US011958861B2

(12) United States Patent
Shepard et al.

(10) Patent No.: US 11,958,861 B2
(45) Date of Patent: Apr. 16, 2024

(54) SPIROCYCLIC LACTAMS AS JAK2 V617F INHIBITORS

(71) Applicant: Incyte Corporation, Wilmington, DE (US)

(72) Inventors: Stacey Shepard, Wilmington, DE (US); Charles Cole, Wilmington, DE (US); Nikoo Falahatpisheh, Wilmington, DE (US); Kai Liu, Chadds Ford, PA (US); Lixin Shao, Wilmington, DE (US); Darius Vrubliauskas, Wilmington, DE (US); Liangxing Wu, Wilmington, DE (US); Wenqing Yao, Chadds Ford, PA (US); Eddy W. Yue, Landenberg, PA (US)

(73) Assignee: Incyte Corporation, Wilmington, DE (US)

( * ) Notice: Subject to any disclaimer, the term of this patent is extended or adjusted under 35 U.S.C. 154(b) by 0 days.

(21) Appl. No.: 17/680,002

(22) Filed: Feb. 24, 2022

(65) Prior Publication Data
US 2022/0281887 A1  Sep. 8, 2022

Related U.S. Application Data

(60) Provisional application No. 63/153,600, filed on Feb. 25, 2021.

(51) Int. Cl.
*C07D 471/22* (2006.01)
*A61P 35/00* (2006.01)
*C07D 471/18* (2006.01)
*C07D 471/20* (2006.01)
*C07D 491/22* (2006.01)
*C07D 519/00* (2006.01)

(52) U.S. Cl.
CPC ............ *C07D 491/22* (2013.01); *A61P 35/00* (2018.01); *C07D 471/18* (2013.01); *C07D 471/20* (2013.01); *C07D 471/22* (2013.01); *C07D 519/00* (2013.01)

(58) Field of Classification Search
CPC .. C07D 471/22; C07D 471/20; C07D 491/22; A61K 31/438; A61K 31/46; A61K 31/506
USPC ....... 544/230; 546/15; 514/212.02, 256, 278
See application file for complete search history.

(56) References Cited

U.S. PATENT DOCUMENTS

| | | | |
|---|---|---|---|
| 4,698,341 A | 10/1987 | Satzinger et al. | |
| 6,339,099 B1 | 1/2002 | Lam et al. | |
| 6,951,865 B2 | 10/2005 | Hibi et al. | |
| 7,429,456 B2 | 9/2008 | Vainchenker et al. | |
| 7,781,199 B2 | 8/2010 | Vainchenker et al. | |
| 7,879,844 B2 | 2/2011 | Inoue et al. | |
| 8,163,767 B2 | 4/2012 | Inoue et al. | |
| 8,524,867 B2 | 9/2013 | Bernett et al. | |
| 8,637,235 B2 | 1/2014 | Vainchenker et al. | |
| 8,785,639 B2 | 7/2014 | Wishart et al. | |
| 8,852,931 B2 | 10/2014 | Vainchenker et al. | |
| 9,115,133 B2 | 8/2015 | Barawkar et al. | |
| 9,233,985 B2 | 1/2016 | Van Zandt et al. | |
| 9,321,730 B2 | 4/2016 | Chan et al. | |
| 9,493,419 B2 | 11/2016 | Tang et al. | |
| 10,065,974 B2 | 9/2018 | Sjogren et al. | |
| 10,155,987 B2 | 12/2018 | Sattler et al. | |
| 10,287,303 B2 | 4/2019 | Sjogren et al. | |
| 10,377,759 B2 | 8/2019 | Yamamoto et al. | |
| 11,753,413 B2 | 9/2023 | Yu et al. | |
| 11,767,323 B2 | 9/2023 | Liu et al. | |
| 11,780,840 B2 | 10/2023 | Ai et al. | |
| 2003/0139431 A1 | 7/2003 | Kawakami et al. | |
| 2004/0209902 A1 | 10/2004 | Lin et al. | |
| 2005/0182060 A1 | 8/2005 | Kelly et al. | |
| 2006/0004043 A1 | 1/2006 | Bhagwat et al. | |
| 2007/0049610 A1 | 3/2007 | Dillon et al. | |
| 2007/0161670 A1 | 7/2007 | Staab et al. | |
| 2008/0004297 A1 | 1/2008 | Cai et al. | |
| 2008/0004318 A1 | 1/2008 | Chelliah et al. | |
| 2008/0188467 A1 | 8/2008 | Wong et al. | |
| 2008/0280879 A1 | 11/2008 | Brickner et al. | |
| 2008/0293739 A1 | 11/2008 | Trede | |
| 2009/0246198 A1 | 10/2009 | Dong et al. | |
| 2010/0105661 A1 | 4/2010 | Shirakami et al. | |
| 2010/0160355 A1 | 6/2010 | DeGoey et al. | |
| 2011/0182812 A1 | 7/2011 | Szardenings et al. | |
| 2011/0269740 A1 | 11/2011 | Sunny et al. | |
| 2011/0313003 A1 | 12/2011 | Shi et al. | |
| 2012/0065188 A1 | 3/2012 | Brickner et al. | |
| 2012/0165370 A1 | 7/2012 | Tang et al. | |
| 2012/0214842 A1 | 8/2012 | Donello et al. | |
| 2012/0282233 A1 | 11/2012 | Rolshausen et al. | |
| 2013/0267521 A1 | 10/2013 | Castro et al. | |

(Continued)

FOREIGN PATENT DOCUMENTS

| | | |
|---|---|---|
| CN | 102838600 | 12/2012 |
| CN | 102838601 | 12/2012 |

(Continued)

OTHER PUBLICATIONS

Atzrodt et al., "The Renaissance of H/D Exchange," Angew Chem Int Ed., 2007, 7744-7765.

(Continued)

*Primary Examiner* — Jeffrey H Murray

(74) *Attorney, Agent, or Firm* — Fish & Richardson P.C.

(57) ABSTRACT

The present application provides spirocyclic lactam compounds that modulate the activity of the V617F variant of JAK2, which are useful in the treatment of various diseases, including cancer.

61 Claims, No Drawings
Specification includes a Sequence Listing.

(56) References Cited

U.S. PATENT DOCUMENTS

| | | | |
|---|---|---|---|
| 2013/0281399 A1 | 10/2013 | McLure et al. | |
| 2013/0302248 A1 | 11/2013 | Gangadharmath et al. | |
| 2014/0142102 A1 | 4/2014 | Fairfax et al. | |
| 2014/0225082 A1 | 8/2014 | Park et al. | |
| 2014/0249204 A1 | 9/2014 | Vainchenker et al. | |
| 2014/0286964 A1 | 9/2014 | Hubbard et al. | |
| 2014/0288048 A1 | 9/2014 | Castro et al. | |
| 2016/0016914 A1 | 1/2016 | Ladziata et al. | |
| 2016/0118600 A1 | 4/2016 | Kim et al. | |
| 2016/0220592 A1 | 8/2016 | Franz et al. | |
| 2017/0107216 A1 | 4/2017 | Wu et al. | |
| 2017/0121346 A1 | 5/2017 | Sprengler et al. | |
| 2017/0145025 A1 | 5/2017 | Li et al. | |
| 2017/0174671 A1 | 6/2017 | Wu et al. | |
| 2017/0174679 A1 | 6/2017 | Lajkiewicz et al. | |
| 2017/0226095 A1 | 8/2017 | Tazi et al. | |
| 2017/0298040 A1 | 10/2017 | Bennett et al. | |
| 2017/0320875 A1 | 11/2017 | Li et al. | |
| 2017/0342060 A1 | 11/2017 | Lu et al. | |
| 2017/0362253 A1 | 12/2017 | Xiao et al. | |
| 2018/0016260 A1 | 1/2018 | Yu et al. | |
| 2018/0031557 A1 | 2/2018 | Scherrer et al. | |
| 2018/0086719 A1 | 3/2018 | Chandrasekhar et al. | |
| 2018/0104245 A1 | 4/2018 | Hansen | |
| 2018/0179159 A1 | 6/2018 | Becknell et al. | |
| 2018/0237797 A1 | 8/2018 | Loh | |
| 2019/0152913 A1 | 5/2019 | Becknell et al. | |
| 2019/0152988 A1 | 5/2019 | Sprengler et al. | |
| 2019/0256492 A1 | 8/2019 | Tu et al. | |
| 2021/0395251 A1 | 12/2021 | Shepard et al. | |
| 2021/0395257 A1 | 12/2021 | Yu et al. | |
| 2022/0002299 A1 | 1/2022 | Liu et al. | |
| 2022/0064165 A1 | 3/2022 | Liu et al. | |
| 2022/0169649 A1 | 6/2022 | Ai et al. | |
| 2022/0213108 A1 | 7/2022 | Buesking et al. | |

FOREIGN PATENT DOCUMENTS

| | | |
|---|---|---|
| CN | 104311426 | 1/2015 |
| CN | 104725249 | 6/2015 |
| CN | 105461714 | 4/2016 |
| CN | 105481765 | 4/2016 |
| CN | 105732591 | 7/2016 |
| CN | 109575022 | 4/2019 |
| CN | 109608504 | 4/2019 |
| CN | 111484480 | 8/2020 |
| EP | 0329012 | 8/1989 |
| EP | 0481448 | 4/1992 |
| EP | 0652218 | 5/1995 |
| EP | 1692281 | 10/2005 |
| EP | 2309567 | 10/2010 |
| EP | 3277293 | 2/2018 |
| EP | 3277820 | 2/2018 |
| EP | 3578555 | 12/2019 |
| FR | 2996129 | 4/2014 |
| JP | 62209062 | 9/1987 |
| JP | 07089957 | 4/1995 |
| JP | 2000123973 | 4/2000 |
| JP | 2003107641 | 4/2003 |
| JP | 2004196702 | 7/2004 |
| KR | 20140111166 | 9/2014 |
| KR | 20150002266 | 1/2015 |
| KR | 20160123112 | 10/2016 |
| KR | 20170003469 | 6/2017 |
| WO | WO 93/17681 | 9/1993 |
| WO | WO 93/17682 | 9/1993 |
| WO | WO 95/18127 | 7/1995 |
| WO | WO 97/34893 | 9/1997 |
| WO | WO 97/47601 | 12/1997 |
| WO | WO 98/16184 | 4/1998 |
| WO | WO 98/40373 | 9/1998 |
| WO | WO 99/61444 | 12/1999 |
| WO | WO 99/64400 | 12/1999 |
| WO | WO 2000/041695 | 7/2000 |
| WO | WO 2000/067754 | 11/2000 |
| WO | WO 2000/068230 | 11/2000 |
| WO | WO 2001/023389 | 4/2001 |
| WO | WO 2001/042247 | 6/2001 |
| WO | WO 2001/047891 | 7/2001 |
| WO | WO 2001/058899 | 8/2001 |
| WO | WO 2001/070229 | 9/2001 |
| WO | WO 2002/000196 | 1/2002 |
| WO | WO 2002/091830 | 11/2002 |
| WO | WO 2003/062209 | 7/2003 |
| WO | WO 2003/074045 | 9/2003 |
| WO | WO 2004/014866 | 2/2004 |
| WO | WO 2004/024693 | 3/2004 |
| WO | WO 2004/030635 | 4/2004 |
| WO | WO 2004/031161 | 4/2004 |
| WO | WO 2004/039806 | 5/2004 |
| WO | WO 2004/055004 | 7/2004 |
| WO | WO 2004/080463 | 9/2004 |
| WO | WO 2005/003100 | 1/2005 |
| WO | WO 2005/007658 | 1/2005 |
| WO | WO 2005/009967 | 2/2005 |
| WO | WO 2005/028478 | 3/2005 |
| WO | WO 2005/061460 | 7/2005 |
| WO | WO 2005/072412 | 8/2005 |
| WO | WO 2005/080377 | 9/2005 |
| WO | WO 2005/082367 | 9/2005 |
| WO | WO 2005/110410 | 11/2005 |
| WO | WO 2005/112932 | 12/2005 |
| WO | WO 2005/117890 | 12/2005 |
| WO | WO 2005/121138 | 12/2005 |
| WO | WO 2006/021448 | 3/2006 |
| WO | WO 2006/032470 | 3/2006 |
| WO | WO 2006/039718 | 4/2006 |
| WO | WO 2006/045096 | 4/2006 |
| WO | WO 2006/045827 | 5/2006 |
| WO | WO 2006/065842 | 6/2006 |
| WO | WO 2006/072828 | 7/2006 |
| WO | WO 2006/074147 | 7/2006 |
| WO | WO 2006/108107 | 10/2006 |
| WO | WO 2006/122156 | 11/2006 |
| WO | WO 2007/002781 | 1/2007 |
| WO | WO 2007/007919 | 1/2007 |
| WO | WO 2007/016525 | 2/2007 |
| WO | WO 2007/022946 | 3/2007 |
| WO | WO 2007/038209 | 4/2007 |
| WO | WO 2007/047653 | 4/2007 |
| WO | WO 2007/051062 | 5/2007 |
| WO | WO 2007/076092 | 5/2007 |
| WO | WO 2007/077949 | 7/2007 |
| WO | WO 2007/110868 | 10/2007 |
| WO | WO 2007/112347 | 10/2007 |
| WO | WO 2007/113565 | 10/2007 |
| WO | WO 2007/125405 | 11/2007 |
| WO | WO 2007/133637 | 11/2007 |
| WO | WO 2007/136465 | 11/2007 |
| WO | WO 2007/140222 | 12/2007 |
| WO | WO 2007/147217 | 12/2007 |
| WO | WO 2008/000409 | 1/2008 |
| WO | WO 2008/005956 | 1/2008 |
| WO | WO 2008/007127 | 1/2008 |
| WO | WO 2008/011109 | 1/2008 |
| WO | WO 2008/011174 | 1/2008 |
| WO | WO 2008/021924 | 2/2008 |
| WO | WO 2008/024977 | 2/2008 |
| WO | WO 2008/046919 | 4/2008 |
| WO | WO 2008/060090 | 5/2008 |
| WO | WO 2008/064107 | 5/2008 |
| WO | WO 2008/079965 | 7/2008 |
| WO | WO 2008/084861 | 7/2008 |
| WO | WO 2008/092231 | 8/2008 |
| WO | WO 2008/112217 | 9/2008 |
| WO | WO 2008/113558 | 9/2008 |
| WO | WO 2008/124083 | 10/2008 |
| WO | WO 2008/135524 | 11/2008 |
| WO | WO 2008/151184 | 12/2008 |
| WO | WO 2009/024095 | 2/2009 |
| WO | WO 2009/042970 | 4/2009 |
| WO | WO 2009/114512 | 9/2009 |
| WO | WO 2010/006130 | 1/2010 |
| WO | WO 2010/026771 | 3/2010 |

(56) References Cited

FOREIGN PATENT DOCUMENTS

| | | |
|---|---|---|
| WO | WO 2010/039518 | 4/2010 |
| WO | WO 2010/042684 | 4/2010 |
| WO | WO 2010/077947 | 7/2010 |
| WO | WO 2010/078229 | 7/2010 |
| WO | WO 2010/080537 | 7/2010 |
| WO | WO 2010/101949 | 9/2010 |
| WO | WO 2010/106436 | 9/2010 |
| WO | WO 2010/107765 | 9/2010 |
| WO | WO 2010/107768 | 9/2010 |
| WO | WO 2010/123975 | 10/2010 |
| WO | WO 2010/125350 | 11/2010 |
| WO | WO 2010/129816 | 11/2010 |
| WO | WO 2010/141062 | 12/2010 |
| WO | WO 2010/143168 | 12/2010 |
| WO | WO 2010/143169 | 12/2010 |
| WO | WO 2010/143170 | 12/2010 |
| WO | WO 2011/004276 | 1/2011 |
| WO | WO 2011/022439 | 2/2011 |
| WO | WO 2011/028864 | 3/2011 |
| WO | WO 2011/047432 | 4/2011 |
| WO | WO 2011/050245 | 4/2011 |
| WO | WO 2011/053861 | 5/2011 |
| WO | WO 2011/068899 | 6/2011 |
| WO | WO 2011/072275 | 6/2011 |
| WO | WO 2011/075630 | 6/2011 |
| WO | WO 2011/078143 | 6/2011 |
| WO | WO 2011/078369 | 6/2011 |
| WO | WO 2011/086053 | 7/2011 |
| WO | WO 2011/097717 | 8/2011 |
| WO | WO 2011/103557 | 8/2011 |
| WO | WO 2011/112687 | 9/2011 |
| WO | WO 2011/123693 | 10/2011 |
| WO | WO 2011/137428 | 11/2011 |
| WO | WO 2011/146882 | 11/2011 |
| WO | WO 2012/061696 | 5/2012 |
| WO | WO 2012/066578 | 5/2012 |
| WO | WO 2012/078902 | 6/2012 |
| WO | WO 2012/085176 | 6/2012 |
| WO | WO 2012/089828 | 7/2012 |
| WO | WO 2012/097479 | 7/2012 |
| WO | WO 2012/116237 | 8/2012 |
| WO | WO 2012/127506 | 9/2012 |
| WO | WO 2013/007765 | 1/2013 |
| WO | WO 2013/033093 | 3/2013 |
| WO | WO 2013/033268 | 3/2013 |
| WO | WO 2013/033270 | 3/2013 |
| WO | WO 2013/033981 | 3/2013 |
| WO | WO 2013/049352 | 4/2013 |
| WO | WO 2013/062987 | 5/2013 |
| WO | WO 2013/067036 | 5/2013 |
| WO | WO 2013/086229 | 6/2013 |
| WO | WO 2013/156869 | 10/2013 |
| WO | WO 2013/158928 | 10/2013 |
| WO | WO 2013/167653 | 11/2013 |
| WO | WO 2013/175281 | 11/2013 |
| WO | WO 2013/191112 | 12/2013 |
| WO | WO 2014/018891 | 1/2014 |
| WO | WO 2014/023377 | 2/2014 |
| WO | WO 2014/051653 | 4/2014 |
| WO | WO 2014/074580 | 5/2014 |
| WO | WO 2014/087165 | 6/2014 |
| WO | WO 2014/120764 | 8/2014 |
| WO | WO 2014/203152 | 12/2014 |
| WO | WO 2014/204263 | 12/2014 |
| WO | WO 2015/001518 | 1/2015 |
| WO | WO 2015/009812 | 1/2015 |
| WO | WO 2015/025228 | 2/2015 |
| WO | WO 2015/036560 | 3/2015 |
| WO | WO 2015/049022 | 4/2015 |
| WO | WO 2015/086523 | 6/2015 |
| WO | WO 2015/124063 | 8/2015 |
| WO | WO 2015/144001 | 10/2015 |
| WO | WO 2015/168079 | 11/2015 |
| WO | WO 2016/009076 | 1/2016 |
| WO | WO 2016/116900 | 7/2016 |
| WO | WO 2016/123627 | 8/2016 |
| WO | WO 2016/128465 | 8/2016 |
| WO | WO 2016/160860 | 10/2016 |
| WO | WO 2016/190847 | 12/2016 |
| WO | WO 2016/197027 | 12/2016 |
| WO | WO 2017/003723 | 1/2017 |
| WO | WO 2017/004134 | 1/2017 |
| WO | WO 2017/029601 | 2/2017 |
| WO | WO 2017/059319 | 4/2017 |
| WO | WO 2017/072039 | 5/2017 |
| WO | WO 2017/072283 | 5/2017 |
| WO | WO 2017/075394 | 5/2017 |
| WO | WO 2017/090002 | 6/2017 |
| WO | WO 2017/103931 | 6/2017 |
| WO | WO 2017/205538 | 11/2017 |
| WO | WO 2017/223452 | 12/2017 |
| WO | WO 2018/009622 | 1/2018 |
| WO | WO 2018/046933 | 3/2018 |
| WO | WO 2018/057805 | 3/2018 |
| WO | WO 2018/068017 | 4/2018 |
| WO | WO 2018/083098 | 5/2018 |
| WO | WO 2018/112382 | 6/2018 |
| WO | WO 2018/140512 | 8/2018 |
| WO | WO 2018/140600 | 8/2018 |
| WO | WO 2018/144478 | 8/2018 |
| WO | WO 2018/204176 | 11/2018 |
| WO | WO 2018/204765 | 11/2018 |
| WO | WO 2018/222901 | 12/2018 |
| WO | WO 2018/231745 | 12/2018 |
| WO | WO 2018/237370 | 12/2018 |
| WO | WO 2019/060860 | 3/2019 |
| WO | WO 2019/070492 | 4/2019 |
| WO | WO 2019/129213 | 7/2019 |
| WO | WO 2019/135920 | 7/2019 |
| WO | WO 2019/177975 | 9/2019 |
| WO | WO 2019/201283 | 10/2019 |
| WO | WO 2019/214546 | 11/2019 |
| WO | WO 2021/018012 | 2/2021 |

OTHER PUBLICATIONS

Baxter et al., "Acquired mutation of the tyrosine kinase JAK2 in human myeloproliferative disorders," Lancet., 2005, 365:1054-1061.

Bennett et al., "Proposals for the classification of the myelodysplastic syndromes," Br J Haematol., 1982, 51:189-199.

Berge et al., "Pharmaceutical Salts," Journal of Pharmaceutical Science, 1977, 66:1-19 pages.

Blom et al., "Preparative LC-MS Purification: Improved Compound Specific Method Optimization," J Combi Chem., 2004, 2004, 6:874-883.

Blom et al., "Optimizing Preparative LC-MS Configurations and Methods for Parallel Synthesis Purification," J Combi Chem., 2003, 5:670.

Blom et al., "Two-Pump at Column Dilution Configuration for Preparative LC-MS," J Combi Chem., 2002, 4:295.

Brunning et al., "Myelodysplastic syndromes/neoplasms," in Chapter 5, Swerdlow, et al, eds. WHO Classification of Tumours of Haematopoietic and Lymphoid Tissues., 4th edition, 2008, 21 pages.

Ceesay et al., "The JAK2 V617F mutation is rare in RARS but common in RARS-T," Leukemia, 2006, 20:2060-2061.

Dommaraju et al., "An efficient catalyst- free chemoselective multicomponent reaction for the synthesis of pyrimidine functionalized pyrrolo-annelated derivatives," RSC Adv., Jan. 1, 2015, 5:24327-24335.

Eisenhauer et al., "New response evaluation criteria in solid tumours: Revised RECIST guideline (version 1.1)," European Journal of Cancer, Jan. 2009, 45(2):228-247.

Harris et al., "World Health Organization classification of neoplastic diseases of the hematopoietic and lymphoid tissues: report of the Clinical Advisory Committee meeting—Airlie House, Virginia, Nov. 1997," J Clin Oncol., 1999, 17:3835-3849.

Hart et al., "Structure-Based Design of Selective Janus Kinase 2 Imidazo[4,5-d]pyrrolo[2,3-b]pyridine Inhibitors," ACS Med Chem Lett., Aug. 13, 2015, 6(8):845-849.

(56) References Cited

OTHER PUBLICATIONS

International Search Report and Written Opinion in International Appln. No. PCT/US2021/037870, dated Aug. 13, 2021, 13 pages.
International Search Report and Written Opinion in International Appln. No. PCT/US2021/037877, dated Aug. 13, 2021, 10 pages.
International Search Report and Written Opinion in International Appln. No. PCT/US2021/040182, dated Sep. 22, 2021, 12 pages.
International Search Report and Written Opinion in International Appln. No. PCT/US2021/040185, dated Sep. 22, 2021, 15 pages.
International Search Report and Written Opinion in International Appln. No. PCT/US2021/047687, dated Nov. 19, 2021, 16 pages.
International Search Report and Written Opinion in International Appln. No. PCT/US2021/064295, dated Mar. 17, 2022, 15 pages.
International Search Report and Written Opinion in International Appln. No. PCT/US2022/017654, dated May 30, 2022, 22 pages.
James et al., "A unique clonal JAK2 mutation leading to constitutive signalling causes polycythaemia vera," Nature, 2005, 434:1144-1148.
Jisha et al., "Exploration of 3,6-dihydroimidazo(4,5-d)pyrrolo(2,3-b)pyridin-2(1H)-one derivatives as JAK inhibitors using various in silico techniques," In Silico Pharmacology, 2017, 5(1):1-23.
Kerekes et al., "Aurora kinase inhibitors based on the imidazo[1,2-a]pyrazine core: fluorine and deuterium incorporation improve oral absorption and exposure," J Med Chem., 2011, 54:201-210.
Khalaf et al., "Structure-based design and synthesis of antiparasitic pyrrolopyrimidines targeting pteridine reductase 1," J Med Chem., Jul. 9, 2014, 57(15):6479-6494.
Kralovics et al., "A gain-of-function mutation of JAK2 in myeloproliferative disorders," N Engl J Med., 2005, 352:1779-1790.
Kulagawski et al., "Identification of imidazo-pyrrolopyridines as novel and potent JAK1 inhibitors," J Med Chem., 2012, 55(12):5901-5921.
Labadie et al., "Design and evaluation of novel 8-oxo-pyridopyrimidine Jak1/2 inhibitors," Bioorg Med Chem Lett., Nov. 2013, 23(21):5923-5930.
Leroy et al., "Differential effect of inhibitory strategies of the V617 mutant of JAK2 on cytokine receptor signaling," Journal of Allergy and Clinical Immunology, Jul. 2019, 144(1):224-235.
Levine et al., "Activating mutation in the tyrosine kinase JAK2 in polycythemia vera, essential thrombocythemia, and myeloid metaplasia with myelofibrosis," Cancer Cell., 2005, 7:387-397.
Ma et al., "Mutation Profile of JAK2 Transcripts in Patients with Chronic Myeloproliferative Neoplasias," J. Mol. Diagn., Jan. 2009, 11(1):49-53.
Remington's Pharmaceutical Sciences, 17th ed., Mack Publishing Company, Easton, Pa., 1985, p. 1418.
STN Search Report, dated Dec. 10, 2019, 379 pages.
STN Search Report, dated Dec. 2019, 1 page.
STN Search Report, dated Dec. 2020, 11 pages.
STN Search Report, dated Jun. 19, 2021, 236 pages.
STN Search Report, dated Jun. 2019, 316 pages.
STN Search Report, dated Jun. 2019, 292 pages.
STN Search Report, dated Jun. 2019, 13 pages.
STN Search Report, dated Jun. 2019, 39 pages.
STN Search Report, dated Oct. 2019, 14 pages.
STN Search Report, dated Sep. 2019, 236 pages.
STN Search Report, dated Sep. 2019, 5 pages.
Vainchecker et al., "JAK inhibitors for the treatment of myeloproliferative neoplasms and other disorders," F1000Research., 2018, 7:82.
Vardiman et al., "The 2008 revision of the World Health Organization (WHO) classification of myeloid neoplasms and acute leukemia: rationale and important changes," Blood 2009, 114:937-951.
Vardiman et al., "The World Health Organization (WHO) classification of the myeloid neoplasms," Blood 2002, 100:2292-2302.
Wilmes et al., "Mechanism of homodimeric cytokine receptor activation and dysregulation by oncogenic mutations," Science, 2020, 367:643-652.
Woods et al., "Activation of JAK/STAT Signaling in Megakaryocytes Sustains Myeloproliferation In Vivo," Clin Cancer Res., 2019, 25(19):5901-5912.
Xu et al., "Design, synthesis and biological evaluation of deuterated nintedanib for improving pharmacokinetic properties," J Label Compd Radiopharm., 2015, 58:308-312.
Yamagishi et al., "Discovery of 3,6-dihydroimidazo[4,5-d]pyrrolo[2,3-b]pyridin-2(1H)-one derivatives as novel JAK inhibitors," Biorg & Med Chem., 2015, 23(15):4846-4859.
Yamagishi et al., "Discovery of tricyclic dipyrrolopyridine derivatives as novel JAK inhibitors," Biorg & Med Chem, 2017, 25(20):5311-5326.
Yang et al., "Three-component reaction for synthesis of 2-amino-6-aryl-5-(phenylamino)-3,7-dihydro-4H-pyrrolo[2,3-d]pyrimidin-4-one derivatives in water," J Hetero Chem., 2020, 57(9):3271-3278.
Zak et al., "Discovery and optimization of C-2 methyl imidazopyrrolopyridines as potent and orally bioavailable JAK1 inhibitors with selectivity over JAK2," J Med Chem., 2012, 55(13):6176-6193.
International Preliminary Report on Patentability in International Application No. PCT/US2021/037870, dated Dec. 29, 2022, 8 pages.
International Preliminary Report on Patentability in International Application No. PCT/US2021/037877, dated Dec. 29, 2022, 8 pages.
International Preliminary Report on Patentability in International Application No. PCT/US2021/040182, dated Jan. 12, 2023, 8 pages.
International Preliminary Report on Patentability in International Application No. PCT/US2021/040185, dated Jan. 12, 2023, 8 pages.
International Preliminary Report on Patentability in International Application No. PCT/US2021/047687, dated Mar. 9, 2023, 8 pages.
Scott et al., "JAK2 Exon 12 Mutations in Polycythemia Vera and Idiopathic Erythrocytosis," The New England Journal of Medicine, Feb. 1, 2007, 356:459-68.
Dommaraju et al., "An efficient catalyst- free chemoselective multicomponent reaction for the synthesis of pyrimidine functionalized pyrrolo-annelated derivatives," Electronic Supplementary Information for RSC Adv., Jan. 1, 2015, 64 pages.
Quiroga et al., "Generation of pyrrolo[2,3-d]pyrimidines. Unexpected products in the multicomponent reaction of 6-aminopyrimidines, dimedone, and arylglyoxal," Tetrahedron Letters, Oct. 2010, 51(41):5443-5447.
European Office Action in European Application No. 22710821.4, dated Oct. 4, 2023, 3 pages.

SPIROCYCLIC LACTAMS AS JAK2 V617F INHIBITORS

TECHNICAL FIELD

The present invention provides spirocyclic lactam compounds that modulate the activity of the V617F variant of JAK2 and are useful in the treatment of diseases related to the V617F variant of JAK2, including cancer.

BACKGROUND

Janus kinase (JAK) 2 plays pivotal roles in signaling by several cytokine receptors. The mutant JAK2 V617F is the most common molecular event associated with myeloproliferative neoplasms. Selective targeting of the JAK2 V617F mutant may be useful for treating various pathologies, while sparing essential JAK2 functions. This application is directed to this need and others.

SUMMARY

The present invention relates to, inter alia, compounds of Formula I:

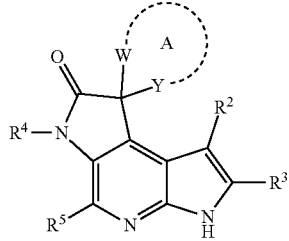

or pharmaceutically acceptable salts thereof, wherein constituent members are defined herein.

The present invention further provides pharmaceutical compositions comprising a compound of Formula I, or a pharmaceutically acceptable salt thereof, and a pharmaceutically acceptable carrier.

The present invention further provides methods of inhibiting an activity of the V617F variant of JAK2 kinase comprising contacting the kinase with a compound of Formula I, or a pharmaceutically acceptable salt thereof.

The present invention further provides methods of treating a disease or a disorder associated with expression or activity of the V617F variant of JAK2 kinase in a patient by administering to a patient a therapeutically effective amount of a compound of Formula I, or a pharmaceutically acceptable salt thereof.

The present invention further provides a compound of Formula I, or a pharmaceutically acceptable salt thereof, for use in any of the methods described herein.

The present invention further provides use of a compound of Formula I, or a pharmaceutically acceptable salt thereof, for the preparation of a medicament for use in any of the methods described herein.

DETAILED DESCRIPTION

The present application provides a compound of Formula I:

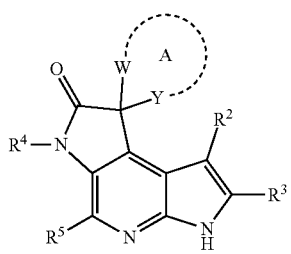

or a pharmaceutically acceptable salt thereof, wherein:

W is $CR^W$, $C(R^W)_2$, N, $NR^W$, O, or S;

Y is $CR^Y$, $C(R^Y)_2$, N, $NR^Y$, O, or S;

wherein at least one of W is $CR^W$ or $C(R^W)_2$ or Y is $CR^Y$ or $C(R^Y)_2$;

each $R^W$ is independently selected from H, oxo, $C_{1-6}$ alkyl, $C_{1-6}$ haloalkyl, $C_{2-6}$ alkenyl, and $C_{2-6}$ alkynyl;

each $R^Y$ is independently selected from H, oxo, $C_{1-6}$ alkyl, $C_{1-6}$ haloalkyl, $C_{2-6}$ alkenyl, and $C_{2-6}$ alkynyl;

Ring A is $C_{3-10}$ cycloalkyl or 4-11 membered heterocycloalkyl, wherein the $C_{3-10}$ cycloalkyl and 4-11 membered heterocycloalkyl of Ring A are each optionally substituted with 1, 2, 3, 4, 5, 6, 7, or 8 independently selected $R^6$ substituents;

$R^2$ is selected from H, halo, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, (4-10 membered heterocycloalkyl)-$C_{1-6}$ alkyl-, CN, $NO_2$, $OR^{a2}$, $SR^{a2}$, $NHOR^{a2}$, $C(O)R^{b2}$, $C(O)NR^{c2}R^{d2}$, $C(O)NR^{c2}(OR^{a2})$, $C(O)OR^{a2}$, $OC(O)R^{b2}$, $OC(O)NR^{c2}R^{d2}$, $NR^{c2}R^{d2}$, $NR^{c2}NR^{c2}R^{d2}$, $NR^{c2}C(O)R^{b2}$, $NR^{c2}C(O)OR^{a2}$, $NR^{c2}C(O)NR^{c2}R^{d2}$, $C(=NR^{e2})R^{b2}$, $C(=NR^{e2})NR^{c2}R^{d2}$, $NR^{c2}C(=NR^{e2})NR^{c2}R^{d2}$, $NR^{c2}C(=NR^{e2})R^{b2}$, $NR^{c2}S(O)R^{b2}$, $NR^{c2}S(O)NR^{c2}R^{d2}$, $NR^{c2}S(O)_2R^{b2}$, $NR^{c2}S(O)(=NR^{e2})R^{b2}$, $NR^{c2}S(O)_2NR^{c2}R^{d2}$, $S(O)R^{b2}$, $S(O)NR^{c2}R^{d2}$, $S(O)_2R^{b2}$, $S(O)_2NR^{c2}R^{d2}$, $OS(O)(=NR^{e2})R^{b2}$, and $OS(O)_2R^{b2}$, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^2$ are each optionally substituted with 1, 2, 3, 4, 5, 6, 7, or 8 independently selected $R^{2A}$ substituents;

each $R^{a2}$, $R^{c2}$, and $R^{d2}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{a2}$, $R^{c2}$ and $R^{d2}$ are each optionally substituted with 1, 2, 3, 4, 5, 6, 7, or 8 independently selected $R^{2A}$ substituents;

or, any $R^{c2}$ and $R^{d2}$ attached to the same N atom, together with the N atom to which they are attached, form a 5-10 membered heteroaryl or a 4-10 membered heterocycloalkyl group, wherein the 5-10 membered heteroaryl or 4-10 membered heterocycloalkyl group is optionally substituted with 1, 2, 3, or 4 independently selected $R^{2A}$ substituents;

each $R^{b2}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{b2}$ are each optionally substituted with 1, 2, 3, 4, 5, 6, 7, or 8 independently selected $R^{2A}$ substituents;

each $R^{e2}$ is independently selected from H, OH, CN, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-;

each $R^{2A}$ is selected from halo, oxo, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, (4-10 membered heterocycloalkyl)-$C_{1-6}$ alkyl-, CN, $NO_2$, $OR^{a21}$, $SR^{a21}$, $NHOR^{a21}$, $C(O)R^{b21}$, $C(O)NR^{c21}R^{d21}$, $C(O)NR^{c21}(OR^{a21})$, $C(O)OR^{a21}$, $OC(O)R^{b21}$, $OC(O)NR^{c21}R^{d21}$, $NR^{c21}R^{d21}$, $NR^{c21}NR^{c21}R^{d21}$, $NR^{c21}C(O)R^{b21}$, $NR^{c21}R^{d21}$, $C(=NR^{e21})R^{b21}$, $C(=NR^{e21})NR^{c21}R^{d21}$, $NR^{c21}C(=NR^{e21})NR^{c21}R^{d21}$, $NR^{c21}C(=NR^{e21})R^{b21}$, $NR^{c21}S(O)R^{b21}$, $NR^{c21}S(O)NR^{c21}R^{d21}$, $NR^{c21}S(O)_2R^{b21}$, $NR^{c21}S(O)(=NR^{e21})R^{b21}$, $NR^{c21}S(O)_2NR^{c21}R^{d21}$, $S(O)R^{b21}$, $S(O)NR^{c21}R^{d21}$, $S(O)_2R^{b21}$, $S(O)_2NR^{c21}R^{d21}$, $OS(O)(=NR)R^{b21}$, and $OS(O)_2R^{b21}$, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{2A}$ are each optionally substituted with 1, 2, 3, 4, 5, 6, 7, or 8 independently selected $R^{2B}$ substituents;

each $R^{a21}$, $R^{c21}$, and $R^{d21}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{a21}$, $R^{c21}$ and $R^{d21}$ are each optionally substituted with 1, 2, 3, 4, 5, 6, 7, or 8 independently selected $R^{2B}$ substituents;

or, any $R^{c21}$ and $R^{d21}$ attached to the same N atom, together with the N atom to which they are attached, form a 5-10 membered heteroaryl or a 4-10 membered heterocycloalkyl group, wherein the 5-10 membered heteroaryl or 4-10 membered heterocycloalkyl group is optionally substituted with 1, 2, 3, or 4 independently selected $R^{2B}$ substituents;

each $R^{b21}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{b21}$ are each optionally substituted with 1, 2, 3, 4, 5, 6, 7, or 8 independently selected $R^{2B}$ substituents;

each $R^{e21}$ is independently selected from H, OH, CN, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-;

each $R^{2B}$ is independently selected from halo, oxo, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, (4-10 membered heterocycloalkyl)-$C_{1-6}$ alkyl-, CN, $NO_2$, $OR^{a22}$, $SR^{a22}$, $NHOR^{a22}$, $C(O)R^{b22}$, $C(O)NR^{c22}R^{d22}$, $C(O)NR^{c22}(OR^{a22})$, $C(O)OR^{a22}$, $OC(O)R^{b22}$, $OC(O)NR^{c22}R^{d22}$, $NR^{c22}R^{d22}$, $NR^{c22}NR^{c22}R^{d22}$, $NR^{c22}C(O)R^{b22}$, $NR^{c22}C(O)OR^{a22}$, $NR^{c22}C(O)NR^{c22}R^{d22}$, $C(=NR^{e22})R^{b22}$, $(=NR^{e22})NR^{c22}R^{d22}$, $NR^{c22}C(=NR^{e22})NR^{c22}R^{d22}$, $NR^{c22}(=NR^{e22})R^{b22}$, $NR^{c22}S(O)R^{b22}$, $NR^{c22}S(O)NR^{c22}R^{d22}$, $NR^{c22}S(O)_2R^{b22}$, $NR^{c22}S(O)(=NR^{e22})R^{b22}$, $NR^{c22}S(O)^2NR^{c22}R^{d22}$, $S(O)R^{b22}$, $S(O)NR^{c22}R^{d22}$, $S(O)_2R^{b22}$, $S(O)_2NR^{c22}R^{d22}$, $OS(O)(=NR^{e22})R^{b22}$, and $OS(O)_2R^{b22}$, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{2B}$ are each optionally substituted with 1, 2, 3, 4, 5, 6, 7, or 8 independently selected $R^{2C}$ substituents;

each $R^{a22}$, $R^{c22}$, and $R^{d22}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{a22}$, $R^{c22}$ and $R^{d22}$ are each optionally substituted with 1, 2, 3, 4, 5, 6, 7, or 8 independently selected $R^{2C}$ substituents;

or, any $R^{c22}$ and $R^{d22}$ attached to the same N atom, together with the N atom to which they are attached, form a 5-10 membered heteroaryl or a 4-10 membered heterocycloalkyl group, wherein the 5-10 membered heteroaryl or 4-10 membered heterocycloalkyl group is optionally substituted with 1, 2, 3, or 4 independently selected $R^{2C}$ substituents;

each $R^{b22}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{b22}$ are each optionally substituted with 1, 2, 3, 4, 5, 6, 7, or 8 independently selected $R^{2C}$ substituents;

each $R^{e22}$ is independently selected from H, OH, CN, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-;

each $R^{2C}$ is independently selected from halo, oxo, $C_{1-6}$ alkyl, $C_{1-6}$ haloalkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, (4-7 membered heterocycloalkyl)-$C_{1-6}$ alkyl-, CN, $NO_2$, $OR^{a23}$, $SR^{a23}$, $NHOR^{a23}$, $C(O)R^{b23}$, $C(O)NR^{c23}R^{d23}$, $C(O)NR^{c23}(OR^{a23})$, $C(O)OR^{a23}$, $OC(O)R^{b23}$, $OC(O)NR^{c23}R^{d23}$, $NR^{c23}R^{d23}$, $NR^{c23}NR^{c23}R^{d23}$, $NR^{c23}C(O)R^{b23}$, $NR^{c23}C(O)OR^{a23}$, $NR^{c23}C(O)NR^{c23}R^{d23}$, $C(=NR^{e23})R^{b23}$, $C(=NR^{e23})NR^{c23}R^{d23}$, $NR^{c23}C(=NR^{e23})NR^{c23}R^{d23}$, $NR^{c23}C(=NR^{e23})R^{b23}$, $NR^{c23}S(O)R^{b23}$, $NR^{c23}S(O)NR^{c23}R^{d23}$, $NR^{c23}S(O)_2R^{b23}$, $NR^{c23}S(O)(=NR^{e23})R^{b23}$, $S(O)R^{b23}$, $S(O)NR^{c23}R^{d23}$, $S(O)_2R^{b23}$, $S(O)_2NR^{c23}R^{d23}$, $OS(O)(=NR^{e23})R^{b23}$, and $OS(O)_2R^{b23}$, wherein the $C_{1-6}$ alkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, (4-7 membered heterocycloalkyl)-$C_{1-6}$ alkyl- of $R^{2C}$ are each optionally substituted with 1, 2, 3, or 4 independently selected $R^M$ substituents;

each $R^{a23}$, $R^{c23}$, and $R^{d23}$ is independently selected from H, $C_{1-6}$ alkyl, $C_{1-6}$ haloalkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl-, wherein the $C_{1-6}$ alkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl- of $R^{a23}$, $R^{c23}$ and $R^{d23}$ are each optionally substituted with 1, 2, 3, or 4 independently selected $R^M$ substituents;

or, any $R^{c23}$ and $R^{d23}$ attached to the same N atom, together with the N atom to which they are attached, form a 5-6 membered heteroaryl or a 4-7 membered heterocycloalkyl group, wherein the 5-6 membered heteroaryl or 4-7 membered heterocycloalkyl group is optionally substituted with 1, 2, 3, or 4 independently selected $R^M$ substituents;

each $R^{b23}$ is independently selected from H, $C_{1-6}$ alkyl, $C_{1-6}$ haloalkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl-, wherein the $C_{1-6}$ alkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl- of $R^{b23}$ are each optionally substituted with 1, 2, 3, or 4 independently selected $R^M$ substituents;

each $R^{e23}$ is independently selected from H, OH, CN, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl-;

$R^3$ is selected from H, halo, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, (4-10 membered heterocycloalkyl)-$C_{1-6}$ alkyl-, CN, $NO_2$, $OR^{a3}$, $SR^{a3}$, $NHOR^{a3}$, $C(O)R^{b3}$, $C(O)NR^{c3}R^{d3}$, $C(O)NR^{c3}(OR^{a3})$, $C(O)OR^{a3}$, $OC(O)R^{b3}$, $OC(O)NR^{c3}R^{d3}$, $NR^{c3}R^{d3}$, $NR^{c3}NR^{c3}R^{d3}$, $NR^{c3}C(O)R^{b3}$, $NR^{c3}C(O)OR^{a3}$, $NR^{c3}C(C)NR^{c3}R^{d3}$, $C(=NR^{e3})R^{b3}$, $C(=NR^{e3})NR^{c3}R^{d3}$, $NR^{c3}C(=NR^{e3})NR^{c3}R^{d3}$, $NR^{c3}C(=NR^{e3})R^{b3}$, $NR^{c3}S(O)R^{b3}$, $NR^{c3}S(C)NR^{c3}R^{d3}$, $NR^{c3}S(O)_2R^{b3}$, $NR^{c3}S(O)(=NR^{e3})R^{b3}$, $NR^{c3}S(O)_2NR^{c3}R^{d3}$, $S(O)R^{b3}$, $S(O)NR^{c3}R^{d3}$, $S(O)_2R^{b3}$, $S(O)_2NR^{c3}R^{d3}$, $OS(O)(=NR^{e3})R^{b3}$, and $OS(O)_2R^{b3}$, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^3$ are each optionally substituted with 1, 2, 3, 4, 5, 6, 7, or 8 independently selected $R^{3A}$ substituents;

each $R^{a3}$, $R^{c3}$, and $R^{d3}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{a3}$, $R^{c3}$ and $R^{d3}$ are each optionally substituted with 1, 2, 3, 4, 5, 6, 7, or 8 independently selected $R^{3A}$ substituents;

or, any $R^{c3}$ and $R^{d3}$ attached to the same N atom, together with the N atom to which they are attached, form a 5-10 membered heteroaryl or a 4-10 membered heterocycloalkyl group, wherein the 5-10 membered heteroaryl or 4-10 membered heterocycloalkyl group is optionally substituted with 1, 2, 3, or 4 independently selected $R^{3A}$ substituents;

each $R^{b3}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{b3}$ are each optionally substituted with 1, 2, 3, 4, 5, 6, 7, or 8 independently selected $R^{3A}$ substituents;

each $R^{e3}$ is independently selected from H, OH, CN, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-;

each $R^{3A}$ is selected from halo, oxo, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, (4-10 membered heterocycloalkyl)-$C_{1-6}$ alkyl-, CN, $NO_2$, $OR^{a31}$, $SR^{a31}$, $NHOR^{a31}$, $C(O)R^{b31}$, $C(O)NR^{c31}(OR^{a31})$, $C(O)OR^{a31}$, $OC(O)R^{b31}$, $OC(O)NR^{c31}R^{d31}$, $NR^{c31}R^{d31}$, $NR^{c31}C(O)R^{b31}$, $NR^{c31}C(O)OR^{a31}$, $NR^{c31}C(O)NR^{c31}R^{d31}$, $C(=NR^{e31})NR^{c31}R^{d31}$, $NR^{c31}C(=NR^{e31})$ $NR^{c31}R^{d31}$, $NR^{c31}C(=NR^{e31})R^{b31}$, $NR^{c31}S(O)R^{b31}$, $NR^{c31}S(O)NR^{c31}R^{d31}$, $NR^{c31}S(O)_2R^{b31}$, $NR^{c31}S(O)_2$ $NR^{c31}R^{d31}$, $S(O)R^{b31}$, $S(O)NR^{c31}R^{d31}$, $S(O)^2R^{b31}$, $S(O)_2NR^{c31}R^{d31}$, $OS(O)(=NR^{e31})R^{b31}$, and $OS(O)_2$ $R^{b31}$, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{3A}$ are each optionally substituted with 1, 2, 3, 4, 5, 6, 7, or 8 independently selected $R^{3B}$ substituents;

each $R^{a31}$, $R^{c31}$, and $R^{d31}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{a31}$, $R^{c31}$ and $R^{d31}$ are each optionally substituted with 1, 2, 3, 4, 5, 6, 7, or 8 independently selected $R^{3B}$ substituents;

or, any $R^{c31}$ and $R^{d31}$ attached to the same N atom, together with the N atom to which they are attached, form a 5-10 membered heteroaryl or a 4-10 membered heterocycloalkyl group, wherein the 5-10 membered heteroaryl or 4-10 membered heterocycloalkyl group is optionally substituted with 1, 2, 3, or 4 independently selected $R^{3B}$ substituents;

each $R^{b31}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{b31}$ are each optionally substituted with 1, 2, 3, 4, 5, 6, 7, or 8 independently selected $R^{3B}$ substituents;

each $R^{e31}$ is independently selected from H, OH, CN, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-;

each $R^{3B}$ is independently selected from halo, oxo, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, (4-10 membered heterocycloalkyl)-$C_{1-6}$ alkyl-, CN, $NO_2$, $OR^{a32}$, $SR^{a32}$, $NHOR^{a32}$, $C(O)R^{b32}$, $C(O)NR^{c32}R^{d32}$, $C(O)NR^{c32}(OR^{a32})$, $C(O)OR^{a32}$, $OC(O)R^{b32}$, $OC(O)NR^{c32}R^{d32}$, $NR^{c32}R^{d32}$, $NR^{c32}NR^{c32}R^{d32}$, $NR^{c32}C(O)R^{b32}$, $NR^{c32}C(O)OR^{a32}$, $NR^{c32}(O)NR^{c32}R^{d32}$, $C(=NR^{e32})R^{b32}$, $(=NR^{e32})NR^{c32}R^{d32}$, $NR^{c32}C(=NR^{e32})NR^{c32}R^{d32}$, $NR^{c32}(=NR^{e32})R^{b32}$, $NR^{c32}S(O)R^{b32}$, $NR^{c32}S(O)NR^{c32}R^{d32}$, $NR^{c32}S(O)_2R^{b32}$, $NR^{c32}S(O)(=NR^{e32})R^{b32}$, $NR^{c32}S(O)_2NR^{c32}R^{d32}$, $S(O)R^{b32}$, $S(O)NR^{c32}R^{d32}$, $S(O)_2R^{b32}$, $S(O)_2NR^{c32}R^{d32}$, $OS(O)(=NR^{e32})R^{b32}$, and $OS(O)_2R^{b32}$, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{3B}$ are each optionally substituted with 1, 2, 3, 4, 5, 6, 7, or 8 independently selected $R^{3C}$ substituents;

each $R^{a32}$, $R^{c32}$, and $R^{d32}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{a32}$, $R^{c32}$ and $R^{d32}$ are each optionally substituted with 1, 2, 3, 4, 5, 6, 7, or 8 independently selected $R^{3C}$ substituents;

or, any $R^{c32}$ and $R^{d32}$ attached to the same N atom, together with the N atom to which they are attached, form a 5-10 membered heteroaryl or a 4-10 membered heterocycloalkyl group, wherein the 5-10 membered heteroaryl or 4-10 membered heterocycloalkyl group is optionally substituted with 1, 2, 3, or 4 independently selected $R^{3C}$ substituents;

each $R^{b32}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_3$ cycloalkyl, 5-10 membered heteroaryl, 4-10 membered heterocycloalkyl, $C_{2-6}$ aryl-$C_{2-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{b32}$ are each optionally substituted with 1, 2, 3, 4, 5, 6, 7, or 8 independently selected $R^{3C}$ substituents;

each $R^{e32}$ is independently selected from H, OH, CN, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-;

each $R^{3C}$ is independently selected from halo, oxo, $C_{1-6}$ alkyl, $C_{1-6}$ haloalkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, (4-7 membered heterocycloalkyl)-$C_{1-6}$ alkyl-, CN, $NO_2$, $OR^{a33}$, $SR^{a33}$, $NHOR^{a33}$, $C(O)R^{b33}$, $C(O)NR^{c33}R^{d33}$, $C(O)NR^{c33}(OR^{a33})$, $C(O)OR^{a33}$, $OC(O)R^{b33}$, $OC(O)NR^{c33}R^{d33}$, $NR^{c33}R^{d33}$, $NR^{c33}NR^{c33}R^{d33}$, $NR^{c33}C(O)R^{b33}$, $NR^{c33}C(O)OR^{a33}$, $NR^{c33}C(O)NR^{c33}R^{d33}$, $C(=NR^{e33})R^{b33}$, $C(=NR^{e33})NR^{c33}R^{d33}$, $NR^{c33}C(=NR^{e33})NR^{c33}R^{d33}$, $NR^{c33}C(=NR^{e33})R^{b33}$, $NR^{c33}S(O)R^{b33}$, $NR^{c33}S(O)NR^{c33}R^{d33}$, $NR^{c33}S(O)R^{b33}$, $NR^{c33}S(O)(=NR^{e33})R^{b33}$, $NR^{c33}S(O)_2NR^{c33}R^{d33}$, $S(O)R^{b33}$, $S(O)NR^{c33}R^{d33}$, $S(O)_2R^{b33}$, $S(O)_2NR^{c33}R^{d33}$, $OS(O)(=NR^{e33})R^{b33}$, and $OS(O)_2R^{b33}$, wherein the $C_{1-6}$ alkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, (4-7 membered heterocycloalkyl)-$C_{1-6}$ alkyl- of $R^{3C}$ are each optionally substituted with 1, 2, 3, or 4 independently selected $R^M$ substituents;

each $R^{a33}$, $R^{c33}$, and $R^{d33}$ is independently selected from H, $C_{1-6}$ alkyl, $C_{1-6}$ haloalkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl-, wherein the $C_{1-6}$ alkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl- of $R^{a33}$, $R^{c33}$ and $R^{d33}$ are each optionally substituted with 1, 2, 3, or 4 independently selected $R^M$ substituents;

or, any $R^{c33}$ and $R^{d33}$ attached to the same N atom, together with the N atom to which they are attached, form a 5-6 membered heteroaryl or a 4-7 membered heterocycloalkyl group, wherein the 5-6 membered heteroaryl or 4-7 membered heterocycloalkyl group is optionally substituted with 1, 2, 3, or 4 independently selected $R^M$ substituents;

each $R^{b33}$ is independently selected from H, $C_{1-6}$ alkyl, $C_{1-6}$ haloalkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl-, wherein the $C_{1-6}$ alkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl- of $R^{b33}$ are each optionally substituted with 1, 2, 3, or 4 independently selected $R^M$ substituents;

each $R^{e33}$ is independently selected from H, OH, CN, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl-;

$R^4$ is selected from H, $C_{1-6}$ alkyl, $C_{1-6}$ alkoxy, $C_{1-6}$ haloalkyl, $C_{1-6}$ haloalkoxy, OH, $NH_2$, and $NHC_{1-6}$ alkyl, wherein the $C_{1-6}$ alkyl is optionally substituted with OH, CN, and $NH_2$;

$R^5$ is selected from H, halo, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, OH, CN, C(O)OH, $C(O)NHR^{a5}$, $NH_2$, and $NHC_{1-6}$ alkyl, wherein the $C_{1-6}$ alkyl is optionally substituted with OH, CN, and $NH_2$;

$R^{a5}$ is H, $C_{1-6}$ alkyl, $C_{1-6}$ alkoxy, $C_{1-6}$ haloalkyl, $C_{1-6}$ haloalkoxy, OH, $NH_2$, and $NHC_{1-6}$ alkyl, wherein the $C_{1-6}$ alkyl is optionally substituted with OH, CN, and $NH_2$;

each $R^6$ is independently selected from halo, oxo, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, (4-10 membered heterocycloalkyl)-$C_{1-6}$ alkyl-, CN, $NO_2$, $OR^{a6}$, $SR^{a6}$, $NHOR^{a6}$, $C(O)R^{b6}$, $C(O)NR^{c6}R^{d6}$, $C(O)NR^{c6}(OR^{a6})$, $C(O)OR^{a6}$, $OC(O)R^{b6}$, $OC(C)NR^{c6}R^{d6}$, $NR^{c6}R^{d6}$, $NR^{c6}NR^{c6}R^{d6}$, $NR^{c6}C(O)R^{b6}$, $NR^{c6}C(O)OR^{a6}$, $NR^{c6}C(O)NR^{c6}R^{d6}$, $C(=NR^{e6})R^{b6}$, $C(=NR^{e6})NR^{c6}R^{d6}$, $NR^{c6}C(=NR^{e6})NR^{c6}R^{d6}$, $NR^{c6}C(=NR^{e6})R^{b6}$, $NR^{c6}S(O)R^{b6}$, $NR^{c6}S(O)NR^{c6}R^{d6}$, $NR^{c6}S(O)_2R^{b6}$, $NR^{c6}S(O)(=NR^{e6})R^{b6}$, $NR^{c6}S(O)^2NR^{c6}R^{d6}$, $S(O)R^{b6}$, $S(O)NR^{c6}R^{d6}$, $OS(O)(=NR^{e6})R^{b6}$, and $OS(O)_2R^{b6}$, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^6$ are each optionally substituted with 1, 2, 3, 4, 5, 6, 7, or 8 independently selected $R^{6A}$ substituents;

each $R^{a6}$, $R^{c6}$, and $R^{d6}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{a6}$, $R^{c6}$ and $R^{d6}$ are each optionally substituted with 1, 2, 3, 4, 5, 6, 7, or 8 independently selected $R^{6A}$ substituents;

or, any $R^{a6}$ and $R^{d6}$ attached to the same N atom, together with the N atom to which they are attached, form a 5-10 membered heteroaryl or a 4-10 membered heterocycloalkyl group, wherein the 5-10 membered heteroaryl or 4-10 membered heterocycloalkyl group is optionally substituted with 1, 2, 3, or 4 independently selected $R^{6A}$ substituents;

each $R^{b6}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{b6}$ are each optionally substituted with 1, 2, 3, 4, 5, 6, 7, or 8 independently selected $R^{6A}$ substituents;

each $R^{e6}$ is independently selected from H, OH, CN, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-;

each $R^{6A}$ is independently selected from halo, oxo, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, (4-10 membered heterocycloalkyl)-$C_{1-6}$ alkyl-, CN, $NO_2$, $OR^{a61}$, $SR^{a61}$, $NHOR^{a61}$, $C(O)R^{b61}$, $C(O)NR^{c61}R^{d61}$, $C(O)NR^{c61}(OR^{a61})$, $C(O)OR^{a61}$, $OC(O)R^{b61}$, $OC(O)NR^{c61}R^{d61}$, $NR^{c61}R^{d61}$, $NR^{c61}NR^{c61}R^{d61}$, $NR^{c61}C(O)R^{b61}$, $NR^{c61}C(O)OR^{a61}$, $NR^{c61}C(O)NR^{c61}R^{d61}$, $C(=NR^{e61})R^{b61}$, $C(=NR^{e61})NR^{c61}R^{d61}$, $NR^{c61}C(=NR^{e61})NR^{c61}R^{d61}$, $NR^{c61}C(=NR^{e61})R^{b61}$, $NR^{c61}S(O)R^{b61}$, $NR^{c61}S(O)NR^{c61}R^{d61}R^{c61}S(O)_2R^{b61}$, $NR^{c61}$, $OS(O)(=NR^{e61})R^{b61}$, $NR^{c61}S(O)_2NR^{c61}R^{d61}$, $S(O)R^{b61}$, $S(O)NR^{c61}R^{d61}$, $S(O)_2R^{b61}$, $S(O)_2NR^{c61}R^{d61}$, $OS(O)(=NR^{e61})R^{b61}$, and $OS(O)_2R^{b61}$, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{6A}$ are each optionally substituted with 1, 2, 3, 4, 5, 6, 7, or 8 independently selected $R^{6B}$ substituents;

each $R^{a61}$, $R^{c61}$, and $R^{d61}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{a61}$, $R^{c61}$ and $R^{d61}$ are each optionally substituted with 1, 2, 3, 4, 5, 6, 7, or 8 independently selected $R^{6B}$ substituents;

or, any $R^{c61}$ and $R^{d61}$ attached to the same N atom, together with the N atom to which they are attached, form a 5-10 membered heteroaryl or a 4-10 membered heterocycloalkyl group, wherein the 5-10 membered heteroaryl or 4-10 membered heterocycloalkyl group is optionally substituted with 1, 2, 3, or 4 independently selected $R^{6B}$ substituents;

each $R^{b61}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{b61}$ are each optionally substituted with 1, 2, 3, 4, 5, 6, 7, or 8 independently selected $R^{6B}$ substituents;

each $R^{e61}$ is independently selected from H, OH, CN, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-;

each $R^{6B}$ is independently selected from halo, oxo, $C_{1-6}$ alkyl, $C_{1-6}$ haloalkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, (4-7 membered heterocycloalkyl)-$C_{1-6}$ alkyl-, CN, $NO_2$, $OR^{a62}$, $SR^{a62}$, $NHOR^{a62}$, $C(O)R^{b62}$, $C(O)NR^{c62}R^{d62}$, $C(O)NR^{c62}(OR^{a62})$, $C(O)OR^{a62}$, $OC(O)R^{b62}$, $OC(O)NR^{c62}R^{d62}$, $NR^{c62}R^{d62}$, $NR^{c62}NR^{c62}R^{d62}$, $NR^{c62}C(O)R^{b62}$, $NR^{c62}C(O)OR^{a62}$, $NR^{c62}C(O)NR^{c62}R^{d62}$, $C(=NR^{e62})R^{b62}$, $C(=NR^{e62})NR^{c62}R^{d62}$, $NR^{c62}C(=NR^{e62})NR^{c62}R^{d62}$, $NR^{c62}C(=NR^{e62})R^{b62}$, $NR^{c62}S(O)R^{b62}$, $NR^{c62}S(O)NR^{c62}R^{d62}$, $NR^{c62}S(O)_2R^{b62}$, $NR^{c62}S(O)(=NR^{e62})R^{b62}$, $NR^{c62}S(O)R^{b62}$, $S(O)NR^{c62}R^{d62}$, $S(O)_2R^{b62}$, $S(O)_2NR^{c62}R^{d62}$, $OS(O)(=NR^{e62})R^{b62}$, and $OS(O)_2R^{b62}$, wherein the $C_{1-6}$ alkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl- and (4-7 membered heterocycloalkyl)-$C_{1-6}$ alkyl- of $R^{6B}$ are each optionally substituted with 1, 2, 3, or 4 independently selected $R^{6C}$ substituents;

each $R^{a62}$, $R^{c62}$, and $R^{d62}$ and is independently selected from H, $C_{1-6}$ alkyl, $C_{1-6}$ haloalkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl-, wherein the $C_{1-6}$ alkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl- of $R^{a62}$, $R^{c62}$ and $R^{d62}$ are each optionally substituted with 1, 2, 3, or 4 independently selected $R^{6C}$ substituents;

or, any $R^{c62}$ and $R^{d62}$ attached to the same N atom, together with the N atom to which they are attached, form a 5-6 membered heteroaryl or a 4-7 membered heterocycloalkyl group, wherein the 5-6 membered heteroaryl or 4-7 membered heterocycloalkyl group is optionally substituted with 1, 2, 3, or 4 independently selected $R^{6C}$ substituents;

each $R^{b62}$ is independently selected from H, $C_{1-6}$ alkyl, $C_{1-6}$ haloalkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl-, wherein the $C_{1-6}$ alkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl- of $R^{b62}$ are each optionally substituted with 1, 2, 3, or 4 independently selected $R^{6C}$ substituents;

each $R^{e62}$ is independently selected from H, OH, CN, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl-;

each $R^{6C}$ is independently selected from halo, oxo, $C_{1-6}$ alkyl, $C_{1-6}$ haloalkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, (4-7 membered heterocycloalkyl)-$C_{1-6}$ alkyl-, CN, $NO_2$, $OR^{a63}$, $SR^{a63}$, $NHOR^{a63}$, $C(O)R^{b63}$, $C(O)NR^{c63}R^{d63}$, $C(O)NR^{c63}(OR^{a63})$, $C(O)OR^{a63}$, $OC(O)R^{b63}$, $OC(O)NR^{c63}R^{d63}$, $NR^{c63}R^{d63}$, $NR^{c63}NR^{c63}R^{d63}$, $NR^{c63}C(O)R^{b63}$, $NR^{c63}C(O)OR^{a63}$, $NR^{c63}C(O)NR^{c63}R^{d63}$, $C(=NR^{e63})R^{b63}$, $C(=NR^{e63})NR^{c63}R^{d63}$, $NR^{c63}C(=NR^{e63})NR^{c63}R^{d63}$, $NR^{c63}C(=NR^{e63})R^{b63}$, $NR^{c63}S(O)R^{b63}$, $NR^{c63}S(O)NR^{c63}R^{d63}$, $NR^{c63}S(O)_2R^{b63}$, $NR^{c63}S(O)(=NR^{e63})R^{b63}$, $NR^{c63}S(O)_2NR^{c63}R^{d63}$, $S(O)R^{b63}$, $S(O)NR^{c63}R^{d63}$, $S(O)_2R^{b63}$, $S(O)_2NR^{c63}R^{d63}$, $OS(O)(=NR^{e63})R^{b63}$, and $OS(O)_2R^{b63}$, wherein the $C_{1-6}$ alkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl- and (4-7 membered heterocycloalkyl)-$C_{1-6}$ alkyl- of $R^{6C}$ are each optionally substituted with 1, 2, 3, or 4 independently selected $R^M$ substituents;

each $R^{a63}$, $R^{c63}$, and $R^{d63}$ is independently selected from H, $C_{1-6}$ alkyl, $C_{1-6}$ haloalkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl-, wherein the $C_{1-6}$ alkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl- of $R^{a63}$, $R^{c63}$ and $R^{d63}$ are each optionally substituted with 1, 2, 3, or 4 independently selected $R^M$ substituents;

or, any $R^{c63}$ and $R^{d63}$ attached to the same N atom, together with the N atom to which they are attached, form a 5-6 membered heteroaryl or a 4-7 membered heterocycloalkyl group, wherein the 5-6 membered heteroaryl or 4-7 membered heterocycloalkyl group is optionally substituted with 1, 2, 3, or 4 independently selected $R^M$ substituents;

each $R^{b63}$ is independently selected from H, $C_{1-6}$ alkyl, $C_{1-6}$ haloalkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl-, wherein the $C_{1-6}$ alkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl- of $R^{b63}$ are each optionally substituted with 1, 2, 3, or 4 independently selected $R^M$ substituents;

each $R^{e63}$ is independently selected from H, OH, CN, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl-;

each $R^M$ is independently selected from H, OH, halo, oxo, CN, C(O)OH, $C(O)NH_2$, $C(O)NH(C_{1-4}$ alkyl), $C(O)N(C_{1-6}$ alkyl$)_2$, $NH_2$, $NO_2$, $SF_5$, $C_{1-6}$ alkyl, $C_{1-6}$ alkoxy, $C_{1-6}$ haloalkoxy, $C_{1-6}$ haloalkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl-.

In some embodiments:

W is $CR^W$, $C(R^W)_2$, N, $NR^W$, O, or S;

Y is $CR^Y$, $C(R^Y)_2$, N, $NR^Y$, O, or S;

wherein at least one of W is $CR^W$ or $C(R^W)_2$ or Y is $CR^Y$ or $C(R^Y)_2$;

each $R^W$ is independently selected from H, oxo, $C_{1-6}$ alkyl, $C_{1-6}$ haloalkyl, $C_{2-6}$ alkenyl, and $C_{2-6}$ alkynyl;

each $R^Y$ is independently selected from H, oxo, $C_{1-6}$ alkyl, $C_{1-6}$ haloalkyl, $C_{2-6}$ alkenyl, and $C_{2-6}$ alkynyl;

Ring A is $C_{3-10}$ cycloalkyl or 4-10 membered heterocycloalkyl, wherein the $C_{3-10}$ cycloalkyl and 4-10 membered heterocycloalkyl of Ring A are each optionally substituted with 1, 2, 3, 4, 5, 6, 7, or 8 independently selected $R^6$ substituents;

$R^2$ is selected from H, halo, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, (4-10 membered heterocycloalkyl)-$C_{1-6}$ alkyl-, CN, $NO_2$, $OR^{a2}$, $SR^{a2}$, $NHOR^{a2}$, $C(O)R^{b2}$, $C(O)NR^{c2}R^{d2}$, $C(O)NR^{c2}(OR^{a2})$, $C(O)OR^{a2}$, $OC(O)R^{b2}$, $OC(O)NR^{c2}R^{d2}$, $NR^{c2}R^{d2}$, $NR^{c2}NR^{c2}R^{d2}$, $NR^{c2}C(O)R^{b2}$, $NR^{c2}C(O)OR^{a2}$, $NR^{c2}C(O)NR^{c2}R^{d2}$, $C(=NR^{e2})R^{b2}$, $C(=NR^{e2})NR^{c2}R^{d2}$, $NR^{c2}C(=NR^{e2})NR^{c2}R^{d2}$, $NR^{c2}C(NR^{e2})R^{b2}$, $NR^{c2}S(O)R^{b2}$, $NR^{c2}S(O)NR^{c2}R^{d2}$, $NR^{c2}S(O)_2R^{b2}$, $NR^{c2}S(O)(=NR^{e2})R^{b2}$, $NR^{c2}S(O)_2NR^{c2}R^{d2}$, $S(O)R^{b3}$, $S(O)NR^{c2}R^{d2}$, $S(O)_2R^{b2}$, $S(O)_2NR^{c2}R^{d2}$, $OS(O)(=NR^{e2})R^{b2}$, and $OS(O)_2R^{b2}$, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^2$ are each optionally substituted with 1, 2, 3, 4, 5, 6, 7, or 8 independently selected $R^{2A}$ substituents;

each $R^{a2}$, $R^{c2}$, and $R^{d2}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{a2}$, $R^{c2}$ and $R^{d2}$ are each optionally substituted with 1, 2, 3, 4, 5, 6, 7, or 8 independently selected $R^{2A}$ substituents;

or, any $R^{c2}$ and $R^{d2}$ attached to the same N atom, together with the N atom to which they are attached, form a 5-10 membered heteroaryl or a 4-10 membered heterocycloalkyl group, wherein the 5-10 membered heteroaryl or 4-10 membered heterocycloalkyl group is optionally substituted with 1, 2, 3, or 4 independently selected $R^{2A}$ substituents;

each $R^{b2}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{b2}$ are each optionally substituted with 1, 2, 3, 4, 5, 6, 7, or 8 independently selected $R^{2A}$ substituents;

each $R^{e2}$ is independently selected from H, OH, CN, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-;

each $R^{2A}$ is selected from halo, oxo, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, (4-10 membered heterocycloalkyl)-$C_{1-6}$ alkyl-, CN, $NO_2$, $OR^{a21}$, $SR^{a21}$, $NHOR^{a21}$, $C(O)R^{b21}$, $C(O)NR^{c21}R^{d21}$, $C(O)NR^{c21}(OR^{a21})$ $C(O)OR^{a21}$, $OC(O)R^{b21}$, $OC(O)NR^{c21}R^{d21}$, $C(=NR^{e21})R^{d21}$, $NR^{c21}NR^{c21}R^{d21}$, $NR^{c21}C(O)R^{b21}$, $NR^{c21}C(O)OR^{a21}$, $NR^{c21}C(O)NR^{c21}R^{d21}$, $C(=NR^{e21})R^{b21}$, $C(=NR^{e21})NR^{c21}R^{d21}$, $NR^{c21}C(=NR^{e21})NR^{c21}R^{d21}$, $NR^{c21}C(=NR^{e21})R^{b21}$, $NR^{c21}S(O)R^{b21}$, $NR^{c21}S(O)NR^{c21}R^{d21}$, $NR^{c21}S(O)_2R^{b21}$, $NR^{c21}S(O)(=NR^{e21})R^{b21}$, $NR^{c21}S(O)_2NR^{c21}R^{d21}$, $S(O)R^{b21}$, $S(O)NR^{c21}R^{d21}$, $S(O)_2R^{b21}$, $S(O)_2NR^{c21}R^{d21}$, $OS(O)(=NR^{e21})R^{b21}$, and $OS(O)_2R^{b21}$, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{2A}$ are each optionally substituted with 1, 2, 3, 4, 5, 6, 7, or 8 independently selected $R^{2B}$ substituents;

each $R^{a21}$, $R^{c21}$, and $R^{d21}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{a21}$, $R^{c21}$ and $R^{d21}$ are each optionally substituted with 1, 2, 3, 4, 5, 6, 7, or 8 independently selected $R^{2B}$ substituents;

or, any $R^{c21}$ and $R^{d21}$ attached to the same N atom, together with the N atom to which they are attached, form a 5-10 membered heteroaryl or a 4-10 membered heterocycloalkyl group, wherein the 5-10 membered heteroaryl or 4-10 membered heterocycloalkyl group is optionally substituted with 1, 2, 3, or 4 independently selected $R^{2B}$ substituents;

each $R^{b21}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{b21}$ are each optionally substituted with 1, 2, 3, 4, 5, 6, 7, or 8 independently selected $R^{2B}$ substituents;

each $R^{e21}$ is independently selected from H, OH, CN, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-;

each $R^{2B}$ is independently selected from halo, oxo, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, (4-10 membered heterocycloalkyl)-$C_{1-6}$ alkyl-, CN, $NO_2$, $OR^{a22}$, $SR^{a22}$, $NHOR^{a22}$, $C(O)R^{b22}$, $C(O)NR^{c22}R^{d22}$, $C(O)NR^{c22}(OR^{a22})$, $C(O)OR^{a22}$, $OC(O)R^{b22}$, $OC(O)NR^{c22}R^{d22}$, $NR^{c22}R^{d22}$, $NR^{c22}NR^{c22}R^{d22}$, $NR^{c22}C(O)R^{b22}$, $NR^{c22}C(O)OR^{a22}$, $NR^{c22}C(O)NR^{c22}R^{d22}$, $C(=NR^{e22})R^{b22}$, $(=NR^{e22})NR^{c22}R^{d22}$, $NR^{c22}C(=NR^{e22})NR^{c22}R^{d22}$, $NR^{c22}C(=NR^{e22})R^{b22}$, $NR^{c22}S(O)R^{b22}$, $NR^{c22}S(O)NR^{c22}R^{d22}$, $NR^{c22}S(O)_2R^{b22}$, $NR^{c22}S(O)(=NR^{e22})R^{b22}$, $NR^{c22}S(O)^2NR^{c22}R^{d22}$, $S(O)R^{b22}$, $S(O)NR^{c22}R^{d22}$, $S(O)_2R^{22b}$, $S(O)_2NR^{c22}R^{d22}$, $OS(O)(=NR^{e22})R^{b22}$, and $OS(O)_2R^{b22}$, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{2B}$ are each optionally substituted with 1, 2, 3, 4, 5, 6, 7, or 8 independently selected $R^{2C}$ substituents;

each $R^{a22}$, $R^{c22}$, and $R^{d22}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{a22}$, $R^{c22}$ and $R^{d22}$ are each optionally substituted with 1, 2, 3, 4, 5, 6, 7, or 8 independently selected $R^{2C}$ substituents;

or, any $R^{c22}$ and $R^{d22}$ attached to the same N atom, together with the N atom to which they are attached, form a 5-10 membered heteroaryl or a 4-10 membered heterocycloalkyl group, wherein the 5-10 membered heteroaryl or 4-10 membered heterocycloalkyl group is optionally substituted with 1, 2, 3, or 4 independently selected $R^{2C}$ substituents;

each $R^{b22}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_1$-6 alkyl-, $C_{3-30}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{b22}$ are each optionally substituted with 1, 2, 3, 4, 5, 6, 7, or 8 independently selected $R^{2C}$ substituents;

each $R^{e22}$ is independently selected from H, OH, CN, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-;

each $R^{2C}$ is independently selected from halo, oxo, $C_{1-6}$ alkyl, $C_{1-6}$ haloalkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, (4-7 membered heterocycloalkyl)-$C_{1-6}$ alkyl-, CN, $NO_2$, $OR^{a23}$, $SR^{a23}$, $NHOR^{a23}$, $C(O)R^{b23}$, $C(O)NR^{c23}NR^{d23}$, $C(O)NR^{c23}(OR^{a23})$, $C(O)OR^{a23}$, $OC(O)R^{b23}$, $OC(O)NR^{c23}R^{d23}$, $NR^{c23}R^{d23}$, $NR^{c23}NR^{c23}R^{d23}$, $NR^{c23}C(O)R^{b23}$, $NR^{c23}C(O)OR^{a23}$, $NR^{c23}C(O)NR^{c23}R^{d23}$, $C(=NR^{e23})R^{b23}$, $C(=NR^{e23})NR^{c23}R^{d23}$, $NR^{c23}C(=NR^{e23})NR^{c23}R^{d23}$, $NR^{c23}C(=NR^{e23})R^{b23}$, $NR^{c23}S(O)R^{b23}$, $NR^{c23}S(O)NR^{c23}R^{d23}$, $NR^{c23}S(O)_2R^{b23}$, $NR^{c23}S(O)(=NR^{e23})R^{b23}$, $NR^{c23}S(O)_2NR^{c23}R^{d23}$, $S(O)R^{b23}$, $S(O)NR^{c23}R^{d23}$, $S(O)_2R^{b23}$, $S(O)_2NR^{c23}R^{d23}$, $OS(O)(=NR^{e23})R^{b23}$, and $OS(O)_2R^{b23}$, wherein the $C_{1-6}$ alkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, (4-7 membered heterocycloalkyl)-$C_{1-6}$ alkyl- of $R^{2C}$ are each optionally substituted with 1, 2, 3, or 4 independently selected $R^M$ substituents;

each $R^{a23}$, $R^{c23}$, and $R^{d23}$ is independently selected from H, $C_{1-6}$ alkyl, $C_{1-6}$ haloalkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl-, wherein the $C_{1-6}$ alkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl- of $R^{a23}$, $R^{c23}$ and $R^{d23}$ are each optionally substituted with 1, 2, 3, or 4 independently selected $R^M$ substituents;

or, any $R^{c23}$ and $R^{d23}$ attached to the same N atom, together with the N atom to which they are attached, form a 5-6 membered heteroaryl or a 4-7 membered heterocycloalkyl group, wherein the 5-6 membered heteroaryl or 4-7 membered heterocycloalkyl group is optionally substituted with 1, 2, 3, or 4 independently selected $R^M$ substituents;

each $R^{b23}$ is independently selected from H, $C_{1-6}$ alkyl, $C_{1-6}$ haloalkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl-, wherein the $C_{1-6}$ alkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl- of $R^{b23}$ are each optionally substituted with 1, 2, 3, or 4 independently selected $R^M$ substituents;

each $R^{e23}$ is independently selected from H, OH, CN, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl-;

$R^3$ is selected from H, halo, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, (4-10 membered heterocycloalkyl)-$C_{1-6}$ alkyl-, CN, $NO_2$, $OR^{a3}$, $SR^{a3}$, $NHOR^{a3}$, $C(O)R^{b3}$, $C(O)NR^{c3}R^{d3}$, $C(O)NR^{c3}(OR^{a3})$, $C(O)OR^{a3}$, $OC(O)R^{b3}$, $OC(O)NR^{c3}R^{d3}$, $NR^{c3}R^{d3}$, $NR^{c3}NR^{c3}R^{d3}$, $NR^{c3}C(O)R^{b3}$, $NR^{c3}C(O)OR^{a3}$, $NR^{c3}C(O)NR^{c3}R^{d3}$, $C(=NR^{e3})R^{b3}$, $C(=NR^{e3})NR^{c3}R^{d3}$, $NR^{c3}C(=NR^{e3})NR^{c3}R^{d3}$, $NR^{c3}C(=NR^{e3})R^{b3}$, $NR^{c3}S(O)R^{b3}$, $NR^{c3}S(O)NR^{c3}R^{d3}$, $NR^{c3}S(O)_2R^{b3}$, $NR^{c3}S(O)(=NR^{e3})R^{b3}$, $NR^{c3}S(O)_2NR^{c3}R^{d3}$, $S(O)R^{b3}$, $S(O)NR^{c3}R^{d3}$, $S(O)_2R^{b3}$, $S(O)_2NR^{c3}R^{d3}$, $OS(O)(=NR^{e3})R^{b3}$, and $OS(O)_2R^{b3}$, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^3$ are each optionally substituted with 1, 2, 3, 4, 5, 6, 7, or 8 independently selected $R^{3A}$ substituents;

each $R^{a3}$, $R^{c3}$, and $R^{d3}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{a3}$, $R^{c3}$ and $R^{d3}$ are each optionally substituted with 1, 2, 3, 4, 5, 6, 7, or 8 independently selected $R^{3A}$ substituents;

or, any $R^{c3}$ and $R^{d3}$ attached to the same N atom, together with the N atom to which they are attached, form a 5-10 membered heteroaryl or a 4-10 membered heterocycloalkyl group, wherein the 5-10 membered heteroaryl or 4-10 membered heterocycloalkyl group is optionally substituted with 1, 2, 3, or 4 independently selected $R^{3A}$ substituents;

each $R^{b3}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{b3}$ are each optionally substituted with 1, 2, 3, 4, 5, 6, 7, or 8 independently selected $R^{3A}$ substituents;

each $R^{e3}$ is independently selected from H, OH, CN, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-;

each $R^{3A}$ is selected from halo, oxo, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, (4-10 membered heterocycloalkyl)-$C_{1-6}$ alkyl-, CN, $NO_2$, $OR^{a31}$, $SR^{a31}$, $NHOR^{a31}$, $C(O)R^{b31}$, $C(O)NR^{c31}R^{d31}$, $C(O)NR^{c31}(OR^{a31})$, $C(O)OR^{a31}$, $OC(O)R^{b31}$, $OC(O)NR^{c31}R^{d31}$, $NR^{c31}R^{d31}$, $NR^{c31}NR^{c31}R^{d31}$, $NR^{c31}C(O)R^{b31}$, $NR^{c31}C(O)OR^{a31}$, $NR^{c31}C(O)NR^{c31}R^{d31}$, $C(=NR^{e31})R^{b31}$, $C(=NR^{e31})NR^{c31}R^{d31}$, $NR^{c31}C(=NR^{e31})NR^{c31}R^{d31}$, $NR^{c31}C(=NR^{e31})R^{b31}$, $NR^{c31}S(O)R^{b31}$, $NR^{c31}S(O)NR^{c31}R^{d31}$, $NR^{c31}S(O)_2R^{b31}$, $NR^{c31}S(O)(=NR^{e31})R^{b31}$, $NR^{c31}S(O)_2NR^{c31}R^{d31}$, $S(O)R^{b31}$, $S(O)_2NR^{c31}R^{d31}$, $S(O)_2R^{b31}$, $S(O)_2NR^{c31}R^{d31}$, $OS(O)(=NR^{e31})R^{b31}$, and $OS(O)_2R^{b31}$, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{3A}$ are each optionally substituted with 1, 2, 3, 4, 5, 6, 7, or 8 independently selected $R^{3B}$ substituents;

each $R^{a31}$, $R^{c31}$, and $R^{d31}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{a31}$, $R^{c31}$ and $R^{d31}$ are each optionally substituted with 1, 2, 3, 4, 5, 6, 7, or 8 independently selected $R^{3B}$ substituents;

or, any $R^{c31}$ and $R^{d31}$ attached to the same N atom, together with the N atom to which they are attached, form a 5-10 membered heteroaryl or a 4-10 membered heterocycloalkyl group, wherein the 5-10 membered heteroaryl or 4-10 membered heterocycloalkyl group is optionally substituted with 1, 2, 3, or 4 independently selected $R^{3B}$ substituents;

each $R^{b31}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{b31}$ are each optionally substituted with 1, 2, 3, 4, 5, 6, 7, or 8 independently selected $R^{3B}$ substituents;

each $R^{e31}$ is independently selected from H, OH, CN, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-;

each $R^{3B}$ is independently selected from halo, oxo, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, (4-10 membered heterocycloalkyl)-$C_{1-6}$ alkyl-, CN, $NO_2$, $OR^{a32}$, $SR^{a32}$, $NHOR^{a32}$, $C(O)R^{b32}$, $C(O)NR^{c32}R^{d32}$, $C(O)NR^{c32}(OR^{a32})$, $C(O)OR^{a32}$, $OC(O)R^{b32}$, $OC(O)R^{b32}$, $OC(O)NR^{c32}R^{d32}$, $NR^{c32}R^{d32}$, $NR^{c32}NR^{c32}R^{d32}$, $NR^{c32}C(O)R^{b32}$, $NR^{c32}C(O)OR^{a32}$, $NR^{c32}C(O)NR^{c32}R^{d32}$, $C(=NR^{e32})R^{b32}$, $C(=NR^{e32})NR^{c32}R^{d32}$, $NR^{c32}C(=NR^{e32})NR^{c32}R^{d32}$, $NR^{c32}C(=NR^{e32})R^{b32}$, $NR^{c32}S(O)R^{b32}$, $NR^{c32}S(O)NR^{c32}R^{d32}$, $NR^{c32}S(O)_2R^{b32}$, $NR^{c32}S(O)(=NR^{e32})R^{b32}$, $NR^{c32}S(O)_2NR^{c32}R^{d32}$, $S(O)R^{b32}$, $S(O)NR^{c32}R^{d32}$, $S(O)_2R^{b32}$, $S(O)_2NR^{c32}R^{d32}$, $OS(O)(=NR^{e32})R^{b32}$, and $OS(O)_2R^{b32}$, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{3B}$ are each optionally substituted with 1, 2, 3, 4, 5, 6, 7, or 8 independently selected $R_{3C}$ substituents;

each $R^{a32}$, $R^{c32}$, and $R^{d32}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{a32}$, $R^{c32}$ and $R^{d32}$ are each optionally substituted with 1, 2, 3, 4, 5, 6, 7, or 8 independently selected $R^{3C}$ substituents;

or, any $R^{c32}$ and $R^{d32}$ attached to the same N atom, together with the N atom to which they are attached, form a 5-10 membered heteroaryl or a 4-10 membered heterocycloalkyl group, wherein the 5-10 membered heteroaryl or 4-10 membered heterocycloalkyl group is optionally substituted with 1, 2, 3, or 4 independently selected $R^{3C}$ substituents;

each $R^{b32}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{b32}$ are each optionally substituted with 1, 2, 3, 4, 5, 6, 7, or 8 independently selected $R^{3C}$ substituents;

each $R^{e32}$ is independently selected from H, OH, CN, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-;

each $R^{3C}$ is independently selected from halo, oxo, $C_{1-6}$ alkyl, $C_{1-6}$ haloalkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, (4-7 membered heterocycloalkyl)-$C_{1-6}$ alkyl-, CN, $NO_2$, $OR^{a33}$, $SR^{a33}$, $NHOR^{a33}$, $C(O)R^{b33}$, $C(O)NR^{c33}R^{d33}$, $C(O)NR^{c33}(OR^{a33})$, $C(O)OR^{a33}$, $OC(O)R^{b33}$, $OC(O)NR^{c33}R^{d33}$, $NR^{c33}R^{d33}$, $NR^{c33}NR^{c33}R^{d33}$, $NR^{c33}C(O)R^{b33}$, $NR^{c33}C(O)OR^{a33}$, $NR^{c33}C(O)NR^{c33}R^{d33}$, $C(=NR^{e33})R^{b33}$, $C(=NR^{e33})NR^{c33}R^{d33}$, $NR^{c33}C(=NR^{e33})NR^{c33}R^{d33}$, $NR^{c33}C(=NR^{e33})R^{b33}$, $NR^{c33}S(O)R^{b33}$, $NR^{c33}S(C)NR^{c33}R^{d33}$, $NR^{c33}S(O)_2R^{b33}$, $NR^{c33}S(O)(=NR^{e33})R^{b33}$, $NR^{c33}S(O)_2NR^{c33}R^{d33}$, $S(O)R^{b33}$, $S(O)NR^{c33}R^{d33}$, $S(O)^2R^{b33}$, $S(O)_2NR^{c33}R^{d33}$, $OS(O)(=NR^{e33})R^{b33}$, and $OS(O)_2R^{b33}$, wherein the $C_{1-6}$ alkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, (4-7 membered heterocycloalkyl)-$C_{1-6}$ alkyl- of $R^{3C}$ are each optionally substituted with 1, 2, 3, or 4 independently selected $R^M$ substituents;

each $R^{a33}$, $R^{c33}$, and $R^{d33}$ is independently selected from H, $C_{1-6}$ alkyl, $C_{1-6}$ haloalkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl-, wherein the $C_{1-6}$ alkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl- of $R^{a33}$, $R^{c33}$ and $R^{d33}$ are each optionally substituted with 1, 2, 3, or 4 independently selected $R^M$ substituents;

or, any $R^{c33}$ and $R^{d33}$ attached to the same N atom, together with the N atom to which they are attached, form a 5-6 membered heteroaryl or a 4-7 membered heterocycloalkyl group, wherein the 5-6 membered heteroaryl or 4-7 membered heterocycloalkyl group is optionally substituted with 1, 2, 3, or 4 independently selected $R^M$ substituents;

each $R^{b33}$ is independently selected from H, $C_{1-6}$ alkyl, $C_{1-6}$ haloalkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl-, wherein the $C_{1-6}$ alkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl- of $R^{b33}$ are each optionally substituted with 1, 2, 3, or 4 independently selected $R^M$ substituents;

each $R^{e33}$ is independently selected from H, OH, CN, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl-;

$R^4$ is selected from H, $C_{1-6}$ alkyl, $C_{1-6}$ alkoxy, $C_{1-6}$ haloalkyl, $C_{1-6}$ haloalkoxy, OH, $NH_2$, and $NHC_{1-6}$ alkyl, wherein the $C_{1-6}$ alkyl is optionally substituted with OH, CN, and $NH_2$;

$R^5$ is selected from H, halo, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, OH, CN, C(O)OH, $C(O)NHR^{a5}$, $NH_2$, and $NHC_{1-6}$ alkyl, wherein the $C_{1-6}$ alkyl is optionally substituted with OH, CN, and $NH_2$;

$R^{a5}$ is H, $C_{1-6}$ alkyl, $C_{1-6}$ alkoxy, $C_{1-6}$ haloalkyl, $C_{1-6}$ haloalkoxy, OH, $NH_2$, and $NHC_{1-6}$ alkyl, wherein the $C_{1-6}$ alkyl is optionally substituted with OH, CN, and $NH_2$;

each $R^6$ is independently selected from halo, oxo, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, (4-10 membered heterocycloalkyl)-$C_{1-6}$ alkyl-, CN, $NO_2$, $OR^{a6}$, $SR^{a6}$, $NHOR^{a6}$, $C(O)R^{b6}$, $C(O)NR^{c6}R^{d6}$, $C(O)NR^{c6}(OR^{a6})$, $C(O)OR^{a6}$, $OC(O)R^{b6}$, $OC(O)NR^{c6}R^{d6}$, $NR^{c6}R^{d6}$, $NR^{c6}NR^{c6}R^{d6}$, $NR^{c6}C(O)R^{b6}$, $NR^{c6}C(O)OR^{a6}$, $NR^{c6}C(O)NR^{c6}R^{d6}$, $C(=NR^{e6})R^{b6}$, $C(=NR^{e6})NR^{c6}R^{d6}$, $NR^{c6}C(=NR^{e6})NR^{c6}R^{d6}$, $NR^{c6}R^{d6}$, $NR^{c6}C(=NR^{e6})R^{b6}$, $NR^{c6}S(O)R^{b6}$, $NR^{c6}S(O)NR^{c6}R^{d6}$, $NR^{c6}S(O)_2R^{b6}$, $NR^{c6}S(O)(=NR^{e6})R^{b6}$, $NR^{b6}S(O)_2NR^{c6}R^{d6}$, $S(O)R^{b6}$, $S(O)NR^{c6}R^{d6}$, $S(O)_2R^{b6}$, $S(O)_2NR^{c6}R^{d6}$, $OS(O)(=NR^{e6})R^{b6}$, and OS (O)$_2$R$^{b6}$, wherein the C$_{1-6}$ alkyl, C$_{2-6}$ alkenyl, C$_{2-6}$ alkynyl, C$_{6-10}$ aryl, C$_{3-10}$ cycloalkyl, 5-10 membered heteroaryl, 4-10 membered heterocycloalkyl, C$_{6-10}$ aryl-C$_{1-6}$ alkyl-, C$_{3-10}$ cycloalkyl-C$_{1-6}$ alkyl-, (5-10 membered heteroaryl)-C$_{1-6}$ alkyl-, and (4-10 membered heterocycloalkyl)-C$_{1-6}$ alkyl- of R$^6$ are each optionally substituted with 1, 2, 3, 4, 5, 6, 7, or 8 independently selected R$^{6A}$ substituents;

each R$^{a6}$, R$^{c6}$, and R$^{d6}$ is independently selected from H, C$_{1-6}$ alkyl, C$_{1-6}$ haloalkyl, C$_{2-6}$ alkenyl, C$_{2-6}$ alkynyl, C$_{6-10}$ aryl, C$_{3-10}$ cycloalkyl, 5-10 membered heteroaryl, 4-10 membered heterocycloalkyl, C$_{6-10}$ aryl-C$_{1-6}$ alkyl-, C$_{3-10}$ cycloalkyl-C$_{1-6}$ alkyl-, (5-10 membered heteroaryl)-C$_{1-6}$ alkyl-, and (4-10 membered heterocycloalkyl)-C$_{1-6}$ alkyl-, wherein the C$_{1-6}$ alkyl, C$_{2-6}$ alkenyl, C$_{2-6}$ alkynyl, C$_{6-10}$ aryl, C$_{3-10}$ cycloalkyl, 5-10 membered heteroaryl, 4-10 membered heterocycloalkyl, C$_{6-10}$ aryl-C$_{1-6}$ alkyl-, C$_{3-10}$ cycloalkyl-C$_{1-6}$ alkyl-, (5-10 membered heteroaryl)-C$_{1-6}$ alkyl-, and (4-10 membered heterocycloalkyl)-C$_{1-6}$ alkyl- of R$^{a6}$, R$^{c6}$ and R$^{d6}$ are each optionally substituted with 1, 2, 3, 4, 5, 6, 7, or 8 independently selected R$^{6A}$ substituents;

or, any R$^{c6}$ and R$^{d6}$ attached to the same N atom, together with the N atom to which they are attached, form a 5-10 membered heteroaryl or a 4-10 membered heterocycloalkyl group, wherein the 5-10 membered heteroaryl or 4-10 membered heterocycloalkyl group is optionally substituted with 1, 2, 3, or 4 independently selected R$^{6A}$ substituents;

each R$^{b6}$ is independently selected from H, C$_{1-6}$ alkyl, C$_{1-6}$ haloalkyl, C$_{2-6}$ alkenyl, C$_{2-6}$ alkynyl, C$_{6-10}$ aryl, C$_{3-10}$ cycloalkyl, 5-10 membered heteroaryl, 4-10 membered heterocycloalkyl, C$_{6-10}$ aryl-C$_{1-6}$ alkyl-, C$_{3-10}$ cycloalkyl-C$_{1-6}$ alkyl-, (5-10 membered heteroaryl)-C$_{1-6}$ alkyl-, and (4-10 membered heterocycloalkyl)-C$_{1-6}$ alkyl-, wherein the C$_{1-6}$ alkyl, C$_{2-6}$ alkenyl, C$_{2-6}$ alkynyl, C$_{6-10}$ aryl, C$_{3-10}$ cycloalkyl, 5-10 membered heteroaryl, 4-10 membered heterocycloalkyl, C$_{6-10}$ aryl-C$_{1-6}$ alkyl-, C$_{3-10}$ cycloalkyl-C$_{1-6}$ alkyl-, (5-10 membered heteroaryl)-C$_{1-6}$ alkyl-, and (4-10 membered heterocycloalkyl)-C$_{1-6}$ alkyl- of R$^{b6}$ are each optionally substituted with 1, 2, 3, 4, 5, 6, 7, or 8 independently selected R$^{6A}$ substituents;

each R$^{e6}$ is independently selected from H, OH, CN, C$_{1-6}$ alkyl, C$_{1-6}$ alkoxy, C$_{1-6}$ haloalkyl, C$_{1-6}$ haloalkoxy, C$_{2-6}$ alkenyl, C$_{2-6}$ alkynyl, C$_{6-10}$ aryl, C$_{3-10}$ cycloalkyl, 5-10 membered heteroaryl, 4-10 membered heterocycloalkyl, C$_{6-10}$ aryl-C$_{1-6}$ alkyl-, C$_{3-10}$ cycloalkyl-C$_{1-6}$ alkyl-, (5-10 membered heteroaryl)-C$_{1-6}$ alkyl-, and (4-10 membered heterocycloalkyl)-C$_{1-6}$ alkyl-;

each R$^{6A}$ is independently selected from halo, oxo, C$_{1-6}$ alkyl, C$_{1-6}$ haloalkyl, C$_{2-6}$ alkenyl, C$_{2-6}$ alkynyl, C$_{6-10}$ aryl, C$_{3-10}$ cycloalkyl, 5-10 membered heteroaryl, 4-10 membered heterocycloalkyl, C$_{6-10}$ aryl-C$_{1-6}$ alkyl-, C$_{3-10}$ cycloalkyl-C$_{1-6}$ alkyl-, (5-10 membered heteroaryl)-C$_{1-6}$ alkyl-, (4-10 membered heterocycloalkyl)-C$_{1-6}$ alkyl-, CN, NO$_2$, R$^{a61}$, R$^{a61}$, NHOR$^{a61}$, C(O)R$^{b61}$, C(O)NR$^{c61}$R$^{d61}$, C(O)NR$^{c61}$(OR$^{a61}$), C(O)OR$^{a61}$, OC(O)R$^{b61}$, OC(O)NR$^{c61}$R$^{d61}$, NR$^{c61}$R$^{d61}$, NR$^{c61}$NR$^{c61}$R$^{d61}$, NR$^{c61}$C(O)R$^{b61}$, NR$^{c61}$C(O)OR$^{a61}$, NR$^{c61}$C(O)NR$^{c61}$R$^{d61}$, C(=NR$^{e61}$)R$^{b61}$, C(=NR$^{e61}$)NR$^{c61}$R$^{d61}$, NR$^{c61}$C(=NR$^{e61}$)NR$^{c61}$R$^{d61}$, NR$^{c61}$C(=NR$^{e61}$)R$^{b61}$, NR$^{c61}$S(O)R$^{b61}$, NR$^{c61}$S(O)NR$^{c61}$R$^{d61}$, NR$^{c61}$S(O)$_2$R$^{b61}$, NR$^{c61}$S(O)(=NR$^{e61}$)R$^{b61}$, NR$^{c61}$S(O)$_2$NR$^{c61}$R$^{d61}$, S(O)R$^{b61}$, S(O)NR$^{c61}$R$^{d61}$, S(O)$_2$R$^{b61}$, S(O)NR$^{c61}$R$^{d61}$, OS(O)(=NR$^{e61}$)R$^{b61}$, and OS(O)$_2$R$^{b61}$, wherein the C$_{1-6}$ alkyl, C$_{2-6}$ alkenyl, C$_{2-6}$ alkynyl, C$_{6-10}$ aryl, C$_{3-10}$ cycloalkyl, 5-10 membered heteroaryl, 4-10 membered heterocycloalkyl, C$_{6-10}$ aryl-C$_{1-6}$ alkyl-, C$_{3-10}$ cycloalkyl-C$_{1-6}$ alkyl-, (5-10 membered heteroaryl)-C$_{1-6}$ alkyl-, and (4-10 membered heterocycloalkyl)-C$_{1-6}$ alkyl- of R$^{6A}$ are each optionally substituted with 1, 2, 3, 4, 5, 6, 7, or 8 independently selected R$^{6B}$ substituents;

each R$^{a61}$, R$^{c61}$, and R$^{d61}$ is independently selected from H, C$_{1-6}$ alkyl, C$_{1-6}$ haloalkyl, C$_{2-6}$ alkenyl, C$_{2-6}$ alkynyl, C$_{6-10}$ aryl, C$_{3-10}$ cycloalkyl, 5-10 membered heteroaryl, 4-10 membered heterocycloalkyl, C$_{6-10}$ aryl-C$_{1-6}$ alkyl-, C$_{3-10}$ cycloalkyl-C$_{1-6}$ alkyl-, (5-10 membered heteroaryl)-C$_{1-6}$ alkyl-, and (4-10 membered heterocycloalkyl)-C$_{1-6}$ alkyl-, wherein the C$_{1-6}$ alkyl, C$_{2-6}$ alkenyl, C$_{2-6}$ alkynyl, C$_{6-10}$ aryl, C$_{3-10}$ cycloalkyl, 5-10 membered heteroaryl, 4-10 membered heterocycloalkyl, C$_{6-10}$ aryl-C$_{1-6}$ alkyl-, C$_{3-10}$ cycloalkyl-C$_{1-6}$ alkyl-, (5-10 membered heteroaryl)-C$_{1-6}$ alkyl-, and (4-10 membered heterocycloalkyl)-C$_{1-6}$ alkyl- of R$^{a61}$, R$^{c61}$ and R$^{d61}$ are each optionally substituted with 1, 2, 3, 4, 5, 6, 7, or 8 independently selected R$^{6B}$ substituents;

or, any R$^{c61}$ and R$^{d61}$ attached to the same N atom, together with the N atom to which they are attached, form a 5-10 membered heteroaryl or a 4-10 membered heterocycloalkyl group, wherein the 5-10 membered heteroaryl or 4-10 membered heterocycloalkyl group is optionally substituted with 1, 2, 3, or 4 independently selected R$^{6B}$ substituents;

each R$^{b61}$ is independently selected from H, C$_{1-6}$ alkyl, C$_{1-6}$ haloalkyl, C$_{2-6}$ alkenyl, C$_{2-6}$ alkynyl, C$_{6-10}$ aryl, C$_{3-10}$ cycloalkyl, 5-10 membered heteroaryl, 4-10 membered heterocycloalkyl, C$_{6-10}$ aryl-C$_{1-6}$ alkyl-, C$_{3-10}$ cycloalkyl-C$_{1-6}$ alkyl-, (5-10 membered heteroaryl)-C$_{1-6}$ alkyl-, and (4-10 membered heterocycloalkyl)-C$_{1-6}$ alkyl-, wherein the C$_{1-6}$ alkyl, C$_{2-6}$ alkenyl, C$_{2-6}$ alkynyl, C$_{6-10}$ aryl, C$_{3-10}$ cycloalkyl, 5-10 membered heteroaryl, 4-10 membered heterocycloalkyl, C$_{6-10}$ aryl-C$_{1-6}$ alkyl-, C$_{3-10}$ cycloalkyl-C$_{1-6}$ alkyl-, (5-10 membered heteroaryl)-C$_{1-6}$ alkyl-, and (4-10 membered heterocycloalkyl)-C$_{1-6}$ alkyl- of R$^{b61}$ are each optionally substituted with 1, 2, 3, 4, 5, 6, 7, or 8 independently selected R$^{6B}$ substituents;

each R$^{e61}$ is independently selected from H, OH, CN, C$_{1-6}$ alkyl, C$_{1-6}$ alkoxy, C$_{1-6}$ haloalkyl, C$_{1-6}$ haloalkoxy, C$_{2-6}$ alkenyl, C$_{2-6}$ alkynyl, C$_{6-10}$ aryl, C$_{3-10}$ cycloalkyl, 5-10 membered heteroaryl, 4-10 membered heterocycloalkyl, C$_{6-10}$ aryl-C$_{1-6}$ alkyl-, C$_{3-10}$ cycloalkyl-C$_{1-6}$ alkyl-, (5-10 membered heteroaryl)-C$_{1-6}$ alkyl-, and (4-10 membered heterocycloalkyl)-C$_{1-6}$ alkyl-;

each R$^{6B}$ is independently selected from halo, oxo, C$_{1-6}$ alkyl, C$_{1-6}$ haloalkyl, C$_{2-6}$ alkenyl, C$_{2-6}$ alkynyl, phenyl, C$_{3-7}$ cycloalkyl, 5-6 membered heteroaryl, 4-7 membered heterocycloalkyl, phenyl-C$_{1-6}$ alkyl-, C$_{3-7}$ cycloalkyl-C$_{1-6}$ alkyl-, (5-6 membered heteroaryl)-C$_{1-6}$ alkyl-, (4-7 membered heterocycloalkyl)-C$_{1-6}$ alkyl-, CN, NO$_2$, OR$^{a62}$, SR$^{a62}$, NHOR$^{a62}$, C(O)R$^{b62}$, C(O)NR$^{c62}$R$^{d62}$, C(O)NR$^{c62}$(OR$^{a62}$), C(O)OR$^{a62}$, OC(O)R$^{b62}$, OC(O)NR$^{c62}$R$^{d62}$, NR$^{c62}$R$^{d62}$, NR$^{c62}$NR$^{c62}$R$^{d62}$, NR$^{c62}$C(O)R$^{b62}$, NR$^{c62}$C(O)OR$^{a62}$, NR$^{c62}$C(O)NR$^{c62}$R$^{d62}$, C(=NR$^{e62}$)R$^{b62}$, C(=NR$^{e62}$)NR$^{c62}$R$^{d62}$, NR$^{c62}$C(=NR$^{e62}$)NR$^{c62}$R$^{d62}$, NR$^{c62}$C(=NR$^{e62}$)R$^{b62}$, NR$^{c62}$S(O)R$^{b62}$, NR$^{c62}$S(O)NR$^{c62}$R$^{d62}$, NR$^{c62}$S(O)$_2$R$^{b62}$, NR$^{c62}$S(O)(=NR$^{e62}$)R$^{b62}$, NR$^{c62}$S(O)$_2$NR$^{c62}$R$^{d62}$, S(O)R$^{b62}$, S(O)NR$^{c62}$R$^{d62}$, S(O)$_2$R$^{b62}$, S(O)$_2$NR$^{c62}$R$^{d62}$, OS(O)(=NR$^{e62}$)R$^{b62}$, and OS(O)$_2$R$^{b62}$, wherein the C$_{1-6}$ alkyl, C$_{2-6}$ alkenyl, C$_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl- and (4-7 membered heterocycloalkyl)-$C_{1-6}$ alkyl- of $R^{6B}$ are each optionally substituted with 1, 2, 3, or 4 independently selected $R^{6C}$ substituents;

each $R^{a62}$, $R^{c62}$, and $R^{d62}$ is independently selected from H, $C_{1-6}$ alkyl, $C_{1-6}$ haloalkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl-, wherein the $C_{1-6}$ alkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl- of $R^{a62}$, $R^{c62}$ and $R^{d62}$ are each optionally substituted with 1, 2, 3, or 4 independently selected $R^{6C}$ substituents;

or, any $R^{c62}$ and $R^{d62}$ attached to the same N atom, together with the N atom to which they are attached, form a 5-6 membered heteroaryl or a 4-7 membered heterocycloalkyl group, wherein the 5-6 membered heteroaryl or 4-7 membered heterocycloalkyl group is optionally substituted with 1, 2, 3, or 4 independently selected $R^{6C}$ substituents;

each $R^{b62}$ is independently selected from H, $C_{1-6}$ alkyl, $C_{1-6}$ haloalkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl-, wherein the $C_{1-6}$ alkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl- of $R^{b62}$ are each optionally substituted with 1, 2, 3, or 4 independently selected $R^{6C}$ substituents;

each $R^{e62}$ is independently selected from H, OH, CN, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl-;

each $R^{6C}$ is independently selected from halo, oxo, $C_{1-6}$ alkyl, $C_{1-6}$ haloalkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, (4-7 membered heterocycloalkyl)-$C_{1-6}$ alkyl-, CN, $NO_2$, $OR^{a63}$, $SR^{a63}$, $NHOR^{a63}$, $C(O)R^{b63}$, $C(O)NR^{c63}R^{d63}$, $C(O)NR^{c63}(OR^{a63})$, $C(O)OR^{a63}$, $OC(O)R^{b63}$, $OC(O)NR^{c63}R^{d63}$, $NR^{c63}R^{d63}$, $NR^{c63}NR^{c63}R^{d63}$, $NR^{c63}C(O)R^{b63}$, $NR^{c63}C(O)NR^{c63}R^{d63}$, $C(=NR^{e63})R^{b63}$, $C(=NR^{e63})NR^{c63}R^{d63}$, $NR^{c63}C(=NR^{e63})NR^{c63}R^{d63}$, $NR^{c63}C(=NR^{e63})R^{b63}$, $NR^{c63}S(O)R^{b63}$, $NR^{c63}S(O)NR^{c63}R^{d63}$, $NR^{c63}S(O)_2R^{b63}$, $NR^{c63}S(O)(=NR^{e63})R^{b63}$, $NR^{c63}S(O)_2NR^{c63}R^{d63}$, $S(O)R^{b63}$, $S(O)NR^{c63}R^{d63}$, $S(O)_2R^{b63}$, $S(O)_2NR^{c63}R^{d63}$, $OS(O)(=NR^{e63})R^{b63}$, and $OS(O)_2R^{b63}$, wherein the $C_{1-6}$ alkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl- and (4-7 membered heterocycloalkyl)-$C_{1-6}$ alkyl- of $R^{6C}$ are each optionally substituted with 1, 2, 3, or 4 independently selected $R^M$ substituents;

each $R^{a63}$, $R^{c63}$, and $R^{d63}$ is independently selected from H, $C_{1-6}$ alkyl, $C_{1-6}$ haloalkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl-, wherein the $C_{1-6}$ alkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl- of $R^{a63}$, $R^{c63}$ and $R^{d63}$ are each optionally substituted with 1, 2, 3, or 4 independently selected $R^M$ substituents;

or, any $R^{c63}$ and $R^{d63}$ attached to the same N atom, together with the N atom to which they are attached, form a 5-6 membered heteroaryl or a 4-7 membered heterocycloalkyl group, wherein the 5-6 membered heteroaryl or 4-7 membered heterocycloalkyl group is optionally substituted with 1, 2, 3, or 4 independently selected $R^M$ substituents;

each $R^{b63}$ is independently selected from H, $C_{1-6}$ alkyl, $C_{1-6}$ haloalkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl-, wherein the $C_{1-6}$ alkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl- of $R^{b63}$ are each optionally substituted with 1, 2, 3, or 4 independently selected $R^M$ substituents;

each $R^{e63}$ is independently selected from H, OH, CN, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl-;

each $R^M$ is independently selected from H, OH, halo, oxo, CN, C(O)OH, $C(O)NH_2$, $C(O)NH(C_{1-4}$ alkyl), $C(O)N(C_{1-6}$ alkyl$)_2$, $NH_2$, $NO_2$, $SF_5$, $C_{1-6}$ alkyl, $C_{1-6}$ alkoxy, $C_{1-6}$ haloalkoxy, $C_{1-6}$ haloalkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl-.

In some embodiments:

W is $CR^W$, $C(R^W)_2$, N, $NR^W$, O, or S;

Y is $CR^Y$, $C(R^Y)_2$, N, $NR^Y$, O, or S;

wherein at least one of W is $CR^W$ or $C(R^W)_2$ or Y is $CR^Y$ or $C(R^Y)_2$;

each $R^W$ is independently selected from H, oxo, $C_{1-6}$ alkyl, $C_{1-6}$ haloalkyl, $C_{2-6}$ alkenyl, and $C_{2-6}$ alkynyl;

each $R^Y$ is independently selected from H, oxo, $C_{1-6}$ alkyl, $C_{1-6}$ haloalkyl, $C_{2-6}$ alkenyl, and $C_{2-6}$ alkynyl;

Ring A is $C_{3-10}$ cycloalkyl or 4-10 membered heterocycloalkyl, wherein the $C_{3-10}$ cycloalkyl and 4-10 membered heterocycloalkyl of Ring A are each optionally substituted with 1, 2, 3, or 4 independently selected $R^6$ substituents;

$R^2$ is selected from halo, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, (4-10 membered heterocycloalkyl)-$C_{1-6}$ alkyl-, CN, $NO_2$, $OR^{a2}$, $SR^{a2}$, $C(O)R^{b2}$, $C(O)NR^{c2}R^{d2}$, $C(O)NR^{c2}(OR^{a2})$, $C(O)OR^{a2}$, $OC(O)R^{b2}$, $OC(O)NR^{c2}R^{d2}$, $NR^{c2}R^{d2}$, $NR^{c2}C(O)R^{b2}$, $NR^{c2}C(O)OR^{a2}$, $NR^{c2}C(O)NR^{c2}R^{d2}$, $NR^{c2}S(O)R^{b2}$, $NR^{c2}S(O)NR^{c2}R^{d2}$, $NR^{c2}S(O)_2R^{b2}$, $NR^{c2}S(O)_2 NR^{c2}R^{d2}$, $S(O)R^{b2}$, $S(O)NR^{c2}R^{d2}$, $S(O)_2R^{b2}$, $S(O)_2 NR^{c2}R^{d2}$, and $OS(O)_2R^{b2}$, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^2$ are each optionally substituted with 1, 2, 3, or 4 independently selected $R^{2A}$ substituents;

each $R^{a2}$, $R^{c2}$, and $R^{d2}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{a2}$, $R^{c2}$ and $R^{d2}$ are each optionally substituted with 1, 2, 3, or 4 independently selected $R^{2A}$ substituents;

or, any $R^{c2}$ and $R^{d2}$ attached to the same N atom, together with the N atom to which they are attached, form a 5-10 membered heteroaryl or a 4-10 membered heterocycloalkyl group, wherein the 5-10 membered heteroaryl or 4-10 membered heterocycloalkyl group is optionally substituted with 1, 2, 3, or 4 independently selected $R^{2A}$ substituents;

each $R^{b2}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{b2}$ are each optionally substituted with 1, 2, 3, or 4 independently selected $R^{2A}$ substituents;

each $R^{2A}$ is selected from halo, oxo, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, (4-10 membered heterocycloalkyl)-$C_{1-6}$ alkyl-, CN, $NO_2$, $OR^{a21}$, $SR^{a21}$, $C(O)R^{b21}$, $C(O)NR^{c21}R^{d21}$, $C(O)NR^{c21}(OR^{a21})$, $C(O)OR^{a21}$, $OC(O)R^{b21}$, $OC(O)NR^{c21}R^{d21}$, $NR^{c21}R^{d21}$, $NR^{c21}C(O)R^{b21}$, $NR^{c21}C(O)OR^{a21}$, $NR^{c21}C(O)NR^{c21}R^{d21}$, $NR^{c21}S(O)R^{b21}$, $NR^{c21}S(O)NR^{c21}R^{d21}$, $NR^{c21}S(O)_2R^{b21}$, $NR^{c21}S(O)_2 NR^{c21}R^{d21}$, $S(O)R^{b21}$, $S(O)NR^{c21}R^{d21}$, $S(O)_2R^{b21}$, $S(O)_2NR^{c21}R^{d21}$, and $OS(O)_2R^{b21}$, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{2A}$ are each optionally substituted with 1, 2, 3, or 4 independently selected $R^{2B}$ substituents;

each $R^{a21}$, $R^{c21}$, and $R^{d21}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{a21}$, $R^{c21}$ and $R^{d21}$ are each optionally substituted with 1, 2, 3, or 4 independently selected $R^{2B}$ substituents;

or, any $R^{c21}$ and $R^{d21}$ attached to the same N atom, together with the N atom to which they are attached, form a 5-10 membered heteroaryl or a 4-10 membered heterocycloalkyl group, wherein the 5-10 membered heteroaryl or 4-10 membered heterocycloalkyl group is optionally substituted with 1, 2, 3, or 4 independently selected $R^{2B}$ substituents;

each $R^{b21}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{b21}$ are each optionally substituted with 1, 2, 3, or 4 independently selected $R^{2B}$ substituents;

each $R^{2B}$ is independently selected from halo, oxo, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, (4-10 membered heterocycloalkyl)-$C_{1-6}$ alkyl-, CN, $NO_2$, $OR^{a22}$, $SR^{a22}$, $C(O)R^{b22}$, $C(O)NR^{c22}R^{d22}$, $C(O)NR^{c22}(OR^{a22})$, $C(O)OR^{a22}$, $OC(O)R^{b22}$, $OC(O)NR^{c22}R^{d22}$, $NR^{c22}R^{d22}$, $NR^{c22}C(O)R^{b22}$, $NR^{c22}C(O)OR^{a22}$, $NR^{c2}C(O)NR^{c22}R^{d22}$, $NR^{c22}S(O)R^{b22}$, $NR^{c22}S(O)NR^{c22}R^{d22}$, and $NR^{c22}S(O)_2R^{b22}$, $NR^{c22}S(O)_2NR^{c22}R^{d22}$, $S(O)R^{b22}$, $S(O)NR^{c22}R^{d22}$, $S(O)_2R^{b22}$, $S(O)_2NR^{c22}R^{d22}$, and $OS(O)_2R^{b22}$, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{2B}$ are each optionally substituted with 1, 2, 3, or 4 independently selected $R^{2C}$ substituents;

each $R^{a22}$, $R^{c22}$, and $R^{d22}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{a22}$, $R^{c22}$ and $R^{d22}$ are each optionally substituted with 1, 2, 3, or 4 independently selected $R^{2C}$ substituents;

or, any $R^{c22}$ and $R^{d22}$ attached to the same N atom, together with the N atom to which they are attached, form a 5-10 membered heteroaryl or a 4-10 membered heterocycloalkyl group, wherein the 5-10 membered heteroaryl or 4-10 membered heterocycloalkyl group is optionally substituted with 1, 2, 3, or 4 independently selected $R^{2C}$ substituents;

each $R^{b22}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{b22}$ are each optionally substituted with 1, 2, 3, or 4 independently selected $R^{2C}$ substituents;

each $R^{2C}$ is independently selected from halo, oxo, $C_{1-6}$ alkyl, $C_{1-6}$ haloalkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, (4-7 membered heterocycloalkyl)-$C_{1-6}$ alkyl-, CN, $NO_2$, $OR^{a23}$, $SR^{a23}$, $C(O)R^{b23}$, $C(O)NR^{c23}R^{d23}$, $C(O)NR^{c23}(OR^{a23})$, $C(O)OR^{a23}$, $OC(O)R^{b23}$, $OC(O)NR^{c23}R^{d23}$, $NR^{c23}R^{d23}$, $NR^{c23}C(O)R^{b23}$, $NR^{c23}C(O)OR^{a23}$, $NR^{c23}C(O)NR^{c23}R^{d23}$, $NR^{c23}S(O)R^{b23}$, $NR^{c23}S(O)NR^{c23}R^{d23}$, $NR^{c23}S(O)_2R^{b23}$, $NR^{c23}S(O)_2NR^{c23}R^{d23}$, $S(O)R^{b23}$, $S(O)NR^{c23}R^{d23}$, $S(O)_2R^{b23a}$, $S(O)_2NR^{c23}R^{d23}$, and $OS(O)_2R^{b23}$;

each $R^{a23}$, $R^{c23}$, and $R^{d23}$ is independently selected from H, $C_{1-6}$ alkyl, $C_{1-6}$ haloalkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl-;

or, any $R^{c23}$ and $R^{d23}$ attached to the same N atom, together with the N atom to which they are attached, form a 5-6 membered heteroaryl or a 4-7 membered heterocycloalkyl group;

each $R^{b23}$ is independently selected from H, $C_{1-6}$ alkyl, $C_{1-6}$ haloalkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl-;

$R^3$ is selected from halo, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, (4-10 membered heterocycloalkyl)-$C_{1-6}$ alkyl-, CN, $NO_2$, $OR^{a3}$, $SR^{a3}$, $C(O)R^{b3}$, $C(O)NR^{c3}R^{d3}$, $C(O)NR^{c3}(OR^{a3})$, $C(O)OR^{a3}$, $OC(O)R^{b3}$, $OC(O)NR^{c3}R^{d3}$, $NR^{c3}R^{d3}$, $NR^{c3}C(O)R^{b3}$, $NR^{c3}C(O)OR^{a3}$, $NR^{c3}C(O)NR^{c3}R^{d3}$, $NR^{c3}S(O)R^{b3}$, $NR^{c3}S(O)NR^{c3}R^{d3}$, $NR^{c3}S(O)_2R^{b3}$, $NR^{c3}S(O)_2 NR^{c3}R^{d3}$, $S(O)R^{b3}$, $S(O)NR^{c3}R^{d3}$, $S(O)_2R^{b3}$, $S(O)_2 NR^{c3}R^{d3}$, and $OS(O)_2R^{b3}$, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^3$ are each optionally substituted with 1, 2, 3, or 4 independently selected $R^{3A}$ substituents;

each $R^{a3}$, $R^{c3}$, and $R^{d3}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{a3}$, $R^{c3}$ and $R^{d3}$ are each optionally substituted with 1, 2, 3, or 4 independently selected $R^{3A}$ substituents;

or, any $R^{c3}$ and $R^{d3}$ attached to the same N atom, together with the N atom to which they are attached, form a 5-10 membered heteroaryl or a 4-10 membered heterocycloalkyl group, wherein the 5-10 membered heteroaryl or 4-10 membered heterocycloalkyl group is optionally substituted with 1, 2, 3, or 4 independently selected $R^{3A}$ substituents;

each $R^{b3}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{b3}$ are each optionally substituted with 1, 2, 3, or 4 independently selected $R^{3A}$ substituents;

each $R^{3A}$ is selected from halo, oxo, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, (4-10 membered heterocycloalkyl)-$C_{1-6}$ alkyl-, CN, $NO_2$, $OR^{a31}$, $SR^{a31}$, $C(O)R^{b31}$, $C(O)NR^{c31}R^{d31}$, $C(O)NR^{c31}(OR^{a31})$, $C(O)OR^{a31}$, $OC(O)R^{b31}$, $OC(O)NR^{c31}R^{d31}$, $NR^{c31}R^{d31}$, $NR^{c31}C(O)R^{b31}$, $NR^{c31}C(O)OR^{a31}$, $NR^{c31}C(O)NR^{c31}R^{d31}$, $NR^{c31}S(O)R^{b31}$, $NR^{c31}S(O)NR^{c31}R^{d31}$, $NR^{c31}S(O)_2R^{b31}$, $NR^{c31}S(O)_2 NR^{c31}R^{d31}$, $S(O)R^{b31}$, $S(O)NR^{c31}R^{d31}$, $S(O)_2R^{b31}$, $S(O)_2NR^{c31}R^{d31}$, and $OS(O)_2R^{b31}$, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{3A}$ are each optionally substituted with 1, 2, 3, or 4 independently selected $R^{3B}$ substituents;

each $R^{a31}$, $R^{c31}$, and $R^{d31}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{a31}$, $R^{c31}$ and $R^{d31}$ are each optionally substituted with 1, 2, 3, or 4 independently selected $R^{3B}$ substituents;

or, any $R^{c31}$ and $R^{d31}$ attached to the same N atom, together with the N atom to which they are attached, form a 5-10 membered heteroaryl or a 4-10 membered heterocycloalkyl group, wherein the 5-10 membered heteroaryl or 4-10 membered heterocycloalkyl group is optionally substituted with 1, 2, 3, or 4 independently selected $R^{3B}$ substituents;

each $R^{b31}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{b31}$ are each optionally substituted with 1, 2, 3, or 4 independently selected $R^{3B}$ substituents;

each $R^{3B}$ is independently selected from halo, oxo, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, (4-10 membered heterocycloalkyl)-$C_{1-6}$ alkyl-, CN, $NO_2$, $OR^{a32}$, $SR^{a32}$, $C(O)R^{b32}$, $C(O)NR^{c32}R^{d32}$, $C(O)NR^{c32}(OR^{a32})$, $C(O)OR^{a32}$, $OC(O)R^{b32}$, $OC(O)NR^{c32}R^{d32}$, $NR^{c32}R^{d32}$, $NR^{c32}C(O)R^{b32}$, $NR^{c32}C(O)OR^{a32}$, $NR^{c32}C(O)NR^{c32}R^{d32}$, $NR^{c32}S(O)R^{b32}$, $NR^{c32}S(O)NR^{c32}R^{d32}$, $NR^{c32}S(O)_2R^{b32}$, $NR^{c32}S(O)_2NR^{c32}R^{d32}$, $S(O)R^{b32}$, $S(O)NR^{c32}R^{d32}$, $S(O)_2R^{b32}$, $S(O)_2NR^{c32}R^{d32}$, and $OS(O)_2R^{b32}$, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{3B}$ are each optionally substituted with 1, 2, 3, or 4 independently selected $R^{3C}$ substituents;

each $R^{a32}$, $R^{c32}$, and $R^{d32}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{a32}$, $R^{c32}$ and $R^{d32}$ are each optionally substituted with 1, 2, 3, or 4 independently selected $R^{3C}$ substituents;

or, any $R^{a32}$ and $R^{d32}$ attached to the same N atom, together with the N atom to which they are attached, form a 5-10 membered heteroaryl or a 4-10 membered heterocycloalkyl group, wherein the 5-10 membered heteroaryl or 4-10 membered heterocycloalkyl group is optionally substituted with 1, 2, 3, or 4 independently selected $R^{3C}$ substituents;

each $R^{b32}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{b32}$ are each optionally substituted with 1, 2, 3, or 4 independently selected $R^{3C}$ substituents;

each $R^{3C}$ is independently selected from halo, oxo, $C_{1-6}$ alkyl, $C_{1-6}$ haloalkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, (4-7 membered heterocycloalkyl)-$C_{1-6}$ alkyl-, CN, $NO_2$, $OR^{a33}$, $SR^{a33}$, $C(O)R^{b33}$, $C(O)NR^{c33}R^{d33}$, $C(O)NR^{c33}(OR^{a33})$, $C(O)OR^{a33}$, $OC(O)R^{b33}$, $OC(O)NR^{c33}R^{d33}$, $NR^{c33}R^{d33}$, $NR^{c33}C(O)R^{b33}$, $NR^{c33}C(O)OR^{a33}$, $NR^{c33}C(O)NR^{c33}R^{d33}$, $NR^{c33}S(O)R^{b33}$, $NR^{c33}S(O)NR^{c33}R^{d33}$, $NR^{c33}S(O)_2R^{b33}$, $NR^{c33}S(O)_2NR^{c33}R^{d33}$, $S(O)_2R^{b33}$, $S(O)_2NR^{c33}R^{d33}$, and $OS(O)_2R^{b33}$;

each $R^{a33}$, $R^{c33}$, and $R^{d33}$ is independently selected from H, $C_{1-6}$ alkyl, $C_{1-6}$ haloalkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl-;

or, any $R^{c33}$ and $R^{d33}$ attached to the same N atom, together with the N atom to which they are attached, form a 5-6 membered heteroaryl or a 4-7 membered heterocycloalkyl group;

each $R^{b33}$ is independently selected from H, $C_{1-6}$ alkyl, $C_{1-6}$ haloalkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl-;

$R^4$ is selected from H, $C_{1-6}$ alkyl, $C_{1-6}$ alkoxy, $C_{1-6}$ haloalkyl, $C_{1-6}$ haloalkoxy, OH, $NH_2$, and $NHC_{1-6}$ alkyl, wherein the $C_{1-6}$ alkyl is optionally substituted with OH, CN, and $NH_2$;

$R^5$ is selected from H, halo, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, OH, CN, C(O)OH, $C(O)NHR^{a5}$, $NH_2$, and $NHC_{1-6}$ alkyl, wherein the $C_{1-6}$ alkyl is optionally substituted with OH, CN, and $NH_2$;

$R^{a5}$ is H, $C_{1-6}$ alkyl, $C_{1-6}$ alkoxy, $C_{1-6}$ haloalkyl, $C_{1-6}$ haloalkoxy, OH, $NH_2$, and $NHC_{1-6}$ alkyl, wherein the $C_{1-6}$ alkyl is optionally substituted with OH, CN, and $NH_2$;

each $R^6$ is independently selected from halo, oxo, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, (4-10 membered heterocycloalkyl)-$C_{1-6}$ alkyl-, CN, $NO_2$, $OR^{a6}$, $SR^{a6}$, $C(O)R^{b6}$, $C(O)NR^{c6}R^{d6}$, $C(O)NR^{c6}(OR^{a6})$, $C(O)OR^{a6}$, $OC(O)R^{b6}$, $OC(O)NR^{c6}R^{d6}$, $NR^{c6}R^{d6}$, $NR^{c6}C(O)R^{b6}$, $NR^{c6}C(O)OR^{a6}$, $NR^{c6}C(O)NR^{c6}R^{d6}$, $NR^{c6}S(O)R^{b6}$, $NR^{c6}S(O)NR^{c6}R^{d6}$, $NR^{c6}S(O)_2R^{b6}$, $NR^{c6}S(O)_2NR^{c6}R^{d6}$, $S(O)R^{b6}$, $S(O)NR^{c6}R^{d6}$, $S(O)_2R^{b6}$, $S(O)_2NR^{c6}R^{d6}$, and $OS(O)_2R^{b6}$, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^6$ are each optionally substituted with 1, 2, 3, or 4 independently selected $R^{6A}$ substituents;

each $R^{a6}$, $R^{c6}$ and $R^{d6}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{a6}$, $R^{c6}$ and $R^{d6}$ are each optionally substituted with 1, 2, 3, or 4 independently selected $R^{6A}$ substituents;

or, any $R^{c6}$ and $R^{d6}$ attached to the same N atom, together with the N atom to which they are attached, form a 5-10 membered heteroaryl or a 4-10 membered heterocycloalkyl group, wherein the 5-10 membered heteroaryl or 4-10 membered heterocycloalkyl group is optionally substituted with 1, 2, 3, or 4 independently selected $R^{6A}$ substituents;

each $R^{b6}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{b6}$ are each optionally substituted with 1, 2, 3, or 4 independently selected $R^{6A}$ substituents;

each $R^{6A}$ is independently selected from halo, oxo, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, (4-10 membered heterocycloalkyl)-$C_{1-6}$ alkyl-, CN, $NO_2$, $OR^{a61}$, $SR_{a61}$, $C(O)R^{b61}$, $C(O)NR^{c61}R^{d61}$, $C(O)NR^{c61}(OR^{a61})$, $C(O)OR^{a61}$, $OC(O)R^{b61}$, $OC(O)NR^{c61}R^{d61}$, $NR^{c61}R^{d61}$, $NR^{c61}C(O)R^{b61}$, $NR^{c61}C(O)OR^{a61}$, $NR^{c61}C(O)NR^{c61}R^{d61}$, $NR^{c61}S(O)R^{b61}$, $NR^{c61}S(O)NR^{c61}R^{d61}$, $NR^{c61}S(O)_2R^{b61}$, $NR^{c61}S(O)_2NR^{c61}R^{d61}$, $S(O)R^{b61}$, $S(O)NR^{c61}R^{d61}R^{d61}$, $S(O)_2R^{b61}$, $S(O)_2NR^{c61}R^{d61}$, and $OS(O)_2R^{b61}$, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{6A}$ are each optionally substituted with 1, 2, 3, or 4 independently selected $R^{6B}$ substituents;

each $R^{a61}$, $R^{c61}$, and $R^{d61}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{a61}$, $R^{c61}$ and $R^{d61}$ are each optionally substituted with 1, 2, 3, or 4 independently selected $R^{6B}$ substituents;

or, any $R^{c61}$ and $R^{d61}$ attached to the same N atom, together with the N atom to which they are attached, form a 5-10 membered heteroaryl or a 4-10 membered heterocycloalkyl group, wherein the 5-10 membered heteroaryl or 4-10 membered heterocycloalkyl group is optionally substituted with 1, 2, 3, or 4 independently selected $R^{6B}$ substituents;

each $R^{b61}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{b61}$ are each optionally substituted with 1, 2, 3, or 4 independently selected $R^{6B}$ substituents;

each $R^{6B}$ is independently selected from halo, oxo, $C_{1-6}$ alkyl, $C_{1-6}$ haloalkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, (4-7 membered heterocycloalkyl)-$C_{1-6}$ alkyl-, CN, $NO_2$, $OR^{a62}$, $SR^{a62}$, $C(O)R^{b62}$, $C(O)NR^{c62}R^{d62}$, $C(O)NR^{c62}(OR^{a62})$, $C(O)OR^{a62}$, $OC(O)R^{b62}$, $OC(O)NR^{c62}R^{d62}$, $NR^{c62}R^{d62}$, $NR^{c62}C(O)R^{b62}$, $NR^{c62}C(O)OR^{a62}$, $NR^{c62}C(O)NR^{c62}R^{d62}$, $NR^{c62}S(O)R^{b62}$, $NR^{c62}S(O)NR^{c62}R^{d62}$, $NR^{c62}S(O)_2R^{b62}$, $NR^{c62}S(O)_2NR^{c62}R^{d62}$, $S(O)R^{b62}$, $S(O)NR^{c62}R^{d62}$, $S(O)_2R^{b62}$, $S(O)_2NR^{c62}R^{d62}$, and $OS(O)_2R^{b62}$, wherein the $C_{1-6}$ alkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl- and (4-7 membered heterocycloalkyl)-$C_{1-6}$ alkyl- of $R^{6B}$ are each optionally substituted with 1, 2, 3, or 4 independently selected $R^{6C}$ substituents;

each $R^{a62}$, $R^{c62}$, and $R^{d62}$ is independently selected from H, $C_{1-6}$ alkyl, $C_{1-6}$ haloalkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl-, wherein the $C_{1-6}$ alkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl- of $R^{a62}$, $R^{c62}$ and $R^{d62}$ are each optionally substituted with 1, 2, 3, or 4 independently selected $R^{6C}$ substituents;

or, any $R^{c62}$ and $R^{d62}$ attached to the same N atom, together with the N atom to which they are attached, form a 5-6 membered heteroaryl or a 4-7 membered heterocycloalkyl group, wherein the 5-6 membered heteroaryl or 4-7 membered heterocycloalkyl group is optionally substituted with 1, 2, 3, or 4 independently selected $R^{6C}$ substituents;

each $R^{b62}$ is independently selected from H, $C_{1-6}$ alkyl, $C_{1-6}$ haloalkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl-, wherein the $C_{1-6}$ alkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl- of $R^{b62}$ are each optionally substituted with 1, 2, 3, or 4 independently selected $R^{6C}$ substituents;

each $R^{6C}$ is independently selected from halo, oxo, $C_{1-6}$ alkyl, $C_{1-6}$ haloalkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, (4-7 membered heterocycloalkyl)-$C_{1-6}$ alkyl-, CN, $NO_2$, $OR^{a63}$, $SR^{a63}$, $C(O)R^{b63}$, $C(O)NR^{c63}R^{d63}$, $C(O)NR^{c63}(OR^{a63})$, $C(O)OR^{a63}$, $OC(O)R^{b63}$, $OC(O)NR^{c63}R^{d63}$, $NR^{c63}R^{d63}$, $NR^{c63}C(O)R^{b63}$, $NR^{c63}C(O)OR^{a63}$, $NR^{c63}C(O)NR^{c63}R^{d63}$, $NR^{c63}S(O)R^{b63}$, $NR^{c63}S(O)NR^{c63}R^{d63}$, $NR^{c63}S(O)_2R^{b63}$, $NR^{c63}S(O)_2NR^{c63}R^{d63}$, $S(O)R^{b63}$, $S(O)NR^{c63}R^{d63}$, $S(O)_2R^{b63}$, $S(O)_2NR^{c63}R^{d63}$, and $OS(O)_2R^{b63}$;

each $R^{a63}$, $R^{c63}$, and $R^{d63}$ is independently selected from H, $C_{1-6}$ alkyl, $C_{1-6}$ haloalkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl-;

or, any $R^{c63}$ and $R^{d63}$ attached to the same N atom, together with the N atom to which they are attached, form a 5-6 membered heteroaryl or a 4-7 membered heterocycloalkyl group; and each $R^{b63}$ is independently selected from H, $C_{1-6}$ alkyl, $C_{1-6}$ haloalkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl-.

In some embodiments, W is $C(R^W)_2$, $NR^W$, O, or S.
In some embodiments, W is $C(R^W)_2$ or $NR^W$.
In some embodiments, W is $C(R^W)_2$.
In some embodiments, each $R^W$ is independently H or $C_{1-6}$ alkyl.
In some embodiments, each $R^W$ is independently H or $C_{1-6}$ alkyl, wherein one or more hydrogen atoms of $R^W$ are optionally replaced by deuterium atoms.
In some embodiments, each $R^W$ is independently H or $C_{1-3}$ alkyl.
In some embodiments, W is $CH_2$.
In some embodiments, Y is $C(R^Y)_2$, $NR^Y$, O, or S.
In some embodiments, Y is $C(R^Y)_2$ or $NR^Y$.
In some embodiments, Y is $C(R^Y)_2$.
In some embodiments, each $R^Y$ is independently H or $C_{1-6}$ alkyl.
In some embodiments, each $R^Y$ is independently H or $C_{1-6}$ alkyl, wherein one or more hydrogen atoms of $R^Y$ are optionally replaced by deuterium atoms.
In some embodiments, each $R^Y$ is independently H or $C_{1-3}$ alkyl.
In some embodiments, Y is $CH_2$.
In some embodiments:
W is $C(R^W)_2$, $NR^W$, O, or S; and
Y is $C(R^Y)_2$, $NR^Y$, O, or S.
In some embodiments:
W is $C(R^W)_2$ or $NR^W$; and
Y is $C(R^Y)_2$ or $NR^Y$.
In some embodiments:
W is $C(R^W)_2$; and
Y is $C(R^Y)_2$.
In some embodiments:
W is $C(R^W)_2$;
Y is $C(R^Y)_2$;
each $R^W$ is independently H or $C_{1-6}$ alkyl; and
each $R^Y$ is independently H or $C_{1-6}$ alkyl.
In some embodiments:
W is $C(R^W)_2$;
Y is $C(R^Y)_2$;
each $R^W$ is independently H or $C_{1-3}$ alkyl; and
each $R^Y$ is independently H or $C_{1-3}$ alkyl.
In some embodiments, W and Y are each $CH_2$.
In some embodiments, Ring A is $C_{3-10}$ cycloalkyl, which is optionally substituted by 1, 2, 3, 4, 5, 6, 7, or 8 independently selected $R^6$ substituents.
In some embodiments, Ring A is $C_{3-10}$ cycloalkyl, which is optionally substituted by 1, 2, 3, or 4 independently selected $R^6$ substituents.
In some embodiments, Ring A is $C_{8-10}$ cycloalkyl, which is optionally substituted by 1, 2, 3, or 4 independently selected $R^6$ substituents.
In some embodiments, Ring A is $C_{3-7}$ cycloalkyl, which is optionally substituted by 1, 2, 3, or 4 independently selected $R^6$ substituents.
In some embodiments, Ring A is monocyclic $C_{3-7}$ cycloalkyl, which is optionally substituted by 1, 2, 3, or 4 independently selected $R^6$ substituents.
In some embodiments, Ring A is monocyclic $C_{3-7}$ cycloalkyl, which is optionally substituted by 1 or 2 independently selected $R^6$ substituents.
In some embodiments, Ring A is bicyclic $C_{8-10}$ cycloalkyl, which is optionally substituted by 1, 2, 3, or 4 independently selected $R^6$ substituents.
In some embodiments, Ring A is bicyclic $C_{8-10}$ cycloalkyl, which is optionally substituted by 1 or 2 independently selected $R^6$ substituents.

In some embodiments, Ring A is spirocyclic $C_{7-10}$ cycloalkyl, which is optionally substituted by 1, 2, 3, or 4 independently selected $R^6$ substituents.

In some embodiments, Ring A is spirocyclic $C_{7-10}$ cycloalkyl, which is optionally substituted by 1 or 2 independently selected $R^6$ substituents.

In some embodiments, Ring A is selected from cyclobutyl, cyclopentyl, cyclohexyl, and dihydroindenyl, wherein the cyclobutyl, cyclopentyl, cyclohexyl, and dihydroindenyl of Ring A are each optionally substituted by 1, 2, 3, or 4 independently selected $R^6$ substituents.

In some embodiments, Ring A is selected from cyclobutyl, cyclopentyl, cyclohexyl, and 2,3-dihydro-1H-indenyl, wherein the cyclobutyl, cyclopentyl, cyclohexyl, and 2,3-dihydro-1H-indenyl of Ring A are each optionally substituted by 1, 2, 3, or 4 independently selected $R^6$ substituents.

In some embodiments, Ring A is selected from cyclobutyl, cyclopentyl, and cyclohexyl, wherein the cyclobutyl, cyclopentyl, and cyclohexyl of Ring A are each optionally substituted by 1, 2, 3, or 4 independently selected $R^6$ substituents.

In some embodiments, Ring A is selected from cyclobutyl, cyclopentyl, cyclohexyl, and dihydroindenyl, wherein the cyclobutyl, cyclopentyl, cyclohexyl, and dihydroindenyl of Ring A are each optionally substituted by 1 or 2 independently selected $R^6$ substituents.

In some embodiments, Ring A is selected from cyclobutyl, cyclopentyl, cyclohexyl, and 2,3-dihydro-1H-indenyl, wherein the cyclobutyl, cyclopentyl, cyclohexyl, and 2,3-dihydro-1H-indenyl of Ring A are each optionally substituted by 1 or 2 independently selected $R^6$ substituents.

In some embodiments, Ring A is selected from cyclobutyl, cyclopentyl, and cyclohexyl, wherein the cyclobutyl, cyclopentyl, and cyclohexyl of Ring A are each optionally substituted by 1 or 2 independently selected $R^6$ substituents.

In some embodiments, Ring A is unsubstituted $C_{3-10}$ cycloalkyl.

In some embodiments, Ring A is unsubstituted $C_{8-10}$ cycloalkyl.

In some embodiments, Ring A is unsubstituted bicyclic $C_{8-10}$ cycloalkyl.

In some embodiments, Ring A is unsubstituted $C_{3-7}$ cycloalkyl.

In some embodiments, Ring A is unsubstituted monocyclic $C_{3-7}$ cycloalkyl.

In some embodiments, Ring A is selected from cyclobutyl, cyclopentyl, cyclohexyl, and dihydroindenyl.

In some embodiments, Ring A is selected from cyclobutyl, cyclopentyl, cyclohexyl, and 2,3-dihydro-1H-indenyl.

In some embodiments, Ring A is selected from cyclobutyl, cyclopentyl, and cyclohexyl.

In some embodiments, Ring A is 4-11 membered heterocycloalkyl, which is optionally substituted by 1, 2, 3, 4, 5, 6, 7, or 8 independently selected $R^6$ substituents.

In some embodiments, Ring A is 4-10 membered heterocycloalkyl, which is optionally substituted by 1, 2, 3, 4, 5, 6, 7, or 8 independently selected $R^6$ substituents.

In some embodiments, Ring A is 4-11 membered heterocycloalkyl, which is optionally substituted by 1, 2, 3, or 4 independently selected $R^6$ substituents.

In some embodiments, Ring A is 4-10 membered heterocycloalkyl, which is optionally substituted by 1, 2, 3, or 4 independently selected $R^6$ substituents.

In some embodiments, Ring A is monocyclic 4-6 membered heterocycloalkyl or a bicyclic 8-10 membered heterocycloalkyl, wherein the monocyclic 4-6 membered heterocycloalkyl and bicyclic 8-10 membered heterocycloalkyl of Ring A are each optionally substituted by 1, 2, 3, or 4 independently selected $R^6$ substituents.

In some embodiments, Ring A is monocyclic 4-6 membered heterocycloalkyl, a bicyclic 8-10 membered heterocycloalkyl, or a spirocyclic 7-11 membered heterocycloalkyl wherein the monocyclic 4-6 membered heterocycloalkyl, bicyclic 8-10 membered heterocycloalkyl, and spirocyclic 7-11 membered heterocycloalkyl of Ring A are each optionally substituted by 1, 2, 3, or 4 independently selected $R^6$ substituents.

In some embodiments, Ring A is monocyclic 4-6 membered heterocycloalkyl, a bicyclic 8-10 membered heterocycloalkyl, or a spirocyclic 7-10 membered heterocycloalkyl wherein the monocyclic 4-6 membered heterocycloalkyl, bicyclic 8-10 membered heterocycloalkyl, and spirocyclic 7-10 membered heterocycloalkyl of Ring A are each optionally substituted by 1, 2, 3, or 4 independently selected $R^6$ substituents.

In some embodiments, Ring A is selected from $C_{3-10}$ cycloalkyl, monocyclic 4-6 membered heterocycloalkyl, and bicyclic 8-10 membered heterocycloalkyl, wherein the $C_{3-7}$ cycloalkyl, monocyclic 4-6 membered heterocycloalkyl, and bicyclic 8-10 membered heterocycloalkyl of Ring A are each optionally substituted by 1, 2, 3, or 4 independently selected $R^6$ substituents.

In some embodiments, Ring A is selected from $C_{3-7}$ cycloalkyl, monocyclic 4-6 membered heterocycloalkyl, and bicyclic 8-10 membered heterocycloalkyl, wherein the $C_{3-7}$ cycloalkyl, monocyclic 4-6 membered heterocycloalkyl, and bicyclic 8-10 membered heterocycloalkyl of Ring A are each optionally substituted by 1, 2, 3, or 4 independently selected $R^6$ substituents.

In some embodiments, Ring A is selected from monocyclic $C_{3-7}$ cycloalkyl, bicyclic $C_{810}$ cycloalkyl, monocyclic 4-6 membered heterocycloalkyl, bicyclic 8-10 membered heterocycloalkyl, and spirocyclic 7-11 membered heterocycloalkyl, wherein the monocyclic $C_{3-7}$ cycloalkyl, bicyclic $C_{8-10}$ cycloalkyl, monocyclic 4-6 membered heterocycloalkyl, bicyclic 8-10 membered heterocycloalkyl, and spirocyclic 7-11 membered heterocycloalkyl of Ring A are each optionally substituted by 1, 2, 3, or 4 independently selected $R^6$ substituents.

In some embodiments, Ring A is selected from monocyclic $C_{3-7}$ cycloalkyl, bicyclic $C_{8-10}$ cycloalkyl, monocyclic 4-6 membered heterocycloalkyl, bicyclic 8-10 membered heterocycloalkyl, and spirocyclic 7-10 membered heterocycloalkyl, wherein the monocyclic $C_{3-7}$ cycloalkyl, bicyclic $C_{8-10}$ cycloalkyl, monocyclic 4-6 membered heterocycloalkyl, bicyclic 8-10 membered heterocycloalkyl, and spirocyclic 7-10 membered heterocycloalkyl of Ring A are each optionally substituted by 1, 2, 3, or 4 independently selected $R^6$ substituents.

In some embodiments, Ring A is selected from cyclobutyl, cyclopentyl, cyclohexyl, dihydroindenyl, tetrahydro-2H-pyranyl, tetrahydrofuranyl, azetidinyl, piperidinyl, pyrrolidinyl, azepanyl, dihydropyridinyl, azabicyclo[3.2.1]octanyl, 2-azaspiro[3.3]heptanyl, and 7-azaspiro[3.5]nonanyl, wherein the cyclobutyl, cyclopentyl, cyclohexyl, dihydroindenyl, tetrahydro-2H-pyranyl, tetrahydrofuranyl, azetidinyl, piperidinyl, pyrrolidinyl, azepanyl, dihydropyridinyl, azabicyclo[3.2.1]octanyl, 2-azaspiro[3.3]hepta- In some embodiments, Ring A is selected from cyclobutyl, cyclopentyl, cyclohexyl, dihydroindenyl, tetrahydro-2H-pyranyl, tetrahydrofuranyl, azetidinyl, piperidinyl, pyrrolidinyl, azepanyl, dihydropyridinyl, azabicyclo[3.2.1]octanyl, 2-azaspiro[3.3]heptanyl, and 7-azaspiro[3.5]nonanyl, wherein the cyclobutyl, cyclopentyl, cyclohexyl, dihydroindenyl, tetrahydro-2H-pyranyl, tetrahydrofuranyl, azetidinyl, piperidinyl, pyrrolidinyl, azepanyl, dihydropyridinyl, azabicyclo[3.2.1]octanyl, 2-azaspiro[3.3]heptanyl, and 7-azaspiro[3.5]nonanyl of Ring A are each optionally substituted by 1, 2, 3, or 4 independently selected $R^6$ substituents.

In some embodiments, Ring A is selected from cyclobutyl, cyclopentyl, cyclohexyl, 2,3-dihydro-1H-indenyl, tetrahydro-2H-pyranyl, tetrahydrofuranyl, azetidinyl, piperidinyl, pyrrolidinyl, azepanyl, dihydropyridinyl, azabicyclo[3.2.1]octanyl, 2-azaspiro[3.3]heptanyl, and 7-azaspiro[3.5]nonanyl, wherein the cyclobutyl, cyclopentyl, cyclohexyl, 2,3-dihydro-1H-indenyl, tetrahydro-2H-pyranyl, tetrahydrofuranyl, azetidinyl, piperidinyl, pyrrolidinyl, azepanyl, dihydropyridinyl, azabicyclo[3.2.1]octanyl, 2-azaspiro[3.3]heptanyl, and 7-azaspiro[3.5]nonanyl of Ring A are each optionally substituted by 1, 2, 3, or 4 independently selected $R^6$ substituents.

In some embodiments, Ring A is selected from cyclobutyl, cyclopentyl, cyclohexyl, 2,3-dihydro-1H-indenyl, tetrahydro-2H-pyranyl, tetrahydrofuranyl, azetidinyl, piperidinyl, pyrrolidinyl, azepanyl, dihydropyridinyl, azabicyclo[3.2.1]octanyl, 2-azaspiro[3.3]heptanyl, and 7-azaspiro[3.5]nonanyl, wherein the cyclobutyl, cyclopentyl, cyclohexyl, 2,3-dihydro-1H-indenyl, tetrahydro-2H-pyranyl, tetrahydrofuranyl, azetidinyl, piperidinyl, pyrrolidinyl, azepanyl, dihydropyridinyl, azabicyclo[3.2.1]octanyl, 2-azaspiro[3.3]heptanyl, and 7-azaspiro[3.5]nonanyl of Ring A are each optionally substituted by 1, 2, 3, or 4 independently selected $R^6$ substituents.

In some embodiments, Ring A is selected from cyclobutyl, cyclopentyl, cyclohexyl, tetrahydro-2H-pyranyl, tetrahydrofuranyl, azetidinyl, piperidinyl, pyrrolidinyl, and azabicyclo[3.2.1]octanyl, wherein the cyclobutyl, cyclopentyl, cyclohexyl, tetrahydro-2H-pyranyl, tetrahydrofuranyl, azetidinyl, piperidinyl, pyrrolidinyl, and azabicyclo[3.2.1]octanyl of Ring A are each optionally substituted by 1, 2, 3, or 4 independently selected $R^6$ substituents.

In some embodiments, Ring A is selected from cyclobutyl, cyclopentyl, cyclohexyl, dihydroindenyl, tetrahydro-2H-pyranyl, tetrahydrofuranyl, azetidinyl, piperidinyl, pyrrolidinyl, azepanyl, dihydropyridinyl, azabicyclo[3.2.1]octanyl, 2-azaspiro[3.3]heptanyl, and 7-azaspiro[3.5]nonanyl, wherein the cyclobutyl, cyclopentyl, tetrahydro-2H-pyranyl, tetrahydrofuranyl, azetidinyl, piperidinyl, pyrrolidinyl, azepanyl, azabicyclo[3.2.1]octanyl, 2-azaspiro[3.3]heptanyl, and 7-azaspiro[3.5]nonanyl of Ring A are each optionally substituted by 1, 2, 3, or 4 independently selected $R^6$ substituents.

In some embodiments, Ring A is selected from cyclobutyl, cyclopentyl, cyclohexyl, dihydroindenyl, tetrahydro-2H-pyranyl, tetrahydrofuranyl, azetidinyl, piperidinyl, pyrrolidinyl, azepanyl, dihydropyridinyl, azabicyclo[3.2.1]octanyl, 2-azaspiro[3.3]heptanyl, and 7-azaspiro[3.5]nonanyl, wherein the cyclobutyl, cyclopentyl, tetrahydro-2H-pyranyl, tetrahydrofuranyl, azetidinyl, piperidinyl, pyrrolidinyl, azepanyl, azabicyclo[3.2.1]octanyl, 2-azaspiro[3.3]heptanyl, and 7-azaspiro[3.5]nonanyl of Ring A are each optionally substituted by 1, 2, 3, or 4 independently selected $R^6$ substituents.

In some embodiments, Ring A is selected from cyclobutyl, cyclopentyl, cyclohexyl, 2,3-dihydro-1H-indenyl, tetrahydro-2H-pyranyl, tetrahydrofuranyl, azetidinyl, piperidinyl, pyrrolidinyl, azepanyl, dihydropyridinyl, azabicyclo[3.2.1]octanyl, 2-azaspiro[3.3]heptanyl, and 7-azaspiro[3.5]nonanyl, wherein the cyclobutyl, cyclopentyl, tetrahydro-2H-pyranyl, tetrahydrofuranyl, azetidinyl, piperidinyl, pyrrolidinyl, azepanyl, dihydropyridinyl, azabicyclo[3.2.1]octanyl, 2-azaspiro[3.3]heptanyl, and 7-azaspiro[3.5]nonanyl of Ring A are each optionally substituted by 1, 2, 3, or 4 independently selected $R^6$ substituents.

In some embodiments, Ring A is selected from cyclobutyl, cyclopentyl, cyclohexyl, 2,3-dihydro-1H-indenyl, tetrahydro-2H-pyranyl, tetrahydrofuranyl, azetidinyl, piperidinyl, pyrrolidinyl, azepanyl, dihydropyridinyl, azabicyclo[3.2.1]octanyl, 2-azaspiro[3.3]heptanyl, and 7-azaspiro[3.5]nonanyl, wherein the cyclobutyl, cyclopentyl, tetrahydro-2H-pyranyl, tetrahydrofuranyl, azetidinyl, piperidinyl, pyrrolidinyl, azepanyl, dihydropyridinyl, azabicyclo[3.2.1]octanyl, 2-azaspiro[3.3]heptanyl, and 7-azaspiro[3.5]nonanyl of Ring A are each optionally substituted by 1, 2, 3, or 4 independently selected $R^6$ substituents.

In some embodiments, Ring A is selected from cyclobutyl, cyclopentyl, cyclohexyl, tetrahydro-2H-pyranyl, tetrahydrofuranyl, azetidinyl, piperidinyl, pyrrolidinyl, and azabicyclo[3.2.1]octanyl, wherein the tetrahydro-2H-pyranyl, tetrahydrofuranyl, azetidinyl, piperidinyl, pyrrolidinyl, and azabicyclo[3.2.1]octanyl of Ring A are each optionally substituted by 1, 2, 3, or 4 independently selected $R^6$ substituents.

In some embodiments, Ring A is selected from tetrahydro-2H-pyranyl, tetrahydrofuranyl, azetidinyl, piperidinyl, pyrrolidinyl, azepanyl, dihydropyridinyl, azabicyclo[3.2.1]octanyl, 2-azaspiro[3.3]heptanyl, and 7-azaspiro[3.5]nonanyl, wherein the tetrahydro-2H-pyranyl, tetrahydrofuranyl, azetidinyl, piperidinyl, pyrrolidinyl, azepanyl, dihydropyridinyl, azabicyclo[3.2.1]octanyl, 2-azaspiro[3.3]heptanyl, and 7-azaspiro[3.5]nonanyl of Ring A are each optionally substituted by 1, 2, 3, or 4 independently selected $R^6$ substituents.

In some embodiments, Ring A is selected from tetrahydro-2H-pyranyl, tetrahydrofuranyl, azetidinyl, piperidinyl, pyrrolidinyl, azepanyl, dihydropyridinyl, azabicyclo[3.2.1]octanyl, 2-azaspiro[3.3]heptanyl, and 7-azaspiro[3.5]nonanyl, wherein the tetrahydro-2H-pyranyl, tetrahydrofuranyl, azetidinyl, piperidinyl, pyrrolidinyl, azepanyl, dihydropyridinyl, azabicyclo[3.2.1]octanyl, 2-azaspiro[3.3]heptanyl, and 7-azaspiro[3.5]nonanyl of Ring A are each optionally substituted by 1, 2, 3, or 4 independently selected $R^6$ substituents.

In some embodiments, Ring A is selected from tetrahydro-2H-pyranyl, tetrahydrofuranyl, azetidinyl, piperidinyl, pyrrolidinyl, and azabicyclo[3.2.1]octanyl, wherein the tetrahydro-2H-pyranyl, tetrahydrofuranyl, azetidinyl, piperidinyl, pyrrolidinyl, and azabicyclo[3.2.1]octanyl of Ring A are each optionally substituted by 1, 2, 3, or 4 independently selected $R^6$ substituents.

In some embodiments, Ring A is selected from cyclobutyl, cyclopentyl, cyclohexyl, 2,3-dihydro-1H-indenyl, tetrahydro-2H-pyranyl, tetrahydrofuranyl, azetidinyl, piperidinyl, pyrrolidinyl, azepanyl, dihydropyridinyl, azabicyclo[3.2.1]octanyl, 2-azaspiro[3.3]heptanyl, and 7-azaspiro[3.5]nonanyl, wherein the cyclobutyl, cyclopentyl, cyclohexyl, 2,3-dihydro-1H-indenyl, tetrahydro-2H-pyranyl, tetrahydrofuranyl, azetidinyl, piperidinyl, pyrrolidinyl, azepanyl, dihydropyridinyl, azabicyclo[3.2.1]octanyl, 2-azaspiro[3.3]heptanyl, and 7-azaspiro[3.5]nonanyl of Ring A are each optionally substituted by 1 or 2 independently selected $R^6$ substituents.

In some embodiments, Ring A is selected from cyclobutyl, cyclopentyl, cyclohexyl, 2,3-dihydro-1H-indenyl, tetrahydro-2H-pyranyl, tetrahydrofuranyl, azetidinyl, piperidinyl, pyrrolidinyl, azepanyl, dihydropyridinyl, azabicyclo[3.2.1]octanyl, 2-azaspiro[3.3]heptanyl, and 7-azaspiro[3.5]nonanyl, wherein the cyclobutyl, cyclopentyl, cyclohexyl, 2,3-dihydro-1H-indenyl, tetrahydro-2H-pyranyl, tetrahydrofuranyl, azetidinyl, piperidinyl, pyrrolidinyl, azepanyl, dihydropyridinyl, azabicyclo[3.2.1]octanyl, 2-azaspiro[3.3]heptanyl, and 7-azaspiro[3.5]nonanyl of Ring A are each optionally substituted by 1 or 2 independently selected $R^6$ substituents.

In some embodiments, Ring A is selected from cyclobutyl, cyclopentyl, cyclohexyl, tetrahydro-2H-pyranyl, tetrahydrofuranyl, azetidinyl, piperidinyl, pyrrolidinyl, and azabicyclo[3.2.1]octanyl, wherein the cyclobutyl, cyclopentyl, cyclohexyl, tetrahydro-2H-pyranyl, tetrahydrofuranyl, azetidinyl, piperidinyl, pyrrolidinyl, and azabicyclo[3.2.1]octanyl of Ring A are each optionally substituted by 1 or 2 independently selected $R^6$ substituents.

In some embodiments, Ring A is selected from cyclobutyl, cyclopentyl, cyclohexyl, tetrahydro-2H-pyranyl, tetrahydrofuranyl, azetidinyl, piperidinyl, pyrrolidinyl, and azabicyclo[3.2.1]octanyl, wherein the tetrahydro-2H-pyranyl, tetrahydrofuranyl, azetidinyl, piperidinyl, pyrrolidinyl, and azabicyclo[3.2.1]octanyl of Ring A are each optionally substituted by 1 or 2 independently selected $R^6$ substituents.

In some embodiments, Ring A is selected from cyclobutyl, cyclopentyl, cyclohexyl, dihydroindenyl, tetrahydro-2H-pyranyl, tetrahydrofuranyl, azetidinyl, piperidinyl, pyrrolidinyl, azepanyl, dihydropyridinyl, azabicyclo[3.2.1]octanyl, 2-azaspiro[3.3]heptanyl, and 7-azaspiro[3.5]nonanyl, wherein the cyclobutyl, cyclopentyl, tetrahydro-2H-pyranyl, tetrahydrofuranyl, azetidinyl, piperidinyl, pyrrolidinyl, azepanyl, dihydropyridinyl, azabicyclo[3.2.1]octanyl, 2-azaspiro[3.3]heptanyl, and 7-azaspiro[3.5]nonanyl of Ring A are each optionally substituted by 1 or 2 independently selected $R^6$ substituents.

In some embodiments, Ring A is selected from cyclobutyl, cyclopentyl, cyclohexyl, dihydroindenyl, tetrahydro-2H-pyranyl, tetrahydrofuranyl, azetidinyl, piperidinyl, pyrrolidinyl, azepanyl, dihydropyridinyl, azabicyclo[3.2.1]octanyl, 2-azaspiro[3.3]heptanyl, and 7-azaspiro[3.5]nonanyl, wherein the cyclobutyl, cyclopentyl, tetrahydro-2H-pyranyl, tetrahydrofuranyl, azetidinyl, piperidinyl, pyrrolidinyl, azepanyl, dihydropyridinyl, azabicyclo[3.2.1]octanyl, 2-azaspiro[3.3]heptanyl, and 7-azaspiro[3.5]nonanyl of Ring A are each optionally substituted by 1 or 2 independently selected $R^6$ substituents.

In some embodiments, Ring A is selected from cyclobutyl, cyclopentyl, cyclohexyl, 2,3-dihydro-1H-indenyl, tetrahydro-2H-pyranyl, tetrahydrofuranyl, azetidinyl, piperidinyl, pyrrolidinyl, azepanyl, dihydropyridinyl, azabicyclo[3.2.1]octanyl, 2-azaspiro[3.3]heptanyl, and 7-azaspiro[3.5]nonanyl, wherein the cyclobutyl, cyclopentyl, cyclohexyl, 2,3-dihydro-1H-indenyl, tetrahydro-2H-pyranyl, tetrahydrofuranyl, azetidinyl, piperidinyl, pyrrolidinyl, azepanyl, dihydropyridinyl, azabicyclo[3.2.1]octanyl, 2-azaspiro[3.3]heptanyl, and 7-azaspiro[3.5]nonanyl of Ring A are each optionally substituted by 1 or 2 independently selected $R^6$ substituents.

In some embodiments, Ring A is selected from cyclobutyl, cyclopentyl, cyclohexyl, 2,3-dihydro-1H-indenyl, tetrahydro-2H-pyranyl, tetrahydrofuranyl, azetidinyl, piperidinyl, pyrrolidinyl, azepanyl, dihydropyridinyl, azabicyclo[3.2.1]octanyl, 2-azaspiro[3.3]heptanyl, and 7-azaspiro[3.5]nonanyl, wherein the cyclobutyl, cyclopentyl, tetrahydro-2H-pyranyl, tetrahydrofuranyl, azetidinyl, piperidinyl, pyrrolidinyl, azepanyl, dihydropyridinyl, azabicyclo[3.2.1]octanyl, 2-azaspiro[3.3]heptanyl, and 7-azaspiro[3.5]nonanyl of Ring A are each optionally substituted by 1 or 2 independently selected $R^6$ substituents.

In some embodiments, Ring A is selected from tetrahydro-2H-pyranyl, tetrahydrofuranyl, azetidinyl, piperidinyl, pyrrolidinyl, and azabicyclo[3.2.1]octanyl, wherein the tetrahydro-2H-pyranyl, tetrahydrofuranyl, azetidinyl, piperidinyl, pyrrolidinyl, and azabicyclo[3.2.1]octanyl of Ring A are each optionally substituted by 1 or 2 independently selected $R^6$ substituents.

In some embodiments, each $R^6$ is independently selected from $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, (4-10 membered heterocycloalkyl)-$C_{1-6}$ alkyl-, C(O)$R^{b6}$, C(O)NR$^{c6}$R$^{d6}$, C(O)OR$^{a6}$, NR$^{c6}$C(O)R$^{b6}$, NR$^{c6}$S(O)$_2$R$^{b6}$, and S(O)$_2$R$^{b6}$, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^6$ are each optionally substituted with 1, 2, 3, or 4 independently selected $R^{6A}$ substituents.

In some embodiments, each $R^6$ is independently selected from $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, (4-10 membered heterocycloalkyl)-$C_{1-6}$ alkyl-, C(O)$R^{b6}$, C(O)NR$^{c6}$R$^{d6}$, and C(O)OR$_{a6}$, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^6$ are each optionally substituted with 1, 2, 3, or 4 independently selected $R^{6A}$ substituents.

In some embodiments, each $R^6$ is independently selected from $C_{1-6}$ alkyl, $C_{1-6}$ haloalkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, (4-7 membered heterocycloalkyl)-$C_{1-6}$ alkyl-, C(O)$R^{b6}$, C(O)NR$^{c6}$R$^{d6}$, C(O)OR$^{a6}$, NR$^{c6}$C(O)R$^{b6}$, NR$^{c6}$S(O)$_2$R$^{b6}$, and S(O)$_2$R$^{b6}$, wherein the $C_{1-6}$ alkyl, $C_{1-6}$ haloalkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl- of $R^6$ are each optionally substituted with 1, 2, 3, or 4 independently selected $R^{6A}$ substituents.

In some embodiments, each $R^6$ is independently selected from $C_{1-6}$ alkyl, $C_{1-6}$ haloalkyl, $C_{2-6}$ alkenyl, $C_{2-6}$ alkynyl, phenyl, $C_{3-7}$ cycloalkyl, 5-6 membered heteroaryl, 4-6 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, (4-6 membered heterocycloalkyl)-$C_{1-6}$ alkyl-, C(O)$R^{b6}$, C(O)NR$^{c6}$R$^{d6}$, and C(O)OR$^{a6}$, wherein the $C_{1-6}$ alkyl, $C_{2-6}$ alkenyl, $C_{2-6}$ alkynyl, phenyl, $C_{3-7}$ cycloalkyl, 5-6 membered heteroaryl, 4-6 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-6 membered heterocycloalkyl)-$C_{1-6}$ alkyl- of $R^6$ are each optionally substituted with 1, 2, 3, or 4 independently selected $R^{6A}$ substituents.

In some embodiments, each $R^6$ is independently selected from $C_{1-6}$ alkyl, $C_{1-6}$ haloalkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, (4-7 membered heterocycloalkyl)-$C_{1-6}$ alkyl-, $C(O)R^{b6}$, $C(O)NR^{c6}R^{d6}$, $C(O)OR^{a6}$, $NR^{c6}C(O)R^{b6}$, $NR^{c6}S(O)_2R^{b6}$, and $S(O)_2R^{b6}$, wherein the $C_{1-6}$ alkyl, $C_{1-6}$ haloalkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl- of $R^6$ are each optionally substituted with 1 or 2 independently selected $R^{6A}$ substituents.

In some embodiments, each $R^6$ is independently selected from $C_{1-6}$ alkyl, $C_{1-6}$ haloalkyl, $C_{2-6}$ alkenyl, $C_{2-6}$ alkynyl, phenyl, $C_{3-7}$ cycloalkyl, 5-6 membered heteroaryl, 4-6 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, (4-6 membered heterocycloalkyl)-$C_{1-6}$ alkyl-, $C(O)R^{b6}$, $C(O)NR^{c6}R^{d6}$, and $C(O)OR^{a6}$, wherein the $C_{1-6}$ alkyl, $C_{2-6}$ alkenyl, $C_{2-6}$ alkynyl, phenyl, $C_{3-7}$ cycloalkyl, 5-6 membered heteroaryl, 4-6 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-6 membered heterocycloalkyl)-$C_{1-6}$ alkyl- of $R^6$ are each optionally substituted with 1 or 2 independently selected $R^{6A}$ substituents.

In some embodiments, each $R^6$ is independently selected from $C_{1-6}$ alkyl, $C_{1-6}$ haloalkyl, $C_{3-10}$ cycloalkyl, 5-10 membered heteroaryl, 4-10 membered heterocycloalkyl, $C_{3-10}$ cycloalkyl-$C_6$ alkyl-, $C_{6-10}$ aryl-$C_{1-6}$ alkyl-, (5-10 membered heteroaryl)-$C_{1-6}$ alkyl-, (4-10 membered heterocycloalkyl)-$C_{1-6}$ alkyl-, $C(O)R^{b6}$, $C(O)NR^{c6}R^{a6}$, $NR^{c6}C(O)R^{b6}$, $NR^{c6}S(O)_2R^{b6}$, and $S(O)_2R^{b6}$, wherein the $C_{1-6}$ alkyl, $C_{1-6}$ haloalkyl, $C_{3-10}$ cycloalkyl, 5-10 membered heteroaryl, 4-10 membered heterocycloalkyl, $C_{3-10}$ cycloalkyl-$C_{1-6}$ alkyl-, $C_{6-10}$ aryl-$C_{1-6}$ alkyl-, (5-10 membered heteroaryl)-$C_{1-6}$ alkyl-, and (4-10 membered heterocycloalkyl)-$C_{1-6}$ alkyl- of $R^6$ are each optionally substituted with 1, 2, 3, or 4 independently selected $R^{6A}$ substituents.

In some embodiments, each $R^6$ is independently selected from $C_{1-6}$ alkyl, $C_{1-6}$ haloalkyl, 5-10 membered heteroaryl, 4-10 membered heterocycloalkyl, (5-10 membered heteroaryl)-$C_{1-6}$ alkyl-, (4-10 membered heterocycloalkyl)-$C_{1-6}$ alkyl-, $C(O)R^{b6}$, $C(O)NR^{c6}R^{d6}$, and $C(O)OR^{a6}$, wherein the $C_{1-6}$ alkyl, 5-10 membered heteroaryl, 4-10 membered heterocycloalkyl, (5-10 membered heteroaryl)-$C_{1-6}$ alkyl-, and (4-10 membered heterocycloalkyl)-$C_{1-6}$ alkyl- of $R^6$ are each optionally substituted with 1, 2, 3, or 4 independently selected $R^{6A}$ substituents.

In some embodiments, each $R^6$ is independently selected from $C_{1-6}$ alkyl, $C_{1-6}$ haloalkyl, $C_{3-7}$ cycloalkyl, 5-6 membered heteroaryl, 4-7 membered heterocycloalkyl, $C_{3-7}$ cycloalkyl-$C_{1-6}$ alkyl-, (5-6 membered heteroaryl)-$C_{1-6}$ alkyl-, (4-7 membered heterocycloalkyl)-$C_{1-6}$ alkyl-, $C(O)R^{b6}$, $C(O)NR^{c6}R^{d6}$, $C(O)OR^{a6}$, $NR^{c6}C(O)R^{b6}$, $NR^{c6}S(O)_2R^{b6}$, and $S(O)_2R^{b6}$, wherein the $C_{1-6}$ alkyl, $C_{1-6}$ haloalkyl, $C_{3-7}$ cycloalkyl, 5-6 membered heteroaryl, 4-7 membered heterocycloalkyl, $C_{3-7}$ cycloalkyl-$C_{1-6}$ alkyl-, (5-6 membered heteroaryl)-$C_{1-6}$ alkyl- and (4-7 membered heterocycloalkyl)-$C_{1-6}$ alkyl-, of $R^6$ are each optionally substituted with 1, 2, 3, or 4 independently selected $R^{6A}$ substituents.

In some embodiments, each $R^6$ is independently selected from $C_{1-6}$ alkyl, $C_{1-6}$ haloalkyl, 5-6 membered heteroaryl, 4-6 membered heterocycloalkyl, (5-6 membered heteroaryl)-$C_{1-6}$ alkyl-, (4-6 membered heterocycloalkyl)-$C_{1-6}$ alkyl-, $C(O)R^{b6}$, $C(O)NR^{c6}R^{d6}$, and $C(O)OR^{a6}$, wherein the $C_{1-6}$ alkyl, 5-6 membered heteroaryl, 4-6 membered heterocycloalkyl, (5-6 membered heteroaryl)-$C_{1-6}$ alkyl-, and (4-6 membered heterocycloalkyl)-$C_{1-6}$ alkyl- of $R^6$ are each optionally substituted with 1, 2, 3, or 4 independently selected $R^{6A}$ substituents.

In some embodiments, each $R^6$ is independently selected from $C_{1-6}$ alkyl, $C_{1-6}$ haloalkyl, $C_{3-7}$ cycloalkyl, 5-6 membered heteroaryl, 4-7 membered heterocycloalkyl, $C_{3-7}$ cycloalkyl-$C_{1-6}$ alkyl-, (5-6 membered heteroaryl)-$C_{1-6}$ alkyl-, (4-7 membered heterocycloalkyl)-$C_{1-6}$ alkyl-, $C(O)R^{b6}$, $C(O)NR^{c6}R^{d6}$, $C(O)OR^{a6}$, $NR^{c6}C(O)R^{b6}$, $NR^{c6}S(O)_2R^{b6}$, and $S(O)_2R^{b6}$, wherein the $C_{1-6}$ alkyl, $C_{1-6}$ haloalkyl, $C_{3-7}$ cycloalkyl, 5-6 membered heteroaryl, 4-7 membered heterocycloalkyl, $C_{3-7}$ cycloalkyl-$C_{1-6}$ alkyl-, (5-6 membered heteroaryl)-$C_{1-6}$ alkyl- and (4-7 membered heterocycloalkyl)-$C_{1-6}$ alkyl-, of $R^6$ are each optionally substituted with 1 or 2 independently selected $R^{6A}$ substituents.

In some embodiments, each $R^6$ is independently selected from $C_{1-6}$ alkyl, $C_{1-6}$ haloalkyl, 5-6 membered heteroaryl, 4-6 membered heterocycloalkyl, (5-6 membered heteroaryl)-$C_{1-6}$ alkyl-, (4-6 membered heterocycloalkyl)-$C_{1-6}$ alkyl-, $C(O)R^{b6}$, $C(O)NR^{c6}R^{d6}$, and $C(O)OR^{a6}$, wherein the $C_{1-6}$ alkyl, 5-6 membered heteroaryl, 4-6 membered heterocycloalkyl, (5-6 membered heteroaryl)-$C_{1-6}$ alkyl-, and (4-6 membered heterocycloalkyl)-$C_{1-6}$ alkyl- of $R^6$ are each optionally substituted with 1 or 2 independently selected $R^{6A}$ substituents.

In some embodiments, each $R^{a6}$, $R^{b6}$, $R^{c6}$, and $R^{d6}$ is independently selected from H, $C_{1-6}$ alkyl, $C_{1-6}$ haloalkyl, $C_{2-6}$ alkenyl, $C_{2-6}$ alkynyl, $C_{3-10}$ cycloalkyl, $C_{6-10}$ aryl, and 4-10 membered heterocycloalkyl)-$C_{1-6}$ alkyl-, wherein the $C_{1-6}$ alkyl, $C_{1-6}$ haloalkyl, $C_{2-6}$ alkenyl, $C_{2-6}$ alkynyl, $C_{3-10}$ cycloalkyl, $C_{6-10}$ aryl, and 4-10 membered heterocycloalkyl)-$C_{1-6}$ alkyl- of $R^{a6}$, $R^{b6}$, $R^{c6}$, and $R^{d6}$ are each optionally substituted by 1, 2, 3, or 4 independently selected $R^{6A}$ substituents.

In some embodiments, each $R^{a6}$, $R^{b6}$, $R^{c6}$, and $R^{d6}$ is independently selected from H, $C_{1-6}$ alkyl, $C_{1-6}$ haloalkyl, $C_{2-6}$ alkenyl, $C_{2-6}$ alkynyl, $C_{3-7}$ cycloalkyl, phenyl, 4-7 membered heterocycloalkyl)-$C_{1-6}$ alkyl-, wherein the $C_{1-6}$ alkyl, $C_{1-6}$ haloalkyl, $C_{2-6}$ alkenyl, $C_{2-6}$ alkynyl, $C_{3-7}$ cycloalkyl, phenyl, and 4-10 membered heterocycloalkyl)-$C_{1-6}$ alkyl- of $R^{a6}$, $R^{b6}$, $R^{c6}$, and $R^{d6}$ are each optionally substituted by 1, 2, 3, or 4 independently selected $R^{6A}$ substituents.

In some embodiments, each $R^{a6}$, $R^{b6}$, $R^{c6}$, and $R^{d6}$ is independently selected from H, $C_{1-6}$ alkyl, $C_{1-6}$ haloalkyl, $C_{2-6}$ alkenyl, $C_{2-6}$ alkynyl, wherein the $C_{1-6}$ alkyl, $C_{1-6}$ haloalkyl, $C_{2-6}$ alkenyl, and $C_{2-6}$ alkynyl of $R^{a6}$, $R^{b6}$, $R^{c6}$, and $R^{d6}$ are each optionally substituted by 1, 2, 3, or 4 independently selected $R^{6A}$ substituents.

In some embodiments, each $R^{a6}$, $R^{b6}$, $R^{c6}$, and $R^{d6}$ is independently selected from H, $C_{1-6}$ alkyl, $C_{1-6}$ haloalkyl, $C_{2-6}$ alkenyl, $C_{2-6}$ alkynyl, $C_{3-10}$ cycloalkyl, $C_{6-10}$ aryl, and 4-10 membered heterocycloalkyl)-$C_{1-6}$ alkyl-, wherein the $C_{1-6}$ alkyl, $C_{1-6}$ haloalkyl, $C_{2-6}$ alkenyl, $C_{2-6}$ alkynyl, $C_{3-7}$ to cycloalkyl, $C_{6-10}$ aryl, and 4-10 membered heterocycloalkyl)-$C_{1-6}$ alkyl- of $R^{a6}$, $R^{b6}$, $R^{c6}$, and $R^{d6}$ are each optionally substituted by 1 or 2 independently selected $R^{6A}$ substituents.

In some embodiments, each $R^{a6}$, $R^{b6}$, $R^{c6}$, and $R^{d6}$ is independently selected from H, $C_{1-6}$ alkyl, $C_{1-6}$ haloalkyl, $C_{2-6}$ alkenyl, $C_{2-6}$ alkynyl, $C_{3-7}$ cycloalkyl, phenyl, and 4-7 membered heterocycloalkyl)-$C_{1-6}$ alkyl-, wherein the $C_{1-6}$ alkyl, $C_{1-6}$ haloalkyl, $C_{2-6}$ alkenyl, $C_{2-6}$ alkynyl, $C_{3-7}$ cycloalkyl, phenyl, and 4-7 membered heterocycloalkyl)-$C_{1-6}$ alkyl- of $R^{a6}$, $R^{b6}$, $R^{c6}$, and $R^{d6}$ are each optionally substituted by 1 or 2 independently selected $R^{6A}$ substituents.

In some embodiments, each $R^{a6}$, $R^{b6}$, $R^{c6}$, and $R^{d6}$ is independently selected from H, $C_{1-6}$ alkyl, $C_{1-6}$ haloalkyl, $C_{2-6}$ alkenyl, $C_{2-6}$ alkynyl, wherein the $C_{1-6}$ alkyl, $C_{1-6}$ haloalkyl, $C_{2-6}$ alkenyl, $C_{2-6}$ alkynyl of $R^{a6}$, $R^{b6}$, $R^{c6}$, and $R^{d6}$ are each optionally substituted by 1 or 2 independently selected $R^{6A}$ substituents.

In some embodiments, each $R^{a6}$, $R^{b6}$, $R^{c6}$, and $R^{d6}$ is independently selected from H, $C_{1-6}$ alkyl, $C_{3-10}$ cycloalkyl, $C_{6-10}$ aryl, and 4-10 membered heterocycloalkyl)-$C_{1-6}$ alkyl-, wherein the $C_{1-6}$ alkyl, $C_{3-10}$ cycloalkyl, $C_{6-10}$ aryl, and 4-10 membered heterocycloalkyl)-$C_{1-6}$ alkyl- of $R^{a6}$, $R^{b6}$, $R^{c6}$, and $R^{d6}$ are each optionally substituted by 1 or 2 independently selected $R^{6A}$ substituents.

In some embodiments, each $R^{a6}$, $R^{b6}$, $R^{c6}$, and $R^{d6}$ is independently selected from H, $C_{1-6}$ alkyl, $C_{3-7}$ cycloalkyl, phenyl, and 4-7 membered heterocycloalkyl)-$C_{1-6}$ alkyl-, wherein the $C_{1-6}$ alkyl, $C_{3-7}$ cycloalkyl, phenyl, and 4-10 membered heterocycloalkyl)-$C_{1-6}$ alkyl- of $R^{a6}$, $R^{b6}$, $R^{c6}$, and $R^{d6}$ are each optionally substituted by 1 or 2 independently selected $R^{6A}$ substituents.

In some embodiments, each $R^{a6}$, $R^{b6}$, $R^{c6}$, and $R^{d6}$ is independently selected from H or $C_{1-6}$ alkyl, wherein the $C_{1-6}$ alkyl of $R^{a6}$, $R^{b6}$, $R^{c6}$, and $R^{d6}$ are each optionally substituted by 1 or 2 independently selected $R^{6A}$ substituents.

In some embodiments, each $R^{a6}$, $R^{b6}$, $R^{c6}$, and $R^{d6}$ is independently selected from H, $C_{1-6}$ alkyl, cyclopropyl, cyclobutyl, phenyl, and tetrahydropyranylmethyl, wherein the $C_{1-6}$ alkyl, cyclopropyl, cyclobutyl, phenyl, and tetrahydropyranylmethyl of $R^{a6}$, $R^{b6}$, $R^{c6}$, and $R^{d6}$ are each optionally substituted by 1 or 2 independently selected $R^{6A}$ substituents.

In some embodiments, each $R^{a6}$, $R^{b6}$, $R^{c6}$, and $R^{d6}$ is independently selected from H, methyl, ethyl, propyl, cyclopropyl, cyclobutyl, phenyl, and tetrahydropyranylmethyl, wherein the methyl, ethyl, propyl, cyclopropyl, cyclobutyl, phenyl, and tetrahydropyranylmethyl of $R^{a6}$, $R^{b6}$, $R^{c6}$, and $R^{d6}$ are each optionally substituted by 1 or 2 independently selected $R^{6A}$ substituents.

In some embodiments, each $R^6$ is independently selected from $C_{1-6}$ alkyl, $C_{1-6}$ haloalkyl, $C_{3-7}$ cycloalkyl, 5-6 membered heteroaryl, 4-7 membered heterocycloalkyl, $C_{3-7}$ cycloalkyl-$C_{1-6}$ alkyl-, phenyl-$C_{1-6}$ alkyl-, (5-6 membered heteroaryl)-$C_{1-6}$ alkyl-, (4-7 membered heterocycloalkyl)-$C_{1-6}$ alkyl-, $C(O)R^{b6}$, $C(O)NR^{c6}R^{d6}$, $C(O)OR^{a6}$, $NR^{c6}C(O)R^{b6}$, $NR^{c6}S(O)_2R^{b6}$, and $S(O)_2R^{b6}$, wherein the $C_{1-6}$ alkyl, $C_{1-6}$ haloalkyl, $C_{3-7}$ cycloalkyl, 5-6 membered heteroaryl, 4-7 membered heterocycloalkyl, $C_{3-7}$ cycloalkyl-$C_{1-6}$ alkyl-, phenyl-$C_{1-6}$ alkyl-, (5-6 membered heteroaryl)-$C_{1-6}$ alkyl-, and (4-7 membered heterocycloalkyl)-$C_{1-6}$ alkyl- of $R^6$ are each optionally substituted with 1 or 2 independently selected $R^{6A}$ substituents; and
$R^{c6}$ and $R^{d6}$ are each optionally substituted by 1 or 2 independently selected $R^{6A}$ substituents.

In some embodiments, each $R^6$ is independently selected from $C_{1-6}$ alkyl, $C_{1-6}$ haloalkyl, $C_{3-7}$ cycloalkyl, 5-6 membered heteroaryl, 4-7 membered heterocycloalkyl, $C_{3-7}$ cycloalkyl-$C_{1-6}$ alkyl-, phenyl-$C_{1-6}$ alkyl-, (5-6 membered heteroaryl)-$C_{1-6}$ alkyl-, (4-7 membered heterocycloalkyl)-$C_{1-6}$ alkyl-, $C(O)R^{b6}$, $C(O)NR^{c6}R^{d6}$, $C(O)OR^{a6}$, $NR^{c6}C(O)R^{b6}$, $NR^{c6}S(O)_2R^{b6}$, and $S(O)_2R^{b6}$, wherein the $C_{1-6}$ alkyl, $C_{1-6}$ haloalkyl, $C_{3-7}$ cycloalkyl, 5-6 membered heteroaryl, 4-7 membered heterocycloalkyl, $C_{3-7}$ cycloalkyl-$C_{1-6}$ alkyl-, phenyl-$C_{1-6}$ alkyl-, (5-6 membered heteroaryl)-$C_{1-6}$ alkyl-, and (4-7 membered heterocycloalkyl)-$C_{1-6}$ alkyl- of $R^6$ are each optionally substituted with 1 or 2 independently selected $R^{6A}$ substituents; and
each $R^{a6}$, $R^{b6}$, $R^{c6}$, and $R^{d6}$ is independently selected from H, $C_{1-6}$ alkyl, cyclopropyl, cyclobutyl, phenyl, and tetrahydropyranylmethyl, wherein the $C_{1-6}$ alkyl, cyclopropyl, cyclobutyl, phenyl, and tetrahydropyranylmethyl of $R^{a6}$, $R^{b6}$, $R^{c6}$, and $R^{d6}$ are each optionally substituted by 1 or 2 independently selected $R^{6A}$ substituents.

In some embodiments, each $R^6$ is independently selected from $C_{1-6}$ alkyl, $C_{1-6}$ haloalkyl, $C_{3-7}$ cycloalkyl, 5-6 membered heteroaryl, 4-7 membered heterocycloalkyl, $C_{3-7}$ cycloalkyl-$C_{1-6}$ alkyl-, phenyl-$C_{1-6}$ alkyl-, (5-6 membered heteroaryl)-$C_{1-6}$ alkyl-, (4-7 membered heterocycloalkyl)-$C_{1-6}$ alkyl-, $C(O)R^{b6}$, $C(O)NR^{c6}R^{d6}$, $C(O)OR^{a6}$, $NR^{c6}C(O)R^{b6}$, $NR^{c6}S(O)_2R^{b6}$, and $S(O)_2R^{b6}$, wherein the $C_{1-6}$ alkyl, $C_{1-6}$ haloalkyl, $C_{3-7}$ cycloalkyl, 5-6 membered heteroaryl, 4-7 membered heterocycloalkyl, $C_{3-7}$ cycloalkyl-$C_{1-6}$ alkyl-, phenyl-$C_{1-6}$ alkyl-, (5-6 membered heteroaryl)-$C_{1-6}$ alkyl-, and (4-7 membered heterocycloalkyl)-$C_{1-6}$ alkyl- of $R^6$ are each optionally substituted with 1 or 2 independently selected $R^{6A}$ substituents; and
each $R^{a6}$, $R^{b6}$, $R^{c6}$, and $R^{d6}$ is independently selected from H, methyl, ethyl, propyl, cyclopropyl, cyclobutyl, phenyl, and tetrahydropyranylmethyl, wherein the methyl, ethyl, propyl, cyclopropyl, cyclobutyl, phenyl, and tetrahydropyranylmethyl of $R^{a6}$, $R^{b6}$, $R^{c6}$, and $R^{d6}$ are each optionally substituted by 1 or 2 independently selected $R^{6A}$ substituents.

In some embodiments, each $R^6$ is independently selected from $C_{1-6}$ alkyl, $C_{1-6}$ haloalkyl, $C_{3-7}$ cycloalkyl, 5-6 membered heteroaryl, 4-7 membered heterocycloalkyl, $C_{3-7}$ cycloalkyl-$C_{1-6}$ alkyl-, phenyl-$C_{1-6}$ alkyl-, (5-6 membered heteroaryl)-$C_{1-6}$ alkyl-, (4-7 membered heterocycloalkyl)-$C_{1-6}$ alkyl-, $C(O)R^{b6}$, $C(O)NR^{c6}R^{d6}$, $C(O)OR^{a6}$, $NR^{c6}C(O)R^{b6}$, $NR^{c6}S(O)_2R^{b6}$, and $S(O)_2R^{b6}$, wherein the $C_{1-6}$ alkyl, $C_{1-6}$ haloalkyl, $C_{3-7}$ cycloalkyl, 5-6 membered heteroaryl, 4-7 membered heterocycloalkyl, $C_{3-7}$ cycloalkyl-$C_{1-6}$ alkyl-, phenyl-$C_{1-6}$ alkyl-, (5-6 membered heteroaryl)-$C_{1-6}$ alkyl-, and (4-7 membered heterocycloalkyl)-$C_{1-6}$ alkyl- of $R^6$ are each optionally substituted with 1 or 2 independently selected $R^{6A}$ substituents; and
a each $R^{a6}$, $R^{b6}$, $R^{c6}$, and $R^{d6}$ is independently selected from H, methyl, ethyl, propyl, cyclopropyl, cyclobutyl, phenyl, and tetrahydropyranylmethyl.

In some embodiments, each $R^6$ is independently selected from $C_{1-6}$ alkyl, 5-10 membered heteroaryl, 4-10 membered heterocycloalkyl, and $C(O)R^{b6}$, wherein the $C_{1-6}$ alkyl, 5-10 membered heteroaryl, and 4-10 membered heterocycloalkyl of $R^6$ are each optionally substituted with 1, 2, 3, or 4 independently selected $R^{6A}$ substituents; and
each $R^{b6}$ is independently selected from H, $C_{1-6}$ alkyl, $C_{1-6}$ haloalkyl, $C_{2-6}$ alkenyl, $C_{2-6}$ alkynyl, wherein the $C_{1-6}$ alkyl, $C_{1-6}$ haloalkyl, $C_{2-6}$ alkenyl, $C_{2-6}$ alkynyl of $R^{b6}$ are each optionally substituted by 1, 2, 3, or 4 independently selected $R^{6A}$ substituents.

In some embodiments, each $R^6$ is independently selected from $C_{1-6}$ alkyl, 5-6 membered heteroaryl, 4-6 membered heterocycloalkyl, and $C(O)R^{b6}$, wherein the $C_{1-6}$ alkyl, 5-6 membered heteroaryl, and 4-6 membered heterocycloalkyl of $R^6$ are each optionally substituted with 1, 2, 3, or 4 independently selected $R^{6A}$ substituents; and each $R^{b6}$ is independently selected from H, $C_{1-6}$ alkyl, $C_{1-6}$ haloalkyl, $C_{2-6}$ alkenyl, $C_{2-6}$ alkynyl, wherein the $C_{1-6}$ alkyl, $C_{1-6}$ haloalkyl, $C_{2-6}$ alkenyl, $C_{2-6}$ alkynyl of $R^{b6}$ are each optionally substituted by 1, 2, 3, or 4 independently selected $R^{6A}$ substituents.

In some embodiments, each $R^6$ is independently selected from $C_{1-6}$ alkyl, 5-6 membered heteroaryl, 4-6 membered heterocycloalkyl, and $C(O)R^{b6}$, wherein the $C_{1-6}$ alkyl, 5-6 membered heteroaryl, and 4-6 membered heterocycloalkyl of $R^6$ are each optionally substituted with 1 or 2 independently selected $R^{6A}$ substituents; and each $R^{b6}$ is independently selected from H and $C_{1-6}$ alkyl, wherein the $C_{1-6}$ alkyl of $R^{b6}$ are each optionally substituted by 1 or 2 independently selected $R^{6A}$ substituents.

In some embodiments, each $R^6$ is independently selected from $C_{1-6}$ alkyl, cyclopropyl, cyclobutyl, cyclopentyl, cyclohexyl, azetidinyl, tetrahydrothiopheneyl, pyrazolyl, piperidinyl, pyrimidinyl, cyclopropylmethyl, spiro[3.3]heptanylmethyl, phenylmethyl, triazolylisopropyl, azetidinylisopropyl, 2-azabicyclo[2.1.1]hexanyl, bicyclo[1.1.1]pentanyl, $C(O)R^{b6}$, $NR^{c6}C(O)R^{b6}$, $NR^{c6}S(O)_2R^{b6}$, and $S(O)_2R^{b6}$, wherein the $C_{1-6}$ alkyl, cyclopropyl, cyclobutyl, cyclopentyl, cyclohexyl, azetidinyl, tetrahydrothiopheneyl, pyrazolyl, piperidinyl, pyrimidinyl, cyclopropylmethyl, spiro[3.3]heptanylmethyl, phenylmethyl, triazolylisopropyl, azetidinylisopropyl, 2-azabicyclo[2.1.1]hexanyl, and bicyclo[1.1.1]pentanyl of $R^6$ are each optionally substituted with 1 or 2 independently selected $R^{6A}$ substituents.

In some embodiments, each $R^6$ is independently selected from ethyl, tert-butyl, cyclopropyl, cyclobutyl, cyclopentyl, cyclohexyl, azetidinyl, tetrahydrothiopheneyl, pyrazolyl, piperidinyl, pyrimidinyl, cyclopropylmethyl, spiro[3.3]heptanylmethyl, phenylmethyl, triazolylisopropyl, azetidinylisopropyl, 2-azabicyclo[2.1.1]hexanyl, bicyclo[1.1.1]pentanyl, methylcarbonyl, tetrahydropyranylmethylcarbonyl, propylcarbonyl, dimethylaminocarbonyl, methoxycarbonyl, phenylaminocarbonyl, ethylsulfonyl, cyclobutylcarbonylamino, cyclopropylsulfonyl, and cyclopropylsulfonylamino, wherein the ethyl, tert-butyl, cyclopropyl, cyclobutyl, cyclopentyl, cyclohexyl, azetidinyl, tetrahydrothiopheneyl, pyrazolyl, piperidinyl, pyrimidinyl, cyclopropylmethyl, spiro[3.3]heptanylmethyl, phenylmethyl, triazolylisopropyl, azetidinylisopropyl, 2-azabicyclo[2.1.1]hexanyl, bicyclo[1.1.1]pentanyl, methylcarbonyl, tetrahydropyranylmethylcarbonyl, propylcarbonyl, dimethylaminocarbonyl, methoxycarbonyl, phenylaminocarbonyl, ethylsulfonyl, cyclobutylcarbonylamino, cyclopropylsulfonyl, and cyclopropylsulfonylamino of $R^6$ are each optionally substituted with 1 or 2 independently selected $R^{6A}$ substituents.

In some embodiments, each $R^6$ is independently selected from ethyl, tert-butyl, cyclopropyl, cyclobutyl, cyclopentyl, cyclohexyl, azetidinyl, tetrahydrothiopheneyl, pyrazolyl, piperidinyl, pyrimidinyl, cyclopropylmethyl, spiro[3.3]heptanylmethyl, phenylmethyl, triazolylisopropyl, azetidinylisopropyl, 2-azabicyclo[2.1.1]hexanyl, bicyclo[1.1.1]pentanyl, methylcarbonyl, tetrahydropyranylmethylcarbonyl, propylcarbonyl, dimethylaminocarbonyl, methoxycarbonyl, phenylaminocarbonyl, ethylsulfonyl, cyclobutylcarbonylamino, cyclopropylsulfonyl, and cyclopropylsulfonylamino, wherein the ethyl, tert-butyl, cyclopropyl, cyclobutyl, cyclopentyl, cyclohexyl, azetidinyl, tetrahydrothiopheneyl, pyrazolyl, piperidinyl, pyrimidinyl, cyclopropylmethyl, spiro[3.3]heptanylmethyl, phenylmethyl, triazolylisopropyl, azetidinylisopropyl, cyclobutylcarbonylamino, cyclopropylsulfonyl, 2-azabicyclo[2.1.1]hexanyl, and bicyclo[1.1.1]pentanyl of $R^6$ are each optionally substituted with 1 or 2 independently selected $R^{6A}$ substituents.

In some embodiments, each $R^6$ is independently selected from $C_{1-6}$ alkyl, pyrazolyl, piperidinyl, and $C(O)R^{b6}$, wherein the $C_{1-6}$ alkyl, pyrazolyl, and piperidinyl of $R^6$ are each optionally substituted with 1 or 2 independently selected $R^{6A}$ substituents; and each $R^{b6}$ is independently selected from H or $C_{1-6}$ alkyl, wherein the $C_{1-6}$ alkyl of $R^{b6}$ is optionally substituted by 5-6 membered heterocycloalkyl.

In some embodiments, each $R^6$ is independently selected from $C_{1-6}$ alkyl, pyrazolyl, piperidinyl, and $C(O)R^{b6}$, wherein the $C_{1-6}$ alkyl, pyrazolyl, and piperidinyl of $R^6$ are each optionally substituted with 1 or 2 independently selected $R^{6A}$ substituents;

each $R^{b6}$ is independently selected from H or $C_{1-6}$ alkyl, wherein the $C_{1-6}$ alkyl of $R^{b6}$ is optionally substituted by tetrahydropyranyl.

In some embodiments, each $R^{6A}$ is independently selected from $C_{6-10}$ aryl, $C_{3-10}$ cycloalkyl, 5-10 membered heteroaryl, 4-10 membered heterocycloalkyl, CN, $C(O)R^{b61}$, $C(O)NR^{c61}R^{d61}$, $C(O)OR^{a61}$, and $OC(O)R^{b61}$, wherein the $C_{6-10}$ aryl, $C_{3-10}$ cycloalkyl, 5-10 membered heteroaryl, and 4-10 membered heterocycloalkyl of $R^{6A}$ are each optionally substituted with 1, 2, 3, or 4 independently selected $R^{6B}$ substituents.

In some embodiments, each $R^{6A}$ is independently selected from phenyl, $C_{3-7}$ cycloalkyl, 5-6 membered heteroaryl, 4-6 membered heterocycloalkyl, CN, $C(O)R^{b61}$, $C(O)NR^{c61}R^{d61}$, $C(O)OR^{a61}$, and $OC(O)R^{b61}$, wherein the phenyl, $C_{3-7}$ cycloalkyl, 5-6 membered heteroaryl, and 4-6 membered heterocycloalkyl of $R^{6A}$ are each optionally substituted with 1, 2, 3, or 4 independently selected $R^{6B}$ substituents.

In some embodiments, each $R^{6A}$ is independently selected from phenyl, $C_{3-7}$ cycloalkyl, 5-6 membered heteroaryl, 4-6 membered heterocycloalkyl, CN, $C(O)R^{b61}$, $C(O)NR^{c61}R^{d61}$, $C(O)OR^{a61}$, and $OC(O)R^{b61}$, wherein the phenyl, $C_{3-7}$ cycloalkyl, 5-6 membered heteroaryl, and 4-6 membered heterocycloalkyl of $R^{6A}$ are each optionally substituted with 1 or 2 independently selected $R^{6B}$ substituents.

In some embodiments, each $R^{a61}$, $R^{b61}$, $R^{c61}$, and $R^{d61}$ is independently selected from H, $C_{1-6}$ alkyl, $C_{1-6}$ haloalkyl, $C_{2-6}$ alkenyl, $C_{2-6}$ alkynyl, and $C_{6-10}$ aryl, wherein the $C_{1-6}$ alkyl, $C_{1-6}$ haloalkyl, $C_{2-6}$ alkenyl, $C_{2-6}$ alkynyl, and $C_{6-10}$ aryl of $R^{a61}$, $R^{b61}$, $R^{c61}$, and $R^{d61}$ are each optionally substituted by 1, 2, 3, or 4 independently selected $R^{6B}$ substituents.

In some embodiments, each $R^{a61}$, $R^{b61}$, $R^{c61}$, and $R^{d61}$ is independently selected from H, $C_{1-6}$ alkyl, $C_{1-6}$ haloalkyl, $C_{2-6}$ alkenyl, $C_{2-6}$ alkynyl, and $C_{6-10}$ aryl, wherein the $C_{1-6}$ alkyl, $C_{1-6}$ haloalkyl, $C_{2-6}$ alkenyl, $C_{2-6}$ alkynyl, and $C_{6-10}$ aryl of $R^{a61}$, $R^{b61}$, $R^{c61}$, and $R^{d61}$ are each optionally substituted by 1 or 2 independently selected $R^{6B}$ substituents.

In some embodiments, each $R^{a61}$, $R^{b61}$, $R^{c61}$, and $R^{d61}$ is independently selected from H, $C_{1-6}$ alkyl, $C_{1-6}$ haloalkyl, $C_{2-6}$ alkenyl, $C_{2-6}$ alkynyl, and phenyl, wherein the $C_{1-6}$ alkyl, $C_{1-6}$ haloalkyl, $C_{2-6}$ alkenyl, $C_{2-6}$ alkynyl, and phenyl of $R^{a61}$, $R^{b61}$, $R^{c61}$, and $R^{d61}$ are each optionally substituted by 1, 2, 3, or 4 independently selected $R^{6B}$ substituents.

In some embodiments, each $R^{a61}$, $R^{b61}$, $R^{c61}$, and $R^{d61}$ is independently selected from H, $C_{1-6}$ alkyl, $C_{1-6}$ haloalkyl, $C_{2-6}$ alkenyl, $C_{2-6}$ alkynyl, and phenyl, wherein the $C_{1-6}$ alkyl, $C_{1-6}$ haloalkyl, $C_{2-6}$ alkenyl, $C_{2-6}$ alkynyl, and phenyl of $R^{a61}$, $R^{b61}$, $R^{c61}$, and $R^{d61}$ are each optionally substituted by 1 or 2 independently selected $R^{6B}$ substituents.

In some embodiments, each $R^{a61}$, $R^{b61}$, $R^{c61}$, and $R^{d61}$ is independently selected from H, $C_{1-6}$ alkyl, and $C_{6-10}$ aryl, wherein the $C_{1-6}$ alkyl and $C_{6-10}$ aryl of $R^{a61}$, $R^{b61}$, $R^{c61}$ and $R^{d61}$ are each optionally substituted by 1, 2, 3, or 4 independently selected $R^{6B}$ substituents.

In some embodiments, each $R^{a61}$, $R^{b61}$, $R^{c61}$, and $R^{d61}$ is independently selected from H, $C_{1-6}$ alkyl, and $C_{6-10}$ aryl, wherein the $C_{1-6}$ alkyl and $C_{6-10}$ aryl of $R^{a61}$, $R^{b61}$, $R^{c61}$ and $R^{d61}$ are each optionally substituted by 1 or 2 independently selected $R^{6B}$ substituents.

In some embodiments, each $R^{a61}$, $R^{b61}$, $R^{c61}$, and $R^{d61}$ is independently selected from H, $C_{1-6}$ alkyl, and phenyl, wherein the $C_{1-6}$ alkyl and phenyl of $R^{a61}$, $R^{b61}$, $R^{c61}$, and $R^{d61}$ are each optionally substituted by 1, 2, 3, or 4 independently selected $R^{6B}$ substituents.

In some embodiments, each $R^{a61}$, $R^{b61}$, $R^{c61}$, and $R^{d61}$ is independently selected from H, $C_{1-6}$ alkyl, and phenyl wherein the $C_{1-6}$ alkyl and phenyl of $R^{a61}$, $R^{b61}$, $R^{c61}$, and $R^{d61}$ are each optionally substituted by 1 or 2 independently selected $R^{6B}$ substituents.

In some embodiments, each $R^{a61}$, $R^{b61}$, $R^{c61}$, and $R^{d61}$ is independently selected from H, $C_{1-6}$ alkyl, $C_{1-6}$ haloalkyl, $C_{2-6}$ alkenyl, and $C_{2-6}$ alkynyl, wherein the $C_{1-6}$ alkyl, $C_{1-6}$ haloalkyl, $C_{2-6}$ alkenyl, $C_{2-6}$ alkynyl of $R^{a61}$, $R^{b61}$, $R^{c61}$, and $R^{d61}$ are each optionally substituted by 1, 2, 3, or 4 independently selected $R^{6B}$ substituents.

In some embodiments, each $R^{a61}$, $R^{b61}$, $R^{c61}$, and $R^{d61}$ is independently selected from H and $C_{1-6}$ alkyl, wherein the $C_{1-6}$ alkyl of $R^{a61}$, $R^{b61}$, $R^{c61}$, and $R^{d61}$ are each optionally substituted by 1, 2, 3, or 4 independently selected $R^{6B}$ substituents.

In some embodiments, each $R^{a61}$, $R^{b61}$, $R^{c61}$, and $R^{d61}$ is independently selected from H and $C_{1-6}$ alkyl, wherein the $C_{1-6}$ alkyl of $R^{a61}$, $R^{b61}$, $R^{c61}$, and $R^{d61}$ are each optionally substituted by 1 or 2 independently selected $R^{6B}$ substituents.

In some embodiments, each $R^{a61}$, $R^{b61}$, $R^{c61}$, and $R^{d61}$ is independently selected from H, methyl, ethyl, and phenyl.

In some embodiments, each $R^{6A}$ is independently selected from halo, oxo, $C_{1-6}$ alkyl, 4-10 membered heterocycloalkyl, CN, $OR^{a61}$, $C(O)R^{b61}$, $C(O)NR^{c61}R^{d61}$, $C(O)OR^{a61}$, $NR^{c61}C(O)R^{b61}$, $NR^{c61}C(O)OR^{a61}$, $NR^{c61}C(O)NR^{c61}R^{d61}$, $NR^{c61}S(O)_2R^{b61}$, and $S(O)_2R^{b61}$, wherein each $C_{1-6}$ alkyl and 4-10 membered heterocycloalkyl of $R^{6A}$ are optionally substituted with 1, 2, 3, or 4 independently selected $R^{6B}$ substituents; and each $R^{a61}$, $R^{b61}$, $R^{c61}$, and $R^{d61}$ is independently selected from H, $C_{1-6}$ alkyl, and $C_{6-10}$ aryl, wherein the $C_{1-6}$ alkyl and $C_{6-10}$ aryl of $R^{a61}$, $R^{b61}$, $R^{c61}$, and $R^{d61}$ are each optionally substituted by 1 or 2 independently selected $R^{6B}$ substituents.

In some embodiments, each $R^{6A}$ is independently selected from halo, oxo, $C_{1-6}$ alkyl, 4-10 membered heterocycloalkyl, CN, $OR^{a61}$, $C(O)R^{b61}$, $C(O)NR^{c61}R^{d61}$, $C(O)OR^{a61}$, $NR^{c61}C(O)R^{b61}$, $NR^{c61}C(O)NR^{c61}R^{d61}$, $NR^{c61}S(O)_2R^{b61}$, and $S(O)_2R^{b61}$, wherein each $C_{1-6}$ alkyl and 4-10 membered heterocycloalkyl of $R^{6A}$ are optionally substituted with 1, 2, 3, or 4 independently selected $R^{6B}$ substituents; and each $R^{a61}$, $R^{b61}$, $R^{c61}$, and $R^{d61}$ is independently selected from H, $C_{1-6}$ alkyl and $C_{6-10}$ aryl, wherein the $C_{1-6}$ alkyl, and $C_{6-10}$ aryl of $R^{a61}$, $R^{b61}$, $R^{c61}$, and $R^{d61}$ are each optionally substituted by 1 or 2 independently selected $R^{6B}$ substituents.

In some embodiments, each $R^{6A}$ is independently selected from halo, oxo, $C_{1-6}$ alkyl, 4-10 membered heterocycloalkyl, CN, $OR^{a61}$, $C(O)R^{b61}$, $C(O)NR^{c61}R^{d61}$, $C(O)OR^{a61}$, $NR^{c61}C(O)R^{b61}$, $NR^{c61}C(O)OR^{a61}$, $NR^{c61}C(O)NR^{d61}R^{d61}$, $NR^{c61}S(O)_2R^{b61}$, and $S(O)_2R^{b61}$, wherein each $C_{1-6}$ alkyl and 4-10 membered heterocycloalkyl of $R^{6A}$ are optionally substituted with 1, 2, 3, or 4 independently selected $R^{6B}$ substituents; and each $R^{a61}$, $R^{b61}$, $R^{c61}$, and $R^{d61}$ is independently selected from H, $C_{1-6}$ alkyl, and phenyl, wherein the $C_{1-6}$ alkyl and phenyl of $R^{a61}$, $R^{b61}$, $R^{c61}$, and $R^{d61}$ are each optionally substituted by 1 or 2 independently selected $R^{6B}$ substituents.

In some embodiments, each $R^{6A}$ is independently selected from halo, oxo, $C_{1-6}$ alkyl, 4-10 membered heterocycloalkyl, CN, $OR^{a61}$, $C(O)R^{b61}$, $C(O)NR^{c61}R^{d61}$, $C(O)OR^{a61}$, $NR^{c61}C(O)R^{b61}$, $NR^{c61}C(O)OR^{a61}$, $NR^{c61}C(O)NR^{c61}R^{d61}$, $NR^{c61}S(O)_2R^{b61}$, and $S(O)_2R^{b61}$, wherein each $C_{1-6}$ alkyl and 4-10 membered heterocycloalkyl of $R^{6A}$ are optionally substituted with 1, 2, 3, or 4 independently selected $R^{6B}$ substituents; and each $R^{a61}$, $R^{b61}$, $R^{c61}$, and $R^{d61}$ is independently selected from H, methyl, ethyl, and phenyl.

In some embodiments, each $R^{6A}$ is independently selected from 4-10 membered heterocycloalkyl, CN, and $C(O)R^{b61}$, wherein the 4-10 membered heterocycloalkyl of $R^{6A}$ are each optionally substituted with 1, 2, 3, or 4 independently selected $R^{6B}$ substituents; and each $R^{b61}$ is independently selected from H, $C_{1-6}$ alkyl, $C_{1-6}$ haloalkyl, $C_{2-6}$ alkenyl, $C_{2-6}$ alkynyl, wherein the $C_{1-6}$ alkyl, $C_{1-6}$ haloalkyl, $C_{2-6}$ alkenyl, $C_{2-6}$ alkynyl of $R^{b61}$ are each optionally substituted by 1 or 2 independently selected $R^{6B}$ substituents.

In some embodiments, each $R^{6A}$ is independently selected from 4-6 membered heterocycloalkyl, CN, and $C(O)R^{b61}$, wherein the 4-6 membered heterocycloalkyl of $R^{6A}$ are each optionally substituted with 1, 2, 3, or 4 independently selected $R^{6B}$ substituents; and each $R^{b61}$ is independently selected from H, $C_{1-6}$ alkyl, $C_{1-6}$ haloalkyl, $C_{2-6}$ alkenyl, $C_{2-6}$ alkynyl, wherein the $C_{1-6}$ alkyl, $C_{1-6}$ haloalkyl, $C_{2-6}$ alkenyl, $C_{2-6}$ alkynyl of $R^{b61}$ are each optionally substituted by 1 or 2 independently selected $R^{6B}$ substituents.

In some embodiments, each $R^{6A}$ is independently selected from 4-6 membered heterocycloalkyl, CN, and $C(O)R^{b61}$, wherein the 4-6 membered heterocycloalkyl of $R^{6A}$ are each optionally substituted with 1 or 2 independently selected $R^{6B}$ substituents; and each $R^{b61}$ is independently selected from H and $C_{1-6}$ alkyl, wherein the $C_{1-6}$ alkyl, of $R^{b61}$ are each optionally substituted by 1 or 2 independently selected $R^{6B}$ substituents.

In some embodiments, each $R^{6B}$ is independently selected from $C_{1-6}$ alkyl, $C_{1-6}$ haloalkyl, $C_{2-6}$ alkenyl, $C_{2-6}$ alkynyl, CN, and $C(O)NR^{c62}R^{d62}$, wherein the $C_{1-6}$ alkyl, $C_{1-6}$ haloalkyl, $C_{2-6}$ alkenyl, and $C_{2-6}$ alkynyl of $R^{6B}$ are each optionally substituted by 1, 2, 3, or 4 independently selected $R^{6C}$ substituents.

In some embodiments, each $R^{6B}$ is independently selected from $C_{1-6}$ alkyl, $C_{1-6}$ haloalkyl, $C_{2-6}$ alkenyl, and $C_{2-6}$ alkynyl, wherein the $C_{1-6}$ alkyl, $C_{1-6}$ haloalkyl, $C_{2-6}$ alkenyl, and $C_{2-6}$ alkynyl of $R^{6B}$ are each optionally substituted by 1, 2, 3, or 4 independently selected $R^{6C}$ substituents.

In some embodiments, each $R^{6B}$ is independently selected from $C_{1-6}$ alkyl, $C_{1-6}$ haloalkyl, $C_{2-6}$ alkenyl, $C_{2-6}$ alkynyl, and CN, and $C(O)NR^{c62}R^{d62}$, wherein the $C_{1-6}$ alkyl, $C_{1-6}$ haloalkyl, $C_{2-6}$ alkenyl, and $C_{2-6}$ alkynyl of $R^{6B}$ are each optionally substituted by 1 or 2 independently selected $R^{6C}$ substituents; and
each $R^{c62}$ and $R^{d62}$ are independently H or $C_{1-6}$ alkyl.

In some embodiments, each $R^{6B}$ is independently selected from $C_{1-6}$ alkyl, $C_{1-6}$ haloalkyl, $C_{2-6}$ alkenyl, $C_{2-6}$ alkynyl, and CN, and $C(O)NR^{c62}R^{d62}$, wherein the $C_{1-6}$ alkyl, $C_{1-6}$ haloalkyl, $C_{2-6}$ alkenyl, and $C_{2-6}$ alkynyl of $R^{6B}$ are each optionally substituted by 1 or 2 independently selected $R^{6C}$ substituents; and
each $R^{c62}$ and $R^{d62}$ are independently H or $C_{1-3}$ alkyl.

In some embodiments, each $R^{6B}$ is independently selected from $C_{1-6}$ alkyl, $C_{1-6}$ haloalkyl, $C_{2-6}$ alkenyl, and $C_{2-6}$ alkynyl, wherein the $C_{1-6}$ alkyl, $C_{1-6}$ haloalkyl, $C_{2-6}$ alkenyl, and $C_{2-6}$ alkynyl of $R^{6B}$ are each optionally substituted by 1 or 2 independently selected $R^{6C}$ substituents.

In some embodiments, each $R^{6C}$ is independently selected from halo, oxo, $C_{1-6}$ alkyl, $C_{1-6}$ haloalkyl, $C_{2-6}$ alkenyl, $C_{2-6}$ alkynyl, CN, and $NO_2$.

In some embodiments, each $R^{6C}$ is independently selected from halo, $C_{1-6}$ alkyl, $C_{1-6}$ haloalkyl, CN, and $NO_2$.

In some embodiments, each $R^{6C}$ is CN.

In some embodiments, each $R^{6B}$ is independently selected from $C_{1-6}$ alkyl, $C_{1-6}$ haloalkyl, $C_{2-6}$ alkenyl, $C_{2-6}$ alkynyl, CN, and $C(O)NR^{c62}R^{d62}$, wherein the $C_{1-6}$ alkyl, $C_{1-6}$ haloalkyl, $C_{2-6}$ alkenyl, and $C_{2-6}$ alkynyl are each optionally substituted by CN.

In some embodiments, each $R^{6B}$ is independently selected from $C_{1-6}$ alkyl, $C_{1-6}$ haloalkyl, $C_{2-6}$ alkenyl, and $C_{2-6}$ alkynyl, wherein the $C_{1-6}$ alkyl, $C_{1-6}$ haloalkyl, $C_{2-6}$ alkenyl, and $C_{2-6}$ alkynyl are each optionally substituted by CN.

In some embodiments, each $R^{6B}$ is independently selected from $C_{1-6}$ alkyl, CN, and $C(O)NR^{c62}R^{d62}$, wherein the $C_{1-6}$ alkyl of $R^{6B}$ are each optionally substituted by CN, and each $R^{c62}$ and $R^{d62}$ is independently selected from H and $C_{1-3}$ alkyl.

In some embodiments, each $R^{6B}$ is independently selected from $C_{1-6}$ alkyl, CN, and $C(O)NH_2$, wherein the $C_{1-6}$ alkyl of $R^{6B}$ are each optionally substituted by CN.

In some embodiments, each $R^{6B}$ is independently selected from $C_{1-6}$ alkyl, wherein the $C_{1-6}$ alkyl of $R^{6B}$ are each optionally substituted by CN.

In some embodiments, each $R^{6B}$ is independently selected from methyl, CN, and $C(O)NH_2$, wherein each methyl of $R^{6B}$ is optionally substituted by CN.

In some embodiments, each $R^{6C}$ is CN.

In some embodiments, each $R^{6A}$ is independently selected from fluoro, oxo, methyl, CN, methoxy, tetrahydropyranyl, methylcarbonyl, aminocarbonyl, methylcarbonylamino, ethylaminocarbonyl, methoxycarbonyl, methoxycarbonylamino, ethylaminocarbonylamino, ethylsulfonyl, and phenylsulfonylamino, wherein each methyl of $R^{6A}$ is optionally substituted by CN or aminocarbonyl; and wherein each tetrahydropyranyl of $R^{6A}$ is optionally substituted by cyanomethyl.

In some embodiments, each $R^{6A}$ is independently selected from fluoro, oxo, methyl, CN, cyanomethyl, methoxy, tetrahydropyranyl, cyanomethyltetrahydropyranyl, methylcarbonyl, aminocarbonyl, methylcarbonylamino, ethylaminocarbonyl, methoxycarbonyl, methoxycarbonylamino, ethylaminocarbonylamino, ethylsulfonyl, and phenylsulfonylamino.

In some embodiments, each $R^{6A}$ is independently selected from cyano, tetrahydropyranyl, cyanomethyltetrahydropyranyl, and methylcarbonyl.

In some embodiments, $R^2$ is selected from H, $C_{1-6}$ alkyl, $C_{2-6}$ alkenyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^2$ are each optionally substituted with 1, 2, 3, or 4 independently selected $R^{2A}$ substituents.

In some embodiments, $R^2$ is selected from $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^2$ are each optionally substituted with 1, 2, 3, or 4 independently selected $R^{2A}$ substituents.

In some embodiments, $R^2$ is selected from H, $C_{1-6}$ alkyl, $C_{2-6}$ alkenyl, phenyl, $C_{3-10}$ cycloalkyl, 5-10 membered heteroaryl, 4-10 membered heterocycloalkyl, phenyl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, phenyl, $C_{3-10}$ cycloalkyl, 5-10 membered heteroaryl, 4-10 membered heterocycloalkyl, phenyl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^2$ are each optionally substituted with 1 or 2 independently selected $R^{2A}$ substituents.

In some embodiments, $R^2$ is selected from phenyl, $C_{3-10}$ cycloalkyl, 5-10 membered heteroaryl, 4-10 membered heterocycloalkyl, phenyl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the phenyl, $C_{3-10}$ cycloalkyl, 5-10 membered heteroaryl, 4-10 membered heterocycloalkyl, phenyl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^2$ are each optionally substituted with 1 or 2 independently selected $R^{2A}$ substituents.

In some embodiments, $R^2$ is selected from H, $C_{1-6}$ alkyl, $C_{2-6}$ alkenyl, $C_{6-10}$ aryl, 5-10 membered heteroaryl, and 4-10 membered heterocycloalkyl, wherein the $C_{1-6}$ alkyl, $C_{2-6}$ alkenyl, $C_{6-10}$ aryl, 5-10 membered heteroaryl, and 4-10 membered heterocycloalkyl of $R^2$ are each optionally substituted with 1, 2, 3, or 4 independently selected $R^{2A}$ substituents.

In some embodiments, $R^2$ is selected from $C_{6-10}$ aryl and 5-10 membered heteroaryl, wherein the $C_{6-10}$ aryl and 5-10 membered heteroaryl of $R^2$ are each optionally substituted with 1, 2, 3, or 4 independently selected $R^{2A}$ substituents.

In some embodiments, $R^2$ is selected from H, $C_{1-6}$ alkyl, $C_{2-6}$ alkenyl, phenyl, $C_{3-10}$ cycloalkyl, 5-10 membered heteroaryl, and 4-10 membered heterocycloalkyl, wherein the phenyl, $C_{3-10}$ cycloalkyl, 5-10 membered heteroaryl, and 4-10 membered heterocycloalkyl of $R^2$ are each optionally substituted with 1, 2, 3, or 4 independently selected $R^{2A}$ substituents.

In some embodiments, $R^2$ is selected from phenyl, $C_{3-10}$ cycloalkyl, 5-10 membered heteroaryl, and 4-10 membered heterocycloalkyl, wherein the phenyl, $C_{3-10}$ cycloalkyl, 5-10 membered heteroaryl, and 4-10 membered heterocycloalkyl of $R^2$ are each optionally substituted with 1, 2, 3, or 4 independently selected $R^{2A}$ substituents.

In some embodiments, $R^2$ is selected from H, $C_{1-6}$ alkyl, $C_{2-6}$ alkenyl, phenyl, 5-10 membered heteroaryl, and 4-10 membered heterocycloalkyl, wherein the $C_{1-6}$ alkyl, $C_{2-6}$ alkenyl, phenyl, 5-10 membered heteroaryl, and 4-10 membered heterocycloalkyl of $R^2$ are each optionally substituted with 1, 2, 3, or 4 independently selected $R^{2A}$ substituents.

In some embodiments, $R^2$ is selected from phenyl and 5-10 membered heteroaryl, wherein the phenyl and 5-10 membered heteroaryl of $R^2$ are each optionally substituted with 1, 2, 3, or 4 independently selected $R^{2A}$ substituents.

In some embodiments, $R^2$ is selected from H, $C_{1-6}$ alkyl, $C_{2-6}$ alkenyl, phenyl, monocyclic 5-6 membered heteroaryl, bicyclic 8-10 membered heteroaryl, and monocyclic 4-6 membered heterocycloalkyl, wherein the $C_{1-6}$ alkyl, $C_{2-6}$ alkenyl, phenyl, monocyclic 5-6 membered heteroaryl, bicyclic 8-10 membered heteroaryl, and monocyclic 4-6 membered heterocycloalkyl of $R^2$ are each optionally substituted with 1, 2, 3, or 4 independently selected $R^{2A}$ substituents.

In some embodiments, $R^2$ is selected from phenyl and 8-10 membered heteroaryl, wherein the phenyl and 5-10 membered heteroaryl of $R^2$ are each optionally substituted with 1, 2, 3, or 4 independently selected $R^{2A}$ substituents.

In some embodiments, $R^2$ is selected from H, $C_{1-6}$ alkyl, $C_{2-6}$ alkenyl, phenyl, monocyclic 5-6 membered heteroaryl, bicyclic 8-10 membered heteroaryl, and monocyclic 4-6 membered heterocycloalkyl, wherein the $C_{1-6}$ alkyl, $C_{2-6}$ alkenyl, phenyl, monocyclic 5-6 membered heteroaryl, bicyclic 8-10 membered heteroaryl, and monocyclic 4-6 membered heterocycloalkyl of $R^2$ are each optionally substituted with 1 or 2 independently selected $R^{2A}$ substituents.

In some embodiments, $R^2$ is selected from phenyl and 8-10 membered heteroaryl, wherein the phenyl and 5-10 membered heteroaryl of $R^2$ are each optionally substituted with 1 or 2 independently selected $R^{2A}$ substituents.

In some embodiments, $R^2$ is selected from H, ethyl, ethenyl, phenyl, indazolyl, thiazolyl, thieno[3,2-c]pyridinyl, 3,6-dihydro-2H-pyranyl, and indolyl, wherein the ethyl, ethenyl, phenyl, indazolyl, thiazolyl, thieno[3,2-c]pyridinyl, 3,6-dihydro-2H-pyranyl, and indolyl of $R^2$ are each optionally substituted with 1, 2, 3, or 4 independently selected $R^{2A}$ substituents.

In some embodiments, $R^2$ is selected from phenyl and indazolyl, wherein the phenyl and indazolyl of $R^2$ are each optionally substituted with 1, 2, 3, or 4 independently selected $R^{2A}$ substituents.

In some embodiments, $R^2$ is selected from H, ethyl, ethenyl, phenyl, indazolyl, thiazolyl, thieno[3,2-c]pyridinyl, 3,6-dihydro-2H-pyranyl, and indolyl, wherein the ethyl, ethenyl, phenyl, indazolyl, thiazolyl, thieno[3,2-c]pyridinyl, 3,6-dihydro-2H-pyranyl, and indolyl of $R^2$ are each optionally substituted with 1 or 2 independently selected $R^{2A}$ substituents.

In some embodiments, $R^2$ is selected from phenyl and indazolyl, wherein the phenyl and indazolyl of $R^2$ are each optionally substituted with 1 or 2 independently selected $R^{2A}$ substituents.

In some embodiments, each $R^{2A}$ is independently selected from halo, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, (4-10 membered heterocycloalkyl)-$C_{1-6}$ alkyl-, CN, and $OR^{a21}$, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, and (4-10 membered heterocycloalkyl)-$C_{1-6}$ alkyl- of $R^{2A}$ are each optionally substituted with 1, 2, 3, or 4 independently selected $R^{2B}$ substituents.

In some embodiments, each $R^{2A}$ is independently selected from $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, and 4-10 membered heterocycloalkyl, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, and 4-10 membered heterocycloalkyl of $R^{2A}$ are each optionally substituted with 1, 2, 3, or 4 independently selected $R^{2B}$ substituents.

In some embodiments, each $R^{2A}$ is independently selected from halo, $C_{1-6}$ alkyl, $C_{1-6}$ haloalkyl, $C_{2-6}$ alkenyl, $C_{2-6}$ alkynyl, phenyl, $C_{3-7}$ cycloalkyl, 5-6 membered heteroaryl, 4-6 membered heterocycloalkyl, (4-6 membered heterocycloalkyl)-$C_{1-6}$ alkyl-, CN, and $OR^{a21}$, wherein the $C_{1-6}$ alkyl, $C_{2-6}$ alkenyl, $C_{2-6}$ alkynyl, phenyl, $C_{3-6}$ cycloalkyl, 5-6 membered heteroaryl, 4-6 membered heterocycloalkyl, and (4-6 membered heterocycloalkyl)-$C_{1-6}$ alkyl- of $R^{2A}$ are each optionally substituted with 1, 2, 3, or 4 independently selected $R^{2B}$ substituents.

In some embodiments, each $R^{2A}$ is independently selected from $C_{1-6}$ alkyl, $C_{1-6}$ haloalkyl, $C_{2-6}$ alkenyl, $C_{2-6}$ alkynyl, phenyl, $C_{3-7}$ cycloalkyl, 5-6 membered heteroaryl, and 4-6 membered heterocycloalkyl, wherein the $C_{1-6}$ alkyl, $C_{2-6}$ alkenyl, $C_{2-6}$ alkynyl, phenyl, $C_{3-6}$ cycloalkyl, 5-6 membered heteroaryl, and 4-6 membered heterocycloalkyl of $R^{2A}$ are each optionally substituted with 1, 2, 3, or 4 independently selected $R^{2B}$ substituents.

In some embodiments, each $R^{2A}$ is independently selected from halo, $C_{1-6}$ alkyl, $C_{1-6}$ haloalkyl, $C_{2-6}$ alkenyl, $C_{2-6}$ alkynyl, phenyl, $C_{3-7}$ cycloalkyl, 5-6 membered heteroaryl, 4-6 membered heterocycloalkyl, (4-6 membered heterocycloalkyl)-$C_{1-6}$ alkyl-, CN, and $OR^{a21}$, wherein the $C_{1-6}$ alkyl, $C_{2-6}$ alkenyl, $C_{2-6}$ alkynyl, phenyl, $C_{3-6}$ cycloalkyl, 5-6 membered heteroaryl, 4-6 membered heterocycloalkyl, and (4-6 membered heterocycloalkyl)-$C_{1-6}$ alkyl- of $R^{2A}$ are each optionally substituted with 1 or 2 independently selected $R^{2B}$ substituents.

In some embodiments, each $R^{2A}$ is independently selected from halo, $C_{1-6}$ alkyl, $C_{1-6}$ haloalkyl, $C_{2-6}$ alkenyl, $C_{2-6}$ alkynyl, phenyl, $C_{3-7}$ cycloalkyl, 5-6 membered heteroaryl, 4-6 membered heterocycloalkyl, (4-6 membered heterocycloalkyl)-$C_{1-6}$ alkyl-, CN, and $OR^{a21}$, wherein the $C_{1-6}$ alkyl, $C_{2-6}$ alkenyl, $C_{2-6}$ alkynyl, phenyl, $C_{3-6}$ cycloalkyl, 5-6 membered heteroaryl, 4-6 membered heterocycloalkyl, and (4-6 membered heterocycloalkyl)-$C_{1-6}$ alkyl- of $R^{2A}$ are each optionally substituted with 1 or 2 independently selected $R^{2B}$ substituents; and each $R^{a21}$ is independently selected from H, $C_{1-6}$ alkyl, and $C_{1-6}$ haloalkyl.

In some embodiments, each $R^{2A}$ is independently selected from $C_{1-6}$ alkyl, $C_{1-6}$ haloalkyl, $C_{2-6}$ alkenyl, $C_{2-6}$ alkynyl, phenyl, $C_{3-7}$ cycloalkyl, 5-6 membered heteroaryl, and 4-6 membered heterocycloalkyl, wherein the $C_{1-6}$ alkyl, $C_{2-6}$ alkenyl, $C_{2-6}$ alkynyl, phenyl, $C_{3-6}$ cycloalkyl, 5-6 membered heteroaryl, and 4-6 membered heterocycloalkyl of $R^{2A}$ are each optionally substituted with 1 or 2 independently selected $R^{2B}$ substituents.

In some embodiments, each $R^{2A}$ is independently selected from halo, $C_{1-6}$ alkyl, $C_{1-6}$ haloalkyl, $C_{3-10}$ cycloalkyl, 5-10 membered heteroaryl, (4-10 membered heterocycloalkyl)-$C_{1-6}$ alkyl-, CN, and $OR^{a21}$, wherein the $C_{1-6}$ alkyl, $C_{1-6}$ haloalkyl, $C_{3-10}$ cycloalkyl, 5-10 membered heteroaryl, and (4-10 membered heterocycloalkyl)-$C_{1-6}$ alkyl- of $R^{2A}$ are each optionally substituted with 1, 2, 3, or 4 independently selected $R^{2B}$ substituents.

In some embodiments, each $R^{2A}$ is independently selected from $C_{1-6}$ alkyl, and 5-10 membered heteroaryl, wherein the $C_{1-6}$ alkyl and 5-10 membered heteroaryl of $R^{2A}$ are each optionally substituted with 1, 2, 3, or 4 independently selected $R^{2B}$ substituents.

In some embodiments, each $R^{2A}$ is independently selected from halo, $C_{1-6}$ alkyl, $C_{1-6}$ haloalkyl, $C_{3-10}$ cycloalkyl, 5-10 membered heteroaryl, (4-10 membered heterocycloalkyl)-$C_{1-6}$ alkyl-, CN, and $OR^{a21}$, wherein the $C_{1-6}$ alkyl, $C_{1-6}$ haloalkyl, $C_{3-10}$ cycloalkyl, 5-10 membered heteroaryl, and (4-10 membered heterocycloalkyl)-$C_{1-6}$ alkyl- of $R^{2A}$ are each optionally substituted with 1 or 2 independently selected $R^{2B}$ substituents.

In some embodiments, each $R^{2A}$ is independently selected from $C_{1-6}$ alkyl, and 5-10 membered heteroaryl, wherein the $C_{1-6}$ alkyl and 5-10 membered heteroaryl of $R^{2A}$ are each optionally substituted with 1 or 2 independently selected $R^{2B}$ substituents.

In some embodiments, each $R^{2A}$ is independently selected from halo, $C_{1-6}$ alkyl, $C_{1-6}$ haloalkyl, $C_{3-6}$ cycloalkyl, 5-6 membered heteroaryl, (4-6 membered heterocycloalkyl)-$C_{1-6}$ alkyl-, CN, and $OR^{a21}$, wherein the $C_{1-6}$ alkyl, $C_{1-6}$ haloalkyl, $C_{3-6}$ cycloalkyl, 5-6 membered heteroaryl, and (4-6 membered heterocycloalkyl)-$C_{1-6}$ alkyl- of $R^{2A}$ are each optionally substituted with 1 or 2 independently selected $R^{2B}$ substituents.

In some embodiments, each $R^{2A}$ is independently selected from halo, $C_{1-6}$ alkyl, $C_{1-6}$ haloalkyl, $C_{3-6}$ cycloalkyl, 5-6 membered heteroaryl, (4-6 membered heterocycloalkyl)-$C_{1-6}$ alkyl-, CN, and $OR^{a21}$, wherein the $C_{1-6}$ alkyl, $C_{1-6}$ haloalkyl, $C_{3-6}$ cycloalkyl, 5-6 membered heteroaryl, and (4-6 membered heterocycloalkyl)-$C_{1-6}$ alkyl- of $R^{2A}$ are each optionally substituted with 1 or 2 independently selected $R^{2B}$ substituents; and
   each $R^{a21}$ is independently selected from H, $C_{1-6}$ alkyl, and $C_{1-6}$ haloalkyl.

In some embodiments, each $R^{2A}$ is independently selected from $C_{1-6}$ alkyl, and 5-6 membered heteroaryl, wherein the $C_{1-6}$ alkyl and 5-6 membered heteroaryl of $R^{2A}$ are each optionally substituted with 1 or 2 independently selected $R^{2B}$ substituents.

In some embodiments, each $R^{2A}$ is independently selected from fluoro, methyl, $CD_3$, trifluoromethyl, cyclopropyl, pyrazolyl, piperazinylmethyl, cyano, methoxy, and trifluoromethoxy, wherein the methyl, cyclopropyl, pyrazolyl, and piperazinylmethyl are each optionally substituted with 1 or 2 independently selected $R^{2B}$ substituents.

In some embodiments, each $R^{2A}$ is independently selected from methyl and pyrazolyl, wherein the methyl and pyrazolyl are each optionally substituted with 1 or 2 independently selected $R^{2B}$ substituents.

In some embodiments, each $R^{2B}$ is independently selected from halo, oxo, $C_{1-6}$ alkyl, $C_{1-6}$ haloalkyl, $C_{2-6}$ alkenyl, $C_{2-6}$ alkynyl, $S(O)R^{b22}$, and $S(O)_2R^{b22}$, wherein the $C_{1-6}$ alkyl, $C_{2-6}$ alkenyl, and $C_{2-6}$ alkynyl of $R^{2B}$ are each optionally substituted with 1, 2, 3, or 4 independently selected $R^{2C}$ substituents.

In some embodiments, each $R^{2B}$ is independently selected from halo, oxo, $C_{1-6}$ alkyl, $C_{1-6}$ haloalkyl, $C_{2-6}$ alkenyl, $C_{2-6}$ alkynyl, and $S(O)_2R^{b22}$, wherein the $C_{1-6}$ alkyl, $C_{2-6}$ alkenyl, and $C_{2-6}$ alkynyl of $R^{2B}$ are each optionally substituted with 1, 2, 3, or 4 independently selected $R^{2C}$ substituents.

In some embodiments, each $R^{a22}$, $R^{b22}$, $R^{c22}$, and $R^{d22}$ is independently selected from H, $C_{1-6}$ alkyl, $C_{1-6}$ haloalkyl, $C_{2-6}$ alkenyl, and $C_{2-6}$ alkynyl.

In some embodiments, each $R^{2B}$ is independently selected from halo, oxo, $C_{1-6}$ alkyl, $C_{1-6}$ haloalkyl, $C_{2-6}$ alkenyl, $C_{2-6}$ alkynyl, and $S(O)_2R^{b22}$, wherein the $C_{1-6}$ alkyl, $C_{2-6}$ alkenyl, and $C_{2-6}$ alkynyl of $R^{2B}$ are each optionally substituted with 1, 2, 3, or 4 independently selected $R^{2C}$ substituents; and
   each $R^{b22}$ is independently selected from H, $C_{1-6}$ alkyl, $C_{1-6}$ haloalkyl, $C_{2-6}$ alkenyl, and $C_{2-6}$ alkynyl.

In some embodiments, each $R^{2B}$ is independently selected from halo, oxo, $C_{1-6}$ alkyl, $C_{1-6}$ haloalkyl, $C_{2-6}$ alkenyl, $C_{2-6}$ alkynyl, and $S(O)_2R^{b22}$, wherein the $C_{1-6}$ alkyl, $C_{2-6}$ alkenyl, and $C_{2-6}$ alkynyl of $R^{2B}$ are each optionally substituted with 1, 2, 3, or 4 independently selected $R^{2C}$ substituents; and
   each $R^{b22}$ is independently selected from H or $C_{1-6}$ alkyl.

In some embodiments, each $R^{2B}$ is independently selected from halo, oxo, $C_{1-6}$ alkyl, $C_{1-6}$ haloalkyl, $C_{2-6}$ alkenyl, and $C_{2-6}$ alkynyl, wherein the $C_{1-6}$ alkyl, $C_{2-6}$ alkenyl, and $C_{2-6}$ alkynyl of $R^{2B}$ are each optionally substituted with 1, 2, 3, or 4 independently selected $R^{2C}$ substituents.

In some embodiments, each $R^{2B}$ is independently selected from $C_{1-6}$ alkyl and $S(O)_2R^{b22}$, wherein the $C_{1-6}$ alkyl of $R^{2B}$ are each optionally substituted with 1, 2, 3, or 4 independently selected $R^{2C}$ substituents.

In some embodiments, each $R^{2B}$ is independently selected from $C_{1-6}$ alkyl and $S(O)R_2R^{b22}$, wherein the $C_{1-6}$ alkyl of $R^{2B}$ are each optionally substituted with 1, 2, 3, or 4 independently selected $R^{2C}$ substituents; and
   each $R^{b22}$ is independently selected from H or $C_{1-6}$ alkyl.

In some embodiments, each $R^{2B}$ is independently selected from $C_{1-6}$ alkyl, wherein the $C_{1-6}$ alkyl of $R^{2B}$ are each optionally substituted with 1, 2, 3, or 4 independently selected $R^{2C}$ substituents.

In some embodiments, each $R^{2B}$ is independently selected from $C_{1-6}$ alkyl and $S(O)_2R^{b22}$, wherein the $C_{1-6}$ alkyl of $R^{2B}$ are each optionally substituted with 1 or 2 independently selected $R^{2C}$ substituents.

In some embodiments, each $R^{2B}$ is independently selected from $C_{1-6}$ alkyl and $S(O)_2R^{b22}$, wherein the $C_{1-6}$ alkyl of $R^{2B}$ are each optionally substituted with 1 or 2 independently selected $R^{2C}$ substituents; and
   each $R^{b22}$ is independently selected from H or $C_{1-6}$ alkyl.

In some embodiments, each $R^{2B}$ is independently selected from $C_{1-6}$ alkyl, wherein the $C_{1-6}$ alkyl of $R^{2B}$ are each optionally substituted with 1 or 2 independently selected $R^{2C}$ substituents.

In some embodiments, each $R^{2C}$ is independently selected from halo, oxo, $C_{1-6}$ alkyl, $C_{1-6}$ haloalkyl, $C_{2-6}$ alkenyl, $C_{2-6}$ alkynyl, CN, and $NO_2$.

In some embodiments, each $R^{2C}$ is independently selected from halo, $C_{1-6}$ alkyl, $C_{1-6}$ haloalkyl, CN, and $NO_2$.

In some embodiments, each $R^{2C}$ is CN.

In some embodiments, each $R^{2B}$ is independently selected from cyanoisopropyl and $S(O)_2R^{b22}$, wherein each $R^{b22}$ is independently selected from H or $C_{1-6}$ alkyl.

In some embodiments, each $R^{2B}$ is independently selected from cyanomethyl and methylsulfonyl.

In some embodiments, each $R^{2A}$ is independently selected from fluoro, methyl, $CD_3$, trifluoromethyl, cyclopropyl, pyrazolyl, piperazinylmethyl, cyano, methoxy, and trifluoromethoxy, wherein the methyl and pyrazolyl of $R^{2A}$ are each optionally substituted by cyano-$C_{1-6}$ alkyl; and the piperazinylmethyl of $R^{2A}$ is optionally substituted with $S(O)_2 R^{b22}$; and each $R^{b22}$ is independently selected from H or $C_{1-6}$ alkyl.

In some embodiments, each $R^{2A}$ is independently selected from fluoro, methyl, $CD_3$, trifluoromethyl, cyclopropyl, pyrazolyl, piperazinylmethyl, cyano, methoxy, and trifluoromethoxy, wherein the methyl and pyrazolyl of $R^{2A}$ are each optionally substituted by cyano-$C_{1-6}$ alkyl; and the piperazinylmethyl of $R^{2A}$ is optionally substituted with methylsulfonyl.

In some embodiments, each $R^{2A}$ is independently selected from fluoro, methyl, $CD_3$, trifluoromethyl, cyclopropyl, pyrazolyl, piperazinylmethyl, cyano, methoxy, and trifluoromethoxy, wherein the pyrazolyl of $R^{2A}$ is optionally substituted by cyanoisopropyl; and the piperazinylmethyl of $R^{2A}$ is optionally substituted with methylsulfonyl.

In some embodiments, each $R^{2A}$ is independently selected from methyl and pyrazolyl, wherein the methyl and pyrazolyl are each optionally substituted by cyano-$C_{1-6}$ alkyl.

In some embodiments, $R^2$ is selected from H, ethyl, ethenyl, phenyl, indazolyl, thiazolyl, thieno[3,2-d]pyridinyl, 3,6-dihydro-2H-pyranyl, and indolyl, wherein the phenyl and indazolyl of $R^2$ are each optionally substituted with 1 or 2 $R^{2A}$ substituents independently selected from fluoro, methyl, $CD_3$, trifluoromethyl, cyclopropyl, pyrazolyl, piperazinylmethyl, cyano, methoxy, and trifluoromethoxy, wherein the methyl and pyrazolyl of $R^{2A}$ are each optionally substituted by cyano-$C_{1-6}$ alkyl; and the piperazinylmethyl of $R^{2A}$ is optionally substituted with methylsulfonyl.

In some embodiments, $R^2$ is selected from H, ethyl, ethenyl, phenyl, indazolyl, thiazolyl, thieno[3,2-d]pyridinyl, 3,6-dihydro-2H-pyranyl, and indolyl, wherein the phenyl and indazolyl of $R^2$ are each optionally substituted with 1 or 2 $R^{2A}$ substituents independently selected from fluoro, methyl, $CD_3$, trifluoromethyl, cyclopropyl, pyrazolyl, piperazinylmethyl, cyano, methoxy, and trifluoromethoxy, wherein the pyrazolyl of $R^{2A}$ is optionally substituted by cyano-$C_{1-6}$ alkyl; and the piperazinylmethyl of $R^{2A}$ is optionally substituted with methylsulfonyl.

In some embodiments, $R^2$ is selected from H, ethyl, ethenyl, phenyl, indazolyl, thiazolyl, thieno[3,2-c]pyridinyl, 3,6-dihydro-2H-pyranyl, and indolyl, wherein the phenyl and indazolyl of $R^2$ are each optionally substituted with 1 or 2 $R^{2A}$ substituents independently selected from fluoro, methyl, $CD_3$, trifluoromethyl, cyclopropyl, pyrazolyl, piperazinylmethyl, cyano, methoxy, and trifluoromethoxy, wherein the pyrazolyl of $R^{2A}$ is optionally substituted by cyanoisopropyl; and the piperazinylmethyl of $R^{2A}$ is optionally substituted with methylsulfonyl.

In some embodiments, $R^2$ is selected from phenyl and indazolyl, wherein the phenyl and indazolyl of $R^2$ are each optionally substituted with 1 or 2 $R^{2A}$ substituents independently selected from fluoro, methyl, $CD_3$, trifluoromethyl, cyclopropyl, pyrazolyl, piperazinylmethyl, cyano, methoxy, and trifluoromethoxy;
wherein the pyrazolyl of $R^{2A}$ is optionally substituted by cyanoisopropyl; and
wherein the piperazinylmethyl of $R^{2A}$ is optionally substituted with methylsulfonyl.

In some embodiments, $R^2$ is selected from phenyl, methylindazolyl, and trideuteromethylindazolyl, wherein the phenyl of $R^2$ is optionally substituted with 1 or 2 $R^{2A}$ substituents independently selected from fluoro, methyl, $CD_3$, trifluoromethyl, cyclopropyl, pyrazolyl, piperazinylmethyl, cyano, methoxy, and trifluoromethoxy;
wherein the pyrazolyl of $R^{2A}$ is optionally substituted by cyanoisopropyl; and
wherein the piperazinylmethyl of $R^{2A}$ is optionally substituted with methylsulfonyl.

In some embodiments, $R^2$ is selected from phenyl and indazolyl, wherein the phenyl and indazolyl of $R^2$ are each optionally substituted with 1 or 2 $R^{2A}$ substituents independently selected from methyl and pyrazolyl, and wherein the methyl and pyrazolyl of $R^{2A}$ are each optionally substituted by cyano-$C_{1-6}$ alkyl.

In some embodiments, $R^2$ is selected from methylindazolyl and trideuteromethylindazolyl.

In some embodiments, $R^3$ is selected from $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^3$ are each optionally substituted with 1, 2, 3, or 4 independently selected $R^{3A}$ substituents.

In some embodiments, $R^3$ is selected from phenyl, $C_{3-7}$ cycloalkyl, monocylic 5-6 membered heteroaryl, bicyclic 8-10 membered heteroaryl, monocyclic 4-6 membered heterocycloalkyl, bicyclic 8-10 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-6 membered heterocycloalkyl)-$C_{1-6}$ alkyl-, wherein the phenyl, $C_{3-7}$ cycloalkyl, monocyclic 5-6 membered heteroaryl, bicyclic 8-10 membered heteroaryl, monocyclic 4-6 membered heterocycloalkyl, bicyclic 8-10 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-6 membered heterocycloalkyl)-$C_{1-6}$ alkyl- of $R^3$ are each optionally substituted with 1, 2, 3, or 4 independently selected $R^{3A}$ substituents.

In some embodiments, $R^3$ is selected from phenyl, $C_{3-7}$ cycloalkyl, 5-6 membered heteroaryl, 4-6 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-6 membered heterocycloalkyl)-$C_{1-6}$ alkyl-, wherein the phenyl, $C_{3-7}$ cycloalkyl, 5-6 membered heteroaryl, 4-6 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-6 membered heterocycloalkyl)-$C_{1-6}$ alkyl- of $R^3$ are each optionally substituted with 1, 2, 3, or 4 independently selected $R^{3A}$ substituents.

In some embodiments, $R^3$ is selected from phenyl, $C_{3-7}$ cycloalkyl, monocyclic 5-6 membered heteroaryl, bicyclic 8-10 membered heteroaryl, monocyclic 4-6 membered heterocycloalkyl, bicyclic 8-10 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-6 membered heterocycloalkyl)-$C_{1-6}$ alkyl-, wherein the phenyl, $C_{3-7}$ cycloalkyl, monocyclic 5-6 membered heteroaryl, bicyclic 8-10 membered heteroaryl, monocyclic 4-6 membered heterocycloalkyl, bicyclic 8-10 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-6 membered heterocycloalkyl)-$C_{1-6}$ alkyl- of $R^3$ are each optionally substituted with 1 or 2 independently selected $R^{3A}$ substituents.

In some embodiments, $R^3$ is selected from phenyl, $C_{3-7}$ cycloalkyl, 5-6 membered heteroaryl, 4-6 heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-6 membered heterocycloalkyl)-$C_{1-6}$ alkyl-, wherein the phenyl, $C_{3-7}$ cycloalkyl, 5-6 membered heteroaryl, 4-6 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-6 membered heterocycloalkyl)-$C_{1-6}$ alkyl- of $R^3$ are each optionally substituted with 1 or 2 independently selected $R^{3A}$ substituents.

In some embodiments, $R^3$ is selected from $C_{6-10}$ aryl, $C_{3-10}$ cycloalkyl, 5-10 membered heteroaryl, and 4-10 membered heterocycloalkyl, wherein the $C_{6-10}$ aryl, $C_{3-10}$ cycloalkyl, 5-10 membered heteroaryl, and 4-10 membered heterocycloalkyl of $R^3$ are each optionally substituted with 1, 2, 3, or 4 independently selected $R^{3A}$ substituents.

In some embodiments, $R^3$ is selected from $C_{6-10}$ aryl, $C_{3-10}$ cycloalkyl, and 5-10 membered heteroaryl, wherein the $C_{6-10}$ aryl, $C_{3-10}$ cycloalkyl, and 5-10 membered heteroaryl of $R^3$ are each optionally substituted with 1, 2, 3, or 4 independently selected $R^{3A}$ substituents.

In some embodiments, $R^3$ is selected from phenyl, $C_{3-7}$ cycloalkyl, monocyclic 5-6 membered heteroaryl, bicyclic 8-10 membered heteroaryl, and bicyclic 8-10 membered heterocycloalkyl, wherein the phenyl, $C_{3-7}$ cycloalkyl, monocyclic 5-6 membered heteroaryl, bicyclic 8-10 membered heteroaryl, and bicyclic 8-10 membered heterocycloalkyl of $R^3$ are each optionally substituted with 1, 2, 3, or 4 independently selected $R^{3A}$ substituents.

In some embodiments, $R^3$ is selected from phenyl, $C_{3-7}$ cycloalkyl, and 5-6 membered heteroaryl, wherein the phenyl, $C_{3-7}$ cycloalkyl, and 5-6 membered heteroaryl of $R^3$ are each optionally substituted with 1, 2, 3, or 4 independently selected $R^{3A}$ substituents.

In some embodiments, $R^3$ is selected from phenyl, $C_{3-7}$ cycloalkyl, monocyclic 5-6 membered heteroaryl, bicyclic 8-10 membered heteroaryl, and bicyclic 8-10 membered heterocycloalkyl, wherein the phenyl, $C_{3-7}$ cycloalkyl, monocyclic 5-6 membered heteroaryl, bicyclic 8-10 membered heteroaryl, and bicyclic 8-10 membered heterocycloalkyl of $R^3$ are each optionally substituted with 1 or 2 independently selected $R^{3A}$ substituents.

In some embodiments, $R^3$ is selected from phenyl, $C_{3-7}$ cycloalkyl, and 5-6 membered heteroaryl, wherein the phenyl, $C_{3-7}$ cycloalkyl, and 5-6 membered heteroaryl of $R^3$ are each optionally substituted with 1 or 2 independently selected $R^{3A}$ substituents.

In some embodiments, $R^3$ is selected from phenyl, cyclopropyl, cyclohexenyl, pyrazolyl, pyrrolyl, 4,5,6,7-tetrahydropyrazolo[1,5-a]pyridinyl, 6,7-dihydro-5H-pyrazolo[5,1-b][1,3]oxazinyl, 3,4-dihydro-2H-benzo[b][1,4]oxazinyl, 5,6-dihydro-4H-pyrrolo[1,2-b]pyrazolyl, and pyrazolo[1,5-a]pyrimidinyl, wherein the phenyl, cyclopropyl, cyclohexenyl, pyrazolyl, pyrrolyl, 4,5,6,7-tetrahydropyrazolo[1,5-a]pyridinyl, 6,7-dihydro-5H-pyrazolo[5,1-b][1,3]oxazinyl, 3,4-dihydro-2H-benzo[b][1,4]oxazinyl, 5,6-dihydro-4H-pyrrolo[1,2-b]pyrazolyl, and pyrazolo[1,5-a]pyrimidinyl of $R^3$ are each optionally substituted with 1, 2, 3, or 4 independently selected $R^{3A}$ substituents.

In some embodiments, $R^3$ is selected from phenyl, cyclopropyl, cyclohexenyl, pyrazolyl, pyrrolyl, 4,5,6,7-tetrahydropyrazolo[1,5-a]pyridinyl, 6,7-dihydro-5H-pyrazolo[5,1-b][1,3]oxazinyl, 3,4-dihydro-2H-benzo[b][1,4]oxazinyl, 5,6-dihydro-4H-pyrrolo[1,2-b]pyrazolyl, and pyrazolo[1,5-a]pyrimidinyl of $R^3$ are each optionally substituted with 1 or 2 independently selected $R^{3A}$ substituents.

In some embodiments, $R^3$ is selected from phenyl, cyclopropyl, and pyrazolyl, wherein the phenyl, cyclopropyl, and pyrazolyl of $R^3$ are each optionally substituted with 1, 2, 3, or 4 independently selected $R^{3A}$ substituents.

In some embodiments, $R^3$ is selected from phenyl, cyclopropyl, and pyrazolyl, wherein the phenyl and pyrazolyl of $R^3$ are each optionally substituted with 1, 2, 3, or 4 independently selected $R^{3A}$ substituents.

In some embodiments, $R^3$ is selected from phenyl, cyclopropyl, and pyrazolyl, wherein the phenyl and pyrazolyl of $R^3$ are each optionally substituted with 1 or 2 independently selected $R^{3A}$ substituents.

In some embodiments, each $R^{3A}$ is independently selected from oxo, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, (4-10 membered heterocycloalkyl)-$C_{1-6}$ alkyl-, $C(O)R^{b31}$ $C(O)NR^{c31}R^{d31}$, $NR^{c31}R^{d31}$, and $S(O)_2 R^{b31}$, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{3A}$ are each optionally substituted with 1, 2, 3, or 4 independently selected $R^{3B}$ substituents.

In some embodiments, each $R^{a31}$, $R^{b31}$, $R^{c31}$ and $R^{d31}$ is independently selected from H, $C_{1-6}$ alkyl, and 4-10 membered heterocycloalkyl.

In some embodiments, each $R^{3A}$ is independently selected from oxo, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, (4-10 membered heterocycloalkyl)-$C_{1-6}$ alkyl-, $C(O)R^{b31}$, $C(O)NR^{c31}R^{d31}$, $NR^{c31}R^{d31}$, and $S(O)_2 R^{b31}$, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{3A}$ are each optionally substituted with 1, 2, 3, or 4 independently selected $R^{3B}$ substituents; and
  each $R^{a31}$, $R^{b31}$, $R^{c31}$, and $R^{d31}$ is independently selected from H, $C_{1-6}$ alkyl, and 4-10 membered heterocycloalkyl.

In some embodiments, each $R^{a31}$, $R^{b31}$, $R^{c31}$, and $R^{d31}$ is independently selected from H, $C_{1-6}$ alkyl, and 4-6 membered heterocycloalkyl.

In some embodiments, each $R^{a31}$, $R^{b31}$, $R^{c31}$, and $R^{d31}$ is independently selected from H, $C_{1-6}$ alkyl, and 4-6 membered heterocycloalkyl.

In some embodiments, each $R^{a31}$, $R^{b31}$, $R^{c31}$, and $R^{d31}$ is independently selected from H, $C_{1-3}$ alkyl, and 4-6 membered heterocycloalkyl.

In some embodiments, each $R^{a31}$, $R^{b31}$, $R^{c31}$, and $R^{d31}$ is independently selected from H, methyl, ethyl, and morpholinyl.

In some embodiments, each $R^{3A}$ is independently selected from $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{3A}$ are each optionally substituted with 1, 2, 3, or 4 independently selected $R^{3B}$ substituents.

In some embodiments, each $R^{3A}$ is independently selected from oxo, $C_{1-6}$ alkyl, $C_{1-6}$ haloalkyl, $C_{2-6}$ alkenyl, $C_{2-6}$ alkynyl, phenyl, $C_{3-7}$ cycloalkyl, 5-6 membered heteroaryl, 4-6 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, (4-6 membered heterocycloalkyl)-$C_{1-6}$ alkyl-, C(O)$R^{b31}$C(O)NR$^{c31}$R$^{d31}$, NR$^{c31}$R$^{d31}$, and S(O)$_2$R$^{b31}$, wherein the $C_{1-6}$ alkyl, $C_{2-6}$ alkenyl, $C_{2-6}$ alkynyl, phenyl, $C_{3-7}$ cycloalkyl, 5-6 membered heteroaryl, 4-6 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-6 membered heterocycloalkyl)-$C_{1-6}$ alkyl- of $R^{3A}$ are each optionally substituted with 1, 2, 3, or 4 independently selected $R^{3B}$ substituents.

In some embodiments, each $R^{3A}$ is independently selected from oxo, $C_{1-6}$ alkyl, $C_{1-6}$ haloalkyl, $C_{2-6}$ alkenyl, $C_{2-6}$ alkynyl, phenyl, $C_{3-7}$ cycloalkyl, 5-6 membered heteroaryl, 4-6 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, (4-6 membered heterocycloalkyl)-$C_{1-6}$ alkyl-, C(O)$R^{b31}$, C(O)NR$^{c31}$R$^{d31}$, NR$^{c31}$R$^{d31}$, and S(O)$_2$R$^{b31}$, wherein the $C_{1-6}$ alkyl, $C_{2-6}$ alkenyl, $C_{2-6}$ alkynyl, phenyl, $C_{3-7}$ cycloalkyl, 5-6 membered heteroaryl, 4-6 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-6 membered heterocycloalkyl)-$C_{1-6}$ alkyl- of $R^{3A}$ are each optionally substituted with 1, 2, 3, or 4 independently selected $R^{3B}$ substituents; and
  each $R^{a31}$, $R^{b31}$, $R^{c31}$, and $R^{d31}$ is independently selected from H, $C_{1-6}$ alkyl, and 4-10 membered heterocycloalkyl.

In some embodiments, each $R^{3A}$ is independently selected from $C_{1-6}$ alkyl, $C_{1-6}$ haloalkyl, $C_{2-6}$ alkenyl, $C_{2-6}$ alkynyl, phenyl, $C_{3-7}$ cycloalkyl, 5-6 membered heteroaryl, 4-6 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-6 membered heterocycloalkyl)-$C_{1-6}$ alkyl-, wherein the $C_{1-6}$ alkyl, $C_{2-6}$ alkenyl, $C_{2-6}$ alkynyl, phenyl, $C_{3-7}$ cycloalkyl, 5-6 membered heteroaryl, 4-6 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-6 membered heterocycloalkyl)-$C_{1-6}$ alkyl- of $R^{3A}$ are each optionally substituted with 1, 2, 3, or 4 independently selected $R^{3B}$ substituents.

In some embodiments, each $R^{3A}$ is independently selected from oxo, $C_{1-6}$ alkyl, $C_{1-6}$ haloalkyl, $C_{2-6}$ alkenyl, $C_{2-6}$ alkynyl, phenyl, $C_{3-7}$ cycloalkyl, 5-6 membered heteroaryl, 4-6 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, (4-6 membered heterocycloalkyl)-$C_{1-6}$ alkyl-, C(O)$R^{b31}$C(O)NR$^{c31}$R$^{d31}$, NR$^{c31}$R$^{d31}$, and S(O)$_2$R$^{b31}$, wherein the $C_{1-6}$ alkyl, $C_{2-6}$ alkenyl, $C_{2-6}$ alkynyl, phenyl, $C_{3-7}$ cycloalkyl, 5-6 membered heteroaryl, 4-6 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-6 membered heterocycloalkyl)-$C_{1-6}$ alkyl- of $R^{3A}$ are each optionally substituted with 1 or 2 independently selected $R^{3B}$ substituents.

In some embodiments, each $R^{3A}$ is independently selected from oxo, $C_{1-6}$ alkyl, $C_{1-6}$ haloalkyl, $C_{2-6}$ alkenyl, $C_{2-6}$ alkynyl, phenyl, $C_{3-7}$ cycloalkyl, 5-6 membered heteroaryl, 4-6 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, (4-6 membered heterocycloalkyl)-$C_{1-6}$ alkyl-, C(O)$R^{b31}$, C(O)NR$^{c31}$R$^{d31}$, NR$^{c31}$R$^{d31}$, and S(O)$_2$R$^{b31}$, wherein the $C_{1-6}$ alkyl, $C_{2-6}$ alkenyl, $C_{2-6}$ alkynyl, phenyl, $C_{3-7}$ cycloalkyl, 5-6 membered heteroaryl, 4-6 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-6 membered heterocycloalkyl)-$C_{1-6}$ alkyl- of $R^{3A}$ are each optionally substituted with 1 or 2 independently selected $R^{3B}$ substituents; and
  each $R^{b31}$, $R^{c31}$, and $R^{d31}$ is independently selected from H, $C_{1-6}$ alkyl, and 4-10 membered heterocycloalkyl.

In some embodiments, each $R^{3A}$ is independently selected from $C_{1-6}$ alkyl, $C_{1-6}$ haloalkyl, $C_{2-6}$ alkenyl, $C_{2-6}$ alkynyl, phenyl, $C_{3-7}$ cycloalkyl, 5-6 membered heteroaryl, 4-6 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-6 membered heterocycloalkyl)-$C_{1-6}$ alkyl-, wherein the $C_{1-6}$ alkyl, $C_{2-6}$ alkenyl, $C_{2-6}$ alkynyl, phenyl, $C_{3-7}$ cycloalkyl, 5-6 membered heteroaryl, 4-6 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-6 membered heterocycloalkyl)-$C_{1-6}$ alkyl- of $R^{3A}$ are each optionally substituted with 1 or 2 independently selected $R^{3B}$ substituents.

In some embodiments, each $R^{3A}$ is independently selected from oxo, $C_{1-6}$ alkyl, $C_{1-6}$ haloalkyl, $C_{3-10}$ cycloalkyl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, (4-10 membered heterocycloalkyl)-$C_{1-6}$ alkyl-, C(O)$R^{b31}$, C(O)NR$^{c31}$R$^{d31}$, NR$^{c31}$R$^{d31}$, and S(O)$_2$R$^{b31}$, wherein the $C_{1-6}$ alkyl, $C_{3-10}$ cycloalkyl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{3A}$ are each optionally substituted with 1, 2, 3, or 4 independently selected $R^{3B}$ substituents.

In some embodiments, each $R^{3A}$ is independently selected from $C_{1-6}$ alkyl, (5-10 membered heteroaryl)-$C_{1-6}$ alkyl-, and (4-10 membered heterocycloalkyl)-$C_{1-6}$ alkyl-, wherein the $C_{1-6}$ alkyl, (5-10 membered heteroaryl)-$C_{1-6}$ alkyl-, and (4-10 membered heterocycloalkyl)-$C_{1-6}$ alkyl- of $R^{3A}$ are each optionally substituted with 1, 2, 3, or 4 independently selected $R^{3B}$ substituents.

In some embodiments, each $R^{3A}$ is independently selected from oxo, $C_{1-6}$ alkyl, $C_{1-6}$ haloalkyl, $C_{3-7}$ cycloalkyl, 4-6 membered heterocycloalkyl, phenyl-$C_{1-6}$ alkyl-, $C_{3-6}$ cycloalkyl-$C_{1-6}$ alkyl-, (5-6 membered heteroaryl)-$C_{1-6}$ alkyl-, (4-6 membered heterocycloalkyl)-$C_{1-6}$ alkyl-, C(O)$R^{b31}$, C(O)NR$^{c31}$R$^{d31}$, NR$^{c31}$R$^{d31}$, and S(O)$_2$R$^{b31}$, wherein the $C_{1-6}$ alkyl, $C_{3-7}$ cycloalkyl, 4-6 membered heterocycloalkyl, phenyl-$C_{1-6}$ alkyl-, $C_{3-6}$ cycloalkyl-$C_{1-6}$ alkyl-, (5-6 membered heteroaryl)-$C_{1-6}$ alkyl-, and (4-6 membered heterocycloalkyl)-$C_{1-6}$ alkyl- of $R^{3A}$ are each optionally substituted with 1, 2, 3, or 4 independently selected $R^{3B}$ substituents.

In some embodiments, each $R^{3A}$ is independently selected from $C_{1-6}$ alkyl, (5-6 membered heteroaryl)-$C_{1-6}$ alkyl-, and (4-6 membered heterocycloalkyl)-$C_{1-6}$ alkyl-, wherein the $C_{1-6}$ alkyl, (5-6 membered heteroaryl)-$C_{1-6}$ alkyl-, and (4-6 membered heterocycloalkyl)-$C_{1-6}$ alkyl- of $R^{3A}$ are each optionally substituted with 1, 2, 3, or 4 independently selected $R^{3B}$ substituents.

In some embodiments, each $R^{3A}$ is independently selected from oxo, $C_{1-6}$ alkyl, $C_{1-6}$ haloalkyl, $C_{3-7}$ cycloalkyl, 4-6 membered heterocycloalkyl, phenyl-$C_{1-6}$ alkyl-, $C_{3-6}$ cycloalkyl-$C_{1-6}$ alkyl-, (5-6 membered heteroaryl)-$C_{1-6}$ alkyl-, (4-6 membered heterocycloalkyl)-$C_{1-6}$ alkyl-, C(O)$R^{b31}$, C(O)NR$^{c31}$R$^{d31}$, NR$^{c31}$R$^{d31}$, and S(O)$_2$R$^{b31}$, wherein the $C_{1-6}$ alkyl, $C_{3-7}$ cycloalkyl, 4-6 membered heterocycloalkyl, phenyl-$C_{1-6}$ alkyl-, $C_{3-6}$ cycloalkyl-$C_{1-6}$ alkyl-, (5-6 membered heteroaryl)-$C_{1-6}$ alkyl-, and (4-6 membered heterocycloalkyl)-$C_{1-6}$ alkyl- of R$^{3A}$ are each optionally substituted with 1 or 2 independently selected R$^{3B}$ substituents.

In some embodiments, each R$^{3A}$ is independently selected from $C_{1-6}$ alkyl, (5-6 membered heteroaryl)-$C_{1-6}$ alkyl-, and (4-6 membered heterocycloalkyl)-$C_{1-6}$ alkyl-, wherein the $C_{1-6}$ alkyl, (5-6 membered heteroaryl)-$C_{1-6}$ alkyl-, and (4-6 membered heterocycloalkyl)-$C_{1-6}$ alkyl- of R$^{3A}$ are each optionally substituted with 1 or 2 independently selected R$^{3B}$ substituents.

In some embodiments, each R$^{3B}$ is independently selected from halo, oxo, $C_{1-6}$ alkyl, $C_{1-6}$ haloalkyl, $C_{2-6}$ alkenyl, $C_{2-6}$ alkynyl, CN, OR$^{a32}$, C(O)R$^{b32}$, C(O)NR$^{c32}$R$^{d32}$, S(O)R$^{b32}$, S(O)$_2$NR$^{c32}$R$^{d32}$, wherein each R$^{a32}$, R$^{b32}$, R$^{c32}$, and R$^{d32}$ is independently selected from H and $C_{1-6}$ alkyl.

In some embodiments, each R$^{3B}$ is independently selected from halo, oxo, $C_{1-6}$ alkyl, $C_{1-6}$ haloalkyl, $C_{2-6}$ alkenyl, $C_{2-6}$ alkynyl, C(O)R$^{b32}$, C(O)NR$^{c32}$R$^{d32}$, S(O)R$^{b32}$, S(O)NR$^{c32}$R$^{d32}$, S(O)$_2$R$^{b32}$, S(O)$_2$NR$^{c32}$R$^{d32}$, wherein each R$^{b32}$, R$^{c32}$, and R$^{d32}$ is independently selected from H and $C_{1-6}$ alkyl.

In some embodiments, each R$^{3B}$ is independently selected from CN, OR$^{a32}$, C(O)R$^{b32}$, S(O)R$^{b32}$, S(O)NR$^{c32}$R$^{32}$, S(O)$_2$R$^{b32}$, and S(O)$_2$NR$^{c32}$R$^{d32}$, wherein each R$^{a32}$, R$^{b32}$, R$^{c32}$, and R$^{d32}$ is independently selected from H and $C_{1-6}$ alkyl.

In some embodiments, each R$^{3B}$ is independently selected from S(O)R$^{b32}$, S(O)NR$^{c32}$R$^{d32}$, S(O)$_2$R$^{b32}$, and S(O)$_2$NR$^{c32}$R$^{d32}$, wherein each R$^{b32}$, R$^{c32}$, and R$^{d32}$ is independently selected from H and $C_{1-6}$ alkyl.

In some embodiments, each R$^{3B}$ is independently selected from CN, OR$^{a32}$, C(O)R$^{b32}$, and S(O)$_2$R$^{b32}$, wherein each R$^{a32}$ and R$^{b32}$ is independently selected from H and $C_{1-6}$ alkyl.

In some embodiments, each R$^{3B}$ is independently selected from S(O)$_2$R$^{b32}$, wherein each R$^{b32}$ is independently selected from H and $C_{1-6}$ alkyl.

In some embodiments, each R$^{3B}$ is independently selected from hydroxy, methoxy, methylsulfonyl, methylcarbonyl, and cyano.

In some embodiments, each R$^{3B}$ is independently selected from methylsulfonyl.

In some embodiments, each R$^{3A}$ is independently selected from methyl, trideuteromethyl (i.e., —CD$_3$), ethyl, isopropyl, isobutyl, difluoroethyl, trifluoroethyl, methoxy, cyclopropyl, cyclopentyl, piperidinyl, tetrahydrofuranyl, tetrahydropyranyl, cyclopropylmethyl, cyclopropylethyl, phenylmethyl, pyridylmethyl, piperidinylmethyl, morpholinylmethyl, morpholinylethyl, morpholinylcarbonyl, dimethylaminocarbonyl, and ethylsulfonyl, wherein the methyl, ethyl, isopropyl, isobutyl, cyclopropyl, cyclopentyl, piperidinyl, tetrahydrofuranyl, tetrahydropyranyl, cyclopropylmethyl, cyclopropylethyl, phenylmethyl, pyridylmethyl, piperidinylmethyl, morpholinylmethyl, and morpholinylethyl of R$^{3A}$ are each optionally substituted with 1, 2, 3, or 4 independently selected R$^{3B}$ substituents.

In some embodiments, each R$^{3A}$ is independently selected from methyl, trideuteromethyl (i.e., —CD$_3$), ethyl, isopropyl, isobutyl, difluoroethyl, trifluoroethyl, methoxy, cyclopropyl, cyclopentyl, piperidinyl, tetrahydrofuranyl, tetrahydropyranyl, cyclopropylmethyl, cyclopropylethyl, phenylmethyl, pyridylmethyl, piperidinylmethyl, morpholinylmethyl, morpholinylethyl, morpholinylcarbonyl, dimethylaminocarbonyl, and ethylsulfonyl, wherein the methyl, ethyl, isopropyl, isobutyl, cyclopropyl, cyclopentyl, piperidinyl, tetrahydrofuranyl, tetrahydropyranyl, cyclopropylmethyl, cyclopropylethyl, phenylmethyl, pyridylmethyl, piperidinylmethyl, morpholinylmethyl, and morpholinylethyl of R$^{3A}$ are each optionally substituted with 1 or 2 independently selected R$^{3B}$ substituents.

In some embodiments, each R$^{3A}$ is independently selected from methyl, trideuteromethyl (i.e., —CD$_3$), ethyl, isopropyl, isobutyl, difluoroethyl, trifluoroethyl, methoxy, cyclopropyl, cyclopentyl, piperidinyl, tetrahydrofuranyl, tetrahydropyranyl, cyclopropylmethyl, cyclopropylethyl, phenylmethyl, pyridylmethyl, piperidinylmethyl, morpholinylmethyl, morpholinylethyl, morpholinylcarbonyl, dimethylaminocarbonyl, and ethylsulfonyl, wherein the methyl, ethyl, isopropyl, isobutyl, cyclopropyl, cyclopentyl, piperidinyl, tetrahydrofuranyl, tetrahydropyranyl, cyclopropylmethyl, cyclopropylethyl, phenylmethyl, pyridylmethyl, piperidinylmethyl, morpholinylmethyl, and morpholinylethyl of R$^{3A}$ are each optionally substituted with 1, 2, 3, or 4 R$^{3B}$ substituents independently selected from hydroxy, methoxy, methylsulfonyl, methylcarbonyl, and cyano.

In some embodiments, each R$^{3A}$ is independently selected from methyl, trideuteromethyl (i.e., —CD$_3$), ethyl, isopropyl, isobutyl, difluoroethyl, trifluoroethyl, methoxy, cyclopropyl, cyclopentyl, piperidinyl, tetrahydrofuranyl, tetrahydropyranyl, cyclopropylmethyl, cyclopropylethyl, phenylmethyl, pyridylmethyl, piperidinylmethyl, morpholinylmethyl, morpholinylethyl, morpholinylcarbonyl, dimethylaminocarbonyl, and ethylsulfonyl, wherein the methyl, ethyl, isopropyl, isobutyl, cyclopropyl, cyclopentyl, piperidinyl, tetrahydrofuranyl, tetrahydropyranyl, cyclopropylmethyl, cyclopropylethyl, phenylmethyl, pyridylmethyl, piperidinylmethyl, morpholinylmethyl, and morpholinylethyl of R$^{3A}$ are each optionally substituted with 1 or 2 substituents independently selected from hydroxy, methoxy, methylsulfonyl, methylcarbonyl, and cyano.

In some embodiments, each R$^{3A}$ is independently selected from methyl, trideuteromethyl (i.e., —CD$_3$), methylpyridyl, methylpiperidinyl, pyridylmethyl, and piperidinylmethyl, wherein the methylpyridyl, methylpiperidinyl, pyridylmethyl, and piperidinylmethyl of R$^{3A}$ are each optionally substituted by methylsulfonyl.

In some embodiments, each R$^{3A}$ is independently selected from methyl, trideuteromethyl (i.e., —CD$_3$), pyridylmethyl, and piperidinylmethyl, wherein the pyridylmethyl and piperidinylmethyl of R$^{3A}$ are each optionally substituted by methylsulfonyl.

In some embodiments, each R$^{3A}$ is independently selected from methyl, trideuteromethyl (i.e., —CD$_3$), methylpyridyl, and methylpiperidinyl, wherein the methylpyridyl and methylpiperidinyl of R$^{3A}$ are each optionally substituted by methylsulfonyl.

In some embodiments, each R$^{3A}$ is independently selected from methyl, trideuteromethyl (i.e., —CD$_3$), methylpyridyl, and methylpiperidinyl, wherein the methylpiperidinyl of R$^{3A}$ is optionally substituted by methylsulfonyl.

In some embodiments, each R$^{3A}$ is independently selected from methyl, trideuteromethyl (i.e., —CD$_3$), ethyl, isopropyl, isobutyl, difluoroethyl, trifluoroethyl, methoxy, cyclopropyl, cyclopentyl, piperidinyl, tetrahydrofuranyl, tetrahydropyranyl, cyclopropylmethyl, cyclopropylethyl, phenylmethyl, pyridylmethyl, piperidinylmethyl, morpholinylmethyl, morpholinylethyl, morpholinylcarbonyl, dimethylaminocarbonyl, and ethylsulfonyl, wherein the methyl, ethyl, isopropyl, isobutyl, cyclopropyl, cyclopentyl, piperidinyl, tetrahydrofuranyl, tetrahydropyranyl, cyclopropylmethyl, cyclopropylethyl, phenylmethyl, pyridylmethyl, piperidinylmethyl, morpholinylmethyl, and morpholinylethyl of $R^{3A}$ are each optionally substituted with 1 or 2 substituents independently selected from hydroxy, methoxy, methylsulfonyl, methylcarbonyl, and cyano.

In some embodiments, each $R^{3A}$ is independently selected from methyl, trideuteromethyl (i.e., —CD$_3$), isopropyl, difluoroethyl, trifluoroethyl, methoxyethyl, hydroxymethylpropyl, hydroxyisobutyl, methoxyisobutyl, methoxy, cyclopropyl, cyclopentyl, (cyanophenyl)methyl, pyridylmethyl, piperidinylmethyl, morpholinylmethyl, morpholinylethyl, cyclopropylmethyl, cyclopropylethyl, tetrahydrofuranyl, tetrahydropyranyl, methylcarbonylpiperidinyl, morpholinylcarbonyl, dimethylaminocarbonyl, and ethylsulfonyl, wherein the pyridylmethyl and piperidinylmethyl of $R^{3A}$ are each optionally substituted by methylsulfonyl.

In some embodiments, $R^3$ is selected from phenyl, cyclopropyl, cyclohexenyl, pyrazolyl, pyrrolyl, 4,5,6,7-tetrahydropyrazolo[1,5-a]pyridinyl, 6,7-dihydro-5H-pyrazolo[5,1-b][1,3]oxazinyl, 3,4-dihydro-2H-benzo[b][1,4]oxazinyl, 5,6-dihydro-4H-pyrrolo[1,2-b]pyrazolyl, and pyrazolo[1,5-a]pyrimidinyl, wherein the phenyl, cyclopropyl, cyclohexenyl, pyrazolyl, pyrrolyl, 4,5,6,7-tetrahydropyrazolo[1,5-a]pyridinyl, 6,7-dihydro-5H-pyrazolo[5,1-b][1,3]oxazinyl, 3,4-dihydro-2H-benzo[b][1,4]oxazinyl, 5,6-dihydro-4H-pyrrolo[1,2-b]pyrazolyl, and pyrazolo[1,5-a]pyrimidinyl of $R^3$ are each optionally substituted with 1, 2, 3, or 4 independently selected $R^{3A}$ substituents; and each $R^{3A}$ is independently selected from methyl, trideuteromethyl (i.e., —CD$_3$), ethyl, isopropyl, isobutyl, difluoroethyl, trifluoroethyl, methoxy, cyclopropyl, cyclopentyl, piperidinyl, tetrahydrofuranyl, tetrahydropyranyl, cyclopropylmethyl, cyclopropylethyl, phenylmethyl, pyridylmethyl, piperidinylmethyl, morpholinylmethyl, morpholinylethyl, morpholinylcarbonyl, dimethylaminocarbonyl, and ethylsulfonyl, wherein the methyl, ethyl, isopropyl, isobutyl, cyclopropyl, cyclopentyl, piperidinyl, tetrahydrofuranyl, tetrahydropyranyl, cyclopropylmethyl, cyclopropylethyl, phenylmethyl, pyridylmethyl, piperidinylmethyl, morpholinylmethyl, and morpholinylethyl of $R^{3A}$ are each optionally substituted with 1 or 2 substituents independently selected from hydroxy, methoxy, methylsulfonyl, methylcarbonyl, and cyano.

In some embodiments, $R^3$ is selected from phenyl, cyclopropyl, cyclohexenyl, pyrazolyl, pyrrolyl, 4,5,6,7-tetrahydropyrazolo[1,5-a]pyridinyl, 6,7-dihydro-5H-pyrazolo[5,1-b][1,3]oxazinyl, 3,4-dihydro-2H-benzo[b][1,4]oxazinyl, 5,6-dihydro-4H-pyrrolo[1,2-b]pyrazolyl, and pyrazolo[1,5-a]pyrimidinyl of $R^3$ are each optionally substituted with 1 or 2 independently selected $R^{3A}$ substituents; and each $R^{3A}$ is independently selected from methyl, trideuteromethyl (i.e., —CD$_3$), ethyl, isopropyl, isobutyl, difluoroethyl, trifluoroethyl, methoxy, cyclopropyl, cyclopentyl, piperidinyl, tetrahydrofuranyl, tetrahydropyranyl, cyclopropylmethyl, cyclopropylethyl, phenylmethyl, pyridylmethyl, piperidinylmethyl, morpholinylmethyl, morpholinylethyl, morpholinylcarbonyl, dimethylaminocarbonyl, and ethylsulfonyl, wherein the methyl, ethyl, isopropyl, isobutyl, cyclopropyl, cyclopentyl, piperidinyl, tetrahydrofuranyl, tetrahydropyranyl, cyclopropylmethyl, cyclopropylethyl, phenylmethyl, pyridylmethyl, piperidinylmethyl, morpholinylmethyl, and morpholinylethyl of $R^{3A}$ are each optionally substituted with 1 or 2 substituents independently selected from hydroxy, methoxy, methylsulfonyl, methylcarbonyl, and cyano.

In some embodiments, $R^3$ is selected from phenyl, cyclopropyl, and pyrazolyl, wherein the phenyl, cyclopropyl, and pyrazolyl of $R^3$ are each optionally substituted with 1 or 2 $R^{3A}$ substituents selected from methyl, trideuteromethyl, methylpyridyl, and methylpiperidinyl, and wherein the methylpyridyl and methylpiperidinyl of $R^{3A}$ are each optionally substituted by methylsulfonyl.

In some embodiments, $R^4$ is selected from H, $C_{1-6}$ alkyl, $C_{1-6}$ alkoxy, $C_{1-6}$ haloalkyl, $C_{1-6}$ haloalkoxy, OH, NH$_2$, and NHC$_{1-6}$ alkyl, wherein the $C_{1-6}$ alkyl is optionally substituted with OH, CN, and NH$_2$; and wherein each hydrogen atom of $R^4$ (e.g., the H of $R^4$ or each hydrogen of the $C_{1-6}$ alkyl, $C_{1-6}$ alkoxy, $C_{1-6}$ haloalkyl, $C_{1-6}$ haloalkoxy, OH, NH$_2$, and NHC$_{1-6}$ alkyl of $R^4$) is optionally replaced by deuterium atoms.

In some embodiments, $R^4$ is selected from H, $C_{1-6}$ alkyl, $C_{1-6}$ alkoxy, $C_{1-6}$ haloalkyl, and $C_{1-6}$ haloalkoxy.

In some embodiments, $R^4$ is selected from H and $C_{1-6}$ alkyl.

In some embodiments, $R^4$ is H.
In some embodiments, $R^4$ is $C_{1-6}$ alkyl.
In some embodiments, $R^4$ is $C_{1-3}$ alkyl.
In some embodiments, $R^4$ is methyl or CD$_3$.
In some embodiments, $R^4$ is methyl.
In some embodiments, $R^4$ is CD$_3$.
In some embodiments, $R^5$ is selected from H, halo, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, OH, CN, C(O)OH, C(O)NHR$^{a5}$, NH$_2$, and NHC$_{1-6}$ alkyl, wherein the $C_{1-6}$ alkyl is optionally substituted with OH, CN, and NH$_2$;

$R^{a5}$ is H, $C_{1-6}$ alkyl, $C_{1-6}$ alkoxy, $C_{1-6}$ haloalkyl, $C_{1-6}$ haloalkoxy, OH, NH$_2$, and NHC$_{1-6}$ alkyl, wherein the $C_{1-6}$ alkyl is optionally substituted with OH, CN, and NH$_2$; and wherein each hydrogen atom of $R^5$ and $R^{a5}$ (e.g., the H of $R^5$ or each hydrogen of the $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, OH, C(O)OH, C(O)NHR$^{a5}$NH$_2$, and NHC$_{1-6}$ alkyl of $R^5$) is optionally replaced by deuterium atoms.

In some embodiments, $R^5$ is selected from H, $C_{1-6}$ alkyl, $C_{1-6}$ alkoxy, $C_{1-6}$ haloalkyl, $C_{1-6}$ haloalkoxy, $C_{2-6}$ alkenyl, and $C_{2-6}$ alkynyl.

In some embodiments, $R^5$ is selected from H and $C_{1-6}$ alkyl.

In some embodiments, $R^5$ is selected from H and $C_{1-3}$ alkyl.

In some embodiments, $R^5$ is H.
In some embodiments:
$R^4$ is selected from H, $C_{1-6}$ alkyl, $C_{1-6}$ alkoxy, $C_{1-6}$ haloalkyl, and $C_{1-6}$ haloalkoxy; and
$R^5$ is selected from H, $C_{1-6}$ alkyl, $C_{1-6}$ alkoxy, $C_{1-6}$ haloalkyl, $C_{1-6}$ haloalkoxy, $C_{2-6}$ alkenyl, and $C_{2-6}$ alkynyl.
In some embodiments:
$R^4$ is selected from H and $C_{1-6}$ alkyl; and
$R^5$ is selected from H and $C_{1-6}$ alkyl.
In some embodiments:
$R^4$ is selected from H and $C_{1-3}$ alkyl; and
$R^5$ is selected from H and $C_{1-3}$ alkyl.
In some embodiments, $R^4$ is $C_{1-6}$ alkyl and $R^5$ is H.
In some embodiments, $R^4$ is $C_{1-3}$ alkyl and $R^5$ is H.
In some embodiments, $R^4$ is methyl or CD$_3$; and $R^5$ is H.
In some embodiments, $R^4$ is methyl and $R^5$ is H.

In some embodiments, $R^4$ is $CD_3$ and $R^5$ is H.

In some embodiments, each $R^M$ is independently selected from H, OH, halo, oxo, CN, C(O)OH, C(O)NH$_2$, C(O)NH (C$_{1-4}$ alkyl), C(O)N(C$_{1-6}$ alkyl)$_2$, NH$_2$, NO$_2$, SF$_5$, C$_{1-6}$ alkyl, C$_{1-6}$ alkoxy, C$_{1-6}$ haloalkoxy, C$_{1-6}$ haloalkyl, C$_{2-6}$ alkenyl, C$_{2-6}$ alkynyl, phenyl, C$_{3-7}$ cycloalkyl, 5-6 membered heteroaryl, 4-7 membered heterocycloalkyl, phenyl-C$_{1-6}$ alkyl-, C$_{3-7}$ cycloalkyl-C$_{1-6}$ alkyl-, (5-6 membered heteroaryl)-C$_{1-6}$ alkyl-, and (4-7 membered heterocycloalkyl)-C$_{1-6}$ alkyl-; and wherein each hydrogen atom of $R^M$ (e.g., the H of $R^M$ or each hydrogen of the OH, C(O)OH, C(O)NH$_2$, C(O)NH (C$_{1-4}$ alkyl), C(O)N(C$_{1-6}$ alkyl)$_2$, NH$_2$, C$_{1-6}$ alkyl, C$_{1-6}$ alkoxy, C$_{1-6}$ haloalkoxy, C$_{1-6}$ haloalkyl, C$_{2-6}$ alkenyl, C$_{2-6}$ alkynyl, phenyl, C$_{3-7}$ cycloalkyl, 5-6 membered heteroaryl, 4-7 membered heterocycloalkyl, phenyl-C$_{1-6}$ alkyl-, C$_{3-7}$ cycloalkyl-C$_{1-6}$ alkyl-, (5-6 membered heteroaryl)-C$_{1-6}$ alkyl-, and (4-7 membered heterocycloalkyl)-C$_{1-6}$ alkyl- of $R^M$) is optionally replaced by deuterium atoms.

In some embodiments:

W is $C(R^W)_2$;

Y is $C(R^Y)_2$;

each $R^W$ is independently H or C$_{1-6}$ alkyl;

each $R^Y$ is independently H or C$_{1-6}$ alkyl;

Ring A is C$_{3-10}$ cycloalkyl or 4-11 membered heterocycloalkyl, wherein the C$_{3-10}$ cycloalkyl and 4-11 membered heterocycloalkyl of Ring A are each optionally substituted with 1, 2, 3, or 4 independently selected $R^6$ substituents;

$R^2$ is selected from H, C$_{1-6}$ alkyl, C$_{2-6}$ alkenyl, C$_{6-10}$ aryl, C$_{3-10}$ cycloalkyl, 5-10 membered heteroaryl, 4-10 membered heterocycloalkyl, C$_{6-10}$ aryl-C$_{1-6}$ alkyl-, C$_{3-10}$ cycloalkyl-C$_{1-6}$ alkyl-, (5-10 membered heteroaryl)-C$_{1-6}$ alkyl-, and (4-10 membered heterocycloalkyl)-C$_{1-6}$ alkyl-, wherein the C$_{1-6}$ alkyl, C$_{2-6}$ alkenyl, C$_{6-10}$ aryl, C$_{3-10}$ cycloalkyl, 5-10 membered heteroaryl, 4-10 membered heterocycloalkyl, C$_{6-10}$ aryl-C$_{1-6}$ alkyl-, C$_{3-10}$ cycloalkyl-C$_{1-6}$ alkyl-, (5-10 membered heteroaryl)-C$_{1-6}$ alkyl-, and (4-10 membered heterocycloalkyl)-C$_{1-6}$ alkyl- of $R^2$ are each optionally substituted with 1, 2, 3, or 4 independently selected $R^{2A}$ substituents;

each $R^{2A}$ is independently selected from halo, C$_{1-6}$ alkyl, C$_{1-6}$ haloalkyl, C$_{2-6}$ alkenyl, C$_{2-6}$ alkynyl, C$_{6-10}$ aryl, C$_{3-10}$ cycloalkyl, 5-10 membered heteroaryl, 4-10 membered heterocycloalkyl, (4-10 membered heterocycloalkyl)-C$_{1-6}$ alkyl-, CN, and OR$^{a21}$, wherein the C$_{1-6}$ alkyl, C$_{2-6}$ alkenyl, C$_{2-6}$ alkynyl, C$_{6-10}$ aryl, C$_{3-10}$ cycloalkyl, 5-10 membered heteroaryl, 4-10 membered heterocycloalkyl, and (4-10 membered heterocycloalkyl)-C$_{1-6}$ alkyl- of $R^{2A}$ are each optionally substituted with 1, 2, 3, or 4 independently selected $R^{2B}$ substituents;

each $R^{a21}$ is independently selected from H, C$_{1-6}$ alkyl, and C$_{1-6}$ haloalkyl;

each $R^{2B}$ is independently selected from halo, oxo, C$_{1-6}$ alkyl, C$_{1-6}$ haloalkyl, C$_{2-6}$ alkenyl, C$_{2-6}$ alkynyl, S(O)R$^{b22}$, and S(O)$_2$R$^{b22}$, wherein the C$_{1-6}$ alkyl, C$_{2-6}$ alkenyl, and C$_{2-6}$ alkynyl of $R^{2B}$ are each optionally substituted with 1, 2, 3, or 4 independently selected $R^{2C}$ substituents;

each $R^{b22}$ is independently selected from H, C$_{1-6}$ alkyl, C$_{1-6}$ haloalkyl, C$_{2-6}$ alkenyl, and C$_{2-6}$ alkynyl;

each $R^{2C}$ is independently selected from halo, oxo, C$_{1-6}$ alkyl, C$_{1-6}$ haloalkyl, C$_{2-6}$ alkenyl, C$_{2-6}$ alkynyl, CN, and NO$_2$;

$R^3$ is selected from C$_{6-10}$ aryl, C$_{3-10}$ cycloalkyl, 5-10 membered heteroaryl, 4-10 membered heterocycloalkyl, C$_{6-10}$ aryl-C$_{1-6}$ alkyl-, C$_{3-10}$ cycloalkyl-C$_{1-6}$ alkyl-, (5-10 membered heteroaryl)-C$_{1-6}$ alkyl-, and (4-10 membered heterocycloalkyl)-C$_{1-6}$ alkyl-, wherein the C$_{6-10}$ aryl, C$_{3-10}$ cycloalkyl, 5-10 membered heteroaryl, 4-10 membered heterocycloalkyl, C$_{6-10}$ aryl-C$_{1-6}$ alkyl-, C$_{3-10}$ cycloalkyl-C$_{1-6}$ alkyl-, (5-10 membered heteroaryl)-C$_{1-6}$ alkyl-, and (4-10 membered heterocycloalkyl)-C$_{1-6}$ alkyl- of $R^3$ are each optionally substituted with 1, 2, 3, or 4 independently selected $R^{3A}$ substituents;

each $R^{3A}$ is independently selected from oxo, C$_{1-6}$ alkyl, C$_{1-6}$ haloalkyl, C$_{2-6}$ alkenyl, C$_{2-6}$ alkynyl, C$_{6-10}$ aryl, C$_{3-10}$ cycloalkyl, 5-10 membered heteroaryl, 4-10 membered heterocycloalkyl, C$_{6-10}$ aryl-C$_{1-6}$ alkyl-, C$_{3-10}$ cycloalkyl-C$_{1-6}$ alkyl-, (5-10 membered heteroaryl)-C$_{1-6}$ alkyl-, (4-10 membered heterocycloalkyl)-C$_{1-6}$ alkyl-, C(O)R$^{b31}$, C(O)NR$^{c31}$R$^{d31}$, NR$^{c31}$R$^{d31}$, and S(O)$_2$R$^{b31}$, wherein the C$_{1-6}$ alkyl, C$_{2-6}$ alkenyl, C$_{2-6}$ alkynyl, C$_{6-10}$ aryl, C$_{3-10}$ cycloalkyl, 5-10 membered heteroaryl, 4-10 membered heterocycloalkyl, C$_{6-10}$ aryl-C$_{1-6}$ alkyl-, C$_{3-10}$ cycloalkyl-C$_{1-6}$ alkyl-, (5-10 membered heteroaryl)-C$_{1-6}$ alkyl-, and (4-10 membered heterocycloalkyl)-C$_{1-6}$ alkyl- of $R^{3A}$ are each optionally substituted with 1, 2, 3, or 4 independently selected $R^{3B}$ substituents;

each $R^{a31}$, $R^{b31}$, $R^{c31}$, and $R^{d31}$ is independently selected from H, C$_{1-6}$ alkyl, and 4-10 membered heterocycloalkyl;

each $R^{3B}$ is independently selected from halo, oxo, C$_{1-6}$ alkyl, C$_{1-6}$ haloalkyl, C$_{2-6}$ alkenyl, C$_{2-6}$ alkynyl, CN, OR$^{a32}$, C(O)R$^{b32}$, C(O)NR$^{c32}$R$^{d32}$, S(O)R$^{b32}$, S(O) NR$^{c32}$R$^{d32}$, S(O)$_2$R$^{b32}$, S(O)$_2$NR$^{c32}$R$^{d32}$;

each $R^{a32}$, $R^{b32}$, $R^{c32}$, and $R^{d32}$ is independently selected from H and C$_{1-6}$ alkyl;

$R^4$ is selected from H, C$_{1-6}$ alkyl, C$_{1-6}$ alkoxy, C$_{1-6}$ haloalkyl, and C$_{1-6}$ haloalkoxy;

$R^5$ is selected from H, C$_{1-6}$ alkyl, C$_{1-6}$ alkoxy, C$_{1-6}$ haloalkyl, C$_{1-6}$ haloalkoxy, C$_{2-6}$ alkenyl, and C$_{2-6}$ alkynyl;

each $R^6$ is independently selected from C$_{1-6}$ alkyl, C$_{1-6}$ haloalkyl, C$_{2-6}$ alkenyl, C$_{2-6}$ alkynyl, C$_{6-10}$ aryl, C$_{3-10}$ cycloalkyl, 5-10 membered heteroaryl, 4-10 membered heterocycloalkyl, C$_{6-10}$ aryl-C$_{1-6}$ alkyl-, C$_{3-10}$ cycloalkyl-C$_{1-6}$ alkyl-, (5-10 membered heteroaryl)-C$_{1-6}$ alkyl-, (4-10 membered heterocycloalkyl)-C$_{1-6}$ alkyl-, C(O)R$^{b6}$, C(O)NR$^{c6}$R$^{d6}$, C(O)OR$^{a6}$, NR$^{c6}$C(O)R$^{b6}$, NR$^{c6}$S(O)$_2$R$^{b6}$, and S(O)$_2$R$^{b6}$, wherein the C$_{1-6}$ alkyl, C$_{2-6}$ alkenyl, C$_{2-6}$ alkynyl, C$_{6-10}$ aryl, C$_{3-10}$ cycloalkyl, 5-10 membered heteroaryl, 4-10 membered heterocycloalkyl, C$_{6-10}$ aryl-C$_{1-6}$ alkyl-, C$_{3-10}$ to cycloalkyl-C$_{1-6}$ alkyl-, (5-10 membered heteroaryl)-C$_{1-6}$ alkyl-, and (4-10 membered heterocycloalkyl)-C$_{1-6}$ alkyl- of $R^6$ are each optionally substituted with 1, 2, 3, or 4 independently selected $R^{6A}$ substituents;

each $R^{a6}$, $R^{b6}$, $R^{c6}$, and $R^{d6}$ is independently selected from H, C$_{1-6}$ alkyl, C$_{1-6}$ haloalkyl, C$_{2-6}$ alkenyl, C$_{2-6}$ alkynyl, C$_{3-10}$ cycloalkyl, C$_{6-10}$ aryl, and 4-10 membered heterocycloalkyl)-C$_{1-6}$ alkyl-, wherein the C$_{1-6}$ alkyl, C$_{1-6}$ haloalkyl, C$_{2-6}$ alkenyl, C$_{2-6}$ alkynyl, C$_{3-10}$ cycloalkyl, C$_{6-10}$ aryl, and 4-10 membered heterocycloalkyl)-C$_{1-6}$ alkyl- of $R^{a6}$, $R^{b6}$, $R^{c6}$, and $R^{d6}$ are each optionally substituted by 1, 2, 3, or 4 independently selected $R^{6A}$ substituents;

each $R^{6A}$ is independently selected from halo, oxo, C$_{1-6}$ alkyl, 4-10 membered heterocycloalkyl, CN, OR$^{a61}$, C(O)R$^{b61}$, C(O)NR$^{c61}$R$^{d61}$, C(O)OR$^{a61}$, NR$^{c61}$C(O)R$^{b61}$, NR$^{c61}$C(O)OR$^{a61}$, NR$^{c61}$C(O)NR$^{c61}$R$^{d61}$, NR$^{c61}$S(O)$_2$R$^{b61}$, and S(O)$_2$R$^{b61}$, wherein each C$_{1-6}$ alkyl and 4-10 membered heterocycloalkyl of R$^{6A}$ are optionally substituted with 1, 2, 3, or 4 independently selected R$^{6B}$ substituents;

each R$^{a61}$, R$^{b61}$, R$^{c61}$, and R$^{d61}$ is independently selected from H, C$_{1-6}$ alkyl, C$_{1-6}$ haloalkyl, C$_{2-6}$ alkenyl, C$_{2-6}$ alkynyl, and C$_{6-10}$ aryl, wherein the C$_{1-6}$ alkyl, C$_{1-6}$ haloalkyl, C$_{2-6}$ alkenyl, C$_{2-6}$ alkynyl, and C$_{6-10}$ aryl of R$^{a61}$, R$^{b61}$, R$^{c61}$, and R$^{d61}$ are each optionally substituted by 1, 2, 3, or 4 independently selected R$^{6B}$ substituents;

each R$^{6B}$ is independently selected from C$_{1-6}$ alkyl, C$_{1-6}$ haloalkyl, C$_{2-6}$ alkenyl, C$_{2-6}$ alkynyl, CN, and C(O)NR$^{c62}$R$^{d62}$, wherein the C$_{1-6}$ alkyl, C$_{1-6}$ haloalkyl, C$_{2-6}$ alkenyl, and C$_{2-6}$ alkynyl of R$^{6B}$ are each optionally substituted by 1, 2, 3, or 4 independently selected R$^6$ substituents;

each R$^{c62}$ and R$^{d62}$ are independently H or C$_{1-6}$ alkyl; and
each R$^{6C}$ is independently selected from halo, oxo, C$_{1-6}$ alkyl, C$_{1-6}$ haloalkyl, C$_{2-6}$ alkenyl, C$_{2-6}$ alkynyl, CN, and NO$_2$.

In some embodiments:
W is C(R$^W$)$_2$;
Y is C(R$^Y$)$_2$;
each R$^W$ is independently H or C$_{1-6}$ alkyl;
each R$^Y$ is independently H or C$_{1-6}$ alkyl;
Ring A is C$_{3-10}$ cycloalkyl or 4-10 membered heterocycloalkyl, wherein the C$_{3-10}$ cycloalkyl and 4-10 membered heterocycloalkyl of Ring A are each optionally substituted with 1, 2, 3, or 4 independently selected R$^6$ substituents;

R$^2$ is selected from H, C$_{1-6}$ alkyl, C$_{2-6}$ alkenyl, C$_{6-10}$ aryl, C$_{3-10}$ cycloalkyl, 5-10 membered heteroaryl, 4-10 membered heterocycloalkyl, C$_{6-10}$ aryl-C$_{1-6}$ alkyl-, C$_{3-10}$ cycloalkyl-C$_{1-6}$ alkyl-, (5-10 membered heteroaryl)-C$_{1-6}$ alkyl-, and (4-10 membered heterocycloalkyl)-C$_{1-6}$ alkyl-, wherein the C$_{1-6}$ alkyl, C$_{2-6}$ alkenyl, C$_{6-10}$ aryl, C$_{3-10}$ cycloalkyl, 5-10 membered heteroaryl, 4-10 membered heterocycloalkyl, C$_{6-10}$ aryl-C$_{1-6}$ alkyl-, C$_{3-10}$ cycloalkyl-C$_{1-6}$ alkyl-, (5-10 membered heteroaryl)-C$_{1-6}$ alkyl-, and (4-10 membered heterocycloalkyl)-C$_{1-6}$ alkyl- of R$^2$ are each optionally substituted with 1, 2, 3, or 4 independently selected R$^{2A}$ substituents;

each R$^{2A}$ is independently selected from halo, C$_{1-6}$ alkyl, C$_{1-6}$ haloalkyl, C$_{2-6}$ alkenyl, C$_{2-6}$ alkynyl, C$_{6-10}$ aryl, C$_{3-10}$ cycloalkyl, 5-10 membered heteroaryl, 4-10 membered heterocycloalkyl, (4-10 membered heterocycloalkyl)-C$_{1-6}$ alkyl-, CN, and OR$^{a21}$, wherein the C$_{1-6}$ alkyl, C$_{2-6}$ alkenyl, C$_{2-6}$ alkynyl, C$_{6-10}$ aryl, C$_{3-10}$ cycloalkyl, 5-10 membered heteroaryl, 4-10 membered heterocycloalkyl, and (4-10 membered heterocycloalkyl)-C$_{1-6}$ alkyl- of R$^{2A}$ are each optionally substituted with 1, 2, 3, or 4 independently selected R$^{2B}$ substituents;

each R$^{a21}$ is independently selected from H, C$_{1-6}$ alkyl, and C$_{1-6}$ haloalkyl;

each R$^{2B}$ is independently selected from halo, oxo, C$_{1-6}$ alkyl, C$_{1-6}$ haloalkyl, C$_{2-6}$ alkenyl, C$_{2-6}$ alkynyl, S(O)R$^{b22}$, and S(O)$_2$R$^{b22}$, wherein the C$_{1-6}$ alkyl, C$_{2-6}$ alkenyl, and C$_{2-6}$ alkynyl of R$^{2B}$ are each optionally substituted with 1, 2, 3, or 4 independently selected R$^{2C}$ substituents;

each R$^{b22}$ is independently selected from H, C$_{1-6}$ alkyl, C$_{1-6}$ haloalkyl, C$_{2-6}$ alkenyl, and C$_{2-6}$ alkynyl;

each R$^{2C}$ is independently selected from halo, oxo, C$_{1-6}$ alkyl, C$_{1-6}$ haloalkyl, C$_{2-6}$ alkenyl, C$_{2-6}$ alkynyl, CN, and NO$_2$;

R$^3$ is selected from C$_{6-10}$ aryl, C$_{3-10}$ cycloalkyl, 5-10 membered heteroaryl, 4-10 membered heterocycloalkyl, C$_{6-10}$ aryl-C$_{1-6}$ alkyl-, C$_{3-10}$ cycloalkyl-C$_{1-6}$ alkyl-, (5-10 membered heteroaryl)-C$_{1-6}$ alkyl-, and (4-10 membered heterocycloalkyl)-C$_{1-6}$ alkyl-, wherein the C$_{6-10}$ aryl, C$_{3-10}$ cycloalkyl, 5-10 membered heteroaryl, 4-10 membered heterocycloalkyl, C$_{6-10}$ aryl-C$_{1-6}$ alkyl-, C$_{3-10}$ cycloalkyl-C$_{1-6}$ alkyl-, (5-10 membered heteroaryl)-C$_{1-6}$ alkyl-, and (4-10 membered heterocycloalkyl)-C$_{1-6}$ alkyl- of R$^3$ are each optionally substituted with 1, 2, 3, or 4 independently selected R$^{3A}$ substituents;

each R$^{3A}$ is independently selected from oxo, C$_{1-6}$ alkyl, C$_{1-6}$ haloalkyl, C$_{2-6}$ alkenyl, C$_{2-6}$ alkynyl, C$_{6-10}$ aryl, C$_{3-10}$ cycloalkyl, 5-10 membered heteroaryl, 4-10 membered heterocycloalkyl, C$_{6-10}$ aryl-C$_{1-6}$ alkyl-, C$_{3-10}$ cycloalkyl-C$_{1-6}$ alkyl-, (5-10 membered heteroaryl)-C$_{1-6}$ alkyl-, (4-10 membered heterocycloalkyl)-C$_{1-6}$ alkyl-, C(O)R$^{b31}$, C(O)NR$^{c31}$R$^{d31}$, NR$^{c31}$R$^{d31}$, and S(O)$_2$R$^{b31}$, wherein the C$_{1-6}$ alkyl, C$_{2-6}$ alkenyl, C$_{2-6}$ alkynyl, C$_{6-10}$ aryl, C$_{3-10}$ cycloalkyl, 5-10 membered heteroaryl, 4-10 membered heterocycloalkyl, C$_{6-10}$ aryl-C$_{1-6}$ alkyl-, C$_{3-10}$ cycloalkyl-C$_{1-6}$ alkyl-, (5-10 membered heteroaryl)-C$_{1-6}$ alkyl-, and (4-10 membered heterocycloalkyl)-C$_{1-6}$ alkyl- of R$^{3A}$ are each optionally substituted with 1, 2, 3, or 4 independently selected R$^{3B}$ substituents;

each R$^{a31}$, R$^{b31}$, R$^{c31}$, and R$^{d31}$ is independently selected from H, C$_{1-6}$ alkyl, and 4-10 membered heterocycloalkyl;

each R$^{3B}$ is independently selected from halo, oxo, C$_{1-6}$ alkyl, C$_{1-6}$ haloalkyl, C$_{2-6}$ alkenyl, C$_{2-6}$ alkenyl, CN, OR$^{a32}$, C(O)R$^{b32}$, C(O)NR$^{c32}$R$^{d32}$, S(O)R$^{b32}$, S(O)NR$^{c32}$R$^{d32}$, S(O)$_2$R$^{b32}$, S(O)$_2$NR$^{c32}$R$^{d32}$;

each R$^{a32}$, R$^{b32}$, R$^{c32}$, and R$^{d32}$ is independently selected from H and C$_{1-6}$ alkyl;

R$^4$ is selected from H, C$_{1-6}$ alkyl, C$_{1-6}$ alkoxy, C$_{1-6}$ haloalkyl, and C$_{1-6}$ haloalkoxy;

R$^5$ is selected from H, C$_{1-6}$ alkyl, C$_{1-6}$ alkoxy, C$_{1-6}$ haloalkyl, C$_{1-6}$ haloalkoxy, C$_{2-6}$ alkenyl, and C$_{2-6}$ alkynyl;

each R$^6$ is independently selected from C$_{1-6}$ alkyl, C$_{1-6}$ haloalkyl, C$_{2-6}$ alkenyl, C$_{2-6}$ alkynyl, C$_{6-10}$ aryl, C$_{3-10}$ cycloalkyl, 5-10 membered heteroaryl, 4-10 membered heterocycloalkyl, C$_{6-10}$ aryl-C$_{1-6}$ alkyl-, C$_{3-10}$ cycloalkyl-C$_{1-6}$ alkyl-, (5-10 membered heteroaryl)-C$_{1-6}$ alkyl-, (4-10 membered heterocycloalkyl)-C$_{1-6}$ alkyl-, C(O)R$^{b6}$, C(O)NR$^{c6}$R$^{d6}$, C(O)OR$^{a6}$, NR$^{c6}$C(O)R$^{b6}$, NR$^{c6}$S(O)$_2$R$^{b6}$, and S(O)$_2$R$^{b6}$, wherein the C$_{1-6}$ alkyl, C$_{2-6}$ alkenyl, C$_{2-6}$ alkynyl, C$_{6-10}$ aryl, C$_{3-10}$ cycloalkyl, 5-10 membered heteroaryl, 4-10 membered heterocycloalkyl, C$_{6-10}$ aryl-C$_{1-6}$ alkyl-, C$_{3-10}$ cycloalkyl-C$_{1-6}$ alkyl-, (5-10 membered heteroaryl)-C$_{1-6}$ alkyl-, and (4-10 membered heterocycloalkyl)-C$_{1-6}$ alkyl- of R$^6$ are each optionally substituted with 1, 2, 3, or 4 independently selected R$^{6A}$ substituents;

each R$^{a6}$, R$^{b6}$, R$^{c6}$, and R$^{d6}$ is independently selected from H, C$_{1-6}$ alkyl, C$_{1-6}$ haloalkyl, C$_{2-6}$ alkenyl, C$_{2-6}$ alkynyl, C$_{3-10}$ cycloalkyl, C$_{6-10}$ aryl, and 4-10 membered heterocycloalkyl)-C$_{1-6}$ alkyl-, wherein the C$_{1-6}$ alkyl, C$_{1-6}$ haloalkyl, C$_{2-6}$ alkenyl, C$_{2-6}$ alkynyl, C$_{3-10}$ cycloalkyl, C$_{6-10}$ aryl, and 4-10 membered heterocycloalkyl)-$C_{1-6}$ alkyl- of $R^{a6}$, $R^{b6}$, $R^{c6}$, and $R^{d6}$ are each optionally substituted by 1, 2, 3, or 4 independently selected $R^{6A}$ substituents;

each $R^{6A}$ is independently selected from halo, oxo, $C_{1-6}$ alkyl, 4-10 membered heterocycloalkyl, CN, $OR^{a61}$, $C(O)R^{b61}$, $C(O)NR^{c61}R^{d61}$, $C(O)OR^{a61}$, $NR^{c61}C(O)R^{b61}$, $NR^{c61}C(O)OR^{a61}$, $NR^{c61}C(O)NR^{c61}R^{d61}$, $NR^{c61}S(O)_2R^{b61}$, and $S(O)_2R^{b61}$, wherein each $C_{1-6}$ alkyl and 4-10 membered heterocycloalkyl of $R^{6A}$ are optionally substituted with 1, 2, 3, or 4 independently selected $R^{6B}$ substituents;

each $R^{a61}$, $R^{b61}$, $R^{c61}$, and $R^{d61}$ is independently selected from H, $C_{1-6}$ alkyl, $C_{1-6}$ haloalkyl, $C_{2-6}$ alkenyl, $C_{2-6}$ alkynyl, and $C_{6-10}$ aryl, wherein the $C_{1-6}$ alkyl, $C_{1-6}$ haloalkyl, $C_{2-6}$ alkenyl, $C_{2-6}$ alkynyl, and $C_{6-10}$ aryl of $R^{a61}$, $R^{b61}$, $R^{c61}$, and $R^{d61}$ are each optionally substituted by 1, 2, 3, or 4 independently selected $R^{6B}$ substituents;

each $R^{6B}$ is independently selected from $C_{1-6}$ alkyl, $C_{1-6}$ haloalkyl, $C_{2-6}$ alkenyl, $C_{2-6}$ alkynyl, CN, and $C(O)NR^{c62}R^{d62}$, wherein the $C_{1-6}$ alkyl, $C_{1-6}$ haloalkyl, $C_{2-6}$ alkenyl, and $C_{2-6}$ alkynyl of $R^{6B}$ are each optionally substituted by 1, 2, 3, or 4 independently selected $R^6$ substituents;

each $R^{c62}$ and $R^{d62}$ are independently H or $C_{1-6}$ alkyl; and each $R^{6C}$ is independently selected from halo, oxo, $C_{1-6}$ alkyl, $C_{1-6}$ haloalkyl, $C_{2-6}$ alkenyl, $C_{2-6}$ alkynyl, CN, and $NO_2$.

In some embodiments:

W is $C(R^W)_2$;

Y is $C(R^Y)_2$;

each $R^W$ is independently H or $C_{1-6}$ alkyl;

each $R^Y$ is independently H or $C_{1-6}$ alkyl;

Ring A is $C_{3-10}$ cycloalkyl or 4-10 membered heterocycloalkyl, wherein the $C_{3-10}$ cycloalkyl and 4-10 membered heterocycloalkyl of Ring A are each optionally substituted with 1, 2, 3, or 4 independently selected $R^6$ substituents;

$R^2$ is selected from H, $C_{1-6}$ alkyl, $C_{2-6}$ alkenyl, $C_{6-10}$ aryl, 5-10 membered heteroaryl, and 4-10 membered heterocycloalkyl, wherein the $C_{1-6}$ alkyl, $C_{2-6}$ alkenyl, $C_{6-10}$ aryl, 5-10 membered heteroaryl, and 4-10 membered heterocycloalkyl of $R^2$ are each optionally substituted with 1, 2, 3, or 4 independently selected $R^{2A}$ substituents;

each $R^{2A}$ is independently selected from halo, $C_{1-6}$ alkyl, $C_{1-6}$ haloalkyl, $C_{2-6}$ alkenyl, $C_{2-6}$ alkynyl, phenyl, $C_{3-7}$ cycloalkyl, 5-6 membered heteroaryl, 4-6 membered heterocycloalkyl, (4-6 membered heterocycloalkyl)-$C_{1-6}$ alkyl-, CN, and $OR^{a21}$, wherein the $C_{1-6}$ alkyl, $C_{2-6}$ alkenyl, $C_{2-6}$ alkynyl, phenyl, $C_{3-6}$ cycloalkyl, 5-6 membered heteroaryl, 4-6 membered heterocycloalkyl, and (4-6 membered heterocycloalkyl)-$C_{1-6}$ alkyl- of $R^{2A}$ are each optionally substituted with 1, 2, 3, or 4 independently selected $R^{2B}$ substituents;

each $R^{a21}$ is independently selected from H, $C_{1-6}$ alkyl, and $C_{1-6}$ haloalkyl each $R^{2B}$ is independently selected from halo, oxo, $C_{1-6}$ alkyl, $C_{1-6}$ haloalkyl, $C_{2-6}$ alkenyl, $C_{2-6}$ alkynyl, and $S(O)_2R^{b22}$, wherein the $C_{1-6}$ alkyl, $C_{2-6}$ alkenyl, and $C_{2-6}$ alkynyl of $R^{2B}$ are each optionally substituted with 1, 2, 3, or 4 independently selected $R^{2C}$ substituents;

each $R^{b22}$ is independently selected from H, $C_{1-6}$ alkyl, $C_{1-6}$ haloalkyl, $C_{2-6}$ alkenyl, $C_{2-6}$ alkynyl;

each $R^{2C}$ is independently selected from halo, $C_{1-6}$ alkyl, $C_{1-6}$ haloalkyl, CN, and $NO_2$;

$R^3$ is selected from phenyl, $C_{3-7}$ cycloalkyl, monocyclic 5-6 membered heteroaryl, bicyclic 8-10 membered heteroaryl, and bicyclic 8-10 membered heterocycloalkyl, wherein the phenyl, $C_{3-7}$ cycloalkyl, monocyclic 5-6 membered heteroaryl, bicyclic 8-10 membered heteroaryl, and bicyclic 8-10 membered heterocycloalkyl of $R^3$ are each optionally substituted with 1, 2, 3, or 4 independently selected $R^{3A}$ substituents;

each $R^{3A}$ is independently selected from oxo, $C_{1-6}$ alkyl, $C_{1-6}$ haloalkyl, $C_{3-7}$ cycloalkyl, 4-6 membered heterocycloalkyl, phenyl-$C_{1-6}$ alkyl-, $C_{3-6}$ cycloalkyl-$C_{1-6}$ alkyl-, (5-6 membered heteroaryl)-$C_{1-6}$ alkyl-, (4-6 membered heterocycloalkyl)-$C_{1-6}$ alkyl-, $C(O)R^{b31}$, $C(O)NR^{c31}R^{d31}$, $NR^{c31}R^{d31}$, and $S(O)_2R^{b31}$, wherein the $C_{1-6}$ alkyl, $C_{3-7}$ cycloalkyl, 4-6 membered heterocycloalkyl, phenyl-$C_{1-6}$ alkyl-, $C_{3-6}$ cycloalkyl-$C_{1-6}$ alkyl-, (5-6 membered heteroaryl)-$C_{1-6}$ alkyl-, and (4-6 membered heterocycloalkyl)-$C_{1-6}$ alkyl- of $R^{3A}$ are each optionally substituted with 1, 2, 3, or 4 independently selected $R^{3B}$ substituents;

each $R^{b31}$, $R^{c31}$, and $R^{d31}$ is independently selected from H, $C_{1-6}$ alkyl, and 4-10 membered heterocycloalkyl;

each $R^{3B}$ is independently selected from CN, $OR^{a32}$, $C(O)R^{b32}$, $S(O)R^{b32}$, $S(O)NR^{c32}R^{d32}$, $S(O)_2R^{b32}$, and $S(O)_2NR^{c32}R^{d32}$, each $R^{a32}$, $R^{b32}$, $R^{c32}$, and $R^{d32}$ is independently selected from H and $C_{1-6}$ alkyl;

$R^4$ is selected from H and $C_{1-6}$ alkyl;

$R^5$ is selected from H and $C_{1-6}$ alkyl;

each $R^6$ is independently selected from $C_{1-6}$ alkyl, $C_{1-6}$ haloalkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, (4-7 membered heterocycloalkyl)-$C_{1-6}$ alkyl-, $C(O)R^{b6}$, $C(O)NR^{c6}R^{d6}$, $C(O)OR^{a6}$, $NR^{c6}C(O)R^{b6}$, $NR^{c6}S(O)_2R^{b6}$, and $S(O)_2R^{b6}$, wherein the $C_{1-6}$ alkyl, $C_{1-6}$ haloalkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl- of $R^6$ are each optionally substituted with 1, 2, 3, or 4 independently selected $R^{6A}$ substituents;

each $R^{a6}$, $R^{b6}$, $R^{c6}$, and $R^{d6}$ is independently selected from H, $C_{1-6}$ alkyl, $C_{1-6}$ haloalkyl, $C_{2-6}$ alkenyl, $C_{2-6}$ alkynyl, $C_{3-7}$ cycloalkyl, phenyl, 4-7 membered heterocycloalkyl)-$C_{1-6}$ alkyl-, wherein the $C_{1-6}$ alkyl, $C_{1-6}$ haloalkyl, $C_{2-6}$ alkenyl, $C_{2-6}$ alkynyl, $C_{3-7}$ cycloalkyl, phenyl, and 4-10 membered heterocycloalkyl)-$C_{1-6}$ alkyl- of $R^{a6}$, $R^{b6}$, $R^{c6}$, and $R^{d6}$ are each optionally substituted by 1, 2, 3, or 4 independently selected $R^{6A}$ substituents;

each $R^{6A}$ is independently selected from halo, oxo, $C_{1-6}$ alkyl, 4-10 membered heterocycloalkyl, CN, $OR^{a61}$, $C(O)R^{b61}$, $C(O)NR^{c61}R^{d61}$, $C(O)OR^{a61}$, $NR^{c61}C(O)R^{b61}$, $NR^{c61}C(O)OR^{a61}$, $NR^{c61}C(O)NR^{c61}R^{d61}$, $NR^{c61}S(O)_2R^{b61}$, and $S(O)_2R^{b61}$, wherein each $C_{1-6}$ alkyl and 4-10 membered heterocycloalkyl of $R^{6A}$ are optionally substituted with 1, 2, 3, or 4 independently selected $R^{6B}$ substituents;

each $R^{a61}$, $R^{b61}$, $R^{c61}$, and $R^{d61}$ is independently selected from H, $C_{1-6}$ alkyl, and phenyl, wherein the $C_{1-6}$ alkyl and phenyl of $R^{a61}$, $R^{b61}$, $R^{c61}$, and $R^{d61}$ are each optionally substituted by 1 or 2 independently selected $R^{6B}$ substituents;

each $R^{6B}$ is independently selected from $C_{1-6}$ alkyl, CN, and $C(O)NR^{c62}R^{d62}$, wherein each $C_{1-6}$ alkyl of $R^{6B}$ is optionally substituted by CN; and each $R^{c62}$ and $R^{d62}$ is independently selected from H and $C_{1-3}$ alkyl.

In some embodiments:

W is $CH_2$;

Y is $CH_2$;

Ring A is selected from cyclobutyl, cyclopentyl, cyclohexyl, dihydroindenyl, tetrahydro-2H-pyranyl, tetrahydrofuranyl, azetidinyl, piperidinyl, pyrrolidinyl, azepanyl, dihydropyridinyl, azabicyclo[3.2.1]octanyl, 2-azaspiro[3.3]heptanyl, and 7-azaspiro[3.5]nonanyl, wherein the cyclobutyl, cyclopentyl, tetrahydro-2H-pyranyl, tetrahydrofuranyl, azetidinyl, piperidinyl, pyrrolidinyl, azepanyl, dihydropyridinyl, azabicyclo[3.2.1]octanyl, 2-azaspiro[3.3]heptanyl, and 7-azaspiro[3.5]nonanyl of Ring A are each optionally substituted by 1 or 2 independently selected $R^6$ substituents;

$R^2$ is selected from H, ethyl, ethenyl, phenyl, indazolyl, thiazolyl, thieno[3,2-c]pyridinyl, 3,6-dihydro-2H-pyranyl, and indolyl, wherein the ethyl, ethenyl, phenyl, indazolyl, thiazolyl, thieno[3,2-c]pyridinyl, 3,6-dihydro-2H-pyranyl, and indolyl of $R^2$ are each optionally substituted with 1, 2, 3, or 4 independently selected $R^{2A}$ substituents;

each $R^{2A}$ is independently selected from fluoro, methyl, $CD_3$, trifluoromethyl, cyclopropyl, pyrazolyl, piperazinylmethyl, cyano, methoxy, and trifluoromethoxy, wherein the methyl, cyclopropyl, pyrazolyl, and piperazinylmethyl are each optionally substituted with 1 or 2 independently selected $R^{2B}$ substituents;

each $R^{2B}$ is independently selected from $C_{1-6}$ alkyl and $S(O)_2R^{b22}$, wherein the $C_{1-6}$ alkyl of $R^{2B}$ are each optionally substituted with CN;

each $R^{b22}$ is independently selected from H or $C_{1-6}$ alkyl;

$R^3$ is selected from phenyl, cyclopropyl, cyclohexenyl, pyrazolyl, pyrrolyl, 4,5,6,7-tetrahydropyrazolo[1,5-a]pyridinyl, 6,7-dihydro-5H-pyrazolo[5,1-b][1,3]oxazinyl, 3,4-dihydro-2H-benzo[b][1,4]oxazinyl, 5,6-dihydro-4H-pyrrolo[1,2-b]pyrazolyl, and pyrazolo[1,5-a]pyrimidinyl, wherein the phenyl, cyclopropyl, cyclohexenyl, pyrazolyl, pyrrolyl, 4,5,6,7-tetrahydropyrazolo[1,5-a]pyridinyl, 6,7-dihydro-5H-pyrazolo[5,1-b][1,3]oxazinyl, 3,4-dihydro-2H-benzo[b][1,4]oxazinyl, 5,6-dihydro-4H-pyrrolo[1,2-b]pyrazolyl, and pyrazolo[1,5-a]pyrimidinyl of $R^3$ are each optionally substituted with 1, 2, 3, or 4 independently selected $R^{3A}$ substituents;

each $R^{3A}$ is independently selected from methyl, trideuteromethyl, ethyl, isopropyl, isobutyl, difluoroethyl, trifluoroethyl, methoxy, cyclopropyl, cyclopentyl, piperidinyl, tetrahydrofuranyl, tetrahydropyranyl, cyclopropylmethyl, cyclopropylethyl, phenylmethyl, pyridylmethyl, piperidinylmethyl, morpholinylmethyl, morpholinylethyl, morpholinylcarbonyl, dimethylaminocarbonyl, and ethylsulfonyl, wherein the methyl, ethyl, isopropyl, isobutyl, cyclopropyl, cyclopentyl, piperidinyl, tetrahydrofuranyl, tetrahydropyranyl, cyclopropylmethyl, cyclopropylethyl, phenylmethyl, pyridylmethyl, piperidinylmethyl, morpholinylmethyl, and morpholinylethyl of $R^{3A}$ are each optionally substituted with 1, 2, 3, or 4 independently selected $R^{3B}$ substituents;

each $R^{3B}$ is independently selected from hydroxy, methoxy, methylsulfonyl, methylcarbonyl, and cyano;

$R^4$ is selected from H and $C_{1-6}$ alkyl;

$R^5$ is selected from H and $C_{1-6}$ alkyl;

each $R^6$ is independently selected from ethyl, tert-butyl, cyclopropyl, cyclobutyl, cyclopentyl, cyclohexyl, azetidinyl, tetrahydrothiopheneyl, pyrazolyl, piperidinyl, pyrimidinyl, cyclopropylmethyl, spiro[3.3]heptanylmethyl, phenylmethyl, triazolylisopropyl, azetidinylisopropyl, 2-azabicyclo[2.1.1]hexanyl, bicyclo[1.1.1]pentanyl, methylcarbonyl, tetrahydropyranylmethylcarbonyl, propylcarbonyl, dimethylaminocarbonyl, methoxycarbonyl, phenylaminocarbonyl, ethylsulfonyl, cyclobutylcarbonylamino, cyclopropylsulfonyl, and cyclopropylsulfonylamino, wherein the ethyl, tert-butyl, cyclopropyl, cyclobutyl, cyclopentyl, cyclohexyl, azetidinyl, tetrahydrothiopheneyl, pyrazolyl, piperidinyl, pyrimidinyl, cyclopropylmethyl, spiro[3.3]heptanylmethyl, phenylmethyl, triazolylisopropyl, azetidinylisopropyl, 2-azabicyclo[2.1.1]hexanyl, bicyclo[1.1.1]pentanyl, methylcarbonyl, tetrahydropyranylmethylcarbonyl, propylcarbonyl, dimethylaminocarbonyl, methoxycarbonyl, phenylaminocarbonyl, ethylsulfonyl, cyclobutylcarbonylamino, cyclopropylsulfonyl, and cyclopropylsulfonylamino of $R^6$ are each optionally substituted with 1 or 2 independently selected $R^{6A}$ substituents; and each $R^{6A}$ is independently selected from fluoro, oxo, methyl, CN, methoxy, tetrahydropyranyl, methylcarbonyl, aminocarbonyl, methylcarbonylamino, ethylaminocarbonyl, methoxycarbonyl, methoxycarbonylamino, ethylaminocarbonylamino, ethylsulfonyl, and phenylsulfonylamino, wherein each methyl of $R^{6A}$ is optionally substituted by CN or aminocarbonyl; and wherein each tetrahydropyranyl of $R^{6A}$ is optionally substituted by cyanomethyl.

In some embodiments:

W is $CH_2$;

Y is $CH_2$;

Ring A is selected from cyclobutyl, cyclopentyl, cyclohexyl, dihydroindenyl, tetrahydro-2H-pyranyl, tetrahydrofuranyl, azetidinyl, piperidinyl, pyrrolidinyl, azepanyl, dihydropyridinyl, azabicyclo[3.2.1]octanyl, 2-azaspiro[3.3]heptanyl, and 7-azaspiro[3.5]nonanyl, wherein the cyclobutyl, cyclopentyl, tetrahydro-2H-pyranyl, tetrahydrofuranyl, azetidinyl, piperidinyl, pyrrolidinyl, azepanyl, dihydropyridinyl, azabicyclo[3.2.1]octanyl, 2-azaspiro[3.3]heptanyl, and 7-azaspiro[3.5]nonanyl of Ring A are each optionally substituted by 1 or 2 independently selected $R^6$ substituents;

$R^2$ is selected from H, ethyl, ethenyl, phenyl, indazolyl, thiazolyl, thieno[3,2-c]pyridinyl, 3,6-dihydro-2H-pyranyl, and indolyl, wherein the ethyl, ethenyl, phenyl, indazolyl, thiazolyl, thieno[3,2-c]pyridinyl, 3,6-dihydro-2H-pyranyl, and indolyl of $R^2$ are each optionally substituted with 1, 2, 3, or 4 independently selected $R^{2A}$ substituents;

each $R^{2A}$ is independently selected from fluoro, methyl, $CD_3$, trifluoromethyl, cyclopropyl, pyrazolyl, piperazinylmethyl, cyano, methoxy, and trifluoromethoxy, wherein the methyl, cyclopropyl, pyrazolyl, and piperazinylmethyl are each optionally substituted with 1 or 2 independently selected $R^{2B}$ substituents;

each $R^{2B}$ is independently selected from $C_{1-6}$ alkyl and $S(O)_2R^{b22}$, wherein the $C_{1-6}$ alkyl of $R^{2B}$ are each optionally substituted with CN;

each $R^{b22}$ is independently selected from H or $C_{1-6}$ alkyl;

$R^3$ is selected from phenyl, cyclopropyl, cyclohexenyl, pyrazolyl, pyrrolyl, 4,5,6,7-tetrahydropyrazolo[1,5-a]

pyridinyl, 6,7-dihydro-5H-pyrazolo[5,1-b][1,3]oxazinyl, 3,4-dihydro-2H-benzo[b][1,4]oxazinyl, 5,6-dihydro-4H-pyrrolo[1,2-b]pyrazolyl, and pyrazolo[1,5-a]pyrimidinyl, wherein the phenyl, cyclopropyl, cyclohexenyl, pyrazolyl, pyrrolyl, 4,5,6,7-tetrahydropyrazolo[1,5-a]pyridinyl, 6,7-dihydro-5H-pyrazolo[5,1-b][1,3]oxazinyl, 3,4-dihydro-2H-benzo[b][1,4]oxazinyl, 5,6-dihydro-4H-pyrrolo[1,2-b]pyrazolyl, and pyrazolo[1,5-a]pyrimidinyl of $R^3$ are each optionally substituted with 1, 2, 3, or 4 independently selected $R^{3A}$ substituents;

each $R^{3A}$ is independently selected from methyl, trideuteromethyl, ethyl, isopropyl, isobutyl, difluoroethyl, trifluoroethyl, methoxy, cyclopropyl, cyclopentyl, piperidinyl, tetrahydrofuranyl, tetrahydropyranyl, cyclopropylmethyl, cyclopropylethyl, phenylmethyl, pyridylmethyl, piperidinylmethyl, morpholinylmethyl, morpholinylethyl, morpholinylcarbonyl, dimethylaminocarbonyl, and ethylsulfonyl, wherein the methyl, ethyl, isopropyl, isobutyl, cyclopropyl, cyclopentyl, piperidinyl, tetrahydrofuranyl, tetrahydropyranyl, cyclopropylmethyl, cyclopropylethyl, phenylmethyl, pyridylmethyl, piperidinylmethyl, morpholinylmethyl, and morpholinylethyl of $R^{3A}$ are each optionally substituted with 1, 2, 3, or 4 independently selected $R^{3B}$ substituents;

each $R^{3B}$ is independently selected from hydroxy, methoxy, methylsulfonyl, methylcarbonyl, and cyano;

$R^4$ is selected from H and $C_{1-6}$ alkyl;

$R^5$ is selected from H and $C_{1-6}$ alkyl;

each $R^6$ is independently selected from ethyl, tert-butyl, cyclopropyl, cyclobutyl, cyclopentyl, cyclohexyl, azetidinyl, tetrahydrothiopheneyl, pyrazolyl, piperidinyl, pyrimidinyl, cyclopropylmethyl, spiro[3.3]heptanylmethyl, phenylmethyl, triazolylisopropyl, azetidinylisopropyl, 2-azabicyclo[2.1.1]hexanyl, bicyclo[1.1.1]pentanyl, methylcarbonyl, tetrahydropyranylmethylcarbonyl, propylcarbonyl, dimethylaminocarbonyl, methoxycarbonyl, phenylaminocarbonyl, ethylsulfonyl, cyclobutylcarbonylamino, cyclopropylsulfonyl, and cyclopropylsulfonylamino, wherein the ethyl, tert-butyl, cyclopropyl, cyclobutyl, cyclopentyl, cyclohexyl, azetidinyl, tetrahydrothiopheneyl, pyrazolyl, piperidinyl, pyrimidinyl, cyclopropylmethyl, spiro[3.3]heptanylmethyl, phenylmethyl, triazolylisopropyl, azetidinylisopropyl, 2-azabicyclo[2.1.1]hexanyl, bicyclo[1.1.1]pentanyl, methylcarbonyl, tetrahydropyranylmethylcarbonyl, propylcarbonyl, dimethylaminocarbonyl, methoxycarbonyl, phenylaminocarbonyl, ethylsulfonyl, cyclobutylcarbonylamino, cyclopropylsulfonyl, and cyclopropylsulfonylamino of $R^6$ are each optionally substituted with 1 or 2 independently selected $R^{6A}$ substituents; and each $R^{6A}$ is independently selected from fluoro, oxo, methyl, CN, methoxy, tetrahydropyranyl, methylcarbonyl, aminocarbonyl, methylcarbonylamino, ethylaminocarbonyl, methoxycarbonyl, methoxycarbonylamino, ethylaminocarbonylamino, ethylsulfonyl, and phenylsulfonylamino, wherein each methyl of $R^{6A}$ is optionally substituted by CN or aminocarbonyl; and wherein each tetrahydropyranyl of $R^{6A}$ is optionally substituted by cyanomethyl.

In some embodiments:

W is $C(R^W)_2$;

Y is $C(R^Y)_2$;

each $R^W$ is independently H or $C_{1-6}$ alkyl;

each $R^Y$ is independently H or $C_{1-6}$ alkyl;

Ring A is $C_{3-10}$ cycloalkyl or 4-10 membered heterocycloalkyl, wherein the $C_{3-10}$ cycloalkyl and 4-10 membered heterocycloalkyl of Ring A are each optionally substituted with 1, 2, 3, or 4 independently selected $R^6$ substituents;

$R^2$ is selected from $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^2$ are each optionally substituted with 1, 2, 3, or 4 independently selected $R^{2A}$ substituents;

each $R^{2A}$ is independently selected from $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, and 4-10 membered heterocycloalkyl, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, and 4-10 membered heterocycloalkyl of $R^{2A}$ are each optionally substituted with 1, 2, 3, or 4 independently selected $R^{2B}$ substituents;

each $R^{2B}$ is independently selected from H, $C_{1-6}$ alkyl, $C_{1-6}$ haloalkyl, $C_{2-6}$ alkenyl, $C_{2-6}$ alkynyl, wherein the $C_{1-6}$ alkyl, $C_{1-6}$ haloalkyl, $C_{2-6}$ alkenyl, $C_{2-6}$ alkynyl of $R^{2B}$ is each optionally substituted by cyano;

$R^3$ is selected from $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^3$ are each optionally substituted with 1, 2, 3, or 4 independently selected $R^{3A}$ substituents;

each $R^{3A}$ is independently selected from $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{3A}$ are each optionally substituted with 1, 2, 3, or 4 independently selected $R^{3B}$ substituents;

each $R^{3B}$ is independently selected from $S(O)_2R^{b32}$;

each $R^{b32}$ is independently selected from H and $C_{1-6}$ alkyl;

$R^4$ is selected from H, $C_{1-6}$ alkyl, $C_{1-6}$ alkoxy, $C_{1-6}$ haloalkyl, and $C_{1-6}$ haloalkoxy;

$R^5$ is selected from H, $C_{1-6}$ alkyl, $C_{1-6}$ alkoxy, $C_{1-6}$ haloalkyl, $C_{1-6}$ haloalkoxy, $C_{2-6}$ alkenyl, and $C_{2-6}$ alkynyl;

each $R^6$ is independently selected from $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, (4-10 membered heterocycloalkyl)-$C_{1-6}$ alkyl-, $C(O)R^{b6}$, $C(O)NR^{c6}R^{d6}$, and $C(O)OR^{a6}$, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^6$ are each optionally substituted with 1, 2, 3, or 4 independently selected $R^{6A}$ substituents;

each $R^{a6}$, $R^{b6}$, $R^{c6}$, and $R^{d6}$ is independently selected from H, $C_{1-6}$ alkyl, $C_{1-6}$ haloalkyl, $C_{2-6}$ alkenyl, $C_{2-6}$ alkynyl, wherein the $C_{1-6}$ alkyl, $C_{1-6}$ haloalkyl, $C_{2-6}$ alkenyl, $C_{2-6}$ alkynyl of $R^{a6}$, $R^{b6}$, $R^{c6}$, and $R^{d6}$ are each optionally substituted by 1, 2, 3, or 4 independently selected $R^{6A}$ substituents;

each $R^{6A}$ is independently selected from $C_{6-10}$ aryl, $C_{3-10}$ cycloalkyl, 5-10 membered heteroaryl, 4-10 membered heterocycloalkyl, CN, $C(O)R^{b61}$, $C(O)NR^{c61}R^{d61}$, $C(O)OR^{a61}$, and $OC(O)R^{b61}$, wherein the $C_{6-10}$ aryl, $C_{3-10}$ cycloalkyl, 5-10 membered heteroaryl, and 4-10 membered heterocycloalkyl of $R^{6A}$ are each optionally substituted with 1, 2, 3, or 4 independently selected $R^{6B}$ substituents;

each $R^{a61}$, $R^{b61}$, $R^{c61}$, and $R^{d61}$ is independently selected from H, $C_{1-6}$ alkyl, $C_{1-6}$ haloalkyl, $C_{2-6}$ alkenyl, $C_{2-6}$ alkynyl, wherein the $C_{1-6}$ alkyl, $C_{1-6}$ haloalkyl, $C_{2-6}$ alkenyl, $C_{2-6}$ alkynyl of $R^{a61}$, $R^{b61}$, $R^{c61}$, and $R^{d61}$ are each optionally substituted by 1, 2, 3, or 4 independently selected $R^{6B}$ substituents; and each $R^{6B}$ is independently selected from $C_{1-6}$ alkyl, $C_{1-6}$ haloalkyl, $C_{2-6}$ alkenyl, and $C_{2-6}$ alkynyl, wherein the $C_{1-6}$ alkyl, $C_{1-6}$ haloalkyl, $C_{2-6}$ alkenyl, and $C_{2-6}$ alkynyl are each optionally substituted by CN.

In some embodiments:

W is $C(R^W)_2$;

Y is $C(R^Y)_2$;

each $R^W$ is independently H or $C_{1-6}$ alkyl;

each $R^Y$ is independently H or $C_{1-6}$ alkyl;

Ring A is $C_{3-10}$ cycloalkyl or 4-10 membered heterocycloalkyl, wherein the $C_{3-10}$ cycloalkyl and 4-10 membered heterocycloalkyl of Ring A are each optionally substituted with 1, 2, 3, or 4 independently selected $R^6$ substituents;

$R^2$ is selected from $C_{6-10}$ aryl and 5-10 membered heteroaryl, wherein the $C_{6-10}$ aryl and 5-10 membered heteroaryl of $R^2$ are each optionally substituted with 1, 2, 3, or 4 independently selected $R^{2A}$ substituents;

each $R^{2A}$ is independently selected from $C_{1-6}$ alkyl, and 5-10 membered heteroaryl, wherein the $C_{1-6}$ alkyl and 5-10 membered heteroaryl of $R^{2A}$ are each optionally substituted with 1 or 2 independently selected $R^{2B}$ substituents;

each $R^{2B}$ is independently selected from H and $C_{1-6}$ alkyl, wherein the $C_{1-6}$ alkyl of $R^{2B}$ is optionally substituted by cyano;

$R^3$ is selected from $C_{6-10}$ aryl, $C_{3-10}$ cycloalkyl, and 5-10 membered heteroaryl, wherein the $C_{6-10}$ aryl, $C_{3-10}$ cycloalkyl, and 5-10 membered heteroaryl of $R^3$ are each optionally substituted with 1, 2, 3, or 4 independently selected $R^{3A}$ substituents;

each $R^{3A}$ is independently selected from $C_{1-6}$ alkyl, (5-10 membered heteroaryl)-$C_{1-6}$ alkyl-, and (4-10 membered heterocycloalkyl)-$C_{1-6}$ alkyl-, wherein the $C_{1-6}$ alkyl, (5-10 membered heteroaryl)-$C_{1-6}$ alkyl-, and (4-10 membered heterocycloalkyl)-$C_{1-6}$ alkyl- of $R^{3A}$ are each optionally substituted with 1, 2, 3, or 4 independently selected $R^{3B}$ substituents;

each $R^{3B}$ is independently selected from $S(O)_2R^{b32}$;

each $R^{b32}$ is independently selected from H and $C_{1-6}$ alkyl;

$R^4$ is selected from H and $C_{1-6}$ alkyl;

$R^5$ is selected from H and $C_{1-6}$ alkyl;

each $R^6$ is independently selected from $C_{1-6}$ alkyl, $C_{1-6}$ haloalkyl, 5-10 membered heteroaryl, 4-10 membered heterocycloalkyl, (5-10 membered heteroaryl)-$C_{1-6}$ alkyl-, (4-10 membered heterocycloalkyl)-$C_{1-6}$ alkyl-, $C(O)R^{b6}$, $C(O)NR^{c6}R^{d6}$, and $C(O)OR^{a6}$, wherein the $C_{1-6}$ alkyl, 5-10 membered heteroaryl, 4-10 membered heterocycloalkyl, (5-10 membered heteroaryl)-$C_{1-6}$ alkyl-, and (4-10 membered heterocycloalkyl)-$C_{1-6}$ alkyl- of $R^6$ are each optionally substituted with 1, 2, 3, or 4 independently selected $R^{6A}$ substituents;

each $R^{a6}$, $R^{b6}$, $R^{c6}$, and $R^{d6}$ is independently selected from H, $C_{1-6}$ alkyl, $C_{1-6}$ haloalkyl, $C_{2-6}$ alkenyl, $C_{2-6}$ alkynyl, wherein the $C_{1-6}$ alkyl, $C_{1-6}$ haloalkyl, $C_{2-6}$ alkenyl, $C_{2-6}$ alkynyl of $R^{a6}$, $R^{b6}$, $R^{c6}$, and $R^{d6}$ are each optionally substituted by 1, 2, 3, or 4 independently selected $R^{6A}$ substituents;

each $R^{6A}$ is independently selected from $C_{6-10}$ aryl, $C_{3-10}$ cycloalkyl, 5-10 membered heteroaryl, 4-10 membered heterocycloalkyl, CN, $C(O)R^{b61}$, $C(O)NR^{c61}R^{d61}$, $C(O)OR^{a61}$, and $OC(O)R^{b61}$, wherein the $C_{6-10}$ aryl, $C_{3-10}$ cycloalkyl, 5-10 membered heteroaryl, and 4-10 membered heterocycloalkyl of $R^{6A}$ are each optionally substituted with 1, 2, 3, or 4 independently selected $R^{6B}$ substituents;

each $R^{a61}$, $R^{b61}$, $R^{c61}$, and $R^{d61}$ is independently selected from H, $C_{1-6}$ alkyl, $C_{1-6}$ haloalkyl, $C_{2-6}$ alkenyl, $C_{2-6}$ alkynyl, wherein the $C_{1-6}$ alkyl, $C_{1-6}$ haloalkyl, $C_{2-6}$ alkenyl, $C_{2-6}$ alkynyl of $R^{a61}$, $R^{b61}$, $R^{c61}$, and $R^{d61}$ are each optionally substituted by 1, 2, 3, or 4 independently selected $R^{6B}$ substituents; and each $R^{6B}$ is independently selected from $C_{1-6}$ alkyl, $C_{1-6}$ haloalkyl, $C_{2-6}$ alkenyl, and $C_{2-6}$ alkynyl, wherein the $C_{1-6}$ alkyl, $C_{1-6}$ haloalkyl, $C_{2-6}$ alkenyl, and $C_{2-6}$ alkynyl are each optionally substituted by CN.

In some embodiments:

W is $CH_2$;

Y is $CH_2$;

Ring A is selected from $C_{3-7}$ cycloalkyl, monocyclic 4-6 membered heterocycloalkyl, and bicyclic 8-10 membered heterocycloalkyl, wherein the $C_{3-7}$ cycloalkyl, monocyclic 4-6 membered heterocycloalkyl, and bicyclic 8-10 membered heterocycloalkyl of Ring A are each optionally substituted by 1, 2, 3, or 4 independently selected $R^6$ substituents;

$R^2$ is selected from phenyl and indazolyl, wherein the phenyl and indazolyl of $R^2$ are each optionally substituted with 1, 2, 3, or 4 independently selected $R^{2A}$ substituents;

each $R^{2A}$ is independently selected from $C_{1-6}$ alkyl, and 5-10 membered heteroaryl, wherein the $C_{1-6}$ alkyl and 5-10 membered heteroaryl of $R^{2A}$ are each optionally substituted with 1 or 2 independently selected $R^{2B}$ substituents;

each $R^{2B}$ is independently selected from H and $C_{1-6}$ alkyl, wherein the $C_{1-6}$ alkyl of $R^{2B}$ is optionally substituted by CN;

$R^3$ is selected from phenyl, cyclopropyl, and pyrazolyl, wherein the phenyl, cyclopropyl, and pyrazolyl of $R^3$ are each optionally substituted with 1, 2, 3, or 4 independently selected $R^{3A}$ substituents;

each $R^{3A}$ is independently selected from $C_{1-6}$ alkyl, (5-10 membered heteroaryl)-$C_{1-6}$ alkyl-, and (4-10 membered heterocycloalkyl)-$C_{1-6}$ alkyl-, wherein the $C_{1-6}$ alkyl, (5-10 membered heteroaryl)-$C_{1-6}$ alkyl-, and (4-10 membered heterocycloalkyl)-$C_{1-6}$ alkyl- of $R^{3A}$ are each optionally substituted with 1, 2, 3, or 4 independently selected $R^{3B}$ substituents;

each $R^{3B}$ is independently selected from $S(O)_2R^{b32}$;

each $R^{b32}$ is independently selected from H and $C_{1-6}$ alkyl;

$R^4$ is selected from H and $C_{1-6}$ alkyl;

$R^5$ is selected from H and $C_{1-6}$ alkyl;

each $R^6$ is independently selected from $C_{1-6}$ alkyl, 5-10 membered heteroaryl, 4-10 membered heterocycloalkyl, and $C(O)R^{b6}$, wherein the $C_{1-6}$ alkyl, 5-10 membered heteroaryl, and 4-10 membered heterocycloalkyl of $R^6$ are each optionally substituted with 1, 2, 3, or 4 independently selected $R^{6A}$ substituents;

each $R^{b6}$ is independently selected from H, $C_{1-6}$ alkyl, $C_{1-6}$ haloalkyl, $C_{2-6}$ alkenyl, $C_{2-6}$ alkynyl, wherein the $C_{1-6}$ alkyl, $C_{1-6}$ haloalkyl, $C_{2-6}$ alkenyl, $C_{2-6}$ alkynyl of $R^{b6}$ are each optionally substituted by 1, 2, 3, or 4 independently selected $R^{6A}$ substituents;

each $R^{6A}$ is independently selected from 4-10 membered heterocycloalkyl, CN, and $C(O)R^{b61}$, wherein the 4-10 membered heterocycloalkyl of $R^{6A}$ are each optionally substituted with 1, 2, 3, or 4 independently selected $R^{6B}$ substituents;

each $R^{b61}$ is independently selected from H, $C_{1-6}$ alkyl, $C_{1-6}$ haloalkyl, $C_{2-6}$ alkenyl, $C_{2-6}$ alkynyl, wherein the $C_{1-6}$ alkyl, $C_{1-6}$ haloalkyl, $C_{2-6}$ alkenyl, $C_{2-6}$ alkynyl of $R^{b61}$ are each optionally substituted by 1 or 2 independently selected $R^{6B}$ substituents;

each $R^{6B}$ is independently selected from $C_{1-6}$ alkyl, wherein the $C_{1-6}$ alkyl of $R^{6B}$ is optionally substituted by CN.

In some embodiments:

W is $CH_2$;

Y is $CH_2$;

Ring A is selected from cyclobutyl, cyclopentyl, cyclohexyl, tetrahydro-2H-pyranyl, tetrahydrofuranyl, azetidinyl, piperidinyl, pyrrolidinyl, and azabicyclo[3.2.1]octanyl, wherein the cyclobutyl, cyclopentyl, cyclohexyl, tetrahydro-2H-pyranyl, tetrahydrofuranyl, azetidinyl, piperidinyl, pyrrolidinyl, and azabicyclo[3.2.1]octanyl of Ring A are each optionally substituted by 1, 2, 3, or 4 independently selected $R^6$ substituents;

$R^2$ is selected from phenyl and indazolyl, wherein the phenyl and indazolyl of $R^2$ are each optionally substituted with 1, 2, 3, or 4 independently selected $R^{2A}$ substituents;

each $R^{2A}$ is independently selected from $C_{1-6}$ alkyl, and 5-10 membered heteroaryl, wherein the $C_{1-6}$ alkyl and 5-10 membered heteroaryl of $R^{2A}$ are each optionally substituted with 1 or 2 independently selected $R^{2B}$ substituents;

each $R^{2B}$ is independently selected from H and $C_{1-6}$ alkyl, wherein the $C_{1-6}$ alkyl of $R^{2B}$ is optionally substituted by CN;

$R^3$ is selected from phenyl, cyclopropyl, and pyrazolyl, wherein the phenyl, cyclopropyl, and pyrazolyl of $R^3$ are each optionally substituted with 1, 2, 3, or 4 independently selected $R^{3A}$ substituents;

each $R^{3A}$ is independently selected from $C_{1-6}$ alkyl, (5-10 membered heteroaryl)-$C_{1-6}$ alkyl-, and (4-10 membered heterocycloalkyl)-$C_{1-6}$ alkyl-, wherein the $C_{1-6}$ alkyl, (5-10 membered heteroaryl)-$C_{1-6}$ alkyl-, and (4-10 membered heterocycloalkyl)-$C_{1-6}$ alkyl- of $R^{3A}$ are each optionally substituted with 1, 2, 3, or 4 independently selected $R^{3B}$ substituents;

each $R^{3B}$ is independently selected from $S(O)_2R^{b32}$;

each $R^{b32}$ is independently selected from H and $C_{1-6}$ alkyl;

$R^4$ is selected from H and $C_{1-6}$ alkyl;

$R^5$ is selected from H and $C_{1-6}$ alkyl;

each $R^6$ is independently selected from $C_{1-6}$ alkyl, 5-10 membered heteroaryl, 4-10 membered heterocycloalkyl, and $C(O)R^{b6}$, wherein the $C_{1-6}$ alkyl, 5-10 membered heteroaryl, and 4-10 membered heterocycloalkyl of $R^6$ are each optionally substituted with 1, 2, 3, or 4 independently selected $R^{6A}$ substituents;

each $R^{b6}$ is independently selected from H, $C_{1-6}$ alkyl, $C_{1-6}$ haloalkyl, $C_{2-6}$ alkenyl, $C_{2-6}$ alkynyl, wherein the $C_{1-6}$ alkyl, $C_{1-6}$ haloalkyl, $C_{2-6}$ alkenyl, $C_{2-6}$ alkynyl of $R^{b6}$ are each optionally substituted by 1, 2, 3, or 4 independently selected $R^{6A}$ substituents;

each $R^{6A}$ is independently selected from 4-10 membered heterocycloalkyl, CN, and $C(O)R^{b61}$, wherein the 4-10 membered heterocycloalkyl of $R^{6A}$ are each optionally substituted with 1, 2, 3, or 4 independently selected $R^{6B}$ substituents;

each $R^{b61}$ is independently selected from H, $C_{1-6}$ alkyl, $C_{1-6}$ haloalkyl, $C_{2-6}$ alkenyl, $C_{2-6}$ alkynyl, wherein the $C_{1-6}$ alkyl, $C_{1-6}$ haloalkyl, $C_{2-6}$ alkenyl, $C_{2-6}$ alkynyl of $R^{b61}$ are each optionally substituted by 1 or 2 independently selected $R^{6B}$ substituents;

each $R^{6B}$ is independently selected from $C_{1-6}$ alkyl, wherein the $C_{1-6}$ alkyl of $R^{6B}$ is optionally substituted by CN.

In some embodiments, the compound of Formula I is a compound of Formula II:

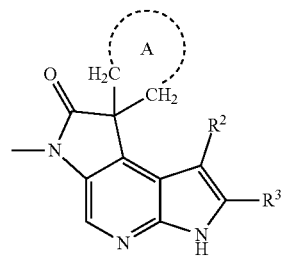

or a pharmaceutically acceptable salt thereof.

In some embodiments, the compound of Formula I is a compound of Formula IIa:

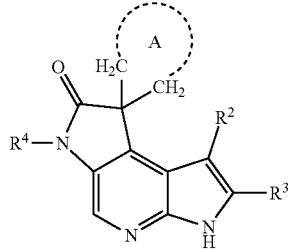

IIa or a pharmaceutically acceptable salt thereof.

In some embodiments, the compound of Formula I is a compound of Formula IIb:

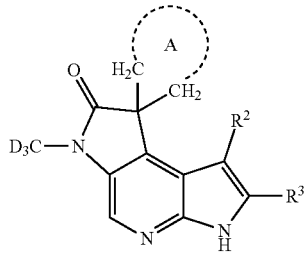

IIb or a pharmaceutically acceptable salt thereof.

In some embodiments, the compound of Formula I is a compound of Formula III:

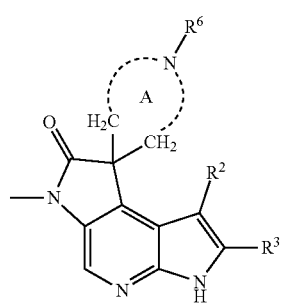

III or a pharmaceutically acceptable salt thereof.

In some embodiments, the compound of Formula I is a compound of Formula IIIa:

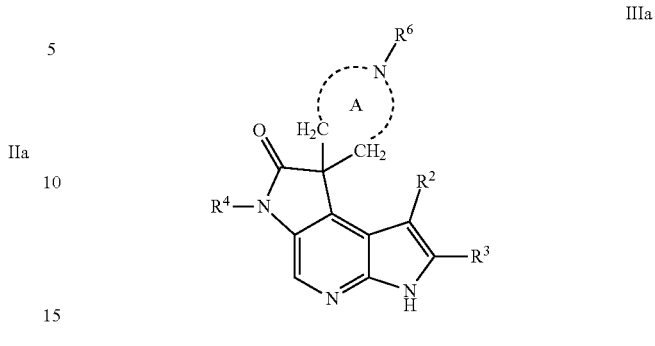

IIIa or a pharmaceutically acceptable salt thereof.

In some embodiments, the compound of Formula I is a compound of Formula IIIb:

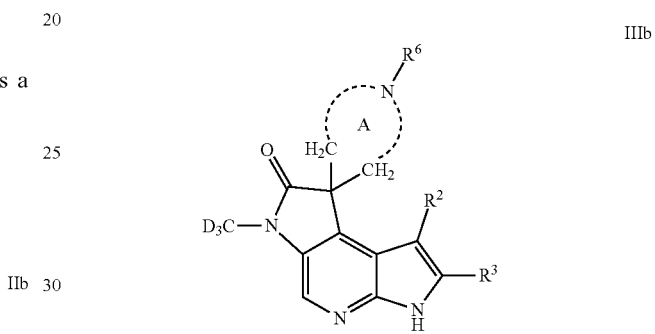

IIIb or a pharmaceutically acceptable salt thereof.

In some embodiments, the compound of Formula I is a compound of Formula IV:

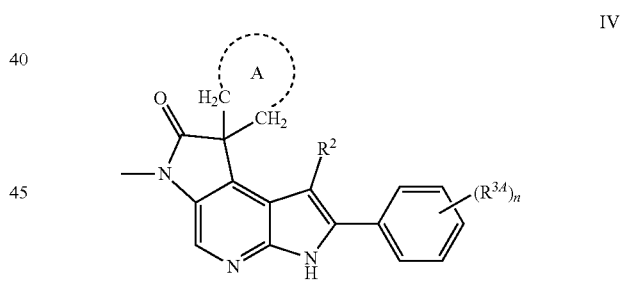

IV or a pharmaceutically acceptable salt thereof, wherein n is 0, 1, 2, 3, 4, or 5.

In some embodiments, the compound of Formula I is a compound of Formula IVa:

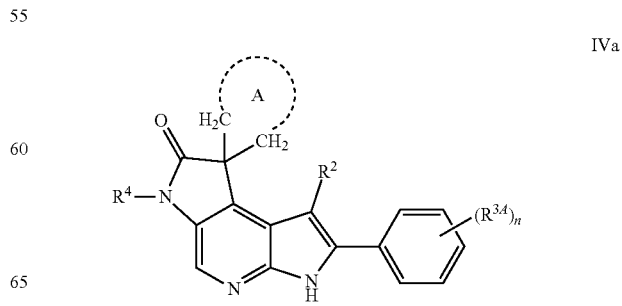

IVa or a pharmaceutically acceptable salt thereof, wherein n is 0, 1, 2, 3, 4, or 5.

In some embodiments, the compound of Formula I is a compound of Formula IVb:

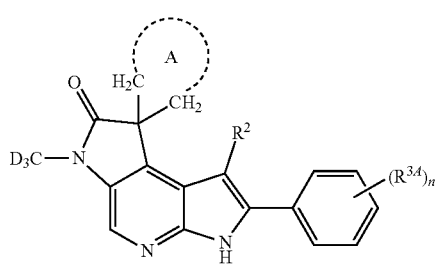

IVb or a pharmaceutically acceptable salt thereof, wherein n is 0, 1, 2, 3, 4, or 5.

In some embodiments, the compound of Formula I is a compound of Formula V:

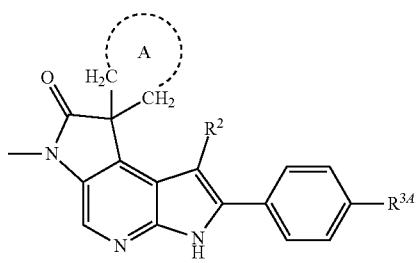

V or a pharmaceutically acceptable salt thereof.

In some embodiments, the compound of Formula I is a compound of Formula Va:

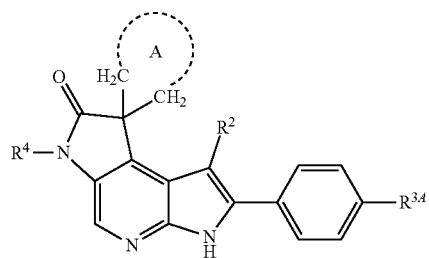

Va or a pharmaceutically acceptable salt thereof.

In some embodiments, the compound of Formula I is a compound of Formula Vb:

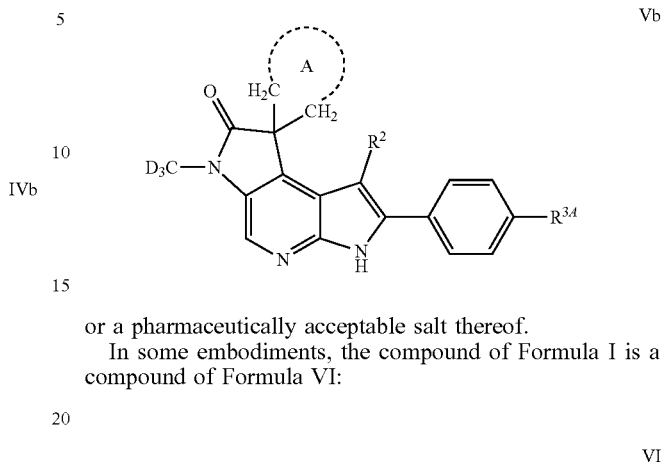

Vb or a pharmaceutically acceptable salt thereof.

In some embodiments, the compound of Formula I is a compound of Formula VI:

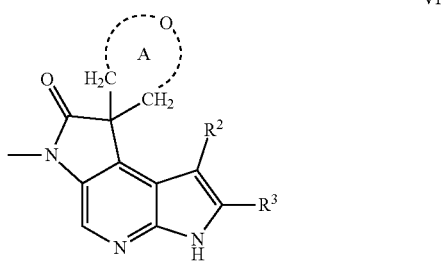

VI or a pharmaceutically acceptable salt thereof.

In some embodiments, the compound of Formula I is a compound of Formula VIa:

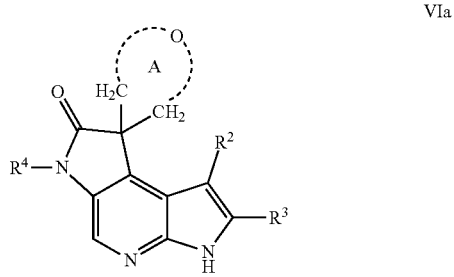

VIa or a pharmaceutically acceptable salt thereof.

In some embodiments, the compound of Formula I is a compound of Formula VIb:

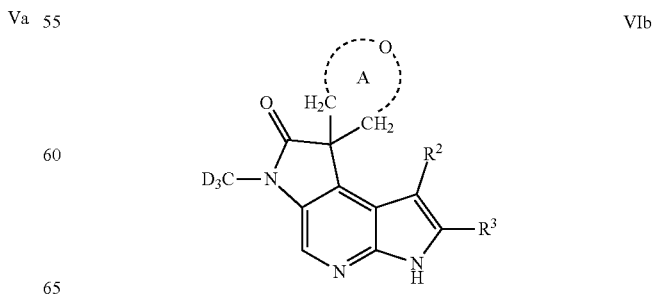

VIb or a pharmaceutically acceptable salt thereof.

In some embodiments, the compound of Formula I is a compound of Formula VII:

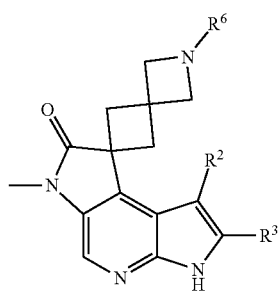

VII or a pharmaceutically acceptable salt thereof.

In some embodiments, the compound of Formula I is a compound of Formula VIIa:

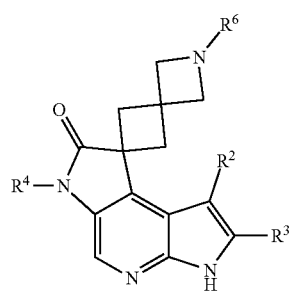

VIIa or a pharmaceutically acceptable salt thereof.

In some embodiments, the compound of Formula I is a compound of Formula VIIb:

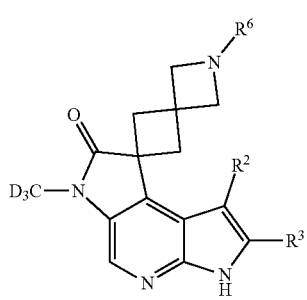

VIIb or a pharmaceutically acceptable salt thereof.

In some embodiments, the compound of Formula I is a compound of Formula VIII:

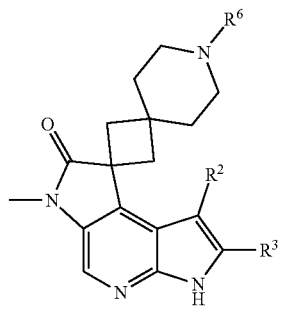

VIII or a pharmaceutically acceptable salt thereof.

In some embodiments, the compound of Formula I is a compound of Formula VIIIa:

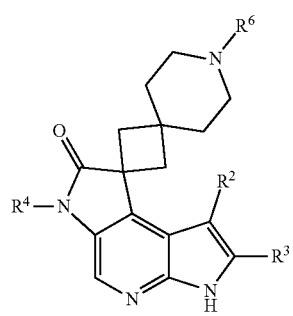

VIIIa or a pharmaceutically acceptable salt thereof.

In some embodiments, the compound of Formula I is a compound of Formula VIIIb:

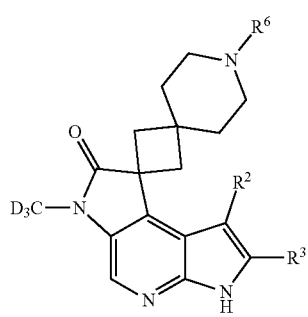

VIIIb or a pharmaceutically acceptable salt thereof.

In some embodiments, the compound of Formula I is a compound of Formula IX:

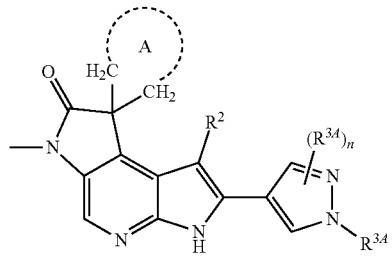

IX or a pharmaceutically acceptable salt thereof, where n is 0, 1, or 2.

In some embodiments, the compound of Formula I is a compound of Formula IXa:

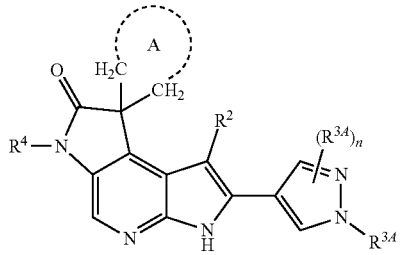

IXa or a pharmaceutically acceptable salt thereof, where n is 0, 1, or 2.

In some embodiments, the compound of Formula I is a compound of Formula IXb:

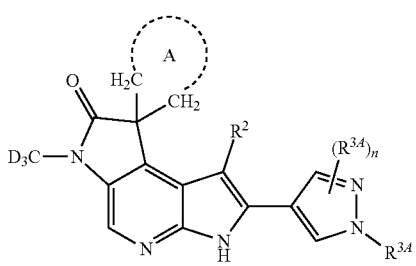

IXb or a pharmaceutically acceptable salt thereof, where n is 0, 1, or 2.

In some embodiments, the compound of Formula I is a compound of Formula X:

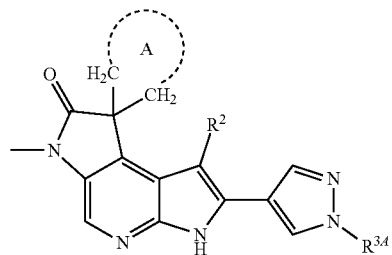

X or a pharmaceutically acceptable salt thereof.

In some embodiments, the compound of Formula I is a compound of Formula Xa:

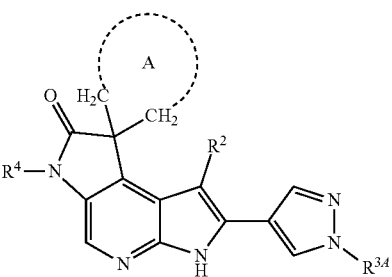

Xa or a pharmaceutically acceptable salt thereof.

In some embodiments, the compound of Formula I is a compound of Formula Xb:

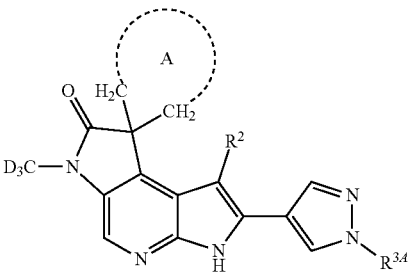

Xb or a pharmaceutically acceptable salt thereof.

In some embodiments, the compound provided herein (e.g., the compound of any of Formulas I-Xb), or a pharmaceutically acceptable salt thereof, comprises at least one deuterium atom.

In some embodiments, the compound provided herein (e.g., the compound of any of Formulas I-Xb), or a pharmaceutically acceptable salt thereof, comprises two or more deuterium atoms.

In some embodiments, all of the hydrogen atoms in the compound provided herein (e.g., the compound of any of Formulas I-Xb), or a pharmaceutically acceptable salt thereof, are replaced by deuterium atoms.

In some embodiments, the compound provided herein is selected from:

6-methyl-2-(4-((4-(methylsulfonyl)piperidin-1-yl)methyl) phenyl)-1-phenyl-2',3,3',5',6,6'-hexahydro-7H-spiro [dipyrrolo[2,3-b:3',2'-d]pyridine-8,4'-pyran]-7-one;

6-methyl-2-(4-((4-(methylsulfonyl)piperidin-1-yl)methyl) phenyl)-1-phenyl-3',4',5',6-tetrahydro-2'H,7H-spiro [dipyrrolo[2,3-b:3',2'-d]pyridine-8,3'-furan]-7-one;

1-(1-acetylpiperidin-4-yl)-6'-methyl-2'-(4-((4-(methylsulfonyl)piperidin-1-yl)methyl)phenyl)-1'-phenyl-3',6'-dihydro-7'H-spiro[azetidine-3,8'-dipyrrolo[2,3-b:3',2'-d]pyridin]-7'-one;

3-(6-methyl-2-(4-((4-(methylsulfonyl)piperidin-1-yl) methyl)phenyl)-7-oxo-1-phenyl-6,7-dihydro-3H-spiro [dipyrrolo[2,3-b:3',2'-d]pyridine-8,4'-piperidin]-1'-yl) propanenitrile;

3-(6-methyl-1-(1-methyl-1H-indazol-5-yl)-2-(4-((4-(methylsulfonyl)piperidin-1-yl)methyl)phenyl)-7-oxo-6,7-dihydro-3H-spiro[dipyrrolo[2,3-b:3',2'-d]pyridine-8,4'-piperidin]-1'-yl)propanenitrile;

2-(4-(4-(6-methyl-2-(1-methyl-1H-pyrazol-4-yl)-7-oxo-1-phenyl-6,7-dihydro-3H-spiro[dipyrrolo[2,3-b:3',2'-d] pyridine-8,4'-piperidin]-1'-yl)-1H-pyrazol-1-yl)tetrahydro-2H-pyran-4-yl)acetonitrile;

3-(6-methyl-1-(1-methyl-1H-indazol-5-yl)-2-(1-(methyl-d3)-1H-pyrazol-4-yl)-7-oxo-6,7-dihydro-3H-spiro[dipyrrolo[2,3-b:3',2'-d]pyridine-8,4'-piperidin]-1'-yl)propanenitrile;

6'-methyl-1'-(1-methyl-1H-indazol-5-yl)-2'-(1-(pyridin-4-ylmethyl)-1H-pyrazol-4-yl)-3',6'-dihydro-7'H-spiro[cyclopentane-1,8'-dipyrrolo[2,3-b:3',2'-d]pyridin]-7'-one;

2'-cyclopropyl-6'-methyl-1'-(1-methyl-1H-indazol-5-yl)-3',6'-dihydro-7'H-spiro[cyclopentane-1,8'-dipyrrolo[2,3-b:3',2'-d]pyridin]-7'-one;

6'-methyl-2'-(4-((4-(methylsulfonyl)piperidin-1-yl)methyl) phenyl)-1'-phenyl-3',6'-dihydro-7'H-spiro[cyclobutane-1,8'-dipyrrolo[2,3-b:3',2'-d]pyridin]-7'-one;

6'-methyl-2'-(4-((4-(methylsulfonyl)piperidin-1-yl)methyl) phenyl)-1'-phenyl-3',6'-dihydro-7'H-spiro[cyclohexane-1,8'-dipyrrolo[2,3-b:3',2'-d]pyridin]-7'-one;

6-methyl-2-(4-((4-(methylsulfonyl)piperidin-1-yl)methyl) phenyl)-1-phenyl-1'-(2-(tetrahydro-2H-pyran-4-yl) acetyl)-3,6-dihydro-7H-spiro[dipyrrolo[2,3-b:3',2'-d] pyridine-8,3'-pyrrolidin]-7-one;

8-acetyl-6'-methyl-2'-(4-((4-(methylsulfonyl)piperidin-1-yl) methyl)phenyl)-1'-phenyl-3',6'-dihydro-7'H-8-azaspiro [bicyclo[3.2.1]octane-3,8'-dipyrrolo[2,3-b:3',2'-d]pyridin]-7'-one;

3-(4-(4-(6'-methyl-2'-(1-methyl-1H-pyrazol-4-yl)-7'-oxo-6',7'-dihydro-3'H-spiro[cyclopentane-1,8'-dipyrrolo[2,3-b:3',2'-d]pyridin]-1'-yl)phenyl)-1H-pyrazol-1-yl)butanenitrile;

6-methyl-2-(4-((4-(methylsulfonyl)piperidin-1-yl)methyl) phenyl)-1-phenyl-1'-(pyrimidin-4-yl)-3,6-dihydro-7H-spiro[dipyrrolo[2,3-b:3',2'-d]pyridine-8,4'-piperidin]-7-one;

(1R,3r,5S)-6'-methyl-2'-(4-((4-(methylsulfonyl)piperidin-1-yl)methyl)phenyl)-1'-phenyl-8-(pyrimidin-4-yl)-3',6'-dihydro-7'H-8-azaspiro[bicyclo[3.2.1]octane-3,8'-dipyrrolo[2,3-b:3',2'-d]pyridin]-7'-one;

6-methyl-2-(1-methyl-1H-pyrazol-4-yl)-1-(2-methylthiazol-5-yl)-1'-(pyrimidin-4-yl)-3,6-dihydro-7H-spiro [dipyrrolo[2,3-b:3',2'-d]pyridine-8,4'-piperidin]-7-one;

6-methyl-2-(1-methyl-1H-pyrazol-4-yl)-1'-(pyrimidin-4-yl)-1-vinyl-3,6-dihydro-7H-spiro[dipyrrolo[2,3-b:3',2'-d] pyridine-8,4'-piperidin]-7-one;

1-ethyl-6-methyl-2-(1-methyl-1H-pyrazol-4-yl)-1'-(pyrimidin-4-yl)-3,6-dihydro-7H-spiro[dipyrrolo[2,3-b:3',2'-d] pyridine-8,4'-piperidin]-7-one;

1-(3,6-dihydro-2H-pyran-4-yl)-6-methyl-2-(1-methyl-1H-pyrazol-4-yl)-1'-(pyrimidin-4-yl)-3,6-dihydro-7H-spiro [dipyrrolo[2,3-b:3',2'-d]pyridine-8,4'-piperidin]-7-one;

N-(3-methoxyphenyl)-6-methyl-2-(4-((4-(methylsulfonyl) piperidin-1-yl)methyl)phenyl)-7-oxo-1-phenyl-6,7-dihydro-3H-spiro[dipyrrolo[2,3-b:3',2'-d]pyridine-8,4'-piperidine]-1'-carboxamide;

6'-methyl-2'-(1-methyl-1H-pyrazol-4-yl)-1'-(4-((4-(methylsulfonyl)piperazin-1-yl)methyl)phenyl)-3',6'-dihydro-7'H-spiro[cyclopentane-1,8'-dipyrrolo[2,3-b:3',2'-d]pyridin]-7'-one;

2-(1-(ethylsulfonyl)-3-(6-methyl-2-(1-methyl-1H-pyrazol-4-yl)-7-oxo-1-phenyl-6,7-dihydro-3H-spiro[dipyrrolo[2,3-b:3',2'-d]pyridine-8,4'-piperidin]-1'-yl)azetidin-3-yl)acetonitrile;

2-(1-acetyl-3-(6-methyl-2-(1-methyl-1H-pyrazol-4-yl)-7-oxo-1-phenyl-6,7-dihydro-3H-spiro[dipyrrolo[2,3-b:3',2'-d]pyridine-8,4'-piperidin]-1'-yl)azetidin-3-yl)acetonitrile;

3-(cyanomethyl)-N-ethyl-3-(6-methyl-2-(1-methyl-1H-pyrazol-4-yl)-7-oxo-1-phenyl-6,7-dihydro-3H-spiro [dipyrrolo[2,3-b:3',2'-d]pyridine-8,4'-piperidin]-1'-yl) azetidine-1-carboxamide;

2-(4-fluorophenyl)-2-(6-methyl-2-(1-methyl-1H-pyrazol-4-yl)-7-oxo-1-phenyl-6,7-dihydro-3H-spiro[dipyrrolo[2,3-b:3',2'-d]pyridine-8,4'-piperidin]-1'-yl)acetamide;

methyl (3-(cyanomethyl)-3-(6-methyl-2-(1-methyl-1H-pyrazol-4-yl)-7-oxo-1-phenyl-6,7-dihydro-3H-spiro [dipyrrolo[2,3-b:3',2'-d]pyridine-8,4'-piperidin]-1'-yl)cyclobutyl)carbamate;

1-(3-(cyanomethyl)-3-(6-methyl-2-(1-methyl-1H-pyrazol-4-yl)-7-oxo-1-phenyl-6,7-dihydro-3H-spiro[dipyrrolo[2,3-b:3',2'-d]pyridine-8,4'-piperidin]-1'-yl)cyclobutyl)-3-ethylurea;

N-(3-(cyanomethyl)-3-(6-methyl-2-(1-methyl-1H-pyrazol-4-yl)-7-oxo-1-phenyl-6,7-dihydro-3H-spiro[dipyrrolo[2,3-b:3',2'-d]pyridine-8,4'-piperidin]-1'-yl)cyclobutyl)benzenesulfonamide;

2-(1-(2-(1-(2,2-difluoroethyl)-1H-pyrazol-4-yl)-6-methyl-1-(1-methyl-1H-indazol-5-yl)-7-oxo-6,7-dihydro-3H-spiro[dipyrrolo[2,3-b:3',2'-d]pyridine-8,4'-piperidin]-1'-yl)cyclobutyl)acetonitrile;

2-(1-(6-methyl-1-(1-methyl-1H-indazol-5-yl)-2-(1-methyl-1H-pyrazol-4-yl)-7-oxo-6,7-dihydro-3H-spiro[dipyrrolo [2,3-b:3',2'-d]pyridine-8,4'-piperidin]-1'-yl)cyclobutyl) acetonitrile;

2-(1-(2-(1-(2-hydroxy-2-methylpropyl)-1H-pyrazol-4-yl)-6-methyl-1-(1-methyl-1H-indazol-5-yl)-7-oxo-6,7-dihydro-3H-spiro[dipyrrolo[2,3-b:3',2'-d]pyridine-8,4'-piperidin]-1'-yl)cyclobutyl)acetonitrile;

2-(1-(6-methyl-1-(1-methyl-1H-indazol-5-yl)-7-oxo-2-(1-(2,2,2-trifluoroethyl)-1H-pyrazol-4-yl)-6,7-dihydro-3H-spiro[dipyrrolo[2,3-b:3',2'-d]pyridine-8,4'-piperidin]-1'-yl)cyclobutyl)acetonitrile;

2-(1-(6-methyl-1-(1-methyl-1H-indazol-5-yl)-2-(4-(morpholine-4-carbonyl)cyclohex-1-en-1-yl)-7-oxo-6,7-dihydro-3H-spiro[dipyrrolo[2,3-b:3',2'-d]pyridine-8,4'-piperidin]-1'-yl)cyclobutyl)acetonitrile;

2-(1-(2-(4-(ethylsulfonyl)phenyl)-6-methyl-1-(1-methyl-1H-indazol-5-yl)-7-oxo-6,7-dihydro-3H-spiro[dipyrrolo [2,3-b:3',2'-d]pyridine-8,4'-piperidin]-1'-yl)cyclobutyl) acetonitrile;

2-(1-(2-(1-(2-methoxyethyl)-1H-pyrazol-4-yl)-6-methyl-1-(1-methyl-1H-indazol-5-yl)-7-oxo-6,7-dihydro-3H-spiro [dipyrrolo[2,3-b:3',2'-d]pyridine-8,4'-piperidin]-1'-yl)cyclobutyl)acetonitrile;

2-(1-(2-(1-(1-hydroxy-2-methylpropan-2-yl)-1H-pyrazol-4-yl)-6-methyl-1-(1-methyl-1H-indazol-5-yl)-7-oxo-6,7-dihydro-3H-spiro[dipyrrolo[2,3-b:3',2'-d]pyridine-8,4'-piperidin]-1'-yl)cyclobutyl)acetonitrile;

2-(1-(6-methyl-1-(1-methyl-1H-indazol-5-yl)-2-(1-(2-morpholinoethyl)-1H-pyrazol-4-yl)-7-oxo-6,7-dihydro-3H-spiro[dipyrrolo[2,3-b:3',2'-d]pyridine-8,4'-piperidin]-1'-yl)cyclobutyl)acetonitrile;

2-(1-(2-(1-(cyclopropylmethyl)-1H-pyrazol-4-yl)-6-methyl-1-(1-methyl-1H-indazol-5-yl)-7-oxo-6,7-dihydro-3H-spiro[dipyrrolo[2,3-b:3',2'-d]pyridine-8,4'-piperidin]-1'-yl)cyclobutyl)acetonitrile;

2-(1-(2-(3-cyclopropyl-1-methyl-1H-pyrazol-4-yl)-6-methyl-1-(1-methyl-1H-indazol-5-yl)-7-oxo-6,7-dihydro-3H-spiro[dipyrrolo[2,3-b:3',2'-d]pyridine-8,4'-piperidin]-1'-yl)cyclobutyl)acetonitrile;

2-(1-(2-(1-(1-acetylpiperidin-4-yl)-1H-pyrazol-4-yl)-6-methyl-1-(1-methyl-1H-indazol-5-yl)-7-oxo-6,7-dihydro-3H-spiro[dipyrrolo[2,3-b:3',2'-d]pyridine-8,4'-piperidin]-1'-yl)cyclobutyl)acetonitrile;

2-(1-(6-methyl-1-(1-methyl-1H-indazol-5-yl)-2-(1-methyl-1H-pyrrol-3-yl)-7-oxo-6,7-dihydro-3H-spiro[dipyrrolo[2,3-b:3',2'-d]pyridine-8,4'-piperidin]-1'-yl)cyclobutyl)acetonitrile;

2-(1-(6-methyl-1-(1-methyl-1H-indazol-5-yl)-7-oxo-2-(4,5,6,7-tetrahydropyrazolo[1,5-a]pyridin-3-yl)-6,7-dihydro-3H-spiro[dipyrrolo[2,3-b:3',2'-d]pyridine-8,4'-piperidin]-1'-yl)cyclobutyl)acetonitrile;

2-(1-(2-(1-(2-methoxy-2-methylpropyl)-1H-pyrazol-4-yl)-6-methyl-1-(1-methyl-1H-indazol-5-yl)-7-oxo-6,7-dihydro-3H-spiro[dipyrrolo[2,3-b:3',2'-d]pyridine-8,4'-piperidin]-1'-yl)cyclobutyl)acetonitrile;

2-(1-(6-methyl-1-(1-methyl-1H-indazol-5-yl)-7-oxo-2-(1-(tetrahydrofuran-3-yl)-1H-pyrazol-4-yl)-6,7-dihydro-3H-spiro[dipyrrolo[2,3-b:3',2'-d]pyridine-8,4'-piperidin]-1'-yl)cyclobutyl)acetonitrile;

2-(1-(2-(1-(2-methoxyethyl)-1H-pyrazol-4-yl)-6-methyl-1-(1-(methyl-d$_3$)-1H-indol-5-yl)-7-oxo-6,7-dihydro-3H-spiro[dipyrrolo[2,3-b:3',2'-d]pyridine-8,4'-piperidin]-1'-yl)cyclobutyl)acetonitrile;

2-(1-(1-(3,5-difluoro-4-methoxyphenyl)-2-(1-(2-hydroxy-2-methylpropyl)-1H-pyrazol-4-yl)-6-methyl-7-oxo-6,7-dihydro-3H-spiro[dipyrrolo[2,3-b:3',2'-d]pyridine-8,4'-piperidin]-1'-yl)cyclobutyl)acetonitrile;

2-(1-(2-(1-(2-hydroxy-2-methylpropyl)-1H-pyrazol-4-yl)-6-methyl-7-oxo-1-(thieno[3,2-c]pyridin-2-yl)-6,7-dihydro-3H-spiro[dipyrrolo[2,3-b:3',2'-d]pyridine-8,4'-piperidin]-1'-yl)cyclobutyl)acetonitrile;

2-(1-(1-(4-cyclopropylphenyl)-2-(1-(2-hydroxy-2-methylpropyl)-1H-pyrazol-4-yl)-6-methyl-7-oxo-6,7-dihydro-3H-spiro[dipyrrolo[2,3-b:3',2'-d]pyridine-8,4'-piperidin]-1'-yl)cyclobutyl)acetonitrile;

2-(1-(2-(1-(2-hydroxy-2-methylpropyl)-1H-pyrazol-4-yl)-6-methyl-7-oxo-1-(4-(trifluoromethoxy)phenyl)-6,7-dihydro-3H-spiro[dipyrrolo[2,3-b:3',2'-d]pyridine-8,4'-piperidin]-1'-yl)cyclobutyl)acetonitrile;

4-(1'-(1-(cyanomethyl)cyclobutyl)-2-(1-(2,2-difluoroethyl)-1H-pyrazol-4-yl)-6-methyl-7-oxo-6,7-dihydro-3H-spiro[dipyrrolo[2,3-b:3',2'-d]pyridine-8,4'-piperidin]-1'-yl)benzonitrile;

2-(1-(2-(1-(2-hydroxy-2-methylpropyl)-1H-pyrazol-4-yl)-6-methyl-7-oxo-1-(4-(trifluoromethyl)phenyl)-6,7-dihydro-3H-spiro[dipyrrolo[2,3-b:3',2'-d]pyridine-8,4'-piperidin]-1'-yl)cyclobutyl)acetonitrile;

(R)-1-(ethylsulfonyl)-2'-(1-isopropyl-1H-pyrazol-4-yl)-6'-methyl-1'-(1-methyl-1H-indazol-5-yl)-3',6'-dihydro-7'H-spiro[azepane-4,8'-dipyrrolo[2,3-b:3',2'-d]pyridin]-7'-one;

(S)-1-(ethylsulfonyl)-2'-(1-isopropyl-1H-pyrazol-4-yl)-6'-methyl-1'-(1-methyl-1H-indazol-5-yl)-3',6'-dihydro-7'H-spiro[azepane-4,8'-dipyrrolo[2,3-b:3',2'-d]pyridin]-7'-one;

1-(ethylsulfonyl)-2''-(1-isopropyl-1H-pyrazol-4-yl)-6''-methyl-1''-(1-methyl-1H-indazol-5-yl)-3'',6''-dihydro-7''H-dispiro[azetidine-3,1'-cyclobutane-3',8''-dipyrrolo[2,3-b:3',2'-d]pyridin]-7''-one;

N-((1S,3R)-6'-methyl-1'-(1-methyl-1H-indazol-5-yl)-2'-(1-methyl-1H-pyrazol-4-yl)-7'-oxo-6',7'-dihydro-3'H-spiro[cyclopentane-1,8'-dipyrrolo[2,3-b:3',2'-d]pyridin]-3-yl)cyclopropanesulfonamide;

N-((1R,3S)-6'-methyl-1'-(1-methyl-1H-indazol-5-yl)-2'-(1-methyl-1H-pyrazol-4-yl)-7'-oxo-6',7'-dihydro-3'H-spiro[cyclopentane-1,8'-dipyrrolo[2,3-b:3',2'-d]pyridin]-3-yl)cyclopropanesulfonamide;

N-((1S,3S)-6'-methyl-1'-(1-(methyl-d$_3$)-1H-indazol-5-yl)-2'-(1-methyl-1H-pyrazol-4-yl)-7'-oxo-6',7'-dihydro-3'H-spiro[cyclopentane-1,8'-dipyrrolo[2,3-b:3',2'-d]pyridin]-3-yl)cyclopropanesulfonamide;

N-((1R,3R)-6'-methyl-1'-(1-(methyl-d$_3$)-1H-indazol-5-yl)-2'-(1-methyl-1H-pyrazol-4-yl)-7'-oxo-6',7'-dihydro-3'H-spiro[cyclopentane-1,8'-dipyrrolo[2,3-b:3',2'-d]pyridin]-3-yl)cyclopropanesulfonamide;

6-methyl-2-(4-((4-(methylsulfonyl)piperidin-1-yl)methyl)phenyl)-1',3,3',6-tetrahydro-7H-spiro[dipyrrolo[2,3-b:3',2'-d]pyridine-8,2'-inden]-7-one;

methyl 6-methyl-2-(1-methyl-1H-pyrazol-4-yl)-1-(1-(methyl-d$_3$)-1H-indazol-5-yl)-7-oxo-6,7-dihydro-3H-dispiro[dipyrrolo[2,3-b:3',2'-d]pyridine-8,1'-cyclobutane-3',4''-piperidine]-1''-carboxylate;

1''-butyryl-6-methyl-1-(1-methyl-1H-indazol-5-yl)-2-(1-methyl-1H-pyrazol-4-yl)-3,6-dihydro-7H-dispiro[dipyrrolo[2,3-b:3',2'-d]pyridine-8,1'-cyclobutane-3',4''-piperidin]-7-one;

N,N,6-trimethyl-1-(1-methyl-1H-indazol-5-yl)-2-(1-methyl-1H-pyrazol-4-yl)-7-oxo-6,7-dihydro-3H-dispiro[dipyrrolo[2,3-b:3',2'-d]pyridine-8,1'-cyclobutane-3',4''-piperidine]-1''-carboxamide;

methyl 6-methyl-1-(1-methyl-1H-indazol-5-yl)-2-(1-methyl-1H-pyrazol-4-yl)-7-oxo-6,7-dihydro-3H-dispiro[dipyrrolo[2,3-b:3',2'-d]pyridine-8,1'-cyclobutane-3',4''-piperidine]-1''-carboxylate;

1''-((2-methoxy ethyl)sulfonyl)-6-methyl-2-(1-methyl-1H-pyrazol-4-yl)-1-phenyl-3,6-dihydro-7H-dispiro[dipyrrolo[2,3-b:3',2'-d]pyridine-8,1'-cyclobutane-3',4''-piperidin]-7-one;

4-(1''-butyryl-6-methyl-1-(1-methyl-1H-indazol-5-yl)-7-oxo-6,7-dihydro-3H-dispiro[dipyrrolo[2,3-b:3',2'-d]pyridine-8,1'-cyclobutane-3',4''-piperidin]-2-yl)-N,N-dimethyl cyclohex-3-ene-1-carboxamide;

1''-butyryl-6-methyl-1-(1-methyl-1H-indazol-5-yl)-2-(1-methyl-1H-pyrrol-3-yl)-3,6-dihydro-7H-dispiro[dipyrrolo[2,3-b:3',2'-d]pyridine-8,1'-cyclobutane-3',4''-piperidin]-7-one;

(R)-2-(1-((6-methyl-1-(1-methyl-1H-indazol-5-yl)-2-(1-methyl-1H-pyrazol-4-yl)-7-oxo-6,7-dihydro-3H-spiro[dipyrrolo[2,3-b:3',2'-d]pyridine-8,3'-pyrrolidin]-1'-yl)methyl)cyclopropyl)acetonitrile;

(S)-2-(1-((6-methyl-1-(1-methyl-1H-indazol-5-yl)-2-(1-methyl-1H-pyrazol-4-yl)-7-oxo-6,7-dihydro-3H-spiro[dipyrrolo[2,3-b:3',2'-d]pyridine-8,3'-pyrrolidin]-1'-yl)methyl)cyclopropyl)acetonitrile;

2-(1-(((6-methyl-1-(1-methyl-1H-indazol-5-yl)-7-oxo-2-(3-oxo-3,4-dihydro-2H-benzo[b][1,4]oxazin-7-yl)-6,7-dihydro-3H-spiro[dipyrrolo[2,3-b:3',2'-d]pyridine-8,3'-pyrrolidin]-1'-yl)methyl)cyclopropyl)acetonitrile;

2-(1-((6-methyl-1-(1-methyl-1H-indazol-5-yl)-7-oxo-2-(pyrazolo[1,5-a]pyrimidin-3-yl)-6,7-dihydro-3H-spiro[dipyrrolo[2,3-b:3',2'-d]pyridine-8,3'-pyrrolidin]-1'-yl)methyl)cyclopropyl)acetonitrile;

4-((4-(1'-((1-(cyanomethyl)cyclopropyl)methyl)-6-methyl-1-(1-methyl-1H-indazol-5-yl)-7-oxo-6,7-dihydro-3H-spiro[dipyrrolo[2,3-b:3',2'-d]pyridine-8,3'-pyrrolidin]-2-yl)-1H-pyrazol-1-yl)methyl)benzonitrile;

2-(2-((6-methyl-1-(1-methyl-1H-indazol-5-yl)-2-(1-methyl-1H-pyrazol-4-yl)-7-oxo-6,7-dihydro-3H-spiro[dipyrrolo[2,3-b:3',2'-d]pyridine-8,3'-pyrrolidin]-1'-yl)methyl)spiro[3.3]heptan-2-yl)acetonitrile;

2-(1-((6-methyl-1-(1-methyl-1H-indazol-5-yl)-2-(1-methyl-1H-pyrazol-4-yl)-7-oxo-6,7-dihydro-3H-spiro[dipyrrolo[2,3-b:3',2'-d]pyridine-8,3'-pyrrolidin]-1'-yl)sulfonyl)cyclopropyl)acetonitrile;

2-(1-((6-methoxy-1-(1-methyl-1H-indazol-5-yl)-2-(1-methyl-1H-pyrazol-4-yl)-7-oxo-6,7-dihydro-3H-spiro[dipyrrolo[2,3-b:3',2'-d]pyridine-8,3'-pyrrolidin]-1'-yl)methyl)cyclopropyl)acetonitrile;

2-(1-(6-methyl-1-(1-methyl-1H-indazol-5-yl)-2-(1-methyl-1H-pyrazol-4-yl)-7-oxo-6,7-dihydro-3H-spiro[dipyrrolo[2,3-b:3',2'-d]pyridine-8,4'-piperidin]-1'-yl)cyclopentyl)acetonitrile;

2-(1-(6-methyl-1-(1-methyl-1H-indazol-5-yl)-2-(1-methyl-1H-pyrazol-4-yl)-7-oxo-6,7-dihydro-1'H,3H-spiro[dipyrrolo[2,3-b:3',2'-d]pyridine-8,4'-pyridin]-1'-yl)cyclopropyl)acetonitrile;

2-(4-methoxy-1-(6-methyl-1-(1-methyl-1H-indazol-5-yl)-2-(1-methyl-1H-pyrazol-4-yl)-7-oxo-6,7-dihydro-3H-spiro[dipyrrolo[2,3-b:3',2'-d]pyridine-8,4'-piperidin]-1'-yl)cyclohexyl)acetonitrile;

1'-(2-(1H-1,2,3-triazol-4-yl)propan-2-yl)-6-methyl-1-(1-methyl-1H-indazol-5-yl)-2-(1-methyl-1H-pyrazol-4-yl)-3,6-dihydro-7H-spiro[dipyrrolo[2,3-b:3',2'-d]pyridine-8,4'-piperidin]-7-one;

1'-(2-(4H-1,2,4-triazol-3-yl)propan-2-yl)-6-methyl-1-(1-methyl-1H-indazol-5-yl)-2-(1-methyl-1H-pyrazol-4-yl)-3,6-dihydro-7H-spiro[dipyrrolo[2,3-b:3',2'-d]pyridine-8,4'-piperidin]-7-one;

6-methyl-1'-(3-methyl-1,1-dioxidotetrahydrothiophen-3-yl)-1-(1-methyl-1H-indazol-5-yl)-2-(1-methyl-1H-pyrazol-4-yl)-3,6-dihydro-7H-spiro[dipyrrolo[2,3-b:3',2'-d]pyridine-8,4'-piperidin]-7-one;

2-(1-(2-(5,6-dihydro-4H-pyrrolo[1,2-b]pyrazol-3-yl)-6-methyl-1-(1-(methyl-d₃)-1H-indazol-5-yl)-7-oxo-6,7-dihydro-3H-spiro[dipyrrolo[2,3-b:3',2'-d]pyridine-8,4'-piperidin]-1'-yl)cyclopentyl)acetonitrile;

(R)-4-methoxy-3-methyl-3-(6-methyl-2-(1-methyl-1H-pyrazol-4-yl)-1-(1-(methyl-d₃)-1H-indazol-5-yl)-7-oxo-6,7-dihydro-3H-spiro[dipyrrolo[2,3-b:3',2'-d]pyridine-8,4'-piperidin]-1'-yl)butanenitrile;

(S)-4-methoxy-3-methyl-3-(6-methyl-2-(1-methyl-1H-pyrazol-4-yl)-1-(1-(methyl-d₃)-1H-indazol-5-yl)-7-oxo-6,7-dihydro-3H-spiro[dipyrrolo[2,3-b:3',2'-d]pyridine-8,4'-piperidin]-1'-yl)butanenitrile;

methyl 4-(cyanomethyl)-4-(6-methyl-1-(1-methyl-1H-indazol-5-yl)-2-(1-methyl-1H-pyrazol-4-yl)-7-oxo-6,7-dihydro-3H-spiro[dipyrrolo[2,3-b:3',2'-d]pyridine-8,4'-piperidin]-1'-yl)piperidine-1-carboxylate;

N-(3-(6-methyl-1-(1-methyl-1H-indazol-5-yl)-2-(1-methyl-1H-pyrazol-4-yl)-7-oxo-6,7-dihydro-3H-spiro[dipyrrolo[2,3-b:3',2'-d]pyridine-8,4'-piperidin]-1'-yl)bicyclo[1.1.1]pentan-1-yl)acetamide;

methyl 4-(6-methyl-1-(1-methyl-1H-indazol-5-yl)-2-(1-methyl-1H-pyrazol-4-yl)-7-oxo-6,7-dihydro-3H-spiro[dipyrrolo[2,3-b:3',2'-d]pyridine-8,4'-piperidin]-1'-yl)-2-azabicyclo[2.1.1]hexane-2-carboxylate;

1'-(2-(azetidin-3-yl)propan-2-yl)-6-methyl-1-(1-methyl-1H-indazol-5-yl)-2-(1-methyl-1H-pyrazol-4-yl)-3,6-dihydro-7H-spiro[dipyrrolo[2,3-b:3',2'-d]pyridine-8,4'-piperidin]-7-one;

1-(ethylsulfonyl)-6"-methyl-1"-(1-(methyl-d₃)-1H-indazol-5-yl)-2"-(4-(morpholinomethyl)phenyl)-3",6"-dihydro-7"H-dispiro[azetidine-3,1'-cyclobutane-3',8"-dipyrrolo[2,3-b:3',2'-d]pyridin]-7"-one;

1-(ethylsulfonyl)-6"-methyl-1"-(1-methyl-1H-indazol-5-yl)-2"-(1-methyl-1H-pyrazol-4-yl)-3",6"-dihydro-7"H-dispiro[azetidine-3,1'-cyclobutane-3',8"-dipyrrolo[2,3-b:3',2'-d]pyridin]-7"-one;

2"-(1-(cyclopropylmethyl)-1H-pyrazol-4-yl)-1-(ethyl sulfonyl)-6"-methyl-1"-(1-methyl-1H-indazol-5-yl)-3",6"-dihydro-7"H-dispiro[azetidine-3,1'-cyclobutane-3',8"-dipyrrolo[2,3-b:3',2'-d]pyridin]-7"-one;

1-(ethylsulfonyl)-2"-(1-(2-methoxyethyl)-1H-pyrazol-4-yl)-6"-methyl-1"-(1-methyl-1H-indazol-5-yl)-3",6"-dihydro-7"H-dispiro[azetidine-3,1'-cyclobutane-3',8"-dipyrrolo[2,3-b:3',2'-d]pyridin]-7"-one;

1-(ethylsulfonyl)-2"-(1-isopropyl-1H-pyrazol-4-yl)-6"-(methyl-d₃)-1"-(1-methyl-1H-indazol-5-yl)-3",6"-dihydro-7"H-dispiro[azetidine-3,1'-cyclobutane-3',8"-dipyrrolo[2,3-b:3',2'-d]pyridin]-7"-one;

2"-(1-cyclopentyl-1H-pyrazol-4-yl)-1-(e thyl sulfonyl)-6"-methyl-1"-(1-methyl-1H-indazol-5-yl)-3",6"-dihydro-7"H-dispiro[azetidine-3,1'-cyclobutane-3',8"-dipyrrolo[2,3-b:3',2'-d]pyridin]-7"-one;

1-(4-(1-(ethylsulfonyl)-6"-methyl-1"-(1-(methyl-d₃)-1H-indazol-5-yl)-7"-oxo-6",7"-dihydro-3"H-dispiro[azetidine-3,1'-cyclobutane-3',8"-dipyrrolo[2,3-b:3',2'-d]pyridin]-2"-yl)benzyl)piperidine-4-carbonitrile;

1-(ethylsulfonyl)-1"-(4-methoxyphenyl)-6"-(methyl-d₃)-2"-(4-(morpholinomethyl)phenyl)-3",6"-dihydro-7"H-dispiro[azetidine-3,1'-cyclobutane-3',8"-dipyrrolo[2,3-b:3',2'-d]pyridin]-7"-one;

2"-(1-(2,2-difluoroethyl)-1H-pyrazol-4-yl)-1-(ethylsulfonyl)-6"-methyl-1"-(1-methyl-1H-indazol-5-yl)-3",6"-dihydro-7"H-dispiro[azetidine-3,1'-cyclobutane-3',8"-dipyrrolo[2,3-b:3',2'-d]pyridin]-7"-one;

2"-(5,6-dihydro-4H-pyrrolo[1,2-b]pyrazol-3-yl)-1-(ethylsulfonyl)-6"-methyl-1"-(1-methyl-1H-indazol-5-yl)-3",6"-dihydro-7"H-dispiro[azetidine-3,1'-cyclobutane-3',8"-dipyrrolo[2,3-b:3',2'-d]pyridin]-7"-one;

2"-(1-ethyl-1H-pyrazol-4-yl)-1-(ethylsulfonyl)-1"-(4-methoxyphenyl)-6"-(methyl-d₃)-3",6"-dihydro-7"H-dispiro[azetidine-3,1'-cyclobutane-3',8"-dipyrrolo[2,3-b:3',2'-d]pyridin]-7"-one;

1-(ethylsulfonyl)-2"-(1-(2-methoxy-2-methylpropyl)-1H-pyrazol-4-yl)-6"-methyl-1"-(1-(methyl-d₃)-1H-indazol-5-yl)-3",6"-dihydro-7"H-dispiro[azetidine-3,1'-cyclobutane-3',8"-dipyrrolo[2,3-b:3',2'-d]pyridin]-7"-one;

1-(ethylsulfonyl)-6"-methyl-1"-(1-methyl-1H-indazol-5-yl)-2"-(1-((tetrahydro-2H-pyran-4-yl)methyl)-1H-pyrazol-4-yl)-3",6"-dihydro-7"H-dispiro[azetidine-3,1'-cyclobutane-3',8"-dipyrrolo[2,3-b:3',2'-d]pyridin]-7"-one;

2"-(6,7-dihydro-5H-pyrazolo[5,1-b][1,3]oxazin-3-yl)-1-(ethylsulfonyl)-6"-methyl-1"-(1-(methyl-d₃)-1H-indazol-5-yl)-3",6"-dihydro-7"H-dispiro[azetidine-3,1'-cyclobutane-3',8"-dipyrrolo[2,3-b:3',2'-d]pyridin]-7"-one;

1-(ethylsulfonyl)-2"-(3-methoxy-1-methyl-1H-pyrazol-4-yl)-6"-methyl-1"-(1-(methyl-d₃)-1H-indazol-5-yl)-3",6"-dihydro-7"H-dispiro[azetidine-3,1'-cyclobutane-3',8"-dipyrrolo[2,3-b:3',2'-d]pyridin]-7"-one;

1-(2-amino-2-oxoethyl)-N-((1S,3S)-6'-methyl-2'-(1-methyl-1H-pyrazol-4-yl)-1'-(1-(methyl-d$_3$)-1H-indazol-5-yl)-7'-oxo-6',7'-dihydro-3'H-spiro[cyclopentane-1,8'-dipyrrolo[2,3-b:3',2'-d]pyridin]-3-yl)cyclobutane-1-carboxamide;

1-(2-amino-2-oxoethyl)-N-((1R,3R)-6'-methyl-2'-(1-methyl-1H-pyrazol-4-yl)-1'-(1-(methyl-d$_3$)-1H-indazol-5-yl)-7'-oxo-6',7'-dihydro-3'H-spiro[cyclopentane-1,8'-dipyrrolo[2,3-b:3',2'-d]pyridin]-3-yl)cyclobutane-1-carboxamide;

1''-butyryl-6-methyl-1-(1-methyl-1H-indazol-5-yl)-2-(1-(methyl-d$_3$)-1H-pyrrol-3-yl)-3,6-dihydro-7H-dispiro[dipyrrolo[2,3-b:3',2'-d]pyridine-8,1'-cyclobutane-3',4''-piperidin]-7-one;

1''-butyryl-6-methyl-1-(1-(methyl-d$_3$)-1H-indazol-5-yl)-2-(1-(methyl-d$_3$)-1H-pyrrol-3-yl)-3,6-dihydro-7H-dispiro[dipyrrolo[2,3-b:3',2'-d]pyridine-8,1'-cyclobutane-3',4''-piperidin]-7-one;

2'-(1-isopropyl-1H-pyrazol-4-yl)-6'-(methyl-d$_3$)-1'-(1-methyl-1H-indazol-5-yl)-1-(1-methylcyclopropyl)sulfonyl)-3',6'-dihydro-7'H-spiro[azepane-4,8'-dipyrrolo[2,3-b:3',2'-d]pyridin]-7'-one; and 2'-(1-(1-cyclopropylethyl)-1H-pyrazol-4-yl)-1-(ethylsulfonyl)-6'-(methyl-d$_3$)-1'-(1-methyl-1H-indazol-5-yl)-3',6'-dihydro-7'H-spiro[azepane-4,8'-dipyrrolo[2,3-b:3',2'-d]pyridin]-7'-one;

or a pharmaceutically acceptable salt thereof.

It is further appreciated that certain features of the invention, which are, for clarity, described in the context of separate embodiments, can also be provided in combination in a single embodiment. Conversely, various features of the invention which are, for brevity, described in the context of a single embodiment, can also be provided separately or in any suitable subcombination.

At various places in the present specification, divalent linking substituents are described. It is specifically intended that each divalent linking substituent include both the forward and backward forms of the linking substituent. For example, —NR(CR'R'')$_n$— includes both —NR(CR'R'')$_n$— and —(CR'R'')$_n$NR—. Where the structure clearly requires a linking group, the Markush variables listed for that group are understood to be linking groups.

The term "n-membered" where n is an integer typically describes the number of ring-forming atoms in a moiety where the number of ring-forming atoms is n. For example, piperidinyl is an example of a 6-membered heterocycloalkyl ring, pyrazolyl is an example of a 5-membered heteroaryl ring, pyridyl is an example of a 6-membered heteroaryl ring, and 1,2,3,4-tetrahydro-naphthalene is an example of a 10-membered cycloalkyl group.

As used herein, the phrase "optionally substituted" means unsubstituted or substituted. The substituents are independently selected, and substitution may be at any chemically accessible position. As used herein, the term "substituted" means that a hydrogen atom is removed and replaced by a substituent. A single divalent substituent, e.g., oxo, can replace two hydrogen atoms. It is to be understood that substitution at a given atom is limited by valency.

As used herein, the phrase "each 'variable' is independently selected from" means substantially the same as wherein "at each occurrence 'variable' is selected from."

Throughout the definitions, the terms "C$_{n-m}$" and "C$_{n-m}$" indicates a range which includes the endpoints, wherein n and m are integers and indicate the number of carbons. Examples include C$_{1-3}$, C$_{1-4}$, C$_{1-6}$, and the like.

As used herein, the term "C$_{n-m}$ alkyl", employed alone or in combination with other terms, refers to a saturated hydrocarbon group that may be straight-chain or branched, having n to m carbons. Examples of alkyl moieties include, but are not limited to, chemical groups such as methyl (Me), ethyl (Et), n-propyl (n-Pr), isopropyl (iPr), n-butyl, tert-butyl, isobutyl, sec-butyl; higher homologs such as 2-methyl-1-butyl, n-pentyl, 3-pentyl, n-hexyl, 1,2,2-trimethylpropyl, and the like. In some embodiments, the alkyl group contains from 1 to 6 carbon atoms, from 1 to 4 carbon atoms, from 1 to 3 carbon atoms, from 2 to 6 carbon atoms, from 2 to 4 carbon atoms, from 2 to 3 carbon atoms, or 1 to 2 carbon atoms.

As used herein, "C$_{n-m}$ alkenyl" refers to an alkyl group having one or more double carbon-carbon bonds and having n to m carbons. Example alkenyl groups include, but are not limited to, ethenyl, n-propenyl, isopropenyl, n-butenyl, sec-butenyl, and the like. In some embodiments, the alkenyl moiety contains 2 to 6, 2 to 4, or 2 to 3 carbon atoms.

As used herein, "C$_{n-m}$ alkynyl" refers to an alkyl group having one or more triple carbon-carbon bonds and having n to m carbons. Example alkynyl groups include, but are not limited to, ethynyl, propyn-1-yl, propyn-2-yl, and the like. In some embodiments, the alkynyl moiety contains 2 to 6, 2 to 4, or 2 to 3 carbon atoms.

As used herein, the term "C$_{n-m}$ alkoxy", employed alone or in combination with other terms, refers to a group of formula —O-alkyl, wherein the alkyl group has n to m carbons. Example alkoxy groups include, but are not limited to, methoxy, ethoxy, propoxy (e.g., n-propoxy and isopropoxy), butoxy (e.g., n-butoxy and tert-butoxy), and the like. In some embodiments, the alkyl group has 1 to 6, 1 to 4, or 1 to 3 carbon atoms.

As used herein, the term "aryl," employed alone or in combination with other terms, refers to an aromatic hydrocarbon group, which may be monocyclic or polycyclic (e.g., having 2, 3 or 4 fused rings). The term "C$_{n-m}$ aryl" refers to an aryl group having from n to m ring carbon atoms. Aryl groups include, e.g., phenyl, naphthyl, anthracenyl, phenanthrenyl, indanyl, indenyl, and the like. In some embodiments, aryl groups have from 5 to 10 carbon atoms. In some embodiments, the aryl group is phenyl or naphthyl. In some embodiments, the aryl is phenyl.

As used herein, "halo" refers to F, Cl, Br, or I. In some embodiments, a halo is F, Cl, or Br. In some embodiments, a halo is F or Cl. In some embodiments, a halo is F. In some embodiments, a halo is Cl.

As used herein, "C$_{n-m}$ haloalkoxy" refers to a group of formula —O-haloalkyl having n to m carbon atoms. Example haloalkoxy groups include OCF$_3$ and OCHF$_2$. In some embodiments, the haloalkoxy group is fluorinated only. In some embodiments, the alkyl group has 1 to 6, 1 to 4, or 1 to 3 carbon atoms.

As used herein, the term "C$_{n-m}$ haloalkyl", employed alone or in combination with other terms, refers to an alkyl group having from one halogen atom to 2s+1 halogen atoms which may be the same or different, where "s" is the number of carbon atoms in the alkyl group, wherein the alkyl group has n to m carbon atoms. In some embodiments, the haloalkyl group is fluorinated only. In some embodiments, the alkyl group has 1 to 6, 1 to 4, or 1 to 3 carbon atoms. Example haloalkyl groups include CF$_3$, C$_2$F$_5$, CHF$_2$, CH$_2$F, CCl$_3$, CHCl$_2$, C$_2$Cl$_5$ and the like.

As used herein, "cycloalkyl" refers to non-aromatic cyclic hydrocarbons including cyclized alkyl and alkenyl groups. Cycloalkyl groups can include mono- or polycyclic (e.g., having 2 fused rings) groups, spirocycles, and bridged rings (e.g., a bridged bicycloalkyl group). Ring-forming carbon atoms of a cycloalkyl group can be optionally substituted by oxo or sulfido (e.g., C(O) or C(S)). Also included in the definition of cycloalkyl are moieties that have one or more aromatic rings fused (i.e., having a bond in common with) to the cycloalkyl ring, for example, benzo or thienyl derivatives of cyclopentane, cyclohexane, and the like. A cycloalkyl group containing a fused aromatic ring can be attached through any ring-forming atom including a ring-forming atom of the fused aromatic ring. Cycloalkyl groups can have 3, 4, 5, 6, 7, 8, 9, or 10 ring-forming carbons (i.e., $C_{3-10}$). In some embodiments, the cycloalkyl is a Cmomonocyclic or bicyclic cycloalkyl. In some embodiments, the cycloalkyl is a $C_{3-7}$ monocyclic cycloalkyl. In some embodiments, the cycloalkyl is a $C_{4-7}$ monocyclic cycloalkyl. In some embodiments, the cycloalkyl is a $C_{4-10}$ spirocycle or bridged cycloalkyl (e.g., a bridged bicycloalkyl group). Example cycloalkyl groups include cyclopropyl, cyclobutyl, cyclopentyl, cyclohexyl, cycloheptyl, cyclopentenyl, cyclohexenyl, cyclohexadienyl, cycloheptatrienyl, norbornyl, norpinyl, norcarnyl, cubane, adamantane, bicyclo[1.1.1]pentyl, bicyclo[2.1.1]hexyl, bicyclo[2.2.1]heptanyl, bicyclo[3.1.1]heptanyl, bicyclo[2.2.2]octanyl, spiro[3.3]heptanyl, and the like. In some embodiments, cycloalkyl is cyclopropyl, cyclobutyl, cyclopentyl, or cyclohexyl.

As used herein, "heteroaryl" refers to a monocyclic or polycyclic (e.g., having 2 fused rings) aromatic heterocycle having at least one heteroatom ring member selected from N, O, S and B. In some embodiments, the heteroaryl ring has 1, 2, 3, or 4 heteroatom ring members independently selected from N, O, S and B. In some embodiments, any ring-forming N in a heteroaryl moiety can be an N-oxide. In some embodiments, the heteroaryl is a 5-10 membered monocyclic or bicyclic heteroaryl having 1, 2, 3, or 4 heteroatom ring members independently selected from N, O, S, and B. In some embodiments, the heteroaryl is a 5-, 7-, 8-, 9-, or 10-membered monocyclic or bicyclic heteroaryl having 1, 2, 3, or 4 heteroatom ring members independently selected from N, O, S, and B. In some embodiments, the heteroaryl is a 5-10 membered monocyclic or bicyclic heteroaryl having 1, 2, 3, or 4 heteroatom ring members independently selected from N, O, and S. In some embodiments, the heteroaryl is a 5-, 7-, 8-, 9-, or 10-membered monocyclic or bicyclic heteroaryl having 1, 2, 3, or 4 heteroatom ring members independently selected from N, O, and S. In some embodiments, the heteroaryl is a 5-6 membered monocyclic heteroaryl having 1 or 2 heteroatom ring members independently selected from N, O, S, and B. In some embodiments, the heteroaryl is a 5 membered monocyclic heteroaryl having 1 or 2 heteroatom ring members independently selected from N, O, S, and B. In some embodiments, the heteroaryl is a 5 membered monocyclic heteroaryl having 1 or 2 heteroatom ring members independently selected from N, O, and S. In some embodiments, the heteroaryl group contains 5 to 10, 5 to 7, 3 to 7, or 5 to 6 ring-forming atoms. In some embodiments, the heteroaryl group has 1 to 4 ring-forming heteroatoms, 1 to 3 ring-forming heteroatoms, 1 to 2 ring-forming heteroatoms or 1 ring-forming heteroatom. When the heteroaryl group contains more than one heteroatom ring member, the heteroatoms may be the same or different. Example heteroaryl groups include, but are not limited to, thienyl (or thiophenyl), furyl (or furanyl), pyrrolyl, imidazolyl, thiazolyl, oxazolyl, pyrazolyl, isothiazolyl, isoxazolyl, 1,2,3-triazolyl, tetrazolyl, 1,2,3-thiadiazolyl, 1,2,3-oxadiazolyl, 1,2,4-triazolyl, 1,2,4-thiadiazolyl, 1,2,4-oxadiazolyl, 1,3,4-triazolyl, 1,3,4-thiadiazolyl, 1,3,4-oxadiazolyl and 1,2-dihydro-1,2-azaborine, pyridinyl, pyrimidinyl, pyrazinyl, pyridazinyl, azolyl, triazolyl, thiadiazolyl, quinolinyl, isoquinolinyl, indolyl, benzothiophenyl, benzofuranyl, benzisoxazolyl, imidazo[1,2-b]thiazolyl, purinyl, triazinyl, thieno[3,2-b]pyridinyl, imidazo[1,2-a]pyridinyl, 1,5-naphthyridinyl, 1H-pyrazolo[4,3-b]pyridinyl, triazolo[4,3-a]pyridinyl, 1H-pyrrolo[3,2-b]pyridinyl, 1H-pyrrolo[2,3-b]pyridinyl, pyrazolo[1,5-a]pyridinyl, indazolyl, and the like.

As used herein, "heterocycloalkyl" refers to monocyclic or polycyclic heterocycles having at least one non-aromatic ring (saturated or partially unsaturated ring), wherein one or more of the ring-forming carbon atoms of the heterocycloalkyl is replaced by a heteroatom selected from N, O, S, and B, and wherein the ring-forming carbon atoms and heteroatoms of a heterocycloalkyl group can be optionally substituted by one or more oxo or sulfido (e.g., C(O), S(O), C(S), or $S(O)_2$, etc.). When a ring-forming carbon atom or heteroatom of a heterocycloalkyl group is optionally substituted by one or more oxo or sulfide, the O or S of said group is in addition to the number of ring-forming atoms specified herein (e.g., a 1-methyl-6-oxo-1,6-dihydropyridazin-3-yl is a 6-membered heterocycloalkyl group, wherein a ring-forming carbon atom is substituted with an oxo group, and wherein the 6-membered heterocycloalkyl group is further substituted with a methyl group). Heterocycloalkyl groups include monocyclic and polycyclic (e.g., having 2 fused rings) systems. Included in heterocycloalkyl are monocyclic and polycyclic 3 to 10, 4 to 10, 5 to 10, 4 to 7, 5 to 7, or 5 to 6 membered heterocycloalkyl groups. Heterocycloalkyl groups can also include spirocycles and bridged rings (e.g., a 5 to 10 membered bridged biheterocycloalkyl ring having one or more of the ring-forming carbon atoms replaced by a heteroatom independently selected from N, O, S, and B). The heterocycloalkyl group can be attached through a ring-forming carbon atom or a ring-forming heteroatom. In some embodiments, the heterocycloalkyl group contains 0 to 3 double bonds. In some embodiments, the heterocycloalkyl group contains 0 to 2 double bonds.

Also included in the definition of heterocycloalkyl are moieties that have one or more aromatic rings fused (i.e., having a bond in common with) to the non-aromatic heterocyclic ring, for example, benzo or thienyl derivatives of piperidine, morpholine, azepine, etc. A heterocycloalkyl group containing a fused aromatic ring can be attached through any ring-forming atom including a ring-forming atom of the fused aromatic ring.

In some embodiments, the heterocycloalkyl group contains 3 to 10 ring-forming atoms, 4 to 10 ring-forming atoms, 4 to 8 ring-forming atoms, 3 to 7 ring-forming atoms, or 5 to 6 ring-forming atoms. In some embodiments, the heterocycloalkyl group has 1 to 4 heteroatoms, 1 to 3 heteroatoms, 1 to 2 heteroatoms or 1 heteroatom. In some embodiments, the heterocycloalkyl is a monocyclic 4-6 membered heterocycloalkyl having 1 or 2 heteroatoms independently selected from N, O, S and B and having one or more oxidized ring members. In some embodiments, the heterocycloalkyl is a monocyclic or bicyclic 5-10 membered heterocycloalkyl having 1, 2, 3, or 4 heteroatoms independently selected from N, O, S, and B and having one or more oxidized ring members. In some embodiments, the heterocycloalkyl is a monocyclic or bicyclic 5 to 10 membered heterocycloalkyl having 1, 2, 3, or 4 heteroatoms independently selected from N, O, and S and having one or more oxidized ring members. In some embodiments, the heterocycloalkyl is a monocyclic 5 to 6 membered heterocycloalkyl having 1, 2, 3, or 4 heteroatoms independently selected from N, O, and S and having one or more oxidized ring members.

Example heterocycloalkyl groups include pyrrolidin-2-one (or 2-oxopyrrolidinyl), 1,3-isoxazolidin-2-one, pyranyl, tetrahydropyran, oxetanyl, azetidinyl, morpholino, thiomorpholino, piperazinyl, tetrahydrofuranyl, tetrahydrothienyl, piperidinyl, pyrrolidinyl, isoxazolidinyl, isothiazolidinyl, pyrazolidinyl, oxazolidinyl, thiazolidinyl, imidazolidinyl, azepanyl, 1,2,3,4-tetrahydroisoquinoline, tetrahydrothiopheneyl, tetrahydrothiopheneyl 1,1-dioxide, benzazapene, azabicyclo[3.1.0]hexanyl, diazabicyclo[3.1.0]hexanyl, oxobicyclo[2.1.1]hexanyl, azabicyclo[2.2.1]heptanyl, diazabicyclo[2.2.1]heptanyl, azabicyclo[3.1.1]heptanyl, diazabicyclo[3.1.1]heptanyl, azabicyclo[3.2.1]octanyl, diazabicyclo[3.2.1]octanyl, oxobicyclo[2.2.2]octanyl, azabicyclo[2.2.2]octanyl, azaadamantanyl, diazaadamantanyl, oxoadamantanyl, azaspiro[3.3]heptanyl, 2-azaspiro[3.3]heptanyl, diazaspiro[3.3]heptanyl, azaspiro[3.5]nonanyl, 7-azaspiro[3.5]nonanyl, oxo-azaspiro[3.3]heptanyl, azaspiro[3.4]octanyl, diazaspiro[3.4]octanyl, oxo-azaspiro[3.4]octanyl, azaspiro[2.5]octanyl, diazaspiro[2.5]octanyl, azaspiro[4.4]nonanyl, diazaspiro[4.4]nonanyl, oxo-azaspiro[4.4]nonanyl, azaspiro[4.5]decanyl, diazaspiro[4.5]decanyl, diazaspiro[4.4]nonanyl, oxo-diazaspiro[4.4]nonanyl, oxo-dihydropyridazinyl, oxo-2,6-diazaspiro[3.4]octanyl, oxo-hexahydropyrrolo[1,2-a]pyrazinyl, 3-oxopiperazinyl, oxo-pyrrolidinyl, oxo-pyridinyl, and the like.

As used herein, "$C_{o-p}$ cycloalkyl-$C_{n-m}$ alkyl-" refers to a group of formula cycloalkyl-alkylene-, wherein the cycloalkyl has o to p carbon atoms and the alkylene linking group has n to m carbon atoms.

As used herein "$C_{o-p}$ aryl-$C_{n-m}$ alkyl-" refers to a group of formula aryl-alkylene-, wherein the aryl has o to p carbon atoms and the alkylene linking group has n to m carbon atoms.

As used herein, "heteroaryl-$C_{n-m}$ alkyl-" refers to a group of formula heteroaryl-alkylene-, wherein alkylene linking group has n to m carbon atoms.

As used herein "heterocycloalkyl-$C_{n-m}$ alkyl-" refers to a group of formula heterocycloalkyl-alkylene-, wherein alkylene linking group has n to m carbon atoms.

As used herein, an "alkyl linking group" or "alkylene linking group" is a bivalent straight chain or branched alkyl linking group ("alkylene group"). For example, "$C_{o-p}$ cycloalkyl-$C_{n-m}$ alkyl-", "$C_{o-p}$ aryl-$C_{n-m}$ alkyl-", "phenyl-$C_{n-m}$ alkyl-", "heteroaryl-$C_{n-m}$ alkyl-", and "heterocycloalkyl-$C_{n-m}$ alkyl-" contain alkyl linking groups. Examples of "alkyl linking groups" or "alkylene groups" include methylene, ethan-1,1-diyl, ethan-1,2-diyl, propan-1,3-diyl, propan-1,2-diyl, propan-1,1-diyl and the like.

At certain places, the definitions or embodiments refer to specific rings (e.g., an azetidine ring, a pyridine ring, etc.). Unless otherwise indicated, these rings can be attached to any ring member provided that the valency of the atom is not exceeded. For example, an azetidine ring may be attached at any position of the ring, whereas a pyridin-3-yl ring is attached at the 3-position.

As used herein, the term "oxo" refers to an oxygen atom (i.e., =O) as a divalent substituent, forming a carbonyl group when attached to a carbon (e.g., C=O or C(O)), or attached to a nitrogen or sulfur heteroatom forming a nitroso, sulfinyl, or sulfonyl group.

As used herein, the term "independently selected from" means that each occurrence of a variable or substituent (e.g., each $R^M$), are independently selected at each occurrence from the applicable list.

The compounds described herein can be asymmetric (e.g., having one or more stereocenters). All stereoisomers, such as enantiomers and diastereomers, are intended unless otherwise indicated. Compounds of the present disclosure that contain asymmetrically substituted carbon atoms can be isolated in optically active or racemic forms. Methods on how to prepare optically active forms from optically inactive starting materials are known in the art, such as by resolution of racemic mixtures or by stereoselective synthesis. Many geometric isomers of olefins, C=N double bonds, and the like can also be present in the compounds described herein, and all such stable isomers are contemplated in the present invention. Cis and trans geometric isomers of the compounds of the present disclosure are described and may be isolated as a mixture of isomers or as separated isomeric forms. In some embodiments, the compound has the (R)-configuration. In some embodiments, the compound has the (S)-configuration. The Formulas (e.g., Formula I, Formula II, etc.) provided herein include stereoisomers of the compounds.

Resolution of racemic mixtures of compounds can be carried out by any of numerous methods known in the art. An example method includes fractional recrystallizaion using a chiral resolving acid which is an optically active, salt-forming organic acid. Suitable resolving agents for fractional recrystallization methods are, for example, optically active acids, such as the D and L forms of tartaric acid, diacetyltartaric acid, dibenzoyltartaric acid, mandelic acid, malic acid, lactic acid or the various optically active camphorsulfonic acids such as β-camphorsulfonic acid. Other resolving agents suitable for fractional crystallization methods include stereoisomerically pure forms of a-methylbenzylamine (e.g., S and R forms, or diastereomerically pure forms), 2-phenylglycinol, norephedrine, ephedrine, N-methylephedrine, cyclohexylethylamine, 1,2-diaminocyclohexane, and the like.

Resolution of racemic mixtures can also be carried out by elution on a column packed with an optically active resolving agent (e.g., dinitrobenzoylphenylglycine). Suitable elution solvent composition can be determined by one skilled in the art.

Compounds provided herein also include tautomeric forms. Tautomeric forms result from the swapping of a single bond with an adjacent double bond together with the concomitant migration of a proton. Tautomeric forms include prototropic tautomers which are isomeric protonation states having the same empirical formula and total charge. Example prototropic tautomers include keton—enol pairs, amide-imidic acid pairs, lactam—lactim pairs, enamine—imine pairs, and annular forms where a proton can occupy two or more positions of a heterocyclic system, for example, 1H- and 3H-imidazole, 1H-, 2H- and 4H-1,2,4-triazole, 1H- and 2H-isoindole, 2-hydroxypyridine and 2-pyridone, and 1H- and 2H-pyrazole. Tautomeric forms can be in equilibrium or sterically locked into one form by appropriate substitution.

All compounds, and pharmaceutically acceptable salts thereof, can be found together with other substances such as water and solvents (e.g. hydrates and solvates) or can be isolated.

In some embodiments, preparation of compounds can involve the addition of acids or bases to affect, for example, catalysis of a desired reaction or formation of salt forms such as acid addition salts.

In some embodiments, the compounds provided herein, or salts thereof, are substantially isolated. By "substantially isolated" is meant that the compound is at least partially or substantially separated from the environment in which it was formed or detected. Partial separation can include, for example, a composition enriched in the compounds provided herein. Substantial separation can include compositions containing at least about 50%, at least about 60%, at least about 70%, at least about 80%, at least about 90%, at least about 95%, at least about 97%, or at least about 99% by weight of the compounds provided herein, or salt thereof.

The term "compound" as used herein is meant to include all stereoisomers, geometric isomers, tautomers, and isotopes of the structures depicted. Compounds herein identified by name or structure as one particular tautomeric form are intended to include other tautomeric forms unless otherwise specified.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The present application also includes pharmaceutically acceptable salts of the compounds described herein. As used herein, "pharmaceutically acceptable salts" refers to derivatives of the disclosed compounds wherein the parent compound is modified by converting an existing acid or base moiety to its salt form. Examples of pharmaceutically acceptable salts include, but are not limited to, mineral or organic acid salts of basic residues such as amines; alkali or organic salts of acidic residues such as carboxylic acids; and the like. The pharmaceutically acceptable salts of the present disclosure include the conventional non-toxic salts of the parent compound formed, for example, from non-toxic inorganic or organic acids. The pharmaceutically acceptable salts of the present disclosure can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, non-aqueous media like ether, ethyl acetate, alcohols (e.g., methanol, ethanol, iso-propanol, or butanol) or acetonitrile (ACN) are preferred. Lists of suitable salts are found in Remington's Pharmaceutical Sciences, 17th ed., Mack Publishing Company, Easton, Pa., 1985, p. 1418 and Journal of Pharmaceutical Science, 66, 2 (1977), each of which is incorporated herein by reference in its entirety.

Synthesis

As will be appreciated by those skilled in the art, the compounds provided herein, including salts and stereoisomers thereof, can be prepared using known organic synthesis techniques and can be synthesized according to any of numerous possible synthetic routes.

For example, compounds of Formula I can be prepared as shown in Scheme 1 (see e.g., compound 1-13 of Scheme 1). A mixture of ortho-substituted nitro compound 1-1, wherein $Y^1$ is a suitable leaving group such as halogen (e.g., F, Cl) and $P^1$ is a suitable protecting group (e.g., phenylsulfonyl or SEM), and ester 1-2, wherein R is a suitable alkyl group (e.g., $CH_3$ or $CH_2CH_3$), can be treated with a suitable base (e.g., LiHMDS) in a suitable solvent (e.g., THF) at low temperature (e.g., −20° C.) to afford intermediate 1-3. Reduction of the nitro group in 1-3 under suitable reaction conditions, such as by treating with a reducing agent (e.g., iron) in a suitable solvent (e.g., water and ethanol) in the presence of ammonium chloride), affords the lactam 1-4.

Intermediate 1-4 can be converted to intermediate 1-6 via alkylation with 1-5 wherein X is a suitable leaving group, such as halogen (e.g., Cl, Br or I) or pseudohalogen (e.g., OMs or OTs). A handle for optional substitution at $R^2$ can be introduced via halogenation of 1-6 with suitable halogenating reagents (e.g., N-bromosuccinimide, N-iodosuccinimide, or $Br_2$) to afford compound 1-7 wherein $Y^2$ is a suitable halogen (e.g., Br or I). Subsequent coupling of compound 1-7 with $R^2$-$M^1$ (1-8), where $M^1$ is a boronic acid, boronate ester, potassium trifluoroborate, or an appropriately substituted metal, such as $Sn(Bu)_3$ or Zn, under standard Suzuki conditions (e.g., in the presence of a palladium catalyst, such as tetrakis(triphenylphosphine)palladium(0) or [1,1'-bis(diphenylphosphino)ferrocene]dichloropalladium (II) and a base (e.g., sodium carbonate)) or standard Stille conditions (e.g., in the presence of a palladium(0) catalyst, such as tetrakis(triphenylphosphine)palladium(0)) or standard Negishi conditions (e.g., in the presence of a palladium catalyst, such as tetrakis(triphenylphosphine)palladium(0) or [1,1'-bis(diphenylphosphino)ferrocene]dichloropalladium (II)), affords compound 1-9.

A handle for optional substitution at $R^3$ can be introduced by treating intermediate 1-9 with a suitable base (e.g., LDA) in a suitable solvent (e.g., THF) at low temperature (e.g., −78° C.), followed by addition of an electrophilic source of halogen (e.g., 1,2-dibromo-1,1,2,2-tetrachloroethane) to afford intermediate 1-10. Coupling of compound 1-10 with $R^3$-$M^2$ (1-11), where $M^2$ is a boronic acid, boronate ester, potassium trifluoroborate, or an appropriately substituted metal such as $Sn(Bu)_3$ or Zn, under standard Suzuki conditions (e.g., in the presence of a palladium catalyst, such as tetrakis(triphenylphosphine)palladium(0) or [1,1'-bis(diphenylphosphino)ferrocene]dichloropalladium (II) and a base (e.g., sodium carbonate)) or standard Stille conditions (e.g., in the presence of a palladium(0) catalyst, such as tetrakis (triphenylphosphine)palladium(0)) or standard Negishi conditions (e.g., in the presence of a palladium catalyst, such as tetrakis(triphenylphosphine)palladium(0) or [1,1'-bis(diphenylphosphino)ferrocene]dichloropalladium (II)), affords compound 1-12. Removal of the protecting group $P^1$ from intermediate 1-12 under conditions suitable for the protecting group chosen (e.g., NaOH for $P^1$=phenylsulfonyl; or TFA followed by ethylenediamine for $P^1$=SEM) affords compounds of 1-13.

Where appropriate, if $R^2$, $R^3$, $R^4$, $R^5$ or $R^6$ bears a suitable handle for further functionalization, such transformations can be carried out at any stage before or after their installation using reactions known to one skilled in the art if the reactions planned are compatible with the reactivity of the intermediates. One skilled in the art will recognize that installation of $R^3$ can precede the installation of $R^2$ via appropriate rearrangement of the steps in the synthetic sequence if the reactions planned are compatible with the reactivity of the intermediates. One skilled in the art will also recognize that deprotection of $P^1$ can be carried out at an earlier stage if the reactions planned are compatible with the reactivity of the intermediates.

Scheme 1.

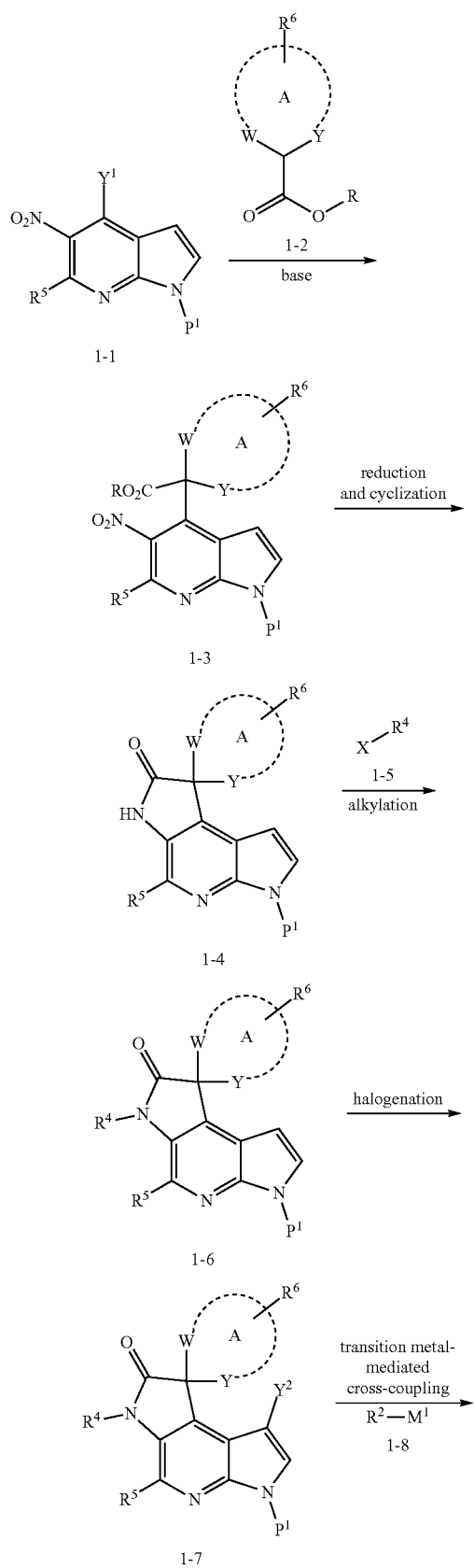

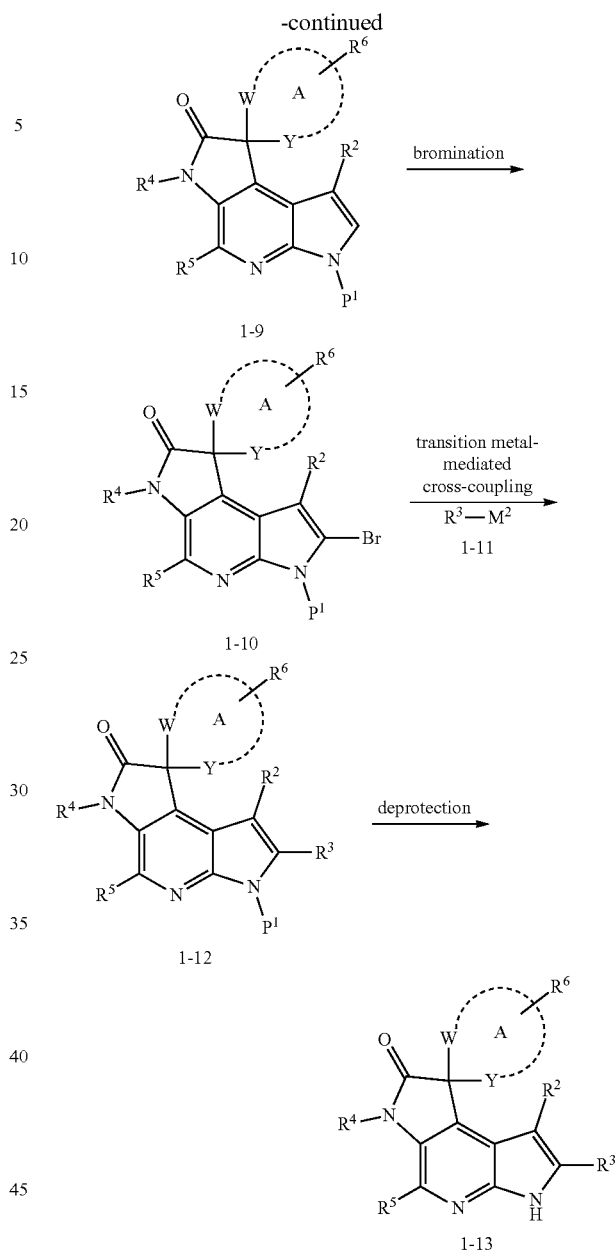

Compounds of Formula I can also be prepared, for example, as shown in Scheme 2 (see e.g., compound 2-4 of Scheme 2). A suitably protected intermediate 2-1 that bears a nitrogen in ring A can be selectively deprotected (e.g., with acid, such as HCl or TFA) to afford intermediate 2-2. Intermediate 2-2 is a suitable starting material for various reactions to install a group $R^6$, such as, but not limited to, alkylation, nucleophilic aromatic substitution, acylation, sulfonylation, reductive amination, arylation, or Michael addition with suitable reactants to afford corresponding functionalized intermediate 2-3. Removal of the protecting group $P^1$ from intermediate 2-3 under suitable conditions (e.g., NaOH) affords compounds 2-4. Alternatively, one skilled in the art would recognize that protecting group $P^1$ can be selectively removed at an earlier step in the synthetic sequence, and deprotection and functionalization of the piperidine nitrogen can be performed as final steps if desired and if the reactions planned are compatible with the reactivity of the intermediates.

Scheme 2.

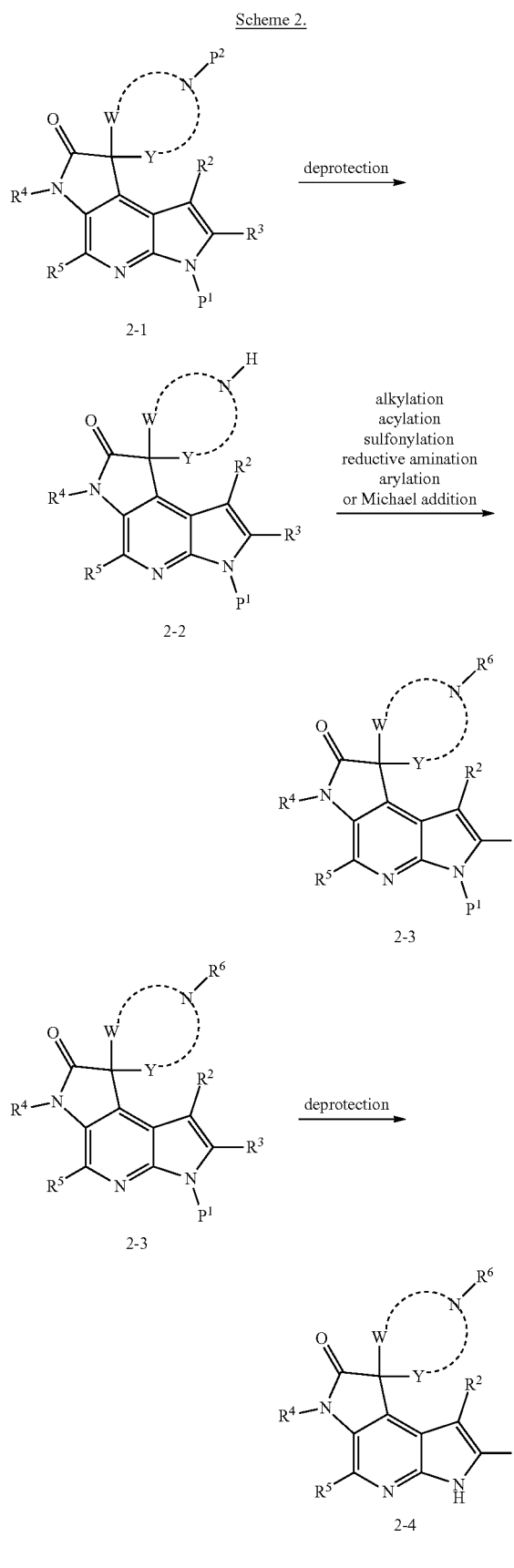

One skilled in the art would recognize that the Steps of Schemes 1 and 2 can be performed in different orders (e.g., if desired and reactivity of the reagents and intermediates permit, the position $R^3$ can be functionalized before $R^2$ is functionalized; deprotection of $P^2$, installation of $R^6$ and deprotection of $P^1$ can also occur at any stage that is compatible with the reactivity of the reagents and intermediates used).

Scheme 3.

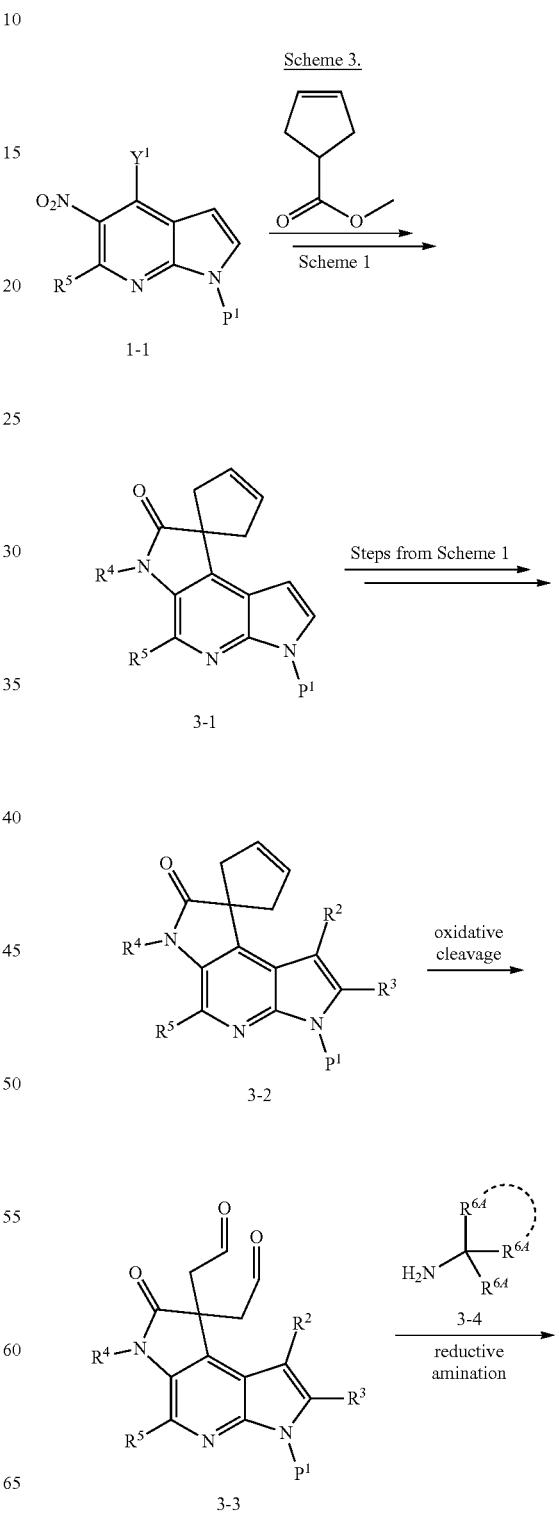

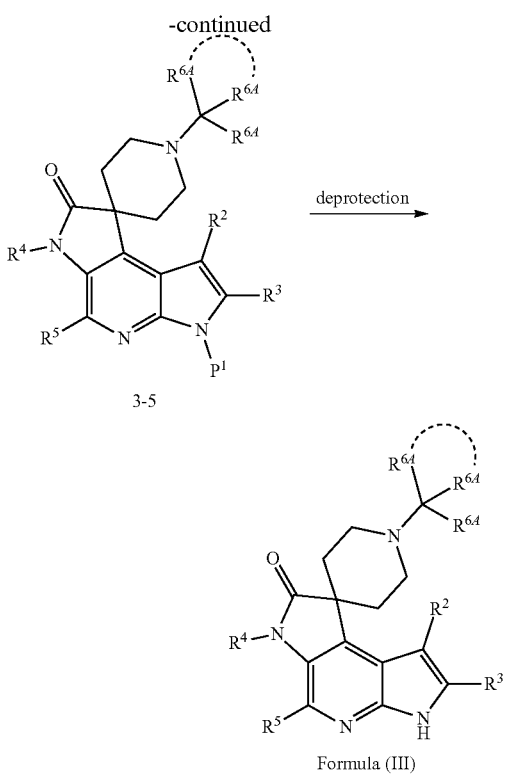

Formula (III)

Compounds of Formula (III) can be prepared as shown in Scheme 3. A suitably protected intermediate 3-2 (e.g., protected with a phenylsulfonyl group) can be synthesized by the same procedure described in Scheme 1, using methyl cyclopent-3-ene-1-carboxylate as starting material and suitable base (e.g., lithium bis(trimethylsilyl)amide) in the first step. The intermediate 3-2 can then be converted to 3-3 using oxidative cleavage conditions (e.g., potassium osmate and sodium periodate). Compound 3-5 can be obtained by reductive amination reactions between 3-3 and 3-4 (e.g., sodium triacetoxyborohydride in the presence of TFA). Finally, deprotecting of the protecting group $P^1$ using a suitable reagent (e.g., NaOH) would gave the desired compound in Formula (III). Alternatively, one skilled in the art would recognize that protecting group $P^1$ can be selectively removed at an earlier step in the synthetic sequence, and deprotection and functionalization of the piperidine nitrogen can be performed as final steps if desired and if the reactions planned are compatible with the reactivity of the intermediates.

The reactions for preparing compounds described herein can be carried out in suitable solvents which can be readily selected by one of skill in the art of organic synthesis. Suitable solvents can be substantially non-reactive with the starting materials (reactants), the intermediates, or products at the temperatures at which the reactions are carried out, (e.g., temperatures which can range from the solvent's freezing temperature to the solvent's boiling temperature). A given reaction can be carried out in one solvent or a mixture of more than one solvent. Depending on the particular reaction step, suitable solvents for a particular reaction step can be selected by the skilled artisan.

The expressions, "ambient temperature" or "room temperature" or "rt" as used herein, are understood in the art, and refer generally to a temperature, e.g., a reaction temperature, that is about the temperature of the room in which the reaction is carried out, for example, a temperature from about 20° C. to about 30° C.

Preparation of compounds described herein can involve the protection and deprotection of various chemical groups. The need for protection and deprotection, and the selection of appropriate protecting groups, can be readily determined by one skilled in the art. The chemistry of protecting groups can be found, for example, in T. W. Greene and P. G. M. Wuts, Protective Groups in Organic Synthesis, $3^{rd}$ Ed., Wiley & Sons, Inc., New York (1999).

Reactions can be monitored according to any suitable method known in the art. For example, product formation can be monitored by spectroscopic means, such as nuclear magnetic resonance spectroscopy (e.g., $^1$H or $^{13}$C), infrared spectroscopy, spectrophotometry (e.g., UV-visible), mass spectrometry, or by chromatographic methods such as high performance liquid chromatography (HPLC), liquid chromatography-mass spectroscopy (LCMS), or thin layer chromatography (TLC). Compounds can be purified by those skilled in the art by a variety of methods, including high performance liquid chromatography (HPLC) and normal phase silica chromatography.

Methods of Use

The compounds described herein can inhibit the activity of the V617F variant of the protein-tyrosine kinase JAK2 (i.e., "V617F" or "JAK2V617F"). Compounds which inhibit V617F are useful in providing a means of preventing the growth or inducing apoptosis in tumors, particularly by inhibiting angiogenesis. It is therefore anticipated that the compounds of the disclosure are useful in treating or preventing proliferative disorders such as cancers. In particular tumors with activating mutants of receptor tyrosine kinases or upregulation of receptor tyrosine kinases may be particularly sensitive to the inhibitors.

In certain embodiments, the disclosure provides a method for treating a V617F-related disorder in a patient in need thereof, comprising the step of administering to said patient a compound of the disclosure, or a pharmaceutically acceptable composition thereof.

Myeloproliferative diseases (MPD) are multipotent hematopoietic stem cell disorders characterized by excess production of various blood cells. MPNs include polycythemia vera (PV), essential thrombocythemia (ET), and idiopathic myelofibrosis (IMF). JAK2 V617F mutation is reported in about 95% of patients with PV, in 35% to 70% of patients with ET, and 50% of patients with IMF. Also, JAK2 exon 12 mutations are detected in some of the V617F-negative PV patients (Ma et al., J. Mol. Diagn., 11: 49-53, 2009). In some embodiments, the compounds of the disclosure can be useful in the treatment of myeloproliferative disorders (e.g., myeloproliferative neoplasms) in a patient in need thereof, such as polycythemia vera, essential thrombocythemia, myelofibrosis with myeloid metaplasia (MMM), primary myelofibrosis (PMF), chronic myelogenous leukemia (CML), chronic myelomonocytic leukemia (CMML), hypereosinophilic syndrome (HES), systemic mast cell disease (SMCD), and the like.

In some embodiments, the myeloproliferative disorder is a myeloproliferative neoplasm.

In some embodiments, the myeloproliferative disorder is myelofibrosis (e.g., primary myelofibrosis (PMF) or post polycythemia vera/essential thrombocythemia myelofibrosis (Post-PV/ET MF)).

In some embodiments, the myeloproliferative disorder is primary myelofibrosis (PMF).

In some embodiments, the myeloproliferative disorder is post-essential thrombocythemia myelofibrosis (Post-ET MF).

In some embodiments, the myeloproliferative disorder is post polycythemia vera myelofibrosis (Post-PV MF).

In some embodiments, the myeloproliferative disorder is selected from primary myelofibrosis (PMF), polycythemia vera (PV), and essential thrombocythemia (ET).

In some embodiments, the myeloproliferative neoplasm is primary myelofibrosis (PMF).

In some embodiments, the myeloproliferative neoplasm is polycythemia vera (PV).

In some embodiments, the myeloproliferative neoplasm is essential thrombocythemia (ET).

Myeloproliferative diseases include disorders of a bone marrow or lymph node-derived cell type, such as a white blood cell. A myeloproliferative disease can manifest by abnormal cell division resulting in an abnormal level of a particular hematological cell population. The abnormal cell division underlying a proliferative hematological disorder is typically inherent in the cells and not a normal physiological response to infection or inflammation. Leukemia is a type of myeloproliferative disease. Exemplary myeloproliferative diseases include, but are not limited to, acute myeloid leukemia (AML), acute lymphoblastic leukemia (ALL), chronic lymphocytic leukemia (CLL), myelodysplastic syndrome (MDS), chronic myeloid leukemia (CML), hairy cell leukemia, leukemic manifestations of lymphomas, multiple myeloma, polycythemia vera (PV), essential thrombocythemia (ET), idiopathic myelofibrosis (IMF), hypereosinophilic syndrome (HES), chronic neutrophilic leukemia (CNL), myelofibrosis with myeloid metaplasia (MMM), chronic myelomonocytic leukemia (CMML), juvenile myelomonocytic leukemia, chronic basophilic leukemia, chronic eosinophilic leukemia, systemic mastocytosis (SM), and unclassified myeloproliferative diseases (UMPD or MPD-NC). Lymphoma is a type of proliferative disease that mainly involves lymphoid organs, such as lymph nodes, liver, and spleen. Exemplary proliferative lymphoid disorders include lymphocytic lymphoma (also called chronic lymphocytic leukemia), follicular lymphoma, large cell lymphoma, Burkitt's lymphoma, marginal zone lymphoma, lymphoblastic lymphoma (also called acute lymphoblastic lymphoma).

For example, the compounds of the disclosure are useful in the treatment of cancer. Example cancers include bladder cancer (e.g., urothelial carcinoma, squamous cell carcinoma, adenocarcinoma), breast cancer (e.g., hormone R positive, triple negative), cervical cancer, colorectal cancer, cancer of the small intestine, colon cancer, rectal cancer, cancer of the anus, endometrial cancer, gastric cancer (e.g., gastrointestinal stromal tumors), head and neck cancer (e.g., cancers of the larynx, hypopharynx, nasopharynx, oropharynx, lips, and mouth, squamous head and neck cancers), kidney cancer (e.g., renal cell carcinoma, urothelial carcinoma, sarcoma, Wilms tumor), liver cancer (e.g., hepatocellular carcinoma, cholangiocellular carcinoma (e.g., intrahepatic, hilar or perihilar, distal extrahepatic), liver angiosarcoma, hepatoblastoma), lung cancer (e.g., adenocarcinoma, small cell lung cancer and non-small cell lung carcinomas, parvicellular and non-parvicellular carcinoma, bronchial carcinoma, bronchial adenoma, pleuropulmonary blastoma), ovarian cancer, prostate cancer, testicular cancer, uterine cancer, vulvar cancer, esophageal cancer, gall bladder cancer, pancreatic cancer (e.g. exocrine pancreatic carcinoma), stomach cancer, thyroid cancer, parathyroid cancer, neuroendocrine cancer (e.g., pheochromocytoma, Merkel cell cancer, neuroendocrine carcinoma), skin cancer (e.g., squamous cell carcinoma, Kaposi sarcoma, Merkel cell skin cancer), and brain cancer (e.g., astrocytoma, medulloblastoma, ependymoma, neuro-ectodermal tumors, pineal tumors).

Further example cancers include hematopoietic malignancies such as leukemia or lymphoma, multiple myeloma, chronic lymphocytic lymphoma, adult T cell leukemia, acute myeloid leukemia (AML), B-cell lymphoma, cutaneous T-cell lymphoma, acute myelogenous leukemia, Hodgkin's or non-Hodgkin's lymphoma, myeloproliferative neoplasms (e.g., 8p11 myeloproliferative syndrome, polycythemia vera (PV), essential thrombocythemia (ET), and primary myelofibrosis (PMF)), myelodysplastic syndrome, chronic eosinophilic leukemia, Waldenstrom's Macroglubulinemia, hairy cell lymphoma, chronic myelogenic lymphoma, acute lymphoblastic lymphoma, AIDS-related lymphomas, and Burkitt's lymphoma.

In certain embodiments, provided herein is a method of treating cancer comprising administering to a patient in need thereof a therapeutically effect amount of a compound of the disclosure. In certain embodiments, the cancer is selected from T lymphoblastic lymphoma, glioblastoma, melanoma, rhabdosarcoma, lymphosarcoma, and osteosarcoma.

Other cancers treatable with the compounds of the disclosure include tumors of the eye, glioblastoma, melanoma, leiomyosarcoma, and urothelial carcinoma (e.g., ureter, urethra, bladder, urachus).

The compounds of the disclosure can also be useful in the inhibition of tumor metastases.

In some embodiments, the compounds of the disclosure as described herein can be used to treat Alzheimer's disease, HIV, or tuberculosis.

In some embodiments, the compounds of the disclosure can be useful in the treatment of myelodysplastic syndrome (MDS) in a patient in need thereof. In some embodiments, said patient having the myelodysplastic syndrome (MDS) is red blood cell transfusion dependent.

As used herein, myelodysplastic syndromes are intended to encompass heterogeneous and clonal hematopoietic disorders that are characterized by ineffective hematopoiesis on one or more of the major myeloid cell lineages. Myelodysplastic syndromes are associated with bone marrow failure, peripheral blood cytopenias, and a propensity to progress to acute myeloid leukemia (AML). Moreover, clonal cytogenetic abnormalities can be detected in about 50% of cases with MDS. In 1997, The World Health Organization (WHO) in conjunction with the Society for Hematopathology (SH) and the European Association of Hematopathology (EAHP) proposed new classifications for hematopoietic neoplasms (Harris, et al., *J Clin Oncol* 1999; 17:3835-3849; Vardiman, et al., *Blood* 2002; 100:2292-2302). For MDS, the WHO utilized not only the morphologic criteria from the French-American-British (FAB) classification but also incorporated available genetic, biologic, and clinical characteristics to define subsets of MDS (Bennett, et al., *Br J Haematol*. 1982; 51:189-199). In 2008, the WHO classification of MDS (Table 1) was further refined to allow precise and prognostically relevant subclassification of unilineage dysplasia by incorporating new clinical and scientific information (Vardiman, et al., *Blood* 2009; 114:937-951; Swerdlow, et al., *WHO Classification of Tumours of Haematopoietic and Lymphoid Tissues*. 4th Edition. Lyon France: IARC Press; 2008:88-103; Bunning and Germing, "Myelodysplastic syndromes/neoplasms" in Chapter 5, Swerdlow, et al, eds. *WHO Classification of Tumours of Haematopoietic and Lymphoid Tissues*. (ed. 4th edition): Lyon, France: IARC Press; 2008: 88-103).

TABLE 1

| 2008 WHO Classification for De Novo Myelodysplastic Syndrome | | |
|---|---|---|
| Subtype | Blood | Bone Marrow |
| Refractory cytopenia with unilineage dysplasia (RCUD) | Single or Bicytopenia | Dysplasia in ≥10% of 1 cell line, <5% blasts |
| Refractory anemia with ring sideroblasts (RARS) | Anemia, no blasts | ≥15% of erythroid precursors w/ring sideroblasts, erythroid dysplasia only, <5% blasts |
| Refractory cytopenia with multilineage dysplasia | Cytopenia(s), <1 × $10^9$/L monocytes | Dysplasia in ≥10% of cells in ≥2 hematopoietic lineages, ±15% ring sideroblasts, <5% blasts |
| Refractory anemia with excess blasts-1 (RAEB-1) | Cytopenia(s), ≤2% to 4% blasts, <1 × $10^9$/L monocytes | Unilineage or multilineage dysplasia, No Auer rods, 5% to 9% blasts |
| Refractory anemia with excess blasts-2 (RAEB-2) | Cytopenia(s), ≤5% to 19% blasts, <1 × $10^9$/L monocytes | Unilineage or multilineage dysplasia, ±Auer rods, 10% to 19% blasts |
| Myelodysplastic syndrome, unclassified (MDS-U) | Cytopenias | Unilineage or no dysplasia but characteristic MDS cytogenetics, <5% blasts |
| MDS associated with isolated del (5q) | Anemia, platelets normal or increased | Unilineage erythroid. Isolated del (5q), <5% blasts |

In some embodiments, the myelodysplastic syndrome is refractory cytopenia with unilineage dysplasia (RCUD).

In some embodiments, the myelodysplastic syndrome is refractory anemia with ring sideroblasts (RARS).

In some embodiments, the myelodysplastic syndrome is refractory anemia with ring sideroblasts associated with thrombocytosis (RARS-T).

In some embodiments, the myelodysplastic syndrome is refractory cytopenia with multilineage dysplasia.

In some embodiments, the myelodysplastic syndrome is refractory anemia with excess blasts-1 (RAEB-1).

In some embodiments, the myelodysplastic syndrome is refractory anemia with excess blasts-2 (RAEB-2).

In some embodiments, the myelodysplastic syndrome is myelodysplastic syndrome, unclassified (MDS-U).

In some embodiments, the myelodysplastic syndrome is myelodysplastic syndrome associated with isolated del(5q).

In some embodiments, the myelodysplastic syndrome is refractory to erythropoiesis-stimulating agents.

In some embodiments, the compounds of the disclosure can be useful in the treatment of myeloproliferative disorder/myelodysplastic overlap syndrome (MPD/MDS overlap syndrome).

In some embodiments, the compounds of the disclosure can be useful in the treatment of leukemia.

In some embodiments, the compounds of the disclosure can be useful in the treatment of acute myeloid leukemia (AML).

In addition to oncogenic neoplasms, the compounds of the disclosure can be useful in the treatment of skeletal and chondrocyte disorders including, but not limited to, achrondroplasia, hypochondroplasia, dwarfism, thanatophoric dysplasia (TD) (clinical forms TD I and TD II), Apert syndrome, Crouzon syndrome, Jackson-Weiss syndrome, Beare-Stevenson cutis gyrate syndrome, Pfeiffer syndrome, and craniosynostosis syndromes.

The compounds provided herein may further be useful in the treatment of fibrotic diseases, such as where a disease symptom or disorder is characterized by fibrosis. Example fibrotic diseases include liver cirrhosis, glomerulonephritis, pulmonary fibrosis, systemic fibrosis, rheumatoid arthritis, and wound healing.

In some embodiments, the compounds provided herein can be used in the treatment of a hypophosphatemia disorder such as, for example, X-linked hypophosphatemic rickets, autosomal recessive hypophosphatemic rickets, and autosomal dominant hypophosphatemic rickets, or tumor-induced osteromalacia.

In some embodiments, provided herein is a method of increasing survival or progression-free survival in a patient, comprising administering a compound provided herein to the patient. In some embodiments, the patient has cancer. In some embodiments, the patient has a disease or disorder described herein. As used herein, progression-free survival refers to the length of time during and after the treatment of a solid tumor that a patient lives with the disease but it does not get worse. Progression-free survival can refer to the length of time from first administering the compound until the earlier of death or progression of the disease. Progression of the disease can be defined by RECIST v. 1.1 (Response Evaluation Criteria in Solid Tumors), as assessed by an independent centralized radiological review committee. In some embodiments, administering of the compound results in a progression free survival that is greater than about 1 month, about 2 months, about 3 months, about 4 months, about 5 months, about 6 months, about 8 months, about 9 months, about 12 months, about 16 months, or about 24 months. In some embodiments, the administering of the compound results in a progression free survival that is at least about 1 month, about 2 months, about 3 months, about 4 months, about 5 months, about 6 months, about 8 months, about 9 months, or about 12 months; and less than about 24 months, about 16 months, about 12 months, about 9 months, about 8 months, about 6 months, about 5 months, about 4 months, about 3 months, or about 2 months. In some embodiments, the administering of the compound results in an increase of progression free survival that is at least about 1 month, about 2 months, about 3 months, about 4 months, about 5 months, about 6 months, about 8 months, about 9 months, or about 12 months; and less than about 24 months, about 16 months, about 12 months, about 9 months, about 8 months, about 6 months, about 5 months, about 4 months, about 3 months, or about 2 months.

The present disclosure further provides a compound described herein, or a pharmaceutically acceptable salt thereof, for use in any of the methods described herein.

The present disclosure further provides use of a compound described herein, or a pharmaceutically acceptable salt thereof, for the preparation of a medicament for use in any of the methods described herein.

As used herein, the term "cell" is meant to refer to a cell that is in vitro, ex vivo or in vivo. In some embodiments, an ex vivo cell can be part of a tissue sample excised from an organism such as a mammal. In some embodiments, an in vitro cell can be a cell in a cell culture. In some embodiments, an in vivo cell is a cell living in an organism such as a mammal.

As used herein, the term "contacting" refers to the bringing together of indicated moieties in an in vitro system or an in vivo system. For example, "contacting" a V617F variant with a compound described herein includes the administration of a compound described herein to an individual or patient, such as a human, having a V617F variant, as well as, for example, introducing a compound described herein into a sample containing a cellular or purified preparation containing the V617F variant.

As used herein, the term "individual" or "patient," used interchangeably, refers to any animal, including mammals, preferably mice, rats, other rodents, rabbits, dogs, cats, swine, cattle, sheep, horses, or primates, and most preferably humans.

As used herein, the phrase "therapeutically effective amount" refers to the amount of active compound or pharmaceutical agent such as an amount of any of the solid forms or salts thereof as disclosed herein that elicits the biological or medicinal response in a tissue, system, animal, individual or human that is being sought by a researcher, veterinarian, medical doctor or other clinician. An appropriate "effective" amount in any individual case may be determined using techniques known to a person skilled in the art.

The phrase "pharmaceutically acceptable" is used herein to refer to those compounds, materials, compositions, and/or dosage forms which are, within the scope of sound medical judgment, suitable for use in contact with the tissues of human beings and animals without excessive toxicity, irritation, allergic response, immunogenicity or other problem or complication, commensurate with a reasonable benefit/risk ratio.

As used herein, the phrase "pharmaceutically acceptable carrier or excipient" refers to a pharmaceutically-acceptable material, composition, or vehicle, such as a liquid or solid filler, diluent, solvent, or encapsulating material. Excipients or carriers are generally safe, non-toxic and neither biologically nor otherwise undesirable and include excipients or carriers that are acceptable for veterinary use as well as human pharmaceutical use. In one embodiment, each component is "pharmaceutically acceptable" as defined herein. See, e.g., *Remington: The Science and Practice of Pharmacy,* 21st ed.; Lippincott Williams & Wilkins: Philadelphia, Pa., 2005; *Handbook of Pharmaceutical Excipients, 6th ed*; Rowe et al., Eds.; The Pharmaceutical Press and the American Pharmaceutical Association: 2009; *Handbook of Pharmaceutical Additives, 3rd ed.*; Ash and Ash Eds.; Gower Publishing Company: 2007; *Pharmaceutical Preformulation and Formulation, 2nd ed.*; Gibson Ed.; CRC Press LLC: Boca Raton, Fla., 2009.

As used herein, the term "treating" or "treatment" refers to inhibiting the disease; for example, inhibiting a disease, condition or disorder in an individual who is experiencing or displaying the pathology or symptomatology of the disease, condition or disorder (i.e., arresting further development of the pathology and/or symptomatology) or ameliorating the disease; for example, ameliorating a disease, condition or disorder in an individual who is experiencing or displaying the pathology or symptomatology of the disease, condition or disorder (i.e., reversing the pathology and/or symptomatology) such as decreasing the severity of disease.

In some embodiments, the compounds of the invention are useful in preventing or reducing the risk of developing any of the diseases referred to herein; e.g., preventing or reducing the risk of developing a disease, condition or disorder in an individual who may be predisposed to the disease, condition or disorder but does not yet experience or display the pathology or symptomatology of the disease.

It is appreciated that certain features of the disclosure, which are, for clarity, described in the context of separate embodiments, can also be provided in combination in a single embodiment (while the embodiments are intended to be combined as if written in multiply dependent form). Conversely, various features of the disclosure which are, for brevity, described in the context of a single embodiment, can also be provided separately or in any suitable subcombination.

Combination Therapies

One or more additional pharmaceutical agents or treatment methods such as, for example, anti-viral agents, chemotherapeutics or other anti-cancer agents, immune enhancers, immunosuppressants, radiation, anti-tumor and anti-viral vaccines, cytokine therapy (e.g., IL2, GM-CSF, etc.), and/or tyrosine kinase inhibitors can be used in combination with compounds described herein for treatment or prevention of V617F-associated diseases, disorders or conditions, or diseases or conditions as described herein. The agents can be combined with the present compounds in a single dosage form, or the agents can be administered simultaneously or sequentially as separate dosage forms.

Compounds described herein can be used in combination with one or more other kinase inhibitors for the treatment of diseases, such as cancer, that are impacted by multiple signaling pathways. For example, a combination can include one or more inhibitors of the following kinases for the treatment of cancer: Akt1, Akt2, Akt3, TGF-βR, Pim, PKA, PKG, PKC, CaM-kinase, phosphorylase kinase, MEKK, ERK, MAPK, mTOR, EGFR, HER2, HER3, HER4, INS-R, IGF-1R, IR-R, PDGFαR, PDGFβR, CSFIR, KIT, FLK-II, KDR/FLK-1, FLK-4, flt-1, FGFR1, FGFR2, FGFR3, FGFR4, c-Met, Ron, Sea, TRKA, TRKB, TRKC, FLT3, VEGFR/Flt2, Flt4, EphA1, EphA2, EphA3, EphB2, EphB4, Tie2, Src, Fyn, Lck, Fgr, Btk, Fak, SYK, FRK, JAK, ABL, ALK and B-Raf. Additionally, the solid forms of the inhibitor as described herein can be combined with inhibitors of kinases associated with the PIK3/Akt/mTOR signaling pathway, such as PI3K, Akt (including Akt1, Akt2 and Akt3) and mTOR kinases.

In some embodiments, compounds described herein can be used in combination with one or more inhibitors of the enzyme or protein receptors such as HPK1, SBLB, TUT4, A2A/A2B, CD19, CD47, CDK2, STING, ALK2, LIN28, ADAR1, MAT2a, RIOK1, HDAC8, WDR5, SMARCA2, and DCLK1 for the treatment of diseases and disorders. Exemplary diseases and disorders include cancer, infection, inflammation and neurodegenerative disorders.

In some embodiments, compounds described herein can be used in combination with a therapeutic agent that targets an epigenetic regulator. Examples of epigenetic regulators include bromodomain inhibitors, the histone lysine methyltransferases, histone arginine methyl transferases, histone demethylases, histone deacetylases, histone acetylases, and DNA methyltransferases. Histone deacetylase inhibitors include, e.g., vorinostat.

For treating cancer and other proliferative diseases, compounds described herein can be used in combination with targeted therapies, including JAK kinase inhibitors (ruxolitinib, additional JAK1/2 and JAK1-selective, baricitinib or itacitinib), Pim kinase inhibitors (e.g., LGH447, INCB053914 and SGI-1776), PI3 kinase inhibitors including PI3K-delta selective and broad spectrum PI3K inhibitors (e.g., parsaclisib and INCB50797), PI3K-gamma inhibitors such as PI3K-gamma selective inhibitors, MEK inhibitors, CSF1R inhibitors (e.g., PLX3397 and LY3022855), TAM receptor tyrosine kinases inhibitors (Tyro-3, Axl, and Mer; e.g., INCB81776), angiogenesis inhibitors, interleukin receptor inhibitors, Cyclin Dependent kinase inhibitors, BRAF inhibitors, mTOR inhibitors, proteasome inhibitors (Bortezomib, Carfilzomib), HDAC-inhibitors (panobinostat, vorinostat), DNA methyl transferase inhibitors, dexamethasone, bromo and extra terminal family members inhibitors (for example, bromodomain inhibitors or BET inhibitors, such as OTX015, CPI-0610, INCB54329 or INCB57643), LSD1 inhibitors (e.g., GSK2979552, INCB59872 and INCB60003), arginase inhibitors (e.g., INCB1158), indoleamine 2,3-dioxygenase inhibitors (e.g., epacadostat, NLG919 or BMS-986205), PARP inhibiors (e.g., olaparib or rucaparib), and inhibitors of BTK such as ibrutinib.

For treating cancer and other proliferative diseases, compounds described herein can be used in combination with chemotherapeutic agents, agonists or antagonists of nuclear receptors, or other anti-proliferative agents. Compounds described herein can also be used in combination with a medical therapy such as surgery or radiotherapy, e.g., gamma-radiation, neutron beam radiotherapy, electron beam radiotherapy, proton therapy, brachytherapy, and systemic radioactive isotopes.

Examples of suitable chemotherapeutic agents include any of: abarelix, abiraterone, afatinib, aflibercept, aldesleukin, alemtuzumab, alitretinoin, allopurinol, altretamine, amidox, amsacrine, anastrozole, aphidicolon, arsenic trioxide, asparaginase, axitinib, azacitidine, bevacizumab, bexarotene, baricitinib, bendamustine, bicalutamide, bleomycin, bortezombi, bortezomib, brivanib, buparlisib, busulfan intravenous, busulfan oral, calusterone, camptosar, capecitabine, carboplatin, carmustine, cediranib, cetuximab, chlorambucil, cisplatin, cladribine, clofarabine, crizotinib, cyclophosphamide, cytarabine, dacarbazine, dacomitinib, dactinomycin, dalteparin sodium, dasatinib, dactinomycin, daunorubicin, decitabine, degarelix, denileukin, denileukin diftitox, deoxycoformycin, dexrazoxane, didox, docetaxel, doxorubicin, droloxafine, dromostanolone propionate, eculizumab, enzalutamide, epidophyllotoxin, epirubicin, epothilones, erlotinib, estramustine, etoposide phosphate, etoposide, exemestane, fentanyl citrate, filgrastim, floxuridine, fludarabine, fluorouracil, flutamide, fulvestrant, gefitinib, gemcitabine, gemtuzumab ozogamicin, goserelin acetate, histrelin acetate, ibritumomab tiuxetan, idarubicin, idelalisib, ifosfamide, imatinib mesylate, interferon alfa 2a, irinotecan, lapatinib ditosylate, lenalidomide, letrozole, leucovorin, leuprolide acetate, levamisole, lonafarnib, lomustine, meclorethamine, megestrol acetate, melphalan, mercaptopurine, methotrexate, methoxsalen, mithramycin, mitomycin C, mitotane, mitoxantrone, nandrolone phenpropionate, navelbene, necitumumab, nelarabine, neratinib, nilotinib, nilutamide, niraparib, nofetumomab, oserelin, oxaliplatin, paclitaxel, pamidronate, panitumumab, panobinostat, pazopanib, pegaspargase, pegfilgrastim, pemetrexed disodium, pentostatin, pilaralisib, pipobroman, plicamycin, ponatinib, porfimer, prednisone, procarbazine, quinacrine, ranibizumab, rasburicase, regorafenib, reloxafine, revlimid, rituximab, rucaparib, ruxolitinib, sorafenib, streptozocin, sunitinib, sunitinib maleate, tamoxifen, tegafur, temozolomide, teniposide, testolactone, tezacitabine, thalidomide, thioguanine, thiotepa, tipifarnib, topotecan, toremifene, tositumomab, trastuzumab, tretinoin, triapine, trimidox, triptorelin, uracil mustard, valrubicin, vandetanib, vinblastine, vincristine, vindesine, vinorelbine, vorinostat, veliparib, talazoparib, and zoledronate.

In some embodiments, compounds described herein can be used in combination with immune checkpoint inhibitors. Exemplary immune checkpoint inhibitors include inhibitors against immune checkpoint molecules such as CD27, CD28, CD40, CD122, CD96, CD73, CD47, OX40, GITR, CSF1R, JAK, PI3K delta, PI3K gamma, TAM, arginase, CD137 (also known as 4-1BB), ICOS, A2AR, B7-H3, B7-H4, BTLA, CTLA-4, LAG3 (e.g., INCAGN2385), TIM3 (e.g., INCB2390), VISTA, PD-1, PD-L1 and PD-L2. In some embodiments, the immune checkpoint molecule is a stimulatory checkpoint molecule selected from CD27, CD28, CD40, ICOS, OX40 (e.g., INCAGN1949), GITR (e.g., INCAGN1876) and CD137. In some embodiments, the immune checkpoint molecule is an inhibitory checkpoint molecule selected from A2AR, B7-H3, B7-H4, BTLA, CTLA-4, IDO, KIR, LAG3, PD-1, TIM3, and VISTA. In some embodiments, the compounds provided herein can be used in combination with one or more agents selected from KIR inhibitors, TIGIT inhibitors, LAIR1 inhibitors, CD160 inhibitors, 2B4 inhibitors and TGFR beta inhibitors.

In some embodiments, the inhibitor of an immune checkpoint molecule is a small molecule PD-L1 inhibitor. In some embodiments, the small molecule PD-L1 inhibitor has an IC50 less than 1 µM, less than 100 nM, less than 10 nM or less than 1 nM in a PD-L1 assay described in US Patent Publication Nos. US 20170107216, US 20170145025, US 20170174671, US 20170174679, US 20170320875, US 20170342060, US 20170362253, and US 20180016260, each of which is incorporated by reference in its entirety for all purposes.

In some embodiments, the inhibitor of an immune checkpoint molecule is an inhibitor of PD-1, e.g., an anti-PD-1 monoclonal antibody. In some embodiments, the anti-PD-1 monoclonal antibody is retifanimab (also known as MGA012), nivolumab, pembrolizumab (also known as MK-3475), pidilizumab, SHR-1210, PDR001, ipilumimab or AMP-224. In some embodiments, the anti-PD-1 monoclonal antibody is nivolumab or pembrolizumab. In some embodiments, the anti-PD1 antibody is pembrolizumab. In some embodiments, the anti-PD1 antibody is nivolumab. In some embodiments, the anti-PD-1 monoclonal antibody is retifanimab (also known as MGA012). In some embodiments, the anti-PD1 antibody is SHR-1210. Other anticancer agent(s) include antibody therapeutics such as 4-1BB (e.g. urelumab, utomilumab).

In some embodiments, the compounds of the disclosure can be used in combination with INCB086550.

In some embodiments, the inhibitor of an immune checkpoint molecule is an inhibitor of PD-L1, e.g., an anti-PD-L1 monoclonal antibody. In some embodiments, the anti-PD-L1 monoclonal antibody is BMS-935559, MEDI4736, MPDL3280A (also known as RG7446), or MSB0010718C. In some embodiments, the anti-PD-L1 monoclonal antibody is MPDL3280A or MEDI4736.

In some embodiments, the inhibitor of an immune checkpoint molecule is an inhibitor of CTLA-4, e.g., an anti-CTLA-4 antibody. In some embodiments, the anti-CTLA-4 antibody is ipilimumab, tremelimumab, AGEN1884, or CP-675,206.

In some embodiments, the inhibitor of an immune checkpoint molecule is an inhibitor of LAG3, e.g., an anti-LAG3 antibody. In some embodiments, the anti-LAG3 antibody is BMS-986016, LAG525, or INCAGN2385.

In some embodiments, the inhibitor of an immune checkpoint molecule is an inhibitor of TIM3, e.g., an anti-TIM3 antibody. In some embodiments, the anti-TIM3 antibody is INCAGN2390, MBG453, or TSR-022.

In some embodiments, the inhibitor of an immune checkpoint molecule is an inhibitor of GITR, e.g., an anti-GITR antibody. In some embodiments, the anti-GITR antibody is TRX518, MK-4166, INCAGN1876, MK-1248, AMG228, BMS-986156, GWN323, or MEDI1873.

In some embodiments, the inhibitor of an immune checkpoint molecule is an agonist of OX40, e.g., OX40 agonist antibody or OX40L fusion protein. In some embodiments, the anti-OX40 antibody is MEDI0562, MOXR-0916, PF-04518600, GSK3174998, or BMS-986178. In some embodiments, the OX40L fusion protein is MEDI6383.

In some embodiments, the inhibitor of an immune checkpoint molecule is an inhibitor of CD20, e.g., an anti-CD20 antibody. In some embodiments, the anti-CD20 antibody is obinutuzumab or rituximab.

The compounds of the present disclosure can be used in combination with bispecific antibodies. In some embodiments, one of the domains of the bispecific antibody targets PD-1, PD-L1, CTLA-4, GITR, OX40, TIM3, LAG3, CD137, ICOS, CD3 or TGFβ receptor.

In some embodiments, the compounds of the disclosure can be used in combination with one or more metabolic enzyme inhibitors. In some embodiments, the metabolic enzyme inhibitor is an inhibitor of IDO1, TDO, or arginase. Examples of IDO1 inhibitors include epacadostat, NLG919, BMS-986205, PF-06840003, IOM2983, RG-70099 and LY338196.

In some embodiments, the compounds described herein can be used in combination with one or more agents for the treatment of diseases such as cancer. In some embodiments, the agent is an alkylating agent, a proteasome inhibitor, a corticosteroid, or an immunomodulatory agent. Examples of an alkylating agent include cyclophosphamide (CY), melphalan (MEL), and bendamustine. In some embodiments, the proteasome inhibitor is carfilzomib. In some embodiments, the corticosteroid is dexamethasone (DEX). In some embodiments, the immunomodulatory agent is lenalidomide (LEN) or pomalidomide (POM).

Suitable antiviral agents contemplated for use in combination with compounds of the present disclosure can comprise nucleoside and nucleotide reverse transcriptase inhibitors (NRTIs), non-nucleoside reverse transcriptase inhibitors (NNRTIs), protease inhibitors and other antiviral drugs.

Example suitable NRTIs include zidovudine (AZT); didanosine (ddI); zalcitabine (ddC); stavudine (d4T); lamivudine (3TC); abacavir (1592U89); adefovir dipivoxil [bis(POM)-PMEA]; lobucavir (BMS-180194); BCH-10652; emitricitabine [(−)-FTC]; beta-L-FD4 (also called beta-L-D4C and named beta-L-2′,3′-dicleoxy-5-fluoro-cytidene); DAPD, ((−)-beta-D-2,6,-diamino-purine dioxolane); and lodenosine (FddA). Typical suitable NNRTIs include nevirapine (BI-RG-587); delaviradine (BHAP, U-90152); efavirenz (DMP-266); PNU-142721; AG-1549; MKC-442 (1-(ethoxy-methyl)-5-(1-methylethyl)-6-(phenylmethyl)-(2,4 (1H,3H)-pyrimidinedione); and (+)-calanolide A (NSC-675451) and B. Typical suitable protease inhibitors include saquinavir (Ro 31-8959); ritonavir (ABT-538); indinavir (MK-639); nelfnavir (AG-1343); amprenavir (141W94); lasinavir (BMS-234475); DMP-450; BMS-2322623; ABT-378; and AG-1 549. Other antiviral agents include hydroxyurea, ribavirin, IL-2, IL-12, pentafuside and Yissum Project No. 11607.

Suitable agents for use in combination with compounds described herein for the treatment of cancer include chemotherapeutic agents, targeted cancer therapies, immunotherapies or radiation therapy. Compounds described herein may be effective in combination with anti-hormonal agents for treatment of breast cancer and other tumors. Suitable examples are anti-estrogen agents including but not limited to tamoxifen and toremifene, aromatase inhibitors including but not limited to letrozole, anastrozole, and exemestane, adrenocorticosteroids (e.g. prednisone), progestins (e.g. megastrol acetate), and estrogen receptor antagonists (e.g. fulvestrant). Suitable anti-hormone agents used for treatment of prostate and other cancers may also be combined with compounds described herein. These include anti-androgens including but not limited to flutamide, bicalutamide, and nilutamide, luteinizing hormone-releasing hormone (LHRH) analogs including leuprolide, goserelin, triptorelin, and histrelin, LHRH antagonists (e.g. degarelix), androgen receptor blockers (e.g. enzalutamide) and agents that inhibit androgen production (e.g. abiraterone).

The compounds described herein may be combined with or in sequence with other agents against membrane receptor kinases especially for patients who have developed primary or acquired resistance to the targeted therapy. These therapeutic agents include inhibitors or antibodies against EGFR, Her2, VEGFR, c-Met, Ret, IGFR1, or Flt-3 and against cancer-associated fusion protein kinases such as Bcr-Abl and EML4-Alk. Inhibitors against EGFR include gefitinib and erlotinib, and inhibitors against EGFR/Her2 include but are not limited to dacomitinib, afatinib, lapitinib and neratinib. Antibodies against the EGFR include but are not limited to cetuximab, panitumumab and necitumumab. Inhibitors of c-Met may be used in combination with FGFR inhibitors. These include onartumzumab, tivantnib, and capmatinib (also known as INC-280). Agents against Abl (or Bcr-Abl) include imatinib, dasatinib, nilotinib, and ponatinib and those against Alk (or EML4-ALK) include crizotinib.

Angiogenesis inhibitors may be efficacious in some tumors in combination with inhibitors described herein. These include antibodies against VEGF or VEGFR or kinase inhibitors of VEGFR. Antibodies or other therapeutic proteins against VEGF include bevacizumab and aflibercept. Inhibitors of VEGFR kinases and other anti-angiogenesis inhibitors include but are not limited to sunitinib, sorafenib, axitinib, cediranib, pazopanib, regorafenib, brivanib, and vandetanib Activation of intracellular signaling pathways is frequent in cancer, and agents targeting components of these pathways have been combined with receptor targeting agents to enhance efficacy and reduce resistance. Examples of agents that may be combined with compounds described herein include inhibitors of the PI3K-AKT-mTOR pathway, inhibitors of the Raf-MAPK pathway, inhibitors of JAK-STAT pathway, and inhibitors of protein chaperones and cell cycle progression.

Agents against the PI3 kinase include but are not limited topilaralisib, idelalisib, buparlisib. Inhibitors of mTOR such as rapamycin, sirolimus, temsirolimus, and everolimus may be combined with compounds described herein. Other suitable examples include but are not limited to vemurafenib and dabrafenib (Raf inhibitors) and trametinib, selumetinib and GDC-0973 (MEK inhibitors). Inhibitors of one or more JAKs (e.g., ruxolitinib, baricitinib, tofacitinib), Hsp90 (e.g., tanespimycin), cyclin dependent kinases (e.g., palbociclib), HDACs (e.g., panobinostat), PARP (e.g., olaparib), and proteasomes (e.g., bortezomib, carfilzomib) can also be combined with compounds described herein. In some embodiments, the JAK inhibitor is selective for JAK1 over JAK2 and JAK3.

Other suitable agents for use in combination with compounds described herein include chemotherapy combinations such as platinum-based doublets used in lung cancer and other solid tumors (cisplatin or carboplatin plus gemcitabine; cisplatin or carboplatin plus docetaxel; cisplatin or carboplatin plus paclitaxel; cisplatin or carboplatin plus pemetrexed) or gemcitabine plus paclitaxel bound particles.

Suitable chemotherapeutic or other anti-cancer agents include, for example, alkylating agents (including, without limitation, nitrogen mustards, ethylenimine derivatives, alkyl sulfonates, nitrosoureas and triazenes) such as uracil mustard, chlormethine, cyclophosphamide, ifosfamide, melphalan, chlorambucil, pipobroman, triethylene-melamine, triethylenethio-phosphoramine, busulfan, carmustine, lomustine, streptozocin, dacarbazine, and temozolomide.

Other suitable agents for use in combination with compounds described herein include steroids including 17 alpha-ethinylestradiol, diethylstilbestrol, testosterone, prednisone, fluoxymesterone, methylprednisolone, methyltestosterone, prednisolone, triamcinolone, chlorotrianisene, hydroxyprogesterone, aminoglutethimide, and medroxyprogesteroneacetate.

Other suitable agents for use in combination with compounds described herein include: dacarbazine (DTIC), optionally, along with other chemotherapy drugs such as carmustine (BCNU) and cisplatin; the "Dartmouth regimen," which consists of DTIC, BCNU, cisplatin and tamoxifen; a combination of cisplatin, vinblastine, and DTIC; or temozolomide. Compounds described herein may also be combined with immunotherapy drugs, including cytokines such as interferon alpha, interleukin 2, and tumor necrosis factor (TNF) in.

Suitable chemotherapeutic or other anti-cancer agents include, for example, antimetabolites (including, without limitation, folic acid antagonists, pyrimidine analogs, purine analogs and adenosine deaminase inhibitors) such as methotrexate, 5-fluorouracil, floxuridine, cytarabine, 6-mercaptopurine, 6-thioguanine, fludarabine phosphate, pentostatine, and gemcitabine.

Suitable chemotherapeutic or other anti-cancer agents further include, for example, certain natural products and their derivatives (e.g., vinca alkaloids, antitumor antibiotics, enzymes, lymphokines and epipodophyllotoxins) such as vinblastine, vincristine, vindesine, bleomycin, dactinomycin, daunorubicin, doxorubicin, epirubicin, idarubicin, ara-C, paclitaxel, mithramycin, deoxycoformycin, mitomycin-C, L-asparaginase, interferons (especially IFN-a), etoposide, and teniposide.

Other cytotoxic agents include navelbene, CPT-11, anastrazole, letrazole, capecitabine, reloxafine, cyclophosphamide, ifosamide, and droloxafine Also suitable are cytotoxic agents such as epidophyllotoxin; an antineoplastic enzyme; a topoisomerase inhibitor; procarbazine; mitoxantrone; platinum coordination complexes such as cis-platin and carboplatin; biological response modifiers; growth inhibitors; antihormonal therapeutic agents; leucovorin; tegafur; and haematopoietic growth factors.

Other anti-cancer agent(s) include antibody therapeutics such as trastuzumab (Herceptin), antibodies to costimulatory molecules such as CTLA-4, 4-1BB, PD-L1 and PD-1 antibodies, or antibodies to cytokines (IL-10, TGF-β, etc.).

Other anti-cancer agents also include those that block immune cell migration such as antagonists to chemokine receptors, including CCR2 and CCR4.

Other anti-cancer agents also include those that augment the immune system such as adjuvants or adoptive T cell transfer.

Anti-cancer vaccines include dendritic cells, synthetic peptides, DNA vaccines and recombinant viruses. In some embodiments, tumor vaccines include the proteins from viruses implicated in human cancers such as Human Papilloma Viruses (HPV), Hepatitis Viruses (HBV and HCV) and Kaposi's Herpes Sarcoma Virus (KHSV). Non-limiting examples of tumor vaccines that can be used include peptides of melanoma antigens, such as peptides of gp100, MAGE antigens, Trp-2, MARTI and/or tyrosinase, or tumor cells transfected to express the cytokine GM-CSF.

The compounds of the present disclosure can be used in combination with bone marrow transplant for the treatment of a variety of tumors of hematopoietic origin (see e.g., U.S. Pat. Nos. 9,233,985, 10,065,974, 10,287,303, 8,524,867, the disclosures of which are incorporated by reference herein in their entireties).

Methods for the safe and effective administration of most of these chemotherapeutic agents are known to those skilled in the art. In addition, their administration is described in the standard literature. For example, the administration of many of the chemotherapeutic agents is described in the "Physicians' Desk Reference" (PDR, e.g., 1996 edition, Medical Economics Company, Montvale, NJ), the disclosure of which is incorporated herein by reference as if set forth in its entirety.

As provided throughout, the additional compounds, inhibitors, agents, etc. can be combined with the present compound in a single or continuous dosage form, or they can be administered simultaneously or sequentially as separate dosage forms.

Pharmaceutical Formulations and Dosage Forms

When employed as pharmaceuticals, the compounds of the disclosure can be administered in the form of pharmaceutical compositions. These compositions can be prepared in a manner well known in the pharmaceutical art, and can be administered by a variety of routes, depending upon whether local or systemic treatment is desired and upon the area to be treated. Administration may be topical (including transdermal, epidermal, ophthalmic and to mucous membranes including intranasal, vaginal and rectal delivery), pulmonary (e.g., by inhalation or insufflation of powders or aerosols, including by nebulizer; intratracheal or intranasal), oral, or parenteral. Parenteral administration includes intravenous, intraarterial, subcutaneous, intraperitoneal intramuscular or injection or infusion; or intracranial, e.g., intrathecal or intraventricular, administration. Parenteral administration can be in the form of a single bolus dose, or may be, for example, by a continuous perfusion pump. Pharmaceutical compositions and formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable.

This disclosure also includes pharmaceutical compositions which contain, as the active ingredient, the compound of the disclosure or a pharmaceutically acceptable salt thereof, in combination with one or more pharmaceutically acceptable carriers (excipients). In some embodiments, the composition is suitable for topical administration. In making the compositions of the disclosure, the active ingredient is typically mixed with an excipient, diluted by an excipient or enclosed within such a carrier in the form of, for example, a capsule, sachet, paper, or other container. When the excipient serves as a diluent, it can be a solid, semi-solid, or liquid material, which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, for example, up to 10% by weight of the active compound, soft and hard gelatin capsules, suppositories, sterile injectable solutions, and sterile packaged powders.

In preparing a formulation, the active compound can be milled to provide the appropriate particle size prior to combining with the other ingredients. If the active compound is substantially insoluble, it can be milled to a particle size of less than 200 mesh. If the active compound is substantially water soluble, the particle size can be adjusted by milling to provide a substantially uniform distribution in the formulation, e.g. about 40 mesh.

The compounds of the disclosure may be milled using known milling procedures such as wet milling to obtain a particle size appropriate for tablet formation and for other formulation types. Finely divided (nanoparticulate) preparations of the compounds of the disclosure can be prepared by processes known in the art, e.g., see International App. No. WO 2002/000196.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup, and methyl cellulose. The formulations can additionally include: lubricating agents such as talc, magnesium stearate, and mineral oil; wetting agents; emulsifying and suspending agents; preserving agents such as methyl- and propylhydroxy-benzoates; sweetening agents; and flavoring agents. The compositions of the disclosure can be formulated so as to provide quick, sustained or delayed release of the active ingredient after administration to the patient by employing procedures known in the art.

The compositions can be formulated in a unit dosage form, each dosage containing from about 5 to about 1000 mg (1 g), more usually about 100 to about 500 mg, of the active ingredient. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient.

In some embodiments, the compositions of the disclosure contain from about 5 to about 50 mg of the active ingredient. One having ordinary skill in the art will appreciate that this embodies compositions containing about 5 to about 10, about 10 to about 15, about 15 to about 20, about 20 to about 25, about 25 to about 30, about 30 to about 35, about 35 to about 40, about 40 to about 45, or about 45 to about 50 mg of the active ingredient.

In some embodiments, the compositions of the disclosure contain from about 50 to about 500 mg of the active ingredient. One having ordinary skill in the art will appreciate that this embodies compositions containing about 50 to about 100, about 100 to about 150, about 150 to about 200, about 200 to about 250, about 250 to about 300, about 350 to about 400, or about 450 to about 500 mg of the active ingredient.

In some embodiments, the compositions of the disclosure contain from about 500 to about 1000 mg of the active ingredient. One having ordinary skill in the art will appreciate that this embodies compositions containing about 500 to about 550, about 550 to about 600, about 600 to about 650, about 650 to about 700, about 700 to about 750, about 750 to about 800, about 800 to about 850, about 850 to about 900, about 900 to about 950, or about 950 to about 1000 mg of the active ingredient.

Similar dosages may be used of the compounds described herein in the methods and uses of the disclosure.

The active compound can be effective over a wide dosage range and is generally administered in a pharmaceutically effective amount. It will be understood, however, that the amount of the compound actually administered will usually be determined by a physician, according to the relevant circumstances, including the condition to be treated, the chosen route of administration, the actual compound administered, the age, weight, and response of the individual patient, the severity of the patient's symptoms, and the like.

For preparing solid compositions such as tablets, the principal active ingredient is mixed with a pharmaceutical excipient to form a solid preformulation composition containing a homogeneous mixture of a compound of the present disclosure. When referring to these preformulation compositions as homogeneous, the active ingredient is typically dispersed evenly throughout the composition so that the composition can be readily subdivided into equally effective unit dosage forms such as tablets, pills and capsules. This solid preformulation is then subdivided into unit dosage forms of the type described above containing from, for example, about 0.1 to about 1000 mg of the active ingredient of the present disclosure.

The tablets or pills of the present disclosure can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

The liquid forms in which the compounds and compositions of the present disclosure can be incorporated for administration orally or by injection include aqueous solutions, suitably flavored syrups, aqueous or oil suspensions, and flavored emulsions with edible oils such as cottonseed oil, sesame oil, coconut oil, or peanut oil, as well as elixirs and similar pharmaceutical vehicles.

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as described supra. In some embodiments, the compositions are administered by the oral or nasal respiratory route for local or systemic effect. Compositions can be nebulized by use of inert gases. Nebulized solutions may be breathed directly from the nebulizing device or the nebulizing device can be attached to a face mask, tent, or intermittent positive pressure breathing machine. Solution, suspension, or powder compositions can be administered orally or nasally from devices which deliver the formulation in an appropriate manner.

Topical formulations can contain one or more conventional carriers. In some embodiments, ointments can contain water and one or more hydrophobic carriers selected from, for example, liquid paraffin, polyoxyethylene alkyl ether, propylene glycol, white Vaseline, and the like. Carrier compositions of creams can be based on water in combination with glycerol and one or more other components, e.g. glycerinemonostearate, PEG-glycerinemonostearate and cetylstearyl alcohol. Gels can be formulated using isopropyl alcohol and water, suitably in combination with other components such as, for example, glycerol, hydroxyethyl cellulose, and the like. In some embodiments, topical formulations contain at least about 0.1, at least about 0.25, at least about 0.5, at least about 1, at least about 2, or at least about 5 wt % of the compound of the disclosure. The topical formulations can be suitably packaged in tubes of, for example, 100 g which are optionally associated with instructions for the treatment of the select indication, e.g., psoriasis or other skin condition.

The amount of compound or composition administered to a patient will vary depending upon what is being administered, the purpose of the administration, such as prophylaxis or therapy, the state of the patient, the manner of administration, and the like. In therapeutic applications, compositions can be administered to a patient already suffering from a disease in an amount sufficient to cure or at least partially arrest the symptoms of the disease and its complications. Effective doses will depend on the disease condition being treated as well as by the judgment of the attending clinician depending upon factors such as the severity of the disease, the age, weight and general condition of the patient, and the like.

The compositions administered to a patient can be in the form of pharmaceutical compositions described above. These compositions can be sterilized by conventional sterilization techniques, or may be sterile filtered. Aqueous solutions can be packaged for use as is, or lyophilized, the lyophilized preparation being combined with a sterile aqueous carrier prior to administration. The pH of the compound preparations typically will be between 3 and 11, more preferably from 5 to 9 and most preferably from 7 to 8. It will be understood that use of certain of the foregoing excipients, carriers, or stabilizers will result in the formation of pharmaceutical salts.

The therapeutic dosage of a compound of the present disclosure can vary according to, for example, the particular use for which the treatment is made, the manner of administration of the compound, the health and condition of the patient, and the judgment of the prescribing physician. The proportion or concentration of a compound of the disclosure in a pharmaceutical composition can vary depending upon a number of factors including dosage, chemical characteristics (e.g., hydrophobicity), and the route of administration. For example, the compounds of the disclosure can be provided in an aqueous physiological buffer solution containing about 0.1 to about 10% w/v of the compound for parenteral administration. Some typical dose ranges are from about 1 µg/kg to about 1 g/kg of body weight per day. In some embodiments, the dose range is from about 0.01 mg/kg to about 100 mg/kg of body weight per day. The dosage is likely to depend on such variables as the type and extent of progression of the disease or disorder, the overall health status of the particular patient, the relative biological efficacy of the compound selected, formulation of the excipient, and its route of administration. Effective doses can be extrapolated from dose-response curves derived from in vitro or animal model test systems.

The compositions of the disclosure can further include one or more additional pharmaceutical agents such as a chemotherapeutic, steroid, anti-inflammatory compound, or immunosuppressant, examples of which are listed herein.

Labeled Compounds and Assay Methods

Another aspect of the present disclosure relates to labeled compounds of the disclosure (radio-labeled, fluorescent-labeled, etc.) that would be useful not only in imaging techniques but also in assays, both in vitro and in vivo, for localizing and quantitating V617F in tissue samples, including human, and for identifying V617F inhibitors by binding of a labeled compound. Substitution of one or more of the atoms of the compounds of the present disclosure can also be useful in generating differentiated ADME (Adsorption, Distribution, Metabolism and Excretion.) Accordingly, the present disclosure includes V617F assays that contain such labeled or substituted compounds.

The present disclosure further includes isotopically-labeled compounds of the disclosure. An "isotopically" or "radio-labeled" compound is a compound of the disclosure where one or more atoms are replaced or substituted by an atom having an atomic mass or mass number different from the atomic mass or mass number typically found in nature (i.e., naturally occurring). Suitable radionuclides that may be incorporated in compounds of the present disclosure include but are not limited to $^{2}$H (also written as D for deuterium), $^{3}$H (also written as T for tritium), $^{11}$C, $^{13}$C, $^{14}$C, $^{13}$N, $^{15}$N, $^{15}$O, $^{17}$O, $^{18}$O, $^{18}$F, $^{35}$S, $^{36}$Cl, $^{82}$Br, $^{75}$Br, $^{76}$Br, $^{123}$I, $^{124}$I, $^{125}$I and $^{131}$I. For example, one or more hydrogen atoms in a compound of the present disclosure can be replaced by deuterium atoms (e.g., one or more hydrogen atoms of a $C_{1-6}$ alkyl group of Formula I can be optionally substituted with deuterium atoms, such as —CD$_3$ being substituted for —CH$_3$). In some embodiments, alkyl groups of the disclosed Formulas (e.g., Formula I) can be perdeuterated.

One or more constituent atoms of the compounds presented herein can be replaced or substituted with isotopes of the atoms in natural or non-natural abundance. In some embodiments, the compound includes at least one deuterium atom. For example, one or more hydrogen atoms in a compound presented herein can be replaced or substituted by deuterium (e.g., one or more hydrogen atoms of a $C_{1-6}$ alkyl group can be replaced by deuterium atoms, such as —CD$_3$ being substituted for —CH$_3$). In some embodiments, the compound includes two or more deuterium atoms. In some embodiments, the compound includes 1-2, 1-3, 1-4, 1-5, 1-6, 1-8, 1-10, 1-12, 1-14, 1-16, 1-18, or 1-20 deuterium atoms. In some embodiments, all of the hydrogen atoms in a compound can be replaced or substituted by deuterium atoms.

In some embodiments, each hydrogen atom of the compounds provided herein, such as hydrogen atoms attached to carbon atoms of alkyl, alkenyl, alkynyl, aryl, phenyl, cycloalkyl, heterocycloalkyl, or heteroaryl substituents or —$C_{1-4}$ alkyl-, alkylene, alkenylene, and alkynylene linking groups, as described herein, is optionally replaced by deuterium atoms.

In some embodiments, each hydrogen atom of the compounds provided herein, such as hydrogen atoms to carbon atoms of alkyl, alkenyl, alkynyl, aryl, phenyl, cycloalkyl, heterocycloalkyl, or heteroaryl substituents or —$C_{1-4}$ alkyl-, alkylene, alkenylene, and alkynylene linking groups, as described herein, is replaced by deuterium atoms (i.e., the alkyl, alkenyl, alkynyl, aryl, phenyl, cycloalkyl, heterocycloalkyl, or heteroaryl substituents, or —$C_{1-4}$ alkyl-, alkylene, alkenylene, and alkynylene linking groups are perdeuterated).

In some embodiments, 1, 2, 3, 4, 5, 6, 7, 8, 9, 10, 11, or 12 hydrogen atoms, attached to carbon atoms of alkyl, alkenyl, alkynyl, aryl, phenyl, cycloalkyl, heterocycloalkyl, or heteroaryl substituents or —$C_{1-4}$ alkyl-, alkylene, alkenylene, and alkynylene linking groups, as described herein, are optionally replaced by deuterium atoms.

In some embodiments, 1, 2, 3, 4, 5, 6, 7, or 8 hydrogen atoms, attached to carbon atoms of alkyl, alkenyl, alkynyl, aryl, phenyl, cycloalkyl, heterocycloalkyl, or heteroaryl substituents or —$C_{1-4}$ alkyl-, alkylene, alkenylene, and alkynylene linking groups, as described herein, are optionally replaced by deuterium atoms.

In some embodiments, the compound provided herein (e.g., the compound of any of Formulas I-Xb), or a pharmaceutically acceptable salt thereof, comprises at least one deuterium atom.

In some embodiments, the compound provided herein (e.g., the compound of any of Formulas I-Xb), or a pharmaceutically acceptable salt thereof, comprises two or more deuterium atoms.

In some embodiments, the compound provided herein (e.g., the compound of any of Formulas I-Xb), or a pharmaceutically acceptable salt thereof, comprises three or more deuterium atoms.

In some embodiments, for a compound provided herein (e.g., the compound of any of Formulas I-Xb), or a pharmaceutically acceptable salt thereof, all of the hydrogen atoms are replaced by deuterium atoms (i.e., the compound is "perdeuterated").

Synthetic methods for including isotopes into organic compounds are known in the art (Deuterium Labeling in Organic Chemistry by Alan F Thomas (New York, N.Y., Appleton-Century-Crofts, 1971; The Renaissance of H/D Exchange by Jens Atzrodt, Volker Derdau, Thorsten Fey and Jochen Zimmermann, Angew. Chem. Int. Ed. 2007, 7744-7765; The Organic Chemistry of Isotopic Labelling by James R. Hanson, Royal Society of Chemistry, 2011). Isotopically labeled compounds can be used in various studies such as NMR spectroscopy, metabolism experiments, and/or assays.

Substitution with heavier isotopes, such as deuterium, may afford certain therapeutic advantages resulting from greater metabolic stability, for example, increased in vivo half-life or reduced dosage requirements, and hence may be preferred in some circumstances. (see e.g., A. Kerekes et. al. *J. Med. Chem.* 2011, 54, 201-210; R. Xu et. al. *J. Label Compd. Radiopharm.* 2015, 58, 308-312). In particular, substitution at one or more metabolism sites may afford one or more of the therapeutic advantages.

The radionuclide that is incorporated in the instant radiolabeled compounds will depend on the specific application of that radio-labeled compound. For example, for in vitro V617F labeling and competition assays, compounds that incorporate $^3$H, $^{14}$C, $^{82}$Br, $^{125}$I, $^{131}$I or $^{35}$S can be useful. For radio-imaging applications $^{11}$C, $^{18}$F, $^{125}$I, $^{123}$I, $^{124}$I, $^{131}$I, $^{75}$Br, $^{76}$Br or $^{77}$Br can be useful.

It is understood that a "radio-labeled" or "labeled compound" is a compound that has incorporated at least one radionuclide. In some embodiments, the radionuclide is selected from the group consisting of $^3$H, $^{14}$C, $^{125}$I, $^{35}$S and $^{82}$Br.

The present disclosure can further include synthetic methods for incorporating radio-isotopes into compounds of the disclosure. Synthetic methods for incorporating radio-isotopes into organic compounds are well known in the art, and an ordinary skill in the art will readily recognize the methods applicable for the compounds of disclosure.

A labeled compound of the disclosure can be used in a screening assay to identify/evaluate compounds. For example, a newly synthesized or identified compound (i.e., test compound) which is labeled can be evaluated for its ability to bind V617F by monitoring its concentration variation when contacting with V617F, through tracking of the labeling. For example, a test compound (labeled) can be evaluated for its ability to reduce binding of another compound which is known to bind to V617F (i.e., standard compound). Accordingly, the ability of a test compound to compete with the standard compound for binding to V617F directly correlates to its binding affinity. Conversely, in some other screening assays, the standard compound is labeled and test compounds are unlabeled. Accordingly, the concentration of the labeled standard compound is monitored in order to evaluate the competition between the standard compound and the test compound, and the relative binding affinity of the test compound is thus ascertained.

Kits

The present disclosure also includes pharmaceutical kits useful, for example, in the treatment or prevention of V617F-associated diseases or disorders as described herein, which include one or more containers containing a pharmaceutical composition comprising a therapeutically effective amount of a compound of the disclosure. Such kits can further include, if desired, one or more of various conventional pharmaceutical kit components, such as, for example, containers with one or more pharmaceutically acceptable carriers, additional containers, etc., as will be readily apparent to those skilled in the art. Instructions, either as inserts or as labels, indicating quantities of the components to be administered, guidelines for administration, and/or guidelines for mixing the components, can also be included in the kit.

The invention will be described in greater detail by way of specific examples. The following examples are offered for illustrative purposes, and are not intended to limit the invention in any manner. Those of skill in the art will readily recognize a variety of non-critical parameters which can be changed or modified to yield essentially the same results.

EXAMPLES

Preparatory LC-MS purifications of some of the compounds prepared were performed on Waters mass directed fractionation systems. The basic equipment setup, protocols, and control software for the operation of these systems have been described in detail in the literature (see e.g. "Two-Pump At Column Dilution Configuration for Preparative LC-MS", K. Blom, *J. Combi. Chem.*, 4, 295 (2002); "Optimizing Preparative LC-MS Configurations and Methods for Parallel Synthesis Purification", K. Blom, R. Sparks, J. Doughty, G. Everlof, T. Hague, A. Combs, *J. Combi. Chem.*, 5, 670 (2003); and "Preparative LC-MS Purification: Improved Compound Specific Method Optimization", K. Blom, B. Glass, R. Sparks, A. Combs, *J. Combi. Chem.*, 6, 874-883 (2004)). The compounds separated were typically subjected to analytical liquid chromatography mass spectrometry (LCMS) for purity analysis under the following conditions: Instrument; Agilent 1100 series, LC/MSD, Column: Waters Sunfire™ $C_{18}$ 5 μm, 2.1×50 mm, Buffers: mobile phase A: 0.025% TFA in water and mobile phase B: acetonitrile; gradient 2% to 80% of B in 3 minutes with flow rate 2.0 mL/minute.

Some of the compounds prepared were also separated on a preparative scale by reverse-phase high performance liquid chromatography (RP-HPLC) with MS detector or flash chromatography (silica gel) as indicated in the Examples. Typical preparative reverse-phase high performance liquid chromatography (RP-HPLC) column conditions are as follows:

pH=2 purifications: Waters Sunfire™ $C_{18}$ 5 µm, 19×100 mm, eluting with mobile phase A: 0.1% TFA (trifluoroacetic acid) in water and mobile phase B: acetonitrile; the flow rate was 30 mL/minute, the separating gradient was optimized for each compound using the Compound Specific Method Optimization protocol as described in the literature (see e.g. "Preparative LCMS Purification: Improved Compound Specific Method Optimization", K. Blom, B. Glass, R. Sparks, A. Combs, *J. Comb. Chem.*, 6, 874-883 (2004)). For purifications using a 30×100 mm column, the flow rate was 60 mL/minute.

pH=10 purifications: Waters XBridge™ $C_{18}$ 5 µm, 19×100 mm column, eluting with mobile phase A: 0.15% $NH_4OH$ in water and mobile phase B: acetonitrile; the flow rate was 30 mL/minute, the separating gradient was optimized for each compound using the Compound Specific Method Optimization protocol as described in the literature (see e.g. "Preparative LCMS Purification: Improved Compound Specific Method Optimization", K. Blom, B. Glass, R. Sparks, A. Combs, *J. Comb. Chem.*, 6, 874-883 (2004)). For purifications using a 30×100 mm column, the flow rate was 60 mL/minute.

The invention will be described in greater detail by way of specific examples. The following examples are offered for illustrative purposes, and are not intended to limit the invention in any manner. Those of skill in the art will readily recognize a variety of noncritical parameters which can be changed or modified to yield essentially the same results.

Example 1

6-Methyl-2-(4-((4-(methylsulfonyl)piperidin-1-yl)methyl)phenyl)-1-phenyl-2',3,3',5',6,6'-hexahydro-7H-spiro[dipyrrolo[2,3-b:3',2'-d]pyridine-8,4'-pyran]-7-one

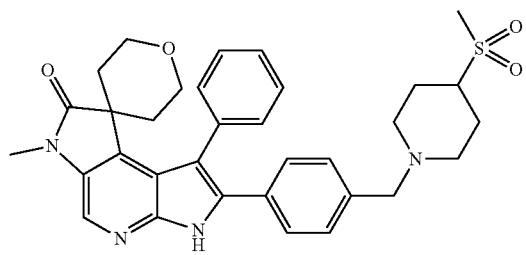 [SMILES: CN1C(=O)C2(CCOCC2)c2c1cnc1[nH]c(-c3ccc(CN4CCC(S(C)(=O)=O)CC4)cc3)c(-c3ccccc3)c21]

Step 1. 4-(Methylsulfonyl)-1-(4-(4,4,5,5-tetramethyl-1,3,2-dioxaborolan-2-yl)benzyl)piperidine

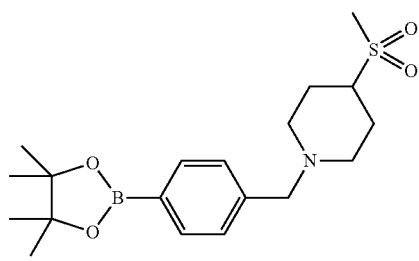 [SMILES: CC1(C)OB(c2ccc(CN3CCC(S(C)(=O)=O)CC3)cc2)OC1(C)C]

To a solution of 2-(4-(bromomethyl)phenyl)-4,4,5,5-tetramethyl-1,3,2-dioxaborolane (6.25 g, 21.0 mmol, Combi-Blocks, BB-2488) in DMF (50 mL) was added $K_2CO_3$ (8.7 g, 63 mmol) and 4-(methylsulfonyl)piperidine (3.6 g, 22 mmol, Combi-Blocks, OT-2818). The resulting solution was stirred at room temperature for 1 hour. The reaction mixture was diluted with EtOAc and was washed with water. The aqueous layer was extracted with EtOAc and the combined organic layers were washed twice with brine (i.e., a saturated aqueous NaCl solution), dried over $MgSO_4$, filtered and concentrated. The product was used without further purification (6.2 g, 77%). LCMS for $C_{19}H_{31}BNO_4S$ $(M+H)^+$: calculated m/z=380.2; found 380.2.

Step 2. Methyl 4-(5-nitro-1-(phenylsulfonyl)-1H-pyrrolo[2,3-b]pyridin-4-yl)tetrahydro-2H-pyran-4-carboxylate

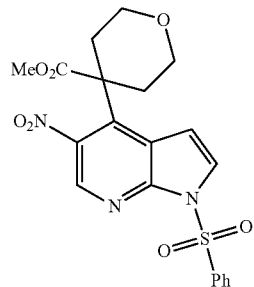

A mixture of 4-chloro-5-nitro-1-(phenylsulfonyl)-1H-pyrrolo[2,3-b]pyridine (1.0 g, 3.0 mmol, AstaTech, Inc., P12207) and methyl tetrahydro-2H-pyran-4-carboxylate (0.40 mL, 3.0 mmol, Sigma-Aldrich, 40199) was azeotroped with toluene to remove moisture. The residue was then dissolved in THF (14.8 mL) and was cooled to −78° C. Lithium bis(trimethylsilyl)amide (LiHMDS) in THF (1.0 M, 5.9 mL, 5.9 mmol) was added. The reaction temperature was raised to −20° C. over 30 min. The cold reaction mixture was then poured into dilute HCl and EtOAc. The aqueous layer was further extracted with EtOAc. The combined organic extracts were dried over $Na_2SO_4$, filtered and concentrated. The product was purified via flash column chromatography on silica gel, eluting with a gradient from 0-100% EtOAc in hexanes to afford the title compound (0.59 g, 45%). LCMS for $C_{20}H_{20}N_3O_7S$ $(M+H)^+$: calculated m/z=446.1; found 446.1.

Step 3. 3-(Phenylsulfonyl)-2',3,3',5',6,6'-hexahydro-7H-spiro[dipyrrolo[2,3-b:2',3'-d]pyridine-8,4'-pyran]-7-one

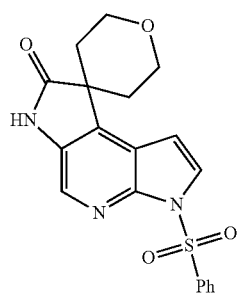 [SMILES: O=C1Nc2cnc3c(ccn3S(=O)(=O)c3ccccc3)c2C12CCOCC2]

A mixture of methyl 4-(5-nitro-1-(phenylsulfonyl)-1H-pyrrolo[2,3-b]pyridin-4-yl)tetrahydro-2H-pyran-4-carboxylate (0.59 g, 1.3 mmol), iron (0.74 g, 13 mmol), and ammonium chloride (1.4 g, 26 mmol) in water (7.1 mL) and ethanol (11 mL) was heated at 60° C. for 3 hours. Upon cooling to room temperature, the reaction mixture was diluted with water and methanol, was filtered through Celite®, and the Celite® was washed with additional EtOAc. The filtrate was partitioned between EtOAc and brine. The organic layer was dried over $Na_2SO_4$, filtered and concentrated. The product was used without further purification in Step 4. Theoretical yield was assumed. LCMS for $C_{19}H_{18}N_3O_4S$ (M+H)$^+$: calculated m/z=384.1; found 384.1.

Step 4. 6-Methyl-3-(phenylsulfonyl)-2',3,3',5',6,6'-hexahydro-7H-spiro[dipyrrolo[2,3-b:3',2'-c]pyridine-8,4'-pyran]-7-one

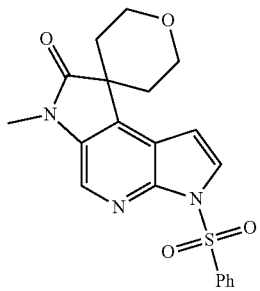 [SMILES: CN1C(=O)C2(CCOCC2)c2c1cnc1c2ccn1S(=O)(=O)c1ccccc1]

To a solution of 3-(phenylsulfonyl)-2',3,3',5',6,6'-hexahydro-7H-spiro[dipyrrolo[2,3-b:3',2'-d]pyridine-8,4'-pyran]-7-one (0.50 g, 1.3 mmol) in DMF (7.7 mL) was added $Cs_2CO_3$ (1.1 g, 3.3 mmol) and iodomethane (0.097 mL, 1.6 mmol). The mixture was heated at 50° C. for 1 hour. Additional iodomethane was added (0.10 mL, 1.6 mmol) and heating at 50° C. was continued for 35 min. Upon cooling to room temperature, the reaction mixture was diluted with saturated $NH_4Cl$ solution and was extracted with EtOAc (3×). The combined organic extracts were washed with brine, dried over $Na_2SO_4$, filtered and concentrated. The product was used without further purification in Step 5. Theoretical yield was assumed. LCMS for $C_{20}H_{20}N_3O_4S$ (M+H)$^+$: calculated m/z=398.1; found 398.1.

Step 5. 1-Bromo-6-methyl-3-(phenylsulfonyl)-2',3,3',5',6,6'-hexahydro-7H-spiro[dipyrrolo[2,3-b:3',2'-c]pyridine-8,4'-pyran]-7-one

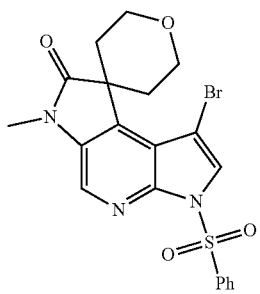 [SMILES: CN1C(=O)C2(CCOCC2)c2c1cnc1c2c(Br)cn1S(=O)(=O)c1ccccc1]

A solution of 6-methyl-3-(phenylsulfonyl)-2',3,3',5',6,6'-hexahydro-7H-spiro[dipyrrolo[2,3-b:3',2'-d]pyridine-8,4'-pyran]-7-one (0.52 g, 1.3 mmol) and N-bromosuccinimide (NBS) (0.26 g, 1.4 mmol) in DMF (6.5 mL) was stirred at 40° C. for 1 hour. Upon cooling to room temperature, the reaction mixture was diluted with EtOAc and washed sequentially with saturated $NaHCO_3$ solution, water, and brine. The solution was dried over $Na_2SO_4$, filtered and concentrated. The product was purified via flash column chromatography on silica gel, eluting with a gradient of 0-100% EtOAc in hexanes to afford the title compound (180 mg, 29%). LCMS for $C_{20}H_{19}BrN_3O_4S$ (M+H)$^+$: calculated m/z=476.0, 478.0; found 476.0, 478.0.

Step 6. 6-Methyl-1-phenyl-3-(phenylsulfonyl)-2',3,3',5',6,6'-hexahydro-7H-spiro[dipyrrolo[2,3-b:3',2'-d]pyridine-8,4'-pyran]-7-one

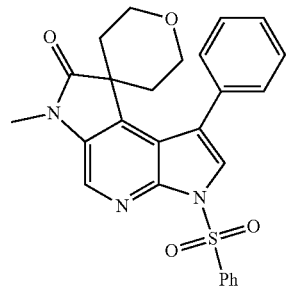 [SMILES: CN1C(=O)C2(CCOCC2)c2c1cnc1c2c(-c2ccccc2)cn1S(=O)(=O)c1ccccc1]

A mixture of 1-bromo-6-methyl-3-(phenylsulfonyl)-2',3,3',5',6,6'-hexahydro-7H-spiro[dipyrrolo[2,3-b:3',2'-d]pyridine-8,4'-pyran]-7-one (0.085 g, 0.18 mmol), phenylboronic acid (0.033 g, 0.27 mmol), $Na_2CO_3$ solution (1.0 M in water, 0.54 mL, 0.54 mmol) and tetrakis(triphenylphosphine)palladium(0) (0.021 g, 0.018 mmol) in DMF (1.8 mL) was degassed by sparging with nitrogen, then was sealed and heated at 120° C. in a microwave for 30 min. Upon cooling to room temperature, the reaction mixture was diluted with EtOAc, washed sequentially with saturated $NaHCO_3$, water, and brine, dried over $Na_2SO_4$, filtered, and concentrated. The product was purified via preparative HPLC-MS (pH=10 method) and the fractions containing product were concentrated to dryness and then azeotroped with toluene to afford the title compound (72 mg, 85%). LCMS for $C_{26}H_{24}N_3O_4S$ (M+H)$^+$: calculated m/z=474.1; found 474.2.

Step 7. 2-Bromo-6-methyl-1-phenyl-3-(phenylsulfonyl)-2',3,3',5',6,6'-hexahydro-7H-spiro[dipyrrolo[2,3-b:3',2'-d]pyridine-8,4'-pyran]-7-one

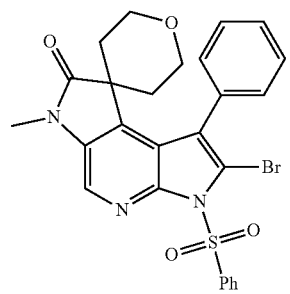 [SMILES: CN1C(=O)C2(CCOCC2)c2c1cnc1c2c(-c2ccccc2)c(Br)n1S(=O)(=O)c1ccccc1]

A solution of 6-methyl-1-phenyl-3-(phenylsulfonyl)-2',3, 3',5',6,6'-hexahydro-7H-spiro[dipyrrolo[2,3-b:3',2'-d]pyridine-8,4'-pyran]-7-one (72 mg, 0.15 mmol) in dry THF (5.1 mL) at −78° C. under $N_2$ was treated with lithium diisopropylamide solution (LDA) (2.0M THF/heptane/ethylbenzene, 0.27 mL, 0.53 mmol). The reaction mixture was stirred at −78° C. for 30 minutes. A solution of 1,2-dibromo-1,1,2,2-tetrachloroethane (0.17 g, 0.53 mmol) in THF (1.0 mL) was then added. The reaction mixture was stirred at −78° C. for 30 min. The reaction mixture was quenched by pouring into saturated aqueous $NH_4Cl$ solution. The resulting mixture was diluted with water and was extracted with EtOAc. The organic layer was separated, and the aqueous layer was extracted with two further portions of EtOAc. The combined organic extracts were dried over $Na_2SO_4$, filtered, and concentrated. The product was purified via flash column chromatography on silica gel, eluting with a gradient from 0-100% EtOAc in hexanes to afford the title compound (0.50 g, 60%). LCMS for $C_{26}H_{23}BrN_3O_4S$ $(M+H)^+$: calculated m/z=552.1, 554.1; found 552.2, 554.1.

Step 8. 6-Methyl-2-((4-(4-(methylsulfonyl)piperidin-1-yl)methyl)phenyl)-1-phenyl-2',3,3',5,6,6'-hexahydro-7H-spiro[dipyrrolo[2,3-b:3,2'-d]pyridine-8,4'-pyran]-7-one A mixture of 2-bromo-6-methyl-1-phenyl-3-(phenylsulfonyl)-2',3,3',5',6,6'-hexahydro-7H-spiro[dipyrrolo[2,3-b:3',2'-d]pyridine-8,4'-pyran]-7-one (21 mg, 0.038 mmol), 4-(methylsulfonyl)-1-(4-(4,4,5,5-tetramethyl-1,3,2-dioxaborolan-2-yl)benzyl)piperidine (22 mg, 0.057 mmol, from Example 1, Step 1), $PdCl_2(dppf)-CH_2Cl_2$ adduct (3.1 mg, 3.8 μmol) and $Na_2CO_3$ (1.0 M in water, 0.11 mL, 0.11 mmol) in dioxane (0.63 mL) was degassed by sparging with $N_2$, then was heated at 100° C. for 2 hours. Upon cooling to room temperature, the reaction mixture was diluted with 1:1 THF:MeOH (1.0 mL), and NaOH solution (1.0 N in water, 0.25 mL, 0.25 mmol) was added. The reaction was stirred for 2 hours. Additional NaOH solution (3.0 N, 0.20 mL, 0.60 mmol) was added and the reaction was stirred overnight. The reaction mixture was diluted with MeCN and MeOH and filtered, then was purified via preparative HPLC-MS (pH=2 method). Fractions containing product were combined and concentrated to dryness. The residue was dissolved in MeOH and was purified via preparative HPLC-MS (pH=10 method) to afford the title compound (5.0 mg, 23%). LCMS for $C_{33}H_{37}N_4O_4S$ $(M+H)^+$: calculated m/z=585.3; found 585.3. $^1H$ NMR (400 MHz, DMSO-$d_6$) δ 12.16 (s, 1H), 8.09 (s, 1H), 7.49-7.37 (m, 5H), 7.34 (d, J=8.0 Hz, 2H), 7.18 (d, J=8.0 Hz, 2H), 3.99 (t, J=11.5 Hz, 2H), 3.42 (s, 2H), 3.31-3.27 (m, 2H), 3.19 (s, 3H), 3.02 (tt, J=12.3, 3.6 Hz, 1H), 2.90 (s, 3H), 2.91-2.84 (m, 2H), 1.95 (m, 6H), 1.59 (qd, J=13.0, 3.8 Hz, 2H), 1.27 (d, J=13.4 Hz, 2H).

Example 2

6-Methyl-2-(4-((4-(methylsulfonyl)piperidin-1-yl)methyl)phenyl)-1-phenyl-3,4',5',6-tetrahydro-2'H,7H-spiro[dipyrrolo[2,3-b:3',2'-d]pyridine-8,3'-furan]-7-one trifluoroacetate salt (Racemic Mixture Prepared)

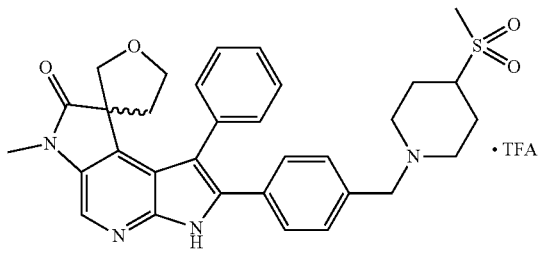 [SMILES: CN1C(=O)C2(CCOC2)c2c1cnc1[nH]c(-c3ccc(CN4CCC(S(C)(=O)=O)CC4)cc3)c(-c3ccccc3)c21]

The title compound was prepared by following a procedure analogous to that described for Example 1, starting with 4-chloro-5-nitro-1-(phenylsulfonyl)-1H-pyrrolo[2,3-b]pyridine (2.0 g, 5.9 mmol) and methyl tetrahydrofuran-3-carboxylate (0.77 g, 5.9 mmol, Ark Pharm, AK137950) in place of methyl tetrahydro-2H-pyran-4-carboxylate in Step 2 with the following differences: The product obtained in Step 6 was purified via flash column chromatography on silica gel, eluting with a gradient from 0-100% EtOAc in hexanes rather than via preparative HPLC-MS, and the final product that was obtained in Step 8 was purified via preparative HPLC-MS (pH=2 method) to afford the title compound as the trifluoroacetate salt (10 mg). LCMS for $C_{32}H_{35}N_4O_4S$ $(M+H)^+$: calculated m/z=571.2; found 571.2. $^1H$ NMR (400 MHz, DMSO-$d_6$) δ 12.34 (s, 1H), 9.57 (s, 1H), 8.14 (s, 1H), 7.51-7.42 (m, 7H), 7.39 (d, J=8.2 Hz, 2H), 4.25 (s, 2H), 3.74 (s, 2H), 3.70 (q, J=8.3, 7.5 Hz, 1H), 3.50 (d, J=12.2 Hz, 2H), 3.39 (tt, J=12.2, 3.4 Hz, 1H), 3.21 (s, 3H), 3.04-2.90 (m, 2H), 2.99 (s, 3H), 2.60 (td, J=8.0, 5.3 Hz, 1H), 2.23 (d, J=13.7 Hz, 2H), 2.11-1.93 (m, 2H), 1.91-1.75 (m, 2H).

Example 3

1-(1-Acetylpiperidin-4-yl)-6'-methyl-2'-(4-04-(methylsulfonyl)piperidin-1-yl)methyl)phenyl)-1'-phenyl-3',6'-dihydro-7'H-spiro[azetidine-3,8'-dipyrrolo[2,3-b:3',2'-d]pyridin]-7'-one

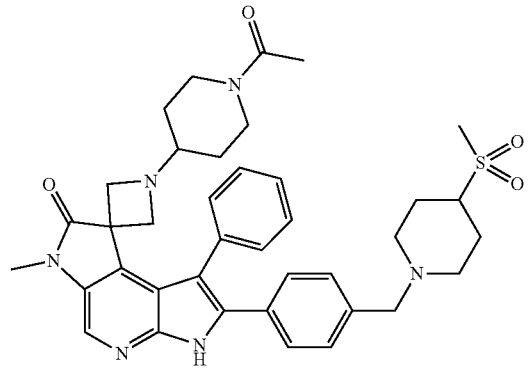 [SMILES: CC(=O)N1CCC(N2CC3(C2)C(=O)N(C)c2cnc4[nH]c(-c5ccc(CN6CCC(S(C)(=O)=O)CC6)cc5)c(-c5ccccc5)c4c23)CC1]

Step 1. tert-Butyl 2'-bromo-6'-methyl-7'-oxo-1'-phenyl-3'-(phenylsulfonyl)-6',7'-dihydro-3'H-spiro[azetidine-3,8'-dipyrrolo[2,3-b:3',2'-d]pyridine]-1-carboxylate

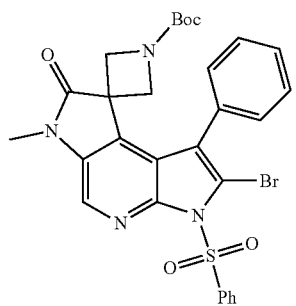 [SMILES: CN1C(=O)C2(CN(C(=O)OC(C)(C)C)C2)c2c1cnc1c2c(-c2ccccc2)c(Br)n1S(=O)(=O)c1ccccc1]

The title compound was prepared by following the procedures described in Example 1, Steps 2 through 7, using 4-chloro-5-nitro-1-(phenylsulfonyl)-1H-pyrrolo[2,3-b]pyridine (2.4 g, 7.2 mmol) and 1-(tert-butyl) 3-methyl azetidine-1,3-dicarboxylate (1.9 g, 8.7 mmol, AstaTech, Inc., BL007805) instead of methyl tetrahydro-2H-pyran-4-carboxylate in Step 2, and the product obtained in Step 7 was used without further purification in Step 8. LCMS for $C_{29}H_{28}BrN_4O_5S$ (M+H)$^+$: calculated m/z=623.1, 625.1; found 623.2, 625.2.

Step 2. tert-Butyl 2'-bromo-6'-methyl-7'-oxo-1'-phenyl-6',7'-dihydro-3'H-spiro[azetidine-3,8'-pyrrolo[2,3-b:3',2'-d]pyridine]-1-carboxylate

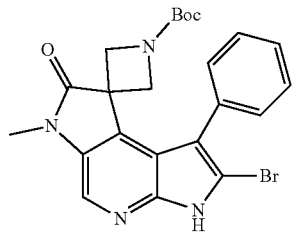 [SMILES: CN1C(=O)C2(CN(C(=O)OC(C)(C)C)C2)c2c1cnc1[nH]c(Br)c(-c3ccccc3)c21]

To tert-butyl 2'-bromo-6'-methyl-7'-oxo-1'-phenyl-3'-(phenyl sulfonyl)-6',7'-dihydro-3'H-spiro[azetidine-3,8'-dipyrrolo[2,3-b:3',2'-d]pyridine]-1-carboxylate (0.15 g, 0.24 mmol) in 1:1 THF:MeOH (4.8 mL) was added NaOH solution (1.0 N, 1.2 mL, 1.2 mmol). The reaction was stirred for 2 hours, then was diluted with water and brine and the mixture was extracted with EtOAc (3×). The combined organic extracts were dried over Na$_2$SO$_4$, filtered and concentrated. The product was purified via flash column chromatography on silica gel, eluting with a gradient from 0-100% EtOAc in hexanes to afford the title compound (0.055 g, 48%). LCMS for $C_{23}H_{24}BrN_4O_3$ (M+H)$^+$: calculated m/z=483.1, 485.1; found 483.2, 485.2.

Step 3. tert-Butyl 6'-methyl-2'-((4-(methylsulfonyl)piperidin-1-yl)methyl)phenyl)-7'-oxo-1'-phenyl-6,7'-dihydro-3'H-spiro[azetidine-3,8pyrrolo[2,3-b:3,2'-d]pyridine]-1-carboxylate

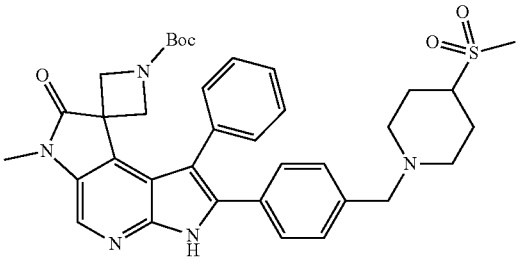

A mixture of tert-butyl 2'-bromo-6'-methyl-7'-oxo-1'-phenyl-6',7'-dihydro-3'H-spiro[azetidine-3,8'-dipyrrolo[2,3-b:3',2'-d]pyridine]-1-carboxylate (0.17 g, 0.35 mmol), 4-(methylsulfonyl)-1-(4-(4,4,5,5-tetramethyl-1,3,2-dioxaborolan-2-yl)benzyl)piperidine (0.20 g, 0.53 mmol, from Example 1, Step 1), PdCl$_2$(dppf)-CH$_2$Cl$_2$ adduct (0.029 g, 0.035 mmol) and Na$_2$CO$_3$ solution (1.0 M in water, 1.1 mL, 1.1 mmol) in dioxane (3.5 mL) was degassed by sparging with N$_2$, then was heated at 100° C. for 2 h. Upon cooling to room temperature, the reaction mixture was diluted with EtOAc and water, then was filtered through Celite®. The layers were separated and the organic layer was washed with brine, dried over Na$_2$SO$_4$, filtered, and concentrated. The product was purified via flash column chromatography on silica gel, eluting with a gradient from 0-100% EtOAc then with a gradient from 0-10% MeOH in DCM to afford the title compound which was used directly in the next step, assuming theoretical yield. LCMS for $C_{36}H_{42}N_5O_5S$ (M+H)$^+$: calculated m/z=656.3; found 656.4.

Step 4. 6'-Methyl-2'-((4-(methylsulfonyl)piperidin-1-yl)methyl)phenyl)-1'-phenyl-3',6'-dihydro-7'H-spiro[azetidine-3,8'-dipyrrolo[2,3-b:3',2'-d]pyridin]-7'-one

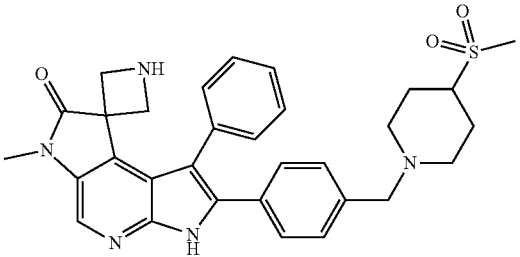

A solution of tert-butyl 6'-methyl-2'-(4-((4-(methylsulfonyl)piperidin-1-yl)methyl)phenyl)-7'-oxo-1'-phenyl-6',7'-dihydro-3'H-spiro[azetidine-3,8'-dipyrrolo[2,3-b:3',2'-d]pyridine]-1-carboxylate (0.23 g, 0.35 mmol) in trifluoroacetic acid (1.5 mL) and CH$_2$Cl$_2$ (2.0 mL) was stirred at room temperature for 1 hour. Volatiles were removed in vacuo to afford the product as the TFA salt. The residue was dissolved in MeOH and filtered, then purified via preparative HPLC-MS (pH=10 method) to afford the title compound (0.037 g, 19% over 2 steps). LCMS for $C_{31}H_{34}N_5O_3S$ (M+H)$^+$: calculated m/z=556.2; found 556.3.

Step 5. 6'-Methyl-2'-((4-(methylsulfonyl)piperidin-1-yl)methyl)phenyl)-1'-phenyl-1-(piperadin-4-yl)-3',6'-dihydro-7'H-spiro[azetidine-3,8'-dipyrrolo[2,3-b:3',2'-d]pyridin]-7'-one trifluoroacetate salt

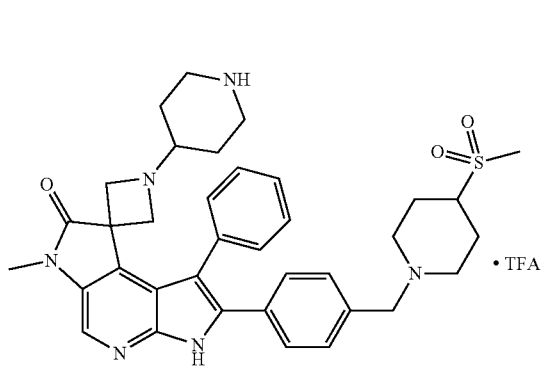

A solution of 6'-methyl-2'-(4-((4-(methylsulfonyl)piperidin-1-yl)methyl)phenyl)-1'-phenyl-3',6'-dihydro-7'H-spiro[azetidine-3,8'-dipyrrolo[2,3-b:3',2'-d]pyridin]-7'-one (0.037 g, 0.067 mmol) and tert-butyl 4-oxopiperidine-1-carboxylate (0.027 g, 0.13 mmol, Sigma-Aldrich, 461350) was stirred for 15 min, at which time sodium triacetoxyborohydride (0.042 g, 0.20 mmol) was added and the reaction was stirred overnight. Additional tert-butyl 4-oxopiperidine-1-carboxylate (0.027 g, 0.13 mmol) and sodium triacetoxyborohydride (0.042 g, 0.20 mmol) were added and the reaction was stirred for 3 hours. The reaction was quenched by the addition of saturated NaHCO$_3$ solution, and the mixture was extracted with EtOAc (3×). The combined organic extracts were washed with brine, dried over Na$_2$SO$_4$, filtered and concentrated. The crude product was stirred in TFA:DCM (1:1, 2 mL) for 1 hour. Volatiles were removed in vacuo and the residue was purified via preparative HPLC-MS (pH=2 method) to afford the title compound (5.0 mg). LCMS for C$_{36}$H$_{43}$N$_6$O$_3$S (M+H)$^+$: calculated m/z=639.3; found 639.6.

Step 6. 1-(1-Acetylpiperidin-4-yl)-6'-methyl-2'-((4(4-(methylsulfonyl)piperidin-1-yl)methyl)phenyl)-1'-phenyl-3',6'-dihydro-7'H-spiro[azetidine-3,8'-dipyrrolo[2,3-b:3',2'-d]pyridin]-7'-one To 6'-methyl-2'-(4-((4-(methylsulfonyl)piperidin-1-yl)methyl)phenyl)-1'-phenyl-1-(piperidin-4-yl)-3',6'-dihydro-7'H-spiro[azetidine-3,8'-dipyrrolo[2,3-b:3',2'-d]pyridin]-7'-one (5.0 mg, 7.8 µmol) in acetonitrile (0.16 mL) was added diisopropylethylamine (DIPEA) (4.1 µL, 0.023 mmol), followed by acetyl chloride (0.67 µL, 9.4 µmol, as an aliquot of a stock solution in acetonitrile). After stirring for 20 min, the reaction mixture was diluted with MeCN and purified via preparative HPLC-MS (pH=10 method) to afford the title compound (1.4 mg, 26%). LCMS for C$_{38}$H$_{45}$N$_6$O$_4$S (M+H)$^+$: calculated m/z=681.3; found 681.4.

Example 4

3-(6-Methyl-2-((4(4-(methylsulfonyl)piperidin-1-yl)methyl)phenyl)-7-oxo-1-phenyl-6,7-dihydro-3H-spiro[dipyrrolo[2,3-b:3',2'-d]pyridine-8,4'-piperidin]-1'-yl)propanenitrile trifluoroacetate salt

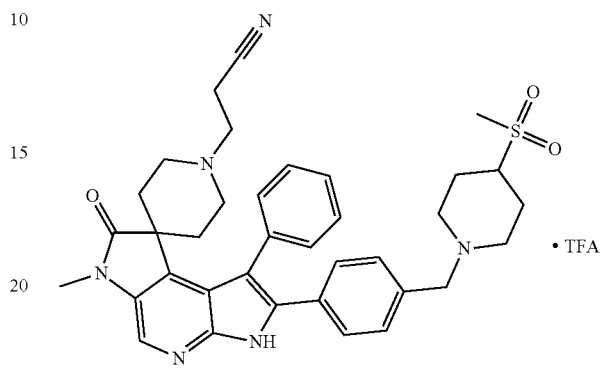

Step 1. 1-(tert-Butyl) 4-methyl 4-(5-nitro-1-(phenylsulfonyl)-1H-pyrrolo[2,3-b]pyridin-4-yl)piperidine-1,4-dicarboxylate

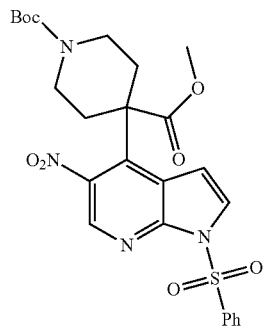 [SMILES: COC(=O)C1(c2c([N+](=O)[O-])cnc3c2ccn3S(=O)(=O)c2ccccc2)CCN(C(=O)OC(C)(C)C)CC1]

A mixture of 4-chloro-5-nitro-1-(phenyl sulfonyl)-1H-pyrrolo[2,3-b]pyridine (1.5 g, 4.4 mmol, Enamine EN300-386169) and 1-(tert-butyl) 4-methyl piperidine-1,4-dicarboxylate (1.3 g, 5.3 mmol, Oxchem AX8014276) was azeotroped with toluene to provide dry starting materials. The residue was dissolved in THF (80.0 mL), and the solution was cooled to −78° C. LiHMDS (1.0 M in THF, 8.9 mL, 8.9 mmol) was added. The mixture was then allowed to warm up to −20° C. slowly over a period of 1.5 hours. The mixture was quenched by the addition of aq. HCl (1.0 N) at −20° C. The reaction mixture was then diluted with water and was extracted with EtOAc. The organic layer was washed successively with water and brine, then was dried over Na$_2$SO$_4$, filtered and concentrated. Purification on a 120 g silica gel column, eluting with a gradient of 0-40% EtOAc in hexanes, afforded the title compound (1.4 g, 56%). LCMS for C$_{20}$H$_{21}$N$_4$O$_6$S (M-Boc+H)$^+$: calculated m/z=445.1; found 445.3.

Step 2. tert-Butyl 7-oxo-3-(phenylsulfonyl)-6,7-dihydro-3H-spiro[dipyrrolo[2,3-b:3,2'-b]pyridine-8,4'-piperidine]-1'-carboxylate

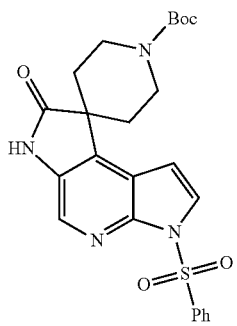

A mixture of 1-(tert-butyl) 4-methyl 4-(5-nitro-1-(phenylsulfonyl)-1H-pyrrolo[2,3-b]pyridin-4-yl)piperidine-1,4-dicarboxylate (1.4 g, 2.5 mmol), iron powder (1.4 g, 25 mmol), NH$_4$Cl (2.7 g, 50.0 mmol), water (1.5 mL) and ethanol (24 mL) was heated at 60° C. for 80 min. Upon cooling to room temperature, the reaction mixture was diluted with water and MeOH, was filtered through Celite®, and the Celite® was rinsed with EtOAc. To the filtrate was added brine, and the layers were shaken and separated. The organic layer was washed again with brine, dried over Na$_2$SO$_4$, filtered and concentrated. Purification on a 120 g silica gel column, eluting with a gradient of 0-60% EtOAc in hexanes, afforded the title compound (0.94 g, 78%). LCMS for C$_{24}$H$_{27}$H$_4$O$_5$S (M+H)$^+$: calculated m/z=483.2; found 483.2.

Step 3. tert-Butyl 6-methyl-7-oxo-3-(phenylsulfonyl)-6,7-dihydro-3H-spiro[dipyrrolo[2,3-b:3',2'-d]pyridine-8,4'-piperidine]-1'-carboxylate

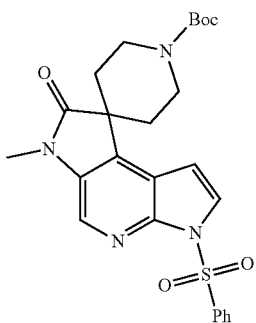 [SMILES: CN1C(=O)C2(CCN(C(=O)OC(C)(C)C)CC2)c2c1cnc1c2ccn1S(=O)(=O)c1ccccc1]

To a solution of tert-butyl 7-oxo-3-(phenylsulfonyl)-6,7-dihydro-3H-spiro[dipyrrolo[2,3-b:3',2'-d]pyridine-8,4'-piperidine]-1'-carboxylate (2.3 g, 4.8 mmol) in DMF (24 mL) was added Cs$_2$CO$_3$ (3.9 g, 12 mmol) and iodomethane (0.59 mL, 9.5 mmol). The mixture was sealed in a pressure vessel and heated at 50° C. in oil bath for 35 min. Upon cooling to room temperature, the reaction mixture was diluted with EtOAc, was filtered through Celite®, and the filtrate was evaporated. The residue was purified by flash chromatography on a 120 g silica gel column, eluting with a gradient of 0-60% EtOAc in hexanes, to afford the title compound (1.7 g, 74%). LCMS for C$_{25}$H$_{29}$N$_4$O$_5$S (M+H)$^+$: calculated m/z=497.2; found 497.3. $^1$H NMR (400 MHz, DMSO-d$_6$) δ 8.17 (s, 1H), 8.15-8.09 (m, 2H), 8.02 (d, J=4.1 Hz, 1H), 7.73 (t, J=7.4 Hz, 1H), 7.63 (t, J=7.7 Hz, 2H), 6.86 (d, J=4.2 Hz, 1H), 3.96-3.76 (m, 2H), 3.68-3.39 (m, 2H), 3.19 (s, 3H), 2.06-1.94 (m, 2H), 1.76-1.64 (m, 2H), 1.46 (s, 9H).

Step 4. tert-Butyl 1-bromo-6-methyl-7-oxo-3-(phenylsulfonyl)-6,7-dihydro-3H-spiro[dipyrrolo[2,3-b:3',2'-c]pyridine-8,4'-piperidine]-1'-carboxylate

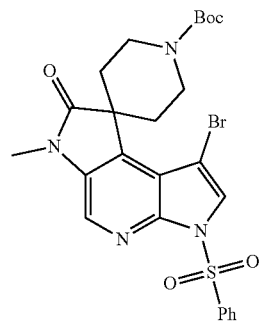 [SMILES: CN1C(=O)C2(CCN(C(=O)OC(C)(C)C)CC2)c2c1cnc1c2c(Br)cn1S(=O)(=O)c1ccccc1]

To a solution of tert-butyl 6-methyl-7-oxo-3-(phenylsulfonyl)-6,7-dihydro-3H-spiro[dipyrrolo[2,3-b:3',2'-d]pyridine-8,4'-piperidine]-1'-carboxylate (1.0 g, 2.0 mmol) in DMF (12 mL) was added NBS (0.39 g, 2.2 mmol). The mixture was stirred at room temperature for 40 min. Additional NBS (0.036 g, 0.20 mmol) was added. The mixture was stirred at room temperature for 20 min, then was diluted with EtOAc, washed sequentially with saturated NaHCO$_3$, water and brine, was dried over Na$_2$SO$_4$ and evaporated. The residue was purified on a 40 g silica gel column with a gradient of 0-60% EtOAc in hexanes to afford a brown solid (1.1 g, 97%). LCMS for C$_{25}$H$_{28}$BrN$_4$O$_5$S (M+H)$^+$: calculated monoisotopic m/z=575.1; found 575.1. $^1$H NMR (400 MHz, DMSO-d$_6$) δ 8.35 (s, 1H), 8.26 (s, 1H), 8.16 (d, J=7.9 Hz, 2H), 7.76 (t, J=7.4 Hz, 1H), 7.65 (t, J=7.7 Hz, 2H), 4.06-3.81 (m, 2H), 3.71-3.41 (m, 2H), 3.19 (s, 3H), 2.66-2.43 (m, 2H), 1.70-1.59 (m, 2H), 1.43 (s, 9H).

Step 5. tert-Butyl 6-methyl-7-oxo-1-phenyl-3-(phenylsulfonyl)-6,7-dihydro-3H-spiro[dipyrrolo[2,3-b:3',2'-d]pyridine-8,4'-piperidine]-1'-carboxylate

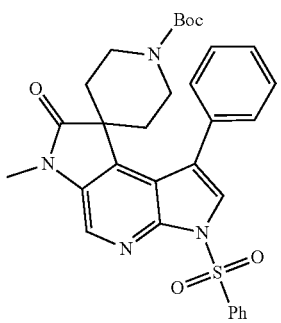 [SMILES: CN1C(=O)C2(CCN(C(=O)OC(C)(C)C)CC2)c2c1cnc1c2c(-c2ccccc2)cn1S(=O)(=O)c1ccccc1]

A mixture of tert-butyl 1-bromo-6-methyl-7-oxo-3-(phenylsulfonyl)-6,7-dihydro-3H-spiro[dipyrrolo[2,3-b:3',2'-d]pyridine-8,4'-piperidine]-1'-carboxylate (0.50 g, 0.87 mmol), phenylboronic acid (0.16 g, 1.3 mmol), Na₂CO₃ solution (1.0 M in water, 2.6 mL, 2.6 mmol) and tetrakis(triphenylphosphine)palladium(0) (0.10 g, 0.087 mmol) in DMF (8.0 mL) was degassed by sparging with N₂, then the reaction vessel was sealed and heated at 120° C. in a microwave for 30 min. Upon cooling to room temperature, the mixture was partitioned between EtOAc and water. The organic layer was washed with water, followed by brine, dried over Na₂SO₄, and evaporated. Purification on a 40 g silica gel column with a gradient of 0-60% EtOAc in hexanes afforded the title compound (0.39 g, 78%). LCMS for $C_{31}H_{33}N_4O_5S$ (M+H)⁺: calculated m/z=573.2; found 573.3. ¹H NMR (400 MHz, DMSO-d₆) δ 8.25-8.17 (m, 3H), 7.89 (s, 1H), 7.77 (t, J=7.4 Hz, 1H), 7.68 (t, J=7.8 Hz, 2H), 7.47-7.35 (m, 5H), 3.66-3.41 (m, 2H), 3.36-3.11 (m, 2H), 3.16 (s, 3H), 1.76-1.52 (m, 2H), 1.48-1.34 (m, 2H), 1.42 (s, 9H).

Step 6. tert-Butyl 2-bromo-6-methyl-7-oxo-1-phenyl-3-(phenylsulfonyl)-6,7-dihydro-3H-spiro[dipyrrolo[2,3-b:3',2'-d]pyridine-8,4'-piperidine]-1'-carboxylate

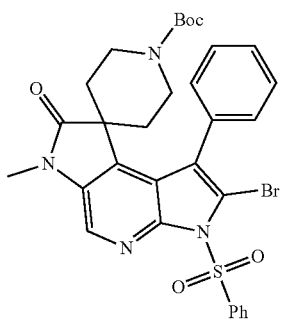 [SMILES: CN1C(=O)C2(CCN(C(=O)OC(C)(C)C)CC2)c2c1cnc1c2c(-c2ccccc2)c(Br)n1S(=O)(=O)c1ccccc1]

A solution of tert-butyl 6-methyl-7-oxo-1-phenyl-3-(phenylsulfonyl)-6,7-dihydro-3H-spiro[dipyrrolo[2,3-b:3',2'-d]pyridine-8,4'-piperidine]-1'-carboxylate (0.39 g, 0.68 mmol) in dry THF (15 mL) was treated with LDA (2.0 M in THF/heptane/ethylbenzene, 0.82 mL, 1.6 mmol) at −78° C. under a nitrogen atmosphere. The reaction mixture was stirred at the same temperature for 30 minutes. 1,2-Dibromo-1,1,2,2-tetrachloroethane (0.53 g, 1.6 mmol) was then added in one portion. The reaction mixture was stirred at −78° C. for 30 min, then quenched by the addition of saturated aqueous NH₄Cl at −78° C. The resulting mixture was diluted with EtOAc and water. The organic layer was separated, washed with brine, dried over Na₂SO₄, filtered, and concentrated. Purification on a 120 g silica gel column, eluting with a gradient of 0-50% EtOAc in hexanes afforded the title compound (0.44 g, 98%). LCMS for $C_{31}H_{32}BrN_4O_5S$ (M+H)⁺: calculated monoisotopic m/z=651.1; found 651.2.

Step 7. tert-Butyl 6-methyl-2-((4-(methylsulfonyl)piperidin-1-yl)methyl)phenyl)-7-oxo-1-phenyl-3-(phenylsulfonyl)-6,7-dihydro-3H-spiro[dipyrrolo[2,3-b:3',2'-c]pyridine-8,4'-piperidine]-1'-carboxylate

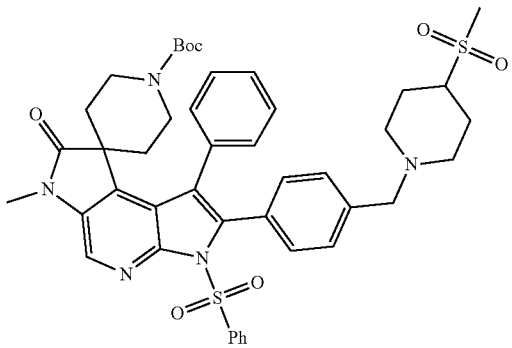 [SMILES: CN1C(=O)C2(CCN(C(=O)OC(C)(C)C)CC2)c2c1cnc1c2c(-c2ccccc2)c(-c2ccc(CN3CCC(S(C)(=O)=O)CC3)cc2)n1S(=O)(=O)c1ccccc1]

A mixture of tert-butyl 2-bromo-6-methyl-7-oxo-1-phenyl-3-(phenylsulfonyl)-6,7-dihydro-3H-spiro[dipyrrolo[2,3-b:3',2'-d]pyridine-8,4'-piperidine]-1'-carboxylate (0.22 g, 0.34 mmol), 4-(methylsulfonyl)-1-(4-(4,4,5,5-tetramethyl-1,3,2-dioxaborolan-2-yl)benzyl)piperidine (0.19 g, 0.50 mmol, from Example 1, Step 1), PdCl₂(dppf)-CH₂Cl₂ adduct (27 mg, 0.034 mmol) and Na₂CO₃ solution (1.0 M in water, 1.0 mL, 1.0 mmol) in dioxane (4.0 mL) was degassed by sparging with N₂, then the reaction vessel was sealed and heated at 100° C. in an oil bath for 55 min. Upon cooling to room temperature, the mixture was diluted with EtOAc and water, filtered over Celite®. The EtOAc layer was washed with brine, dried over Na₂SO₄, filtered and concentrated. Purification on a 40 g silica gel column with a gradient of 0-100% EtOAc in hexanes, followed by 5% MeOH in EtOAc afforded the desired compound as a brown oil (170 mg, 61%). LCMS for $C_{44}H_{50}N_5O_7S_2$ (M+H)⁺: calculated m/z=824.3; found 824.4.

Step 8. 6-Methyl-2-(4-((4-(methylsulfonyl)piperidin-1-yl)methyl)phenyl)-1-phenyl-3-(phenylsulfonyl)-3,6-dihydro-7H-spiro[dipyrrolo[2,3-b:3,2'-d]pyridine-8,4'-piperidin]-7-one hydrochloric acid Salt

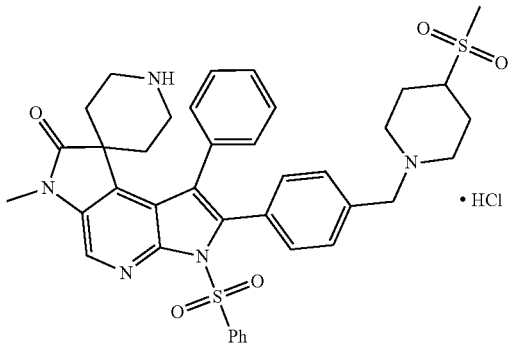 [SMILES: CN1C(=O)C2(CCNCC2)c2c1cnc1c2c(-c2ccccc2)c(-c2ccc(CN3CCC(S(C)(=O)=O)CC3)cc2)n1S(=O)(=O)c1ccccc1 ; "· HCl"]

To a solution of tert-butyl 6-methyl-2-(4-((4-(methylsulfonyl)piperidin-1-yl)methyl)phenyl)-7-oxo-1-phenyl-3-(phenylsulfonyl)-6,7-dihydro-3H-spiro[dipyrrolo[2,3-b:3',2'-d]pyridine-8,4'-piperidine]-1'-carboxylate (0.16 g, 0.19 mmol) in DCM (1.0 mL) was added HCl solution (4.0 M in dioxane, 0.97 mL, 3.9 mmol). The mixture was stirred at room temperature for one hour, then was evaporated to afford the title compound, which was used without further purification (theoretical yield assumed). LCMS for $C_{39}H_{42}N_5O_5S_2(M+H)^+$: calculated m/z=724.3; found 724.4.

Step 9. 3-(6-Methyl-2-(4-((4-(methylsulfonyl)piperidin-1-yl)methyl)phenyl)-7-oxo-1-phenyl-6,7-dihydro-3H-spiro[dipyrrolo[2,3-b:3',2'-d]pyridine-8,4'-piperidin]-1'-yl)propanenitrile, trifluoroacetate salt To a mixture of 6-methyl-2-(4-((4-(methylsulfonyl)piperidin-1-yl)methyl)phenyl)-1-phenyl-3-(phenylsulfonyl)-3,6-dihydro-7H-spiro[dipyrrolo[2,3-b:3',2'-d]pyridine-8,4'-piperidin]-7-one, HCl salt (12 mg, 0.015 mmol) in acetonitrile (0.20 mL) was added DIPEA (0.010 mL, 0.060 mmol), followed by acrylonitrile (1.6 mg, 0.030 mmol) and 1,8-diazabicyclo[5.4.0]undec-7-ene (DBU) (0.0023 mL, 0.015 mmol). The mixture was stirred at room temperature for one hour. DMF (0.10 mL) was added, followed by $Cs_2CO_3$ (15 mg, 0.045 mmol). The mixture was stirred at room temperature for 3 days. To the mixture was added THF (0.50 mL) and MeOH (0.50 mL), followed by NaOH solution (3.0 M in water, 0.050 mL, 0.15 mmol). The mixture was stirred at 40° C. for 30 min, then was diluted with MeOH and filtered. Purification via preparative HPLC-MS (pH=2 method) afforded the title compound (3.0 mg). A portion of this material was repurified via preparative HPLC-MS (pH=10) to afford the free base for characterization via NMR. LCMS for $C_{36}H_{41}N_6O_3S$ (M+H)$^+$: calculated m/z=637.3; found 637.5. $^1$H NMR (free base) (600 MHz, DMSO-d$_6$) δ 12.13 (s, 1H), 8.07 (s, 1H), 7.47-7.41 (m, 3H), 7.40-7.36 (m, 2H), 7.35-7.31 (m, 2H), 7.17 (d, J=8.2 Hz, 2H), 3.42 (s, 2H), 3.17 (s, 3H), 3.02 (tt, J=12.3, 3.7 Hz, 1H), 2.91-2.85 (m, 2H), 2.90 (s, 3H), 2.81-2.74 (m, 2H), 2.46 (t, J=6.7 Hz, 2H), 2.38-2.28 (m, 4H), 2.00-1.90 (m, 6H), 1.59 (qd, J=12.8, 12.2, 3.4 Hz, 2H), 1.33-1.27 (m, 2H).

Example 5

3-(6-Methyl-1-(1-methyl-1H-indazol-5-yl)-2-(4-((4-(methylsulfonyl)piperidin-1-yl)methyl)phenyl)-7-oxo-6,7-dihydro-3H-spiro[dipyrrolo[2,3-b:3',2'-d]pyridine-8,4'-piperidin]-1'-yl)propanenitrile trifluoroacetate salt

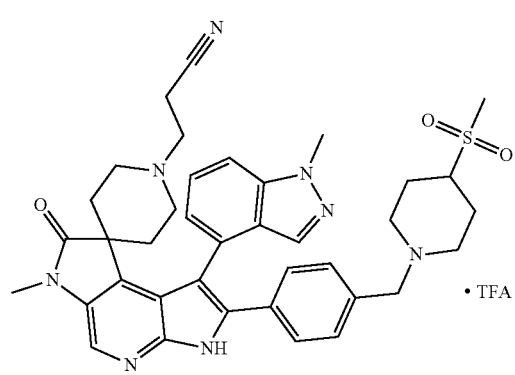 [SMILES: CN1C(=O)C2(CCN(CCC#N)CC2)c2c1cnc1[nH]c(-c3ccc(CN4CCC(S(C)(=O)=O)CC4)cc3)c(-c3cccc4c3cnn4C)c21 ; "· TFA"]

Step 1. tert-Butyl 6-methyl-1-(1-methyl-1H-indazol-5-yl)-7-oxo-3-(phenylsulfonyl)-6,7-dihydro-3H-spiro[dipyrrolo[2,3-b:3',2'-d]pyridine-8,4'-piperidine]-1'-carboxylate

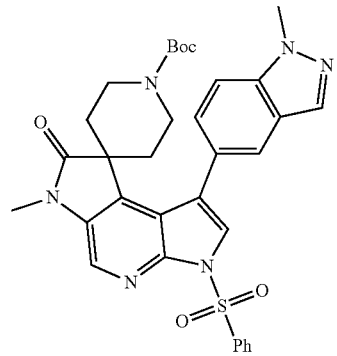 [SMILES: CN1C(=O)C2(CCN(C(=O)OC(C)(C)C)CC2)c2c1cnc1c2c(-c2ccc3c(cnn3C)c2)cn1S(=O)(=O)c1ccccc1]

A mixture of tert-butyl 1-bromo-6-methyl-7-oxo-3-(phenylsulfonyl)-6,7-dihydro-3H-spiro[dipyrrolo[2,3-b:3',2'-d]pyridine-8,4'-piperidine]-1'-carboxylate (0.26 g, 0.45 mmol, prepared as in Example 4, Step 4), 1-methyl-5-(4,4,5,5-tetramethyl-1,3,2-dioxaborolan-2-yl)-1H-indazole (0.18 g, 0.68 mmol, AstaTech 64501), $Na_2CO_3$ solution (1.0 M in water, 1.8 mL, 1.8 mmol) and tetrakis(triphenylphosphine)palladium(0) (52 mg, 0.045 mmol) in dioxane (4.0 mL) was degassed by sparging with $N_2$, then the reaction vessel was sealed and heated at 100° C. in an oil bath for 1 h. Upon cooling to room temperature, the reaction mixture was diluted with EtOAc, washed sequentially with water and brine, dried over $Na_2SO_4$, filtered and concentrated. Purification on a 40 g silica gel column, eluting with a gradient of 0-100% EtOAc in hexanes, afforded the title compound (0.22 g, 79%). LCMS for $C_{33}H_{35}N_6O_5S$ (M+H)$^+$: calculated m/z=627.2; found 627.2.

Step 2. tert-Butyl 2-bromo-6-methyl-1-(1-methyl-1H-indazol-5-yl)-7-oxo-3-(phenylsulfonyl)-6,7-dihydro-3H-spiro[dipyrrolo[2,3-b:3',2'-d]pyridine-8,4'-piperidine]-1'-carboxylate

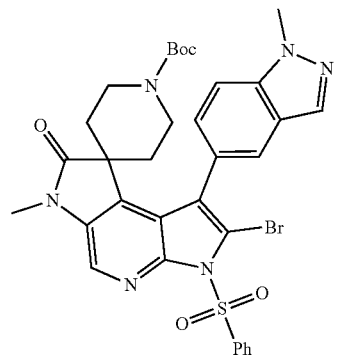 [SMILES: CN1C(=O)C2(CCN(C(=O)OC(C)(C)C)CC2)c2c1cnc1c2c(-c2ccc3c(cnn3C)c2)c(Br)n1S(=O)(=O)c1ccccc1]

The procedure of Example 4, Step 6 was followed with 1.9 equivalent of LDA and 1,2-dibromo-1,1,2,2-tetrachloroethane, using tert-butyl 6-methyl-1-(1-methyl-1H-indazol-5-yl)-7-oxo-3-(phenylsulfonyl)-6,7-dihydro-3H-spiro[dipyrrolo[2,3-b:3',2'-d]pyridine-8,4'-piperidine]-1'-carboxylate (0.22 g, 0.36 mmol) in place of tert-butyl 6-methyl-7-oxo-1-phenyl-3-(phenylsulfonyl)-6,7-dihydro-3H-spiro[dipyrrolo[2,3-b:3',2'-d]pyridine-8,4'-piperidine]-1'-carboxylate. Purification on a 40 g silica gel column with a gradient of 0-100% EtOAc in hexanes afforded the title compound (0.21 g, 83%). LCMS for $C_{33}H_{34}BrN_6O_5S$ $(M+H)^+$: calculated monoisotopic m/z=705.1; found 705.2.

Step 3. 2-Bromo-6-methyl-1-(1-methyl-1H-indazol-5-yl)-3-(phenylsulfonyl)-3,6-dihydro-7H-spiro[dipyrrolo[2,3-b:3',2'-d]pyridine-8,4'-piperidin]-7-one

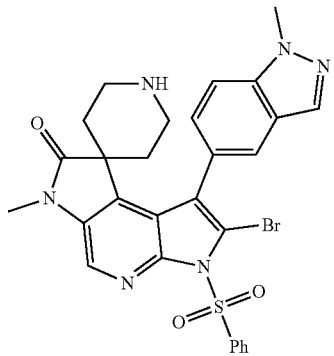 [SMILES: CN1C(=O)C2(CCNCC2)c2c1cnc1c2c(-c2ccc3c(cnn3C)c2)c(Br)n1S(=O)(=O)c1ccccc1]

To a mixture of tert-butyl 2-bromo-6-methyl-1-(1-methyl-1H-indazol-5-yl)-7-oxo-3-(phenylsulfonyl)-6,7-dihydro-3H-spiro[dipyrrolo[2,3-b:3',2'-d]pyridine-8,4'-piperidine]-1'-carboxylate (0.21 g, 0.30 mmol) in DCM (5.0 mL) was added TFA (1.1 mL, 15 mmol). The mixture was stirred at room temperature for one hour, then volatiles were removed in vacuo. The residue was dissolved in DCM and was treated with saturated $NaHCO_3$ solution. The layers were separated, and the aqueous layer was extracted with two further portions of DCM. The combined organic extracts were dried over $Na_2SO_4$, filtered and concentrated to afford the title compound (0.18 g, 100%). LCMS for $C_{28}H_{26}BrN_6O_3S$ $(M+H)^+$: calculated monoisotopic m/z=605.1; found 605.2.

Step 4. 3-(2-Bromo-6-methyl-1-(1-methyl-1H-indazol-5-yl-7-oxo-3-(phenylsulfonyl)-6,7-dihydro-3H-spiro[dipyrrolo[2,3-b:3',2'-d]pyridine-8,4'-piperidin]-1'-yl)propanenitrile

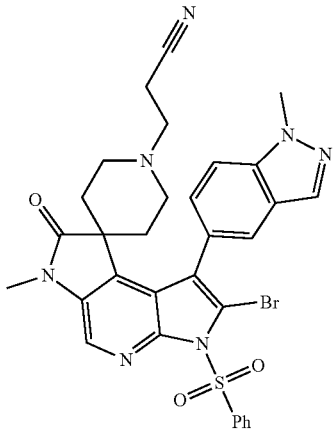 [SMILES: CN1C(=O)C2(CCN(CCC#N)CC2)c2c1cnc1c2c(-c2ccc3c(cnn3C)c2)c(Br)n1S(=O)(=O)c1ccccc1]

A mixture of 2-bromo-6-methyl-1-(1-methyl-1H-indazol-5-yl)-3-(phenylsulfonyl)-3,6-dihydro-7H-spiro[dipyrrolo[2,3-b:3',2'-d]pyridine-8,4'-piperidin]-7-one (0.080 g, 0.13 mmol) and acrylonitrile (0.087 mL, 1.3 mmol) in EtOH (3.0 mL) was sealed and heated at 70° C. overnight to give a white slurry. The slurry was cooled to room temperature and the product was isolated by filtration. The filter cake was washed with a small amount of EtOH, then was air-dried to afford the title compound (71 mg, 82%). LCMS for $C_{31}H_{29}BrN_7O_3S$ $(M+H)^+$: calculated monoisotopic m/z=658.1; found 658.1.

Step 5. 3-(6-Methyl-1-(1-methyl-1H-indazol-5-yl-2-(4-((4-(methylsulfonyl)piperidin-1-yl)methyl)phenyl)-7-oxo-6,7-dihydro-3H-spiro[dipyrrolo[2,3-b:3',2'-d]pyridine-8,4'-piperidin]-1'-yl)propanenitrile trifluoroacetate salt A mixture of 3-(2-bromo-6-methyl-1-(1-methyl-1H-indazol-5-yl)-7-oxo-3-(phenylsulfonyl)-6,7-dihydro-3H-spiro[dipyrrolo[2,3-b:3',2'-d]pyridine-8,4'-piperidin]-1'-yl)propanenitrile (8.0 mg, 0.012 mmol), 4-(methylsulfonyl)-1-(4-(4,4,5,5-tetramethyl-1,3,2-dioxaborolan-2-yl)benzyl)piperidine (6.9 mg, 0.018 mmol, from Example 1, Step 1), $PdCl_2(dppf)-CH_2Cl_2$ adduct (0.99 mg, 0.0012 mmol) and $K_2CO_3$ solution (1.0 M in water, 0.036 mL, 0.036 mmol) in dioxane (0.50 mL) was degassed by sparging with $N_2$, then was heated at 100° C. in an oil bath for one hour. Upon cooling to room temperature, MeOH (0.50 mL) was added, followed by NaOH solution (3.0 M in water, 0.040 mL, 0.12 mmol). The mixture was heated at 40° C. for 30 min. Upon cooling to room temperature, the reaction mixture was diluted with MeOH and filtered. Purification via preparative HPLC-MS (pH=2 method) afforded the title compound (5.7 mg). A portion of this material was repurified via preparative HPLC-MS (pH=10) to afford the free base for characterization via $^1H$ NMR. LCMS for $C_{38}H_{43}N_8O_3S$ $(M+H)^+$: calculated m/z=691.3; found 691.3. $^1H$ NMR (free base) (600 MHz, DMSO-$d_6$) δ 12.12 (s, 1H), 8.07 (s, 1H), 8.03 (s, 1H), 7.75 (s, 1H), 7.66 (d, J=8.5 Hz, 1H), 7.39 (dd, J=8.5, 1.6 Hz, 1H), 7.37-7.32 (m, 2H), 7.13 (d, J=8.2 Hz, 2H), 4.11 (s, 3H), 3.38 (s, 2H), 3.16 (s, 3H), 3.00 (tt, J=12.5, 3.7 Hz, 1H), 2.89 (s, 3H), 2.87-2.82 (m, 2H), 2.70-2.61 (m, 2H), 2.22-2.17 (m, 1H), 2.15-1.99 (m, 4H), 1.97-1.88 (m, 5H), 1.87-1.79 (m, 2H), 1.56 (qd, J=11.9, 3.9 Hz, 2H), 1.31-1.22 (m, 2H).

Example 6

2-(4-(4-(6-Methyl-2-(1-methyl-1H-pyrazol-4-yl)-7-oxo-1-phenyl-6,7-dihydro-3H-spiro[dipyrrolo[2,3-b:3',2'-d]pyridine-8,4'-piperidin]-1'-yl)-1H-pyrazol-1-yl)tetrahydro-2H-pyran-4-yl)acetonitrile trifluoroacetate salt

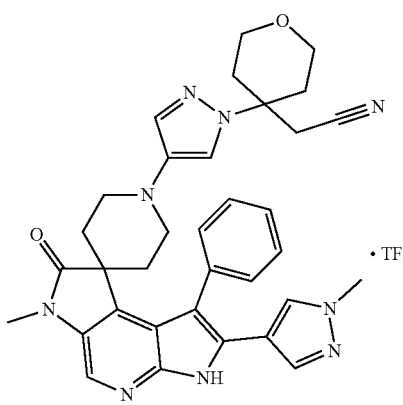

145

Step 1. Ethyl 1-(1-(tetrahydro-2H-pyran-2-yl)-1H-pyrazol-4-yl)piperidine-4-carboxylate

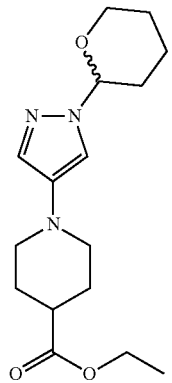 [SMILES: CCOC(=O)C1CCN(c2cnn(C3CCCCO3)c2)CC1]

A mixture of 4-iodo-1-(tetrahydro-2H-pyran-2-yl)-1H-pyrazole (10.0 g, 36 mmol, Combi-Blocks QI-5237), ethyl piperidine-4-carboxylate (11 g, 72 mmol, Combi-Blocks AM-1894), $K_2CO_3$ (9.9 g, 72 mmol) and copper(I) iodide (1.4 g, 7.2 mmol) in DMSO (35 mL) was degassed by sparging with $N_2$, then was sealed and heated at 100° C. for 18 hours. Upon cooling to room temperature, the reaction mixture was diluted with EtOAc and water, and filtered through Celite®. The organic layer was washed twice with brine, dried over $Na_2SO_4$, filtered and concentrated. The residue was purified on a 330 g silica gel column, eluting with a gradient of 0-100% EtOAc in hexanes to afford the title compound (5.2 g, 47%). LCMS for $C_{16}H_{26}N_3O_3$ (M+H)$^+$: calculated m/z=308.2; found 308.2. $^1$H NMR (400 MHz, DMSO-d$_6$) δ 7.37 (s, 1H), 7.24 (s, 1H), 5.22 (dd, J=10.1, 2.5 Hz, 1H), 4.08 (q, J=7.1 Hz, 2H), 3.92-3.84 (m, 1H), 3.63-3.53 (m, 1H), 3.27 (dt, J=12.1, 4.1 Hz, 2H), 2.57-2.47 (m, 2H), 2.40 (tt, J=11.1, 3.9 Hz, 1H), 2.11-1.97 (m, 1H), 1.96-1.79 (m, 4H), 1.73-1.56 (m, 3H), 1.55-1.44 (m, 2H), 1.19 (t, J=7.1 Hz, 3H).

Step 2. Ethyl 4-(5-nitro-1-(phenylsulfonyl)-1H-pyrrolo[2,3-b]pyridin-4-yl)-1-(1-(tetrahydro-2H-pyran-2-yl)-1H-pyrazol-4-yl)piperidine-4-carboxylate

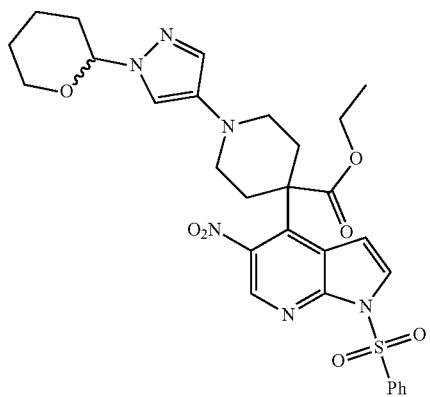 [SMILES: CCOC(=O)C1(c2c([N+](=O)[O-])cnc3c2ccn3S(=O)(=O)c2ccccc2)CCN(c2cnn(C3CCCCO3)c2)CC1]

146

A mixture of 4-chloro-5-nitro-1-(phenylsulfonyl)-1H-pyrrolo[2,3-b]pyridine (4.9 g, 14 mmol, Enamine EN300-386169) and ethyl 1-(1-(tetrahydro-2H-pyran-2-yl)-1H-pyrazol-4-yl)piperidine-4-carboxylate (3.2 g, 10.0 mmol) was azeotroped with toluene to provide dry starting materials. The residue was dissolved in THF (100.0 mL), and the solution was cooled to −78° C. LiHMDS (1.0 M in THF, 26 mL, 26 mmol) was added. The mixture was then allowed to warm up to −12° C. slowly over a period of 1.5 hours. The mixture was quenched by the addition of saturated ammonium chloride solution at −12° C. The reaction mixture was then diluted with water and was extracted with EtOAc. The organic layer was washed successively with water and brine, then was dried over $Na_2SO_4$, filtered and concentrated. Purification on a 120 g silica gel column, eluting with a gradient of 0-100% EtOAc in hexanes, afforded the title compound (2.4 g, 38%). LCMS for $C_{29}H_{33}N_6O_7S$ (M+H)$^+$: calculated m/z=609.2; found 609.3.

Step 3. 3-(Phenylsulfonyl)-1'-(1-(tetrahydro-2H-pyran-2-yl)-1H-pyrazol-4-yl)-3,6-dihydro-7H-spiro[dipyrrolo[2,3-b:3',2'-c]pyridine-8,4'-piperidin]-7-one

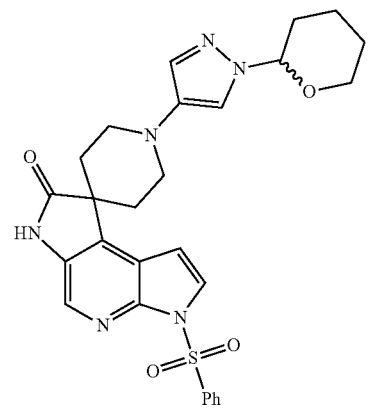 [SMILES: O=C1Nc2cnc3c(ccn3S(=O)(=O)c3ccccc3)c2C12CCN(c1cnn(C3CCCCO3)c1)CC2]

A mixture of ethyl 4-(5-nitro-1-(phenylsulfonyl)-1H-pyrrolo[2,3-b]pyridin-4-yl)-1-(1-(tetrahydro-2H-pyran-2-yl)-1H-pyrazol-4-yl)piperidine-4-carboxylate (3.3 g, 5.5 mmol), iron (3.1 g, 55 mmol), NH$_4$Cl (5.9 g, 110 mmol), water (14 mL) and ethanol (40.0 mL) was heated at 60° C. overnight. Upon cooling to room temperature, the mixture was diluted with water and acetonitrile, then filtered through Celite®. The filter cake was washed with MeOH. The filtrate was then partitioned between EtOAc and brine. The organic layer was washed again with brine, was dried over $Na_2SO_4$, filtered and concentrated to give a solid residue. Purification on a 120 g silica gel column, eluting with a gradient of 0-100% EtOAc in hexanes, then 5% MeOH in EtOAc afforded the title compound (1.0 g, 35%). LCMS for $C_{27}H_{29}N_6O_4S$ (M+H)$^+$: calculated m/z=533.2; found 533.2.

Step 4. 6-Methyl-3-(phenylsulfonyl)-1'-(1-(tetrahydro-2H-pyran-2-yl)-1H-pyrazol-4-yl)-3,6-dihydro-7H-spiro[dipyrrolo[2,3-b:3',2'-c]pyridine-8,4'-piperidin]-7-one

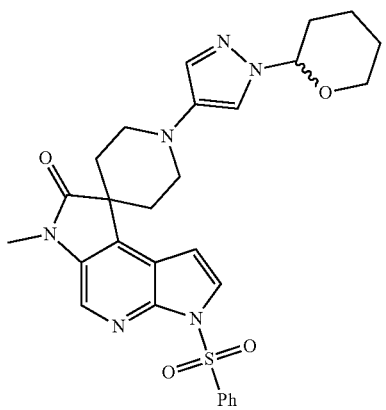 [SMILES: CN1C(=O)C2(CCN(c3cnn(C4CCCCO4)c3)CC2)c2c1cnc1c2ccn1S(=O)(=O)c1ccccc1]

To a solution of 3-(phenylsulfonyl)-1'-(1-(tetrahydro-2H-pyran-2-yl)-1H-pyrazol-4-yl)-3,6-dihydro-7H-spiro[dipyrrolo[2,3-b:3',2'-d]pyridine-8,4'-piperidin]-7-one (1.0 g, 1.9 mmol) in DMF (35 mL) was added $Cs_2CO_3$ (1.25 g, 3.8 mmol), followed by iodomethane (0.10 mL, 1.6 mmol). The mixture was stirred at room temperature for one hour, then was diluted with EtOAc and filtered over Celite®. The filtrate was washed twice with brine, dried over $Na_2SO_4$, filtered and concentrated. The residue was purified on a 120 g silica gel column, eluting with a gradient of 0-100% EtOAc in hexanes to afford the title compound (0.78 g, 75%). LCMS for $C_{28}H_{31}N_6O_4S$ $(M+H)^+$: calculated m/z=547.2; found 547.2. $^1H$ NMR (400 MHz, DMSO-$d_6$) δ 8.17 (s, 1H), 8.15-8.10 (m, 2H), 8.00 (d, J=4.1 Hz, 1H), 7.73 (t, J=7.4 Hz, 1H), 7.63 (t, J=7.8 Hz, 2H), 7.46 (s, 1H), 7.32 (s, 1H), 6.85 (d, J=4.1 Hz, 1H), 5.27 (dd, J=10.0, 2.4 Hz, 1H), 3.96-3.85 (m, 1H), 3.68-3.54 (m, 1H), 3.38-3.21 (m, 4H), 3.18 (s, 3H), 2.36-2.19 (m, 2H), 2.14-2.01 (m, 1H), 1.98-1.81 (m, 2H), 1.80-1.59 (m, 3H), 1.58-1.44 (m, 2H).

Step 5. 1-Bromo-6-methyl-3-(phenylsulfonyl)-1'-(1-(tetrahydro-2H-pyran-2-yl)-1H-pyrazol-4-yl)-3,6-dihydro-7H-spiro[dipyrrolo[2,3-b:3',2'-d]pyridine-8,4'-piperidin]-7-one

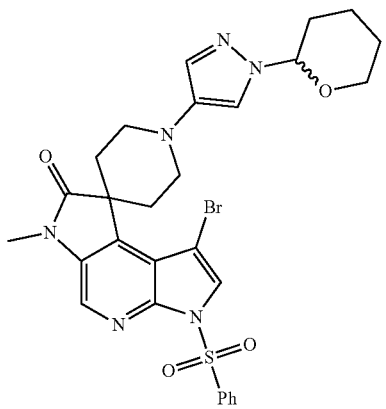 [SMILES: CN1C(=O)C2(CCN(c3cnn(C4CCCCO4)c3)CC2)c2c1cnc1c2c(Br)cn1S(=O)(=O)c1ccccc1]

A solution of 6-methyl-3-(phenylsulfonyl)-1'-(1-(tetrahydro-2H-pyran-2-yl)-1H-pyrazol-4-yl)-3,6-dihydro-7H-spiro[dipyrrolo[2,3-b:3',2'-d]pyridine-8,4'-piperidin]-7-one (0.78 g, 1.4 mmol) in DMF (24 mL) was cooled to 0° C. N-Bromosuccinimide (0.20 g, 1.1 mmol) was added, and the mixture was stirred at 0° C. for 20 min. Saturated $NaHCO_3$ was added to give a slurry. The mixture was then partitioned between EtOAc and brine. The organic layer was washed again with brine, dried over $Na_2SO_4$, filtered and concentrated. Purification on a 120 g silica gel column, eluting with a gradient of 0-80% EtOAc in hexanes afforded the title compound (0.54 g, 60%). LCMS for $C_{28}H_{30}BrN_6O_4S$ $(M+H)^+$: calculated monoisotopic m/z=625.1; found 625.2.

Step 6. 6-Methyl-1-phenyl-3-(phenylsulfonyl)-1'-(1-(tetrahydro-2H-pyran-2-yl)-1H-pyrazol-4-yl)-3,6-dihydro-7H-spiro[dipyrrolo[2,3-b:3',2'-d]pyridine-8,4'-piperidin]-7-one

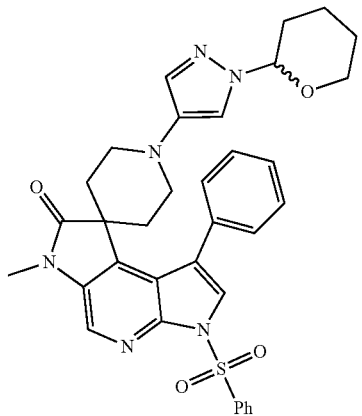 [SMILES: CN1C(=O)C2(CCN(c3cnn(C4CCCCO4)c3)CC2)c2c1cnc1c2c(-c2ccccc2)cn1S(=O)(=O)c1ccccc1]

A mixture of 1-bromo-6-methyl-3-(phenylsulfonyl)-1'-(1-(tetrahydro-2H-pyran-2-yl)-1H-pyrazol-4-yl)-3,6-dihydro-7H-spiro[dipyrrolo[2,3-b:3',2'-d]pyridine-8,4'-piperidin]-7-one (0.54 g, 0.86 mmol), phenylboronic acid (0.32 g, 2.6 mmol), $Na_2CO_3$ solution (1.0 M in water, 3.5 mL, 3.5 mmol) and tetrakis(triphenylphosphine)palladium(0) (0.10 g, 0.086 mmol) in dioxane (11 mL) was degassed by sparging with $N_2$, then was sealed and heated at 90° C. in an oil bath for 5 hours. Upon cooling to room temperature, the reaction mixture was diluted with EtOAc, washed successively with water and brine, dried over $Na_2SO_4$, filtered and concentrated. Purification on a 120 g silica gel column, eluting with a gradient of 0-80% EtOAc in hexanes afforded the title compound (0.44 g, 82%). LCMS for $C_{34}H_{35}N_6O_4S$ $(M+H)^+$: calculated m/z=623.2; found 623.2.

Step 7. 2-Bromo-6-methyl-1-phenyl-3-(phenylsulfonyl)-1'-(1-(tetrahydro-2H-pyran-2-yl)-1H-pyrazol-4-yl)-3,6-dihydro-7H-spiro[dipyrrolo[2,3-b:3',2'-d]pyridine-8,4'-piperidin]-7-one

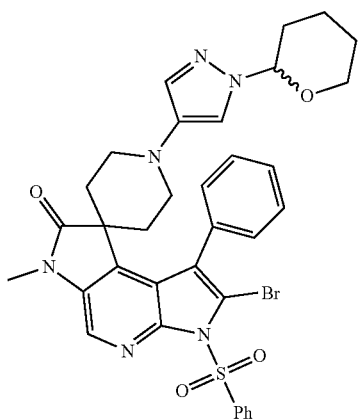 [SMILES: CN1C(=O)C2(CCN(c3cnn(C4CCCCO4)c3)CC2)c2c1cnc1c2c(-c2ccccc2)c(Br)n1S(=O)(=O)c1ccccc1]

The procedure of Example 4, Step 6 was followed with 2.0 equivalents of LDA and 1,2-dibromo-1,1,2,2-tetrachloroethane, using 6-methyl-1-phenyl-3-(phenylsulfonyl)-1'-(1-(tetrahydro-2H-pyran-2-yl)-1H-pyrazol-4-yl)-3,6-dihydro-7H-spiro[dipyrrolo[2,3-b:3',2'-d]pyridine-8,4'-piperidin]-7-one (0.44 g, 0.71 mmol) in place of tert-butyl 6-methyl-7-oxo-1-phenyl-3-(phenylsulfonyl)-6,7-dihydro-3H-spiro[dipyrrolo[2,3-b:3',2'-d]pyridine-8,4'-piperidine]-1'-carboxylate. Purification on a 40 g silica gel column, eluting with a gradient of 0-70% EtOAc in hexanes afforded the title compound (0.42 g, 84%). LCMS for $C_{34}H_{34}BrN_6O_4S$ $(M+H)^+$: calculated monoisotopic m/z=701.2; found 701.1.

Step 8. 6-Methyl-2-(1-methyl-1H-pyrazol-4-yl)-1-phenyl-3-(phenylsulfonyl)-1'-(1-(tetrahydro-2H-pyran-2-yl)-1H-pyrazol-4-yl)-3,6-dihydro-7H-spiro[dipyrrolo[2,3-b:3',2'-c]pyridine-8,4'-piperidin]-7-one

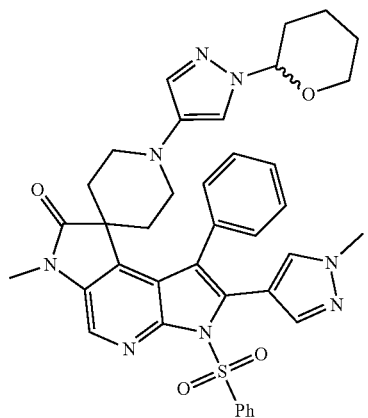

The procedure of Example 4, Step 7 was followed, using 2-bromo-6-methyl-1-phenyl-3-(phenylsulfonyl)-1'-(1-(tetrahydro-2H-pyran-2-yl)-1H-pyrazol-4-yl)-3,6-dihydro-7H-spiro[dipyrrolo[2,3-b:3',2'-d]pyridine-8,4'-piperidin]-7-one (0.10 g, 0.15 mmol) in place of tert-butyl 2-bromo-6-methyl-7-oxo-1-phenyl-3-(phenylsulfonyl)-6,7-dihydro-3H-spiro[dipyrrolo[2,3-b:3',2'-d]pyridine-8,4'-piperidine]-1'-carboxylate, and 1-methyl-4-(4,4,5,5-tetramethyl-1,3,2-dioxaborolan-2-yl)-1H-pyrazole (0.076 g, 0.37 mmol, Sigma-Aldrich 595314) in place of 4-(methylsulfonyl)-1-(4-(4,4,5,5-tetramethyl-1,3,2-dioxaborolan-2-yl)benzyl)piperidine. Purification on a 20 g silica gel column, eluting with a gradient of 0-100% EtOAc in hexanes, then 5% MeOH in EtOAc afforded the title compound (0.046 g, 44%). LCMS for $C_{38}H_{39}N_8O_4S$ $(M+H)^+$: calculated m/z=703.3; found 703.2.

Step 9. 6-Methyl-2-(1-methyl-1H-pyrazol-4-yl)-1-phenyl-3-(phenylsulfonyl)-1'-(1H-pyrazol-4-yl)-3,6-dihydro-7H-spiro[dipyrrolo[2,3-b:3',2'-c]pyridine-8,4'-piperidin]-7-one trifluoroacetate salt

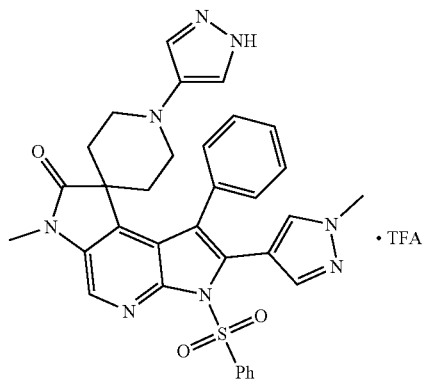

To a solution of 6-methyl-2-(1-methyl-1H-pyrazol-4-yl)-1-phenyl-3-(phenylsulfonyl)-1'-(1-(tetrahydro-2H-pyran-2-yl)-1H-pyrazol-4-yl)-3,6-dihydro-7H-spiro[dipyrrolo[2,3-b:3',2'-d]pyridine-8,4'-piperidin]-7-one (45 mg, 0.064 mmol) in DCM (1.0 mL) was added TFA (0.25 mL, 3.2 mmol). The mixture was stirred at room temperature for one hour, then volatiles were removed in vacuo. Purification via preparative HPLC-MS (pH=2 method) afforded the title compound (23 mg). LCMS for $C_{33}H_{31}N_8O_3S$ $(M+H)^+$: calculated m/z =619.2; found 619.3.

Step 10. 2-(4-(4-(6-Methyl-2-(1-methyl-1H-pyrazol-4-yl)-7-oxo-1-phenyl-6,7-dihydro-3H-spiro[dipyrrolo[2,3-b:3',2'-d]pyridine-8,4'-piperidin]-1'-yl)-1H-pyrazol-1-yl)tetrahydro-2H-pyran-4-yl)acetonitrile trifluoroacetate salt To a solution of 6-methyl-2-(1-methyl-1H-pyrazol-4-yl)-1-phenyl-3-(phenylsulfonyl)-1'-(1H-pyrazol-4-yl)-3,6-dihydro-7H-spiro[dipyrrolo[2,3-b:3',2'-d]pyridine-8,4'-piperidin]-7-one trifluoroacetate salt (6.0 mg) in DMF (0.10 mL) was added triethylamine (5.6 4, 0.040 mmol, as an aliquot of a stock solution in DMF) and DBU (6.1 µL, 0.0040 mmol, as an aliquot of a stock solution in DMF), followed by 2-(tetrahydro-4H-pyran-4-ylidene)acetonitrile (10.0 mg, 0.081 mmol, Combi-Blocks AM-1621). The mixture was heated at 80° C. for 20 hours. Upon cooling to room temperature, MeOH (0.50 mL) and THF (0.50 mL) were added, followed by NaOH solution (3.0 M in water, 0.054 mL, 0.16 mmol). The mixture was heated at 60° C. for one hour, then was cooled to room temperature, diluted with MeOH and filtered. Purification via preparative HPLC-MS (pH=2 method) afforded the title compound (2.1 mg). LCMS for $C_{34}H_{36}N_9O_2(M+H)^+$: calculated m/z=602.3; found 602.3. $^1$H NMR (400 MHz, DMSO-$d_6$) δ 11.96 (s, 1H), 8.26 (s, 1H), 8.11-8.04 (m, 2H), 8.06 (s, 1H), 7.95 (s, 1H), 7.94 (s, 1H), 7.47 (t, J=7.7 Hz, 2H), 7.35-7.26 (m, 1H), 6.71 (s, 1H), 3.92 (s, 3H), 3.85-3.75 (m, 2H), 3.49-3.35 (m, 4H), 3.21 (s, 3H), 3.19 (s, 2H), 3.19-3.08 (m, 2H), 2.65-2.55 (m, 2H), 2.44-2.31 (m, 2H), 2.07-1.99 (m, 2H), 1.85-1.76 (m, 2H).

Example 7

3-(6-Methyl-1-(1-methyl-1H-indazol-5-yl)-2-(1-(methyl-$d_3$)-1H-pyrazol-4-yl)-7-oxo-6,7-dihydro-3H-spiro[dipyrrolo[2,3-b:3',2'-d]pyridine-8,4'-piperidin]-1'-yl)propanenitrile

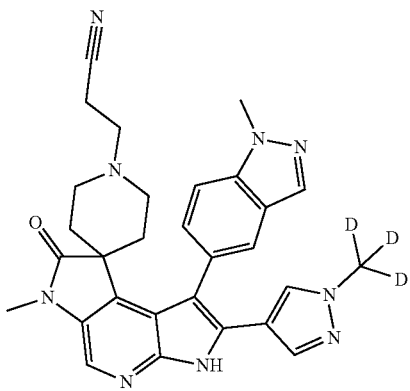 [SMILES: [2H]C([2H])([2H])n1cc(-c2[nH]c3ncc4c(c3c2-c2ccc3c(cnn3C)c2)C2(CCN(CCC#N)CC2)C(=O)N4C)cn1]

Step 1. 1-(Methyl-$d_3$)-4-(4,4,5,5-tetramethyl-1,3,2-dioxaborolan-2-yl)-1H-pyrazole

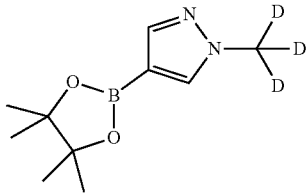 [SMILES: [2H]C([2H])([2H])n1cc(B2OC(C)(C)C(C)(C)O2)cn1]

To a solution of 4-(4,4,5,5-tetramethyl-1,3,2-dioxaborolan-2-yl)-1H-pyrazole (0.60 g, 3.1 mmol, Combi-Blocks, PN-8851) in DMF (10.0 mL) was added iodomethane-$d_3$ (0.54 g, 3.7 mmol, Oakwood Chemical, 043255) and Cs$_2$CO$_3$ (1.3 g, 4.0 mmol). The mixture was stirred at room temperature for 3 hours, then was taken up in EtOAc, washed sequentially with water and brine, dried over Na$_2$SO$_4$, filtered and concentrated to afford the product, which was used without further purification (0.42 g, 64%). LCMS for $C_{10}H_{15}D_3BN_2O_2(M+H)^+$: calculated m/z=212.2; found 212.2.

Step 2. 3-(6-Methyl-1-(1-methyl-1H-indazol-5-yl)-2-(1-(methyl-$d_3$)-1H-pyrazol-4-yl)-7-oxo-6,7-dihydro-3H-spiro[dipyrrolo[2,3-b:3',2'-c]pyridine-8,4'-piperidin]-1'-yl)propanenitrile A mixture of 3-(2-bromo-6-methyl-1-(1-methyl-1H-indazol-5-yl)-7-oxo-3-(phenylsulfonyl)-6,7-dihydro-3H-spiro[dipyrrolo[2,3-b:3',2'-d]pyridine-8,4'-piperidin]-1'-yl)propanenitrile (14 mg, 0.021 mmol, from Example 5, Step 4), 1-(methyl-$d_3$)-4-(4,4,5,5-trimethyl-1,3,2-dioxaborolan-2-yl)-1H-pyrazole (17 mg, 0.085 mmol), PdCl$_2$(dppf)-CH$_2$Cl$_2$ adduct (1.7 mg, 0.0021 mmol) and K$_2$CO$_3$ solution (1.0 M in water, 0.085 mL, 0.085 mmol) in dioxane (0.70 mL) was degassed by sparging with N$_2$, then was heated at 100° C. in an oil bath for 30 min. Upon cooling to room temperature, MeOH (0.50 mL) was added, followed by NaOH solution (3.0 M in water, 0.071 mL, 0.21 mmol). The mixture was heated at 40° C. for 30 min. Upon cooling to room temperature, the reaction mixture was diluted with MeOH and filtered. Purification via preparative HPLC-MS (pH=2 method) first, followed by preparative HPLC-MS (pH=10 method) afforded the title compound (5.9 mg, 53%). LCMS for $C_{29}H_{27}D_3N_9O(M+H)^+$: calculated m/z=523.3; found 523.3. $^1$H NMR (400 MHz, DMSO-$d_6$) δ 12.00 (s, 1H), 8.08 (s, 1H), 7.98 (s, 1H), 7.77-7.70 (m, 2H), 7.40 (s, 1H), 7.35 (dd, J=8.4, 1.6 Hz, 1H), 7.00 (s, 1H), 4.14 (s, 3H), 3.15 (s, 3H), 2.77-2.68 (m, 2H), 2.26-2.17 (m, 1H), 2.14-1.98 (m, 4H), 1.96-1.73 (m, 3H), 1.32-1.22 (m, 2H).

Example 8

6'-Methyl-1'-(1-methyl-1H-indazol-5-yl)-2'-(1-(pyridin-4-ylmethyl)-1H-pyrazol-4-yl)-3',6'-dihydro-7'H-spiro[cyclopentane-1,8'-dipyrrolo[2,3-b:3',2'-d]pyridin]-7'-one trifluoroacetate salt

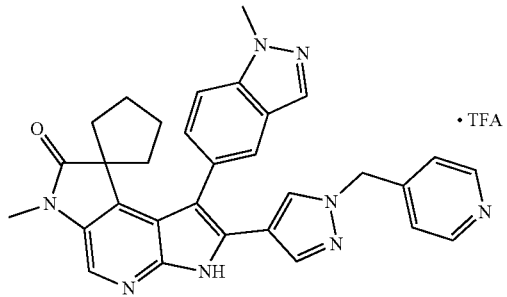 [SMILES: CN1C(=O)C2(CCCC2)c2c1cnc1[nH]c(-c3cnn(Cc4ccncc4)c3)c(-c3ccc4c(cnn4C)c3)c21]

Step 1. Methyl 1-(5-nitro-1-(phenylsulfonyl)-1H-pyrrolo[2,3-b]pyridin-4-yl)cyclopentane-1-carboxylate

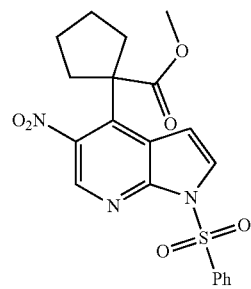 [SMILES: COC(=O)C1(c2c([N+](=O)[O-])cnc3c2ccn3S(=O)(=O)c2ccccc2)CCCC1]

A mixture of 4-chloro-5-nitro-1-(phenylsulfonyl)-1H-pyrrolo[2,3-b]pyridine (7.0 g, 21 mmol, Astatech P12207) and methyl cyclopentanecarboxylate (3.2 g, 25 mmol, Lancaster L00741) was dissolved in THF (130 mL) and cooled to −78° C. LiHMDS (1.0 M in THF, 42 mL, 42 mmol) was added. The mixture was then allowed to warm to room temperature and stir overnight. The mixture was cooled to −20° C. and was quenched by the addition of 1.0 N HCl. The mixture was diluted with more water and was extracted with EtOAc. The organic layer was washed with brine, dried over Na$_2$SO$_4$, filtered and concentrated. Purification via flash column chromatography on silica gel, eluting with a gradient of 0-40% EtOAc in hexanes, afforded the title compound (5.0 g, 56%). LCMS for C$_2$H$_{20}$N$_3$O$_6$S (M+H)$^+$: calculated m/z=430.1; found 430.1.

Step 2. 3'-(Phenylsulfonyl)-3',6'-dihydro-7'H-spiro[cyclopentane-1,8'-dipyrrolo[2,3-b:3',2'-d]pyridin]-7'-one

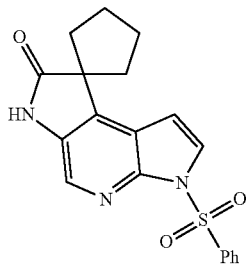 [SMILES: O=C1Nc2cnc3c(ccn3S(=O)(=O)c3ccccc3)c2C12CCCC2]

A mixture of methyl 1-(5-nitro-1-(phenylsulfonyl)-1H-pyrrolo[2,3-b]pyridin-4-yl)cyclopentane-1-carboxylate (5.0 g, 12 mmol), iron (6.5 g, 12 mmol), ammonium chloride (12.5 g, 233 mmol), water (15 mL) and ethanol (40.0 mL) was heated at 60° C. for 4 hours. The reaction mixture was cooled to room temperature, diluted with water and MeOH, filtered through Celite®, and the Celite® was washed with EtOAc. The filtrate was partitioned between EtOAc and brine. The organic extract was washed with additional brine, dried over Na$_2$SO$_4$, filtered and concentrated. Purification via flash column chromatography on silica gel, eluting with a gradient of 0-60% EtOAc in hexanes, afforded the title compound (3.0 g, 70%). LCMS for C$_{19}$H$_{18}$N$_3$O$_3$S (M+H)$^+$: calculated m/z=368.1; found 368.1.

Step 3. 6'-Methyl-3'-(phenylsulfonyl)-3',6'-dihydro-7'H-spiro[cyclopentane-1,8'-dipyrrolo[2,3-b:3',2'-d]pyridin]-7'-one

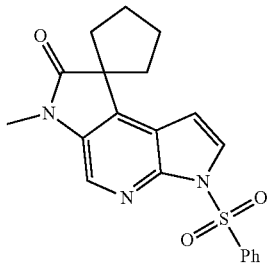 [SMILES: CN1C(=O)C2(CCCC2)c2c1cnc1c2ccn1S(=O)(=O)c1ccccc1]

To a solution of 3'-(phenylsulfonyl)-3',6'-dihydro-7'H-spiro[cyclopentane-1,8'-dipyrrolo[2,3-b:3',2'-d]pyridin]-7'-one (3.0 g, 8.2 mmol) in DMF (50.0 mL) was added Cs$_2$CO$_3$ (6.6 g, 20 mmol) and iodomethane (0.56 mL, 9.0 mmol, Aldrich 18507). The mixture was sealed and stirred at 50° C. for 35 min. Upon cooling to room temperature, the reaction mixture was diluted with EtOAc, filtered through Celite®, and the filtrate was concentrated. Purification via flash column chromatography on silica gel, eluting with a gradient of 0-60% EtOAc in hexanes, afforded the title compound (2.2 g, 71%). LCMS for C$_{20}$H$_{20}$N$_3$O$_3$S (M+H)$^+$: calculated m/z=382.1; found 382.1.

Step 4. 1'-Bromo-6'-methyl-3'-(phenylsulfonyl)-3',6'-dihydro-7'H-spiro[cyclopentane-1,8'-dipyrrolo[2,3-b:3',2'-d]pyridin]-7'-one

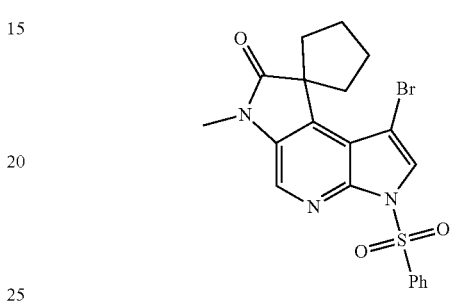

To a mixture of 6'-methyl-3'-(phenylsulfonyl)-3',6'-dihydro-7'H-spiro[cyclopentane-1,8'-dipyrrolo[2,3-b:3',2'-d]pyridin]-7'-one (1.0 g, 2.6 mmol) in DMF (20.0 mL) was added NBS (0.51 g, 2.9 mmol, Aldrich B81255). The reaction was heated at 40° C. for 1 hour. Upon cooling to room temperature, the reaction mixture was diluted with EtOAc, washed sequentially with saturated NaHCO$_3$ and brine, dried over Na$_2$SO$_4$, filtered and concentrated. Purification via flash column chromatography on silica gel, eluting with a gradient of 0-60% EtOAc in hexanes, afforded the title compound (1.1 g, 91%). LCMS for C$_{20}$H$_{19}$BrN$_3$O$_3$S (M+H)$^+$: calculated monoisotopic m/z=460.0; found 460.0.

Step 5. 6'-Methyl-1'-(1-methyl-1H-indazol-5-yl)-3'-(phenylsulfonyl)-3',6'-dihydro-7'H-spiro[cyclopentane-1,8'-dipyrrolo[2,3-b:3',2'-d]pyridin]-7'-one

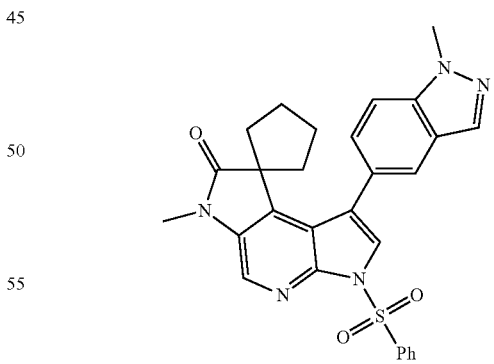

A mixture of 1'-bromo-6'-methyl-3'-(phenylsulfonyl)-3',6'-dihydro-7'H-spiro[cyclopentane-1,8'-dipyrrolo[2,3-b:3',2'-d]pyridin]-7'-one (0.20 g, 0.44 mmol), 1-methyl-5-(4,4,5,5-tetramethyl-1,3,2-dioxaborolan-2-yl)-1H-indazole (0.12 g, 0.65 mmol, AstaTech 64501), PdCl$_2$(dppf)-CH$_2$Cl$_2$ adduct (25 mg, 0.03 mmol) and Na$_2$CO$_3$ (1.0 M in water, 1.3 mL, 1.3 mmol) in dioxane (4.0 mL) was degassed and heated at 100° C. for 1 hour. Upon cooling to room temperature, the reaction mixture was diluted with EtOAc and water, filtered through Celite®, and the Celite® was washed with EtOAc. The filtrate was partitioned between EtOAc and brine. The organic extract was washed with additional brine, dried over $Na_2SO_4$, filtered and concentrated. Purification via preparative HPLC-MS (pH=2) afforded the title compound (0.17 g, 76%). LCMS for $C_{28}H_{26}N_5O_3S$ (M+H)$^+$: calculated m/z=512.2; found 512.3.

Step 6. 2'-Bromo-6'-methyl-1'-(1-methyl-1H-indazol-5-yl)-3'-(phenylsulfonyl)-3',6'-dihydro-7'H-spiro [cyclopentane-1,8'-dipyrrolo[2,3-b:3',2'-c]pyridin]-7'-one

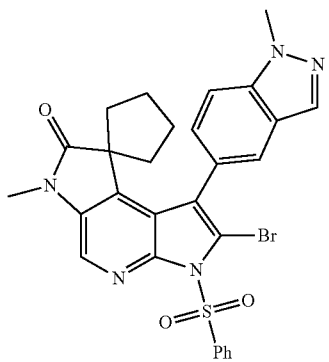 [SMILES: CN1C(=O)C2(CCCC2)c2c1cnc1c2c(-c2ccc3c(cnn3C)c2)c(Br)n1S(=O)(=O)c1ccccc1]

A solution of 6'-methyl-1'-(1-methyl-1H-indazol-5-yl)-3'-(phenylsulfonyl)-3',6'-dihydro-7'H-spiro[cyclopentane-1,8'-dipyrrolo[2,3-b:3',2'-d]pyridin]-7'-one (0.17 g, 0.33 mmol) in dry THF (3.0 mL) at −78° C. under $N_2$ was treated with LDA (2.0 M in THF/heptane/ethylbenzene, 0.33 mL, 0.66 mmol). The reaction mixture was stirred at −78° C. for 30 minutes before the addition of 1,2-dibromo-1,1,2,2-tetrachloroethane (0.16 g, 0.50 mmol, Aldrich 133396). The reaction mixture was stirred at −78° C. for 30 minutes, then was quenched by the addition of saturated aqueous $NH_4Cl$. The reaction mixture was diluted with water and was extracted with ethyl acetate. The organic extract was washed with brine, dried over $Na_2SO_4$, filtered, and concentrated. Purification via flash column chromatography on silica gel, eluting with a gradient of 0-100% EtOAc in hexanes afforded the title compound (0.13 g, 66%). LCMS for $C_{28}H_{25}BrN_5O_3S$ (M+H)$^+$: calculated monoisotopic m/z=590.1; found 590.2.

Step 7. 2'-Bromo-6'-methyl-1'-(1-methyl-1H-indazol-5-yl)-3',6'-dihydro-7'H-spiro[cyclopentane-1,8'-dipyrrolo[2,3-b:3',2'-c]pyridin]-7'-one

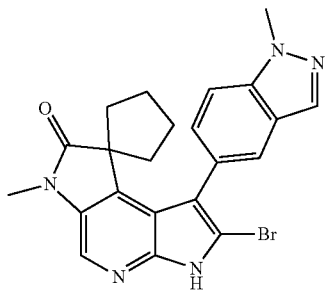 [SMILES: CN1C(=O)C2(CCCC2)c2c1cnc1[nH]c(Br)c(-c3ccc4c(cnn4C)c3)c21]

To a solution of 2'-bromo-6'-methyl-1'-(1-methyl-1H-indazol-5-yl)-3'-(phenylsulfonyl)-3',6'-dihydro-7'H-spiro[cyclopentane-1,8'-dipyrrolo[2,3-b:3',2'-d]pyridin]-7'-one (0.15 g, 0.25 mmol) in THF (1.0 mL) and MeOH (1.0 mL) was added NaOH (3.0 N solution in water, 0.40 mL, 1.2 mmol) and the reaction mixture was stirred at room temperature overnight. The reaction mixture was diluted with water and was extracted with EtOAc. The organic extract was dried over $MgSO_4$, filtered and concentrated to afford the title compound (0.010 g, 87%). LCMS for $C_{22}H_{21}BrN_5O$ (M+H)$^+$: calculated monoisotopic m/z=450.1; found 450.2.

Step 8. 6'-Methyl-1'-(1-methyl-1H-indazol-5-yl)-2'-(1-(pyridin-4-ylmethyl)-1H-pyrazol-4-yl)-3',6'-dihydro-7'H-spiro[cyclopentane-1,8'-dipyrrolo[2,3-b:3',2'-d]pyridin]-7'-one trifluoroacetate salt A mixture of 2'-bromo-6'-methyl-1'-(1-methyl-1H-indazol-5-yl)-3',6'-dihydro-7'H-spiro[cyclopentane-1,8'-dipyrrolo[2,3-b:3',2'-d]pyridin]-7'-one (0.010 g, 0.022 mmol), 4-((4-(4,4,5,5-tetramethyl-1,3,2-dioxaborolan-2-yl)-1H-pyrazol-1-yl)methyl)pyridine (9.5 mg, 0.033 mmol, Combi-Block PN-5620), $PdCl_2(dppf)\cdot CH_2Cl_2$ adduct (1.8 mg, 0.0022 mmol) and $K_2CO_3$ (1.0 M in water, 0.067 mL, 0.067 mmol) in dioxane (0.30 mL) was degassed by sparging with $N_2$ and was heated at 100° C. for 2 hours. The reaction mixture was diluted with acetonitrile and was filtered. Purification via preparative HPLC-MS (pH=2) afforded the title compound (3.0 mg).

LCMS for $C_{31}H_{29}N_8O$ (M+H)$^+$: calculated m/z=529.2; found 529.2. $^1$H NMR (400 MHz, DMSO-d$_6$) δ 12.06 (s, 1H), 8.60 (d, J=5.6 Hz, 2H), 8.09 (s, 1H), 7.98 (s, 1H), 7.80 (s, 1H), 7.75 (d, J=8.6 Hz, 1H), 7.56 (s, 1H), 7.38 (d, J=8.6 Hz, 1H), 7.22 (d, J=5.4 Hz, 2H), 7.11 (s, 1H), 5.42 (s, 2H), 4.13 (s, 3H), 3.16 (s, 3H), 2.00-1.86 (m, 1H), 1.79-1.63 (m, 3H), 1.49-1.45 (m, 2H), 0.43-0.38 (m, 2H).

Example 9

2'-Cyclopropyl-6'-methyl-1'-(1-methyl-1H-indazol-5-yl)-3',6'-dihydro-7'H-spiro[cyclopentane-1,8'-dipyrrolo[2,3-b:3',2'-d]pyridin]-7'-one, trifluoroacetate salt

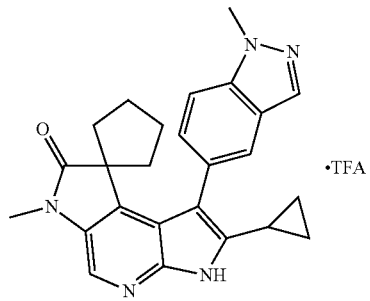 [SMILES: CN1C(=O)C2(CCCC2)c2c1cnc1[nH]c(C3CC3)c(-c3ccc4c(cnn4C)c3)c21]

The title compound was prepared by a procedure analogous to that described for Example 8, Step 8, utilizing 2'-bromo-6'-methyl-1'-(1-methyl-1H-indazol-5-yl)-3',6'-dihydro-7'H-spiro[cyclopentane-1,8'-dipyrrolo[2,3-b:3',2'-d] pyridin]-7'-one (10.0 mg, 0.022 mmol, from Example 8, Step 7) and cyclopropylboronic acid (2.9 mg, 0.034 mmol, Combi-Block BB-2007) in place of 4-((4-(4,4,5,5-tetramethyl-1,3,2-dioxaborolan-2-yl)-1H-pyrazol-1-yl)methyl)

pyridine. Purification via preparative HPLC-MS (pH=2) afforded the title compound (3.0 mg). LCMS for $C_{25}H_{26}N_5O$ (M+H)$^+$: calculated m/z=412.2; found 412.3. $^1$H NMR (500 MHz, DMSO-d$_6$) δ 11.25 (s, 1H), 8.07 (s, 1H), 7.88 (s, 1H), 7.77 (s, 1H), 7.68 (d, J=8.6 Hz, 1H), 7.39 (dd, J=8.6, 1.5 Hz, 1H), 4.10 (s, 3H), 3.14 (s, 3H), 1.91-1.87 (m, 1H), 1.76-1.72 (m, 1H), 1.67-1.63 (m, 2H), 1.61-1.52 (m, 1H), 1.48-1.44 (m, 2H), 0.95-0.83 (m, 2H), 0.83-0.76 (m, 2H), 0.45-0.41 (m, 2H).

Example 10

6'-Methyl-2'-(4-((4-(methylsulfonyl)piperidin-1-yl)methyl)phenyl)-1'-phenyl-3',6'-dihydro-7'H-spiro[cyclobutane-1,8'-dipyrrolo[2,3-b:3',2'-d]pyridin]-7'-one trifluoroacetate salt

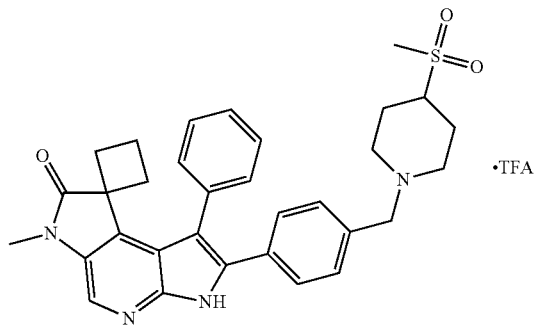 [SMILES: CN1C(=O)C2(CCC2)c2c1cnc1[nH]c(-c3ccc(CN4CCC(S(C)(=O)=O)CC4)cc3)c(-c3ccccc3)c21]

Step 1. Methyl 1-(5-nitro-1-(phenylsulfonyl)-1H-pyrrolo[2,3-b]pyridin-4-yl)cyclobutane-1-carboxylate

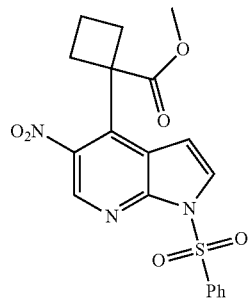 [SMILES: COC(=O)C1(c2c([N+](=O)[O-])cnc3c2ccn3S(=O)(=O)c2ccccc2)CCC1]

To a mixture of methyl cyclobutanecarboxylate (0.40 g, 3.5 mmol, Acros S851957) in THF (20.0 mL) at −78° C. was added LDA (2.0 Min THF/heptane/ethylbenzene, 1.8 mL, 3.6 mmol). The reaction was stirred at −78° C. for 40 min. To the reaction mixture was added 4-chloro-5-nitro-1-(phenylsulfonyl)-1H-pyrrolo[2,3-b]pyridine (1.0 g, 2.9 mmol, AstaTech P12207), then the reaction mixture was warmed to room temperature and was stirred at room temperature for 1 hour. The reaction mixture was quenched by the addition of saturated aqueous NH$_4$Cl. The mixture was diluted with water and was extracted with EtOAc. The organic extract was washed with brine, dried over MgSO$_4$, filtered, and concentrated. Purification via flash column chromatography on silica gel, eluting with a gradient of 0-50% EtOAc in hexanes, afforded the title compound (0.35 g, 28%). LCMS for $C_{19}H_{18}N_3O_6S$ (M+H)$^+$: calculated m/z=416.1; found 416.1.

Step 2. 3'-(Phenylsulfonyl)-3',6'-dihydro-7'H-spiro[cyclobutane-1,8'-dipyrrolo[2,3-b:3',2'-d]pyridin]-7'-one

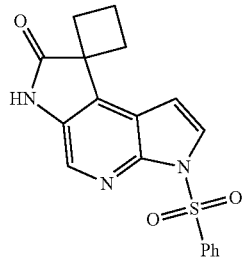

The title compound was prepared by a procedure analogous to that described for Example 8, Step 2, utilizing methyl 1-(5-nitro-1-(phenylsulfonyl)-1H-pyrrolo[2,3-b]pyridin-4-yl)cyclobutane-1-carboxylate (0.35 g, 0.84 mmol) in place of methyl 1-(5-nitro-1-(phenylsulfonyl)-1H-pyrrolo[2,3-b]pyridin-4-yl)cyclopentane-1-carboxylate. Purification via flash column chromatography on silica gel, eluting with a gradient of 0-60% EtOAc in hexanes, afforded the title compound (0.17 g, 57%). LCMS for $C_{18}H_{16}N_3O_3S$ (M+H)$^+$: calculated m/z=354.1; found 354.1.

Step 3. 6'-Methyl-3'-(phenylsulfonyl)-3',6'-dihydro-7'H-spiro[cyclobutane-1,8'-dipyrrolo[2,3-b:3',2'-c]pyridin]-7'-one

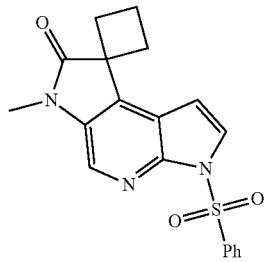 [SMILES: CN1C(=O)C2(CCC2)c2c1cnc1c2ccn1S(=O)(=O)c1ccccc1]

The title compound was prepared by a procedure analogous to that described for Example 8, Step 3, utilizing 3'-(phenylsulfonyl)-3',6'-dihydro-7'H-spiro[cyclobutane-1,8'-dipyrrolo[2,3-b:3',2'-d]pyridin]-7'-one (0.17 g, 0.48 mmol) in place of 3'-(phenylsulfonyl)-3',6'-dihydro-7'H-spiro[cyclopentane-1,8'-dipyrrolo[2,3-b:3',2'-d]pyridin]-7'-one. Purification via flash column chromatography on silica gel, eluting with a gradient of 0-60% EtOAc in hexanes, afforded the title compound (0.15 g, 85%). LCMS for $C_{19}H_{18}N_3O_3S$ (M+H)$^+$: calculated m/z=368.1; found 368.2.

Step 4. 1'-Bromo-6'-methyl-3'-(phenylsulfonyl)-3', 6'-dihydro-7'H-spiro[cyclobutane-1,8'-dipyrrolo[2,3-b:3',2'-c]pyridin]-7'-one

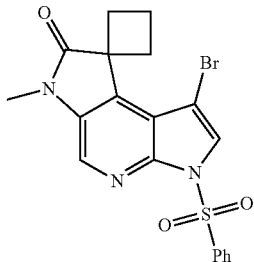 [SMILES: CN1C(=O)C2(CCC2)c2c1cnc1c2c(Br)cn1S(=O)(=O)c1ccccc1]

The title compound was prepared by a procedure analogous to that described for Example 8, Step 4, utilizing 6'-methyl-3'-(phenylsulfonyl)-3',6'-dihydro-7'H-spiro[cyclobutane-1,8'-dipyrrolo[2,3-b:3',2'-d]pyridin]-7'-one (0.15 g, 0.41 mmol) in place of 6'-methyl-3'-(phenylsulfonyl)-3',6'-dihydro-7'H-spiro[cyclopentane-1,8'-dipyrrolo[2,3-b:3',2'-d]pyridin]-7'-one. Purification via flash column chromatography on silica gel, eluting with a gradient of 0-60% EtOAc in hexanes, afforded the title compound (0.11 g, 60%). LCMS for $C_{19}H_{17}BrN_3O_3S$ $(M+H)^+$: calculated monoisotopic m/z=446.1; found 446.0.

Step 5. 6'-Methyl-1'-phenyl-3'-(phenylsulfonyl)-3,6'-dihydro-7'H-spiro[cyclobutane-1,8'-dipyrrolo[2,3-b:3',2'-c]pyridin]-7'-one

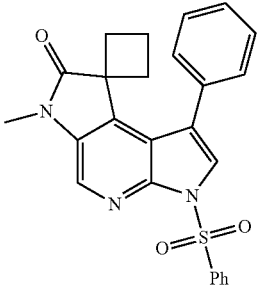 [SMILES: CN1C(=O)C2(CCC2)c2c1cnc1c2c(-c2ccccc2)cn1S(=O)(=O)c1ccccc1]

A mixture of 1'-bromo-6'-methyl-3'-(phenylsulfonyl)-3',6'-dihydro-7'H-spiro[cyclobutane-1,8'-dipyrrolo[2,3-b:3',2'-d]pyridin]-7'-one (0.05 g, 0.11 mmol), phenylboronic acid (0.021 g, 0.17 mmol, Aldrich P20009), Na₂CO₃ (1.0 M in water, 0.34 mL, 0.34 mmol) and tetrakis(triphenylphosphine)palladium(0) (0.013 g, 0.011 mmol) in DMF (1.0 mL) was degassed by sparging with N₂. The reaction was sealed and was heated at 120° C. in a microwave for 30 min. Upon cooling to room temperature, the reaction mixture was partitioned between EtOAc and water. The organic extract was washed sequentially with water and brine, dried over Na₂SO₄, filtered, and concentrated. Purification via flash column chromatography on silica gel, eluting with a gradient of 0-60% EtOAc in hexanes, afforded the title compound (0.03 g, 60%). LCMS for $C_{25}H_{22}N_3O_3S$ $(M+H)^+$: calculated m/z=444.1; found 444.1.

Step 6. 2'-Bromo-6'-methyl-1'-phenyl-3'-(phenylsulfonyl)-3',6'-dihydro-7'H-spiro[cyclobutane-1,8'-dipyrrolo[2,3-b:3',2'-d]pyridin]-7'-one

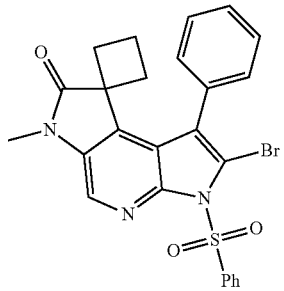 [SMILES: CN1C(=O)C2(CCC2)c2c1cnc1c2c(-c2ccccc2)c(Br)n1S(=O)(=O)c1ccccc1]

The title compound was prepared by a procedure analogous to that described for Example 8, Step 6, utilizing 6'-methyl-1'-phenyl-3'-(phenylsulfonyl)-3',6'-dihydro-7'H-spiro[cyclobutane-1,8'-dipyrrolo[2,3-b:3',2'-d]pyridin]-7'-one (0.03 g, 0.07 mmol) in place of 6'-methyl-1'-(1-methyl-1H-indazol-5-yl)-3'-(phenylsulfonyl)-3',6'-dihydro-7'H-spiro[cyclopentane-1,8'-dipyrrolo[2,3-b:3',2'-d]pyridin]-7'-one. Purification via flash column chromatography on silica gel, eluting with a gradient of 0-50% EtOAc in hexanes, afforded the title compound in a mixture containing some overbrominated products (0.02 g). LCMS for $C_{25}H_{21}BrN_3O_3S$ $(M+H)^+$: calculated monoisotopic m/z=522.0; found 522.0.

Step 7. 2'-Bromo-6'-methyl-1'-phenyl-3',6'-dihydro-7'H-spiro[cyclobutane-1,8'-dipyrrolo[2,3-b:3',2'-d]pyridin]-7'-one

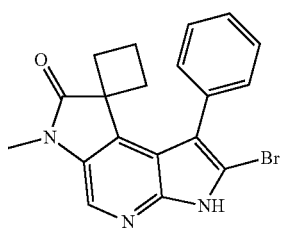 [SMILES: CN1C(=O)C2(CCC2)c2c1cnc1[nH]c(Br)c(-c3ccccc3)c21]

This compound was prepared by a procedure analogous to that described for Example 8, Step 7, utilizing 2'-bromo-6'-methyl-1'-phenyl-3'-(phenylsulfonyl)-3',6'-dihydro-7'H-spiro[cyclobutane-1,8'-dipyrrolo[2,3-b:3',2'-d]pyridin]-7'-one (0.02 g, 0.04 mmol) in place of 2'-bromo-6'-methyl-1'-(1-methyl-1H-indazol-5-yl)-3'-(phenylsulfonyl)-3',6'-dihydro-7'H-spiro[cyclopentane-1,8'-dipyrrolo[2,3-b:3',2'-d]pyridin]-7'-one. Purification via flash column chromatography on silica gel, eluting with a gradient of 0-5% MeOH in DCM, afforded the title compound (0.01 g, 70%). LCMS for $C_{19}H_{17}BrN_3O$ $(M+H)^+$: calculated monoisotopic m/z=382.1; found 382.1.

Step 8. 6'-Methyl-2'-((4-(methylsulfonyl)piperidin-1-yl)methyl)phenyl)-1'-phenyl-3',6'-dihydro-7'H-spiro[cyclobutane-1,8'-dipyrrolo[2,3-b:3',2'-d]pyridin]-7'-one trifluoroacetate salt The title compound was prepared by a procedure analogous to that described for Example 8, Step 8, utilizing 2'-bromo-6'-methyl-1'-phenyl-3',6'-dihydro-7'H-spiro[cyclobutane-1,8'-dipyrrolo[2,3-b:3',2'-d]pyridin]-7'-one (0.01 g, 0.03 mmol) in place of 2'-bromo-6'-methyl-F-(1-methyl-1H-indazol-5-yl)-3',6'-dihydro-7'H-spiro[cyclopentane-1,8'-dipyrrolo[2,3-b:3',2'-d]pyridin]-7'-one and 4-(methylsulfonyl)-1-(4-(4,4,5,5-tetramethyl-1,3,2-dioxaborolan-2-yl)benzyl)piperidine (0.015 g, 0.040 mmol, Example 1, Step 1) in place of 4-((4-(4,4,5,5-tetramethyl-1,3,2-dioxaborolan-2-yl)-1H-pyrazol-1-yl)methyl)pyridine. Purification via preparative HPLC-MS (pH=2) afforded the title compound (4 mg). LCMS for $C_{32}H_{35}N_4O_3S$ (M+H)$^+$: calculated m/z=555.2; found 555.3. $^1$H NMR (400 MHz, DMSO-d$_6$) δ 12.28 (s, 1H), 8.08 (s, 1H), 7.65-7.58 (m, 2H), 7.57-7.44 (m, 5H), 7.40 (d, J=8.1 Hz, 2H), 4.26 (s, 2H), 3.55-3.47 (m, 2H), 3.44-3.33 (m, 1H), 3.19 (s, 3H), 3.00-2.90 (m, 2H), 2.99 (s, 3H), 2.33-2.20 (m, 4H), 2.12-2.01 (m, 2H), 1.99-1.80 (m, 3H), 0.69 (d, J=10.5 Hz, 1H).

Example 11

6'-Methyl-2'-((4(4-(methylsulfonyl)piperidin-1-yl)methyl)phenyl)-1'-phenyl-3',6'-dihydro-7'H-spiro[cyclohexane-1,8'-dipyrrolo[2,3-b:3',2'-d]pyridin]-7'-one trifluoroacetate salt

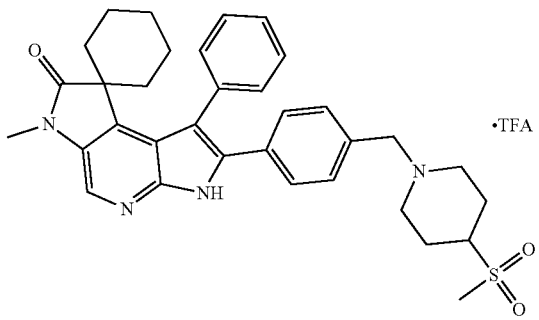 [SMILES: CN1C(=O)C2(CCCCC2)c2c1cnc1[nH]c(-c3ccc(CN4CCC(S(C)(=O)=O)CC4)cc3)c(-c3ccccc3)c21]

Step 1. Methyl 1-(5-nitro-1-(phenylsulfonyl)-1H-pyrrolo[2,3-b]pyridin-4-yl)cyclohexane-1-carboxylate

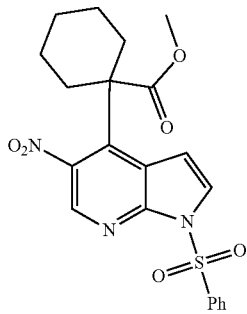 [SMILES: COC(=O)C1(c2c([N+](=O)[O-])cnc3c2ccn3S(=O)(=O)c2ccccc2)CCCCC1]

The title compound was prepared by a procedure analogous to that described for Example 8, Step 1, utilizing 4-chloro-5-nitro-1-(phenylsulfonyl)-1H-pyrrolo[2,3-b]pyridine (3.0 g, 8.9 mmol, AstaTech P12207) and methyl cyclohexanecarboxylate (1.5 g, 11 mmol, Aldrich W35680-8) in place of methyl cyclopentanecarboxylate. Purification via flash column chromatography on silica gel, eluting with a gradient of 0-40% EtOAc in hexanes, afforded the title compound (2.0 g, 51%). LCMS for $C_{21}H_{22}N_3O_6S$ (M+H)$^+$: calculated m/z=444.1; found 444.2.

Step 2. 3'-(Phenylsulfonyl)-3',6'-dihydro-7'H-spiro[clohexane-1,8'-dipyrrolo[2,3-b:3',2'-d]pyridin]-7'-one

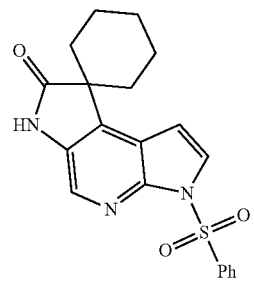 [SMILES: O=C1Nc2cnc3c(ccn3S(=O)(=O)c3ccccc3)c2C12CCCCC2]

The title compound was prepared by a procedure analogous to that described for Example 8, Step 2, utilizing methyl 1-(5-nitro-1-(phenylsulfonyl)-1H-pyrrolo[2,3-b]pyridin-4-yl)cyclohexane-1-carboxylate (2.0 g, 4.5 mmol) in place of methyl 1-(5-nitro-1-(phenylsulfonyl)-1H-pyrrolo[2,3-b]pyridin-4-yl)cyclopentane-1-carboxylate. Purification via flash column chromatography on silica gel, eluting with a gradient of 0-60% EtOAc in hexanes, afforded the title compound (1.0 g, 58%). LCMS for $C_{20}H_{20}N_3O_3S$ (M+H)$^+$: calculated m/z=382.1; found 382.2.

Step 3. 6'-Methyl-3'-(phenylsulfonyl)-3',6'-dihydro-7'H-spiro[cyclohexane-1,8'-dipyrrolo[2,3-b:3',2'-c]pyridin]-7'-one

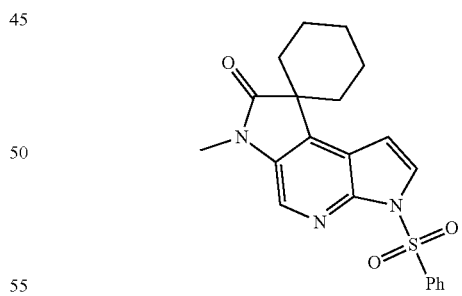

The title compound was prepared by a procedure analogous to that described for Example 8, Step 3, utilizing 3'-(phenyl sulfonyl)-3',6'-dihydro-7'H-spiro[cyclohexane-1,8'-dipyrrolo[2,3-b:3',2'-d]pyridin]-7'-one (1.0 g, 2.6 mmol) in place of 3'-(phenylsulfonyl)-3',6'-dihydro-7'H-spiro[cyclopentane-1,8'-dipyrrolo[2,3-b:3',2'-d]pyridin]-7'-one. Purification via flash column chromatography on silica gel, eluting with a gradient of 0-60% EtOAc in hexanes, afforded the title compound (0.95 g, 92%). LCMS for $C_{21}H_{22}N_3O_3S$ (M+H)$^+$: calculated m/z=396.1; found 396.2.

Step 4. 1'-Bromo-6'-methyl-3'-(phenylsulfonyl)-3', 6'-dihydro-7'H-spiro[cyclohexane-1,8'-dipyrrolo[2,3-b:3',2'-c]pyridin]-7'-one

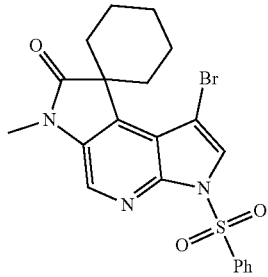 [SMILES: CN1C(=O)C2(CCCCC2)c2c1cnc1c2c(Br)cn1S(=O)(=O)c1ccccc1]

The title compound was prepared by a procedure analogous to that described for Example 8, step 4, utilizing 6'-methyl-3'-(phenylsulfonyl)-3',6'-dihydro-7'H-spiro[cyclohexane-1,8'-dipyrrolo[2,3-b:3',2'-d]pyridin]-7'-one (0.41 g, 1.1 mmol) in place of 6'-methyl-3'-(phenylsulfonyl)-3',6'-dihydro-7'H-spiro[cyclopentane-1,8'-dipyrrolo[2,3-b:3',2'-d]pyridin]-7'-one. Purification via flash column chromatography on silica gel, eluting with a gradient of 0-60% EtOAc in hexanes, afforded the title compound (0.35 g, 71%). LCMS for $C_{21}H_{21}BrN_3O_3S$ (M+H)$^+$: calculated monoisotopic m/z=474.0; found 474.1.

Step 5. 6'-Methyl-1'-phenyl-3'-(phenylsulfonyl)-3,6'-dihydro-7'H-spiro[cyclohexane-1,8'-dipyrrolo[2,3-b:3',2'-d]pyridin]-7'-one

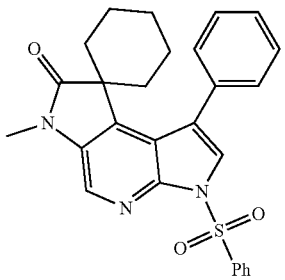 [SMILES: CN1C(=O)C2(CCCCC2)c2c1cnc1c2c(-c2ccccc2)cn1S(=O)(=O)c1ccccc1]

The title compound was prepared by a procedure analogous to that described for Example 8, Step 5, utilizing 1'-bromo-6'-methyl-3'-(phenylsulfonyl)-3',6'-dihydro-7'H-spiro[cyclohexane-1,8'-dipyrrolo[2,3-b:3',2'-d]pyridin]-7'-one (0.10 g, 0.21 mmol) in place of 1'-bromo-6'-methyl-3'-(phenylsulfonyl)-3',6'-dihydro-7'H-spiro[cyclopentane-1,8'-dipyrrolo[2,3-b:3',2'-d]pyridin]-7'-one. Purification via flash column chromatography, eluting with a gradient of 0-80% EtOAc in hexanes, afforded the title compound (0.05 g, 50%). LCMS for $C_{27}H_{26}N_3O_3S$ (M+H)$^+$: calculated m/z=472.2; found 472.2.

Step 6. 2'-Bromo-6'-methyl-1'-phenyl-3'-(phenylsulfonyl)-3',6'-dihydro-7'H-spiro[cyclohexane-1, 8'-dipyrrolo[2,3-b:3',2'-d]pyridin]-7'-one

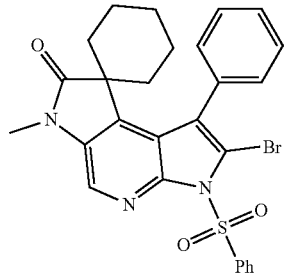 [SMILES: CN1C(=O)C2(CCCCC2)c2c1cnc1c2c(-c2ccccc2)c(Br)n1S(=O)(=O)c1ccccc1]

The title compound was prepared by a procedure analogous to that described for Example 8, Step 6, utilizing 6'-methyl-1'-phenyl-3'-(phenylsulfonyl)-3',6'-dihydro-7'H-spiro[cyclohexane-1,8'-dipyrrolo[2,3-b:3',2'-d]pyridin]-7'-one (0.04 g, 0.08 mmol) in place of 6'-methyl-1'-(1-methyl-1H-indazol-5-yl)-3'-(phenylsulfonyl)-3',6'-dihydro-7'H-spiro[cyclopentane-1,8'-dipyrrolo[2,3-b:3',2'-d]pyridin]-7'-one. Purification via flash column chromatography on silica gel, eluting with a gradient of 0-100% EtOAc in hexanes, afforded the title compound in a mixture containing some over brominated products (0.4 g). LCMS for $C_{27}H_{25}BrN_3O_3S$ (M+H)$^+$: calculated monoisotopic m/z=550.1; found 550.2.

Step 7. 2'-Bromo-6'-methyl-1'-phenyl-3',6'-dihydro-7'H-spiro[cyclohexane-1,8'-dipyrrolo[2,3-b:3',2'-d] pyridin]-7'-one

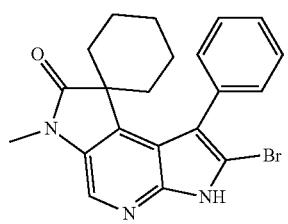 [SMILES: CN1C(=O)C2(CCCCC2)c2c1cnc1[nH]c(Br)c(-c3ccccc3)c21]

The title compound was prepared by a procedure analogous to that described for Example 8, Step 7, utilizing 2'-bromo-6'-methyl-1'-phenyl-3'-(phenylsulfonyl)-3',6'-dihydro-7'H-spiro[cyclohexane-1,8'-dipyrrolo[2,3-b:3',2'-d] pyridin]-7'-one (0.02 g, 0.04 mmol) in place of 2'-bromo-6'-methyl-1'-(1-methyl-1H-indazol-5-yl)-3'-(phenylsulfonyl)-3',6'-dihydro-7'H-spiro[cyclopentane-1,8'-dipyrrolo[2,3-b:3',2'-d]pyridin]-7'-one. Purification via flash column chromatography on silica gel, eluting with a gradient of 0-5% MeOH in DCM, afforded the title compound (0.01 g, 70%). LCMS for $C_{21}H_{21}BrN_3O$ (M+H)$^+$: calculated monoisotopic m/z=410.1; found 410.1.

Step 8. 6'-Methyl-2'-((4-(methylsulfonyl)piperidin-1-yl)methyl)phenyl)-1'-phenyl-3',6'-dihydro-7'H-spiro[cyclohexane-1,8'-dipyrrolo[2,3-b:3',2'-d]pyridin]-7'-one trifluoroacetate salt The title compound was prepared by a procedure analogous to that described for Example 8, Step 8, utilizing 2'-bromo-6'-methyl-1'-phenyl-3',6'-dihydro-7'H-spiro[cyclohexane-1,8'-dipyrrolo[2,3-b:3',2'-d]pyridin]-7'-one (0.01 g, 0.02 mmol) in place of 2'-bromo-6'-methyl-F-(1-methyl-1H-indazol-5-yl)-3',6'-dihydro-7'H-spiro[cyclopentane-1,8'-dipyrrolo[2,3-b:3',2'-d]pyridin]-7'-one and 4-(methylsulfonyl)-1-(4-(4,4,5,5-tetramethyl-1,3,2-dioxaborolan-2-yl)benzyl)piperidine (0.01 g, 0.04 mmol, Example 1, Step 1) in place of 4-((4-(4,4,5,5-tetramethyl-1,3,2-dioxaborolan-2-yl)-1H-pyrazol-1-yl)methyl)pyridine. Purification via preparative HPLC-MS (pH=2) afforded the title compound (4 mg). LCMS for $C_{34}H_{39}N_4O_3S$ (M+H)$^+$: calculated m/z=583.3; found 583.4. $^1$H NMR (500 MHz, DMSO-d$_6$) δ 12.25 (s, 1H), 8.10 (s, 1H), 7.51-7.48 (m, 3H), 7.48-7.45 (m, 4H), 7.38 (d, J=8.1 Hz, 2H), 4.24 (s, 2H), 3.50-3.38 (m, 3H), 3.18 (s, 3H), 3.00-2.90 (m, 2H), 2.98 (s, 3H), 2.24 (d, J=13.4 Hz, 2H), 2.01-1.78 (m, 4H), 1.71 (td, J=13.5, 4.2 Hz, 2H), 1.43-1.33 (m, 3H), 1.16-1.09 (m, 2H), 0.29-0.17 (m, 1H).

Example 12

6-Methyl-2-(4-((4-(methylsulfonyl)piperidin-1-yl)methyl)phenyl)-1-phenyl-1'-(2-(tetrahydro-2H-pyran-4-yl)acetyl)-3,6-dihydro-7H-spiro[dipyrrolo[2,3-b:3',2'-d]pyridine-8,3'-pyrrolidin]-7-one trifluoroacetate salt (Racemic Mixture Prepared)

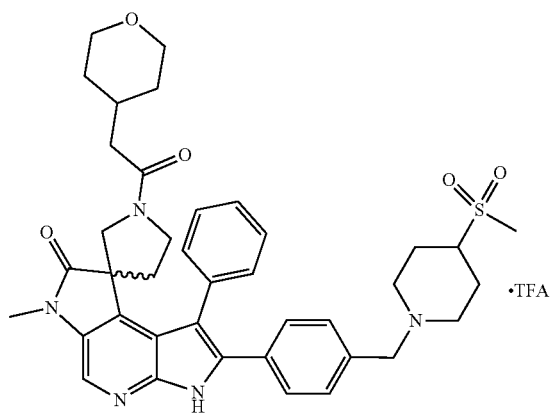

Step 1. 1-(tert-Butyl) 3-ethyl 3-(5-nitro-1-(phenylsulfonyl)-1H-pyrrolo[2,3-b]pyridin-4-yl)pyrrolidine-1,3-dicarboxylate (Racemic Mixture Prepared)

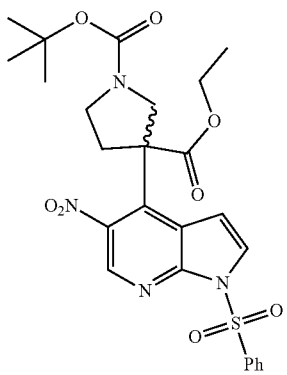 [SMILES: CCOC(=O)C1(c2c([N+](=O)[O-])cnc3c2ccn3S(=O)(=O)c2ccccc2)CCN(C(=O)OC(C)(C)C)C1]

The title compound was prepared by a procedure analogous to that described for Example 8, Step 1, utilizing 4-chloro-5-nitro-1-(phenylsulfonyl)-1H-pyrrolo[2,3-b]pyridine (2.0 g, 5.9 mmol, AstaTech P12207) and 1-(tert-butyl) 3-ethyl pyrrolidine-1,3-dicarboxylate (1.7 g, 7.1 mmol, AstaTech 60872) in place of methyl cyclopentanecarboxylate. Purification via flash column chromatography on silica gel, eluting with a gradient of 0-80% EtOAc in hexanes, afforded the title compound (1.4 g, 43%). LCMS for $C_{25}H_{29}N_4O_8S$ (M+H)$^+$: calculated m/z=545.2 found 545.3.

Step 2. tert-Butyl 7-oxo-3-(phenylsulfonyl)-6,7-dihydro-3H-spiro[dipyrrolo[2,3-b:3',2'-d]pyridine-8,3'-pyrrolidine]-1'-carboxylate (Racemic Mixture Prepared)

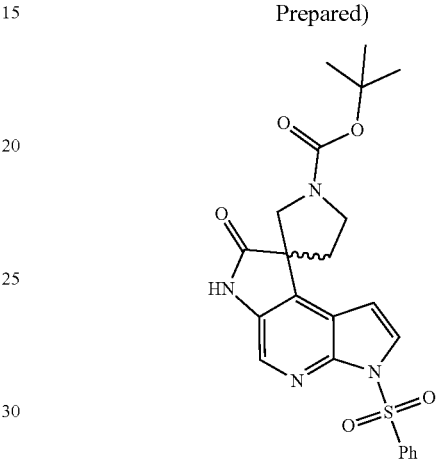

The title compound was prepared by a procedure analogous to that described for Example 8, Step 2, utilizing 1-(tert-butyl) 3-ethyl 3-(5-nitro-1-(phenylsulfonyl)-1H-pyrrolo[2,3-b]pyridin-4-yl)pyrrolidine-1,3-dicarboxylate (1.4 g, 2.6 mmol) in place of methyl 1-(5-nitro-1-(phenylsulfonyl)-1H-pyrrolo[2,3-b]pyridin-4-yl)cyclopentane-1-carboxylate. Purification via flash column chromatography on silica gel, eluting with a gradient of 0-60% EtOAc in hexanes, afforded the title compound (0.9 g, 70%). LCMS for $C_{23}H_{25}N_4O_5S$ (M+H)$^+$: calculated m/z=469.2; found 469.2.

Step 3. tert-Butyl 6-methyl-7-oxo-3-(phenylsulfonyl)-6,7-dihydro-3H-spiro[dipyrrolo[2,3-b:3',2'-d]pyridine-8,3'-pyrrolidine]-1'-carboxylate (Racemic Mixture Prepared)

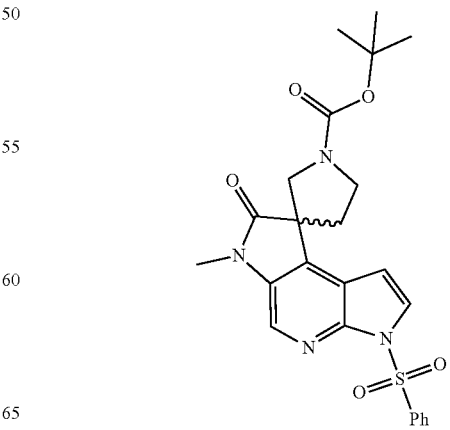

This compound was prepared by a procedure analogous to that described for Example 8, Step 3, utilizing tert-butyl 7-oxo-3-(phenylsulfonyl)-6,7-dihydro-3H-spiro[dipyrrolo[2,3-b:3',2'-d]pyridine-8,3'-pyrrolidine]-1'-carboxylate (0.090 g, 1.9 mmol) in place of 3'-(phenylsulfonyl)-3',6'-dihydro-7'H-spiro[cyclopentane-1,8'-dipyrrolo[2,3-b:3',2'-d]pyridin]-7'-one. Purification via flash column chromatography on silica gel, eluting with a gradient of 0-60% EtOAc in hexanes, afforded the title compound (0.80 g, 86%). LCMS for $C_{24}H_{27}N_4O_5S$ (M+H)$^+$: calculated m/z=483.2; found 483.1.

Step 4. tert-Butyl 1-bromo-6-methyl-7-oxo-3-(phenylsulfonyl)-6,7-dihydro-3H-spiro[dipyrrolo[2,3-b:3,2'-d]pyridine-8,3'-pyrrolidine]-1'-carboxylate (Racemic Mixture Prepared)

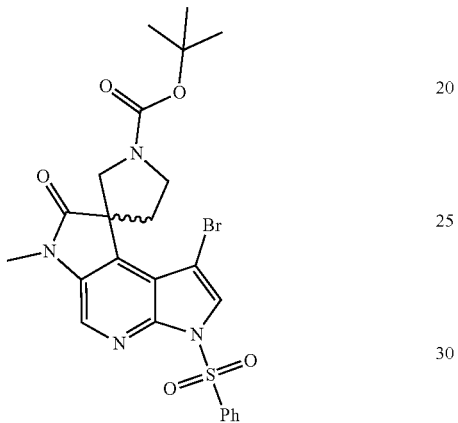

The title compound was prepared by a procedure analogous to that described for Example 8, Step 4, utilizing tert-butyl 6-methyl-7-oxo-3-(phenylsulfonyl)-6,7-dihydro-3H-spiro[dipyrrolo[2,3-b:3',2'-d]pyridine-8,3'-pyrrolidine]-1'-carboxylate (0.40 g, 0.83 mmol) in place of 6'-methyl-3'-(phenylsulfonyl)-3',6'-dihydro-7'H-spiro[cyclopentane-1,8'-dipyrrolo[2,3-b:3',2'-d]pyridin]-7'-one. Purification via flash column chromatography on silica gel column, eluting with a gradient of 0-80% EtOAc in hexanes, afforded the title compound (0.35 g, 75%). LCMS for $C_{24}H_{26}BrN_4O_5S$ (M+H)$^+$: calculated monoisotopic m/z=561.1; found 561.2.

Step 5. tert-Butyl 6-methyl-7-oxo-1-phenyl-3-(phenylsulfonyl)-6,7-dihydro-3H-spiro[dipyrrolo[2,3-b:3,2'-d]pyridine-8,3'-pyrrolidine]-1'-carboxylate (Racemic Mixture Prepared)

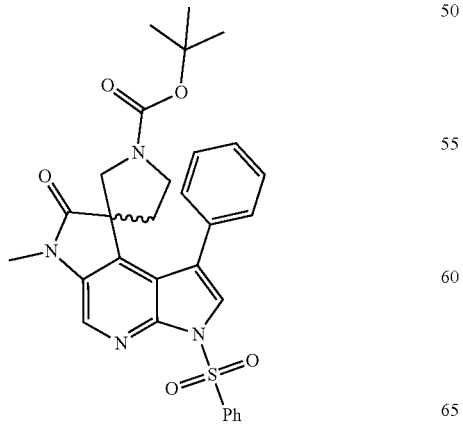

The title compound was prepared by a procedure analogous to that described for Example 10, Step 5, utilizing tert-butyl 1-bromo-6-methyl-7-oxo-3-(phenylsulfonyl)-6,7-dihydro-3H-spiro[dipyrrolo[2,3-b:3',2'-d]pyridine-8,3'-pyrrolidine]-1'-carboxylate (0.35 g, 0.62 mmol) in place of 1'-bromo-6'-methyl-3'-(phenylsulfonyl)-3',6'-dihydro-7'H-spiro[cyclobutane-1,8'-dipyrrolo[2,3-b:3',2'-d]pyridin]-7'-one. Purification via flash column chromatography on silica gel, eluting with a gradient of 0-80% EtOAc in hexanes, afforded the title compound (0.28 g, 80%). LCMS for $C_{30}H_{31}N_4O_5S$ (M+H)$^+$: calculated m/z=559.2; found 559.2.

Step 6. tert-Butyl 2-bromo-6-methyl-7-oxo-1-phenyl-3-(phenylsulfonyl)-6,7-dihydro-3H-spiro[dipyrrolo[2,3-b:3',2'-d]pyridine-8,3'-pyrrolidine]-1'-carboxylate (Racemic Mixture Prepared)

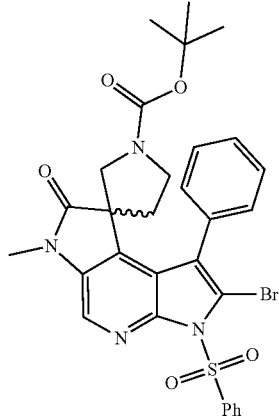 [SMILES: CN1C(=O)C2(CCN(C(=O)OC(C)(C)C)C2)c2c1cnc1c2c(-c2ccccc2)c(Br)n1S(=O)(=O)c1ccccc1]

The title compound was prepared by a procedure analogous to that described for Example 8, Step 6, utilizing tert-butyl 6-methyl-7-oxo-1-phenyl-3-(phenylsulfonyl)-6,7-dihydro-3H-spiro[dipyrrolo[2,3-b:3',2'-d]pyridine-8,3'-pyrrolidine]-1'-carboxylate (0.18 g, 0.32 mmol) in place of 6'-methyl-1'-(1-methyl-1H-indazol-5-yl)-3'-(phenylsulfonyl)-3',6'-dihydro-7'H-spiro[cyclopentane-1,8'-dipyrrolo[2,3-b:3',2'-d]pyridin]-7'-one. Purification via flash column chromatography on silica gel, eluting with a gradient of 0-100% EtOAc in hexanes, afforded the title compound (0.10 g, 48%). LCMS for $C_{30}H_{30}BrN_4O_5S$ (M+H)$^+$: calculated monoisotopic m/z=637.1; found 637.0.

Step 7. tert-Butyl 2-bromo-6-methyl-7-oxo-1-phenyl-6,7-dihydro-3H-spiro[dipyrrolo[2,3-b:3',2'-d]pyridine-8,3'-pyrrolidine]-1'-carboxylate (Racemic Mixture Prepared)

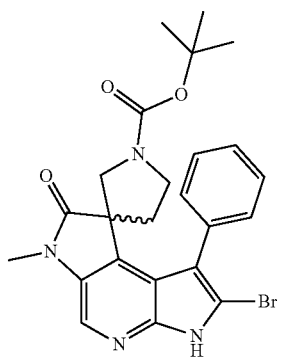 [SMILES: CN1C(=O)C2(CCN(C(=O)OC(C)(C)C)C2)c2c1cnc1[nH]c(Br)c(-c3ccccc3)c21]

The title compound was prepared by a procedure analogous to that described for Example 8, Step 7, utilizing tert-butyl 2-bromo-6-methyl-7-oxo-1-phenyl-3-(phenylsulfonyl)-6,7-dihydro-3H-spiro[dipyrrolo[2,3-b:3',2'-d]pyridine-8,3'-pyrrolidine]-1'-carboxylate (0.06 g, 0.09 mmol) in place of 2'-bromo-6'-methyl-1'-(1-methyl-1H-indazol-5-yl)-3'-(phenylsulfonyl)-3',6'-dihydro-7'H-spiro[cyclopentane-1,8'-dipyrrolo[2,3-b:3',2'-d]pyridin]-7'-one. Purification via flash column chromatography on silica gel, eluting with a gradient of 0-100% EtOAc in hexanes, afforded the title compound (0.02 g, 40%). LCMS for C$_{24}$H$_{26}$BrN$_4$O$_3$ (M+H)$^+$: calculated monoisotopic m/z=497.1; found 496.9.

Step 8. tert-Butyl 6-methyl-2-((4-(methylsulfonyl)piperidin-1-yl)methyl)phenyl)-7-oxo-1-phenyl-6,7-dihydro-3H-spiro[dipyrrolo[2,3-b:3,2'-d]pyridine-8,3'-pyrrolidine]-1'-carboxylate (Racemic Mixture Prepared)

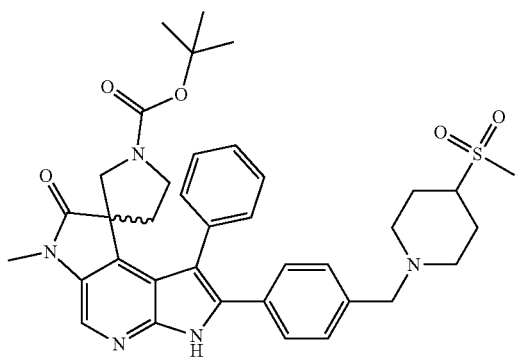

The title compound was prepared by a procedure analogous to that described for Example 8, Step 8, utilizing tert-butyl 2-bromo-6-methyl-7-oxo-1-phenyl-6,7-dihydro-3H-spiro[dipyrrolo[2,3-b:3',2'-d]pyridine-8,3'-pyrrolidine]-1'-carboxylate (0.02 g, 0.04 mmol) in place of 2'-bromo-6'-methyl-1'-(1-methyl-1H-indazol-5-yl)-3'-(phenylsulfonyl)-3',6'-dihydro-7'H-spiro[cyclopentane-1,8'-dipyrrolo[2,3-b:3',2'-d]pyridin]-7'-one and 4-(methylsulfonyl)-1-(4-(4,4,5,5-tetramethyl-1,3,2-dioxaborolan-2-yl)benzyl)piperidine (0.02 g, 0.06 mmol, Example 1, Step 1) in place of 4-((4-(4,4,5,5-tetramethyl-1,3,2-dioxaborolan-2-yl)-1H-pyrazol-1-yl)methyl)pyridine. Purification via flash column chromatography on silica gel, eluting with a gradient of 0-5% MeOH in DCM, afforded the title compound (0.02 g, 70%). LCMS for C$_{37}$H$_{44}$N$_5$O$_5$S (M+H)$^+$: calculated m/z=670.3; found 670.3.

Step 9. 6-Methyl-2-((4-(4-(methylsulfonyl)piperidin-1-yl)methyl)phenyl)-1-phenyl-3,6-dihydro-7H-spiro[dipyrrolo[2,3-b:3',2'-d]pyridine-8,3'-pyrrolidin]-7-one hydrochloric acid salt (Racemic Mixture Prepared)

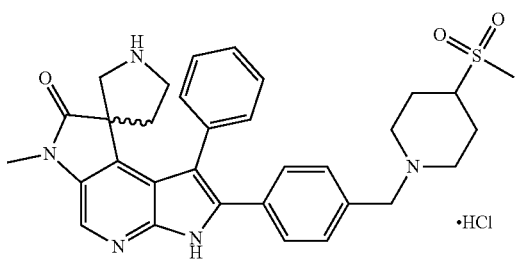

To a mixture of tert-butyl 6-methyl-2-(4-((4-(methylsulfonyl)piperidin-1-yl)methyl)phenyl)-7-oxo-1-phenyl-6,7-dihydro-3H-spiro[dipyrrolo[2,3-b:3',2'-d]pyridine-8,3'-pyrrolidine]-1'-carboxylate (0.02 g, 0.03 mmol) in DCM (0.5 mL) was added HCl solution (4.0 N in dioxane, 80 μL, 0.3 mmol). The reaction mixture was stirred for 30 min and volatiles were removed in vacuo to afford the title compound (0.02 g, 100%). LCMS for C$_{32}$H$_{36}$N$_5$O$_3$S (M+H)$^+$: calculated m/z=570.3; found 570.2.

Step 10. 6-Methyl-2-((4-(methylsulfonyl)piperidin-1-yl)methyl)phenyl)-1-phenyl-1'-(2-(tetrahydro-2H-pyran-4-yl)acetyl)-3,6-dihydro-7H-spiro[dipyrrolo[2,3-b:3,2'-d]pyridine-8,3'-pyrrolidin]-7-one trifluoroacetate salt (Racemic Mixture Prepared)

To a mixture of 6-methyl-2-(4-((4-(methylsulfonyl)piperidin-1-yl)methyl)phenyl)-1-phenyl-3,6-dihydro-7H-spiro[dipyrrolo[2,3-b:3',2'-d]pyridine-8,3'-pyrrolidin]-7-one, HCl salt (8.0 mg, 0.013 mmol), 2-(tetrahydro-2H-pyran-4-yl)acetic acid, HCl salt (3.6 mg, 0.020 mmol) and HATU (5.0 mg, 0.013 mmol) in DMF (0.2 mL) was added DIPEA (9 4, 0.05 mmol), and the reaction mixture was stirred for 1 hour. The reaction mixture was diluted with water and was extracted with EtOAc. The organic extract was concentrated, and the residue was reconstituted with acetonitrile and filtered. Purification via preparative HPLC-MS (pH=2) afforded the title compound (1.2 mg). LCMS for C$_{39}$H$_{46}$N$_5$O$_5$S (M+H)$^+$: calculated m/z=696.3; found 696.3. $^1$H NMR (rotamers, 500 MHz, DMSO-d$_6$) δ 12.37 (s, 0.5H), 12.35 (s, 0.5H), 8.16 (s, 0.5H), 8.15 (s, 0.5H), 7.53-7.34 (m, 9H), 4.25 (s, 2H), 3.91-3.78 (m, 2H), 3.58-3.26 (m, 9H), 3.20 (s, 1.5H), 3.19 (s, 1.5H), 2.93-3.0 (m, 2H), 2.98 (s, 3H), 2.27-2.19 (m, 2H), 2.18-1.84 (m, 7H), 1.68-1.51 (m, 2H), 1.30-1.11 (m, 2H).

Example 13

8-Acetyl-6'-methyl-2'-((4(4-(methylsulfonyl)piperidin-1-yl)methyl)phenyl)-1'-phenyl-3',6'-dihydro-7'H-8-azaspiro[bicyclo[3.2.1]octane-3,8'-dipyrrolo[2,3-b:3',2'-d]pyridin]-7'-one trifluoroacetate salt

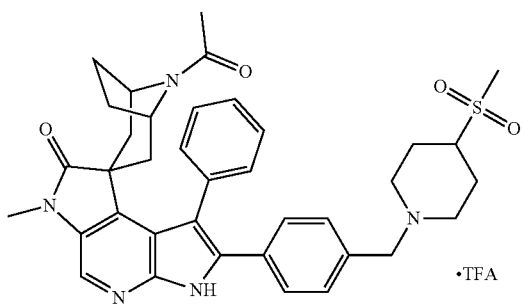 [SMILES: CC(=O)N1C2CCC1CC1(C2)C(=O)N(C)c2cnc3[nH]c(-c4ccc(CN5CCC(S(C)(=O)=O)CC5)cc4)c(-c4ccccc4)c3c21 ; "·TFA"]

Step 1. 8-(tert-Butyl) 3-methyl 3-(5-nitro-1-(phenylsulfonyl)-1H-pyrrolo[2,3-b]pyridin-4-yl)-8-azabicyclo[3.2.1]octane-3,8-dicarboxylate

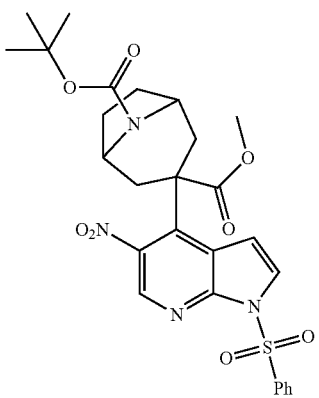 [SMILES: COC(=O)C1(c2c([N+](=O)[O-])cnc3c2ccn3S(=O)(=O)c2ccccc2)CC2CCC(C1)N2C(=O)OC(C)(C)C]

The title compound was prepared by a procedure analogous to that described for Example 12, Step 1, utilizing 4-chloro-5-nitro-1-(phenylsulfonyl)-1H-pyrrolo[2,3-b]pyridine (0.61 g, 1.8 mmol, AstaTech P12207) and 8-(tert-butyl) 3-methyl 8-azabicyclo[3.2.1]octane-3,8-dicarboxylate (0.57 g, 2.1 mmol, PharmaBlock PBZ9959) in place of 1-(tert-butyl) 3-ethyl pyrrolidine-1,3-dicarboxylate. Purification via flash column chromatography on silica gel, eluting with a gradient of 0-40% EtOAc in hexanes, afforded the title compound (0.78 g, 74%). LCMS for $C_{27}H_{31}N_4O_8S$ (M+H)$^+$: calculated m/z=571.2; found 571.2.

Step 2. tert-Butyl 7'-oxo-3'-(phenylsulfonyl)-6',7'-dihydro-3'H-8-azaspiro[bicyclo[3.2.1]octane-3,8'-dipyrrolo[2,3-b:3',2'-c]pyridine]-8-carboxylate

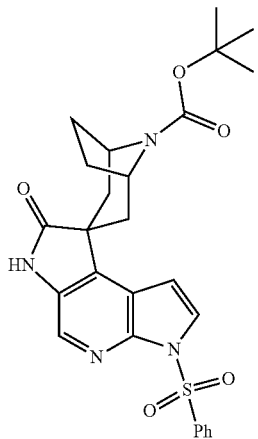 [SMILES: CC(C)(C)OC(=O)N1C2CCC1CC1(C2)C(=O)Nc2cnc3c(ccn3S(=O)(=O)c3ccccc3)c21]

The title compound was prepared by a procedure analogous to that described for Example 12, Step 2, utilizing 8-(tert-butyl) 3-methyl 3-(5-nitro-1-(phenylsulfonyl)-1H-pyrrolo[2,3-b]pyridin-4-yl)-8-azabicyclo[3.2.1]octane-3,8-dicarboxylate (0.76 g, 1.3 mmol) in place of 1-(tert-butyl) 3-ethyl 3-(5-nitro-1-(phenylsulfonyl)-1H-pyrrolo[2,3-b]pyridin-4-yl)pyrrolidine-1,3-dicarboxylate. Purification via flash column chromatography on silica gel, eluting with a gradient of 0-60% EtOAc in hexanes, afforded the title compound (0.60 g, 89%). LCMS for $C_{26}H_{29}N_4O_5S$ (M+H)$^+$: calculated m/z=509.2; found 509.2.

Step 3. tert-Butyl 6'-methyl-7'-oxo-3'-(phenylsulfonyl)-6',7'-dihydro-3'H-8-azaspiro[bicyclo[3.2.1]octane-3,8'-dipyrrolo[2,3-b:3',2'-d]pyridine]-8-carboxylate

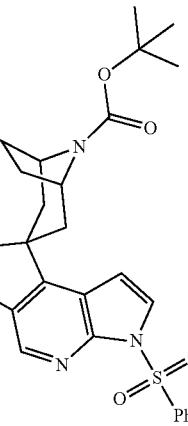

The title compound was prepared by a procedure analogous to that described for Example 12, Step 3, utilizing tert-butyl 7'-oxo-3'-(phenylsulfonyl)-6',7'-dihydro-3'H-8-azaspiro[bicyclo[3.2.1]octane-3,8'-dipyrrolo[2,3-b:3',2'-d]pyridine]-8-carboxylate (0.60 g, 1.2 mmol) in place of tert-butyl 7-oxo-3-(phenylsulfonyl)-6,7-dihydro-3H-spiro[dipyrrolo[2,3-b:3',2'-d]pyridine-8,3'-pyrrolidine]-1'-carboxylate. Purification via flash column chromatography on silica gel, eluting with a gradient of 0-60% EtOAc in hexanes, afforded the title compound (0.40 g, 65%). LCMS for $C_{27}H_{31}N_4O_5S$ (M+H)$^+$: calculated m/z=523.2; found 523.2.

Step 4. tert-Butyl 1'-bromo-6'-methyl-7'-oxo-3'-(phenylsulfonyl)-6',7'-dihydro-3'H-8-azaspiro[bicyclo[3.2.1]octane-3,8'-dipyrrolo[2,3-b:3',2'-d]pyridine]-8-carboxylate

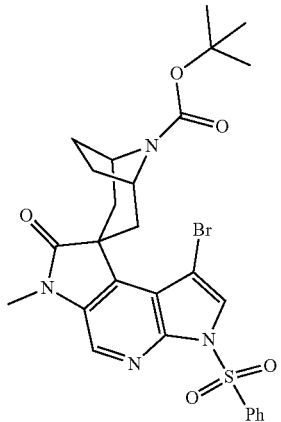 [SMILES: CN1C(=O)C2(CC3CCC(C2)N3C(=O)OC(C)(C)C)c2c1cnc1c2c(Br)cn1S(=O)(=O)c1ccccc1]

The title compound was prepared by a procedure analogous to that described for Example 12, Step 4, utilizing tert-butyl 6'-methyl-7'-oxo-3'-(phenylsulfonyl)-6',7'-dihydro-3'H-8-azaspiro[bicyclo[3.2.1]octane-3,8'-dipyrrolo[2,3-b:3',2'-d]pyridine]-8-carboxylate (0.40 g, 0.76 mmol) in place of tert-butyl 6-methyl-7-oxo-3-(phenylsulfonyl)-6,7-dihydro-3H-spiro[dipyrrolo[2,3-b:3',2'-d]pyridine-8,3'-pyrrolidine]-1'-carboxylate. Purification via flash column chromatography on silica gel, eluting with a gradient of 0-60% EtOAc in hexanes, afforded the title compound (0.23 g, 50%). LCMS for $C_{27}H_{30}BrN_4O_5S$ (M+H)$^+$: calculated monoisotopic m/z=601.1; found 601.1.

Step 5. tert-Butyl 6'-methyl-7'-oxo-1'-phenyl-3'-(phenylsulfonyl)-6',7'-dihydro-3'H-8-azaspiro[bicyclo[3.2.1]octane-3,8'-dipyrrolo[2,3-b:3',2'-d]pyridine]-8-carboxylate

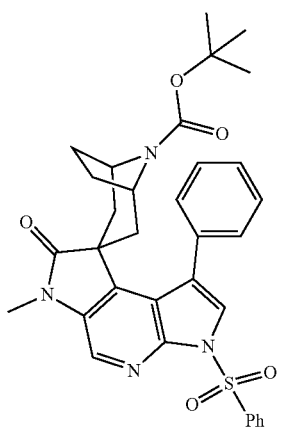 [SMILES: CN1C(=O)C2(CC3CCC(C2)N3C(=O)OC(C)(C)C)c2c1cnc1c2c(-c2ccccc2)cn1S(=O)(=O)c1ccccc1]

The title compound was prepared by a procedure analogous to that described for Example 12, Step 5, utilizing tert-butyl 1'-bromo-6'-methyl-7'-oxo-3'-(phenylsulfonyl)-6',7'-dihydro-3'H-8-azaspiro[bicyclo[3.2.1]octane-3,8'-dipyrrolo[2,3-b:3',2'-d]pyridine]-8-carboxylate (0.23 g, 0.38 mmol) in place of tert-butyl 1-bromo-6-methyl-7-oxo-3-(phenylsulfonyl)-6,7-dihydro-3H-spiro[dipyrrolo[2,3-b:3',2'-d]pyridine-8,3'-pyrrolidine]-1'-carboxylate. Purification via flash column chromatography on silica gel, eluting with a gradient of 0-60% EtOAc in hexanes, afforded the title compound (0.15 g, 65%). LCMS for $C_{33}H_{35}N_4O_5S$ (M+H)$^+$: calculated m/z=599.2; found 599.2.

Step 6. tert-Butyl 2'-bromo-6'-methyl-7'-oxo-1'-phenyl-3'-(phenylsulfonyl)-6',7'-dihydro-3'H-8-azaspiro[bicyclo[3.2.1]octane-3,8'-dipyrrolo[2,3-b:3',2'-c]pyridine]-8-carboxylate

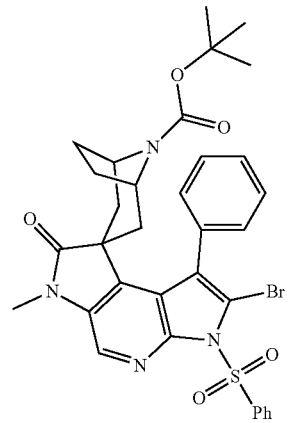 [SMILES: CN1C(=O)C2(CC3CCC(C2)N3C(=O)OC(C)(C)C)c2c1cnc1c2c(-c2ccccc2)c(Br)n1S(=O)(=O)c1ccccc1]

The title compound was prepared by a procedure analogous to that described for Example 12, Step 6, utilizing tert-butyl 6'-methyl-7'-oxo-1'-phenyl-3'-(phenylsulfonyl)-6',7'-dihydro-3'H-8-azaspiro[bicyclo[3.2.1]octane-3,8'-dipyrrolo[2,3-b:3',2'-d]pyridine]-8-carboxylate (150 mg, 0.25 mmol) in place of tert-butyl 6-methyl-7-oxo-1-phenyl-3-(phenylsulfonyl)-6,7-dihydro-3H-spiro[dipyrrolo[2,3-b:3',2'-d]pyridine-8,3'-pyrrolidine]-1'-carboxylate. Purification via flash column chromatography on silica gel, eluting with a gradient of 0-80% EtOAc in hexanes, afforded the title compound (0.14 g, 82%). LCMS for $C_{33}H_{34}BrN_4O_5S$ (M+H)$^+$: calculated monoisotopic m/z=677.1; found 677.0.

Step 7. tert-Butyl 6'-methyl-2'-((4-(4-(methylsulfonyl)piperidin-1-yl)methyl)phenyl)-7'-oxo-1'-phenyl-3'-(phenylsulfonyl)-6',7'-dihydro-3'H-8-azaspiro[bicyclo[3.2.1]octane-3,8'-dipyrrolo[2,3-b:3',2'-d]pyridine]-8-carboxylate

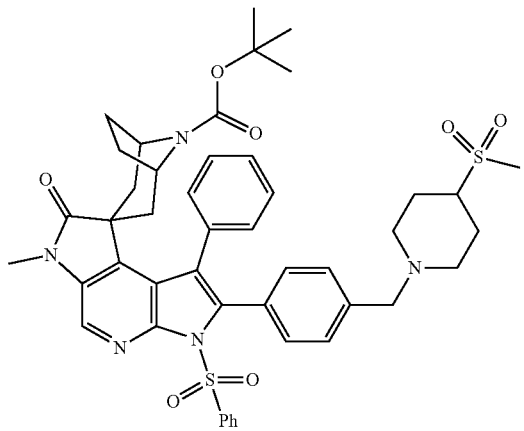

The title compound was prepared by a procedure analogous to that described for Example 12, Step 8, utilizing 4-(methylsulfonyl)-1-(4-(4,4,5,5-tetramethyl-1,3,2-dioxaborolan-2-yl)benzyl)piperidine (120 mg, 0.31 mmol, Example 1, Step 1) and tert-butyl 2'-bromo-6'-methyl-7'-oxo-1'-phenyl-3'-(phenylsulfonyl)-6',7'-dihydro-3'H-8-azaspiro[bicyclo[3.2.1]octane-3,8'-dipyrrolo[2,3-b:3',2'-d]pyridine]-8-carboxylate (0.14 g, 0.20 mmol) in place of tert-butyl 2-bromo-6-methyl-7-oxo-1-phenyl-6,7-dihydro-3H-spiro[dipyrrolo[2,3-b:3',2'-d]pyridine-8,3'-pyrrolidine]-1'-carboxylate. Purification via flash column chromatography on silica gel, eluting with a gradient of 0-100% EtOAc in hexanes, afforded the title compound (0.10 g, 56%). LCMS for $C_{46}H_{52}N_5O_7S_2$ (M+H)$^+$: calculated m/z=850.3; found 850.2.

Step 8. 6'-Methyl-2'-((4-(methylsulfonyl)piperidin-1-yl)methyl)phenyl)-1'-phenyl-3'-(phenylsulfonyl)-3',6'-dihydro-7'H-8-azaspiro[bicyclo[3.2.1]octane-3,8'-dipyrrolo[2,3-b:3',2'-d]pyridin]-7'-one hydrochloric acid salt

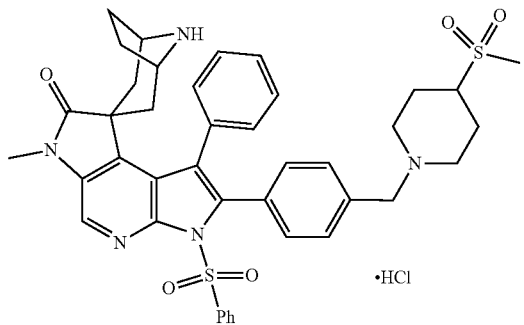

A procedure analogous to that described for Example 12, Step 9 was followed, utilizing tert-butyl 6'-methyl-2'-(4-((4-(methylsulfonyl)piperidin-1-yl)methyl)phenyl)-7'-oxo-1'-phenyl-3'-(phenylsulfonyl)-6',7'-dihydro-3'H-8-azaspiro[bicyclo[3.2.1]octane-3,8'-dipyrrolo[2,3-b:3',2'-d]pyridine]-8-carboxylate (0.10 g, 0.12 mmol) in place of tert-butyl 6-methyl-2-(4-((4-(methylsulfonyl)piperidin-1-yl)methyl)phenyl)-7-oxo-1-phenyl-6,7-dihydro-3H-spiro[dipyrrolo[2,3-b:3',2'-d]pyridine-8,3'-pyrrolidine]-1'-carboxylate to afford the title compound (0.090 g, 99%). LCMS for $C_{41}H_{44}N_5O_5S_2$ (M+H)$^+$: calculated m/z=750.3; found 750.3.

Step 9. 8-Acetyl-6'-methyl-2'-(4-((4-(methylsulfonyl)piperidin-1-yl)methyl)phenyl)-1'-phenyl-3'-(phenylsulfonyl)-3',6'-dihydro-7'H-8-azaspiro[bicyclo[3.2.1]octane-3,8'-dipyrrolo[2,3-b:3',2'-d]pyridin]-7'-one

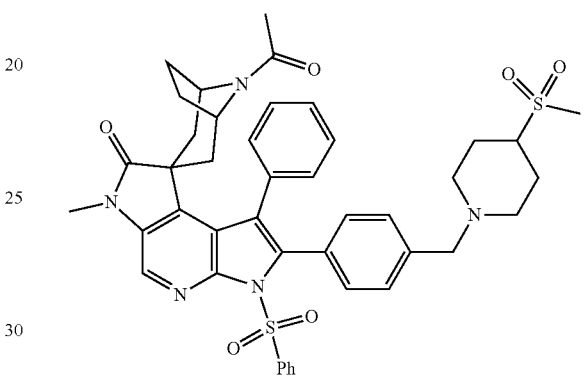

To a mixture of 6'-methyl-2'-(4-((4-(methylsulfonyl)piperidin-1-yl)methyl)phenyl)-1'-phenyl-3'-(phenylsulfonyl)-3',6'-dihydro-7'H-8-azaspiro[bicyclo[3.2.1]octane-3,8'-dipyrrolo[2,3-b:3',2'-d]pyridin]-7'-one, HCl salt (0.010 g, 0.013 mmol) in DCM (0.20 mL) was added triethylamine (10.0 mL, 0.076 mmol), followed by acetyl chloride (1.5 mg, 0.019 mmol), and the resulting mixture was stirred for 1 hour. Volatiles were removed in vacuo to afford the title compound, which was used without further purification. LCMS for $C_{43}H_{46}N_5O_6S_2$ (M+H)$^+$: calculated m/z=792.3; found 792.3.

Step 10. 8-Acetyl-6'-methyl-2'-((4(4-(methylsulfonyl)piperidin-1-yl)methyl)phenyl)-1'-phenyl-3',6'-dihydro-7'H-8-azaspiro[bicyclo[3.2.1]octane-3,8'-dipyrrolo[2,3-b:3,2'-d]pyridin]-7'-one trifluoroacetate salt The title compound was prepared by a procedure analogous to that described for Example 8, Step 7, utilizing 8-acetyl-6'-methyl-2'-(4-((4-(methylsulfonyl)piperidin-1-yl)methyl)phenyl)-1'-phenyl-3'-(phenylsulfonyl)-3',6'-dihydro-7'H-8-azaspiro[bicyclo[3.2.1]octane-3,8'-dipyrrolo[2,3-b:3',2'-d]pyridin]-7'-one (0.010 g, 0.013 mmol) in place of 2'-bromo-6'-methyl-1'-(1-methyl-1H-indazol-5-yl)-3'-(phenylsulfonyl)-3',6'-dihydro-7'H-spiro[cyclopentane-1,8'-dipyrrolo[2,3-b:3',2'-d]pyridin]-7'-one. Preparative HPLC-MS (pH=2) afforded the title compound (4.0 mg). LCMS for $C_{37}H_{42}N_5O_4S$ (M+H)$^+$: calculated m/z=652.3; found 652.3. $^1$H NMR (500 MHz, DMSO-$d_6$) δ 12.29 (s, 1H), 8.07 (s, 1H), 7.40-7.33 (m, 3H), 7.35-7.27 (m, 4H), 7.20 (d, J=8.0 Hz, 2H), 4.43-4.39 (m, 1H), 4.23 (s, 2H), 3.91-3.88 (m, 1H), 3.50-3.46 (m, 2H), 3.39-3.32 (m, 1H), 3.19 (s, 3H), 3.00-2.90 (m, 2H), 2.99 (s, 3H), 2.46-2.27 (m, 4H), 2.27-2.20 (m, 2H), 1.89-1.80 (m, 2H), 1.80-1.72 (m, 2H), 1.66 (s, 3H), 1.57-1.47 (m, 1H), 1.46-1.37 (m, 1H).

Example 14

3-(4-(4-(6'-Methyl-2'-(1-methyl-1H-pyrazol-4-yl)-7'-oxo-6',7'-dihydro-3'H-spiro[cyclopentane-1,8'-dipyrrolo[2,3-b:3',2'-d]pyridin]-1'-yl)phenyl)-1H-pyrazol-1-yl)butanenitrile trifluoroacetate salt (Racemic Mixture Prepared)

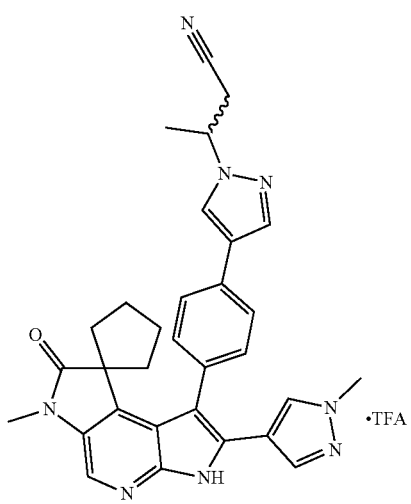

Step 1. 4-(4-Bromophenyl)-1-(tetrahydro-2H-pyran-2-yl)-1H-pyrazole

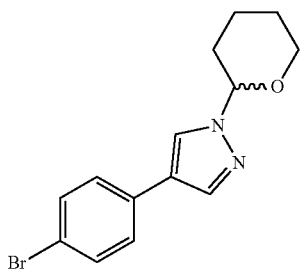 [SMILES: Brc1ccc(-c2cnn(C3CCCCO3)c2)cc1]

A mixture of 1-(tetrahydro-2H-pyran-2-yl)-4-(4,4,5,5-tetramethyl-1,3,2-dioxaborolan-2-yl)-1H-pyrazole (1.0 g, 3.6 mmol, AstaTech 82915), 1-bromo-4-iodobenzene (1.0 g, 3.6 mmol, Aldrich 238090), PdCl$_2$(dppf)-CH$_2$Cl$_2$ adduct (0.23 g, 0.36 mmol) and Na$_2$CO$_3$ (1.0 M in water, 9.0 mL, 9.0 mmol) in dioxane (25 mL) was degassed, and the reaction mixture was heated at 100° C. for 1 hour. Upon cooling to room temperature, the reaction mixture was diluted with EtOAc and water, filtered through Celite®, and the layers of the filtrate were separated. The organic layer was washed with brine, dried over Na$_2$SO$_4$, filtered and concentrated. Purification via flash column chromatography on silica gel, eluting with a gradient of 0-50% EtOAc in hexanes, afforded the title compound (0.89 g, 81%). LCMS for C$_{14}$H$_{16}$BrN$_2$O (M+H)$^+$: calculated monoisotopic m/z=307.0; found 307.1.

Step 2. 1-(Tetrahydro-2H-pyran-2-yl)-4-(4-(4,4,5,5-tetramethyl-1,3,2-dioxaborolan-2-yl)phenyl)-1H-pyrazole

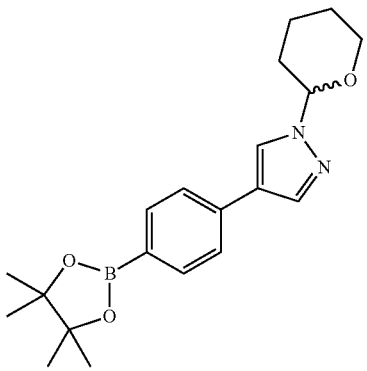 [SMILES: CC1(C)OB(c2ccc(-c3cnn(C4CCCCO4)c3)cc2)OC1(C)C]

A mixture of 4-(4-bromophenyl)-1-(tetrahydro-2H-pyran-2-yl)-1H-pyrazole (0.90 g, 2.9 mmol), anhydrous KOAc (1.1 g, 12 mmol), bis(pinacolato)diboron (1.1 g, 4.4 mmol) and 1,1'-bis(diphenylphosphino)ferrocene-palladium(II)dichloride dichloromethane adduct (0.30 g, 0.30 mmol) in dioxane (8.0 mL) was degassed and then was heated at 90° C. overnight. Upon cooling to room temperature, the reaction mixture was diluted with water and extracted with EtOAc. The organic extract was dried over MgSO$_4$, filtered and concentrated. Purification via flash column chromatography on silica gel, eluting with a gradient of 0-50% EtOAc in hexanes, afforded the title compound (0.83 g, 80%). LCMS for C$_{20}$H$_{28}$BN$_2$O$_3$ (M+H)$^+$: calculated m/z=355.2; found 355.2.

Step 3. 6'-Methyl-3'-(phenylsulfonyl)-1'-(4-(1-(tetrahydro-2H-pyran-2-yl)-1H-pyrazol-4-yl)phenyl)-3',6'-dihydro-7'H-spiro[cyclopentane-1,8'-dipyrrolo[2,3-b:3',2'-c]pyridin]-7'-one

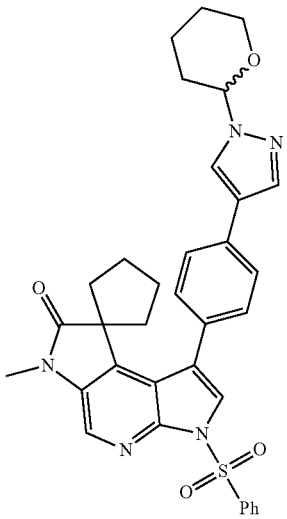 [SMILES: CN1C(=O)C2(CCCC2)c2c1cnc1c2c(-c2ccc(-c3cnn(C4CCCCO4)c3)cc2)cn1S(=O)(=O)c1ccccc1]

The title compound was prepared by a procedure analogous to that described for Example 8, Step 5, utilizing 1'-bromo-6'-methyl-3'-(phenylsulfonyl)-3',6'-dihydro-7'H-spiro[cyclopentane-1,8'-dipyrrolo[2,3-b:3',2'-d]pyridin]-7'-one (0.20 g, 0.43 mmol, Example 8, Step 4) and 1-(tetrahydro-2H-pyran-2-yl)-4-(4-(4,4,5,5-tetramethyl-1,3,2-dioxaborolan-2-yl)phenyl)-1H-pyrazole (0.23 g, 0.65 mmol, Example 14, Step 2) in place of 1-methyl-5-(4,4,5,5-tetramethyl-1,3,2-dioxaborolan-2-yl)-1H-indazole. Purification via flash column chromatography on silica gel, eluting with a gradient of 0-60% EtOAc in hexanes, afforded the title compound (0.20 g, 76%). LCMS for $C_{34}H_{34}N_5O_4S$ $(M+H)^+$: calculated m/z=608.2; found 608.3.

Step 4. 2'-Bromo-6'-methyl-3'-(phenylsulfonyl)-1'-(4-(1-(tetrahydro-2H-pyran-2-yl)-1H-pyrazol-4-yl)phenyl)-3',6'-dihydro-7'H-spiro[cyclopentane-1,8'-dipyrrolo[2,3-b:3',2'-d]pyridin]-7'-one

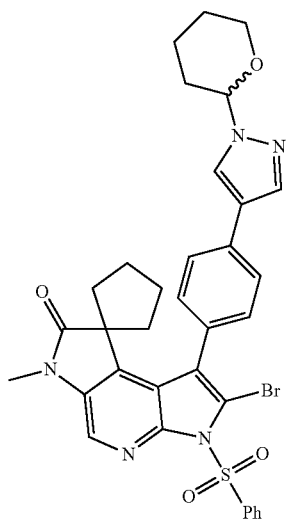 [SMILES: CN1C(=O)C2(CCCC2)c2c1cnc1c2c(-c2ccc(-c3cnn(C4CCCCO4)c3)cc2)c(Br)n1S(=O)(=O)c1ccccc1]

The title compound was prepared by a procedure analogous to that described for Example 8, Step 6, utilizing 6'-methyl-3'-(phenylsulfonyl)-1'-(4-(1-(tetrahydro-2H-pyran-2-yl)-1H-pyrazol-4-yl)phenyl)-3',6'-dihydro-7'H-spiro[cyclopentane-1,8'-dipyrrolo[2,3-b:3',2'-d]pyridin]-7'-one (0.10 g, 0.16 mmol) in place of 6'-methyl-1'-(1-methyl-1H-indazol-5-yl)-3'-(phenyl sulfonyl)-3',6'-dihydro-7'H-spiro[cyclopentane-1,8'-dipyrrolo[2,3-b:3',2'-d]pyridin]-7'-one. Purification via flash column chromatography on silica gel, eluting with a gradient of 0-100% EtOAc in hexanes, afforded the title compound (0.080 g, 70%). LCMS for $C_{34}H_{33}BrN_5O_4S$ $(M+H)^+$: calculated monoisotopic m/z=686.1; found 686.3.

Step 5. 6'-Methyl-2'-(1-methyl-1H-pyrazol-4-yl)-3'-(phenylsulfonyl)-1'-(4-(1-(tetrahydro-2H-pyran-2-yl)-1H-pyrazol-4-yl)phenyl)-3',6'-dihydro-7'H-spiro[cyclopentane-1,8'-dipyrrolo[2,3-b:3',2'-c]pyridin]-7'-one

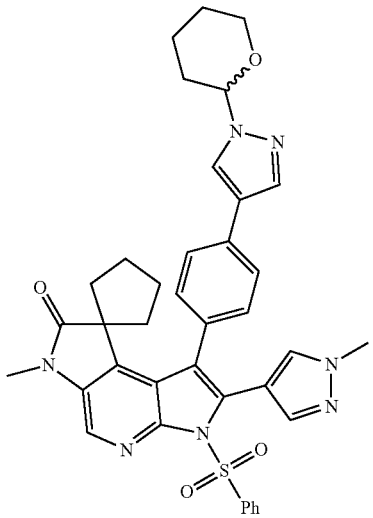

The title compound was prepared by a procedure analogous to that described for Example 13, Step 7, utilizing 2'-bromo-6'-methyl-3'-(phenylsulfonyl)-1'-(4-(1-(tetrahydro-2H-pyran-2-yl)-1H-pyrazol-4-yl)phenyl)-3',6'-dihydro-7'H-spiro[cyclopentane-1,8'-dipyrrolo[2,3-b:3',2'-d]pyridin]-7'-one (0.082 g, 0.12 mmol) in place of tert-butyl 2'-bromo-6'-methyl-7'-oxo-1'-phenyl-3'-(phenylsulfonyl)-6',7'-dihydro-3'H-8-azaspiro[bicyclo[3.2.1]octane-3,8'-dipyrrolo[2,3-b:3',2'-d]pyridine]-8-carboxylate and 1-methyl-4-(4,4,5,5-tetramethyl-1,3,2-dioxaborolan-2-yl)-1H-pyrazole (0.036 g, 0.17 mmol, Combi-Blocks PN-5112) in place of 4-(methylsulfonyl)-1-(4-(4,4,5,5-tetramethyl-1,3,2-dioxaborolan-2-yl)benzyl)piperidine. Purification via flash column chromatography on silica gel, eluting with a gradient of 0-5% MeOH in DCM, afforded the title compound (0.062 g, 75%). LCMS for $C_{38}H_{38}N_7O_4S$ $(M+H)^+$: calculated m/z=688.3; found 688.3.

Step 6. 1'-(4-(1H-Pyrazol-4-yl)phenyl)-6'-methyl-2'-(1-methyl-1H-pyrazol-4-yl)-3'-(phenylsulfonyl)-3',6'-dihydro-7'H-spiro[cyclopentane-1,8'-dipyrrolo[2,3-b:3',2'-d]pyridin]-7'-one hydrochloric acid salt

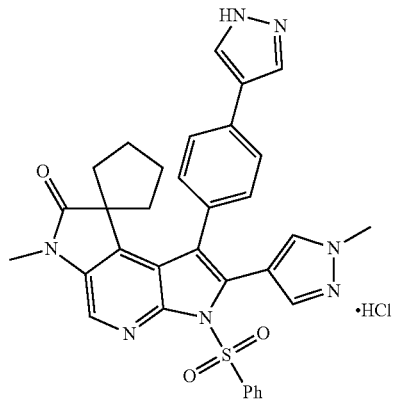

A procedure analogous to that described for Example 12, Step 9 was followed, utilizing 6'-methyl-2'-(1-methyl-1H-pyrazol-4-yl)-3'-(phenylsulfonyl)-1'-(4-(1-(tetrahydro-2H- pyran-2-yl)-1H-pyrazol-4-yl)phenyl)-3',6'-dihydro-7'H-spiro[cyclopentane-1,8'-dipyrrolo[2,3-b:3',2'-d]pyridin]-7'-one (0.05 g, 0.07 mmol) in place of tert-butyl 6-methyl-2-(4-((4-(methylsulfonyl)piperidin-1-yl)methyl)phenyl)-7-oxo-1-phenyl-6,7-dihydro-3H-spiro[dipyrrolo[2,3-b:3',2'-d]pyridine-8,3'-pyrrolidine]-1'-carboxylate to afford the title compound (0.041 g, 98%). LCMS for $C_{33}H_{30}N_7O_3S$ (M+H)$^+$: calculated m/z=604.2; found 604.1.

Step 7. 3-(4-(4-(6'-methyl-2'-(1-methyl-1H-pyrazol-4-yl)-7'-oxo-3'-(phenylsulfonyl)-6',7'-dihydro-3'H-spiro[cyclopentane-1,8'-dipyrrolo[2,3-b:3,2'-d]pyridin]-1'-yl)phenyl)-1H-pyrazol-1-yl)butanenitrile
(Racemic Mixture Prepared)

3-(4-(4-(6'-methyl-2'-(1-methyl-1H-pyrazol-4-yl)-7'-oxo-3'-(phenylsulfonyl)-6',7'-dihydro-3'H-spiro[cyclopentane-1,8'-dipyrrolo[2,3-b:3',2'-d]pyridin]-1'-yl)phenyl)-1H-pyrazol-1-yl)butanenitrile (10 mg, 0.02 mmol) in place of 2'-bromo-6'-methyl-1'-(1-methyl-1H-indazol-5-yl)-3'-(phenylsulfonyl)-3',6'-dihydro-7'H-spiro[cyclopentane-1,8'-dipyrrolo[2,3-b:3',2'-d]pyridin]-7'-one. Purification via preparative HPLC-MS (pH=2 method) afforded the title compound (3.0 mg). LCMS for $C_{31}H_{31}N_8O$ (M+H)$^+$: calculated m/z=531.3; found 531.3. $^1$H NMR (400 MHz, DMSO-$d_6$) δ 11.99 (s, 1H), 8.42 (s, 1H), 8.08 (s, 1H), 7.96 (s, 1H), 7.75 (d, J=7.9 Hz, 2H), 7.46 (s, 1H), 7.40 (d, J=7.9 Hz, 2H), 7.13 (s, 1H), 5.76 (s, 2H), 4.79 (p, J=6.6 Hz, 1H), 3.74 (s, 3H), 3.16 (s, 3H), 1.93-1.88 (m, 2H), 1.75-1.67 (m, 2H), 1.66-1.60 (m, 2H), 1.58 (d, J=6.7 Hz, 3H), 0.89-0.76 (m, 2H).

Example 15

6-Methyl-2-(4-((4-(methylsulfonyl)piperidin-1-yl)methyl)phenyl)-1-phenyl-1'-(pyrimidin-4-yl)-3,6-dihydro-7H-spiro[dipyrrolo[2,3-b:3',2'-d]pyridine-8,4'-piperidin]-7-one, trifluoroacetate salt

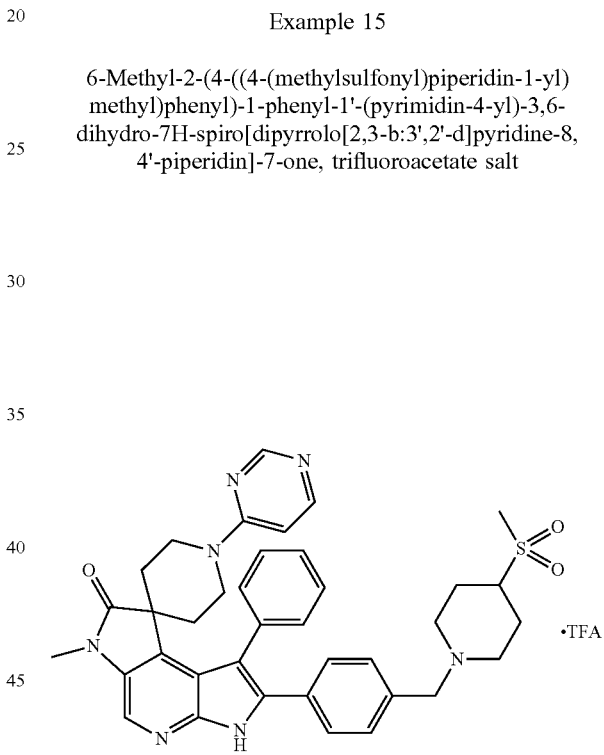

To a mixture of 1'-(4-(1H-pyrazol-4-yl)phenyl)-6'-methyl-2'-(1-methyl-1H-pyrazol-4-yl)-3'-(phenylsulfonyl)-3',6'-dihydro-7'H-spiro[cyclopentane-1,8'-dipyrrolo[2,3-b:3',2'-d]pyridin]-7'-one hydrochloric acid salt (0.010 g, 0.017 mmol), but-2-enenitrile (1.3 mg, 0.019 mmol, Aldrich, 252522, mixture of cis and trans) in acetonitrile (0.30 mL) was added 1,8-diazabicyclo[5.4.0]undec-7-ene (5.0 μL, 0.033 mmol), and the reaction was stirred at room temperature for 5 hours. The reaction mixture was concentrated to afford the product, which was used without further purification. LCMS for $C_{37}H_{35}N_8O_3S$ (M+H)$^+$: calculated m/z=671.3; found 671.3.

Step 8. 3-(4-(4-(6'-methyl-2'-(1-methyl-1H-pyrazol-4-yl)-7'-oxo-6',7'-dihydro-3'H-spiro[cyclopentane-1,8'-dipyrrolo[2,3-b:3',2'-d]pyridin]-1'-yl)phenyl)-1H-pyrazol-1-yl)butanenitrile trifluoroacetate salt
(Racemic Mixture Prepared)

The title compound was prepared by a procedure analogous to that described for Example 8, Step 7, utilizing A mixture of 6-methyl-2-(4-((4-(methylsulfonyl)piperidin-1-yl)methyl)phenyl)-1-phenyl-3-(phenylsulfonyl)-3,6-dihydro-7H-spiro[dipyrrolo[2,3-b:3',2'-d]pyridine-8,4'-piperidin]-7-one, HCl salt (from Example 4, Step 8, 10.0 mg, 0.013 mmol), 4-chloropyrimidine, HCl salt (3.8 mg, 0.025 mmol, J&W Pharmlab 70R0111S), and DIPEA (18 μL, 0.10 mmol) in EtOH (0.20 mL) was stirred at 85° C. for 40 min. Upon cooling to room temperature, the reaction mixture was diluted with THF:MeOH (1:1, 1.0 mL), and NaOH (3.0 N in water, 42 μL, 0.13 mmol) was added. The reaction was heated at 40° C. for 30 min. Upon cooling to room temperature, the reaction mixture was diluted with MeOH and filtered. Purification via preparative HPLC-MS (pH=2) afforded the title compound (5.8 mg) as a TFA salt. LCMS for $C_{37}H_{40}N_7O_3S$ (M+H)$^+$: calculated m/z=662.3; found 662.2.

Example 16

(1R,3r,5S)-6'-Methyl-2'-((4(4-(methylsulfonyl)piperidin-1-yl)methyl)phenyl)-1'-phenyl-8-(pyrimidin-4-yl)-3',6'-dihydro-7'H-8-azaspiro[bicyclo[3.2.1]octane-3,8'-dipyrrolo[2,3-b:3',2'-d]pyridin]-7'-one, trifluoroacetate salt

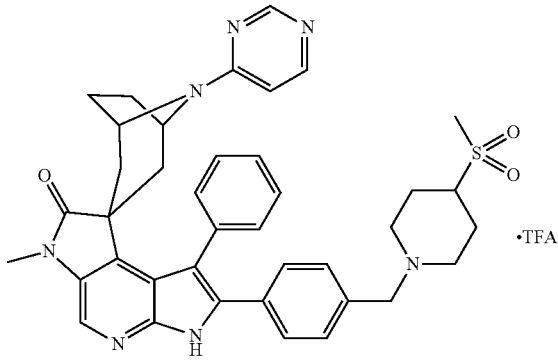 [SMILES: CN1C(=O)C2(CC3CCC(C2)N3c2ccncn2)c2c1cnc1[nH]c(-c3ccc(CN4CCC(S(C)(=O)=O)CC4)cc3)c(-c3ccccc3)c21]

The procedure of Example 15 was followed, using (1R,3r,5S)-6'-methyl-2'-(4-((4-(methyl sulfonyl)piperidin-1-yl)methyl)phenyl)-1'-phenyl-3'-(phenylsulfonyl)-3',6'-dihydro-7'H-8-azaspiro[bicyclo[3.2.1]octane-3,8'-dipyrrolo[2,3-b:3',2'-d]pyridin]-7'-one, HCl salt (from Example 13, Step 8, 10.0 mg, 0.012 mmol) in place of 6-methyl-2-(4-((4-(methyl sulfonyl)piperidin-1-yl)methyl)phenyl)-1-phenyl-3-(phenylsulfonyl)-3,6-dihydro-7H-spiro[dipyrrolo[2,3-b:3',2'-d]pyridine-8,4'-piperidin]-7-one, HCl salt, to afford the title compound (5.0 mg) as a TFA salt. LCMS for $C_{39}H_{42}N_7O_3S$ (M+H)$^+$: calculated m/z=688.3; found 688.3.

Example 17

6-Methyl-2-(1-methyl-1H-pyrazol-4-yl)-1-(2-methylthiazol-5-yl)-1'-(pyrimidin-4-yl)-3,6-dihydro-7H-spiro[dipyrrolo[2,3-b:3',2'-d]pyridine-8,4'-piperidin]-7-one, trifluoroacetate salt

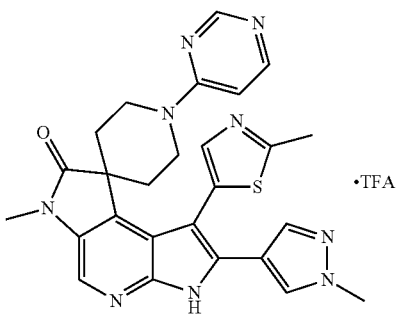

Step 1. tert-Butyl 2-bromo-6-methyl-7-oxo-3-(phenylsulfonyl)-6,7-dihydro-3H-spiro[dipyrrolo[2,3-b:3',2'-d]pyridine-8,4'-piperidin]-1'-carboxylate

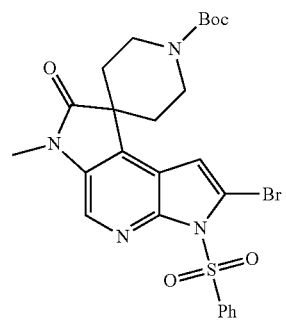 [SMILES: CN1C(=O)C2(CCN(C(=O)OC(C)(C)C)CC2)c2c1cnc1c2cc(Br)n1S(=O)(=O)c1ccccc1]

The procedure of Example 4, Step 6 was followed using tert-butyl 6-methyl-7-oxo-3-(phenylsulfonyl)-6,7-dihydro-3H-spiro[dipyrrolo[2,3-b:3',2'-d]pyridine-8,4'-piperidine]-1'-carboxylate (from Example 4, Step 3, 0.40 g, 0.81 mmol) in place of tert-butyl 6-methyl-7-oxo-1-phenyl-3-(phenylsulfonyl)-6,7-dihydro-3H-spiro[dipyrrolo[2,3-b:3',2'-d]pyridine-8,4'-piperidine]-1'-carboxylate, and utilizing 2.5 eq each of LDA and 1,2-dibromo-1,1,2,2-tetrachloroethane to afford the title compound (0.20 g, 43%). LCMS for $C_{25}H_{28}BrN_4O_5S$ (M+H)$^+$: calculated m/z=575.1; found 575.1.

Step 2. tert-Butyl 6-methyl-2-(1-methyl-1H-pyrazol-4-yl)-7-oxo-3-(phenylsulfonyl)-6,7-dihydro-3H-spiro[dipyrrolo[2,3-b:3,2'-d]pyridine-8,4'-piperidine]-1'-carboxylate

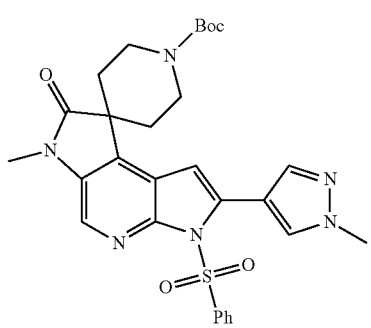

The procedure of Example 4, Step 7 was followed using tert-butyl 2-bromo-6-methyl-7-oxo-3-(phenylsulfonyl)-6,7-dihydro-3H-spiro[dipyrrolo[2,3-b:3',2'-d]pyridine-8,4'-piperidine]-1'-carboxylate (0.20 g, 0.35 mmol) in place of tert-butyl 2-bromo-6-methyl-7-oxo-1-phenyl-3-(phenyl sulfonyl)-6,7-dihydro-3H-spiro[dipyrrolo[2,3-b:3',2'-d]pyridine-8,4'-piperidine]-1'-carboxylate and using 1-methyl-4-(4,4,5,5-tetramethyl-1,3,2-dioxaborolan-2-yl)-1H-pyrazole (0.11 g, 0.52 mmol) in place of 4-(methyl sulfonyl)-1-(4-(4,4,5,5-tetramethyl-1,3,2-dioxaborolan-2-yl)benzyl)piperidine to afford the title compound (0.15 g, 75%). LCMS for $C_{29}H_{33}N_6O_5S$ (M+H)$^+$: calculated m/z=577.2; found 577.2.

Step 3. tert-Butyl 1-bromo-6-methyl-2-(1-methyl-1H-pyrazol-4-yl)-7-oxo-3-(phenylsulfonyl)-6,7-dihydro-3H-spiro[dipyrrolo[2,3-b:3',2'-d]pyridine-8,4'-piperidin]-1'-carboxylate

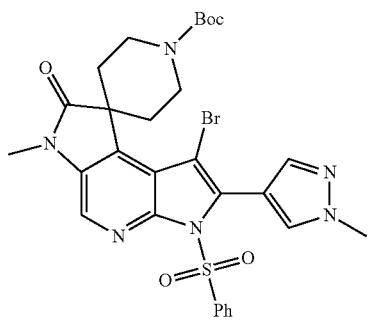

The procedure of Example 4, Step 4 was followed using tert-butyl 6-methyl-2-(1-methyl-1H-pyrazol-4-yl)-7-oxo-3-(phenylsulfonyl)-6,7-dihydro-3H-spiro[dipyrrolo[2,3-b:3',2'-d]pyridine-8,4'-piperidine]-1'-carboxylate (0.14 g, 0.24 mmol) in place of tert-butyl 6-methyl-7-oxo-3-(phenylsulfonyl)-6,7-dihydro-3H-spiro[dipyrrolo[2,3-b:3',2'-d]pyridine-8,4'-piperidine]-1'-carboxylate and the reaction was performed at 40° C. for 30 min. Purification via flash column chromatography, eluting with a gradient from 0-100% EtOAc in hexanes afforded the title compound (0.13 g, 83%). LCMS for $C_{29}H_{32}BrN_6O_5S$ (M+H)$^+$: calculated monoisotopic m/z=655.1; found 655.1.

Step 4. 1-Bromo-6-methyl-2-(1-methyl-1H-pyrazol-4-yl)-3-(phenylsulfonyl)-3,6-dihydro-7H-spiro[dipyrrolo[2,3-b:3',2'-d]pyridine-8,4'-piperidin]-7-one, trifluoroacetate salt

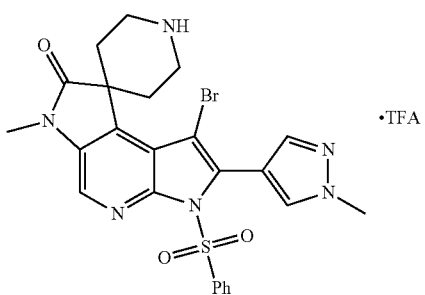

tert-Butyl 1-bromo-6-methyl-2-(1-methyl-1H-pyrazol-4-yl)-7-oxo-3-(phenylsulfonyl)-6,7-dihydro-3H-spiro[dipyrrolo[2,3-b:3',2'-d]pyridine-8,4'-piperidine]-1'-carboxylate (0.13 g, 0.20 mmol) in DCM (3.0 mL) was treated with TFA (0.76 mL, 9.9 mmol) at room temperature for 30 min. Volatiles were removed in vacuo and the product was used without further purification. LCMS for $C_{24}H_{24}BrN_6O_3S$ (M+H)$^+$: calculated monoisotopic m/z=555.1; found 555.0.

Step 5. 1-Bromo-6-methyl-2-(1-methyl-1H-pyrazol-4-yl)-3-(phenylsulfonyl)-1'-(pyrimidin-4-yl)-3,6-dihydro-7H-spiro[dipyrrolo[2,3-b:3',2'-d]pyridine-8,4'-piperidin]-7-one

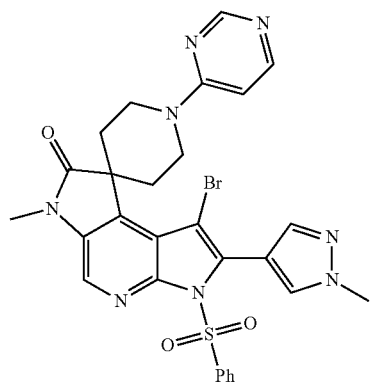

The procedure of Example 15 was followed, using 1-bromo-6-methyl-2-(1-methyl-1H-pyrazol-4-yl)-3-(phenylsulfonyl)-3,6-dihydro-7H-spiro[dipyrrolo[2,3-b:3',2'-d]pyridine-8,4'-piperidin]-7-one, TFA salt, (0.11 g, 0.20 mmol) in place of 6-methyl-2-(4-((4-(methylsulfonyl)piperidin-1-yl)methyl)phenyl)-1-phenyl-3-(phenylsulfonyl)-3,6-dihydro-7H-spiro[dipyrrolo[2,3-b:3',2'-d]pyridine-8,4'-piperidin]-7-one, HCl salt and the reaction was performed at 90° C. for 2 hours. Upon cooling to room temperature, the reaction mixture was concentrated in vacuo and diluted with water. The precipitated product was isolated by filtration, washed with water and dried under vacuum to afford the title compound (0.11 g, 87%). LCMS for $C_{28}H_{26}BrN_8O_3S$ (M+H)$^+$: calculated monoisotopic m/z=633.1; found 633.1.

Step 6. 6-Methyl-2-(1-methyl-1H-pyrazol-4-yl)-1-(2-methylthiazol-5-yl)-1'-(pyrimidin-4-yl)-3,6-dihydro-7H-spiro[dipyrrolo[2,3-b:3',2'-d]pyridine-8,4'-piperidin]-7-one, trifluoroacetate salt A degassed mixture of 1-bromo-6-methyl-2-(1-methyl-1H-pyrazol-4-yl)-3-(phenyl sulfonyl)-1'-(pyrimidin-4-yl)-3,6-dihydro-7H-spiro[dipyrrolo[2,3-b:3',2'-d]pyridine-8,4'-piperidin]-7-one (0.010 g, 0.016 mmol), 2-methyl-5-(4,4,5,5-tetramethyl-1,3,2-dioxaborolan-2-yl)thiazole (5.3 mg, 0.024 mmol), PdCl$_2$(dppf)-CH$_2$Cl$_2$ adduct (1.9 mg, 2.4 μmol) and K$_2$CO$_3$ (1.0 M in water, 47 μL, 0.047 mmol) in dioxane (0.50 mL) was heated at 100° C. for 1 hr. Additional 2-methyl-5-(4,4,5,5-tetramethyl-1,3,2-dioxaborolan-2-yl)thiazole (5.3 mg, 0.024 mmol) and PdCl$_2$(dppf)-CH$_2$Cl$_2$ adduct (1.9 mg, 2.4 μmol) were added and the reaction was heated at 110° C. for 1 hr. Upon cooling to room temperature, the reaction mixture was diluted with MeOH (0.50 mL) and treated with NaOH (3.0 N, 53 μL, 0.16 mmol). The mixture was heated at 50° C. for 30 min. Purification via preparative HPLC-MS (pH=2) afforded the title compound as a TFA salt (2.1 mg). LCMS for $C_{26}H_{26}N_9OS$ (M+H)$^+$: calculated monoisotopic m/z=512.2; found 512.5.

Example 18

6-Methyl-2-(1-methyl-1H-pyrazol-4-yl)-1'-(pyrimidin-4-yl)-1-vinyl-3,6-dihydro-7H-spiro[dipyrrolo[2,3-b:3',2'-d]pyridine-8,4'-piperidin]-7-one, trifluoroacetate salt

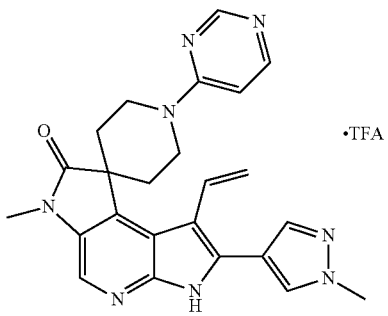

The procedure of Example 17, Step 6 was followed, utilizing 1-bromo-6-methyl-2-(1-methyl-1H-pyrazol-4-yl)-3-(phenylsulfonyl)-1'-(pyrimidin-4-yl)-3,6-dihydro-7H-spiro[dipyrrolo[2,3-b:3',2'-d]pyridine-8,4'-piperidin]-7-one (15 mg, 0.024 mmol) and using 4,4,5,5-tetramethyl-2-vinyl-1,3,2-dioxaborolane (15 mg, 0.095 mmol) in place of 2-methyl-5-(4,4,5,5-tetramethyl-1,3,2-dioxaborolan-2-yl)thiazole and conducting the reaction at 100° C. overnight to afford the title compound (7.3 mg) as a TFA salt. LCMS for $C_{24}H_{25}N_8O$ (M+H)$^+$: calculated m/z=441.2; found 441.2.

Example 19

1-Ethyl-6-methyl-2-(1-methyl-1H-pyrazol-4-yl)-1'-(pyrimidin-4-yl)-3,6-dihydro-7H-spiro[dipyrrolo[2,3-b:3',2'-d]pyridine-8,4'-piperidin]-7-one, trifluoroacetate salt

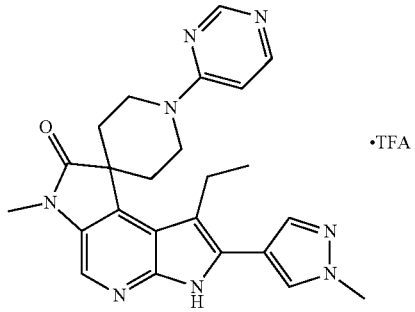

To a solution of 6-methyl-2-(1-methyl-1H-pyrazol-4-yl)-1'-(pyrimidin-4-yl)-1-vinyl-3,6-dihydro-7H-spiro[dipyrrolo[2,3-b:3',2'-d]pyridine-8,4'-piperidin]-7-one, TFA salt (from Example 18, 5.1 mg, 7.6 μmol) in MeOH (1.0 mL) was added palladium on carbon (10%, 4.1 mg, 3.8 μmol) and the mixture was degassed. The reaction mixture was stirred for two hours under an atmosphere of hydrogen provided by a balloon. The reaction mixture was filtered and the filtrate was purified via preparative HPLC-MS (pH=2) to afford the title compound (2.2 mg). LCMS for $C_{24}H_{27}N_8O$ (M+H)$^+$: calculated m/z=443.2; found 443.2.

Example 20

1-(3,6-Dihydro-2H-pyran-4-yl)-6-methyl-2-(1-methyl-1H-pyrazol-4-yl)-(1-(pyrimidin-4-yl))-3,6-dihydro-7H-spiro[dipyrrolo[2,3-b:3',2'-d]pyridine-8,4'-piperidin]-7-one, trifluoroacetate salt

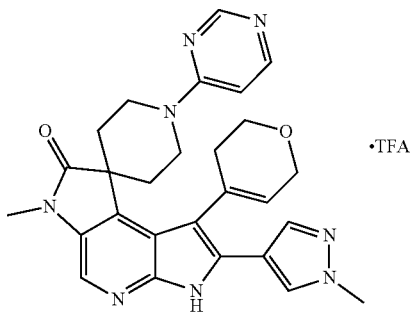

The procedure of Example 17, Step 6 was followed, utilizing 2-(3,6-dihydro-2H-pyran-4-yl)-4,4,5,5-tetramethyl-1,3,2-dioxaborolane (12 mg, 0.057 mmol) in place of 2-methyl-5-(4,4,5,5-tetramethyl-1,3,2-dioxaborolan-2-yl)thiazole to afford the title compound as a TFA salt (4.3 mg). LCMS for $C_{27}H_{29}N_8O_2$ (M+H)$^+$: calculated m/z=497.2; found 497.3.

Example 21

N-(3-Methoxyphenyl)-6-methyl-2-(4-((4-(methylsulfonyl)piperidin-1-yl)methyl)phenyl)-7-oxo-1-phenyl-6,7-dihydro-3H-spiro[dipyrrolo[2,3-b:3',2'-d]pyridine-8,4'-piperidine]-1'-carboxamide, trifluoroacetate salt

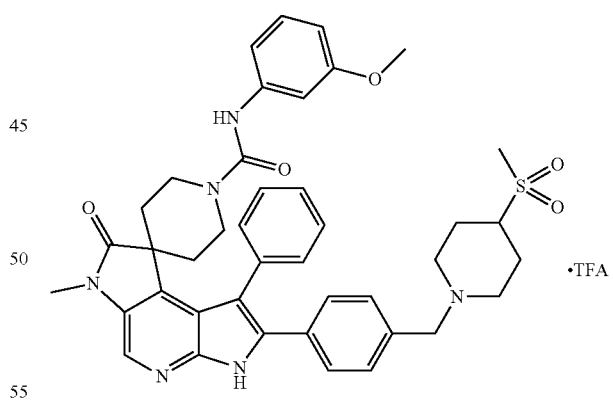

To a mixture of 6-methyl-2-(4-((4-(methylsulfonyl)piperidin-1-yl)methyl)phenyl)-1-phenyl-3-(phenylsulfonyl)-3,6-dihydro-7H-spiro[dipyrrolo[2,3-b:3',2'-d]pyridine-8,4'-piperadin]-7-one, HCl salt (from Example 4, Step 8, 10.0 mg, 0.013 mmol) in DCM (0.20 mL) was added triethylamine (11 μL, 0.075 mmol), followed by 1-isocyanato-3-methoxybenzene (2.8 mg, 0.019 mmol). The reaction mixture was stirred at room temperature for 1 hour, then volatiles were removed in vacuo. The residue was dissolved in THF:MeOH (1:1, 1.0 mL) and NaOH (3.0 N, 42 μL, 0.13 mmol) was added. The mixture was stirred at 40° C. for one hour, then was cooled to room temperature, diluted with MeOH and filtered. The product was purified via preparative HPLC-MS (pH=2) to afford the title compound (5.9 mg) as a TFA salt. LCMS for $C_{41}H_{45}N_6O_5S$ (M+H)$^+$: calculated m/z=733.3; found 733.6.

Example 22

6'-Methyl-2'-(1-methyl-1H-pyrazol-4-yl)-1'-(4-((4-(methylsulfonyl)piperazin-1-yl)methyl)phenyl)-3',6'-dihydro-7'H-spiro[cyclopentane-1,8'-dipyrrolo[2,3-b:3',2'-d]pyridin]-7'-one, trifluoroacetate salt

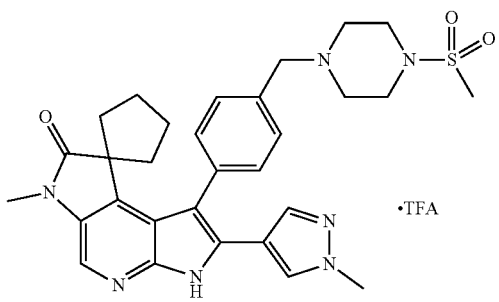 [SMILES: CN1C(=O)C2(CCCC2)c2c1cnc1[nH]c(-c3cnn(C)c3)c(-c3ccc(CN4CCN(S(C)(=O)=O)CC4)cc3)c21]

Step 1. tert-Butyl 4-(4-(6'-methyl-7'-oxo-3'-(phenylsulfonyl)-6',7'-dihydro-3'H-spiro[cyclopentane-1,8'-dipyrrolo[2,3-b:3',2'-d]pyridin]-1'-yl)benzyl)piperazine-1-carboxylate

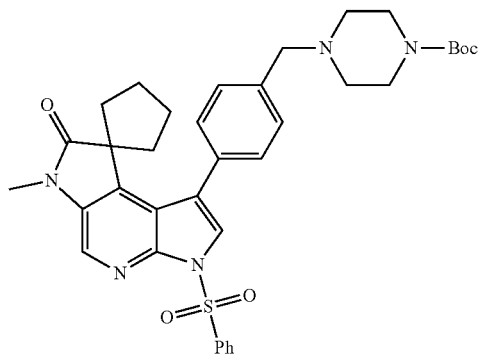 [SMILES: CN1C(=O)C2(CCCC2)c2c1cnc1c2c(-c2ccc(CN3CCN(C(=O)OC(C)(C)C)CC3)cc2)cn1S(=O)(=O)c1ccccc1]

The procedure of Example 8, Step 5 was followed utilizing 1'-bromo-6'-methyl-3'-(phenylsulfonyl)-3',6'-dihydro-7'H-spiro[cyclopentane-1,8'-dipyrrolo[2,3-b:3',2'-d]pyridin]-7'-one (from Example 8, Step 4, 0.050 g, 0.11 mmol) and using tert-butyl 4-(4-(4,4,5,5-tetramethyl-1,3,2-dioxaborolan-2-yl)benzyl)piperazine-1-carboxylate (66 mg, 0.16 mmol) in place of 1-methyl-5-(4,4,5,5,-tetramethyl-1,3,2-dioxaborolan-2-yl)-1H-indazole. Purification of the reaction mixture via flash column chromatography, eluting with a gradient of 0-80% EtOAc in hexanes, afforded the title compound (0.060 g, 84%). LCMS for $C_{36}H_{42}N_5O_5S$ (M+H)$^+$: calculated m/z=656.3; found 656.3.

Step 2. tert-Butyl 4-(4-(2'-bromo-6'-methyl-7'-oxo-3'-(phenylsulfonyl)-6',7'-dihydro-3'H-spiro[cyclopentane-1,8'-pyrrolo[2,3-b:3',2'-d]pyridin]-1'-yl)benzyl)piperazine-1-carboxylate

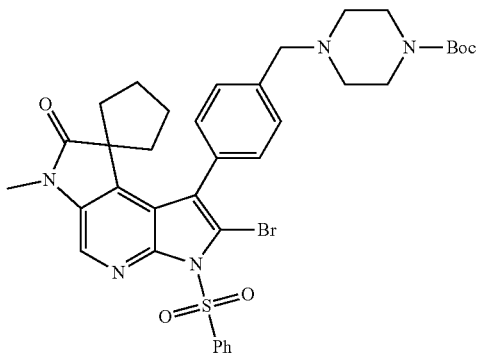 [SMILES: CN1C(=O)C2(CCCC2)c2c1cnc1c2c(-c2ccc(CN3CCN(C(=O)OC(C)(C)C)CC3)cc2)c(Br)n1S(=O)(=O)c1ccccc1]

The procedure of Example 8, Step 6 was followed utilizing tert-butyl 4-(4-(6'-methyl-7'-oxo-3'-(phenylsulfonyl)-6',7'-dihydro-3'H-spiro[cyclopentane-1,8'-dipyrrolo[2,3-b:3',2'-d]pyridin]-1'-yl)benzyl)piperazine-1-carboxylate (0.060 g, 0.091 mmol) in place of 6'-methyl-1'-(1-methyl-1H-indazol-5-yl)-3'-(phenylsulfonyl)-3',6'-dihydro-7'H-spiro[cyclopentane-1,8'-dipyrrolo[2,3-b:3',2'-d]pyridin]-7'-one to afford the title compound (0.030 g, 44%). LCMS for $C_{36}H_{41}BrN_5O_5S$ (M+H)$^+$: calculated monoisotopic m/z=734.2; found 734.2.

Step 3. 6'-Methyl-2'-(1-methyl-1H-pyrazol-4-yl)-3'-(phenylsulfonyl)-1'-(4-(piperazin-1-ylmethyl)phenyl)-3',6'-dihydro-7'H-spiro[cyclopentane-1,8'-dipyrrolo[2,3-b:3',2'-d]pyridin]-7'-one, HCl salt

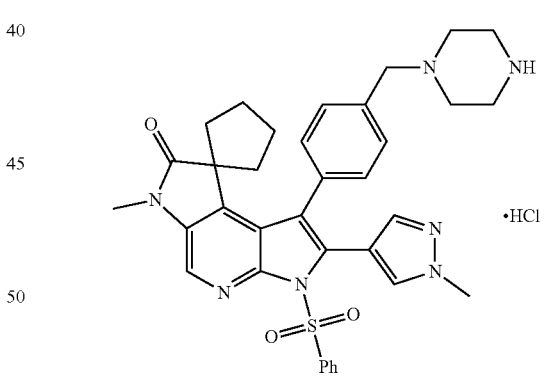

The procedure of Example 8, Step 8 was followed utilizing tert-butyl 4-(4-(2'-bromo-6'-methyl-7'-oxo-3'-(phenylsulfonyl)-6',7'-dihydro-3'H-spiro[cyclopentane-1,8'-dipyrrolo[2,3-b:3',2'-d]pyridin]-1'-yl)benzyl)piperazine-1-carboxylate (0.030 g, 0.041 mmol) in place of 2'-bromo-6'-methyl-1'-(1-methyl-1H-indazol-5-yl)-3'-(phenylsulfonyl)-3',6'-dihydro-7'H-spiro[cyclopentane-1,8'-dipyrrolo[2,3-b:3',2'-d]pyridin]-7'-one, and using 1-methyl-4-(4,4,5,5-tetramethyl-1,3,2-dioxaborolan-2-yl)-1H-pyrazole (0.017 g, 0.082 mmol) in place of 4-44-(4,4,5,5-tetramethyl-1,3,2-dioxaborolan-2-yl)-1H-pyrazol-1-yl)methyl)pyridine. Purification via flash column chromatography, eluting with a gradient from 0-100% EtOAc in hexanes afforded the desired intermediate, tert-butyl 4-(4-(6'-methyl-2'-(1-methyl-1H-pyrazol-4-yl)-7'-oxo-3'-(phenylsulfonyl)-6',7'-dihydro-3'H-spiro[cyclopentane-1,8'-dipyrrolo[2,3-b:3',2'-d]pyridin]-1'-yl)benzyl)piperazine-1-carboxylate (18 mg, 60%). LCMS for $C_{40}H_{46}N_7O_5S$ (M+H)$^+$: calculated m/z=736.3; found 736.2. This intermediate was dissolved in dioxane (1.0 mL) and was treated with HCl (4.0 N in dioxane, 1.0 mL, 4.0 mmol) for 1 hour. Volatiles were removed in vacuo to afford the title compound as an HCl salt (18 mg, 69%). LCMS for $C_{35}H_{38}N_7O_3S$ (M+H)$^+$: calculated m/z=636.3; found 636.2.

Step 4. 6'-Methyl-2'-(1-methyl-1H-pyrazol-4-yl)-1'-(4-((4-(methylsulfonyl)piperazin-1-yl)methyl)phenyl)-3',6'-dihydro-7'H-spiro[cyclopentane-1,8'-dipyrrolo[2,3-b:3',2'-d]pyridin]-7'-one, trifluoroacetate salt To a mixture of 6'-methyl-2'-(1-methyl-1H-pyrazol-4-yl)-3'-(phenylsulfonyl)-1'-(4-(piperazin-1-ylmethyl)phenyl)-3',6'-dihydro-7'H-spiro[cyclopentane-1,8'-dipyrrolo[2,3-b:3',2'-d]pyridin]-7'-one, HCl salt (15 mg, 0.024 mmol) in DCM (0.2 mL) and triethylamine (7 μL, 0.05 mmol) at 0° C. was added methanesulfonyl chloride (3.2 mg, 0.028 mmol). The reaction mixture was stirred for 30 min, then was diluted with water and extracted with EtOAc. The organic layer was dried over MgSO$_4$, filtered and concentrated to provide crude 6'-methyl-2'-(1-methyl-1H-pyrazol-4-yl)-1'-(4-((4-(methylsulfonyl)piperazin-1-yl)methyl)phenyl)-3'-(phenylsulfonyl)-3',6'-dihydro-7'H-spiro[cyclopentane-1,8'-dipyrrolo[2,3-b:3',2'-d]pyridin]-7'-one. The crude product was dissolved in THF:MeOH (1:1, 0.40 mL) and was treated with NaOH (3.0 N in water, 39 μL, 0.12 mmol) overnight. The reaction mixture was filtered and purified via preparative HPLC-MS (pH=2) to afford the title compound as a TFA salt (3.0 mg). LCMS for $C_{30}H_{36}N_7O_3S$ (M+H)$^+$: calculated m/z=574.3; found 574.2.

Example 23

2-(1-(Ethylsulfonyl)-3-(6-methyl-2-(1-methyl-1H-pyrazol-4-yl)-7-oxo-1-phenyl-6,7-dihydro-3H-spiro[dipyrrolo[2,3-b:3',2'-d]pyridine-8,4'-piperidin]-1'-yl)azetidin-3-yl)acetonitrile, trifluoroacetate salt

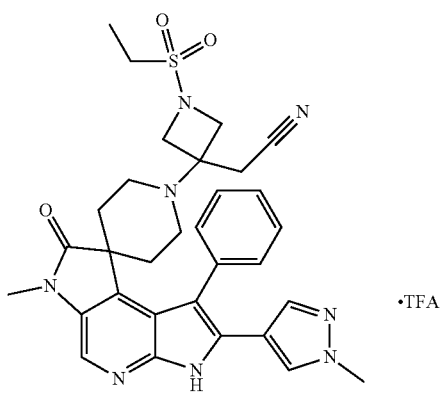

Step 1. tert-Butyl 6-methyl-2-(1-methyl-1H-pyrazol-4-yl)-7-oxo-1-phenyl-3-(phenylsulfonyl)-6,7-dihydro-3H-spiro[dipyrrolo[2,3-b:3',2'-d]pyridine-8,4'-piperidin]-1'-carboxylate

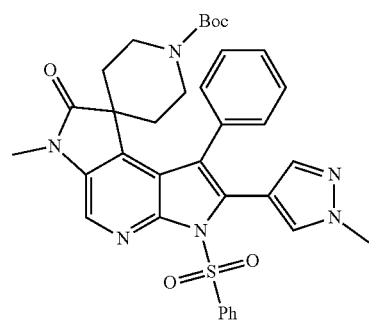

The procedure of Example 4, Step 7 was followed utilizing tert-butyl 2-bromo-6-methyl-7-oxo-1-phenyl-3-(phenylsulfonyl)-6,7-dihydro-3H-spiro[dipyrrolo[2,3-b:3',2'-d]pyridine-8,4'-piperidine]-1'-carboxylate (from Example 4, Step 6, 0.68 g, 0.10 mmol) and using 1-methyl-4-(4,4,5,5-tetramethyl-1,3,2-dioxaborolan-2-yl)-1H-pyrazole (0.43 g, 2.1 mmol) in place of 4-(methylsulfonyl)-1-(4-(4,4,5,5-tetramethyl-1,3,2-dioxaborolan-2-yl)benzyl)piperidine to afford the title compound (0.41 g, 60%). LCMS for $C_{35}H_{37}N_6O_5S$ (M+H)$^+$: calculated m/z=653.3; found 653.2.

Step 2. 6-Methyl-2-(1-methyl-1H-pyrazol-4-yl)-1-phenyl-3-(phenylsulfonyl)-3,6-dihydro-7H-spiro[dipyrrolo[2,3-b:3',2'-d]pyridine-8,4'-piperidin]-7-one

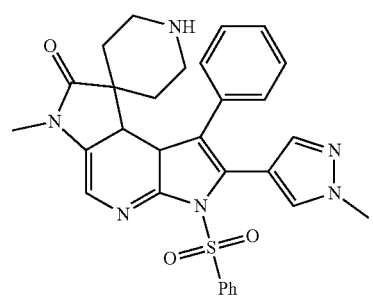

The procedure of Example 5, Step 3 was followed, utilizing tert-butyl 6-methyl-2-(1-methyl-1H-pyrazol-4-yl)-7-oxo-1-phenyl-3-(phenylsulfonyl)-6,7-dihydro-3H-spiro[dipyrrolo[2,3-b:3',2'-d]pyridine-8,4'-piperidine]-1'-carboxylate (0.41 g, 0.63 mmol) in place of tert-butyl 2-bromo-6-methyl-1-(1-methyl-1H-indazol-5-yl)-7-oxo-3-(phenylsulfonyl)-6,7-dihydro-3H-spiro[dipyrrolo[2,3-b:3',2'-d]pyridine-8,4'-piperidine]-1'-carboxylate to afford the title compound (0.33 g, 95%). LCMS for $C_{30}H_{29}N_6O_3S$ (M+H)$^+$: calculated m/z=553.2; found 553.3.

Step 3. tert-Butyl 3-(cyanomethyl)-3-(6-methyl-2-(1-methyl-1H-pyrazol-4-yl)-7-oxo-1-phenyl-3-(phenylsulfonyl)-6,7-dihydro-3H-spiro[dipyrrolo[2,3-b:3',2'-d]pyridine-8,4'-piperidin]-1'-yl)azetidine-1-carboxylate

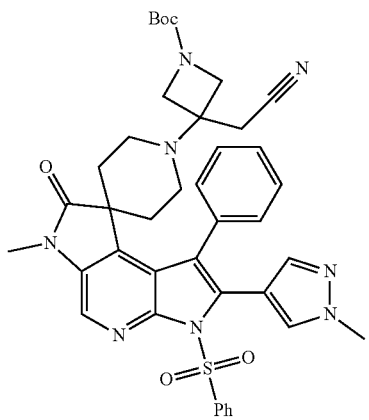

A mixture of 6-methyl-2-(1-methyl-1H-pyrazol-4-yl)-1-phenyl-3-(phenylsulfonyl)-3,6-dihydro-7H-spiro[dipyrrolo[2,3-b:3',2'-d]pyridine-8,4'-piperidin]-7-one (0.060 g, 0.11 mmol) and DBU (5 μL, 0.03 mmol) in a combination of MeOH, MeCN and EtOH as solvents at a concentration of 0.1 M to 0.36 M (as solvents were evaporated and added) was treated with tert-butyl 3-(cyanomethylene)azetidine-1-carboxylate (prepared as described in WO2009/11451 284 mg, 0.44 mmol, added in four equal portions over the reaction period) and heated in the range of 65-80° C. over a period of 6 days. Upon cooling to room temperature, the reaction mixture was subjected to flash column chromatography, eluting with a gradient from 0-100% EtOAc in hexanes to afford the title compound (34 mg, 40%). LCMS for $C_{40}H_{43}N_8O_5S$ (M+H)$^+$: calculated m/z=747.3; found 747.3.

Step 4. 2-(3-(6-Methyl-2-(1-methyl-1H-pyrazol-4-yl)-7-oxo-1-phenyl-3-(phenylsulfonyl)-6,7-dihydro-3H-spiro[dipyrrolo[2,3-b:3',2'-d]pyridine-8,4'-piperidin]-1'-yl)azetidin-3-yl)acetonitrile

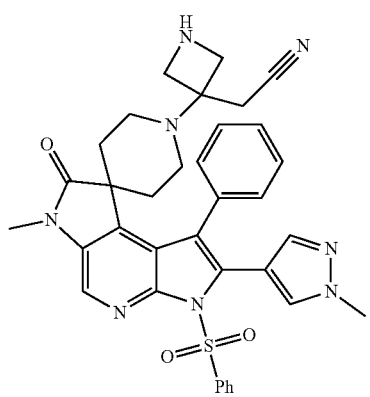

A solution of tert-butyl 3-(cyanomethyl)-3-(6-methyl-2-(1-methyl-1H-pyrazol-4-yl)-7-oxo-1-phenyl-3-(phenylsulfonyl)-6,7-dihydro-3H-spiro[dipyrrolo[2,3-b:3',2'-d]pyridine-8,4'-piperidin]-1'-yl)azetidine-1-carboxylate (34 mg, 0.046 mmol) in DCM (1.0 mL) was treated with HCl in dioxane (4.0 M, 230 μL, 0.91 mmol) for 1 hour. Volatiles were removed in vacuo and the residue was dissolved in DCM and washed with saturated NaHCO$_3$ solution. The aqueous layer was back extracted with DCM (2×). The combined organic extracts were dried over Na$_2$SO$_4$, filtered and evaporated to afford the title compound (28 mg, 97%). LCMS for $C_{35}H_{35}N_8O_3S$ (M+H)$^+$: calculated m/z=647.3; found 647.2.

Step 5. 2-(1-(Ethylsulfonyl)-3-(6-methyl-2-(1-methyl-1H-pyrazol-4-yl)-7-oxo-1-phenyl-6,7-dihydro-3H-spiro[dipyrrolo[2,3-b:3',2'-d]pyridine-8,4'-piperidin]-1'-yl)azetidin-3-yl)acetonitrile, trifluoroacetate salt To a solution of 2-(3-(6-methyl-2-(1-methyl-1H-pyrazol-4-yl)-7-oxo-1-phenyl-3-(phenylsulfonyl)-6,7-dihydro-3H-spiro[dipyrrolo[2,3-b:3',2'-d]pyridine-8,4'-piperidin]-1'-yl)azetidin-3-yl)acetonitrile (7.0 mg, 11 μmol) in DCM (1.0 mL) was added DIPEA (6 μL, 0.03 mmol), followed by ethanesulfonyl chloride (1.5 μL, 0.016 mmol) from a stock solution prepared in DCM (0.10 mL). The mixture was stirred at room temperature for 30 min, then solvent was removed in vacuo. The residue was dissolved in THF:MeOH (1:1, 0.60 mL), NaOH (3.0 N, 36 μL, 0.11 mmol) was added and the reaction mixture was heated at 50° C. for 30 min. Upon cooling to room temperature, the reaction mixture was diluted with MeOH, filtered and purified via preparative HPLC-MS (pH=2) to afford the title compound as a TFA salt (3.3 mg). LCMS for $C_{31}H_{35}N_8O_3S$ (M+H)$^+$: calculated m/z=599.3; found 599.2.

Examples 24-25

Examples 24-25 were prepared by the method of Example 23, substituting acetyl chloride or ethylisocyanate in place of ethanesulfonyl chloride as appropriate in Step 5.

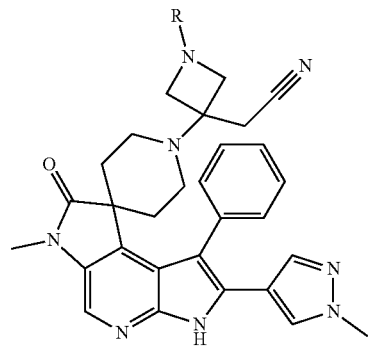

| Ex. No. | Compound Name | R | LCMS |
|---|---|---|---|
| 24 | 2-(1-Acetyl-3-(6-methyl-2-(1-methyl-1H-pyrazol-4-yl)-7-oxo-1-phenyl-6,7-dihydro-3H-spiro[dipyrrolo[2,3-b:3',2'-d]pyridine-8,4'-piperidin]-1'-yl)azetidin-3-yl)acetonitrile, trifluoroacetate salt | | Calculated for $C_{31}H_{33}N_8O_2$ $(M + H)^+$: m/z = 549.3, found: 549.2 |
| 25 | 3-(Cyanomethyl)-N-ethyl-3-(6-methyl-2-(1-methyl-1H-pyrazol-4-yl)-7-oxo-1-phenyl-6,7-dihydro-3H-spiro[dipyrrolo[2,3-b:3',2'-d]pyridine-8,4'-piperidin]-1'-yl)azetidine-1-carboxamide, trifluoroacetate salt | | Calculated for $C_{32}H_{36}N_9O_2$ $(M + H)^+$: m/z = 578.3, found: 578.3 |

Example 26

2-(4-Fluorophenyl)-2-(6-methyl-2-(1-methyl-1H-pyrazol-4-yl)-7-oxo-1-phenyl-6,7-dihydro-3H-spiro[dipyrrolo[2,3-b:3',2'-d]pyridine-8,4'-piperidin]-1'-yl)acetamide, trifluoroacetate salt (Racemic Mixture Prepared)

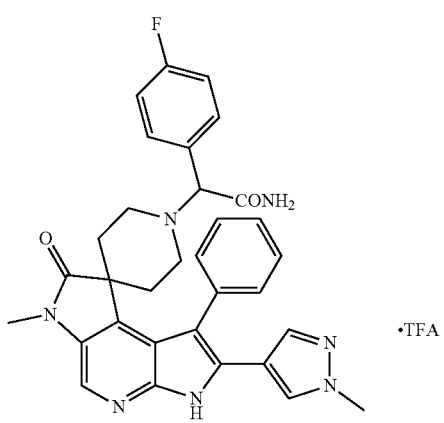

A mixture of 6-methyl-2-(1-methyl-1H-pyrazol-4-yl)-1-phenyl-3-(phenylsulfonyl)-3,6-dihydro-7H-spiro[dipyrrolo[2,3-b:3',2'-d]pyridine-8,4'-piperidin]-7-one (from Example 23, Step 2, 0.020 g, 0.036 mmol), 2-bromo-2-(4-fluorophenyl)acetamide (Enamine #EN300-24512, 17 mg, 0.072 mmol) and Cs$_2$CO$_3$ (24 mg, 0.072 mmol) in DMF (0.36 mL) was heated to 55° C. for 1 hour. Upon cooling to room temperature, the reaction mixture was diluted with THF:MeOH (1:1, 1.0 mL) and was filtered. To the filtrate was added NaOH (3.0 N, 0.24 mL, 0.72 mmol) and the mixture was heated at 55° C. for 1 h, cooled to room temperature, diluted with MeOH, filtered and purified via preparative HPLC-MS (pH=2) to afford the title compound as a TFA salt (15 mg). LCMS for $C_{32}H_{31}FN_7O_2$ $(M+H)^+$: calculated m/z=564.2; found 564.2.

Example 27

Methyl (3-(cyanomethyl)-3-(6-methyl-2-(1-methyl-1H-pyrazol-4-yl)-7-oxo-1-phenyl-6,7-dihydro-3H-spiro[dipyrrolo[2,3-b:3',2'-d]pyridine-8,4'-piperidin]-1'-yl)cyclobutyl)carbamate (Single Diastereomer Isolated)

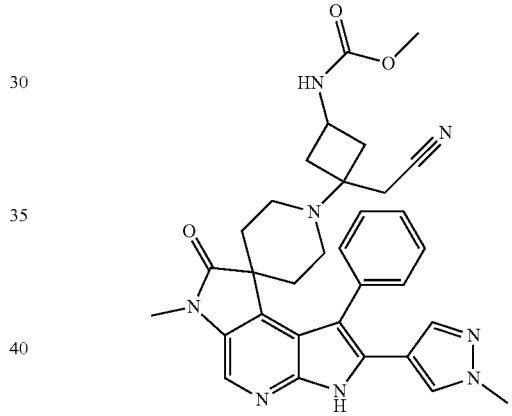

Step 1. tert-Butyl (3-(cyanomethylene)cyclobutyl)carbamate

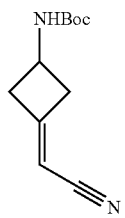 [SMILES: CC(C)(C)OC(=O)NC1CC(=CC#N)C1]

To a solution of diethyl (cyanomethyl)phosphonate (0.51 mL, 3.2 mmol) in dry THF (20.0 mL) at 0° C. was added potassium tert-butoxide (1.0 M in THF, 3.2 mL, 3.2 mmol). The mixture was stirred for 5 min at 0° C. before the addition of a solution of tert-butyl (3-oxocyclobutyl)carbamate (Combi-Blocks #QA-9986, 0.50 g, 2.7 mmol) in THF (5.0 mL). The mixture was allowed to warm to room temperature and stir for 4 hours, then was quenched by the addition of saturated NH₄Cl and extracted with EtOAc (3×). The combined organic extracts were washed with water, followed by brine, dried over Na₂SO₄, filtered and concentrated. Purification via flash column chromatography, eluting with a gradient of 0-30% EtOAc in hexanes afforded the title compound (0.51 g, 91%). ¹H NMR (400 MHz, CDCl₃) δ 5.28-5.23 (m, 1H), 4.82 (br, 1H), 4.25 (br, 1H), 3.42-3.30 (m, 1H), 3.30-3.12 (m, 1H), 2.99-2.76 (m, 2H), 1.47 (s, 9H).

Step 2. tert-Butyl (3-(cyanomethyl)-3-(6-methyl-2-(1-methyl-1H-pyrazol-4-yl)-7-oxo-1-phenyl-3-(phenylsulfonyl)-6,7-dihydro-3H-spiro[dipyrrolo[2,3-b:3,2'-d]pyridine-8,4'-piperidin]-1'-yl)cyclobutyl)carbamate (Single Diastereomer Isolated)

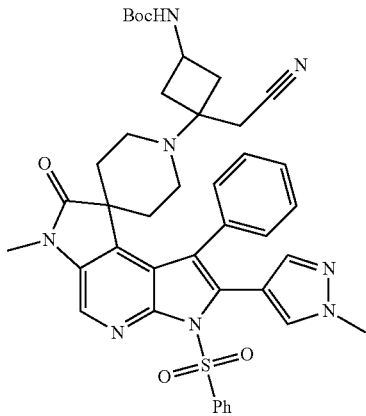

A solution of 6-methyl-2-(1-methyl-1H-pyrazol-4-yl)-1-phenyl-3-(phenylsulfonyl)-3,6-dihydro-7H-spiro[dipyrrolo[2,3-b:3',2'-d]pyridine-8,4'-piperidin]-7-one (from Example 23, Step 2, 0.13 g, 0.24 mmol) and tert-butyl (3-(cyanomethylene)cyclobutyl)carbamate (98 mg, 0.47 mmol) in glycerol (1.0 mL) and ethanol (1.0 mL) was heated at 100° C. for 22 hours. Purification of the reaction mixture via preparative HPLC-MS (pH=2, Waters SunFire C18, 5 µm particle size, 30×100 mm; Aq(0.1% TFA)/MeCN @60 mL/min; 40.8-60.8% B in 5 min) afforded two isomers of the title compound. Peak 1 retention time: 4.71 min (25 mg); Peak 2 retention time: 5.55 min (9.4 mg). Peak 1 was used in the subsequent steps, the stereochemistry was not determined. LCMS for C₄₁H₄₅N₈O₅S (M+H)⁺: calculated m/z=761.3; found 761.3.

Step 3. 2-(3-Amino-1-(6-methyl-2-(1-methyl-1H-pyrazol-4-yl)-7-oxo-1-phenyl-3-(phenylsulfonyl)-6,7-dihydro-3H-spiro[dipyrrolo[2,3-b:3,2'-d]pyridine-8,4'-piperidin]-1'-yl)cyclobutyl)acetonitrile (Single Diastereomer Isolated)

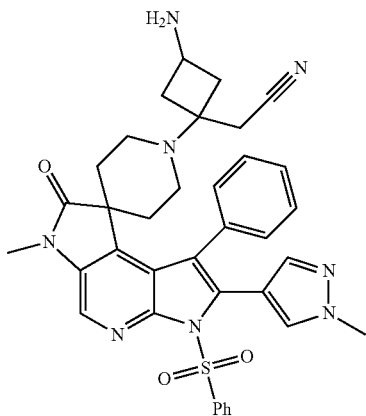

The procedure of Example 5, Step 3 was followed, utilizing tert-butyl (3-(cyanomethyl)-3-(6-methyl-2-(1-methyl-1H-pyrazol-4-yl)-7-oxo-1-phenyl-3-(phenylsulfonyl)-6,7-dihydro-3H-spiro[dipyrrolo[2,3-b:3',2'-d]pyridine-8,4'-piperidin]-1'-yl)cyclobutyl)carbamate (Peak 1 from Step 2, 25 mg, 0.033 mmol) in place of tert-butyl 2-bromo-6-methyl-1-(1-methyl-1H-indazol-5-yl)-7-oxo-3-(phenylsulfonyl)-6,7-dihydro-3H-spiro[dipyrrolo[2,3-b:3',2'-d]pyridine-8,4'-piperidine]-1'-carboxylate to afford the title compound, which was used without further purification (16 mg, 75%). LCMS for C₃₆H₃₇N₈O₃S (M+H)⁺: calculated m/z=661.3; found 661.2.

Step 4. Methyl (3-(cyanomethyl)-3-(6-methyl-2-(1-methyl-1H-pyrazol-4-yl)-7-oxo-1-phenyl-6,7-dihydro-3H-spiro[dipyrrolo[2,3-b:3',2'-d]pyridine-8,4'-piperidin]-1'-yl)cyclobutyl)carbamate, Single Isomer Prepared The procedure of Example 23, Step 5 was followed, utilizing 2-(3-amino-1-(6-methyl-2-(1-methyl-1H-pyrazol-4-yl)-7-oxo-1-phenyl-3-(phenylsulfonyl)-6,7-dihydro-3H-spiro[dipyrrolo[2,3-b:3',2'-d]pyridine-8,4'-piperidin]-1'-yl)cyclobutyl)acetonitrile (4.0 mg, 6.1 µmol) in place of 2-(3-(6-methyl-2-(1-methyl-1H-pyrazol-4-yl)-7-oxo-1-phenyl-3-(phenylsulfonyl)-6,7-dihydro-3H-spiro[dipyrrolo[2,3-b:3',2'-d]pyridine-8,4'-piperidin]-1'-yl)azetidin-3-yl)acetonitrile and methyl chloroformate (0.70 µL, 9.1 µmol) in place of ethanesulfonyl chloride. Purification via preparative HPLC-MS (pH=10) afforded the title compound (1.1 mg). LCMS for C₃₂H₃₅N₈O₃ (M+H)⁺: calculated m/z=579.3; found 579.2.

Examples 28-29

Examples 28-29 were prepared by the method of Example 27, substituting ethyl isocyanate or benzenesulfonyl chloride for methylchloroformate as appropriate in Step 4; and the compounds were purified via preparative HPLC-MS (pH=2).

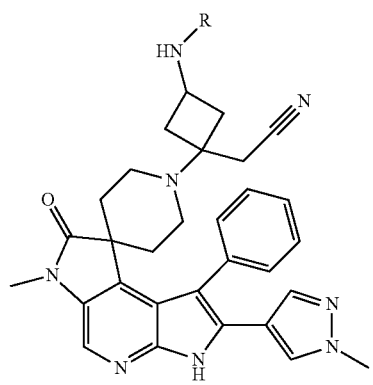

| Ex. No. | Compound Name | R | LCMS |
|---|---|---|---|
| 28 | 1-(3-(Cyanomethyl)-3-(6-methyl-2-(1-methyl-1H-pyrazol-4-yl)-7-oxo-1-phenyl-6,7-dihydro-3H-spiro[dipyrrolo[2,3-b:3',2'-d]pyridine-8,4'-piperidin]-1'-yl)cyclobutyl)-3-ethylurea, trifluoroacetate salt | ![structure with NHEt carbonyl] | Calculated for $C_{33}H_{38}N_9O_2$ $(M + H)^+$: m/z = 592.3, found: 592.4 |
| 29 | N-(3-(Cyanomethyl)-3-(6-methyl-2-(1-methyl-1H-pyrazol-4-yl)-7-oxo-1-phenyl-6,7-dihydro-3H-spiro[dipyrrolo[2,3-b:3',2'-d]pyridine-8,4'-piperidin]-1'-yl)cyclobutyl)benzenesulfonamide, trifluoroacetate salt | ![structure with SO2Ph] | Calculated for $C_{36}H_{37}N_8O_3S$ $(M + H)^+$: m/z = 661.3, found: 661.3 |

Example 30. 2-(1-(2-(1-(2,2-Difluoroethyl)-1H-pyrazol-4-yl)-6-methyl-1-(1-methyl-1H-indazol-5-yl)-7-oxo-6,7-dihydro-3H-spiro[dipyrrolo[2,3-b:3', 2'-d]pyridine-8,4'-piperidin]-1'-yl)cyclobutyl) acetonitrile, trifluoroacetate salt

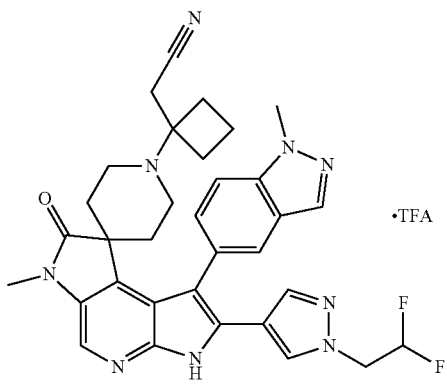 [SMILES: CN1C(=O)C2(CCN(C3(CC#N)CCC3)CC2)c2c1cnc1[nH]c(-c3cnn(CC(F)F)c3)c(-c3ccc4c(cnn4C)c3)c21]

Step 1. tert-Butyl 2-(1-(2,2-difluoroethyl)-1H-pyrazol-4-yl)-6-methyl-1-(1-methyl-1H-indazol-5-yl)-7-oxo-3-(phenylsulfonyl)-6,7-dihydro-3H-spiro[pyrrolo[2,3-b:3',2'-c]pyridine-8,4'-piperidin]-1'-carboxylate

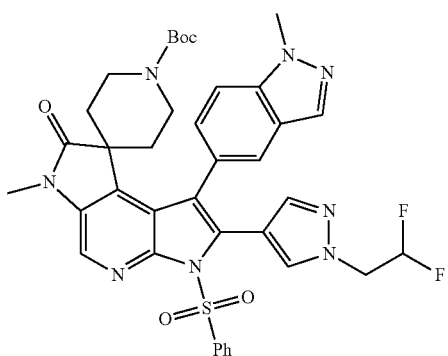 [SMILES: CN1C(=O)C2(CCN(C(=O)OC(C)(C)C)CC2)c2c1cnc1c2c(-c2ccc3c(cnn3C)c2)c(-c2cnn(CC(F)F)c2)n1S(=O)(=O)c1ccccc1]

A degassed mixture of tert-butyl 2-bromo-6-methyl-1-(1-methyl-1H-indazol-5-yl)-7-oxo-3-(phenylsulfonyl)-6,7-dihydro-3H-spiro[dipyrrolo[2,3-b:3',2'-d]pyridine-8,4'-piperidine]-1'-carboxylate (from Example 5, Step 2, 0.10 g, 0.14 mmol), 1-(2,2-difluoroethyl)-4-(4,4,5,5-tetramethyl-1,3,2-dioxaborolan-2-yl)-1H-pyrazole (PharmaBlock #PB07295, 91 mg, 0.35 mmol), PdCl$_2$(dppf)-CH$_2$Cl$_2$ adduct (12 mg, 0.014 mmol) and K$_2$CO$_3$ solution (1.0 M in water, 0.71 mL, 0.71 mmol) in dioxane (2.6 mL) was heated at 100° C. for 1 h. Upon cooling to room temperature, the reaction mixture was diluted with EtOAc, washed with water (2×), followed by brine (1×), dried over Na$_2$SO$_4$, filtered and concentrated. Purification via flash column chromatography, eluting with a gradient of 0-100% EtOAc in hexanes afforded the title compound (0.10 g, 95%). LCMS for $C_{38}H_{39}F_2N_8O_5S$ $(M+H)^+$: calculated m/z=757.3; found 757.3.

Step 2. 2-(1-(2,2-Difluoroethyl)-1H-pyrazol-4-yl)-6-methyl-1-(1-methyl-1H-indazol-5-yl)-3-(phenylsulfonyl)-3,6-dihydro-7H-spiro[dipyrrolo[2,3-b:3, 2'-d]pyridine-8,4'-piperidin]-7-one

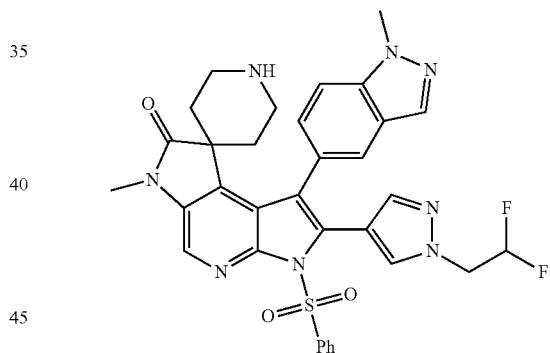

The procedure of Example 5, Step 3 was followed utilizing tert-butyl 2-(1-(2,2-difluoroethyl)-1H-pyrazol-4-yl)-6-methyl-1-(1-methyl-1H-indazol-5-yl)-7-oxo-3-(phenylsulfonyl)-6,7-dihydro-3H-spiro[dipyrrolo[2,3-b:3',2'-d]pyridine-8,4'-piperidine]-1'-carboxylate (0.10 g, 0.14 mmol) in place of tert-butyl 2-bromo-6-methyl-1-(1-methyl-1H-indazol-5-yl)-7-oxo-3-(phenylsulfonyl)-6,7-dihydro-3H-spiro[dipyrrolo[2,3-b:3',2'-d]pyridine-8,4'-piperidine]-1'-carboxylate to afford the title compound, which was used without further purification (84 mg, 95%). LCMS for $C_{33}H_{31}F_2N_8O_3S$ $(M+H)^+$: calculated m/z=657.2; found 657.2.

Step 3. 2-(1-(2-(1-(2,2-Difluoroethyl)-1H-pyrazol-4-yl)-6-methyl-1-(1-methyl-1H-indazol-5-yl)-7-oxo-6, 7-dihydro-3H-spiro[dipyrrolo[2,3-b:3',2'-d]pyridine-8,4'-piperidin]-1'-yl)cyclobutyl)acetonitrile, trifluoroacetate salt A mixture of 2-(1-(2,2-difluoroethyl)-1H-pyrazol-4-yl)-6-methyl-1-(1-methyl-1H-indazol-5-yl)-3-(phenylsulfonyl)-

3,6-dihydro-7H-spiro[dipyrrolo[2,3-b:3',2'-d]pyridine-8,4'-piperidin]-7-one (84 mg, 0.13 mmol) and 2-cyclobutylideneacetonitrile (Enamine #EN300-216219, 0.12 g, 1.3 mmol) in glycerol (0.15 mL) and EtOH (0.15 mL) was heated at 100° C. for 4 hours. Upon cooling to room temperature, volatiles were removed in vacuo. The residue was dissolved in MeOH:THF (1:1, 3.0 mL) and NaOH (3.0 N in water, 0.43 mL, 1.3 mmol) was added. The reaction mixture was heated at 60° C. for 30 min, then was cooled to room temperature and purified via preparative HPLC-MS (pH=2) to afford the title compound as a trifluoroacetate salt (31 mg, 27%). LCMS for $C_{33}H_{34}F_2N_9O$ $(M+H)^+$: calculated m/z=610.3; found 610.4. $^1$H NMR (600 MHz, DMSO-$d_6$) δ 12.14 (s, 1H), 8.14 (s, 1H), 8.00 (s, 1H), 7.81 (s, 1H), 7.79 (d, J=8.6 Hz, 1H), 7.58 (s, 1H), 7.34 (dd, J=8.5, 1.5 Hz, 1H), 7.07 (s, 1H), 6.24 (tt, J=54.5, 3.6 Hz, 1H), 4.54 (td, J=15.4, 3.6 Hz, 2H), 4.13 (s, 3H), 3.15 (s, 3H), 2.72-2.61 (m, 2H), 2.49 (s, 2H), 2.11-2.04 (m, 1H), 2.00-1.90 (m, 2H), 1.74 (td, J=12.5, 4.8 Hz, 1H), 1.68-1.58 (m, 2H), 1.57-1.50 (m, 1H), 1.40-1.30 (m, 3H), 1.08-1.00 (m, 1H), 0.87 (q, J=9.7 Hz, 1H). $^{19}$F NMR (376 MHz, DMSO-$d_6$) δ −74.73, −122.88 (dt, J=54.7, 15.4 Hz).

Examples 31-43

Examples 31-43 were prepared by one of the following two methods:

Method A:

The procedure of Example 30 was followed, substituting the appropriate boronic acid or ester in place of 1-(2,2-difluoroethyl)-4-(4,4,5,5-tetramethyl-1,3,2-dioxaborolan-2-yl)-1H-pyrazole in Step 1.

Method B:

The procedure of Example 30 was followed with the exception that tert-butyl 2-bromo-6-methyl-1-(1-methyl-1H-indazol-5-yl)-7-oxo-3-(phenylsulfonyl)-6,7-dihydro-3H-spiro[dipyrrolo[2,3-b:3',2'-d]pyridine-8,4'-piperidine]-1'-carboxylate was subjected to the procedures of Steps 2-3 and omitting the deprotection of the phenylsulfonyl group in Step 3 prior to performing the Suzuki coupling procedure (with the appropriate boronic acid or ester) of Step 1. After the Suzuki coupling of Step 1 was performed, the deprotection using NaOH was then followed as disclosed in the latter portion of Step 3. Additionally, Example 43 was purified via preparative HPLC-MS (pH=10) to afford the free base.

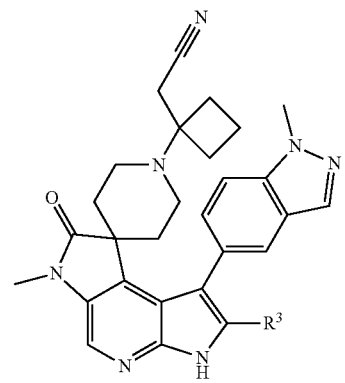

| Ex. No. | Method | Compound Name<br>$^1$H NMR | $R^3$ | LCMS |
|---|---|---|---|---|
| 31 | B | 2-(1-(6-Methyl-1-(1-methyl-1H-indazol-5-yl)-2-(1-methyl-1H-pyrazol-4-yl)-7-oxo-6,7-dihydro-3H-spiro[dipyrrolo[2,3-b:3',2'-d]pyridine-8,4'-piperidin]-1'-yl)cyclobutyl)acetonitrile, trifluoroacetate salt | ![pyrazole with N-methyl] | Calculated for $C_{32}H_{34}N_9O$ $(M + H)^+$: m/z = 560.3, found: 560.3 |
| | | $^1$H NMR (400 MHz, DMSO-$d_6$) δ 12.00 (s, 1H), 8.14 (d, J = 0.9 Hz, 1H), 7.97 (s, 1H), 7.82-7.75 (m, 2H), 7.41 (s, 1H), 7.33 (dd, J = 8.4, 1.6 Hz, 1H), 7.01 (s, 1H), 4.13 (s, 3H), 3.71 (s, 3H), 3.15 (s, 3H), 2.72-2.59 (m, 2H), 2.50 (s, 2H), 2.13-2.02 (m, 1H), 2.02-1.88 (m, 2H), 1.80-1.69 (m, 1H), 1.69-1.60 (m, 2H), 1.60-1.48 (m, 1H), 1.42-1.28 (m, 3H), 1.11-0.98 (m, 1H), 0.94-0.79 (m, 1H). | | |
| 32 | B | 2-(1-(2-(1-(2-Hydroxy-2-methylpropyl)-1H-pyrazol-4-yl)-6-methyl-1-(1-methyl-1H-indazol-5-yl)-7-oxo-6,7-dihydro-3H-spiro[dipyrrolo[2,3-b:3',2'-d]pyridine-8,4'-piperidin]-1'-yl)cyclobutyl)acetonitrile, trifluoroacetate salt | ![pyrazole with CH2C(CH3)2OH] | Calculated for $C_{35}H_{40}N_9O_2$ $(M + H)^+$: m/z = 618.3, found: 618.5 |
| 33 | B | 2-(1-(6-Methyl-1-(1-methyl-1H-indazol-5-yl)-7-oxo-2-(1-(2,2,2-trifluoroethyl)-1H-pyrazol-4-yl)-6,7-dihydro-3H-spiro[dipyrrolo[2,3-b:3',2'-d]pyridine-8,4'-piperidin]-1'-yl)cyclobutyl)acetonitrile, trifluoroacetate salt | ![pyrazole with CH2CF3] | Calculated for $C_{33}H_{33}F_3N_9O$ $(M + H)^+$: m/z = 628.3, found: 628.4 |

-continued

| Ex. No. | Method | Compound Name | R³ | LCMS |
|---|---|---|---|---|
| 34 | B | 2-(1-(6-Methyl-1-(1-methyl-1H-indazol-5-yl)-2-(4-(morpholine-4-carbonyl)cyclohex-1-en-1-yl)-7-oxo-6,7-dihydro-3H-spiro[dipyrrolo[2,3-b:3',2'-d]pyridine-8,4'-piperidin]-1'-yl)cyclobutyl)acetonitrile, trifluoroacetate salt (racemic mixture) | (cyclohexenyl-morpholine carbonyl) | Calculated for $C_{39}H_{45}N_8O_3$ $(M + H)^+$: m/z = 673.4, found: 673.6 |
| 35 | B | 2-(1-(2-(4-(Ethylsulfonyl)phenyl)-6-methyl-1-(1-methyl-1H-indazol-5-yl)-7-oxo-6,7-dihydro-3H-spiro[dipyrrolo[2,3-b:3',2'-d]pyridine-8,4'-piperidin]-1'-yl)cyclobutyl)acetonitrile, trifluoroacetate salt | (4-ethylsulfonylphenyl) | Calculated for $C_{36}H_{38}N_7O_3S$ $(M + H)^+$: m/z = 648.3, found: 648.5 |
| 36 | B | 2-(1-(2-(1-(2-Methoxyethyl)-1H-pyrazol-4-yl)-6-methyl-1-(1-methyl-1H-indazol-5-yl)-7-oxo-6,7-dihydro-3H-spiro[dipyrrolo[2,3-b:3',2'-d]pyridine-8,4'-piperidin]-1'-yl)cyclobutyl)acetonitrile, trifluoroacetate salt | (1-(2-methoxyethyl)pyrazol-4-yl) | Calculated for $C_{34}H_{38}N_9O_2$ $(M + H)^+$: m/z = 604.4, found: 604.3 |

¹H NMR (600 MHz, DMSO-d₆) δ 12.10 (s, 1H), 8.14 (d, J = 0.9 Hz, 1H), 7.98 (s, 1H), 7.83-7.73 (m, 2H), 7.43 (s, 1H), 7.34 (d, J = 8.6 Hz, 1H), 7.07 (s, 1H), 4.13 (s, 3H), 4.11 (t, J = 5.1 Hz, 2H), 3.51 (t, J = 5.0 Hz, 2H), 3.15 (s, 3H), 3.04 (s, 3H), 2.71-2.61 (m, 2H), 2.49 (s, 2H), 2.08 (td, J = 12.5, 4.6 Hz, 1H), 2.01-1.91 (m, 2H), 1.77 (td, J = 12.6, 4.7 Hz, 1H), 1.69-1.59 (m, 2H), 1.57-1.51 (m, 1H), 1.39-1.32 (m, 3H), 1.09-1.01 (m, 1H), 0.86 (q, J = 9.7 Hz, 1H).

| Ex. No. | Method | Compound Name | R³ | LCMS |
|---|---|---|---|---|
| 37 | B | 2-(1-(2-(1-(1-Hydroxy-2-methylpropan-2-yl)-1H-pyrazol-4-yl)-6-methyl-1-(1-methyl-1H-indazol-5-yl)-7-oxo-6,7-dihydro-3H-spiro[dipyrrolo[2,3-b:3',2'-d]pyridine-8,4'-piperidin]-1'-yl)cyclobutyl)acetonitrile, trifluoroacetate salt | (1-(1-hydroxy-2-methylpropan-2-yl)pyrazol-4-yl) | Calculated for $C_{35}H_{40}N_9O_2$ $(M + H)^+$: m/z = 618.3, found: 618.4 |
| 38 | B | 2-(1-(6-Methyl-1-(1-methyl-1H-indazol-5-yl)-2-(1-(2-morpholinoethyl)-1H-pyrazol-4-yl)-7-oxo-6,7-dihydro-3H-spiro[dipyrrolo[2,3-b:3',2'-d]pyridine-8,4'-piperidin]-1'-yl)cyclobutyl)acetonitrile, trifluoroacetate salt | (1-(2-morpholinoethyl)pyrazol-4-yl) | Calculated for $C_{37}H_{43}N_{10}O_2$ $(M + H)^+$: m/z = 659.4, found: 659.3 |
| 39 | B | 2-(1-(2-(1-(Cyclopropylmethyl)-1H-pyrazol-4-yl)-6-methyl-1-(1-methyl-1H-indazol-5-yl)-7-oxo-6,7-dihydro-3H-spiro[dipyrrolo[2,3-b:3',2'-d]pyridine-8,4'-piperidin]-1'-yl)cyclobutyl)acetonitrile, trifluoroacetate salt | (1-(cyclopropylmethyl)pyrazol-4-yl) | Calculated for $C_{35}H_{38}N_9O$ $(M + H)^+$: m/z = 600.3, found: 600.4 |

¹H NMR (500 MHz, DMSO-d₆) δ 12.11 (s, 1H), 8.14 (s, 1H), 7.99 (s, 1H), 7.82-7.78 (m, 2H), 7.49 (s, 1H), 7.34 (d, J = 8.5 Hz, 1H), 7.03 (s, 1H), 4.13 (s, 3H), 3.82 (d, J = 7.1 Hz, 2H), 3.15 (s, 3H), 2.66 (q, J = 12.0 Hz, 2H), 2.50 (s, 2H), 2.10 (td, J = 12.2, 4.3 Hz, 1H), 2.02-1.91 (m, 2H), 1.79 (dt, J = 12.8, 7.0 Hz, 1H), 1.69-1.58 (m, 2H), 1.58-1.48 (m, 1H), 1.42-1.28 (m, 3H), 1.11-0.96 (m, 2H), 0.91-0.80 (m, 1H), 0.43-0.31 (m, 2H), 0.22-0.12 (m, 2H).

| Ex. No. | Method | Compound Name | R³ | LCMS |
|---|---|---|---|---|
| 40 | B | 2-(1-(2-(3-Cyclopropyl-1-methyl-1H-pyrazol-4-yl)-6-methyl-1-(1-methyl-1H-indazol-5-yl)-7-oxo-6,7-dihydro-3H-spiro[dipyrrolo[2,3-b:3',2'-d]pyridine-8,4'-piperidin]-1'-yl)cyclobutyl)acetonitrile, trifluoroacetate salt | (3-cyclopropyl-1-methylpyrazol-4-yl) | Calculated for $C_{35}H_{38}N_9O$ $(M + H)^+$: m/z = 600.3, found: 600.5 |

-continued

| Ex. No. | Method | Compound Name | R³ / ¹H NMR | LCMS |
|---|---|---|---|---|
| 41 | B | 2-(1-(2-(1-(1-Acetylpiperidin-4-yl)-1H-pyrazol-4-yl)-6-methyl-1-(1-methyl-1H-indazol-5-yl)-7-oxo-6,7-dihydro-3H-spiro[dipyrrolo[2,3-b:3',2'-d]pyridine-8-4'-piperidin]-1'-yl)cyclobutyl)acetonitrile, trifluoroacetate salt | (pyrazole-N-piperidine-N-Ac) | Calculated for $C_{38}H_{43}N_{10}O_2$ $(M + H)^+$: m/z = 671.4, found: 671.5 |
| 42 | B | 2-(1-(6-Methyl-1-(1-methyl-1H-indazol-5-yl)-2-(1-methyl-1H-pyrrol-3-yl)-7-oxo-6,7-dihydro-3H-spiro[dipyrrolo[2,3b:3',2'-d]pyridine-8,4'-piperidin]-1'-yl)cyclobutyl)acetonitrile, trifluoroacetate salt | (N-methylpyrrole) | Calculated for $C_{33}H_{35}N_8O$ $(M + H)^+$: m/z = 559.3, found: 559.4 |
| 43 | A | 2-(1-(6-Methyl-1-(1-methyl-1H-indazol-5-yl)-7-oxo-2-(4,5,6,7-tetrahydropyrazolo[1,5-a]pyridin-3-yl)-6,7-dihydro-3H-spiro[dipyrrolo[2,3-b:3',2'-d]pyridine-8,4'-piperidin]-1'-yl)cyclobutyl)acetonitrile | (tetrahydropyrazolo[1,5-a]pyridine) | Calculated for $C_{35}H_{38}N_9O$ $(M + H)^+$: m/z = 600.3, found: 600.5 |

¹H NMR (600 MHz, DMSO-d₆) δ 11.57 (s, 1H), 8.09 (s, 1H), 7.99 (s, 1H), 7.77 (s, 1H), 7.67 (d, J = 8.5 Hz, 1H), 7.33 (dd, J = 8.6, 1.5 Hz, 1H), 6.83 (s, 1H), 4.09 (s, 3H), 3.98 (t, J = 6.1 Hz, 2H), 3.15 (s, 3H), 2.93-2.80 (m, 2H), 2.71-2.61 (m, 2H), 2.49 (s, 2H), 2.07 (td, J = 12.4, 4.6 Hz, 1H), 1.99-1.86 (m, 4H), 1.80-1.72 (m, 3H), 1.69-1.58 (m, 2H), 1.56-1.50 (m, 1H), 1.39-1.28 (m, 3H), 1.09-1.01 (m, 1H), 0.87 (q, J = 9.7 Hz, 1H).

| Ex. No. | Method | Compound Name | R³ | LCMS |
|---|---|---|---|---|
| 44 | B | 2-(1-(2-(1-(2-Methoxy-2-methylpropyl)-1H-pyrazol-4-yl)-6-methyl-1-(1-methyl-1H-indazol-5-yl)-7-oxo-6,7-dihydro-3H-spiro[dipyrrolo[2,3-b:3',2'-d]pyridine-8,4'-piperidin]-1'-yl)cyclobutyl)acetonitrile, trifluoroacetate salt | (pyrazole-CH₂-C(CH₃)₂-OCH₃) | Calculated for $C_{36}H_{42}N_9O_2$ $(M + H)^+$: m/z = 632.3, found: 632.3 |
| 45 | B | 2-(1-(6-Methyl-1-(1-methyl-1H-indazol-5-yl)-7-oxo-2-(1-(tetrahydrofuran-3-yl)-1H-pyrazol-4-yl)-6,7-dihydro-3H-spiro[dipyrrolo[2,3-b:3',2'-d]pyridine-8,4'-piperidin]-1'-yl)cyclobutyl)acetonitrile, trifluoroacetate salt (racemic mixture prepared) | (pyrazole-tetrahydrofuran-3-yl) | Calculated for $C_{35}H_{38}N_9O_2$ $(M + H)^+$: m/z = 616.3, found: 616.4 |

Examples 46-52

Examples 46-52 were prepared by one of the two following methods:

Method A:

The procedure of Example 30 was followed, substituting the appropriate boronic acids or esters in place of 1-(2,2-difluoroethyl)-4-(4,4,5,5-tetramethyl-1,3,2-dioxaborolan-2-yl)-1H-pyrazole in Step 1; in addition, the starting material used in Step 1 of Example 30 (tert-butyl 2-bromo-6-methyl-1-(1-methyl-1H-indazol-5-yl)-7-oxo-3-(phenylsulfonyl)-6,7-dihydro-3H-spiro[dipyrrolo[2,3-b:3',2'-d]pyridine-8,4'-piperidine]-1'-carboxylate) was replaced by intermediates obtained by the procedure of Example 5, Steps 1 through 2, substituting the appropriate boronic esters or acids in place of 1-methyl-5-(4,4,5,5-tetramethyl-1,3,2-dioxaborolan-2-yl)-1H-indazole in Example 5, Step 1.

Method B:

This method follows a procedure similar to Method A, with the difference that that Steps 2 and 3 were performed (omitting the deprotection of the phenylsulfonyl group in Step 3) prior to performing Step 1, and the deprotection using NaOH was then followed as found in the latter portion of Step 3.

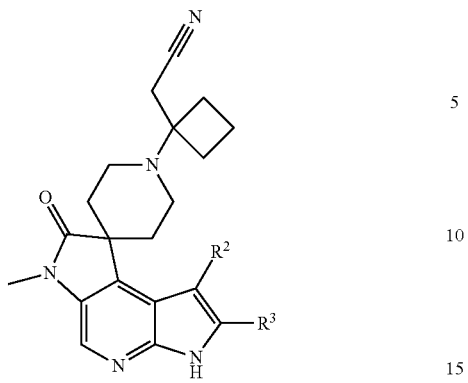

| Ex. No. | Method | Compound Name | R² | R³ | LCMS |
|---|---|---|---|---|---|
| 46 | A | 2-(1-(2-(1-(2-Methoxyethyl)-1H-pyrazol-4-yl)-6-methyl-1-(methyl-d₃)-1H-indol-5-yl)-7-oxo-6,7-dihydro-3H-spiro[dipyrrolo[2,3-b:3',2'-d]pyridine-8,4'-piperidin]-1'-yl)cyclobutyl)acetonitrile, trifluoroacetate salt | D₃C-indol-5-yl | pyrazol-4-yl with N-CH₂CH₂OMe | Calculated for $C_{35}H_{36}D_3N_8O_2$ $(M + H)^+$: m/z = 606.3, found: 606.3 |
| 47 | B | 2-(1-(1-(3,5-Difluoro-4-methoxyphenyl)-2-(1-(2-hydroxy-2-methylpropyl)-1H-pyrazol-4-yl)-6-methyl-7-oxo-6,7-dihydro-3H-spiro[dipyrrolo[2,3-b:3',2'-d]pyridine-8,4'-piperidin]-1'-yl)cyclobutyl)acetonitrile, trifluoroacetate salt | 3,5-difluoro-4-methoxyphenyl | pyrazol-4-yl with N-CH₂C(CH₃)₂OH | Calculated for $C_{34}H_{38}F_2N_7O_3$ $(M + H)^+$: m/z = 630.3, found: 630.4 |
| 48 | B | 2-(1-(2-(1-(2-Hydroxy-2-methylpropyl)-1H-pyrazol-4-yl)-6-methyl-7-oxo-1-(thieno[3,2-c]pyridin-2-yl)-6,7-dihydro-3H-spiro[dipyrrolo[2,3-b:3',2'-d]pyridine-8,4'-piperidin]-1'-yl)cyclobutyl)acetonitrile, trifluoroacetate salt | thieno[3,2-c]pyridin-2-yl | pyrazol-4-yl with N-CH₂C(CH₃)₂OH | Calculated for $C_{34}H_{37}N_8O_2S$ $(M + H)^+$: m/z = 621.3, found: 621.3 |
| 49 | B | 2-(1-(1-(4-Cyclopropylphenyl)-2-(1-(2-hydroxy-2-methylpropyl)-1H-pyrazol-4-yl)-6-methyl-7-oxo-6,7-dihydro-3H-spiro[dipyrrolo[2,3-b:3',2'-d]pyridine-8,4'-piperidin]-1'-yl)cyclobutyl)acetonitrile, trifluoroacetate salt | 4-cyclopropylphenyl | pyrazol-4-yl with N-CH₂C(CH₃)₂OH | Calculated for $C_{36}H_{42}N_7O_2$ $(M + H)^+$: m/z = 604.3, found: 604.3 |

| Ex. No. | Method | Compound Name | R² | R³ | LCMS |
|---|---|---|---|---|---|
| 50 | B | 2-(1-(2-(1-(2-Hydroxy-2-methylpropyl)-1H-pyrazol-4-yl)-6-methyl-7-oxo-1-(4-(trifluoromethoxy)phenyl)-6,7-dihydro-3H-spiro[dipyrrolo[2,3-b:3',2'-d]pyridine-8,4'-piperidin]-1'-yl)cyclobutyl)acetonitrile, trifluoroacetate salt | 4-(OCF₃)phenyl | 1-(2-hydroxy-2-methylpropyl)-1H-pyrazol-4-yl | Calculated for $C_{34}H_{37}F_3N_7O_3$ $(M + H)^+$: m/z = 648.3, found: 648.4 |
| 51 | B | 4-(1'-(1-(Cyanomethyl)cyclobutyl)-2-(1-(2,2-difluoroethyl)-1H-pyrazol-4-yl)-6-methyl-7-oxo-6,7-dihydro-3H-spiro[dipyrrolo[2,3-b:3',2'-d]pyridine-8,4'-piperidin]-1'-yl)cyclobutyl)acetonitrile, trifluoroacetate salt | 4-cyanophenyl | 1-(2,2-difluoroethyl)-1H-pyrazol-4-yl | Calculated for $C_{32}H_{31}F_2N_8O$ $(M + H)^+$: m/z = 581.3, found: 581.3 |
| 52 | B | 2-(1-(2-(1-(2-Hydroxy-2-methylpropyl)-1H-pyrazol-4-yl)-6-methyl-7-oxo-1-(4-(trifluoromethyl)phenyl)-6,7-dihydro-3H-spiro[dipyrrolo[2,3-b:3',2'-d]pyridine-8,4'-piperidin]-1'-yl)cyclobutyl)acetonitrile, trifluoroacetate salt | 4-(CF₃)phenyl | 1-(2-hydroxy-2-methylpropyl)-1H-pyrazol-4-yl | Calculated for $C_{34}H_{37}F_3N_7O_2$ $(M + H)^+$: m/z = 632.3, found: 632.5 |

Example 53a and Example 53b. (R)-1-(Ethylsulfonyl)-2'-(1-isopropyl-1H-pyrazol-4-yl)-6'-methyl-1'-(1-methyl-1H-indazol-5-yl)-3',6'-dihydro-7'H-spiro[azepane-4,8'-dipyrrolo[2,3-b:3',2'-d]pyridin]-7'-one (Example 53a) and (S)-1-(Ethylsulfonyl)-2'-(1-isopropyl-1H-pyrazol-4-yl)-6'-methyl-1'-(1-methyl-1H-indazol-5-yl)-3',6'-dihydro-7'H-spiro[azepane-4,8'-dipyrrolo[2,3-b:3',2'-d]pyridin]-7'-one (Example 53b) (Single Enantiomers Prepared)

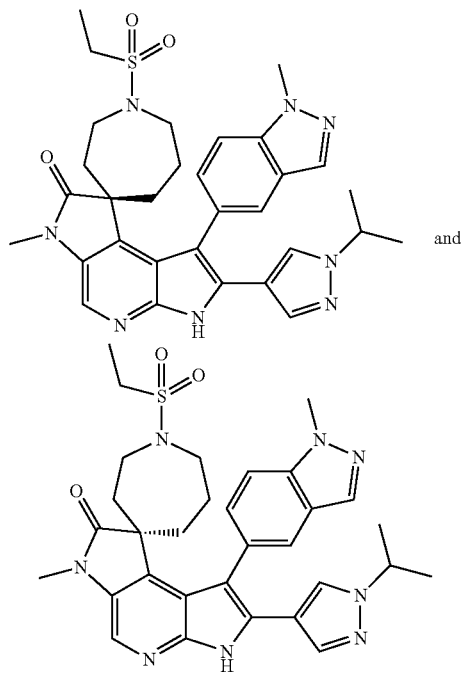

and

Step 1. tert-Butyl 2'-(1-isopropyl-1H-pyrazol-4-yl)-6'-methyl-1'-(1-methyl-1H-indazol-5-yl)-7'-oxo-3'-(phenylsulfonyl)-6',7'-dihydro-3'H-spiro[azepane-4,8'-dipyrrolo[2,3-b:3',2'-d]pyridine]-1-carboxylate (Racemic Mixture Prepared)

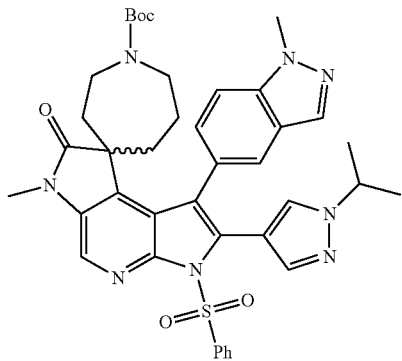 [SMILES: CC(C)n1cc(-c2c(-c3ccc4c(cnn4C)c3)c3c4c(cnc3n2S(=O)(=O)c2ccccc2)N(C)C(=O)C42CCCN(C(=O)OC(C)(C)C)CC2)cn1]

The procedure of Example 13, Steps 1 through 7 were followed, utilizing 1-(tert-butyl) 4-methyl azepane-1,4-dicarboxylate (eNovation Chemicals LLC #D573239) in place of 8-(tert-butyl) 3-methyl 8-azabicyclo[3.2.1]octane-3,8-dicarboxylate in Step 1, utilizing 1-methyl-5-(4,4,5,5-tetramethyl-1,3,2-dioxaborolan-2-yl)-1H-indazole in place of phenylboronic acid in Step 5, and utilizing 1-isopropyl-4-(4,4,5,5-tetramethyl-1,3,2-dioxaborolan-2-yl)-1H-pyrazole in place of 4-(methylsulfonyl)-1-(4-(4,4,5,5-tetramethyl-1,3,2-dioxaborolan-2-yl)benzyl)piperidine in Step 7. Purification via flash column chromatography, eluting with a gradient from 0-100% EtOAc in hexanes afforded the title compound. LCMS for $C_{40}H_{45}N_8O_5S$ (M+H)$^+$: calculated m/z=749.3; found 749.2.

Step 2. 2'-(1-Isopropyl-1H-pyrazol-4-yl)-6'-methyl-1'-(1-methyl-1H-indazol-5-yl)-3'-(phenylsulfonyl)-3',6'-dihydro-7'H-spiro[azepane-4,8'-dipyrrolo[2,3-b:3',2'-d]pyridin]-7'-one (Racemic Mixture Prepared)

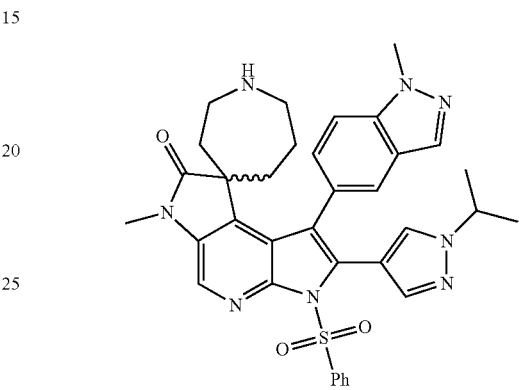

The procedure of Example 5, Step 3 was followed, utilizing tert-butyl 2'-(1-isopropyl-1H-pyrazol-4-yl)-6'-methyl-1'-(1-methyl-1H-indazol-5-yl)-7'-oxo-3'-(phenylsulfonyl)-6',7'-dihydro-3'H-spiro[azepane-4,8'-dipyrrolo[2,3-b:3',2'-d]pyridine]-1-carboxylate in place of tert-butyl 2-bromo-6-methyl-1-(1-methyl-1H-indazol-5-yl)-7-oxo-3-(phenylsulfonyl)-6,7-dihydro-3H-spiro[dipyrrolo[2,3-b:3',2'-d]pyridine-8,4'-piperidine]-1'-carboxylate. LCMS for $C_{35}H_{37}N_8O_3S$ (M+H)$^+$: calculated m/z=649.3; found 649.2.

Step 3. (R)-1-(Ethylsulfonyl)-2'-(1-isopropyl-1H-pyrazol-4-yl)-6'-methyl-1'-(1-methyl-1H-indazol-5-yl)-3',6'-dihydro-7'H-spiro[azepane-4,8'-dipyrrolo[2,3-b:3',2'-d]pyridin]-7'-one and (S)-1-(Ethylsulfonyl)-2'-(1-isopropyl-1H-pyrazol-4-yl)-6'-methyl-1'-(1-methyl-1H-indazol-5-yl)-3',6'-dihydro-7'H-spiro[azepane-4,8'-dipyrrolo[2,3-b:3',2'-d]pyridin]-7'-one (Single Enantiomers Prepared)

The procedure of Example 23, Step 5 was followed, utilizing 2'-(1-isopropyl-1H-pyrazol-4-yl)-6'-methyl-1'-(1-methyl-1H-indazol-5-yl)-3'-(phenylsulfonyl)-3',6'-dihydro-7'H-spiro[azepane-4,8'-dipyrrolo[2,3-b:3',2'-d]pyridin]-7'-one in place of 2-(3-(6-methyl-2-(1-methyl-1H-pyrazol-4-yl)-7-oxo-1-phenyl-3-(phenylsulfonyl)-6,7-dihydro-3H-spiro[dipyrrolo[2,3-b:3',2'-a]pyridine-8,4'-piperidin]-1'-yl)azetidin-3-yl)acetonitrile. Before deprotection with NaOH (as described in Example 23, Step 5), the enantiomers were separated (Phenomenex Lux 5 μm Cellulose-1, 21.2×250 mm, loading 18 mg in 2 mL EtOH and eluting with 45% EtOH in hexanes at 20 mL/min over 22 min). Peak 1 retention time: 13.4 min; Peak 2 retention time: 16.1 min). Peaks 1 and 2 were deprotected separately with NaOH following the method found in Example 23, Step 5 and purified via preparative HPLC-MS (pH=10) to afford the title compounds.

Example 53a (Derived from Peak 1)

LCMS for $C_{31}H_{37}N_8O_3S$ (M+H)$^+$: calculated m/z=601.3; found 601.2. $^1$H NMR (500 MHz, DMSO-d$_6$, 3:2 ratio of atropisomers) δ 11.99 (s, 0.4H), 11.98 (s, 0.6H), 8.07 (s, 0.6H), 8.06 (s, 0.4H), 8.01 (s, 0.4H), 8.01 (s, 0.6H), 7.81 (d, J=8.5 Hz, 0.4H), 7.78 (s, 0.6H), 7.75 (d, J=8.5 Hz, 0.6H), 7.75 (s, 0.4H), 7.66 (s, 0.6H), 7.62 (s, 0.4H), 7.46 (dd, J=8.5, 1.6 Hz, 0.4H), 7.36 (dd, J=8.6, 1.6 Hz, 0.6H), 6.78 (s, 0.6H), 6.69 (s, 0.4H), 4.33 (h, J=6.5 Hz, 1H), 4.13 (s, 1.2H), 4.12 (s, 1.8H), 3.55 (dd, J=14.3, 9.4 Hz, 0.6H), 3.34 (dd, J=14.3, 9.4 Hz, 0.4H), 3.33-3.27 (m, 0.4H), 3.19 (s, 1.2H), 3.18 (s, 1.8H), 3.10 (dt, J=11.7, 3.9 Hz, 0.6H), 2.75 (q, J=7.3 Hz, 1.2H), 2.60 (dd, J=14.1, 7.3 Hz, 0.6H), 2.52 (dq, J=14.5, 7.4 Hz, 0.4H), 2.38 (dq, J=14.5, 7.4 Hz, 0.4H), 2.33-1.88 (m, 3.8H), 1.80 (td, J=11.9, 2.2 Hz, 0.6H), 1.74-1.63 (m, 1H), 1.60-1.51 (m, 1H), 1.43-1.32 (m, 0.4H), 1.32-1.24 (m, 6H), 1.24-1.14 (m, 0.6H), 1.04 (t, J=7.3 Hz, 1.8H), 0.94 (t, J=7.3 Hz, 1.2H).

Example 53b (Derived from Peak 2)

LCMS for $C_{31}H_{37}N_8O_3S$ (M+H)$^+$: calculated m/z=601.3; found 601.3. $^1$H NMR (500 MHz, DMSO-d$_6$, 3:2 ratio of atropisomers) δ 11.99 (s, 0.4H), 11.98 (s, 0.6H), 8.07 (s, 0.6H), 8.06 (s, 0.4H), 8.01 (s, 0.4H), 8.01 (s, 0.6H), 7.81 (d, J=8.5 Hz, 0.4H), 7.78 (s, 0.6H), 7.75 (d, J=8.5 Hz, 0.6H), 7.75 (s, 0.4H), 7.66 (s, 0.6H), 7.62 (s, 0.4H), 7.46 (dd, J=8.5, 1.6 Hz, 0.4H), 7.36 (dd, J=8.6, 1.6 Hz, 0.6H), 6.78 (s, 0.6H), 6.69 (s, 0.4H), 4.33 (h, J=6.5 Hz, 1H), 4.13 (s, 1.2H), 4.12 (s, 1.8H), 3.55 (dd, J=14.3, 9.4 Hz, 0.6H), 3.34 (dd, J=14.3, 9.4 Hz, 0.4H), 3.33-3.27 (m, 0.4H), 3.19 (s, 1.2H), 3.18 (s, 1.8H), 3.10 (dt, J=11.7, 3.9 Hz, 0.6H), 2.75 (q, J=7.3 Hz, 1.2H), 2.60 (dd, J=14.1, 7.3 Hz, 0.6H), 2.52 (dq, J=14.5, 7.4 Hz, 0.4H), 2.38 (dq, J=14.5, 7.4 Hz, 0.4H), 2.33-1.88 (m, 3.8H), 1.80 (td, J=11.9, 2.2 Hz, 0.6H), 1.74-1.63 (m, 1H), 1.60-1.51 (m, 1H), 1.43-1.32 (m, 0.4H), 1.32-1.24 (m, 6H), 1.24-1.14 (m, 0.6H), 1.04 (t, J=7.3 Hz, 1.8H), 0.94 (t, J=7.3 Hz, 1.2H).

Example 54. 1-(Ethylsulfonyl)-2"-(1-isopropyl-1H-pyrazol-4-yl)-6"-methyl-1"'-(1-methyl-1H-indazol-5-yl)-3",6"-dihydro-7"H-dispiro[azetidine-3,1'-cyclobutane-3',8"-dipyrrolo[2,3-b:3',2'-d]pyridin]-7"-one, trifluoroacetate salt

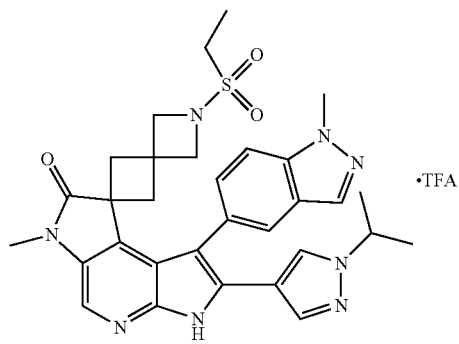 [SMILES: CCS(=O)(=O)N1CC2(C1)CC1(C2)C(=O)N(C)c2cnc3[nH]c(-c4cnn(C(C)C)c4)c(-c4ccc5c(cnn5C)c4)c3c21]

·TFA

The procedure of Example 13, Steps 1 through 7 were followed, utilizing 2-(tert-butyl) 6-methyl 2-azaspiro[3.3]heptane-2,6-dicarboxylate (Synthonix #M11808) in place of 8-(tert-butyl) 3-methyl 8-azabicyclo[3.2.1]octane-3,8-dicarboxylate in Step 1, utilizing 1-methyl-5-(4,4,5,5-tetramethyl-1,3,2-dioxaborolan-2-yl)-1H-indazole in place of phenylboronic acid in Step 5, and utilizing 1-isopropyl-4-(4,4,5,5-tetramethyl-1,3,2-dioxaborolan-2-yl)-1H-pyrazole in place of 4-(methylsulfonyl)-1-(4-(4,4,5,5-tetramethyl-1,3,2-dioxaborolan-2-yl)benzyl)piperidine in Step 7. Deprotection of the Boc protecting group was performed analogously to the procedure found in Example 5, Step 3, and the procedure of Example 23, Step 5 was then followed to afford the title compound. LCMS for $C_{31}H_{35}N_8O_3S$ (M+H)$^+$: calculated m/z=599.3; found 599.3. $^1$H NMR (500 MHz, DMSO-d$_6$) δ 12.00 (s, 1H), 8.14 (s, 1H), 7.95 (s, 1H), 7.91 (s, 1H), 7.87 (d, J=8.5 Hz, 1H), 7.67 (s, 1H), 7.49 (dd, J=8.6, 1.5 Hz, 1H), 6.83 (s, 1H), 4.35 (hept, J=6.7 Hz, 1H), 4.13 (s, 3H), 3.93-3.86 (m, 2H), 3.16 (s, 3H), 2.92-2.81 (m, 2H), 2.48 (d, J=12.3 Hz, 1H), 2.35 (d, J=12.4 Hz, 1H), 2.31 (d, J=8.9 Hz, 1H), 2.25-2.17 (m, 2H), 1.93 (d, J=8.9 Hz, 1H), 1.29 (d, J=6.7 Hz, 6H), 1.08 (t, J=7.3 Hz, 3H).

Example 55. Mixture of N-((1S,3R)-6'-Methyl-1'-(1-methyl-1H-indazol-5-yl)-2'-(1-methyl-1H-pyrazol-4-yl)-7'-oxo-6',7'-dihydro-3'H-spiro[cyclopentane-1,8'-dipyrrolo[2,3-b:3',2'-d]pyridin]-3-yl)cyclopropanesulfonamide, trifluoroacetate salt and N-((1R,3S)-6'-Methyl-1'-(1-methyl-1H-indazol-5-yl)-2'-(1-methyl-1H-pyrazol-4-yl)-7'-oxo-6',7'-dihydro-3'H-spiro[cyclopentane-1,8'-dipyrrolo[2,3-b:3',2'-d]pyridin]-3-yl)cyclopropanesulfonamide, trifluoroacetate salt (Racemic Mixture Prepared)

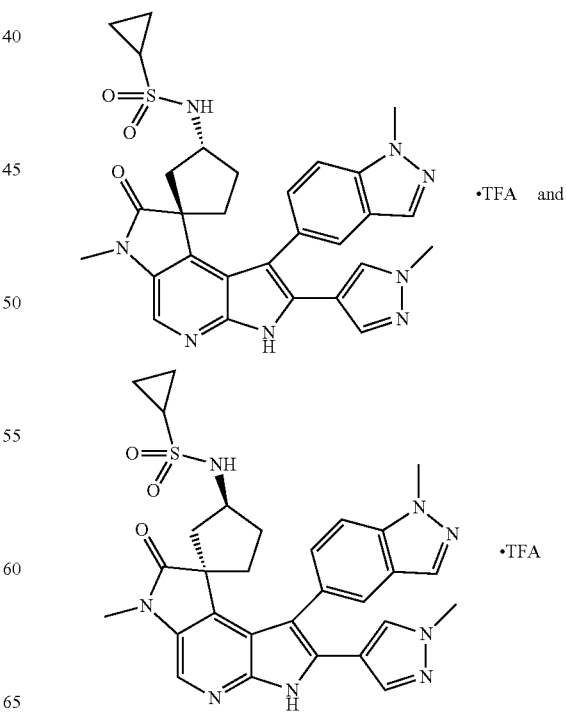

215

Step 1. Methyl 3-((diphenylmethylene)amino)cyclopentane-1-carboxylate

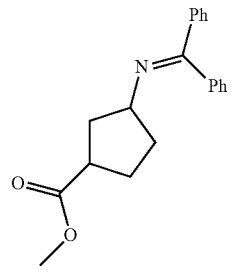 [SMILES: COC(=O)C1CCC(N=C(c2ccccc2)c2ccccc2)C1]

A mixture of methyl 3-aminocyclopentane-1-carboxylate, HCl salt (Combi-Blocks QB-0001—stereochemistry not specified, 3.0 g, 17 mmol) and diphenylmethanimine (Aldrich #293733, 3.0 g, 17 mmol) in DCM (42 mL) was stirred overnight. The reaction mixture was filtered and volatiles were removed in vacuo. Flash column chromatography, eluting with a gradient from 0-60% EtOAc in hexanes afforded the title compound, which was azeotroped with toluene before use in the subsequent step (4.9 g, 95%). LCMS for $C_{20}H_{22}NO_2$ (M+H)$^+$: calculated m/z=308.2; found 308.1.

Step 2. 3-Amino-3'-(phenylsulfonyl)-3',6'-dihydro-7'H-spiro[cyclopentane-1,8'-dipyrrolo[2,3-b:3',2'-d]pyridin]-7'-one (Mixture of Diastereomers Prepared)

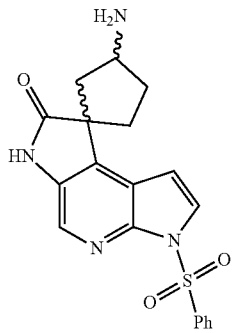 [SMILES: NC1CCC2(C1)C(=O)Nc1cnc3c(ccn3S(=O)(=O)c3ccccc3)c12]

The procedure of Example 1, Steps 2 and 3 were followed, utilizing 4-chloro-5-nitro-1-(phenylsulfonyl)-1H-pyrrolo[2,3-b]pyridine (2.6 g, 7.7 mmol) and methyl 3-((diphenylmethylene)amino)cyclopentane-1-carboxylate (2.4 g, 7.7 mmol) in place of methyl tetrahydro-2H-pyran-4-carboxylate in Step 2, and allowing the reaction mixture to warm to 0° C. instead of −20° C. Workup after following the procedure of Example 1, Step 3 included the additional modifications: removal of organic solvents from the aqueous layer of the filtrate in vacuo, basification (to pH=10) of the aqueous mixture by the addition of NaOH (1.0 N) and further extraction of the mixture with 10% iPrOH/DCM. The product was used without further purification (benzophenone present, theoretical yield assumed). LCMS for $C_{19}H_{19}N_4O_3S$ (M+H)$^+$: calculated m/z=383.1; found 383.1.

216

Step 3. Mixture of tert-Butyl ((1S,3R)-7'-oxo-3'-(phenylsulfonyl)-6',7'-dihydro-3'H-spiro[cyclopentane-1,8'-dipyrrolo[2,3-b:3',2'-d]pyridin]-3-yl)carbamate, tert-Butyl ((1S,3S)-7'-oxo-3'-(phenylsulfonyl)-6',7'-dihydro-3'H-spiro [cyclopentane-1,8'-dipyrrolo[2,3-b:3',2'-d]pyridin]-3-yl)carbamate, tert-Butyl ((1R,3S)-7'-oxo-3'-(phenylsulfonyl)-6',7'-dihydro-3'H-spiro [cyclopentane-1,8'-dipyrrolo[2,3-b:3',2'-d]pyridin]-3-yl)carbamate, tert-Butyl ((1R,3R)-7'-oxo-3'-(phenylsulfonyl)-6',7'-dihydro-3'H-spiro [cyclopentane-1,8'-dipyrrolo[2,3-b:3',2'-d]pyridin]-3-yl)carbamate (Two Diastereomers Isolated, Each as a Racemic Mixture)

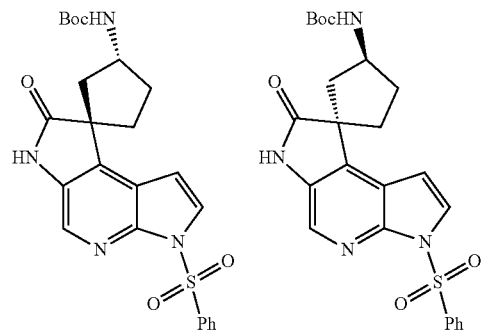

and

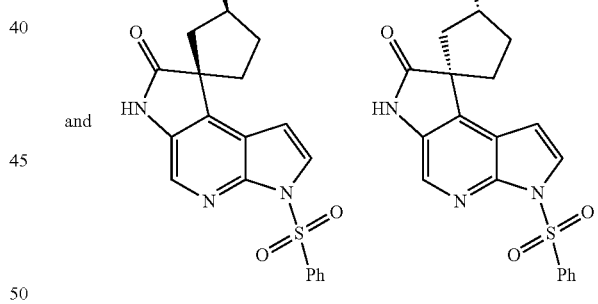

To 3-amino-3'-(phenyl sulfonyl)-3',6'-dihydro-7'H-spiro [cyclopentane-1,8'-dipyrrolo[2,3-b:3',2'-d]pyridin]-7'-one (mixture of diastereomers from Step 2, 1.1 g, 2.8 mmol) in THF (28 mL) was added triethylamine (0.97 mL, 7.0 mmol) and di-tert-butyl dicarbonate (0.71 mL, 3.1 mmol) and the reaction was stirred for 16 hours. Water was added to the reaction mixture and the volatile organic solvent was removed in vacuo. The mixture was extracted with EtOAc (3×) and the combined organic extracts were washed with water, followed by brine, dried over $Na_2SO_4$, filtered and concentrated. The product was purified via flash column chromatography, eluting with a gradient from 0-100% EtOAc in hexanes. Two diastereomers were isolated separately.

Peak 1, first to elute, tert-Butyl ((1S,3R)-7'-oxo-3'-(phenylsulfonyl)-6',7'-dihydro-3'H-spiro[cyclopentane-1,8'-dipyrrolo[2,3-b:3',2'-d]pyridin]-3-yl)carbamate and tert-Butyl ((1R,3S)-7'-oxo-3'-(phenylsulfonyl)-6',7'-dihydro-3'H-spiro[cyclopentane-1,8'-dipyrrolo[2,3-b:3',2'-d]pyridin]-3-yl)carbamate (racemic mixture): 0.26 g, 19%; LCMS for $C_{24}H_{27}N_4O_5S$ (M+H)$^+$: calculated m/z=483.2; found 483.2.

Peak 2, second to elute, tert-Butyl ((1S,3S)-7'-oxo-3'-(phenylsulfonyl)-6',7'-dihydro-3'H-spiro[cyclopentane-1,8'-dipyrrolo[2,3-b:3',2'-d]pyridin]-3-yl)carbamate and tert-Butyl ((1R,3R)-7'-oxo-3'-(phenylsulfonyl)-6',7'-dihydro-3'H-spiro[cyclopentane-1,8'-dipyrrolo[2,3-b:3',2'-d]pyridin]-3-yl)carbamate (racemic mixture): 0.37 g, 28%; LCMS for $C_{24}H_{27}N_4O_5S$ (M+H)$^+$: calculated m/z=483.2; found 483.2.

Step 4. Mixture of N-((1S,3R)-6'-Methyl-1'-(1-methyl-1H-indazol-5-yl)-2'-(1-methyl-1H-pyrazol-4-yl)-7'-oxo-6',7'-dihydro-3'H-spiro[cyclopentane-1,8'-dipyrrolo[2,3-b:3,2'-d]pyridin]-3-yl)cyclopropanesulfonamide, trifluoroacetate salt and N-((1R,3S)-6'-Methyl-1'-(1-methyl-1H-indazol-5-yl)-2'-(1-methyl-1H-pyrazol-4-yl)-7'-oxo-6',7'-dihydro-3'H-spiro[cyclopentane-1,8'-dipyrrolo[2,3-b:3',2'-d]pyridin]-3-yl)cyclopropanesulfonamide, trifluoroacetate salt (Racemic Mixture Prepared)

The procedure of Example 13, Steps 3 through 7 were followed, utilizing tert-Butyl ((1S,3R)-7'-oxo-3'-(phenylsulfonyl)-6',7'-dihydro-3'H-spiro[cyclopentane-1,8'-dipyrrolo[2,3-b:3',2'-d]pyridin]-3-yl)carbamate and tert-Butyl ((1R,3S)-7'-oxo-3'-(phenylsulfonyl)-6',7'-dihydro-3'H-spiro[cyclopentane-1,8'-dipyrrolo[2,3-b:3',2'-d]pyridin]-3-yl)carbamate (Peak 1 from Step 3 of this Example, as a racemic mixture) in place of tert-butyl 7'-oxo-3'-(phenylsulfonyl)-6',7'-dihydro-3'H-8-azaspiro[bicyclo[3.2.1]octane-3,8'-dipyrrolo[2,3-b:3',2'-d]pyridine]-8-carboxylate in Step 3, utilizing 1-methyl-5-(4,4,5,5-tetramethyl-1,3,2-dioxaborolan-2-yl)-1H-indazole in place of phenylboronic acid in Step 5, and utilizing 1-methyl-4-(4,4,5,5-tetramethyl-1,3,2-dioxaborolan-2-yl)-1H-pyrazole in place of 4-(methylsulfonyl)-1-(4-(4,4,5,5-tetramethyl-1,3,2-dioxaborolan-2-yl)benzyl)piperidine in Step 7 to provide tert-butyl ((1S,3R)-6'-methyl-1'-(1-methyl-1H-indazol-5-yl)-2'-(1-methyl-1H-pyrazol-4-yl)-7'-oxo-3'-(phenylsulfonyl)-6',7'-dihydro-3'H-spiro[cyclopentane-1,8'-dipyrrolo[2,3-b:3',2'-d]pyridin]-3-yl)carbamate and tert-butyl ((1R,3S)-6'-methyl-1'-(1-methyl-1H-indazol-5-yl)-2'-(1-methyl-1H-pyrazol-4-yl)-7'-oxo-3'-(phenylsulfonyl)-6',7'-dihydro-3'H-spiro[cyclopentane-1,8'-dipyrrolo[2,3-b:3',2'-d]pyridin]-3-yl)carbamate as a racemic mixture. Deprotection of the Boc protecting group was performed analogously to the procedure found in Example 5, Step 3, then the procedure found in Example 23, Step 5 was applied, utilizing cyclopropanesulfonyl chloride in place of ethanesulfonyl chloride. Purification via preparative HPLC-MS (pH=2) afforded the title compounds as their TFA salts. LCMS for $C_{29}H_{31}N_8O_3S$ (M+H)$^+$: calculated m/z=571.2; found 571.2.

Example 56. Mixture of N-((1S,3S)-6'-Methyl-1'-(1-(methyl-d$_3$)-1H-indazol-5-yl)-2'-(1-methyl-1H-pyrazol-4-yl)-7'-oxo-6',7'-dihydro-3'H-spiro[cyclopentane-1,8'-dipyrrolo[2,3-b:3',2'-d]pyridin]-3-yl)cyclopropanesulfonamide, trifluoroacetate salt and N-((1R,3R)-6'-Methyl-1'-(1-(methyl-d$_3$)-1H-indazol-5-yl)-2'-(1-methyl-1H-pyrazol-4-yl)-7'-oxo-6',7'-dihydro-3'H-spiro[cyclopentane-1,8'-dipyrrolo[2,3-b:3',2'-d]pyridin]-3-yl)cyclopropanesulfonamide, trifluoroacetate salt (Racemic Mixture Prepared)

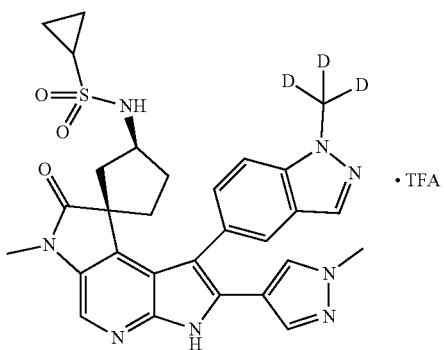

and

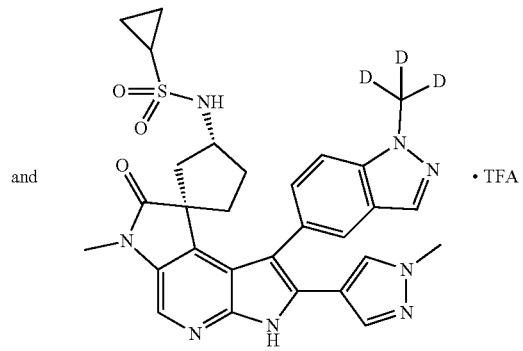

The procedure of Example 55, Step 4 was followed, utilizing Peak 2 from Step 3 as starting material in place of Peak 1, and using (1-(methyl-d$_3$)-1H-indazol-5-yl)boronic acid (Abovchem, #504689) in place of 1-methyl-5-(4,4,5,5-tetramethyl-1,3,2-dioxaborolan-2-yl)-1H-indazole in Step 4. LCMS for $C_{29}H_{28}D_3N_8O_3S$ (M+H)$^+$: calculated m/z=574.2; found 574.1. $^1$H NMR (600 MHz, DMSO-d$_6$) δ 12.05 (s, 1H), 8.14-8.08 (m, 1H), 7.98 (d, J=2.1 Hz, 1H), 7.80-7.76 (m, 1H), 7.45 (dd, J=8.4, 1.6 Hz, 1H), 7.41 (d, J=2.7 Hz, 1H), 7.34 (dd, J=8.5, 1.6 Hz, 1H), 6.98-6.91 (m, 1H), 5.98 (dd, J=11.7, 6.3 Hz, 1H), 4.08-3.84 (m, 3D), 3.71 (s, 3H), 3.21-3.15 (s, 3H), 2.35-2.13 (m, 1H), 2.08-1.96 (m, 2H), 1.92-1.79 (m, 1H), 1.76-1.63 (m, 2H), 1.48 (dt, J=14.5, 8.6 Hz, 1H), 0.90-0.73 (m, 4H), -0.20-0.53 (m, 1H).

Example 57. 6-Methyl-2-(4-((4-(methylsulfonyl) piperidin-1-yl)methyl)phenyl)-1',3,3',6-tetrahydro-7H-spiro[dipyrrolo[2,3-b:3',2'-d]pyridine-8,2'-inden]-7-one

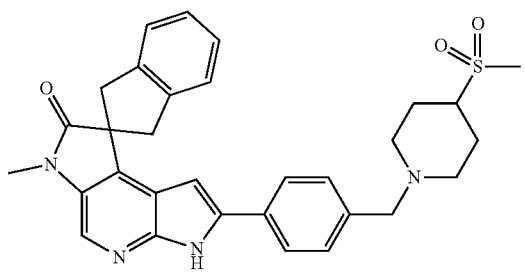

The procedure of Example 1 was followed, utilizing 4-chloro-5-nitro-1-(phenylsulfonyl)-1H-pyrrolo[2,3-b]pyridine (Astatech #P12207, 0.10 g, 0.30 mmol) and methyl 2,3-dihydro-1H-indene-2-carboxylate (Lancaster, Cat #L00741, 63 mg, 0.36 mmol) in place of methyl tetrahydro-2H-pyran-4-carboxylate in Step 2. Steps 5 and 6 were not performed, and in Step 8, the deprotection of the phenylsulfonyl group was performed before the Suzuki coupling. Purification of the final product via preparative HPLC-MS (pH=10) afforded the title compound (0.6 mg). LCMS for $C_{31}H_{33}N_4O_3S$ (M+H)$^+$: calculated m/z=541.2; found 541.1.

Example 58. Methyl 6-methyl-2-(1-methyl-1H-pyrazol-4-yl)-1-(1-(methyl-d$_3$)-1H-indazol-5-yl)-7-oxo-6,7-dihydro-3H-dispiro[dipyrrolo[2,3-b:3',2'-d] pyridine-8,1'-cyclobutane-3',4''-piperidine]-1''-carboxylate, trifluoroacetate salt

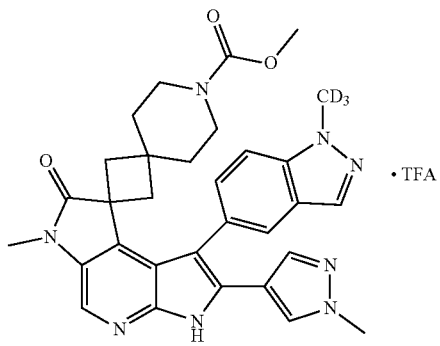

Step 1. 7-(tert-Butyl) 2-methyl 7-azaspiro[3.5]nonane-2,7-dicarboxylate

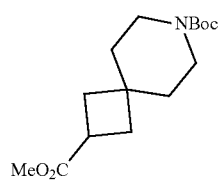

To a mixture of 7-(tert-butoxycarbonyl)-7-azaspiro[3.5] nonane-2-carboxylic acid (4.0 g, 15 mmol, PharmaBlock, PBN2011606) and Cs$_2$CO$_3$ (7.2 g, 22 mmol) in DMF (130 mL) was added CH$_3$I (1.1 mL, 18 mmol) at room temperature. The reaction mixture was stirred at this temperature for 3 hr under nitrogen. The reaction mixture was then diluted with water (500 mL) and extracted with EtOAc (3×). The combined organic layers were washed sequentially with water (4×) and brine, and dried over anhydrous Na$_2$SO$_4$. The solids were removed by filtration and the filtrate concentrated to give 7-(tert-butyl) 2-methyl 7-azaspiro[3.5]nonane-2,7-dicarboxylate (4.0 g, 98%). LCMS for $C_{11}H_{18}NO_4$ (M-$^t$Bu+H)$^+$: calculated m/z=228.1; found 228.1.

Step 2. tert-Butyl 6-methyl-1-(1-(methyl-d$_3$)-1H-indazol-5-yl)-7-oxo-3-(phenylsulfonyl)-6,7-dihydro-3H-dispiro[dipyrrolo[2,3-b:3',2'-d]pyridine-8,1'-cyclobutane-3',4''-piperidin]-1''-carboxylate

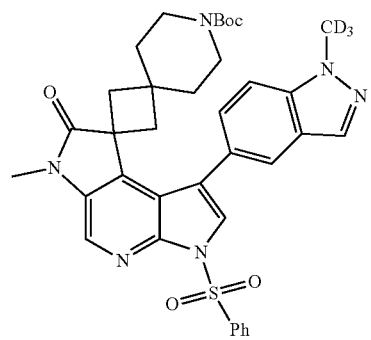 [SMILES: [2H]C([2H])([2H])n1ncc2cc(-c3cn(S(=O)(=O)c4ccccc4)c4ncc5c(c34)C3(CC4(CCN(C(=O)OC(C)(C)C)CC4)C3)C(=O)N5C)ccc21]

The title compound was prepared in a manner analogous to Example 8, Steps 1-5, with the following modifications. In Step 1, 7-(tert-butyl) 2-methyl 7-azaspiro[3.5]nonane-2, 7-dicarboxylate (3.5 g, 12 mmol) was used in place of methyl cyclopentanecarboxylate. In Step 5, (1-(methyl-d$_3$)-1H-indazol-5-yl)boronic acid was used in place of 1-methyl-5-(4,4,5,5-tetramethyl-1,3,2-dioxaborolan-2-yl)-1H-indazole to afford the title compound (0.18 g). LCMS for $C_{36}H_{36}D_3N_6O_5S$ (M+H)$^+$: calculated m/z=670.3; found 670.3.

Step 3. tert-Butyl 2-bromo-6-methyl-1-(1-(methyl-d$_3$)-1H-indazol-5-yl)-7-oxo-3-(phenylsulfonyl)-6,7-dihydro-3H-dispiro[dipyrrolo[2,3-b:3,2'-d]pyridine-8,1'-cyclobutane-3',4''-piperidin]-1''-carboxylate

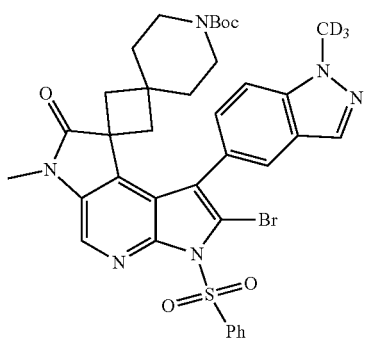 [SMILES: [2H]C([2H])([2H])n1ncc2cc(-c3c(Br)n(S(=O)(=O)c4ccccc4)c4ncc5c(c34)C3(CC4(CCN(C(=O)OC(C)(C)C)CC4)C3)C(=O)N5C)ccc21]

To a vial containing tert-butyl 6-methyl-1-(1-(methyl-d$_3$)-1H-indazol-5-yl)-7-oxo-3-(phenylsulfonyl)-6,7-dihydro-3H-dispiro[dipyrrolo[2,3-b:3',2'-d]pyridine-8,1'-cyclobutane-3',4''-piperidine]-1''-carboxylate (0.21 g, 0.32 mmol) as a solution in THF (13 mL) was added LDA (2.0 M heptane/THF/ethylbenzene) (0.32 mL, 0.64 mmol) at −78° C. The reaction mixture was stirred for 20 min after which time 1,2-dibromo-1,1,2,2-tetrachloroethane (0.11 g, 0.33 mmol) was added in a single portion and the mixture stirred for an additional 20 min. The reaction was quenched by the addition of water, diluted with EtOAc and the layers separated. The aqueous layer was further extracted with EtOAc (2×). The combined organic layers were dried over Na$_2$SO$_4$, filtered and concentrated to give the crude product, which was further purified on a 12 g silica gel column, eluting with a gradient of 0-60% EtOAc in hexanes to afford the title compound. LCMS for C$_{36}$H$_{35}$D$_3$BrN$_6$O$_5$S (M+H)$^+$: calculated m/z=748.2; found 748.2.

Step 4. tert-Butyl 6-methyl-2-(1-methyl-1H-pyrazol-4-yl)-1-(1-(methyl-d$_3$)-1H-indazol-5-yl)-7-oxo-3-(phenylsulfonyl)-6,7-dihydro-3H-dispiro[dipyrrolo[2,3-b:3',2'-d]pyridine-8,1'-cyclobutane-3',4''-piperidine]-1''-carboxylate

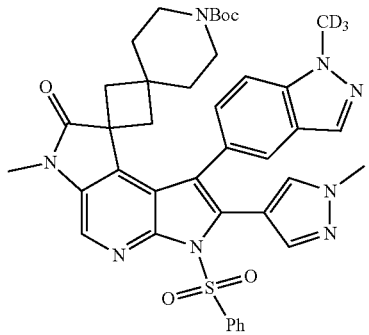

The title compound was prepared by a procedure analogous to that described for Example 12, Step 8, utilizing (1-methyl-1H-pyrazol-4-yl)boronic acid (0.048 g, 0.38 mmol) in place of 4-(methylsulfonyl)-1-(4-(4,4,5,5-tetramethyl-1,3,2-dioxaborolan-2-yl)benzyl)piperidine and tert-butyl 2-bromo-6-methyl-1-(1-(methyl-d$_3$)-1H-indazol-5-yl)-7-oxo-3-(phenylsulfonyl)-6,7-dihydro-3H-dispiro[dipyrrolo[2,3-b:3',2'-d]pyridine-8,1'-cyclobutane-3',4''-piperidine]-1''-carboxylate (0.19 g, 0.25 mmol) in place of tert-butyl 2-bromo-6-methyl-7-oxo-1-phenyl-6,7-dihydro-3H-spiro[dipyrrolo[2,3-b:3',2'-d]pyridine-8,3'-pyrrolidine]-1'-carboxylate. Purification via flash column chromatography on silica gel, eluting with a gradient of 0-100% EtOAc in hexanes, afforded the title compound (0.15 g, 76%). LCMS for C$_{40}$H$_{40}$D$_3$N$_8$O$_5$S (M+H)$^+$: calculated m/z=750.3; found 750.3.

Step 5. 6-Methyl-2-(1-methyl-1H-pyrazol-4-yl)-1-(1-(methyl-d$_3$)-1H-indazol-5-yl)-3-(phenylsulfonyl)-3,6-dihydro-7H-dispiro[dipyrrolo[2,3-b:3,2'-d]pyridine-8,1'-cyclobutane-3',4''-piperidin]-7-one

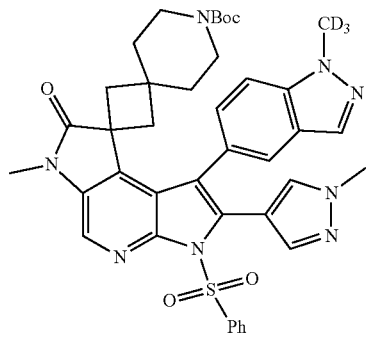

To a 1-dram vial containing tert-butyl 6-methyl-2-(1-methyl-1H-pyrazol-4-yl)-1-(1-(methyl-d$_3$)-1H-indazol-5-yl)-7-oxo-3-(phenyl sulfonyl)-6,7-dihydro-3H-dispiro[dipyrrolo[2,3-b:3',2'-d]pyridine-8,1'-cyclobutane-3',4''-piperidine]-1''-carboxylate (0.15 g, 0.19 mmol) in DCM (3.9 mL) was added TFA (3.9 mL) and the mixture was stirred at 23° C. for 30 min. The reaction was concentrated to remove excess TFA, diluted with DCM and the organics washed with saturated aqueous NaHCO$_3$ (3×). The organic layer was dried and concentrated to afford the title compound (0.22 g, 95%). LCMS for C$_{35}$H$_{32}$D$_3$N$_8$O$_3$S (M+H)$^+$: calculated m/z=650.3; found 650.2.

Step 6. Methyl 6-methyl-2-(1-methyl-1H-pyrazol-4-yl)-1-(1-(methyl-d$_3$)-1H-indazol-5-yl)-7-oxo-6,7-dihydro-3H-dispiro[dipyrrolo[2,3-b:3,2'-d]pyridine-8,1'-cyclobutane-3',4''-piperidin]-1''-carboxylate, trifluoroacetate salt To a vial containing 6-methyl-2-(1-methyl-1H-pyrazol-4-yl)-1-(1-(methyl-d$_3$)-1H-indazol-5-yl)-3-(phenylsulfonyl)-3,6-dihydro-7H-dispiro[dipyrrolo[2,3-b:3',2'-d]pyridine-8,1'-cyclobutane-3',4''-piperidin]-7-one (8.0 mg, 0.012 mmol) was added THF (0.25 mL), Et$_3$N (0.014 mL, 0.098 mmol) and methyl chloroformate (2.3 mg, 0.025 mmol). The reaction was stirred at 23° C. for 30 min after which time MeOH (0.30 mL) and NaOH (3.0 N, 0.10 mL) were added sequentially. The reaction mixture was then heated to 55° C. and stirred at this temperature for an additional 30 min. The mixture was then further diluted with MeOH (4.5 mL) and purified via preparative HPLC-MS (pH=2) to afford the title compound (3.2 mg, 34%). LCMS for C$_{31}$H$_{30}$D$_3$N$_8$O$_3$ (M+H)$^+$: calculated m/z=568.3; found 568.3. $^1$H NMR (500 MHz, DMSO-d$_6$) δ 12.04 (s, 1H), 8.11 (s, 1H), 7.96 (s, 1H), 7.88 (s, 1H), 7.82 (d, J=8.5 Hz, 1H), 7.47 (d, J=8.5, 1H), 7.32 (s, 1H), 6.65 (s, 1H), 3.68 (s, 3H), 3.49 (s, 3H), 3.19 (s, 3H), 3.12 (q, J=5.1 Hz, 2H), 2.28-2.17 (m, 4H), 2.09-1.89 (m, 4H), −0.46-0.61 (m, 2H).

Examples 59-64

Unless otherwise indicated, the Examples 59-64 in the Table below were synthesized according to the procedure described for Example 58, utilizing the appropriate boronic esters or boronic acids in the introduction of R$^2$ and R$^3$ (see e.g., Scheme 1) and utilizing the appropriate acid chloride, carbamoyl chloride, or sulfonyl chloride in the introduction of R[6] (see e.g., Scheme 2). For preparation of Examples 63 and 64, the sequence of Steps 5 and 6 were performed prior to Step 4.

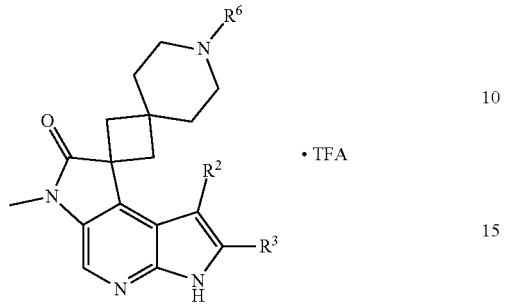

| Ex. No. | Compound Name | R[2] | R[3] | R[6] | LCMS |
|---|---|---|---|---|---|
| | | ¹H NMR | | | |
| 59 | 1″-Butyryl-6-methyl-1-(1-methyl-1H-indazol-5-yl)-2-(1-methyl-1H-pyrazol-4-yl)-3,6-dihydro-7H-dispiro[dipyrrolo[2,3-b:3′,2′-d]pyridine-8,1′-cyclobutane-3′,4″-piperidin]-7-one, trifluoroacetate salt | (1-methyl-1H-indazol-5-yl) | (1-methyl-1H-pyrazol-4-yl) | butyryl | Calculated for $C_{33}H_{37}N_8O_2$ $(M + H)^+$: m/z = 577.3, found: 577.3 |
| | ¹H NMR (500 MHz, DMSO-$d_6$) mixture of rotamers δ 12.06 (s, 1H), 12.04 (s, 1H), 8.13 (s, 1H), 8.10 (s, 1H), 7.97 (s, 2H), 7.90 (s, 1H), 7.88 (s, 1H), 7.83 (d, J = 7.1 Hz, 2H), 7.81 (s, 1H), 7.49 (s, 1H), 7.46 (s, 1H), 7.33 (s, 1H), 7.31 (s, 1H), 6.70 (s, 1H), 6.64 (s, 1H), 4.16 (s, 3H), 4.14 (s, 3H), 3.68 (d, J = 2.2 Hz, 6H), 3.18 (s, 6H), 3.13 (dd, J = 21.6, 11.0 Hz, 5H), 2.33-2.10 (m, 9H), 2.08-1.95 (m, 9H), 1.38 (m, 4H), 0.86 (t, J = 7.3 Hz, 3H), 0.81 (t, J = 7.4 Hz, 3H), −0.37−−0.45 (m, 1H), −0.58 (t, J = 5.7 Hz, 2H), −0.63−−0.70 (m, 1H). | | | | |
| 60 | N,N,6-Trimethyl-1-(1-methyl-1H-indazol-5-yl)-2-(1-methyl-1H-pyrazol-4-yl)-7-oxo-6,7-dihydro-3H-dispiro[dipyrrolo[2,3-b:3′,2′-d]pyridine-8,1′-cyclobutane-3′,4″-piperidine]-1″-carboxamide, trifluoroacetate salt | (1-methyl-1H-indazol-5-yl) | (1-methyl-1H-pyrazol-4-yl) | N,N-dimethylcarbamoyl | Calculated for $C_{32}H_{36}N_9O_2$ $(M + H)^+$: m/z = 578.3, found: 578.3 |
| | ¹H NMR (500 MHz, DMSO-$d_6$) δ 12.05 (s, 1H), 8.12 (s, 1H), 7.97 (s, 1H), 7.89 (s, 1H), 7.83 (d, J = 8.5 Hz, 1H), 7.48 (dd, J = 8.6, 1.5 Hz, 1H), 7.33 (s, 1H), 6.67 (s, 1H), 4.14 (s, 3H), 3.68 (s, 3H), 3.19 (s, 3H), 2.89-2.80 (m, 2H), 2.59 (s, 6H), 2.24 (dd, J = 19.1, 12.1 Hz, 2H), 2.07-1.98 (m, 4H), 1.93 (td, J = 6.8, 4.0 Hz, 2H), −0.41−−0.49 (m, 1H), −0.58 (ddd, J = 12.1, 7.0, 3.7 Hz, 1H). | | | | |
| 61 | Methyl 6-methyl-1-(1-methyl-1H-indazol-5-yl)-2-(1-methyl-1H-pyrazol-4-yl)-7-oxo-6,7-dihydro-3H-dispiro[dipyrrolo[2,3-b:3′,2′-d]pyridine-8,1′-cyclobutane- | (1-methyl-1H-indazol-5-yl) | (1-methyl-1H-pyrazol-4-yl) | methoxycarbonyl | Calculated for $C_{31}H_{33}N_8O_3$ $(M + H)^+$: m/z = 565.3, found: 565.3 |

| Ex. No. | Compound Name | R² | R³ | R⁶ | LCMS |
|---|---|---|---|---|---|
| | | | ¹H NMR | | |

3',4"-piperidine]-1"-carboxylate, trifluoroacetate salt

¹H NMR (500 MHz, DMSO-d₆) δ 12.05 (s, 1H), 8.12 (s, 1H), 7.97 (s, 1H), 7.89 (s, 1H), 7.83 (d, J = 8.5 Hz, 1H), 7.48 (dd, J = 8.5, 1.5 Hz, 1H), 7.33 (s, 1H), 6.65 (s, 1H), 4.15 (s, 3H), 3.68 (s, 3H), 3.50 (s, 3H), 3.19 (s, 3H), 3.13 (q, J = 5.2 Hz, 2H), 2.29-2.18 (m, 4H), 2.11-1.92 (m, 4H), −0.46-−0.60 (m, 2H).

| 62 | 1"-((2-Methoxyethyl)sulfonyl)-6-methyl-2-(1-methyl-1H-pyrazol-4-yl)-1-phenyl-3,6-dihydro-7H-dispiro[dipyrrolo[2,3-b:3',2'-d]pyridine-8,1'-cyclobutane-3',4"-piperidin]-7-one, trifluoroacetate salt | phenyl | 1-methylpyrazol-4-yl | 2-methoxyethylsulfonyl | Calculated for C₃₀H₃₅N₆O₄S (M + H)⁺: m/z = 575.2, found: 575.2 |

¹H NMR (500 MHz, DMSO-d₆) δ 12.07 (s, 1H), 7.97 (s, 1H), 7.60-7.54 (m, 3H), 7.52 (dd, J = 6.5, 3.0 Hz, 2H), 7.14 (s, 1H), 6.83 (s, 1H), 3.71 (s, 3H), 3.61 (t, J = 5.9 Hz, 2H), 3.26 (s, 3H), 3.22 (t, J = 6.0 Hz, 2H), 3.19 (s, 3H), 3.01 (t, J = 5.6 Hz, 2H), 2.58-2.53 (m, 2H), 2.33-2.26 (m, 2H), 2.21 (t, J = 5.4 Hz, 2H), 2.12-2.06 (m, 2H), −0.06 (t, J = 5.5 Hz, 2H).

| 63 | 4-(1"-Butyryl-6-methyl-1-(1-methyl-1H-indazol-5-yl)-7-oxo-6,7-dihydro-3H-dispiro[dipyrrolo[2,3-b:3',2'-d]pyridine-8,1'-cyclobutane-3',4"-piperidin]-2-yl)-N,N-dimethylcyclohex-3-ene-1-carboxamide, trifluoroacetate salt (racemic mixture prepared) | 1-methylindazol-5-yl | 4-(N,N-dimethylcarbamoyl)cyclohex-3-en-1-yl | butyryl | Calculated for C₃₈H₄₆N₇O₃ (M + H)⁺: m/z = 648.4, found: 648.4 |

¹H NMR (500 MHz, DMSO-d₆) mixture of rotamers δ 11.72 (s, 2H), 8.11 (s, 1H), 8.08 (s, 1H), 7.99 (s, 2H), 7.86 (d, J = 12.2 Hz, 1H), 7.83 (d, J = 11.3 Hz, 1H), 7.73 (d, J = 8.2 Hz, 2H), 7.71 (s, 1H), 7.49 (t, J = 7.6 Hz, 1H), 7.45 (d, J = 9.8 Hz, 1H), 5.82 (s, 1H), 5.76 (s, 1H), 4.13 (s, 3H), 4.11 (s, 3H), 3.19 (s, 6H), 2.92 (s, 6H), 2.76 (s, 6H), 2.62-2.54 (m, 2H), 2.33-1.74 (m, 27H), 1.56 (s, 2H), 1.46-1.33 (m, 5H), 1.29 (m, 1H), 1.24 (s, 1H), 1.15 (d, J = 3.2 Hz, 1H), 0.87 (t, J = 7.4 Hz, 3H), 0.82 (t, J = 7.4 Hz, 3H), −0.36-−0.75 (m, 4H).

| 64 | 1"-Butyryl-6-methyl-1-(1-methyl-1H-indazol-5-yl)-2-(1-methyl-1H-pyrrol-3-yl)-3,6-dihydro-7H-dispiro[dipyrrolo[2,3-b:3',2'-d]pyridine-8,1 cyclobutane-3',4"-piperidin]-7-one, trifluoroacetate salt | 1-methylindazol-5-yl | 1-methylindazol-5-yl | butyryl | Calculated for C₃₄H₃₈N₇O₂ (M + H)⁺: m/z = 576.3, found: 576.3 |

¹H NMR (500 MHz, DMSO-d₆) mixture of rotamers δ 11.79 (s, 1H), 11.78 (s, 1H), 8.12 (s, 1H), 8.09 (s, 1H), 7.90 (s, 2H), 7.87 (s, 1H), 7.85 (s, 1H), 7.82 (s, 1H), 7.79 (d, J = 7.7 Hz, 1H), 7.48 (s, 1H), 7.46 (d, J = 8.3Hz, 1H), 6.48 (d, J = 2.4 Hz, 2H), 6.41 (d, J = 11.6 Hz, 2H), 5.53-5.44 (m, 2H), 4.16 (s, 3H), 4.14 (s, 3H), 3.43-3.41 (m, 6H), 3.18 (s, 6H), 3.15 (s, 6H), 2.44-2.11 (m, 9H), 2.07-1.82 (m, 9H), 1.39 (m, 4H), 0.87 (t, J = 7.3 Hz, 3H), 0.82 (t, J = 7.4 Hz, 3H), −0.42 (d, J = 5.3 Hz, 1H), −0.58 (t, J = 5.7 Hz, 2H), −0.66 (s, 1H).

Examples 65 (Peak 1) and 66 (Peak 2). (R)-2-(1-((6-Methyl-1-(1-methyl-1H-indazol-5-yl)-2-(1-methyl-1H-pyrazol-4-yl)-7-oxo-6,7-dihydro-3H-spiro[dipyrrolo[2,3-b:3',2'-d]pyridine-8,3'-pyrrolidin]-1'-yl)methyl)cyclopropyl)acetonitrile (Example 65) and (S)-2-(1-((6-Methyl-1-(1-methyl-1H-indazol-5-yl)-2-(1-methyl-1H-pyrazol-4-yl)-7-oxo-6,7-dihydro-3H-spiro[dipyrrolo[2,3-b:3',2'-d]pyridine-8,3'-pyrrolidin]-1'-yl)methyl)cyclopropyl)acetonitrile (Example 66) (Single Enantiomers Isolated)

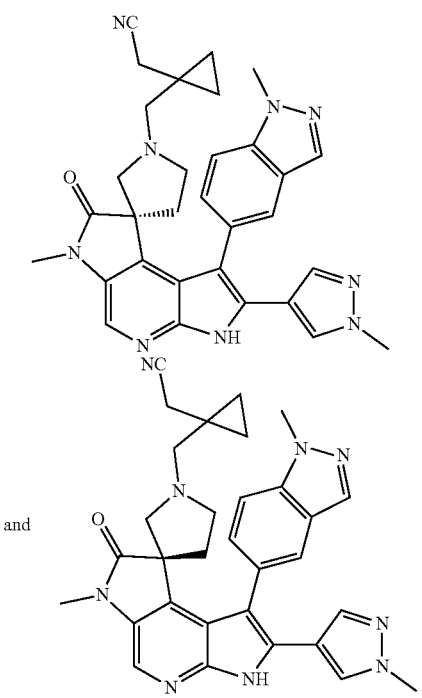

and

Step 1. tert-Butyl 6-methyl-1-(1-methyl-1H-indazol-5-yl)-7-oxo-3-(phenylsulfonyl)-6,7-dihydro-3H-spiro[dipyrrolo[2,3-b:3',2'-d]pyridine-8,3'-pyrrolidine]-1'-carboxylate (Racemic Mixture Prepared

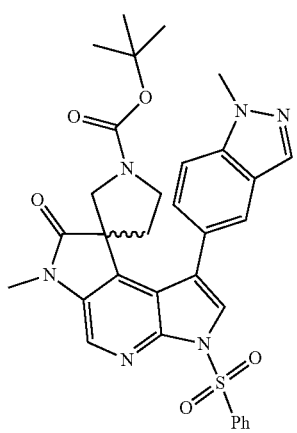 [SMILES: CN1C(=O)C2(CCN(C(=O)OC(C)(C)C)C2)c2c1cnc1c2c(-c2ccc3c(cnn3C)c2)cn1S(=O)(=O)c1ccccc1]

The title compound was prepared by a procedure analogous to that described for Example 8, Step 5, utilizing tert-butyl 1-bromo-6-methyl-7-oxo-3-(phenylsulfonyl)-6,7-dihydro-3H-spiro[dipyrrolo[2,3-b:3',2'-d]pyridine-8,3'-pyrrolidine]-1'-carboxylate (1.2 g, 2.1 mmol, from Example 12, Step 4) in place of F-bromo-6'-methyl-3'-(phenylsulfonyl)-3',6'-dihydro-7H-spiro[cyclopentane-1,8'-dipyrrolo[2,3-b:3',2'-d]pyridin]-7'-one. Purification via flash column chromatography on silica gel, eluting with a gradient of 0-100% EtOAc in hexanes, afforded the title compound (1.1 g, 83%). LCMS for $C_{32}H_{33}N_6O_5S$ (M+H)$^+$: calculated m/z=613.2; found 613.2.

Step 2. tert-Butyl 2-bromo-6-methyl-1-(1-methyl-1H-indazol-5-yl)-7-oxo-3-(phenylsulfonyl)-6,7-dihydro-3H-spiro[dipyrrolo[2,3-b:3',2'-d]pyridine-8,3'-pyrrolidine]-1'-carboxylate (Racemic Mixture Prepared)

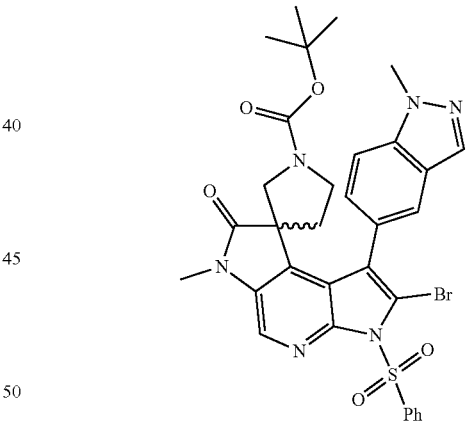

The title compound was prepared by a procedure analogous to that described for Example 8, Step 6, utilizing tert-butyl 6-methyl-1-(1-methyl-1H-indazol-5-yl)-7-oxo-3-(phenylsulfonyl)-6,7-dihydro-3H-spiro[dipyrrolo[2,3-b:3',2'-d]pyridine-8,3'-pyrrolidine]-1'-carboxylate (1.3 g, 2.7 mmol) in place of 6'-methyl-1'-(1-methyl-1H-indazol-5-yl)-3'-(phenylsulfonyl)-3',6'-dihydro-7'H-spiro[cyclopentane-1,8'-dipyrrolo[2,3-b:3',2'-d]pyridin]-7'-one. Purification via flash column chromatography on silica gel, eluting with a gradient of 0-100% EtOAc in hexanes, afforded the title compound (1.2 g, 77%). LCMS for $C_{32}H_{32}BrN_6O_5S$ (M+H)$^+$: calculated monoisotopic m/z=691.1; found 691.1.

Step 3. tert-Butyl 6-methyl-1-(1-methyl-1H-indazol-5-yl)-2-(1-methyl-1H-pyrazol-4-yl)-7-oxo-3-(phenylsulfonyl)-6,7-dihydro-3H-spiro[dipyrrolo[2,3-b:3,2'-d]pyridine-8,3'-pyrrolidine]-1'-carboxylate (Racemic Mixture Prepared)

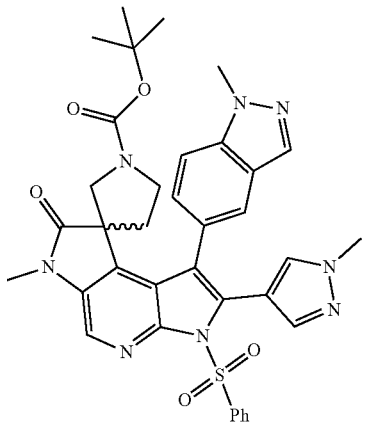

The procedure of Example 4, Step 7 was followed, using tert-butyl 2-bromo-6-methyl-1-(1-methyl-1H-indazol-5-yl)-7-oxo-3-(phenylsulfonyl)-6,7-dihydro-3H-spiro[dipyrrolo[2,3-b:3',2'-d]pyridine-8,3'-pyrrolidine]-1'-carboxylate (1.9 g, 2.7 mmol) in place of tert-butyl 2-bromo-6-methyl-7-oxo-1-phenyl-3-(phenylsulfonyl)-6,7-dihydro-3H-spiro[dipyrrolo[2,3-b:3',2'-d]pyridine-8,4'-piperidine]-1'-carboxylate, and 1-methyl-4-(4,4,5,5-tetramethyl-1,3,2-dioxaborolan-2-yl)-1H-pyrazole (0.84 g, 4.0 mmol) in place of 4-(methylsulfonyl)-1-(4-(4,4,5,5-tetramethyl-1,3,2-dioxaborolan-2-yl)benzyl)piperidine. Purification on a 100 g silica gel column, eluting with a gradient of 0-100% EtOAc in hexanes afforded the title compound (1.3 g, 71%). LCMS for $C_{36}H_{37}N_8O_5S$ (M+H)$^+$: calculated m/z=693.3; found 693.2.

Step 4. 6-Methyl-1-(1-methyl-1H-indazol-5-yl)-2-(1-methyl-1H-pyrazol-4-yl)-3-(phenylsulfonyl)-3,6-dihydro-7H-spiro[dipyrrolo[2,3-b:3',2'-d]pyridine-8,3'-pyrrolidin]-7-one (Racemic Mixture Prepared)

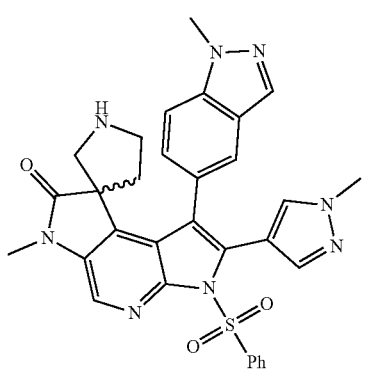

To a 40 mL vial containing tert-butyl 6-methyl-1-(1-methyl-1H-indazol-5-yl)-2-(1-methyl-1H-pyrazol-4-yl)-7-oxo-3-(phenylsulfonyl)-6,7-dihydro-3H-spiro[dipyrrolo[2,3-b:3',2'-d]pyridine-8,3'-pyrrolidine]-F-carboxylate (1.3 g, 1.9 mmol) in DCM (2.0 mL) was added TFA (1.0 mL) and the mixture was stirred at ambient temperature for 1 hour. The reaction mixture was concentrated to remove excess TFA, diluted with DCM and the organics were washed with saturated aqueous NaHCO$_3$ (3×). The organic layer was washed with brine, dried over anhydrous Na$_2$SO$_4$, filtered and concentrated in vacuo to afford the title compound (1.0 g, 89%). LCMS for $C_{31}H_{29}N_8O_3S$ (M+H)$^+$: calculated m/z=593.2; found 593.2.

Step 5. (R)-2-(1-(((6-Methyl-1-(1-methyl-1H-indazol-5-yl)-2-(1-methyl-1H-pyrazol-4-yl)-7-oxo-6,7-dihydro-3H-spiro[dipyrrolo[2,3-b:3',2'-d]pyridine-8,3'-pyrrolidin]-1'-yl)methyl)cyclopropyl)acetonitrile and (S)-2-(1-(((6-Methyl-1-(1-methyl-1H-indazol-5-yl)-2-(1-methyl-1H-pyrazol-4-yl)-7-oxo-6,7-dihydro-3H-spiro[dipyrrolo[2,3-b:3',2'-d]pyridine-8,3'-pyrrolidin]-1'-yl)methyl)cyclopropyl)acetonitrile (Single Enantiomers Isolated)

To a vial containing 6-methyl-1-(1-methyl-1H-indazol-5-yl)-2-(1-methyl-1H-pyrazol-4-yl)-3-(phenylsulfonyl)-3,6-dihydro-7H-spiro[dipyrrolo[2,3-b:3',2'-d]pyridine-8,3'-pyrrolidin]-7-one (0.010 g, 0.017 mmol) was added 2-(1-(bromomethyl)cyclopropyl)acetonitrile (29 mg, 0.17 mmol), Et$_3$N (0.030 mL, 0.22 mmol), and MeCN (0.50 mL). The resulting mixture was stirred at 80° C. for 16 h then was cooled to ambient temperature. Methanol (0.5 mL) and 3.0 N NaOH$_{(aq.)}$ (0.30 mL) were added and the mixture was heated to 55° C. After 1 hour, the reaction mixture was diluted with acetonitrile, filtered and purified via preparative HPLC-MS (pH=2) affording the title compound (4.5 mg) as a racemic mixture. The racemate was resolved via chiral preparative HPLC (i-amylose-1 column, eluted with 90% EtOH in hexanes) giving individual enantiomers as Peak 1 (RT=8.85 min, Example 65) and Peak 2 (RT=12.15 min, Example 66). LCMS for $C_{31}H_{32}N_9O$ (M+H)$^+$: calculated m/z=546.3; found 546.3. $^1$H NMR (400 MHz, DMSO-d$_6$) δ 12.25 (s, 1H), 8.15-8.09 (m, 2H), 7.97 (d, J=9.8 Hz, 1H), 7.86 (d, J=8.5 Hz, 1H), 7.53 (ddd, J=15.7, 8.5, 1.5 Hz, 1H), 7.45 (d, J=4.5 Hz, 1H), 6.98 (d, J=7.1 Hz, 1H), 4.17 (s, 3H), 3.93 (s, 3H), 3.71 (s, 3H), 3.56-3.41 (m, 1H), 3.24 (s, 2H), 2.91-2.65 (m, 2H), 2.61-2.55 (m, 2H), 2.47-1.98 (m, 2H), 1.32 (q, J=9.9 Hz, 1H), 0.69-0.55 (m, 2H), 0.53-0.01 (m, 2H).

Examples 67-69

Examples 67-69 in the following Table were synthesized according to the procedure described for Example 65, with the modification that Steps 4 and 5 (omitting the chiral separation in Step 5) were performed before Step 3, and the appropriate boronic acids or esters were used in place of 1-methyl-4-(4,4,5,5,-tetramethyl-1,3,2-dioxaborolan-2-yl)-1H-pyrazole when performing the procedure of Step 3.

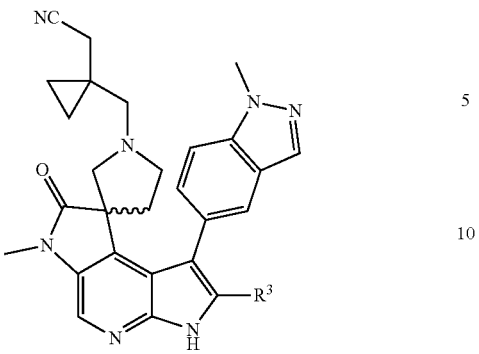

| Ex. No. | Compound Name <br> ¹H NMR | R³ | LCMS |
|---|---|---|---|
| 67 | 2-(1-((6-Methyl-1-(1-methyl-1H-indazol-5-yl)-7-oxo-2-(3-oxo-3,4-dihydro-2H-benzo[b][1,4]oxazin-7-yl)-6,7-dihydro-3H-spiro[dipyrrolo[2,3-b:3',2'-d]pyridine-8,3'-pyrrolidin]-1'-yl)methyl)cyclopropyl) acetonitrile, trifluoroacetate salt (racemic mixture prepared) | 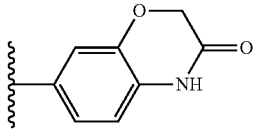 [SMILES: *c1ccc2c(c1)OCC(=O)N2] | Calculated for $C_{35}H_{33}N_8O_3$ $(M + H)^+$: m/z = 613.3, found: 613.2 |

¹H NMR (600 MHz, DMSO-d₆) δ 12.33 (s, 1H), 10.75 (s, 1H), 8.19(s, 1H), 8.16-8.06 (m, 1H), 8.03-7.89 (m, 1H), 7.81 (dd, J = 15.7, 8.6 Hz, 1H), 7.65-7.45 (m, 1H), 6.96-6.92 (m, 1H), 6.91 (s, 1H), 6.70 (dd, J= 8.2, 2.2 Hz, 1H), 4.49 (s, 2H), 4.16 (s, 3H), 3.89 (s, 1H), 3.57-3.40 (m, 2H), 3.25 (s, 3H), 2.74 (d, J = 11.6 Hz, 1H), 2.65-2.56 (m, 2H), 2.34-2.17 (m, 2H), 1.90 (d, J = 13.5 Hz, 1H), 1.45-1.30 (m, 1H), 0.68-0.45 (m, 4H).

| 68 | 2-(1-((6-Methyl-1-(1-methyl-1H-indazol-5-yl)-7-oxo-2-(pyrazolo[1,5-a]pyrimidin-3-yl)-6,7-dihydro-3H-spiro[dipyrrolo[2,3-b:3',2'-d]pyridine-8,3'-pyrrolidin]-1'-yl)methyl)cyclopropyl)acetonitrile, trifluoroacetate salt (racemic mixture prepared) | 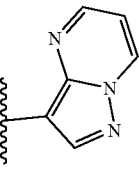 [SMILES: *c1cnn2cccnc12] | Calculated for $C_{33}H_{31}N_{10}O$ $(M + H)^+$: m/z = 583.3, found: 583.3 |

¹H NMR (600 MHz, DMSO-d₆) δ 11.61 (s, 1H), 9.14 (dd, J = 7.0, 1.6 Hz, 1H), 8.75 (dd, J = 4.0, 1.7 Hz, 1H), 8.17 (s, 1H), 8.16-8.09 (m, 1H), 8.07-8.02 (m, 1H), 7.86 (dd, J = 8.5, 3.2 Hz, 1H), 7.66-7.57 (m, 1H), 7.20-7.14 (m, 2H), 4.16 (d, J = 7.5 Hz, 3H), 3.27 (s, 3H), 2.92 (d, 11.7 Hz, 1H), 2.77 (d, J = 11.7 Hz, 1H), 2.40-2.24 (m, 4H), 2.09 (d, J = 13.5 Hz, 1H), 1.64 (d, J = 13.5 Hz, 1H), 1.42-1.24 (m, 2H), 0.68-0.43 (m, 2H), 0.36-0.18 (m, 2H).

| 69 | 4-((4-(1'-((1-(Cyanomethyl)cyclopropyl)methyl)-6-methyl-1-(1-methyl-1H-indazol-5-yl)-7-oxo-6,7-dihydro-3H-spiro[dipyrrolo[2,3-b:3',2'-d]pyridine-8,3'-pyrrolidin]-2-yl)-1H-pyrazol-1-yl)methyl)benzonitrile, trifluoroacetate salt (racemic mixture prepared) | 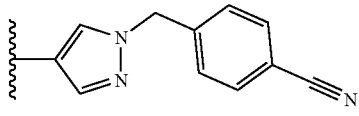 [SMILES: *c1cnn(Cc2ccc(C#N)cc2)c1] | Calculated for $C_{38}H_{35}N_{10}O$ $(M + H)^+$: m/z = 647.3, found: 647.3 |

¹H NMR (600 MHz, DMSO-d₆) δ 12.28 (s, 1H), 8.17-8.07 (m, 2H), 7.98-7.92 (m, 1H), 7.84 (dd, J = 8.6, 2.8 Hz, 1H), 7.79-7.74 (m, 2H), 7.56-7.47 (m, 2H), 7.25 (d, J = 8.1 Hz, 2H), 7.09 (d, J = 9.0 Hz, 1H), 5.34 (s, 2H), 4.17 (s, 3H), 3.99-3.89 (m, 1H), 3.58-3.43 (m, 1H), 3.24 (s, 3H), 2.87 (d, J = 11.8 Hz, 1H), 2.72-2.63 (m, 1H), 2.48-2.36 (m, 2H), 2.36-2.19 (m, 1H), 2.05 (d, J = 13.5 Hz, 1H), 1.59 (d, J = 13.5 Hz, 1H), 1.33 (q, J = 9.9 Hz, 1H), 0.72-0.54 (m, 2H), 0.53--0.03 (m, 2H).

Example 70. 2-(2-(((6-Methyl-1-(1-methyl-1H-indazol-5-yl)-2-(1-methyl-1H-pyrazol-4-yl)-7-oxo-6,7-dihydro-3H-spiro[dipyrrolo[2,3-b:3',2'-d]pyridine-8,3'-pyrrolidin]-1'-yl)methyl)spiro[3.3]heptan-2-yl)acetonitrile (Racemic Mixture Prepared)

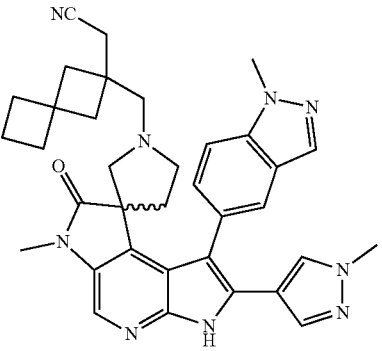 [SMILES: CN1C(=O)C2(CCN(CC3(CC#N)CC4(CCC4)C3)C2)c2c1cnc1[nH]c(-c3cnn(C)c3)c(-c3ccc4c(cnn4C)c3)c21]

Step 1: (2-(Cyanomethyl)spiro[3.3]heptan-2-yl)methyl 4-methylbenzenesulfonate

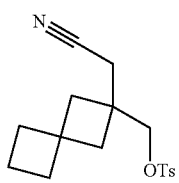 [SMILES: Cc1ccc(S(=O)(=O)OCC2(CC#N)CC3(CCC3)C2)cc1]

To a solution of spiro[3.3]heptane-2,2-diylbis(methylene)bis(4-methylbenzenesulfonate) (0.75 g, 1.6 mmol, prepared as described in Angewandte Chemie, International Edition in English (1996), 35(18), 2137-2139) in DMSO (6.0 mL) was added NaCN (0.079 g, 1.6 mmol). The resulting mixture was stirred at 80° C. for 16 hours. After cooling to ambient temperature, the reaction mixture was diluted with ethyl acetate (25 mL). The organic phase was washed with water (10 mL×3), brine (10 mL), dried over $Na_2SO_4$, filtered, and concentrated in vacuo. Purification of the crude residue on silica gel, eluting with 1:5:14 EtOAc:DCM:hexanes afforded the title compound (0.35 g, 68%). LCMS for $C_{17}H_{21}NO_3SNa$ (M+Na)$^+$: calculated m/z=342.1; found 342.1.

Step 2. 2-(2-(((6-Methyl-1-(1-methyl-1H-indazol-5-yl)-2-(1-methyl-1H-pyrazol-4-yl)-7-oxo-6,7-dihydro-3H-spiro[dipyrrolo[2,3-b:3',2'-d]pyridine-8,3'-pyrrolidin]-1'-yl)methyl)spiro[3.3]heptan-2-yl)acetonitrile (Racemic Mixture Prepared)

The procedure of Example 65 was followed, using (2-(cyanomethyl)spiro[3.3]heptan-2-yl)methyl 4-methylbenzenesulfonate in place of 2-(1-(bromomethyl)cyclopropyl)acetonitrile in Step 5, omitting the chiral separation step, and purification via preparative HPLC-MS (pH=10) to afford the title compound as the racemate. LCMS for $C_{35}H_{38}N_9O$ (M+H)$^+$: calculated m/z=600.3; found 600.3.

Example 71. 2-(1-(((6-Methyl-1-(1-methyl-1H-indazol-5-yl)-2-(1-methyl-1H-pyrazol-4-yl)-7-oxo-6,7-dihydro-3H-spiro[dipyrrolo[2,3-b:3',2'-d]pyridine-8,3'-pyrrolidin]-1'-yl)sulfonyl)cyclopropyl)acetonitrile, trifluoroacetate salt (Racemic Mixture Prepared)

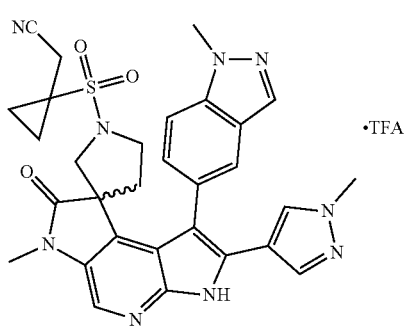 [SMILES: CN1C(=O)C2(CCN(S(=O)(=O)C3(CC#N)CC3)C2)c2c1cnc1[nH]c(-c3cnn(C)c3)c(-c3ccc4c(cnn4C)c3)c21]

Step 1. 1'-((1-(Chloromethyl)cyclopropyl)sulfonyl)-6-methyl-1-(1-methyl-1H-indazol-5-yl)-2-(1-methyl-1H-pyrazol-4-yl)-3-(phenylsulfonyl)-3,6-dihydro-7H-spiro[dipyrrolo[2,3-b:3',2'-d]pyridine-8,3'-pyrrolidin]-7-one (Racemic Mixture Prepared).

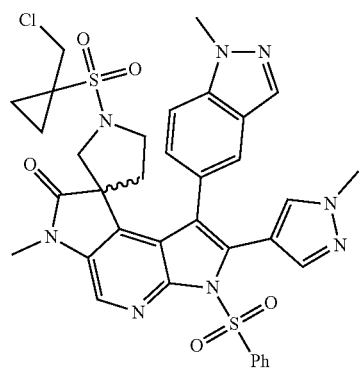

To a 1 dram vial containing 6-methyl-1-(1-methyl-1H-indazol-5-yl)-2-(1-methyl-1H-pyrazol-4-yl)-3-(phenylsulfonyl)-3,6-dihydro-7H-spiro[dipyrrolo[2,3-b:3',2'-d]pyridine-8,3'-pyrrolidin]-7-one (from Example 65, Step 4, 0.10 g, 0.17 mmol) was added DCM (2.0 mL), Et$_3$N (0.050 mL, 0.36 mmol) and 1-(chloromethyl)cyclopropane-1-sulfonyl chloride (0.050 g, 0.26 mmol, Enamine EN300-1700646). The resulting mixture was stirred for 4 hours at ambient temperature then was concentrated in vacuo and directly purified on silica gel, eluting with a gradient of 50-100% EtOAc in hexanes to afford the title compound (0.12 g, 91%). LCMS for $C_{35}H_{34}ClN_8O_5S_2$ (M+H)$^+$: calculated m/z=745.2; found 745.1.

235

Step 2. 1'-((1-(Iodomethyl)cyclopropyl)sulfonyl)-6-methyl-1-(1-methyl-1H-indazol-5-yl)-2-(1-methyl-1H-pyrazol-4-yl)-3-(phenylsulfonyl)-3,6-dihydro-7H-spiro[dipyrrolo[2,3-b:3',2'-d]pyridine-8,3'-pyrrolidin]-7-one (Racemic Mixture Prepared)

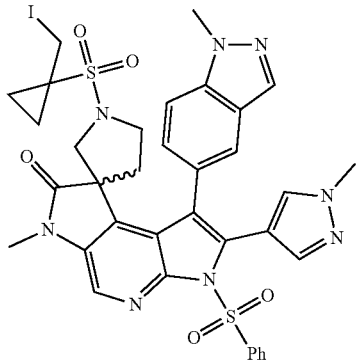 [SMILES: CN1C(=O)C2(CCN(S(=O)(=O)C3(CI)CC3)C2)c2c1cnc1c2c(-c2ccc3c(cnn3C)c2)c(-c2cnn(C)c2)n1S(=O)(=O)c1ccccc1]

To a 1 dram vial containing 1'-((1-(chloromethyl)cyclopropyl)sulfonyl)-6-methyl-1-(1-methyl-1H-indazol-5-yl)-2-(1-methyl-1H-pyrazol-4-yl)-3-(phenylsulfonyl)-3,6-dihydro-7H-spiro[dipyrrolo[2,3-b:3',2'-d]pyridine-8,3'-pyrrolidin]-7-one (0.030 g, 0.040 mmol) was added methyl vinyl ketone (1.0 mL) and NaI (0.050 g, 0.33 mmol). The resulting mixture was stirred at 80° C. for 16 hours, cooled to room temperature, filtered and concentrated in vacuo to afford the title compound (0.034 g, 99%). LCMS for $C_{35}H_{34}IN_8O_5S_2$ (M+H)$^+$: calculated m/z=837.1; found 837.1.

Step 3. 2-(1-((6-Methyl-1-(1-methyl-1H-indazol-5-yl)-2-(1-methyl-1H-pyrazol-4-yl)-7-oxo-6,7-dihydro-3H-spiro[dipyrrolo[2,3-b:3',2'-d]pyridine-8,3'-pyrrolidin]-1'-yl)sulfonyl)cyclopropyl)acetonitrile, trifluoroacetate salt (Racemic Mixture Prepared)

To a 1 dram vial containing 1'-((1-(iodomethyl)cyclopropyl)sulfonyl)-6-methyl-1-(1-methyl-1H-indazol-5-yl)-2-(1-methyl-1H-pyrazol-4-yl)-3-(phenylsulfonyl)-3,6-dihydro-7H-spiro[dipyrrolo[2,3-b:3',2'-d]pyridine-8,3'-pyrrolidin]-7-one (0.015 g, 0.018 mmol) was added DMSO (0.50 mL) and NaCN (0.025 g, 0.51 mmol). The resulting mixture was stirred at 45° C. for 4 hours then MeOH (0.50 mL) and 3.0 N NaOH$_{(aq.)}$ (0.30 mL) were added and the mixture was heated to 55° C. After 1 hour, the reaction mixture was diluted with acetonitrile, filtered and purified via preparative HPLC-MS (pH=2) affording the title compound (7.2 mg). LCMS for $C_{30}H_{30}N_9O_3S$ (M+H)$^+$: calculated m/z=596.2; found 596.2. $^1$H NMR (600 MHz, DMSO-d$_6$) δ 12.13 (s, 1H), 8.09-8.00 (m, 2H), 7.83-7.67 (m, 2H), 7.50-7.32 (m, 2H), 7.22-7.02 (m, 1H), 4.10 (s, 3H), 3.72 (s, 3H), 3.47-3.37 (m, 2H), 3.32 (dd, J=9.9, 7.2 Hz, 1H), 3.19 (s, 3H), 3.13-3.00 (m, 1H), 2.95-2.78 (m, 1H), 2.61-2.26 (m, 1H), 2.21 (ddd, J=13.8, 11.0, 6.9 Hz, 1H), 2.06-1.90 (m, 1H), 1.15-1.00 (m, 2H), 1.00-0.84 (m, 2H).

236

Example 72. 2-(1-((6-Methoxy-1-(1-methyl-1H-indazol-5-yl)-2-(1-methyl-1H-pyrazol-4-yl)-7-oxo-6,7-dihydro-3H-spiro[dipyrrolo[2,3-b:3',2'-d]pyridine-8,3'-pyrrolidin]-1'-yl)methyl)cyclopropyl)acetonitrile, trifluoroacetate salt (Racemic Mixture Prepared)

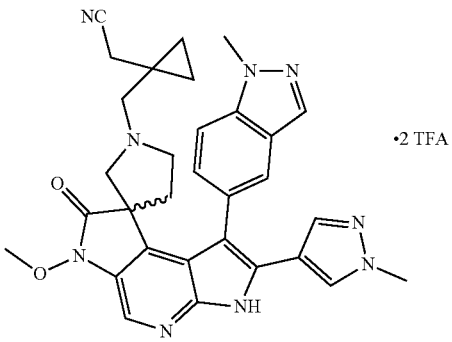

Step 1. tert-Butyl 6-hydroxy-7-oxo-3-(phenylsulfonyl)-6,7-dihydro-3H-spiro[dipyrrolo[2,3-b:3',2'-d]pyridine-8,3'-pyrrolidine]-1'-carboxylate (Racemic Mixture Prepared)

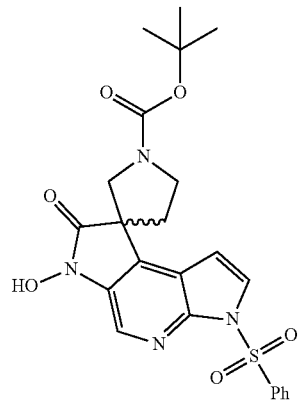 [SMILES: CC(C)(C)OC(=O)N1CCC2(C1)C(=O)N(O)c1cnc3c(ccn3S(=O)(=O)c3ccccc3)c12]

The title compound was prepared in a manner analogous to Example 8, Step 2, using 1-(tert-butyl) 3-ethyl 3-(5-nitro-1-(phenylsulfonyl)-1H-pyrrolo[2,3-b]pyridin-4-yl)pyrrolidine-1,3-dicarboxylate (7.7 g, 14 mmol) in place of methyl 1-(5-nitro-1-(phenylsulfonyl)-1H-pyrrolo[2,3-b]pyridin-4-yl)cyclopentane-1-carboxylate and the reaction was heated at 60° C. for 2 hours instead of 4 hours. Purification via flash column chromatography on silica gel, eluting with a gradient of 10-80% EtOAc in hexanes, afforded the title compound and the compound described in Example 12, step 2 in a ~1:3 ratio (2.1 g). LCMS for $C_{23}H_{25}N_4O_6S$ (M+H)$^+$: calculated m/z=485.1; found 485.1.

Step 2. tert-Butyl 6-methoxy-7-oxo-3-(phenylsulfonyl)-6,7-dihydro-3H-spiro[dipyrrolo[2,3-b:3',2'-d]pyridine-8,3'-pyrrolidine]-1'-carboxylate (Racemic Mixture Prepared)

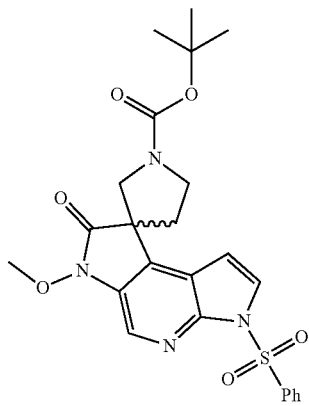 [SMILES: CON1C(=O)C2(CCN(C(=O)OC(C)(C)C)C2)c2c1cnc1c2ccn1S(=O)(=O)c1ccccc1]

This compound was prepared by a procedure analogous to that described for Example 8, Step 3, utilizing a ~1:3 mixture of tert-butyl 6-hydroxy-7-oxo-3-(phenylsulfonyl)-6,7-dihydro-3H-spiro[dipyrrolo[2,3-b:3',2'-d]pyridine-8,3'-pyrrolidine]-1'-carboxylate and tert-butyl 7-oxo-3-(phenylsulfonyl)-6,7-dihydro-3H-spiro[dipyrrolo[2,3-b:3',2'-d]pyridine-8,3'-pyrrolidine]-1'-carboxylate (2.1 g of mixture from Step 1 of this Example) in place of 3'-(phenylsulfonyl)-3',6'-dihydro-7'H-spiro[cyclopentane-1,8'-dipyrrolo[2,3-b:3',2'-d]pyridin]-7'-one. Purification via flash column chromatography on silica gel, eluting with a gradient of 10-60% EtOAc in hexanes, afforded the title compound (0.41 g). LCMS for $C_{24}H_{27}N_4O_6S$ (M+H)$^+$: calculated m/z=499.2; found 499.1.

Step 3. tert-Butyl 1-bromo-6-methoxy-7-oxo-3-(phenylsulfonyl)-6,7-dihydro-3H-spiro[dipyrrolo[2,3-b:3',2'-d]pyridine-8,3'-pyrrolidine]-1'-carboxylate (Racemic Mixture Prepared)

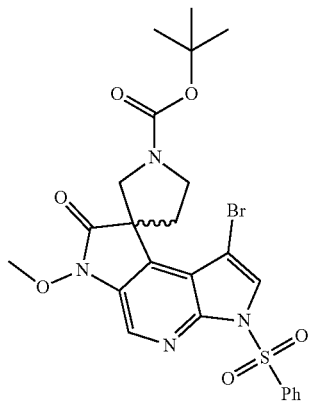 [SMILES: CON1C(=O)C2(CCN(C(=O)OC(C)(C)C)C2)c2c1cnc1c2c(Br)cn1S(=O)(=O)c1ccccc1]

The title compound was prepared by a procedure analogous to that described for Example 8, Step 4, utilizing tert-butyl 6-methoxy-7-oxo-3-(phenylsulfonyl)-6,7-dihydro-3H-spiro[dipyrrolo[2,3-b:3',2'-d]pyridine-8,3'-pyrrolidine]-1'-carboxylate (0.41 g, 0.81 mmol) in place of 6'-methyl-3'-(phenylsulfonyl)-3',6'-dihydro-7'H-spiro[cyclopentane-1,8'-dipyrrolo[2,3-b:3',2'-d]pyridin]-7'-one. Purification via flash column chromatography on silica gel, eluting with a gradient of 10-60% EtOAc in hexanes, afforded the title compound (0.45 g, 96%). LCMS for $C_{24}H_{26}BrN_4O_6S$ (M+H)$^+$: calculated monoisotopic m/z=577.1; found 577.0.

Step 4. tert-Butyl 6-methoxy-1-(1-methyl-1H-indazol-5-yl)-7-oxo-3-(phenylsulfonyl)-6,7-dihydro-3H-spiro[dipyrrolo[2,3-b:3',2'-d]pyridine-8,3'-pyrrolidine]-1'-carboxylate (Racemic Mixture Prepared)

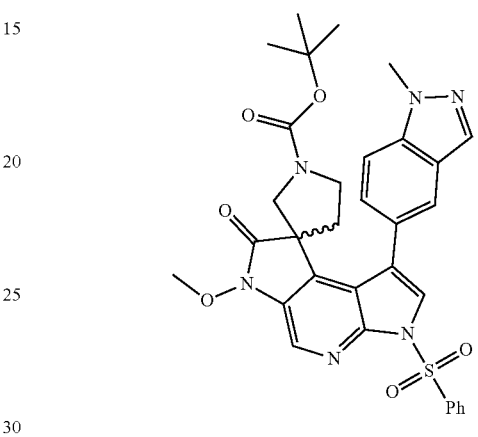

The title compound was prepared by a procedure analogous to that described for Example 8, Step 5, utilizing tert-butyl 1-bromo-6-methoxy-7-oxo-3-(phenylsulfonyl)-6,7-dihydro-3H-spiro[dipyrrolo[2,3-b:3',2'-d]pyridine-8,3'-pyrrolidine]-1'-carboxylate (0.45 g, 0.78 mmol) in place of 1'-bromo-6'-methyl-3'-(phenylsulfonyl)-3',6'-dihydro-7'H-spiro[cyclopentane-1,8'-dipyrrolo[2,3-b:3',2'-d]pyridin]-7'-one. Purification via flash column chromatography on silica gel, eluting with a gradient of 0-100% EtOAc in hexanes, afforded the title compound (0.35 g, 71%). LCMS for $C_{32}H_{33}N_6O_6S$ (M+H)$^+$: calculated m/z=629.2; found 629.2.

Step 5. tert-Butyl 2-bromo-6-methoxy-1-(1-methyl-1H-indazol-5-yl)-7-oxo-3-(phenylsulfonyl)-6,7-dihydro-3H-spiro[dipyrrolo[2,3-b:3',2'-d]pyridine-8,3'-pyrrolidine]-1'-carboxylate (Racemic Mixture Prepared)

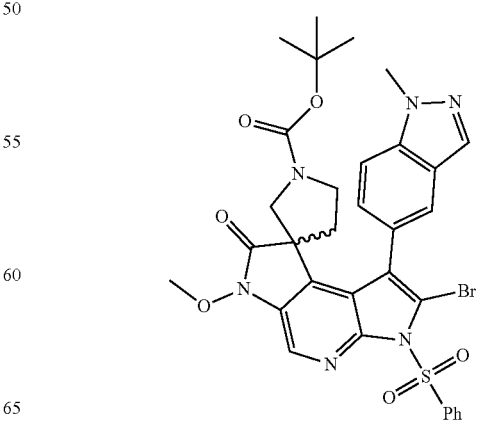

The title compound was prepared by a procedure analogous to that described for Example 8, Step 6, utilizing tert-butyl 6-methoxy-1-(1-methyl-1H-indazol-5-yl)-7-oxo-3-(phenyl sulfonyl)-6,7-dihydro-3H-spiro[dipyrrolo[2,3-b:3',2'-d]pyridine-8,3'-pyrrolidine]-1'-carboxylate (0.35 g, 0.56 mmol) in place of 6'-methyl-1'-(1-methyl-1H-indazol-5-yl)-3'-(phenyl sulfonyl)-3',6'-dihydro-7'H-spiro[cyclopentane-1,8'-dipyrrolo[2,3-b:3',2'-d]pyridin]-7'-one. Purification via flash column chromatography on silica gel, eluting with a gradient of 0-100% EtOAc in hexanes, afforded the title compound (0.28 g, 71%). LCMS for $C_{32}H_{32}BrN_6O_6S$ (M+H)+: calculated monoisotopic m/z=707.1; found 707.1.

Step 6. tert-Butyl 6-methoxy-1-(1-methyl-1H-indazol-5-yl)-2-(1-methyl-1H-pyrazol-4-yl)-7-oxo-3-(phenylsulfonyl)-6,7-dihydro-3H-spiro[dipyrrolo[2,3-b:3',2'-d]pyridine-8,3'-pyrrolidine]-1'-carboxylate (Racemic Mixture Prepared)

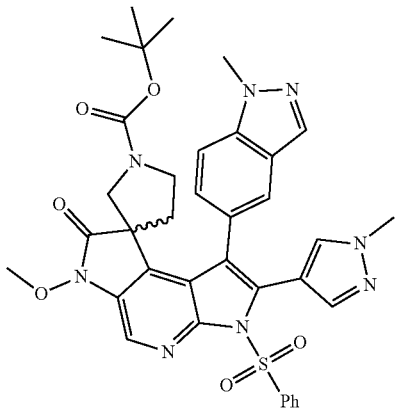

The procedure of Example 4, Step 7 was followed, using tert-butyl 2-bromo-6-methoxy-1-(1-methyl-1H-indazol-5-yl)-7-oxo-3-(phenylsulfonyl)-6,7-dihydro-3H-spiro[dipyrrolo[2,3-b:3',2'-d]pyridine-8,3'-pyrrolidine]-1'-carboxylate (0.28 g, 0.40 mmol) in place of tert-butyl 2-bromo-6-methyl-7-oxo-1-phenyl-3-(phenylsulfonyl)-6,7-dihydro-3H-spiro[dipyrrolo[2,3-b:3',2'-d]pyridine-8,4'-piperidine]-1'-carboxylate, and 1-methyl-4-(4,4,5,5-tetramethyl-1,3,2-dioxaborolan-2-yl)-1H-pyrazole (0.12 g, 0.59 mmol) in place of 4-(methylsulfonyl)-1-(4-(4,4,5,5-tetramethyl-1,3,2-dioxaborolan-2-yl)benzyl)piperidine. Purification on silica gel, eluting with a gradient of 0-100% EtOAc in hexanes afforded the title compound (0.11 g, 39%). LCMS for $C_{36}H_{37}N_8O_6S$ (M+H)+: calculated m/z=709.3; found 709.2.

Step 7. 6-Methoxy-1-(1-methyl-1H-indazol-5-yl)-2-(1-methyl-1H-pyrazol-4-yl)-3-(phenylsulfonyl)-3,6-dihydro-7H-spiro[dipyrrolo[2,3-b:3',2'-d]pyridine-8,3'-pyrrolidin]-7-one (Racemic Mixture Prepared)

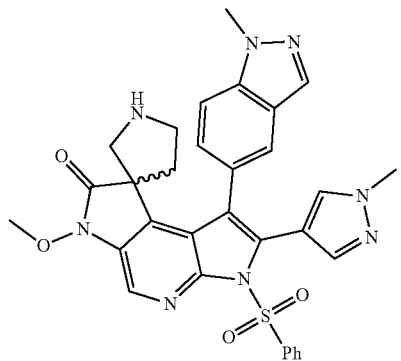

The procedure of Example 65, Step 4 was followed, using tert-butyl 6-methoxy-1-(1-methyl-1H-indazol-5-yl)-2-(1-methyl-1H-pyrazol-4-yl)-7-oxo-3-(phenylsulfonyl)-6,7-dihydro-3H-spiro[dipyrrolo[2,3-b:3',2'-d]pyridine-8,3'-pyrrolidine]-1'-carboxylate (0.11 g, 0.16 mmol) in place of tert-butyl 6-methyl-1-(1-methyl-1H-indazol-5-yl)-2-(1-methyl-1H-pyrazol-4-yl)-7-oxo-3-(phenylsulfonyl)-6,7-dihydro-3H-spiro[dipyrrolo[2,3-b:3',2'-d]pyridine-8,3'-pyrrolidine]-1'-carboxylate to afford the title compound (0.090 g, 95%). LCMS for $C_{31}H_{29}N_8O_4S$ (M+H)+: calculated m/z=609.2; found 609.2.

Step 8. 2-(1-((6-Methoxy-1-(1-methyl-1H-indazol-5-yl)-2-(1-methyl-1H-pyrazol-4-yl)-7-oxo-6,7-dihydro-3H-spiro[dipyrrolo[2,3-b:3',2'-d]pyridine-8,3'-pyrrolidin]-1'-yl)methyl)cyclopropyl)acetonitrile, trifluoroacetate salt (Racemic Mixture Prepared)

The procedure of Example 65, Step 5 was followed, using 6-methoxy-1-(1-methyl-1H-indazol-5-yl)-2-(1-methyl-1H-pyrazol-4-yl)-3-(phenylsulfonyl)-3,6-dihydro-7H-spiro[dipyrrolo[2,3-b:3',2'-d]pyridine-8,3'-pyrrolidin]-7-one (0.015 g, 0.025 mmol) in place of 6-methyl-1-(1-methyl-1H-indazol-5-yl)-2-(1-methyl-1H-pyrazol-4-yl)-3-(phenylsulfonyl)-3,6-dihydro-7H-spiro[dipyrrolo[2,3-b:3',2'-d]pyridine-8,3'-pyrrolidin]-7-one, and the chiral separation step was not performed. Purification via preparative HPLC-MS (pH=2) afforded the title compound as the 2×TFA salt (5.1 mg). LCMS for $C_{31}H_{29}N_8O_3S$ (M+H)+: calculated m/z=593.2; found 593.2. LCMS for $C_{31}H_{32}N_9O_2$ (M+H)+: calculated m/z=562.3; found 562.2. 1H NMR (600 MHz, DMSO-$d_6$) δ 12.06 (s, 1H), 10.75 (s, 1H), 8.17-8.05 (m, 1H), 7.95-7.88 (m, 1H), 7.84 (d, J=8.5 Hz, 1H), 7.54-7.44 (m, 1H), 7.35 (d, J=6.8 Hz, 1H), 6.92 (d, J=9.9 Hz, 1H), 4.16 (s, 3H), 4.01 (s, 3H), 3.69 (s, 3H), 3.11 (qd, J=7.3, 4.8 Hz, 1H), 2.79 (d, J=11.6 Hz, 1H), 2.68-2.54 (m, 2H), 2.43-1.95 (m, 2H), 1.60 (d, J=13.4 Hz, 1H), 1.37-1.22 (m, 2H), 1.18 (t, J=7.3 Hz, 1H), 0.68-0.51 (m, 2H), 0.49-0.05 (m, 2H).

Example 73. 2-(1-(6-Methyl-1-(1-methyl-1H-indazol-5-yl)-2-(1-methyl-1H-pyrazol-4-yl)-7-oxo-6,7-dihydro-3H-spiro[dipyrrolo[2,3-b:3',2'-d]pyridine-8,4'-piperidin]-1'-yl)cyclopentyl)acetonitrile, trifluoroacetate salt

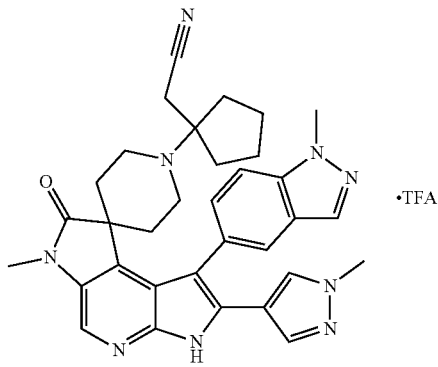

Step 1. 2'-Bromo-6'-methyl-1'-(1-methyl-1H-indazol-5-yl)-3'-(phenylsulfonyl)-3',6'-dihydro-7'H-spiro[cyclopentane-1,8'-dipyrrolo[2,3-b:3',2'-d]pyridin]-3-en-7'-one

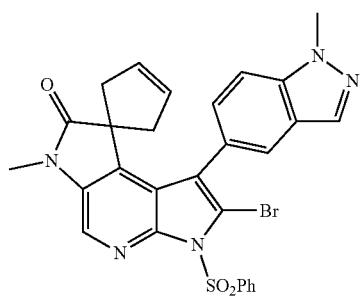

This compound was prepared in the manner of Example 1, Steps 2 through 7, utilizing methyl cyclopent-3-ene-1-carboxylate (Combi-Blocks, OS-7827) in place of methyl tetrahydro-2H-pyran-4-carboxylate in Step 2; and utilizing (1-methyl-1H-indazol-5-yl)boronic acid instead of phenylboronic acid in Step 7. LCMS for $C_{28}H_{23}BrN_5O_3S$ (M+H)$^+$: calculated monoisotopic m/z=588.1; found 588.0.

Step 2. 6'-Methyl-1'-(1-methyl-1H-indazol-5-yl)-2'-(1-methyl-1H-pyrazol-4-yl)-3'-(phenylsulfonyl)-3',6'-dihydro-7'H-spiro[cyclopentane-1,8'-dipyrrolo[2,3-b:3',2'-c]pyridin]-3-en-7'-one

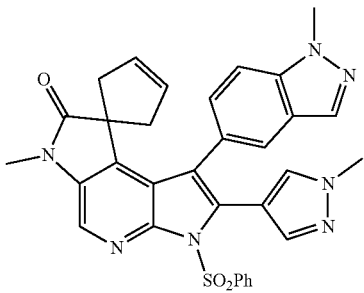

To a solution of 2'-bromo-6'-methyl-1'-(1-methyl-1H-indazol-5-yl)-3'-(phenylsulfonyl)-3',6'-dihydro-7'H-spiro [cyclopentane-1,8'-dipyrrolo[2,3-b:3',2'-d]pyridin]-3-en-7'-one (0.45 g, 0.77 mmol) in dioxane (6.0 mL) and water (1.5 mL) was added 1-methyl-4-(4,4,5,5-tetramethyl-1,3,2-dioxaborolan-2-yl)-1H-pyrazole (0.32 g, 1.5 mmol), [1,1'-bis(diphenylphosphino)ferrocene]dichloropalladium(II) (0.13 g, 0.15 mmol) and Cs$_2$CO$_3$ (0.75 g, 2.3 mmol). N$_2$ was bubbled through the reaction mixture for 1 minute then it was stirred at 90° C. for 1 hour. After this time, it was cooled to r.t., water was removed and the organic layer was concentrated to dryness. The residue was purified by silica gel chromatography using 0-10% MeOH in DCM to afford the desired product. LCMS for $C_{32}H_{28}N_7O_3S$ (M+H)$^+$: calculated m/z=590.2; found 590.1.

Step 3. 2,2'-(6-Methyl-1-(1-methyl-1H-indazol-5-yl)-2-(1-methyl-1H-pyrazol-4-yl)-7-oxo-3-(phenylsulfonyl)-3,6,7,8-tetrahydrodipyrrolo[2,3-b:3',2'-d]pyridine-8,8-diyl)diacetaldehyde

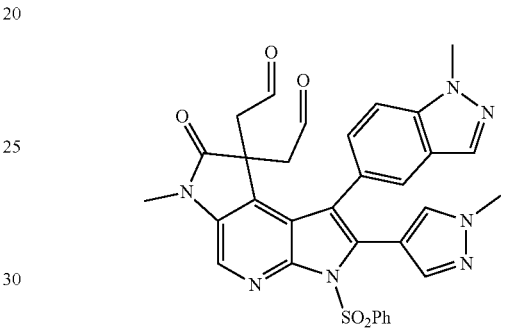

To a solution of 6'-methyl-1'-(1-methyl-1H-indazol-5-yl)-2'-(1-methyl-1H-pyrazol-4-yl)-3'-(phenylsulfonyl)-3',6'-dihydro-7'H-spiro[cyclopentane-1,8'-dipyrrolo[2,3-b:3',2'-d]pyridin]-3-en-7'-one (270 mg, 0.46 mmol) in THF (6.0 mL) and water (4.0 mL) was added sodium periodate (490 mg, 2.3 mmol) and potassium osmate dihydrate (34 mg, 0.092 mmol) then the reaction mixture was stirred at 35° C. for 15 hours. After this time, it was diluted with DCM and then washed with water twice. The organic layer was dried over MgSO$_4$, filtered and then concentrated to dryness. The residue was used in the next step without purification. LCMS for $C_{32}H_{28}N_7O_5S$ (M+H)$^+$: calculated m/z=622.2; found 622.1.

Step 4. 2-(1-(6-Methyl-1-(1-methyl-1H-indazol-5-yl)-2-(1-methyl-1H-pyrazol-4-yl)-7-oxo-6,7-dihydro-3H-spiro[dipyrrolo[2,3-b:3',2'-c]pyridine-8,4'-piperidin]-1'-yl)cyclopentyl)acetonitrile, trifluoroacetate salt To a solution of 2,2'-(6-methyl-1-(1-methyl-1H-indazol-5-yl)-2-(1-methyl-1H-pyrazol-4-yl)-7-oxo-3-(phenylsulfonyl)-3,6,7,8-tetrahydrodipyrrolo[2,3-b:3',2'-d]pyridine-8,8-diyl)diacetaldehyde (0.030 g, 0.048 mmol, Example 73, Step 3) in acetonitrile (5.0 mL) was added 2-(1-aminocyclopentyl)acetonitrile (6.0 mg, 0.048 mmol, Astatech Inc, F30400) and trifluoroacetic acid (0.020 mL). The reaction mixture was then allowed to stir at ambient temperature for 15 hours followed by the addition of sodium triacetoxyborohydride (61 mg, 0.29 mmol) and trifluoroacetic acid (0.10 mL). The resulting solution was stirred at r.t. for 30 minutes, then was concentrated to dryness. The residue was dissolved in MeOH and purified via preparative HPLC-MS (pH=10). The obtained intermediate was then dissolved in MeOH (2.0 mL) and THF (1.0 mL) and 4.0 N NaOH (1.0 mL) was added and the reaction mixture was stirred at 50° C. for 1 hour. After this time, it was cooled to r.t., diluted with MeCN, filtered and purified by preparative HPLC-MS (pH=2) to afford the title compound as a TFA salt. LCMS for $C_{33}H_{36}N_9O$ (M+H)$^+$: calculated m/z=574.3; found 574.2.

Example 74. 2-(1-(6-Methyl-1-(1-methyl-1H-indazol-5-yl)-2-(1-methyl-1H-pyrazol-4-yl)-7-oxo-6,7-dihydro-1'H,3H-spiro[dipyrrolo[2,3-b:3',2'-d]pyridine-8,4'-pyridin]-1'-yl)cyclopropyl)acetonitrile, trifluoroacetate salt

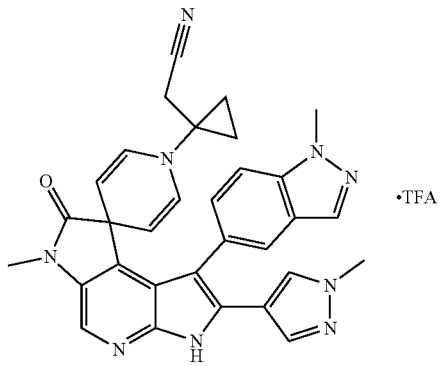

To a solution of 2,2'-(6-methyl-1-(1-methyl-1H-indazol-5-yl)-2-(1-methyl-1H-pyrazol-4-yl)-7-oxo-3-(phenylsulfonyl)-3,6,7,8-tetrahydrodipyrrolo[2,3-b:3',2'-d]pyridine-8,8-diyl)diacetaldehyde (0.030 g, 0.048 mmol, Example 73, Step 3) in acetonitrile (5.0 mL) was added 2-(1-aminocyclopropyl)acetonitrile (6.0 mg, 0.048 mmol, Astatech Inc, E70249) and trifluoroacetic acid (0.020 mL). The reaction mixture was allowed to stir at ambient temperature for 15 hours then was concentrated to dryness. The residue was dissolved in MeOH and purified via preparative HPLC-MS (pH=10). The obtained intermediate was then dissolved in MeOH (2.0 mL) and THF (1.0 mL) then 4.0 N NaOH (1.0 mL) was added and the reaction mixture was stirred at 50° C. for 1 hour. After this time, it was cooled to r.t., diluted with MeCN, filtered and purified via preparative HPLC-MS (pH=2) to afford the title compound as a TFA salt. LCMS for $C_{31}H_{28}N_9O$ (M+H)$^+$: calculated m/z=542.2; found 542.2.

Example 75a and Example 75b 2-(4-Methoxy-1-(6-methyl-1-(1-methyl-1H-indazol-5-yl)-2-(1-methyl-1H-pyrazol-4-yl)-7-oxo-6,7-dihydro-3H-spiro[dipyrrolo[2,3-b:3',2'-d]pyridine-8,4'-piperidin]-1'-yl)cyclohexyl)acetonitrile (cis- and trans-Isomers Isolated)

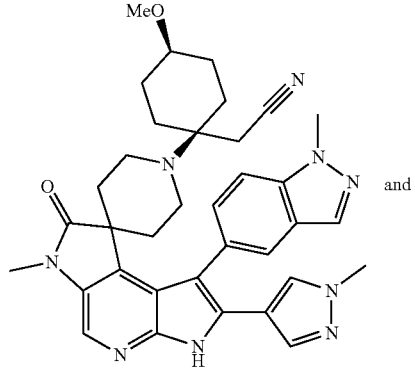

and

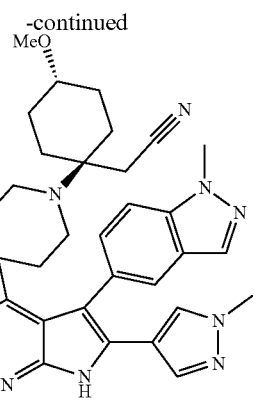

Step 1. 2-(4-Methoxycyclohexylidene)acetonitrile

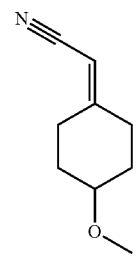

To a solution of diethyl (cyanomethyl)phosphonate (250 mg, 1.4 mmol) in diethyl ether (10.0 mL) at 0° C. was added NaH (60% in mineral oil, 68 mg, 1.7 mmol), and the reaction was stirred for 15 minutes before 4-methoxycyclohexan-1-one (180 mg, 1.4 mmol, Combi-Blocks #QA-6744) was added. The resulting solution was stirred at 0° C. for another 3 hours, then was diluted with water and extracted with diethyl ether. The combined organic layers were washed with brine, dried over MgSO$_4$, filtered and concentrated to dryness to afford the crude product as which was used for next step without purification.

Step 2.
2-(1-Amino-4-methoxycyclohexyl)acetonitrile
(mixture of cis- and trans-Isomers Prepared)

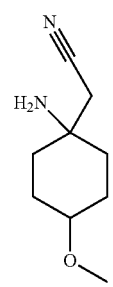

To a solution of 2-(4-methoxycyclohexylidene)acetonitrile (prepared in the previous step) in MeOH (2.0 mL) was added NH$_4$OH$_{(aq.)}$ (28%, 2.0 mL) and the reaction mixture was stirred in a sealed tube at 100° C. for 72 hours. After this time, it was cooled to r.t., concentrated to ⅓ its original volume and then was diluted with MeOH, filtered and the purified by preparative HPLC-MS (pH=10) to afford the desired product as a colorless oil. LCMS for $C_9H_{17}N_2O$ $(M+H)^+$: calculated m/z=169.1; found 169.1

Step 3. 2-(4-Methoxy-1-(6-methyl-1-(1-methyl-1H-indazol-5-yl)-2-(1-methyl-1H-pyrazol-4-yl)-7-oxo-6,7-dihydro-3H-spiro[dipyrrolo[2,3-b:3',2'-d]pyridine-8,4'-piperidin]-1'-yl)cyclohexyl)acetonitrile (cis- and trans-Isomers Isolated)

To a solution of 2,2'-(6-methyl-1-(1-methyl-1H-indazol-5-yl)-2-(1-methyl-1H-pyrazol-4-yl)-7-oxo-3-(phenylsulfonyl)-3,6,7,8-tetrahydrodipyrrolo[2,3-b:3',2'-d]pyridine-8,8-diyl)diacetaldehyde (0.020 g, 0.032 mmol, Example 73, Step 3) in MeCN (5.0 mL) was added 2-(1-amino-4-methoxycyclohexyl)acetonitrile (16 mg, 0.097 mmol) and the reaction mixture was stirred for 20 minutes. Trifluoroacetic anhydride (14 µL, 0.097 mmol) was added and the resulting solution was stirred at r.t. for 15 hours. Then, sodium triacetoxyborohydride (41 mg, 0.19 mmol) and trifluoroacetic acid (74 µL, 0.97 mmol) were added sequentially. The resulting solution was stirred at r.t. for 30 minutes (or until complete consumption of starting material as indicated by LCMS), then volatiles were removed in vacuo. The residue was dissolved in MeOH/THF (2:1, 3.0 mL), then 4.0 N NaOH (1.0 mL) was added and the mixture was stirred at 50° C. for 1 hour. Upon cooling to room temperature, the reaction mixture was neutralized by the addition of 1.0 N HCl, diluted with MeCN, filtered and purified via preparative HPLC-MS (pH=10; 35% to 55% MeCN/H$_2$O containing 0.1% ammonium hydroxide over 5 minutes) to afford the cis- and trans-products as separate peaks. Peak 1 (Example 75a), retention time: 3.45 min; Peak 2 (Example 75b), retention time: 4.31 min. LCMS for $C_{35}H_{40}N_9O_2$ $(M+H)^+$: calculated m/z=618.3; found 618.4

Examples 76-78

Unless otherwise indicated, Examples 76-78 in the Table below were synthesized according to the procedure described for Example 73, utilizing the appropriate amines in place of 2-(1-aminocyclopentyl)acetonitrile in Step 4, and with the modification that the products were purified via preparative HPLC-MS (pH=10).

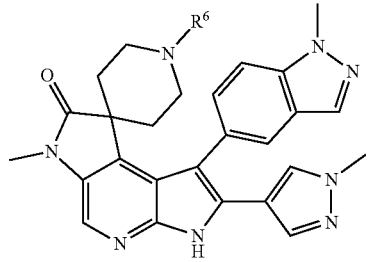

| Ex. No. | Compound Name | R$^6$ | LCMS |
|---|---|---|---|
| 76 | 1'-(2-(1H-1,2,3-Triazol-4-yl)propan-2-yl)-6-methyl-1-(1-methyl-1H-indazol-5-yl)-2-(1-methyl-1H-pyrazol-4-yl)-3,6-dihydro-7H-spiro[dipyrrolo[2,3-b:3',2'-d]pyridine-8,4'-piperidin]-7-one | | Calculated for $C_{31}H_{34}N_{11}O$ $(M + H)^+$: m/z = 576.3, found: 576.3 |
| 77 | 1'-(2-(4H-1,2,4-Triazol-3-yl)propan-2-yl)-6-methyl-1-(1-methyl-1H-indazol-5-yl)-2-(1-methyl-1H-pyrazol-4-yl)-3,6-dihydro-7H-spiro[dipyrrolo[2,3-b:3',2'-d]pyridine-8,4'-piperidin]-7-one | | Calculated for $C_{31}H_{34}N_{11}O$ $(M + H)^+$: m/z = 576.3, found: 576.3 |
| 78 | 6-Methyl-1'-(3-methyl-1,1-dioxidotetrahydrothiophen-3-yl)-1-(1-methyl-1H-indazol-5-yl)-2-(1-methyl-1H-pyrazol-4-yl)-3,6-dihydro-7H-spiro[dipyrrolo[2,3-b:3'-2'-d]pyridine-8,4'-piperidin]-7-one (racemic mixture prepared) | | Calculated for $C_{31}H_{35}N_8O_3S$ $(M + H)^+$: m/z = 599.3, found: 599.2 |

Example 79. 2-(1-(2-(5,6-Dihydro-4H-pyrrolo[1,2-b]pyrazol-3-yl)-6-methyl-1-(1-(methyl-d₃)-1H-indazol-5-yl)-7-oxo-6,7-dihydro-3H-spiro[dipyrrolo[2,3-b:3',2'-d]pyridine-8,4'-piperidin]-1'-yl)cyclopentyl)acetonitrile

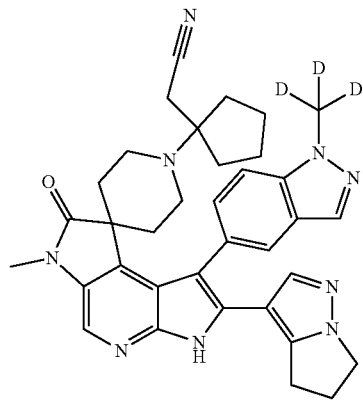 [SMILES: [2H]C([2H])([2H])n1ncc2cc(-c3c(-c4cnn5c4CCC5)[nH]c4ncc5c(c34)C3(CCN(C4(CC#N)CCCC4)CC3)C(=O)N5C)ccc21]

The title compound was prepared in the manner of Example 73, utilizing (1-(methyl-d₃)-1H-indazol-5-yl)boronic acid in place of (1-methyl-1H-indazol-5-yl)boronic acid in Step 1; and utilizing (5,6-dihydro-4H-pyrrolo[1,2-b]pyrazol-3-yl)boronic acid instead of 1-methyl-4-(4,4,5,5-tetramethyl-1,3,2-dioxaborolan-2-yl)-1H-pyrazole in Step 2 and the product was purified via preparative HPLC-MS (pH=10). LCMS for $C_{35}H_{35}D_3N_9O$ (M+H)⁺: calculated m/z=603.3; found 603.3.

Example 80a and Example 80b. (R)-4-Methoxy-3-methyl-3-(6-methyl-2-(1-methyl-1H-pyrazol-4-yl)-1-(1-(methyl-d₃)-1H-indazol-5-yl)-7-oxo-6,7-dihydro-3H-spiro[dipyrrolo[2,3-b:3',2'-d]pyridine-8,4'-piperidin]-1'-yl)butanenitrile (Example 80a) and (S)-4-Methoxy-3-methyl-3-(6-methyl-2-(1-methyl-1H-pyrazol-4-yl)-1-(1-(methyl-d₃)-1H-indazol-5-yl)-7-oxo-6,7-dihydro-3H-spiro[dipyrrolo[2,3-b:3',2'-d]pyridine-8,4'-piperidin]-1'-yl)butanenitrile (Example 80b) (Single Enantiomers Isolated)

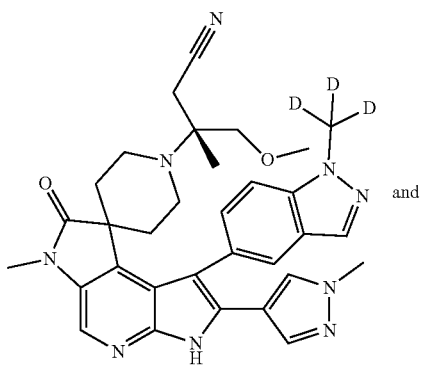

and

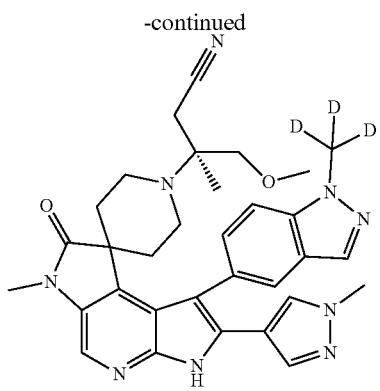

Step 1. 2,2'-(6-Methyl-2-(1-methyl-1H-pyrazol-4-yl)-1-(1-(methyl-d₃)-1H-indazol-5-yl)-7-oxo-3-(phenylsulfonyl)-3,6,7,8-tetrahydrodipyrrolo[2,3-b:3',2'-d]pyridine-8,8-diyl)diacetaldehyde

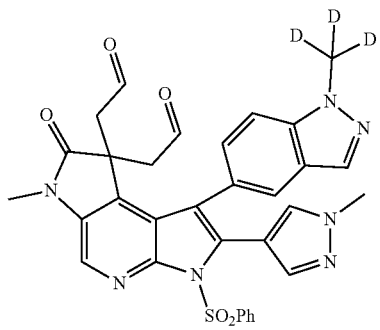

The title compound was prepared in the manner of Example 73, from Step 1 to Step 3, utilizing (1-(methyl-d₃)-1H-indazol-5-yl)boronic acid (Abovchem, AC504689) in place of (1-methyl-1H-indazol-5-yl)boronic acid in Step 1. LCMS for $C_{32}H_{25}D_3N_7O_5S$ (M+H)⁺: calculated m/z=625.2; found 625.2.

Step 2. (R)-4-Methoxy-3-methyl-3-(6-methyl-2-(1-methyl-1H-pyrazol-4-yl)-1-(1-(methyl-d₃)-1H-indazol-5-yl)-7-oxo-6,7-dihydro-3H-spiro[dipyrrolo[2,3-b:3,2'-d]pyridine-8, 4'-piperidin]-1'-yl)butanenitrile and (S)-4-Methoxy-3-methyl-3-(6-methyl-2-(1-methyl-1H-pyrazol-4-yl)-1-(1-(methyl-d₃)-1H-indazol-5-yl)-7-oxo-6,7-dihydro-3H-spiro[dipyrrolo[2,3-b:3',2'-d]pyridine-8,4'-piperidin]-1'-yl)butanenitrile (single enantiomers isolated)

The title compounds were prepared in the manner of Example 75, utilizing 1-methoxypropan-2-one (Sigma Aldrich #117180) instead of 4-methoxycyclohexan-1-one in Step 1 and utilizing 2,2'-(6-methyl-2-(1-methyl-1H-pyrazol-4-yl)-1-(1-(methyl-d₃)-1H-indazol-5-yl)-7-oxo-3-(phenylsulfonyl)-3,6,7,8-tetrahydrodipyrrolo[2,3-b:3',2'-d]pyridine-8,8-diyl)diacetaldehyde prepared from the previous step instead of 2,2'-(6-methyl-1-(1-methyl-1H-indazol-5-yl)-2-(1-methyl-1H-pyrazol-4-yl)-7-oxo-3-(phenylsulfonyl)-3,6,7,8-tetrahydrodipyrrolo[2,3-b:3',2'-d]pyridine-8,8-diyl)diacetaldehyde in Step 3. LCMS for $C_{32}H_{33}D_3N_9O_2$ (M+H)⁺: calculated m/z=581.3; found 581.3. The enantiomers could be separated by Chiral LCMS (Phenomenex Lux 5 μm Cellulose-4, 21.2×250 mm column, eluting with 60% ethanol in hexanes, at flow rate of 20 mL/min). Peak 1 (Example 80a), retention time: 14.6 min; Peak 2 (Example 80b), retention time: 18.5 min.

Example 81. Methyl 4-(cyanomethyl)-4-(6-methyl-1-(1-methyl-1H-indazol-5-yl)-2-(1-methyl-1H-pyrazol-4-yl)-7-oxo-6,7-dihydro-3H-spiro[dipyrrolo[2,3-b:3',2'-d]pyridine-8,4'-piperidin]-1'-yl)piperidine-1-carboxylate

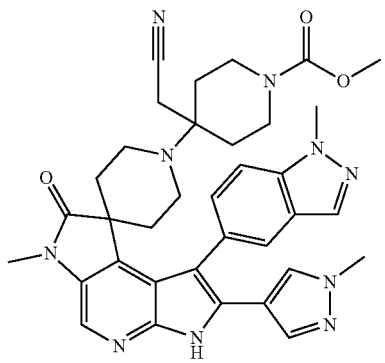

Step 1. 2-(4-(6-Methyl-1-(1-methyl-1H-indazol-5-yl)-2-(1-methyl-1H-pyrazol-4-yl)-7-oxo-3-(phenylsulfonyl)-6,7-dihydro-3H-spiro[dipyrrolo[2,3-b:3,2'-d]pyridine-8,4'-piperidin]-1'-yl)piperidin-4-yl)acetonitrile, trifluoroacetate salt

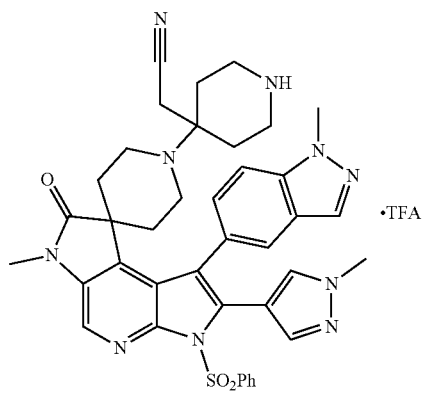

The title compound was prepared in the manner of Example 75, utilizing tert-butyl 4-oxopiperidine-1-carboxylate (Combi-Blocks #AM-1027) instead of 4-methoxycyclohexan-1-one in Step 1, and the following modifications: the NaOH-mediated deprotection was not performed, and the Boc protecting group was removed by treating the intermediate with 1:3 TFA/DCM for 60 minutes followed by removal of volatiles in vacuo. LCMS for $C_{39}H_{41}N_{10}O_3S$ (M+H)$^+$: calculated m/z=729.3; found 729.3.

Step 2. Methyl 4-(cyanomethyl)-4-(6-methyl-1-(1-methyl-1H-indazol-5-yl)-2-(1-methyl-1H-pyrazol-4-yl)-7-oxo-6,7-dihydro-3H-spiro[dipyrrolo[2,3-b:3',2'-d]pyridine-8,4'-piperidin]-1'-yl)piperidin-1-carboxylate To a solution of 2-(4-(6-methyl-1-(1-methyl-1H-indazol-5-yl)-2-(1-methyl-1H-pyrazol-4-yl)-7-oxo-3-(phenylsulfonyl)-6,7-dihydro-3H-spiro[dipyrrolo[2,3-b:3',2'-d]pyridine-8,4'-piperidin]-1'-yl)piperidin-4-yl)acetonitrile, trifluoroacetate salt (5.0 mg, 6.9 μmol) in DCM was added Et$_3$N (4.8 μL, 0.034 mmol) and methyl chloroformate (1.9 mg, 0.021 mmol). The resulting solution was stirred at r.t. for 30 minutes and it was then concentrated to dryness. The residue was dissolved in MeOH/THF (2:1, 3.0 mL), then 4.0 N NaOH (1.0 mL) was added and the reaction mixture was stirred at 50° C. for 1 hour. Upon cooling to room temperature, the reaction mixture was neutralized by the addition of 1.0 N HCl, diluted with MeCN, filtered and purified via preparative HPLC-MS (pH=10) to afford the title compound. LCMS for $C_{35}H_{39}N_{10}O_3$ (M+H)$^+$: calculated m/z=647.3; found 647.3.

Examples 82-83

Unless otherwise indicated, Examples 82-83 in the Table below were synthesized according to the procedure described for Example 81, utilizing the appropriate amines in Step 1 and utilizing appropriate acylating reagents in Step 2.

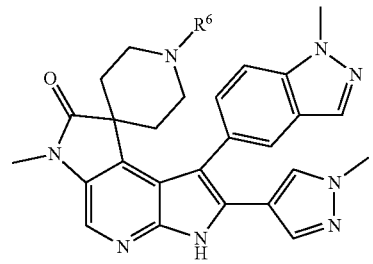

| Ex. No. | Compound Name | R$^6$ | LCMS |
|---|---|---|---|
| 82 | N-(3-(6-Methyl-1-(1-methyl-1H-indazol-5-yl)-2-(1-methyl-1H-pyrazol-4-yl)-7-oxo-6,7-dihydro-3H-spiro [dipyrrolo [2,3-b:3',2'-d]pyridine-8,4'-piperidin ]-1'-yl)bicyclo[1.1.1]pentan-1-yl)acetamide | | Calculated for $C_{33}H_{36}N_9O_2$ (M + H)$^+$: m/z = 590.3, found: 590.2 |

| Ex. No. | Compound Name | R⁶ | LCMS |
|---|---|---|---|
| 83 | Methyl 4-(6-methyl-1-(1-methyl-1H-indazol-5-yl)-2-(1-methyl-1H-pyrazol-4-yl)-7-oxo-6,7-dihydro-3H-spiro[dipyrrolo[2,3-b:3',2'-d]pyridine-8,4'-piperidin]-1'-yl)-2-azabicyclo[2.1.1]hexane-2-carboxylate | | Calculated for $C_{33}H_{36}N_9O_3$ (M + H)⁺: m/z = 606.3, found: 606.3 |

Example 84. 1'-(2-(Azetidin-3-yl)propan-2-yl)-6-methyl-1-(1-methyl-1H-indazol-5-yl)-2-(1-methyl-1H-pyrazol-4-yl)-3,6-dihydro-7H-spiro[dipyrrolo[2,3-b:3',2'-d]pyridine-8,4'-piperidin]-7-one

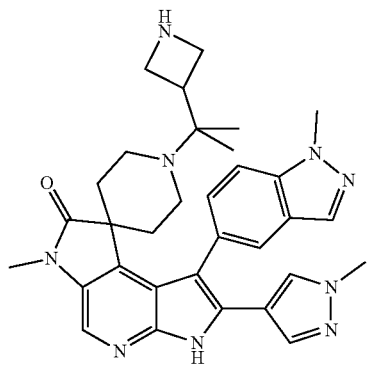

To a solution of 2,2'-(6-methyl-1-(1-methyl-1H-indazol-5-yl)-2-(1-methyl-1H-pyrazol-4-yl)-7-oxo-3-(phenylsulfonyl)-3,6,7,8-tetrahydrodipyrrolo[2,3-b:3',2'-d]pyridine-8,8-diyl)diacetaldehyde (0.020 g, 0.032 mmol, Example 73, Step 3) in MeCN (5.0 mL) was added tert-butyl 3-(2-aminopropan-2-yl)azetidine-1-carboxylate (14 mg, 0.064 mmol, Astatech, Inc. #P14780) and the reaction mixture was stirred for 20 minutes at r.t. followed by addition of trifluoroacetic anhydride (14 µL, 0.097 mmol). The resulting solution was stirred at r.t. for 15 hours then sodium triacetoxyborohydride (41 mg, 0.19 mmol) was added, followed by the addition of trifluoroacetic acid (74 µL, 0.97 mmol). The resulting solution was stirred at r.t. for 30 minutes (or until starting material was consumed as indicated by LCMS) and the reaction mixture was then concentrated to dryness. The residue was dissolved in 1:3 TFA/DCM and stirred for 60 minutes before volatiles were removed in vacuo. The resulting residue was dissolved in MeOH/THF (2:1, 3.0 mL), then 4.0 N NaOH (1.0 mL) was added and the reaction mixture was stirred at 50° C. for 1 hour. Upon cooling to room temperature, the reaction mixture was neutralized by the addition of 1.0 N HCl, diluted with MeCN, filtered and purified via preparative HPLC-MS (pH=10) to afford the title compound. LCMS for $C_{32}H_{38}N_9O$ (M+H)⁺: calculated m/z=564.3; found 564.3..

Examples 85-99

Examples 85-99 of the following table were prepared by one of the two following methods. Method A: The procedure of Example 54 was followed, substituting the appropriate boronic acids or esters in place of 1-methyl-5-(4,4,5,5-tetramethyl-1,3,2-dioxaborolany-2-yl)-1H-indazole for alternate R² groups, and substituting the appropriate boronic acids or esters in place of 1-isopropyl-4-(4,4,5,5-tetramethyl-1,3,2-dioxaborolan-2-yl)-1H-pyrazole for alternate R³ groups. Method B: The procedure of Example 54 was followed with the modification that the Boc deprotection and installation of the ethanesulfonyl group was performed before functionalization to install R² and R³. Where R⁴=CD₃, alkylation was performed with iodomethane-d₃ in place of iodomethane.

| Ex. No. | Method | Compound Name | R⁴ | R² | R³ | LCMS ¹H NMR |
|---|---|---|---|---|---|---|
| 85 | B | 1-(Ethylsulfonyl)-6"-methyl-1"-(1-(methyl-d₃)-1H-indazol-5-yl)-2"-(4-(morpholinomethyl)phenyl)-3",6"-dihydro-7"H-dispiro[azetidine-3,1'-cyclobutane-3',8"-dipyrrolo[2,3-b:3',2'-d]pyridin]-7"-one, trifluoroacetate salt | CH₃ | D₃C-indazol-5-yl | 4-(morpholinomethyl)phenyl | Calculated for $C_{36}H_{37}D_3N_7O_4S$ (M + H)⁺: m/z = 669.3, found: 669.4 |

| Ex. No. | Method | Compound Name | R⁴ | R² | R³ | LCMS |
|---|---|---|---|---|---|---|
| | | | | ¹H NMR | | |
| 86 | A | 1-(Ethylsulfonyl)-6"-methyl-1"-(1-methyl-1H-indazol-5-yl)-2"-(1-methyl-1H-pyrazol-4-yl)-3",6"-dihydro-7"H-dispiro[azetidine-3,1'-cyclobutane-3',8"-dipyrrolo[2,3-b:3',2'-d]pyridin]-7"-one, trifluoroacetate salt | CH₃ | 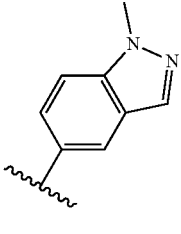 [SMILES: *c1ccc2c(cnn2C)c1] |  | Calculated for $C_{29}H_{31}N_8O_3S$ (M + H)⁺: m/z = 571.2, found: 571.2 |
| 87 | A | 2"-(1-(Cyclopropylmethyl)-1H-pyrazol-4-yl)-1-(ethylsulfonyl)-6"-methyl-1"-(1-methyl-1H-indazol-5-yl)-3",6"-dihydro-7"H-dispiro[azetidine-3,1'-cyclobutane-3',8"-dipyrrolo[2,3-b:3',2'-d]pyridin]-7"-one, trifluoroacetate salt | CH₃ |  | 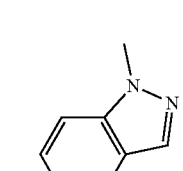 | Calculated for $C_{32}H_{35}N_8O_3S$ (M + H)⁺: m/z = 611.3, found: 611.3 |
| 88 | B | 1-(Ethylsulfonyl)-2"-(1-(2-methoxyethyl)-1H-pyrazol-4-yl)-6"-methyl-1"-(1-methyl-1H-indazol-5-yl)-3",6"-dihydro-7"H-dispiro[azetidine-3,1'-cyclobutane-3',8"-dipyrrolo[2,3-b:3',2'-d]pyridin]-7"-one, trifluoroacetate salt | CH₃ | 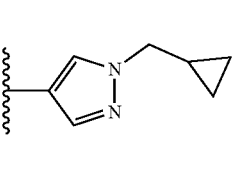 | 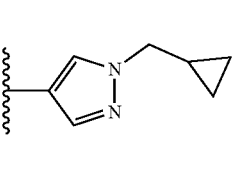 | Calculated for $C_{31}H_{35}N_8O_4S$ (M + H)⁺: m/z = 615.2, found: 615.3 |
| 89 | B | 1-(Ethylsulfonyl)-2"-(1-isopropyl-1H-pyrazol-4-yl)-6"-(methyl-d₃)-1"-(1-methyl-1H-indazol-5-yl)-3",6"-dihydro-7"H-dispiro[azetidine-3,1'-cyclobutane-3',8"-dipyrrolo[2,3-b:3',2'-d]pyridin]-7"-one, trifluoroacetate salt | CH₃ | 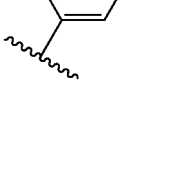 |  | Calculated for $C_{31}H_{32}D_3N_8O_3S$ (M + H)⁺: m/z = 602.3, found: 602.2 |
| 90 | A | 2"-(1-Cyclopentyl-1H-pyrazol-4-yl)-1-(ethylsulfonyl)-6"-methyl-1"-(1-methyl-1H-indazol-5-yl)-3",6"-dihydro-7"H-dispiro[azetidine-3,1'-cyclobutane-3',8"-dipyrrolo[2,3-b:3',2'-d]pyridin]-7"-one, trifluoroacetate salt | CH₃ |  |  | Calculated for $C_{33}H_{37}N_8O_3S$ (M + H)⁺: m/z = 625.3, found: 625.3 |

| Ex. No. | Method | Compound Name | R⁴ | R² | R³ | LCMS ¹H NMR |
|---|---|---|---|---|---|---|
| 91 | B | 1-(4-(1-(Ethylsulfonyl)-6"-methyl-1"-(1-(methy-d₃)-1H-indazol-5-yl)-7"-oxo-6",7"-dihydro-3"H-dispiro[azetidine-3,1'-cyclobutane-3',8"-dipyrrolo[2,3-b:3',2'-d]pyridin]-2"-yl)benzyl)piperidine-4-carbonitrile, trifluoroacetate salt | CH₃ | 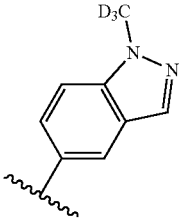 [SMILES: *c1ccc2c(cnn2C([2H])([2H])[2H])c1] | 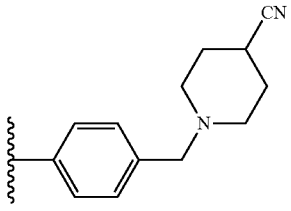 [SMILES: *c1ccc(CN2CCC(C#N)CC2)cc1] | Calculated for C₃₈H₃₈D₃N₈O₃S (M + H)⁺: m/z = 692.3, found: 692.4 |
| 92 | B | 1-(Ethylsulfonyl)-1"-(4-methoxyphenyl)-6"-(methyl-d₃)-2"-(4-(morpholinomethyl)phenyl)-3",6"-dihydro-7"H-dispiro[azetidine-3,1'-cyclobutane-3',8"-dipyrrolo[2,3-b:3',2'-d]pyridin]-7"-one, trifluoroacetate salt | CH₃ | 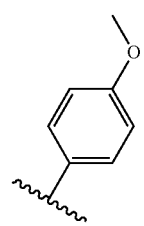 [SMILES: *c1ccc(OC)cc1] | 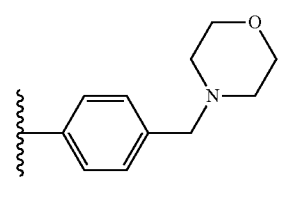 [SMILES: *c1ccc(CN2CCOCC2)cc1] | Calculated for C₃₅H₃₇D₃N₅O₅S (M + H)⁺: m/z = 645.3, found: 645.3 |
| 93 | B | 2"-(1-(2,2-Difluoroethyl)-1H-pyrazol-4-yl)-1-(ethylsulfonyl)-6"-methyl-1"-(1-methyl-1H-indazol-5-yl)-3",6"-dihydro-7"-dispiro[azetidine-3,1'-cyclobutane-3',8"-dipyrrolo[2,3-b:3',2'-d]pyridin]-7"-one, trifluoroacetate salt | CH₃ | 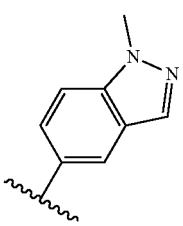 | 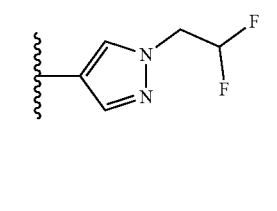 [SMILES: *c1cnn(CC(F)F)c1] | Calculated for C₃₀H₃₁F₂N₈O₃S (M + H)⁺: m/z = 621.3, found: 621.3 |
| 94 | A | 2"-(5,6-Dihydro-4H-pyrrolo[1,2-b]pyrazol-3-yl)-1-(ethylsulfonyl)-6"-methyl-1"-(1-methyl-1H-indazol-5-yl)-3",6"-dihydro-7"-dispiro[azetidine-3,1'-cyclobutane-3',8"-dipyrrolo[2,3-b:3',2'-d]pyridin]-7"-one, trifluoroacetate salt | CH₃ | 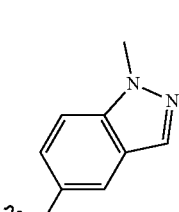 | 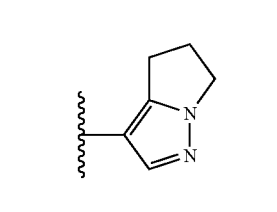 [SMILES: *c1cnn2c1CCC2] | Calculated for C₃₁H₃₅N₈O₄S (M + H)⁺: m/z = 615.2, found: 615.3 |
| 95 | B | 2"-(1-Ethyl-1H-pyrazol-4-yl)-1-(ethylsulfonyl)-1"-(4-methoxyphenyl)-6"-(methyl-d₃)-3",6"-dihydro-7"H-dispiro[azetidine-3,1'-cyclobutane-3',8"-dipyrrolo[2,3-b:3',2'-d]pyridin]-7"-one, trifluoroacetate salt | CD₃ | 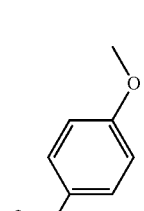 | 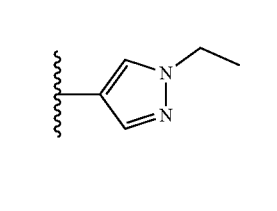 [SMILES: *c1cnn(CC)c1] | Calculated for C₂₉H₃₀D₃N₆O₄S (M + H)⁺: m/z = 564.2, found: 564.2 |

| Ex. No. | Method | Compound Name | R⁴ | R² | R³ | LCMS |
|---|---|---|---|---|---|---|
| | | | | ¹H NMR | | |
| 96 | B | 1-(Ethylsulfonyl)-2"-(1-(2-methoxy-2-methylpropyl)-1H-pyrazol-4-yl)-6"-methyl-1"-(1-(methyl-d₃)-1H-indazol-5-yl)-3",6"-dihydro-7"H-dispiro[azetidine-3,1'-cyclobutane-3',8"-dipyrrolo[2,3-b:3',2'-d]pyridin]-7"-one, trifluoroacetate salt | CH₃ | D₃C-indazole | pyrazole-CH₂-C(CH₃)₂-OMe | Calculated for C₃₆H₃₆D₃N₈O₄S (M + H)⁺: m/z = 646.3, found: 646.4 |
| 97 | B | 1-(Ethylsulfonyl)-6"-methyl-1"-(1-methyl-1H-indazol-5-yl)-2"-(1-((tetrahydro-2H-pyran-4-yl)methyl)-1H-pyrazol-4-yl)-3",6"-dihydro-7"H-dispiro[azetidine-3,1'-cyclobutane-3',8"-dipyrrolo[2,3-b:3',2'-d]pyridin]-7"-one, trifluoroacetate salt | CH₃ | 1-methyl-indazole | pyrazole-CH₂-tetrahydropyran | Calculated for C₃₄H₃₉N₈O₄S (M + H)⁺: m/z = 655.3, found: 655.3 |
| 98 | B | 2"-(6,7-Dihydro-5H-pyrazolo[5,1-b][1,3]oxazin-3-yl)-1-(ethylsulfonyl)-6"-methyl-1"-(1-(methyl-d₃)-1H-indazol-5-yl)-3",6"-dihydro-7"H-dispiro[azetidine-3,1'-cyclobutane-3',8"-dipyrrolo[2,3-b:3',2'-d]pyridin]-7"-one, trifluoroacetate salt | CH₃ | D₃C-indazole | 6,7-dihydro-5H-pyrazolo[5,1-b][1,3]oxazine | Calculated for C₃₁H₃₀D₃N₈O₄S (M + H)⁺: m/z = 616.3, found: 616.3 |
| 99 | B | 1-(Ethylsulfonyl)-2"-(3-methoxy-1-methyl-1H-pyrazol-4-yl)-6"-methyl-1"-(1-(methyl-d₃)-1H-indazol-5-yl)-3",6"-dihydro-7"H-dispiro[azetidine-3,1'-cyclobutane-3',8"-dipyrrolo[2,3-b:3',2'-d]pyridin]-7"-one, trifluoroacetate salt | CH₃ | D₃C-indazole | 3-methoxy-1-methyl-pyrazole | Calculated for C₃₁H₃₅N₈O₄S (M + H)⁺: m/z = 615.2, found: 615.3 |

¹H NMR (500 MHz, DMSO-d₆) δ 11.14 (s, 1H), 8.12 (d, J = 1.0 Hz, 1H), 7.95 (s, 1H), 7.84 (d, J = 1.3 Hz, 1H), 7.80 (d, J = 8.5 Hz, 1H), 7.44 (dd, J = 8.5, 1.5 Hz, 1H), 6.69 (s, 1H), 3.93-3.84 (m, 2H), 3.81 (s, 3H), 3.50 (s, 3H), 3.16 (s, 3H), 2.92-2.81 (m, 2H), 2.42 (d, J = 12.5 Hz, 1H), 2.36-2.28 (m, 2H), 2.21-2.15 (m, 2H), 1.89 (d, J = 8.9 Hz, 1H), 1.08 (t, J = 7.4 Hz, 3H).

Example 100. 1-(2-Amino-2-oxoethyl)-N-((1S,3S)-6'-methyl-2'-(1-methyl-1H-pyrazol-4-yl)-1'-(1-(methyl-d₃)-1H-indazol-5-yl)-7'-oxo-6',7'-dihydro-3'H-spiro[cyclopentane-1,8'-dipyrrolo[2,3-b:3',2'-d]pyridin]-3-yl)cyclobutane-1-carboxamide, trifluoroacetate salt and 1-(2-Amino-2-oxoethyl)-N-((1R,3R)-6'-methyl-2'-(1-methyl-1H-pyrazol-4-yl)-1'-(1-(methyl-d₃)-1H-indazol-5-yl)-7'-oxo-6',7'-dihydro-3'H-spiro[cyclopentane-1,8'-dipyrrolo[2,3-b:3',2'-d]pyridin]-3-yl)cyclobutane-1-carboxamide, trifluoroacetate salt (Racemic Mixture Prepared)

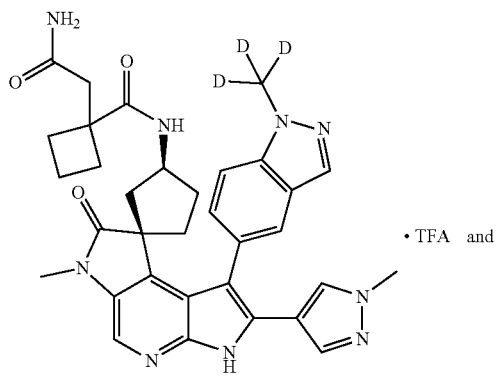

· TFA and

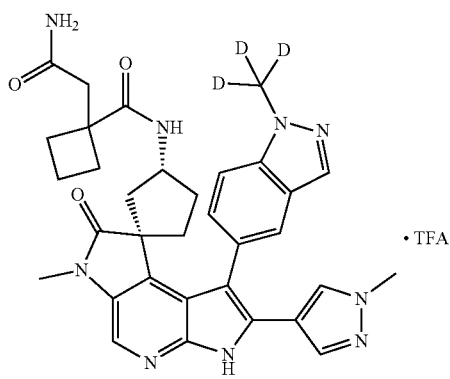

· TFA

Step 1. (1S,3S)-3-amino-6'-methyl-2'-(1-methyl-1H-pyrazol-4-yl)-1'-(1-(methyl-d₃)-1H-indazol-5-yl)-3'-(phenylsulfonyl)-3',6'-dihydro-7'H-spiro[cyclopentane-1,8'-dipyrrolo[2,3-b:3',2'-d]pyridin]-7'-one and (1R,3R)-3-amino-6'-methyl-2'-(1-methyl-1H-pyrazol-4-yl)-1'-(1-(methyl-d₃)-1H-indazol-5-yl)-3'-(phenylsulfonyl)-3',6'-dihydro-7'H-spiro[cyclopentane-1,8'-dipyrrolo[2,3-b:3',2'-d]pyridin]-7'-one (Racemic Mixture)

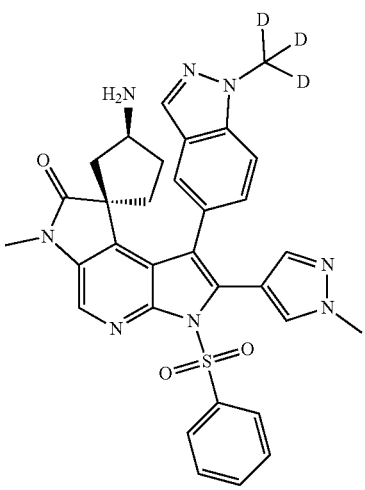

and

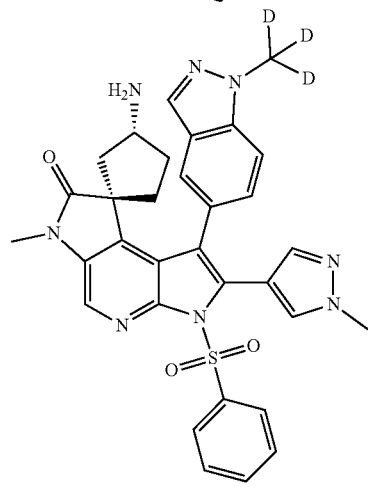

The procedure of Example 55, Step 4 was followed, utilizing Peak 2 from Step 3 as starting material in place of Peak 1, and using (1-(methyl-d₃)-1H-indazol-5-yl)boronic acid (Abovchem, #504689) in place of 1-methyl-5-(4,4,5,5-tetramethyl-1,3,2-dioxaborolan-2-yl)-1H-indazole. Deprotection of the Boc protecting group was performed analogously to the procedure found in Example 5, Step 3 to give (1S,3S)-3-amino-6'-methyl-2'-(1-methyl-1H-pyrazol-4-yl)-1'-(1-(methyl-d₃)-1H-indazol-5-yl)-3'-(phenylsulfonyl)-3',6'-dihydro-7'H-spiro[cyclopentane-1,8'-dipyrrolo[2,3-b:3',2'-d]pyridin]-7'-one and (1R,3R)-3-amino-6'-methyl-2'-(1-methyl-1H-pyrazol-4-yl)-1'-(1-(methyl-d₃)-1H-indazol-5-yl)-3'-(phenylsulfonyl)-3',6'-dihydro-7'H-spiro[cyclopentane-1,8'-dipyrrolo[2,3-b:3',2'-d]pyridin]-7'-one as a racemic mixture.

Step 2. 1-(2-Amino-2-oxoethyl)-N-((1S,3S)-6'-methyl-2'-(1-methyl-1H-pyrazol-4-yl)-1'-(1-(methyl-d3)-1H-indazol-5-yl)-7'-oxo-6',7'-dihydro-3'H-spiro[cyclopentane-1,8'-dipyrrolo[2,3-b:3',2'-d]pyridin]-3-yl)cyclobutane-1-carboxamide, trifluoroacetate salt (Example 100A) and 1-(2-Amino-2-oxoethyl)-N-((1R,3R)-6'-methyl-2'-(1-methyl-1H-pyrazol-4-yl)-1'-(1-(methyl-d₃)-1H-indazol-5-yl)-7'-oxo-6',7'-dihydro-3'H-spiro[cyclopentane-1,8'-dipyrrolo[2,3-b:3',2'-d]pyridin]-3-yl)cyclobutane-1-carboxamide, trifluoroacetate salt (Example 100B) (Racemic Mixture Prepared)

To a solution of (1S,3S)-3-amino-6'-methyl-2'-(1-methyl-1H-pyrazol-4-yl)-1'-(1-(methyl-d₃)-1H-indazol-5-yl)-3'-(phenylsulfonyl)-3',6'-dihydro-7'H-spiro[cyclopentane-1,8'-dipyrrolo[2,3-b:3',2'-d]pyridin]-7'-one and (1R,3R)-3-amino-6'-methyl-2'-(1-methyl-1H-pyrazol-4-yl)-1'-(1-(methyl-d₃)-1H-indazol-5-yl)-3'-(phenylsulfonyl)-3',6'-dihydro-7'H-spiro[cyclopentane-1,8'-dipyrrolo[2,3-b:3',2'-d]pyridin]-7'-one (0.01 g, 0.02 mmol, racemic mixture) in acetonitrile (0.5 mL) was added triethylamine (0.1 mL), 1-(cyanomethyl)cyclobutane-1-carboxylic acid (0.002 g, 0.02 mmol, AstaTech, D79150) and HATU (1-[bis(dimethylamino)methylene]-1H-1,2,3-triazolo[4,5-b]pyridinium 3-oxide hexafluorophosphate) (0.01 g, 0.02 mmol). The resulting mixture was stirred at ambient temperature for 1 hour then diluted with methanol (3.0 mL) and NaOH (3.0 N, 0.5 mL, 1.5 mmol). The reaction mixture was heated at 60° C. for 30 min, then cooled to room temperature and purified via preparative HPLC-MS (pH=2) to afford the title compound as a racemic mixture of trifluoroacetate salts. LCMS for $C_{33}H_{33}D_3N_9O_3$ (M+H)⁺: calculated m/z=609.3; found 609.3.

Examples 101-102

Examples 101-102 in the Table below were synthesized according to the procedure described for Example 58, utilizing the appropriate boronic esters or boronic acids in the introduction of $R^2$ and $R^3$ (see e.g., Scheme 1) and utilizing the appropriate acid chloride, carbamoyl chloride, or sulfonyl chloride in the introduction of $R^6$ (see e.g., Scheme 2).

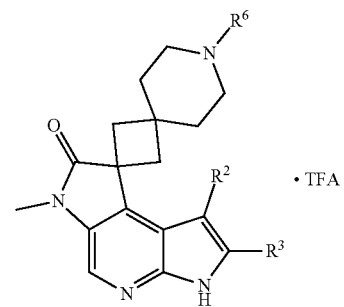

| Ex. No. | Compound Name | $R^2$ | $R^3$ | $R^6$ | LCMS |
|---|---|---|---|---|---|
| 101 | 1''-Butyryl-6-methyl-1-(1-methyl-1H-indazol-5-yl)-2-(1-(methyl-d₃)-1H-pyrrol-3-yl)-3,6-dihydro-7H-dispiro[dipyrrolo[2,3-b:3',2'-d]pyridine-8,1'-cyclobutane-3',4''-piperidin]-7-one, trifluoroacetate salt | | | | Calculated for $C_{34}H_{35}D_3N_7O_2$ (M + H)⁺: m/z = 579.3, found: 579.3 |
| 102 | 1''-Butyryl-6-methyl-1-(1-(methyl-d₃)-1H-indazol-5-yl)-2-(1-(methyl-d₃)-1H-pyrrol-3-yl)-3,6-dihydro-7H-dispiro[dipyrrolo[2,3-b:3',2'-d]pyridine-8,1'-cyclobutane-3',4''-piperidin]-7-one, trifluoroacetate salt | | | | Calculated for $C_{34}H_{32}D_6N_7O_2$ (M + H)⁺: m/z = 582.3, found: 582.3 |

Example 103. 2'-(1-Isopropyl-1H-pyrazol-4-yl)-6'-(methyl-d₃)-1'-(1-methyl-1H-indazol-5-yl)-1-((1-methylcyclopropyl)sulfonyl)-3',6'-dihydro-7'H-spiro[azepane-4,8'-dipyrrolo[2,3-b:3',2'-d]pyridin]-7'-one, trifluoroacetate salt (Single Enantiomer Prepared)

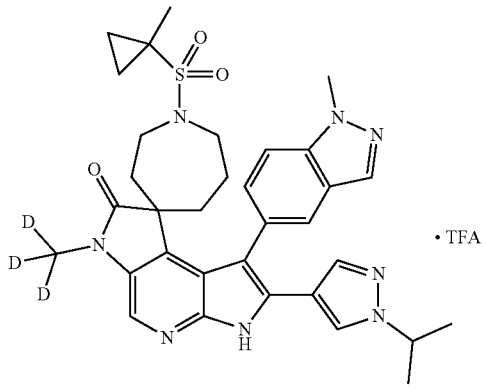 [SMILES: [2H]C([2H])([2H])N1C(=O)C2(CCCN(S(=O)(=O)C3(C)CC3)CC2)c2c1cnc1[nH]c(-c3cnn(C(C)C)c3)c(-c3ccc4c(cnn4C)c3)c21]

Step 1. tert-Butyl 6'-(methyl-d₃)-7'-oxo-3'-(phenylsulfonyl)-6',7'-dihydro-3'H-spiro[azepane-4,8'-dipyrrolo[2,3-b:3',2'-d]pyridine]-1-carboxylate (Single Enantiomers Isolated)

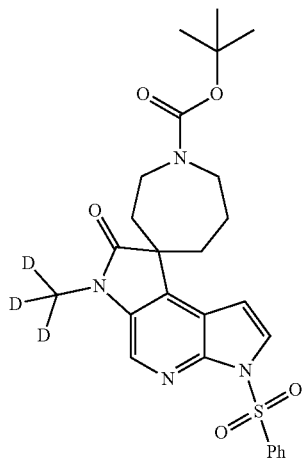 [SMILES: [2H]C([2H])([2H])N1C(=O)C2(CCCN(C(=O)OC(C)(C)C)CC2)c2c1cnc1c2ccn1S(=O)(=O)c1ccccc1]

The procedure of Example 8, Steps 1 through 3 were followed using 1-(tert-butyl) 4-methyl azepane-1,4-dicarboxylate (eNovation Chemicals LLC #D573239) in place of methyl cyclopentane carboxylate in Step 1, and using iodomethane-d₃ in place of iodomethane in Step 3. The enantiomers were separated via chiral SFC (Phenomenex Amylose-1, 5 µm, 30×250 mm, loading 56 mg in 1.8 mL and eluting with 25% MeOH in CO₂ at 100 mL/min over 8 min).

Peak 1 (first to elute, retention time 6.1 min): LCMS for $C_{26}H_{28}D_3N_4O_5S$ (M+H)⁺: calculated m/z=514.2; found 514.3.

Peak 2 (second to elute, retention time 7.8 min): LCMS for $C_{26}H_{28}D_3N_4O_5S$ (M+H)⁺: calculated m/z=514.2; found 514.3.

Step 2. tert-Butyl 2'-bromo-6'-(methyl-d₃)-1'-(1-methyl-1H-indazol-5-yl)-7'-oxo-3'-(phenylsulfonyl)-6',7'-dihydro-3'H-spiro[azepane-4,8'-dipyrrolo[2,3-b:3',2'-d]pyridine]-1-carboxylate (Single Enantiomer Prepared)

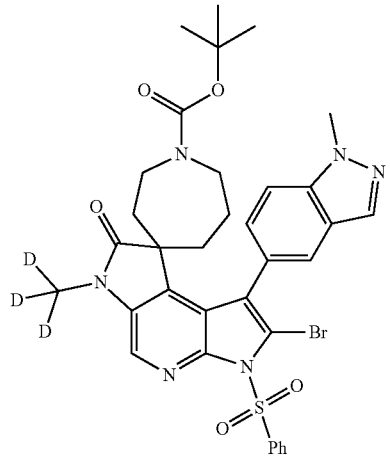 [SMILES: [2H]C([2H])([2H])N1C(=O)C2(CCCN(C(=O)OC(C)(C)C)CC2)c2c1cnc1c2c(-c2ccc3c(cnn3C)c2)c(Br)n1S(=O)(=O)c1ccccc1]

The procedure of Example 8, Steps 4 through 6 were followed using tert-butyl 6'-(methyl-d₃)-7'-oxo-3'-(phenylsulfonyl)-6',7'-dihydro-3'H-spiro[azepane-4,8'-dipyrrolo[2,3-b:3',2'-d]pyridine]-1-carboxylate (Peak 1 from Step 1, 2.22 g, 4.32 mmol) as starting material in place of 6'-methyl-3'-(phenylsulfonyl)-3',6'-dihydro-7'H-spiro [cyclopentane-1,8'-dipyrrolo[2,3-b:3',2'-d]pyridin]-7'-one in Step 4, and using tetrakis(triphenylphosphine)palladium(0) in place of PdCl₂(dppf)-CH₂Cl₂ adduct as catalyst in Step 5. LCMS for $C_{34}H_{33}D_3BrN_6O_5S$ (M+H)⁺: calculated monoisotopic m/z=722.2; found 722.1.

Step 3. 2'-Bromo-6'-(methyl-d₃)-1'-(1-methyl-1H-indazol-5-yl)-3'-(phenylsulfonyl)-3',6'-dihydro-7'H-spiro[azepane-4,8'-dipyrrolo[2,3-b:3',2'-d]pyridin]-7'-one (Single Enantiomer Prepared)

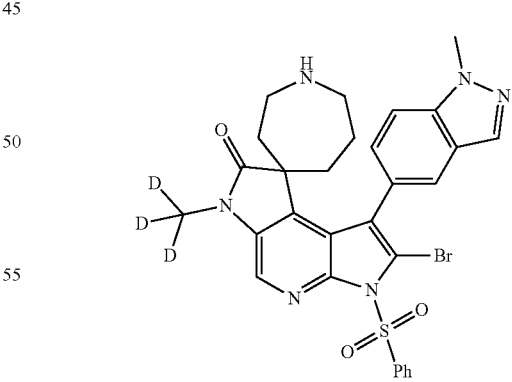

tert-Butyl 2'-bromo-6'-(methyl-d₃)-1'-(1-methyl-1H-indazol-5-yl)-7'-oxo-3'-(phenylsulfonyl)-6',7'-dihydro-3'H-spiro[azepane-4,8'-dipyrrolo[2,3-b:3',2'-d]pyridine]-1-carboxylate (0.11 g, 0.15 mmol) was deprotected by the method described in Example 5, Step 3 to afford the title compound (94 mg, 99%). LCMS for $C_{29}H_{25}D_3BrN_6O_3S$ (M+H)⁺: calculated monoisotopic m/z=622.1; found 622.1.

Step 4. 2'-Bromo-6'-(methyl-d₃)-1'-(1-methyl-1H-indazol-5-yl)-1-((1-methylcyclopropyl)sulfonyl)-3'-(phenylsulfonyl)-3',6'-dihydro-7'H-spiro[azepane-4,8'-dipyrrolo[2,3-b:3',2'-d]pyridin]-7'-one (Single Enantiomer Prepared)

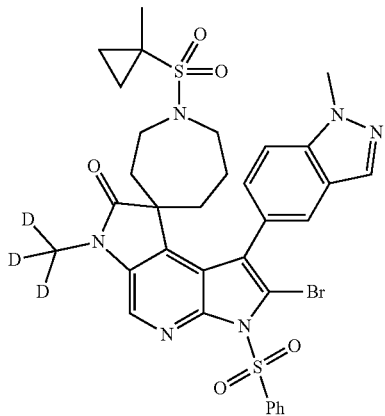 [SMILES: [2H]C([2H])([2H])N1C(=O)C2(CCCN(S(=O)(=O)C3(C)CC3)CC2)c2c1cnc1c2c(-c2ccc3c(cnn3C)c2)c(Br)n1S(=O)(=O)c1ccccc1]

To a solution of 2'-bromo-6'-(methyl-d₃)-1'-(1-methyl-1H-indazol-5-yl)-3'-(phenylsulfonyl)-3',6'-dihydro-7'H-spiro[azepane-4,8'-dipyrrolo[2,3-b:3',2'-d]pyridin]-7'-one (0.014 g, 0.022 mmol) and triethylamine (0.0094 mL, 0.067 mmol) in DCM (0.23 mL) at 0° C. was added 1-methylcyclopropane-1-sulfonyl chloride (5.2 mg, 0.034 mmol, AstaTech #68609) and the mixture was stirred for 10 minutes with warming to room temperature. Saturated NaHCO₃ solution was added, and the resulting mixture was extracted with EtOAc. The organic layer was washed with water, followed by brine, then dried over sodium sulfate, filtered, and concentrated. Purification via flash column chromatography, eluting with a gradient of 0-100% EtOAc in hexanes afforded the title compound (17 mg, 99%). LCMS for $C_{33}H_{31}D_3BrN_6O_5S_2$ (M+H)⁺: calculated monoisotopic m/z=740.1; found 740.2.

Step 5. 2'-(1-Isopropyl-1H-pyrazol-4-yl)-6'-(methyl-d₃)-1'-(1-methyl-1H-indazol-5-yl)-1-((1-methylcyclopropyl)sulfonyl)-3, 6'-dihydro-7'H-spiro[azepane-4,8'-dipyrrolo[2,3-b:3',2'-d]pyridin]-7'-one, trifluoroacetate salt (Single Enantiomer Prepared)

A degassed mixture of 2'-bromo-6'-(methyl-d3)-1'-(1-methyl-1H-indazol-5-yl)-1-((1-methylcyclopropyl)sulfonyl)-3'-(phenylsulfonyl)-3',6'-dihydro-7'H-spiro[azepane-4,8'-dipyrrolo[2,3-b:3',2'-d]pyridin]-7'-one (17 mg, 0.022 mmol), 1-isopropyl-4-(4,4,5,5-tetramethyl-1,3,2-dioxaborolan-2-yl)-1H-pyrazole (11 mg, 0.046 mmol, Combi-Blocks #PN-9153), PdCl₂(dppf)-CH₂Cl₂ adduct (1.9 mg, 0.0023 mmol) and K₂CO₃ (1.0 M in water, 0.069 mL, 0.069 mmol) in dioxane (0.30 mL) was heated at 100° C. for one hour. Upon cooling to room temperature, 1:1 MeOH/THF (1.0 mL) and sodium hydroxide (3.0 N, 0.15 mL, 0.45 mmol) were added and the reaction mixture was heated at 60° C. for 30 min. The resulting mixture was filtered and purified via preparative HPLC-MS (pH=2) to afford the title compound (4.8 mg). LCMS for $C_{33}H_{36}D_3N_8O_3S$ (M+H)⁺: calculated m/z=630.3; found 630.5.

Example 104

The compound of Example 104 was prepared by the method described in Example 103, substituting ethanesulfonyl chloride in place of 1-methylcyclopropane-1-sulfonyl chloride in Step 4, and 1-(1-cyclopropylethyl)-4-(4,4,5,5-tetramethyl-1,3,2-dioxaborolan-2-yl)-1H-pyrazole (racemate) in place of 1-isopropyl-4-(4,4,5,5-tetramethyl-1,3,2-dioxaborolan-2-yl)-1H-pyrazole in Step 5.

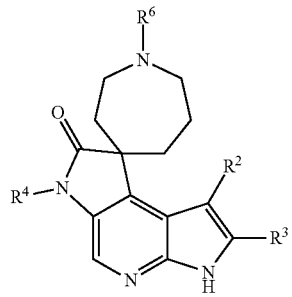

| Ex No. | Compound Name | R⁴ | R⁶ | R² | R³ | LCMS |
|---|---|---|---|---|---|---|
| 104 | 2'-(1-(1-Cyclopropylethyl)-1H-pyrazol-4-yl)-1-(ethylsulfonyl)-6'-(methyl-d₃)-r-(1-methyl-1H-indazol-5-yl)-3',6'-dihydro-7'H-spiro[azepane-4,8'-dipyrrolo[2,3-b:3',2'-d]pyridin]-7'-one, trifluoroacetate salt (mixture of two diastereomers prepared) | CD₃ | (ethylsulfonyl group) | (1-methyl-1H-indazol-5-yl group) | (1-(1-cyclopropylethyl)-1H-pyrazol-4-yl group) | Calculated for $C_{33}H_{36}D_3N_8O_3S$ (M + H)⁺: m/z = 630.3, found: 630.5 |

Example A. JAK2 LanthaScreen JH1 Binding Assay

JAK2 JH1 binding assay utilizes catalytic domain (JH1, amino acids 826-1132) of human JAK2 expressed as N-terminal FLAG-tagged, biotinylated protein in a baculovirus expression system (Carna Biosciences, Product #08-445-20N). The assay was conducted in black 384-well polystyrene plates in a final reaction volume of 20 µL. JAK2 JH1 (1.5 nM) was incubated with compounds (100 nL serially diluted in DMSO) in the presence of 50 nM Fluorescent JAK2-JH1 Tracer and 0.5 nM Streptavidin-Tb cryptate (Cisbio Part #610SATLB) in assay buffer (50 mM Tris, pH=7.5, 10 mM $MgCl_2$, 0.01% Brij-35, 0.1% BSA, 1 mM EGTA, 5% Glycerol and 5 mM DTT). Non-specific binding was accessed in the presence of 2 mM ATP. After incubation for 2 hours at 25° C., LanthaScreen signals were read on a PHERAstar FS plate reader (BMG LABTECH). Data was analyzed with IDBS XLfit and GraphPad Prism 5.0 software using a four parameter dose response curve to determine IC50 for each compound.

Example B. JAK2 LanthaScreen JH2-WT Binding Assay

JAK2 JH2-WT binding assay utilizes pseudo-kinase domain (JH2, amino-acids 536-812 with 3 surface mutations W659A, W777A, F794H) of human Wild Type JAK2 expressed as C-terminal His-Avi-tagged, biotinylated protein in a baculovirus expression system (BPS Bioscience, Catalog #79463). The assay was conducted in black 384-well polystyrene plates in a final reaction volume of 20 µL. JAK2 JH2-WT (0.145 nM) was incubated with compounds (100 nL serially diluted in DMSO) in the presence of 50 nM Fluorescent JAK2-JH2 Tracer (MedChem Express Catalog #HY-102055) and 0.25 nM Streptavidin-Tb cryptate (Cisbio Part #610SATLB) in assay buffer (50 mM Tris, pH=7.5, 10 mM $MgCl_2$, 0.01% Brij-35, 0.1% BSA, 1 mM EGTA, 5% Glycerol and 5 mM DTT). Non-specific binding was accessed in the presence of 2 mM ATP. After incubation for 1 hour at 25° C., LanthaScreen signals were read on a PHERAstar FS plate reader (BMG LABTECH). Data was analyzed with IDBS XLfit and GraphPad Prism 5.0 software using a four parameter dose response curve to determine IC50 for each compound.

Example C. JAK2 LanthaScreen JH2-V617F Binding Assay

JAK2 JH2-V617F binding assay utilizes pseudo-kinase domain (JH2, amino-acids 536-812 with 3 surface mutations W659A, W777A, F794H) of human V617F mutant JAK2 expressed as C-terminal His-Avi-tagged, biotinylated protein in a baculovirus expression system (BPS Bioscience, Catalog #79498). The assay was conducted in black 384-well polystyrene plates in a final reaction volume of 20 µL. JAK2 JH2-V617F (0.26 nM) was incubated with compounds (100 nL serially diluted in DMSO) in the presence of 50 nM Fluorescent JAK2-JH2 Tracer (MedChem Express Catalog #HY-102055) and 0.25 nM Streptavidin-Tb cryptate (Cisbio Part #610SATLB) in assay buffer (50 mM Tris, pH=7.5, 10 mM $MgCl_2$, 0.01% Brij-35, 0.1% BSA, 1 mM EGTA, 5% Glycerol and 5 mM DTT). Non-specific binding was accessed in the presence of 2 mM ATP. After incubation for 1 hour at 25° C., LanthaScreen signals were read on a PHERAstar FS plate reader (BMG LABTECH). Data was analyzed with IDBS XLfit and GraphPad Prism 5.0 software using a four parameter dose response curve to determine IC50 for each compound.

Example D. JAK2 HTRF Enzyme Activity Assay

JAK2 enzyme activity assays utilize catalytic domain (JH1, amino acids 808-1132) of human JAK2 expressed as N-terminal His-tagged protein in a baculovirus expression system (BPS Bioscience, Catalog #40450). The assays was conducted in black 384-well polystyrene plates in a final reaction volume of 20 µL. JAK2 (0.015 nM) was incubated with compounds (100 nL serially diluted in DMSO) in the presence of ATP (30 µM or 1 mM) and 500 nM Biotin-labeled EQEDEPEGDYFEWLE (SEQ ID NO.: 1) peptide (BioSource International, custom synthesis) in assay buffer (50 mM Tris, pH=7.5, 10 mM $MgCl_2$, 0.01% Brij-35, 0.1% BSA, 1 mM EGTA, 5% Glycerol and 5 mM DTT) for 60 minutes at 25° C. The reactions were stopped by the addition of 10 µL of detection buffer (50 mM Tris, pH 7.8, 0.5 mg/mL BSA, 150 mM NaCl), supplemented with EDTA, LANCE Eu-W1024 anti-phosphotyrosine (PY20), (PerkinElmer, Catalog #AD0067) and Streptavidin SureLight APC (PerkinElmer Catalog #CR130-100), for a final concentration of 15 mM, 1.5 nM and 75 nM, respectively. HTRF signals were read after 30 minutes incubation at room temperature on a PHERAstar FS plate reader (BMG LABTECH). Data was analyzed with IDBS XLfit and GraphPad Prism 5.0 software using a four parameter dose response curve to determine IC50 for each compound.

The compounds of the disclosure were tested in one or more of the assays described in Examples A-D, and the resulting data are shown in Table A.

TABLE A

| Ex. No. | V617F JH2 Binding (nM) | WT JH2 Binding (nM) | JH1 Binding (nM) | ENZ 30UMATP (nM) |
|---|---|---|---|---|
| 1 | + | + | ++++ | ++++ |
| 2 | + | + | +++++ | +++++ |
| 3 | ++ | ++ | +++++ | +++++ |
| 4 | + | + | +++ | +++ |
| 5 | + | + | +++ | +++ |
| 6 | + | + | +++++ | +++++ |
| 7 | + | + | ++++ | ++++ |
| 8 | + | + | ++++ | +++++ |
| 9 | ++ | ++ | +++++ | +++++ |
| 10 | + | + | +++++ | +++++ |
| 11 | ++ | ++ | +++++ | +++++ |
| 12 | ++ | ++ | +++++ | +++++ |
| 13 | ++ | + | ++++ | ++++ |
| 14 | ++ | + | +++++ | +++++ |
| 15 | + | + | +++++ | +++++ |
| 16 | + | + | +++++ | +++++ |
| 17 | ++ | ++ | +++++ | +++++ |
| 18 | ++++ | +++ | +++++ | +++++ |
| 19 | ++ | ++ | ++++ | ++++ |
| 20 | ++ | ++ | +++++ | +++++ |
| 21 | + | + | +++++ | +++++ |
| 22 | ++ | + | +++++ | +++++ |
| 23 | + | + | +++ | ++ |
| 24 | + | + | +++ | ++ |
| 25 | + | + | +++ | ++ |
| 26 | + | + | ++ | + |
| 27 | + | + | ++ | ++ |
| 28 | + | + | ++ | ++ |
| 29 | + | + | +++ | +++ |
| 30 | + | + | ++ | ++ |
| 31 | + | + | ++ | ++ |
| 32 | + | + | ++ | ++ |

TABLE A-continued

| Ex. No. | V617F JH2 Binding (nM) | WT JH2 Binding (nM) | JH1 Binding (nM) | ENZ 30UMATP (nM) |
|---|---|---|---|---|
| 33 | + | + | +++ | +++ |
| 34 | + | + | +++ | +++ |
| 35 | + | + | +++ | +++ |
| 36 | + | + | ++ | ++ |
| 37 | + | + | ++ | ++ |
| 38 | + | + | ++ | + |
| 39 | + | + | ++ | ++ |
| 40 | + | + | +++++ | +++++ |
| 41 | + | + | ++ | + |
| 42 | + | + | +++ | ++ |
| 43 | + | + | +++++ | +++++ |
| 44 | + | + | ++ | ++ |
| 45 | + | + | ++ | + |
| 46 | + | + | +++ | +++ |
| 47 | + | + | +++++ | +++++ |
| 48 | + | + | ++ | ++ |
| 49 | + | + | +++++ | +++++ |
| 50 | + | + | +++++ | +++++ |
| 51 | + | + | +++ | +++ |
| 52 | + | + | +++++ | +++++ |
| 53a | +++ | ++ | +++++ | +++++ |
| 53b | + | + | ++ | ++ |
| 54 | + | + | +++ | +++ |
| 55 | + | + | ++++ | +++ |
| 56 | + | + | ++++ | ++++ |
| 57 | +++++ | ++++ | +++++ | +++++ |
| 58 | + | + | ++++ | ++++ |
| 59 | + | + | ++++ | ++++ |
| 60 | + | + | ++++ | ++++ |
| 61 | + | + | +++ | +++ |
| 62 | + | + | +++++ | +++++ |
| 63 | + | + | +++++ | +++++ |
| 64 | + | + | ++++ | ++++ |
| 65 | + | + | +++++ | +++++ |
| 66 | + | + | +++ | +++ |
| 67 | + | + | +++++ | +++++ |
| 68 | + | + | +++++ | +++++ |
| 69 | + | + | +++ | +++ |
| 70 | + | + | +++++ | +++++ |
| 71 | + | + | ++++ | ++++ |
| 72 | ++++ | +++ | +++++ | +++ |
| 73 | + | + | ++ | ++ |
| 74 | + | + | +++ | +++ |
| 75a | + | + | ++ | ++ |
| 75b | + | + | +++ | +++ |
| 76 | + | + | ++ | ++ |
| 77 | + | + | +++ | +++ |
| 78 | + | + | +++ | +++ |
| 79 | + | + | +++++ | ++++ |
| 80a | + | + | ++++ | ++++ |
| 80b | + | + | +++ | +++ |
| 81 | + | + | +++ | +++ |
| 82 | + | + | ++ | ++ |
| 83 | + | + | ++++ | ++++ |
| 84 | + | + | +++ | ++ |
| 85 | + | + | ++++ | ++++ |
| 86 | + | + | +++ | +++ |
| 87 | + | + | ++++ | ++++ |
| 88 | + | + | ++++ | ++++ |
| 89 | + | + | ++++ | ++++ |
| 90 | + | + | ++++ | ++++ |
| 91 | + | + | ++++ | ++++ |
| 92 | + | + | +++++ | +++++ |
| 93 | + | + | ++++ | ++++ |
| 94 | + | + | +++++ | +++++ |
| 95 | + | + | +++ | +++ |
| 96 | + | + | +++++ | +++++ |
| 97 | + | + | ++++ | ++++ |
| 98 | + | + | +++++ | NT |
| 99 | + | + | +++++ | NT |
| 100 | +++ | +++ | +++++ | NT |
| 101 | + | + | ++++ | NT |
| 102 | + | + | +++++ | NT |
| 103 | + | + | ++ | +++ |
| 104 | + | + | ++ | ++ |

+ refers to $IC_{50}$ of ≤100 nM
++ refers to $IC_{50}$ of >100 nM to ≤500 nM
+++ refers to $IC_{50}$ of >500 nM to ≤1250 nM
++++ refers to $IC_{50}$ of >1250 nM to ≤2500 nM
+++++ refers to $IC_{50}$ of >2500 nM
NT refers to "Not Tested"

Example E. Cell Culture and STATS (Tyr694) Phosphorylation Cell Based Assay

Ba/F3 cells expressing human JAK2 V617F/EPOR (mouse JAK2 WT knocked out by CRISPR) are cultured in RPMI media with 10% FBS, 1 μg/mL Puromycin, 1 mg/mL Geneticin (Thermo Fisher). Ba/F3 cells expressing human JAK2 WT/EPOR are cultured in RPMI media with 10% FBS, 1 μg/mL Puromycin, 1 mg/mL Geneticin and 2 ng/mL EPO. 24 hours before the assay, the culture medium for JAK2 V617F/EPOR Ba/F3 cells are changed to RPMI with 10% FBS without antibiotic (assay medium 1). Culture medium for Ba/F3 cells expressing human JAK2 WT/EPOR are changed to RPMI with 10% FBS and 2 ng/mL EPO (R&D systems) without antibiotic (assay medium 2). 50 nL/well test compounds in DMSO are transferred to the 384 white low volume cell culture plate (Greiner Bio-one) by ECHO liquid handler (Labcyte). The cells are centrifuged, resuspended in the corresponding fresh assay medium and dispensed at 10 μL/well ($6\times10^6$ cells/mL) with 0.5% DMSO in the final assay. After the treated cells are incubated at 37° C., 5% $CO_2$ for 2 hours, 4 μL/well supplemented lysis buffer (100× blocking buffer diluted 25 fold in 4× lysis buffer, Perkin—Elmer) are added and incubated at room temperature for 60 min with gentle shaking on orbital shaker at 600 rpm. Phospho-STATS Cryptate antibody and Phospho-STATS d2 antibody (1:1 vol/vol, Perkin—Elmer) are premixed and diluted 20 fold within the detection buffer. 4 μL of the premixed antibody solution are added to each well followed with 16 hours incubation at room temperature. The product activity is determined by measuring the fluorescence at 620 nm and 665 nm on Pherastar microplate reader (BMG Labtech). A ratio is calculated (665/620 nm) for each well. Wells with DMSO serve as the positive controls and wells containing high concentration of control compound are used as negative controls. $IC_{50}$ determination is performed by fitting the curve of percent control activity versus the log of the compound concentration using the Genedata Screener software.

Various modifications of the invention, in addition to those described herein, will be apparent to those skilled in the art from the foregoing description. Such modifications are also intended to fall within the scope of the appended claims. Each reference, including all patent, patent applications, and publications, cited in the present application is incorporated herein by reference in its entirety.

What is claimed is:

1. A compound of Formula I:

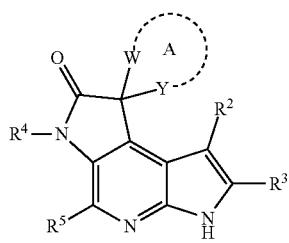

I or a pharmaceutically acceptable salt thereof, wherein:
W is $CR^W$ or $C(R^W)_2$;
Y is $CR^Y$ or $C(R^Y)_2$;
each $R^W$ is independently selected from H, oxo, $C_{1-6}$ alkyl, $C_{1-6}$ haloalkyl, $C_{2-6}$ alkenyl, and $C_{2-6}$ alkynyl;
each $R^Y$ is independently selected from H, oxo, $C_{1-6}$ alkyl, $C_{1-6}$ haloalkyl, $C_{2-6}$ alkenyl, and $C_{2-6}$ alkynyl;
Ring A is $C_{3-10}$ cycloalkyl or 4-10 membered heterocycloalkyl, wherein the $C_{3-10}$ cycloalkyl and 4-10 membered heterocycloalkyl of Ring A are each optionally substituted with 1, 2, 3, 4, 5, 6, 7, or 8 independently selected $R^6$ substituents;
$R^2$ is selected from H, halo, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, (4-10 membered heterocycloalkyl)-$C_{1-6}$ alkyl-, CN, $NO_2$, $OR^{a2}$, $SR^{a2}$, $NHOR^{a2}$, $C(O)R^{b2}$, $C(O)NR^{c2}R^{d2}$, $C(O)NR^{c2}(OR^{a2})$, $C(O)OR^{a2}$, $OC(O)R^{b2}$, $OC(O)NR^{c2}R^{d2}$, $NR^{c2}R^{d2}$, $NR^{c2}NR^{c2}R^{d2}$, $NR^{c2}C(O)R^{b2}$, $NR^{c2}C(O)OR^{a2}$, $NR^{c2}C(O)NR^{c2}R^{d2}$, $C(=NR^{e2})R^{b2}$, $C(=NR^{e2})R^{c2}R^{d2}$, $NR^{c2}C(=NR^{e2})NR^{c2}R^{d2}$, $NR^{c2}C(=NR^{e2})R^{b2}$, $NR^{c2}S(O)R^{b2}$, $NR^{c2}S(O)NR^{c2}R^{d2}$, $NR^{c2}S(O)_2R^{b2}$, $NR^{c2}S(O)(=NR^{e2})R^{b2}$, $NR^{c2}S(O)_2NR^{c2}R^{d2}$, $S(O)R^{b2}$, $S(O)NR^{c2}R^{d2}$, $S(O)_2R^{b2}$, $S(O)_2NR^{c2}R^{d2}$, $OS(O)(=NR^{e2})R^{b2}$, and $OS(O)_2R^{b2}$, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^2$ are each optionally substituted with 1, 2, 3, 4, 5, 6, 7, or 8 independently selected $R^{2A}$ substituents;

each $R^{a2}$, $R^{c2}$, and $R^{d2}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{a2}$, $R^{c2}$ and $R^{d2}$ are each optionally substituted with 1, 2, 3, 4, 5, 6, 7, or 8 independently selected $R^{2A}$ substituents;

or, any $R^{c2}$ and $R^{d2}$ attached to the same N atom, together with the N atom to which they are attached, form a 5-10 membered heteroaryl or a 4-10 membered heterocycloalkyl group, wherein the 5-10 membered heteroaryl or 4-10 membered heterocycloalkyl group is optionally substituted with 1, 2, 3, or 4 independently selected $R^{2A}$ substituents;

each $R^{b2}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{b2}$ are each optionally substituted with 1, 2, 3, 4, 5, 6, 7, or 8 independently selected $R^{2A}$ substituents;

each $R^{e2}$ is independently selected from H, OH, CN, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-;

each $R^{2A}$ is selected from halo, oxo, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, (4-10 membered heterocycloalkyl)-$C_{1-6}$ alkyl-, CN, $NO_2$, $OR^{a21}$, $SR^{a21}$, $NHOR^{a21}$, $C(O)R^{b21}$, $C(O)NR^{c21}R^{d21}$, $C(O)NR^{c21}(OR^{a21})$, $C(O)OR^{a21}$, $OC(O)R^{b21}$, $OC(O)NR^{c21}R^{d21}$, $NR^{c21}R^{d21}$, $NR^{c21}NR^{c21}R^{d21}$, $NR^{c21}C(O)R^{b21}$, $NR^{c21}C(O)OR^{a21}$, $NR^{c21}C(O)NR^{c21}R^{d21}$, $C(=NR^{e21})R^{b21}$, $C(=NR^{e21})NR^{c21}R^{d21}$, $NR^{c21}C(=NR^{e21})NR^{c21}R^{d21}$, $NR^{c21}C(=NR^{e21})R^{b21}$, $NR^{c21}S(O)R^{b21}$, $NR^{c21}S(O)NR^{c21}R^{d21}$, $NR^{c21}S(O)_2R^{b21}$, $NR^{c21}S(O)(=NR^{e21})R^{b21}$, $NR^{c21}S(O)_2NR^{c21}R^{d21}$, $S(O)R^{b21}$, $S(O)NR^{c21}R^{d21}$, $S(O)_2R^{b21}$, $S(O)_2NR^{c21}R^{d21}$, $OS(O)(=NR^{e21})R^{b21}$, and $OS(O)_2R^{b21}$, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{2A}$ are each optionally substituted with 1, 2, 3, 4, 5, 6, 7, or 8 independently selected $R^{2B}$ substituents;

each $R^{a21}$, $R^{c21}$, and $R^{d21}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{a21}$, $R^{c21}$ and $R^{d21}$ are each optionally substituted with 1, 2, 3, 4, 5, 6, 7, or 8 independently selected $R^{2B}$ substituents;

or, any $R^{c21}$ and $R^{d21}$ attached to the same N atom, together with the N atom to which they are attached, form a 5-10 membered heteroaryl or a 4-10 membered heterocycloalkyl group, wherein the 5-10 membered heteroaryl or 4-10 membered heterocycloalkyl group is optionally substituted with 1, 2, 3, or 4 independently selected $R^{2B}$ substituents;

each $R^{b21}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{b21}$ are each optionally substituted with 1, 2, 3, 4, 5, 6, 7, or 8 independently selected $R^{2B}$ substituents;

each $R^{e21}$ is independently selected from H, OH, CN, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-;

each $R^{2B}$ is independently selected from halo, oxo, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, (4-10 membered heterocycloalkyl)-$C_{1-6}$ alkyl-, CN, $NO_2$, $OR^{a22}$, $SR^{a22}$, $NHOR^{a22}$, $C(O)R^{b22}$, $C(O)NR^{c22}R^{d22}$, $C(O)NR^{c22}(OR^{a22})$, $C(O)OR^{a22}$, $OC(O)R^{b22}$, $OC(O)NR^{c22}R^{d22}$, $NR^{c22}R^{d22}$, $NR^{c22}NR^{c22}R^{d22}$, $NR^{c22}C(O)R^{b22}$, $NR^{c22}C(O)OR^{a22}$, $NR^{c22}C(O)NR^{c22}R^{d22}$, $C(=NR^{e22})R^{b22}$, $(=NR^{e22})NR^{c22}R^{d22}$, $NR^{c22}C(=NR^{e22})NR^{c22}R^{d22}$, $NR^{c22}(=NR^{e22})R^{b22}$, $NR^{c22}S(O)R^{b22}$, $NR^{c22}S(O)NR^{c22}R^{d22}$, $NR^{c22}S(O)_2R^{b22}$, $NR^{c22}S(O)(=NR^{e22})R^{b22}$, $NR^{c22}S(O)^2NR^{c22}R^{d22}$, $S(O)R^{b22}$, $S(O)NR^{c22}R^{d22}$, $S(O)_2R^{b22}$, $S(O)_2NR^{c22}R^{d22}$, $S(O)(=NR^{e22})R^{b22}$, and $OS(O)_2R^{b22}$, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{2B}$ are each optionally substituted with 1, 2, 3, 4, 5, 6, 7, or 8 independently selected $R^{2C}$ substituents;

each $R^{a22}$, $R^{c22}$, and $R^{d22}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-o}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{a22}$, $R^{c22}$ and $R^{d22}$ are each optionally substituted with 1, 2, 3, 4, 5, 6, 7, or 8 independently selected $R^{2C}$ substituents;

or, any $R^{c22}$ and $R^{d22}$ attached to the same N atom, together with the N atom to which they are attached, form a 5-10 membered heteroaryl or a 4-10 membered heterocycloalkyl group, wherein the 5-10 membered heteroaryl or 4-10 membered heterocycloalkyl group is optionally substituted with 1, 2, 3, or 4 independently selected $R^{2C}$ substituents;

each $R^{b22}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{b22}$ are each optionally substituted with 1, 2, 3, 4, 5, 6, 7, or 8 independently selected $R^{2C}$ substituents;

each $R^{e22}$ is independently selected from H, OH, CN, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-;

each $R^{2C}$ is independently selected from halo, oxo, $C_{1-6}$ alkyl, $C_{1-6}$ haloalkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, (4-7 membered heterocycloalkyl)-$C_{1-6}$ alkyl-, CN, NO$_2$, OR$^{a23}$, SR$^{a23}$, NHOR$^{a23}$, C(O)R$^{b23}$, C(O)NR$^{c23}$R$^{d23}$, C(O)NR$^{c23}$(OR$^{a23}$), C(O)OR$^{a23}$, OC(O)R$^{b23}$, OC(O)NR$^{c23}$R$^{d23}$, NR$^{c23}$R$^{d23}$, NR$^{c23}$NR$^{c23}$R$^{c23}$, NR$^{c23}$C(O)R$^{b23}$, NR$^{c23}$C(O)OR$^{a23}$, NR$^{c23}$C(O)NR$^{c23}$R$^{23}$, C(=NR$^{e23}$)R$^{b23}$, C(=NR$^{e23}$)NR$^{c23}$R$^{23}$, NR$^{c23}$C(=NR$^{e23}$)NR$^{c23}$R$^{d23}$, NR$^{c23}$C(=NR$^{e23}$)R$^{b23}$, NR$^{c23}$S(O)R$^{b23}$, NR$^{c23}$S(O)NR$^{c23}$R$^{23}$, NR$^{e23}$S(O)$_2$R$^{b23}$, NR$^{e23}$S(O)(=NR$^{e23}$)R$^{b23}$, NR$^{c23}$S(O)$_2$NR$^{c23}$R$^{23}$, S(O)R$^{b23}$, S(O)NR$^{c23}$R$^{d23}$, S(O)$_2$R$^{b23}$, S(O)$_2$NR$^{c23}$R$^{d23}$, OS(O)(=NR$^{e23}$)R$^{b23}$, and OS(O)$_2$R$^{b23}$, wherein the $C_{1-6}$ alkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, (4-7 membered heterocycloalkyl)-$C_{1-6}$ alkyl- of R$^{2C}$ are each optionally substituted with 1, 2, 3, or 4 independently selected R$^M$ substituents;

each R$^{a23}$, R$^{c23}$, and R$^{d23}$ is independently selected from H, $C_{1-6}$ alkyl, $C_{1-6}$ haloalkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl-, wherein the $C_{1-6}$ alkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl- of R$^{a23}$, R$^{e23}$ and R$^{d23}$ are each optionally substituted with 1, 2, 3, or 4 independently selected R$^M$ substituents;

or, any R$^{c23}$ and R$^{d23}$ attached to the same N atom, together with the N atom to which they are attached, form a 5-6 membered heteroaryl or a 4-7 membered heterocycloalkyl group, wherein the 5-6 membered heteroaryl or 4-7 membered heterocycloalkyl group is optionally substituted with 1, 2, 3, or 4 independently selected R$^M$ substituents;

each R$^{b23}$ is independently selected from H, $C_{1-6}$ alkyl, $C_{1-6}$ haloalkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl-, wherein the $C_{1-6}$ alkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl- of R$^{b23}$ are each optionally substituted with 1, 2, 3, or 4 independently selected R$^M$ substituents;

each R$^{e23}$ is independently selected from H, OH, CN, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl-;

R$^3$ is selected from $C_{6-10}$ aryl, $C_{3-10}$ cycloalkyl, 5-10 membered heteroaryl, and 4-10 membered heterocycloalkyl, wherein the $C_{6-10}$ aryl, $C_{3-10}$ cycloalkyl, 5-10 membered heteroaryl, and 4-10 membered heterocycloalkyl of R$^3$ are each optionally substituted with 1, 2, 3, or 4 independently selected R$^{3A}$ substituents;

each R$^{3A}$ is independently selected from oxo, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, (4-10 membered heterocycloalkyl)-$C_{1-6}$ alkyl-, C(O)R$^{b31}$, C(O)NR$^{c31}$R$^{d31}$, NR$^{c31}$R$^{d31}$, and S(O)$_2$R$^{b31}$ wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of R$^{3A}$ are each optionally substituted with 1, 2, 3, or 4 independently selected R$^{3B}$ substituents;

each R$^{b31}$, R$^{c31}$, and R$^{d31}$ is independently selected from H, $C_{1-6}$ alkyl, and 4-10 membered heterocycloalkyl;

each R$^{3B}$ is independently selected from CN, OR$^{a32}$, C(O)R$^{b32}$, and S(O)$_2$R$^{b32}$;

each R$^{a32}$ and R$^{b32}$ is independently selected from H and $C_{1-6}$ alkyl;

R$^4$ is selected from H, $C_{1-3}$ alkyl, and $C_{1-3}$ alkoxy;

R$^5$ is H;

each R$^6$ is independently selected from halo, oxo, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, (4-10 membered heterocycloalkyl)-$C_{1-6}$ alkyl-, CN, NO$_2$, OR$^{a6}$, SR$^{a6}$, NHOR$^{a6}$, C(O)R$^{b6}$, C(O)NR$^{c6}$R$^{d6}$, C(O)NR$^{c6}$(OR$^{a6}$), C(O)OR$^{a6}$, OC(O)R$^{b6}$, OC(O)NR$^{c6}$R$^{d6}$, NR$^{c6}$R$^{d6}$, NR$^{c6}$NR$^{c6}$R$^{d6}$, NR$^{c6}$C(O)R$^{b6}$, NR$^{c6}$C(O)OR$^{a6}$, NR$^{c6}$C(O)NR$^{c6}$R$^{d6}$, C(=NR$^{e6}$)R$^{b6}$, C(=NR$^{e6}$)NR$^{c6}$R$^{d6}$, NR$^{c6}$C(=NR$^{e6}$)NR$^{c6}$R$^{d6}$, NR$^{c6}$C(=NR$^{e6}$)R$^{b6}$, NR$^{c6}$S(O)R$^{b6}$, NR$^{c6}$S(O)NR$^{c6}$R$^{d6}$, NR$^{c6}$S(O)$_2$R$^{b6}$, NR$^{c6}$S(O)(=NR$^{e6}$)R$^{b6}$, NR$^{c6}$S(O)$_2$NR$^{c6}$R$^{d6}$, S(O)R$^{b6}$, S(O)NR$^{c6}$R$^{d6}$, S(O)$_2$R$^{b6}$, S(O)$_2$NR$^{c6}$R$^{d6}$, OS(O)(=NR$^{e6}$)R$^{b6}$, and OS(O)$_2$ R$^{b6}$, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of R$^6$ are each optionally substituted with 1, 2, 3, 4, 5, 6, 7, or 8 independently selected R$^{6A}$ substituents;

each R$^{a6}$, R$^{c6}$, and R$^{d6}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-

$C_{1-6}$ alkyl-, and (4-10 membered heterocycloalkyl)-$C_{1-6}$ alkyl- of $R^{a6}$, $R^{c6}$ and $R^{d6}$ are each optionally substituted with 1, 2, 3, 4, 5, 6, 7, or 8 independently selected $R^{6A}$ substituents;

or, any $R^{c6}$ and $R^{d6}$ attached to the same N atom, together with the N atom to which they are attached, form a 5-10 membered heteroaryl or a 4-10 membered heterocycloalkyl group, wherein the 5-10 membered heteroaryl or 4-10 membered heterocycloalkyl group is optionally substituted with 1, 2, 3, or 4 independently selected $R^{6A}$ substituents;

each $R^{b6}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{b6}$ are each optionally substituted with 1, 2, 3, 4, 5, 6, 7, or 8 independently selected $R^{6A}$ substituents;

each $R^{e6}$ is independently selected from H, OH, CN, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-;

each $R^{6A}$ is independently selected from halo, oxo, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, (4-10 membered heterocycloalkyl)-$C_{1-6}$ alkyl-, CN, $NO_2$, $OR^{a61}$, $SR^{a61}$, $NHOR^{a61}$, $C(O)R^{b61}$, $C(O)NR^{c61}R^{d61}$, $C(O)NR^{c61}(OR^{a61})$, $C(O)OR^{a61}$, $OC(O)R^{b61}$, $OC(O)NR^{c61}R^{d61}$, $NR^{c61}R^{d61}$, $NR^{c61}NR^{c61}R^{d61}$, $NR^{c61}C(O)R^{c61}$, $NR^{c61}C(O)OR^{a61}NR^{c61}C(O)NR^{c61}R^{d61}$, $C(=NR^{e61})R^{b61}$, $C(=NR^{e61})NR^{c61}R^{d61}$, $NR^{c61}C(=NR^{e61})NR^{c61}R^{d61}$, $NR^{c61}C(=NR^{e61})R^{b61}$, $NR^{c61}S(O)R^{b61}$, $NR^{c61}S(O)NR^{c6}R^{d61}$, $NR^{c61}S(O)_2R^{b61}$, $NR^{c61}S(O)(=NR^{e61})R^{b61}$, $NR^{c61}S(O)_2NR^{c61}R^{d61}$, $S(O)R^{b61}$, $S(O)NR^{c61}R^{d61}$, $S(O)_2R^{b61}$, $S(O)_2NR^{c61}R^{d61}$, $OS(O)(=NR^{e61})R^{b61}$, and $OS(O)_2R^{b61}$, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{6A}$ are each optionally substituted with 1, 2, 3, 4, 5, 6, 7, or 8 independently selected $R^{6B}$ substituents;

each $R^{a61}$, $R^{c61}$, and $R^{d61}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{a6}$, $R^{c61}$ and $R^{d61}$ are each optionally substituted with 1, 2, 3, 4, 5, 6, 7, or 8 independently selected $R^{6B}$ substituents;

or, any $R^{c61}$ and $R^{d61}$ attached to the same N atom, together with the N atom to which they are attached, form a 5-10 membered heteroaryl or a 4-10 membered heterocycloalkyl group, wherein the 5-10 membered heteroaryl or 4-10 membered heterocycloalkyl group is optionally substituted with 1, 2, 3, or 4 independently selected $R^{6B}$ substituents;

each $R^{b61}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_6$-10 aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{b61}$ are each optionally substituted with 1, 2, 3, 4, 5, 6, 7, or 8 independently selected $R^{6B}$ substituents;

each $R^{e61}$ is independently selected from H, OH, CN, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-;

each $R^{6B}$ is independently selected from halo, oxo, $C_{1-6}$ alkyl, $C_{1-6}$ haloalkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, (4-7 membered heterocycloalkyl)-$C_{1-6}$ alkyl-, CN, $NO_2$, $OR^{a62}$, $SR^{a62}$, $NHOR^{a62}$, $C(O)R^{b62}C(O)NR^{c62}R^{d62}$, $C(O)NR^{c62}(OR^{a62})$, $C(O)OR^{a62}$, $OC(O)R^{b62}$, $OC(O)NR^{c62}R^{d62}$, $NR^{c6\ 62}NR^{c62}NR^{c62}R^{d62}$, $NR^{c62}C(O)R^{b62}$, $NR^{c62}C(O)OR^{a62}$, $NR^{c62}C(O)NR^{c62}R^{d62}$, $C(=NR^{e62})R^{b62}$, $C(=NR^{e62})NR^{e62}R^{d62}$, $NR^{c62}C(=NR^{e62})NR^{c2}R^{d62}$, $NR^{c62}C(=NR^{e62})R^{b62}$, $NR^{c62}S(O)R^{b62}$, $NR^{c62}S(O)NR^{c62}R^{d62}$, $NR^{c62}S(O)_2R^{b62}$, $NR^{c62}S(O)(=NR^{e62})R^{b62}$, $NR^{c62}S(O)_2NR^{c62}R^{d62}$, $S(O)R^{b62}$, $S(O)NR^{c62}R^{d62}$, $S(O)_2R^{b62}$, $S(O)_2NR^{c62}R^{d62}$, $OS(O)(=NR^{e62})R^{b62}$, and $OS(O)_2R^{b62}$, wherein the $C_{1-6}$ alkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl- and (4-7 membered heterocycloalkyl)-$C_{1-6}$ alkyl- of $R^{6B}$ are each optionally substituted with 1, 2, 3, or 4 independently selected $R^{6C}$ substituents;

each $R^{a62}$, $R^{b62}$, and $R^{d62}$ is independently selected from H, $C_{1-6}$ alkyl, $C_{1-6}$ haloalkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl-, wherein the $C_{1-6}$ alkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl- of $R^{a62}$, $R^{c62}$ and $R^{d62}$ are each optionally substituted with 1, 2, 3, or 4 independently selected $R^{6C}$ substituents;

or, any $R^{c62}$ and $R^{d62}$ attached to the same N atom, together with the N atom to which they are attached, form a 5-6 membered heteroaryl or a 4-7 membered heterocycloalkyl group, wherein the 5-6 membered heteroaryl or 4-7 membered heterocycloalkyl group is optionally substituted with 1, 2, 3, or 4 independently selected $R^{6C}$ substituents;

each $R^{b62}$ is independently selected from H, $C_{1-6}$ alkyl, $C_{1-6}$ haloalkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl-, wherein the $C_{1-6}$ alkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl- of $R^{b62}$ are each optionally substituted with 1, 2, 3, or 4 independently selected $R^{6C}$ substituents;

each $R^{e62}$ is independently selected from H, OH, CN, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl-;

each $R^{6C}$ is independently selected from halo, oxo, $C_{1-6}$ alkyl, $C_{1-6}$ haloalkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, (4-7 membered heterocycloalkyl)-$C_{1-6}$ alkyl-, CN, $NO_2$, $OR^{a63}$, $SR^{a63}$, $NHOR^{a63}$, $C(O)R^{b63}$, $C(O)NR^{c63}R^{d63}$, $C(O)NR^{c63}(OR^{a63})$, $C(O)OR^{a63}$, $OC(O)R^{b63}$, $OC(O)NR^{c63}R^{d63}$, $NR^{c63}R^{d63}$, $NR^{c63}NR^{c63}R^{d63}$, $NR^{c63}C(O)R^{b63}$, $NR^{c63}C(O)OR^{a63}$, $NR^{c63}C(O)NR^{c63}R^{d63}$, $C(=NR^{e63})R^{b63}$, $C(=NR^{e63})NR^{c63}R^{d63}$, $NR^{c63}C(=NR^{e63})NR^{c63}R^{d63}$, $NR^{c63}C(=NR^{e63})R^{b63}$, $NR^{c63}S(O)R^{b63}$, $NR^{c63}S(O)NR^{c63}R^{d63}$, $NR^{c63}S(O)_2R^{b63}$, $NR^{c63}S(O)(=NR^{e63})R^{b63}$, $NR^{c63}S(O)_2NR^{c63}R^{d63}$, $S(O)R^{b63}$, $S(O)NR^{c63}R^{d63}$, $S(O)_2R^{b63}$, $S(O)_2NR^{c63}R^{d63}$, $OS(O)(=NR^{e63})R^{b63}$, and $OS(O)_2R^{b63}$, wherein the $C_{1-6}$ alkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl- and (4-7 membered heterocycloalkyl)-$C_{1-6}$ alkyl- of $R^{6C}$ are each optionally substituted with 1, 2, 3, or 4 independently selected $R^{M}$ substituents;

each $R^{a63}$, $R^{c63}$, and $R^{d63}$ is independently selected from H, $C_{1-6}$ alkyl, $C_{1-6}$ haloalkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl-, wherein the $C_{1-6}$ alkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl- of $R^{a63}$, $R^{c63}$ and $R^{d63}$ are each optionally substituted with 1, 2, 3, or 4 independently selected $R^{M}$ substituents;

or, any $R^{c63}$ and $R^{d63}$ attached to the same N atom, together with the N atom to which they are attached, form a 5-6 membered heteroaryl or a 4-7 membered heterocycloalkyl group, wherein the 5-6 membered heteroaryl or 4-7 membered heterocycloalkyl group is optionally substituted with 1, 2, 3, or 4 independently selected $R^{M}$ substituents;

each $R^{b63}$ is independently selected from H, $C_{1-6}$ alkyl, $C_{1-6}$ haloalkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl-, wherein the $C_{1-6}$ alkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl- of $R^{b63}$ are each optionally substituted with 1, 2, 3, or 4 independently selected $R^{M}$ substituents;

each $R^{e63}$ is independently selected from H, OH, CN, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl-;

each $R^{M}$ is independently selected from H, OH, halo, oxo, CN, C(O)OH, $C(O)NH_2$, $C(O)NH(C_{1-4}$ alkyl), $C(O)N(C_{1-6}$ alkyl$)_2$, $NH_2$, $NO_2$, $SF_5$, $C_{1-6}$ alkyl, $C_{1-6}$ alkoxy, $C_{1-6}$ haloalkoxy, $C_{1-6}$ haloalkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl-; and wherein one or more hydrogen atoms are optionally replaced by deuterium.

2. The compound of claim 1, or a pharmaceutically acceptable salt thereof, wherein W is $C(R^{W})_2$.

3. The compound of claim 1, or a pharmaceutically acceptable salt thereof, wherein each $R^{W}$ is independently H or $C_{1-6}$ alkyl.

4. The compound of claim 1, or a pharmaceutically acceptable salt thereof, wherein W is $CH_2$.

5. The compound of claim 1, or a pharmaceutically acceptable salt thereof, wherein Y is $C(R^{Y})_2$.

6. The compound of claim 1, or a pharmaceutically acceptable salt thereof, wherein each $R^{Y}$ is independently H or $C_{1-6}$ alkyl.

7. The compound of claim 1, or a pharmaceutically acceptable salt thereof, wherein Y is $CH_2$.

8. The compound of claim 1, or a pharmaceutically acceptable salt thereof, wherein W and Y are each $CH_2$.

9. The compound of claim 1, or a pharmaceutically acceptable salt thereof, wherein Ring A is $C_{3-10}$ cycloalkyl, which is optionally substituted by 1, 2, 3, or 4 independently selected $R^6$ substituents.

10. The compound of claim 1, or a pharmaceutically acceptable salt thereof, wherein Ring A is $C_{3-7}$ cycloalkyl, which is optionally substituted by 1, 2, 3, or 4 independently selected $R^6$ substituents.

11. The compound of claim 1 or a pharmaceutically acceptable salt thereof, wherein Ring A is a bicyclic $C_{8-10}$ cycloalkyl or a monocyclic $C_{3-7}$ cycloalkyl, which is optionally substituted by 1, 2, 3, or 4 independently selected $R^6$ substituents.

12. The compound of claim 1, or a pharmaceutically acceptable salt thereof, wherein Ring A is selected from cyclobutyl, cyclopentyl, cyclohexyl and dihydroindenyl, wherein the cyclobutyl, cyclopentyl, cyclohexyl, and dihydroindenyl of Ring A are each optionally substituted by 1, 2, 3, or 4 independently selected $R^6$ substituents.

13. The compound of claim 1, or a pharmaceutically acceptable salt thereof, wherein Ring A is 4-10 membered heterocycloalkyl, which is optionally substituted by 1, 2, 3, or 4 independently selected $R^6$ substituents.

14. The compound of claim 1, or a pharmaceutically acceptable salt thereof, wherein Ring A is monocyclic 4-6 membered heterocycloalkyl, bicyclic 8-10 membered heterocycloalkyl, or spirocyclic 7-10 membered heterocycloalkyl, wherein the monocyclic 4-6 membered heterocycloalkyl, bicyclic 8-10 membered heterocycloalkyl, and spirocyclic 7-10 membered heterocycloalkyl of Ring A are each optionally substituted by 1, 2, 3, or 4 independently selected $R^6$ substituents.

15. The compound of claim 1, or a pharmaceutically acceptable salt thereof, wherein Ring A is selected from tetrahydro-2H-pyranyl, tetrahydrofuranyl, azetidinyl, piperidinyl, pyrrolidinyl, azepanyl, dihydropyridinyl, azabicyclo[3.2.1]octanyl, 2-azaspiro[3.3]heptanyl, and 7-azaspiro[3.5]nonanyl, wherein the tetrahydro-2H-pyranyl, tetrahydrofuranyl, azetidinyl, piperidinyl, pyrrolidinyl, azepanyl, dihydropyridinyl, azabicyclo[3.2.1]octanyl, 2-azaspiro[3.3]heptanyl, and 7-azaspiro[3.5]nonanyl of Ring A are each optionally substituted by 1, 2, 3, or 4 independently selected $R^6$ substituents.

16. The compound of claim 1, or a pharmaceutically acceptable salt thereof, wherein each $R^6$ is independently selected from $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, (4-10 membered heterocycloalkyl)-$C_{1-6}$ alkyl-, $C(O)R^{b6}$, $C(O)NR^{c6}R^{d6}$, $C(O)OR^{a6}$, $NR^{c6}C(O)R^{b6}$, $NR^{c6}S(O)_2R^{b6}$, and $S(O)_2R^{b6}$, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^6$ are each optionally substituted with 1, 2, 3, or 4 independently selected $R^{6A}$ substituents.

17. The compound of claim 1, or a pharmaceutically acceptable salt thereof, wherein each $R^6$ is independently selected from $C_{1-6}$ alkyl, $C_{1-6}$ haloalkyl, $C_{3-10}$ cycloalkyl, 5-10 membered heteroaryl, 4-10 membered heterocycloalkyl, $C_{3-10}$ cycloalkyl-$C_{1-6}$ alkyl-, $C_{6-10}$ aryl-$C_{1-6}$ alkyl-, (5-10 membered heteroaryl)-$C_{1-6}$ alkyl-, (4-10 membered heterocycloalkyl)-$C_{1-6}$ alkyl-, $C(O)R^{b6}$, $C(O)NR^{c6}R^{d6}$, $C(O)OR^{a6}$, $NR^{c6}C(O)R^{b6}$, $NR^{c6}S(O)_2R^{b6}$, and $S(O)_2R^{b6}$, wherein the $C_{1-6}$ alkyl, $C_{1-6}$ haloalkyl, $C_{3-10}$ cycloalkyl, 5-10 membered heteroaryl, 4-10 membered heterocycloalkyl, $C_{3-10}$ cycloalkyl-$C_{1-6}$ alkyl-, $C_{6-10}$ aryl-$C_{1-6}$ alkyl-, (5-10 membered heteroaryl)-$C_{1-6}$ alkyl-, and (4-10 membered heterocycloalkyl)-$C_{1-6}$ alkyl-of $R^6$ are each optionally substituted with 1, 2, 3, or 4 independently selected $R^{6A}$ substituents.

18. The compound of claim 1, or a pharmaceutically acceptable salt thereof, wherein each $R^{a6}$, $R^{b6}$, $R^{c6}$, and $R^{d6}$ is independently selected from H, $C_{1-6}$ alkyl, $C_{1-6}$ haloalkyl, $C_{2-6}$ alkenyl, $C_{2-6}$ alkynyl, $C_{3-10}$ cycloalkyl, $C_{6-10}$ aryl, and 4-10 membered heterocycloalkyl)-$C_{1-6}$ alkyl-, wherein the $C_{1-6}$ alkyl, $C_{1-6}$ haloalkyl, $C_{2-6}$ alkenyl, $C_{2-6}$ alkynyl, $C_{3-10}$ cycloalkyl, $C_{6-10}$ aryl, and 4-10 membered heterocycloalkyl)-$C_{1-6}$ alkyl- of $R^{a6}$, $R^{b6}$, $R^{c6}$, and $R^{d6}$ are each optionally substituted by 1, 2, 3, or 4 independently selected $R^{6A}$ substituents.

19. The compound of claim 1, or a pharmaceutically acceptable salt thereof, wherein each $R^6$ is independently selected from $C_{1-6}$ alkyl, $C_{1-6}$ haloalkyl, $C_{3-10}$ cycloalkyl, 5-10 membered heteroaryl, 4-10 membered heterocycloalkyl, $C_{3-10}$ cycloalkyl-$C_{1-6}$ alkyl-, $C_{6-10}$ aryl-$C_{1-6}$ alkyl-, (5-10 membered heteroaryl)-$C_{1-6}$ alkyl-, (4-10 membered heterocycloalkyl)-$C_{1-6}$ alkyl-, $C(O)R^{b6}$, $C(O)NR^{c6}R^{d6}$, $C(O)OR^{a6}$, $NR^{c6}C(O)R^{b6}$, $NR^{c6}S(O)_2R^{b6}$, and $S(O)_2R^{b6}$, wherein the $C_{1-6}$ alkyl, $C_{1-6}$ haloalkyl, $C_{3-10}$ cycloalkyl, 5-10 membered heteroaryl, 4-10 membered heterocycloalkyl, $C_{3-10}$ cycloalkyl-$C_{1-6}$ alkyl-, $C_{6-10}$ aryl-$C_{1-6}$ alkyl-, (5-10 membered heteroaryl)-$C_{1-6}$ alkyl-, and (4-10 membered heterocycloalkyl)-$C_{1-6}$ alkyl-of $R^6$ are each optionally substituted with 1, 2, 3, or 4 independently selected $R^{6A}$ substituents; and each $R^{a6}$, $R^{b6}$, $R^{c6}$, and $R^{d6}$ is independently selected from H, $C_{1-6}$ alkyl, $C_{1-6}$ haloalkyl, $C_{2-6}$ alkenyl, $C_{2-6}$ alkynyl, $C_{3-10}$ cycloalkyl, $C_{6-10}$ aryl, and 4-10 membered heterocycloalkyl)-$C_{1-6}$ alkyl-, wherein the $C_{1-6}$ alkyl, $C_{1-6}$ haloalkyl, $C_{2-6}$ alkenyl, $C_{2-6}$ alkynyl, $C_{3-10}$ cycloalkyl, $C_{6-10}$ aryl, and 4-10 membered heterocycloalkyl)-$C_{1-6}$ alkyl- of $R^{a6}$, $R^{b6}$, $R^{c6}$, and $R^{d6}$ are each optionally substituted by 1, 2, 3, or 4 independently selected $R^{6A}$ substituents.

20. The compound of claim 1, or a pharmaceutically acceptable salt thereof, wherein each $R^6$ is independently selected from ethyl, tert-butyl, cyclopropyl, cyclobutyl, cyclopentyl, cyclohexyl, azetidinyl, tetrahydrothiopheneyl, pyrazolyl, piperidinyl, pyrimidinyl, cyclopropylmethyl, spiro[3.3]heptanylmethyl, phenylmethyl, triazolylisopropyl, azetidinylisopropyl, 2-azabicyclo[2.1.1]hexanyl, bicyclo[1.1.1]pentanyl, methylcarbonyl, tetrahydropyranylmethylcarbonyl, propylcarbonyl, dimethylaminocarbonyl, methoxycarbonyl, phenylaminocarbonyl, ethylsulfonyl, cyclobutylcarbonylamino, cyclopropylsulfonyl, and cyclopropylsulfonylamino, wherein the ethyl, tert-butyl, cyclopropyl, cyclobutyl, cyclopentyl, cyclohexyl, azetidinyl, tetrahydrothiopheneyl, pyrazolyl, piperidinyl, pyrimidinyl, cyclopropylmethyl, spiro[3.3]heptanylmethyl, phenylmethyl, triazolylisopropyl, azetidinylisopropyl, 2-azabicyclo[2.1.1]hexanyl, bicyclo[1.1.1]pentanyl, methylcarbonyl, tetrahydropyranylmethylcarbonyl, propylcarbonyl, dimethylaminocarbonyl, methoxycarbonyl, phenylaminocarbonyl, ethylsulfonyl, cyclobutylcarbonylamino, cyclopropylsulfonyl, and cyclopropylsulfonylamino of $R^6$ are each optionally substituted with 1 or 2 independently selected $R^{6A}$ substituents.

21. The compound of claim 1, or a pharmaceutically acceptable salt thereof, wherein each $R^{6A}$ is independently selected from halo, oxo, $C_{1-6}$ alkyl, 4-10 membered heterocycloalkyl, CN, OR$^{a61}$, C(O)R$^{b61}$, C(O)NR$^{c61}$R$^{d61}$, C(O)OR$^{a61}$, NR$^{c61}$C(O)R$^{b61}$, NR$^{c61}$C(O)OR$^{a61}$, NR$^{c61}$C(O)NR$^{c61}$R$^{d61}$, NR$^{c61}$S(O)$_2$R$^{b61}$, and S(O)$_2$R$^{b61}$, wherein each C$_{1-6}$ alkyl and 4-10 membered heterocycloalkyl of R$^{6A}$ are optionally substituted with 1, 2, 3, or 4 independently selected R$^{6B}$ substituents.

22. The compound of claim 1, or a pharmaceutically acceptable salt thereof, wherein each R$^{a61}$, R$^{b61}$, R$^{c61}$, and R$^{d61}$ is independently selected from H, C$_{1-6}$ alkyl, C$_{1-6}$ haloalkyl, C$_{2-6}$ alkenyl, C$_{2-6}$ alkynyl, and C$_{6-10}$ aryl, wherein the C$_{1-6}$ alkyl, C$_{1-6}$ haloalkyl, C$_{2-6}$ alkenyl, C$_{2-6}$ alkynyl, and C$_{6-10}$ aryl of R$^{a61}$, R$^{b61}$, R$^{c61}$, and R$^{d61}$ are each optionally substituted by 1, 2, 3, or 4 independently selected R$^{6B}$ substituents.

23. The compound of claim 1, or a pharmaceutically acceptable salt thereof, wherein each R$^{6A}$ is independently selected from halo, oxo, C$_{1-6}$ alkyl, 4-10 membered heterocycloalkyl, CN, OR$^{a61}$, C(O)R$^{b61}$, C(O)NR$^{c61}$R$^{d61}$, C(O)OR$^{a61}$, NR$^{c61}$C(O)R$^{b61}$, NR$^{c61}$C(O)OR$^{a61}$, NR$^{c61}$C(O)NR$^{c61}$R$^{d61}$, NR$^{c61}$S(O)$_2$R$^{b61}$, and S(O)$_2$R$^{b61}$, wherein each C$_{1-6}$ alkyl and 4-10 membered heterocycloalkyl of R$^{6A}$ are optionally substituted with 1, 2, 3, or 4 independently selected R$^{6B}$ substituents; and
each R$^{a61}$, R$^{b61}$, R$^{c61}$, and R$^{d61}$ is independently selected from H, C$_{1-6}$ alkyl, and phenyl, wherein the C$_{1-6}$ alkyl and phenyl of R$^{a61}$, R$^{b61}$, R$^{c61}$, and R$^{d61}$ are each optionally substituted by 1, 2, 3, or 4 independently selected R$^{6B}$ substituents.

24. The compound of claim 1, or a pharmaceutically acceptable salt thereof, wherein each R$^{6B}$ is independently selected from C$_{1-6}$ alkyl, C$_{1-6}$ haloalkyl, C$_{2-6}$ alkenyl, C$_{2-6}$ alkynyl, CN, and C(O)NR$^{c62}$R$^{d62}$, wherein the C$_{1-6}$ alkyl, C$_{1-6}$ haloalkyl, C$_{2-6}$ alkenyl, and C$_{2-6}$ alkynyl are each optionally substituted by CN; and each R$^{c62}$ and R$^{d62}$ are independently H or C$_{1-6}$ alkyl.

25. The compound of claim 1, or a pharmaceutically acceptable salt thereof, wherein each R$^{6A}$ is independently selected from fluoro, oxo, methyl, CN, methoxy, tetrahydropyranyl, methylcarbonyl, aminocarbonyl, methylcarbonylamino, ethylaminocarbonyl, methoxycarbonyl, methoxycarbonylamino, ethylaminocarbonylamino, ethylsulfonyl, and phenylsulfonylamino, wherein each methyl of R$^{6A}$ is optionally substituted by CN or aminocarbonyl; and wherein each tetrahydropyranyl of R$^{6A}$ is optionally substituted by cyanomethyl.

26. The compound of claim 1, or a pharmaceutically acceptable salt thereof, wherein R$^2$ is selected from H, C$_{1-6}$ alkyl, C$_{2-6}$ alkenyl, C$_{6-10}$ aryl, C$_{3-10}$ cycloalkyl, 5-10 membered heteroaryl, 4-10 membered heterocycloalkyl, C$_{6-10}$ aryl-C$_{1-6}$ alkyl-, C$_{3-10}$ cycloalkyl-C$_{1-6}$ alkyl-, (5-10 membered heteroaryl)-C$_{1-6}$ alkyl-, and (4-10 membered heterocycloalkyl)-C$_{1-6}$ alkyl-, wherein the C$_{1-6}$ alkyl, C$_{2-6}$ alkenyl, C$_{6-10}$ aryl, C$_{3-10}$ cycloalkyl, 5-10 membered heteroaryl, 4-10 membered heterocycloalkyl, C$_{6-10}$ aryl-C$_{1-6}$ alkyl-, C$_{3-10}$ cycloalkyl-C$_{1-6}$ alkyl-, (5-10 membered heteroaryl)-C$_{1-6}$ alkyl-, and (4-10 membered heterocycloalkyl)-C$_{1-6}$ alkyl- of R$^2$ are each optionally substituted with 1, 2, 3, or 4 independently selected R$^{2A}$ substituents.

27. The compound of claim 1, or a pharmaceutically acceptable salt thereof, wherein R$^2$ is selected from H, C$_{1-6}$ alkyl, C$_{2-6}$ alkenyl, C$_{6-10}$ aryl, 5-10 membered heteroaryl, and 4-10 membered heterocycloalkyl, wherein the C$_{1-6}$ alkyl, C$_{2-6}$ alkenyl, C$_{6-10}$ aryl, 5-10 membered heteroaryl, and 4-10 membered heterocycloalkyl of R$^2$ are each optionally substituted with 1, 2, 3, or 4 independently selected R$^{2A}$ substituents.

28. The compound of claim 1, or a pharmaceutically acceptable salt thereof, wherein R$^2$ is selected from H, ethyl, ethenyl, phenyl, indazolyl, thiazolyl, thieno[3,2-c]pyridinyl, 3,6-dihydro-2H-pyranyl, and indolyl, wherein the ethyl, ethenyl, phenyl, indazolyl, thiazolyl, thieno[3,2-c]pyridinyl, 3,6-dihydro-2H-pyranyl, and indolyl of R$^2$ are each optionally substituted with 1, 2, 3, or 4 independently selected R$^{2A}$ substituents.

29. The compound of claim 1, or a pharmaceutically acceptable salt thereof, wherein each R$^{2A}$ is independently selected from halo, C$_{1-6}$ alkyl, C$_{1-6}$ haloalkyl, C$_{2-6}$ alkenyl, C$_2$-6 alkynyl, C$_{6-10}$ aryl, C$_{3-10}$ cycloalkyl, 5-10 membered heteroaryl, 4-10 membered heterocycloalkyl, (4-10 membered heterocycloalkyl)-C$_{1-6}$ alkyl-, CN, and OR$^{21}$, wherein the C$_{1-6}$ alkyl, C$_{2-6}$ alkenyl, C$_{2-6}$ alkynyl, C$_{6-10}$ aryl, C$_{3-10}$ cycloalkyl, 5-10 membered heteroaryl, 4-10 membered heterocycloalkyl, and (4-10 membered heterocycloalkyl)-C$_{1-6}$ alkyl- of R$^{2A}$ are each optionally substituted with 1, 2, 3, or 4 independently selected R$^{21}$ substituents.

30. The compound of claim 1, or a pharmaceutically acceptable salt thereof, wherein each R$^{2A}$ is independently selected from halo, C$_{1-6}$ alkyl, C$_{1-6}$ haloalkyl, C$_{3-10}$ cycloalkyl, 5-10 membered heteroaryl, (4-10 membered heterocycloalkyl)-C$_{1-6}$ alkyl-, CN, and OR$^{a21}$, wherein the C$_{1-6}$ alkyl, C$_{1-6}$ haloalkyl, C$_{3-10}$ cycloalkyl, 5-10 membered heteroaryl, and (4-10 membered heterocycloalkyl)-C$_{1-6}$ alkyl- of R$^{2A}$ are each optionally substituted with 1, 2, 3, or 4 independently selected R$^{2B}$ substituents; and
each R$^{a21}$ is independently selected from H, C$_{1-6}$ alkyl, and C$_{1-6}$ haloalkyl.

31. The compound of claim 1, or a pharmaceutically acceptable salt thereof, wherein each R$^{2A}$ is independently selected from fluoro, methyl, CD$_3$, trifluoromethyl, cyclopropyl, pyrazolyl, piperazinylmethyl, cyano, methoxy, and trifluoromethoxy, wherein the methyl, cyclopropyl, pyrazolyl, and piperazinylmethyl are each optionally substituted with 1 or 2 independently selected R$^{2B}$ substituents.

32. The compound of claim 1, or a pharmaceutically acceptable salt thereof, wherein R$^2$ is selected from H, ethyl, ethenyl, phenyl, indazolyl, thiazolyl, thieno[3,2-c]pyridinyl, 3,6-dihydro-2H-pyranyl, and indolyl, wherein the phenyl and indazolyl of R$^2$ are each optionally substituted with 1 or 2 R$^{2A}$ substituents independently selected from fluoro, methyl, CD$_3$, trifluoromethyl, cyclopropyl, pyrazolyl, piperazinylmethyl, cyano, methoxy, and trifluoromethoxy, wherein the methyl and pyrazolyl of R$^{2A}$ are each optionally substituted by cyano-C$_{1-6}$ alkyl; and the piperazinylmethyl of R$^{2A}$ is optionally substituted with methylsulfonyl.

33. The compound of claim 1, or a pharmaceutically acceptable salt thereof, wherein R$^3$ is selected from phenyl, C$_{3-7}$ cycloalkyl, monocyclic 5-6 membered heteroaryl, bicyclic 8-10 membered heteroaryl, monocyclic 4-6 membered heterocycloalkyl, and bicyclic 8-10 membered heterocycloalkyl, wherein the phenyl, C$_{3-7}$ cycloalkyl, monocyclic 5-6 membered heteroaryl, bicyclic 8-10 membered heteroaryl, monocyclic 4-6 membered heterocycloalkyl, and bicyclic 8-10 membered heterocycloalkyl of R$^3$ are each optionally substituted with 1, 2, 3, or 4 independently selected R$^{3A}$ substituents.

34. The compound of claim 1, or a pharmaceutically acceptable salt thereof, wherein R$^3$ is selected from phenyl, cyclopropyl, cyclohexenyl, pyrazolyl, pyrrolyl, 4,5,6,7-tetrahydropyrazolo[1,5-a]pyridinyl, 6,7-dihydro-5H-pyrazolo[5,1-b][1,3]oxazinyl, 3,4-dihydro-2H-benzo[b][1,4]oxazinyl, 5,6-dihydro-4H-pyrrolo[1,2-b]pyrazolyl, and pyrazolo[1,5-a]pyrimidinyl, wherein the phenyl, cyclopropyl, cyclohexenyl, pyrazolyl, pyrrolyl, 4,5,6,7-tetrahydropyrazolo[1,5-a]pyridinyl, 6,7-dihydro-5H-pyrazolo[5,1-b][1,3]oxazinyl, 3,4-dihydro-2H-benzo[b][1,4]oxazinyl, 5,6-dihydro-4H-pyrrolo[1,2-b]pyrazolyl, and pyrazolo[1,5-a]pyrimidinyl of $R^3$ are each optionally substituted with 1, 2, 3, or 4 independently selected $R^{3A}$ substituents.

35. The compound of claim 1, or a pharmaceutically acceptable salt thereof, wherein each $R^{3A}$ is independently selected from oxo, $C_{1-6}$ alkyl, $C_{1-6}$ haloalkyl, $C_{3-10}$ cycloalkyl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, (4-10 membered heterocycloalkyl)-$C_{1-6}$ alkyl-, $C(O)R^{b3}$, $C(O)NR^{c31}R^{d31}$, $NR^{c31}R^{d31}$, and $S(O)_2R^{b31}$, wherein the $C_{1-6}$ alkyl, $C_{3-10}$ cycloalkyl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{3A}$ are each optionally substituted with 1, 2, 3, or 4 independently selected $R^{3B}$ substituents; and
  each $R^{b31}$, $R^{c31}$, and $R^{d31}$ is independently selected from H, $C_{1-6}$ alkyl, and 4-10 membered heterocycloalkyl.

36. The compound of claim 1, or a pharmaceutically acceptable salt thereof, wherein each $R^{3A}$ is independently selected from methyl, $CD_3$, ethyl, isopropyl, isobutyl, difluoroethyl, trifluoroethyl, methoxy, cyclopropyl, cyclopentyl, piperidinyl, tetrahydrofuranyl, tetrahydropyranyl, cyclopropylmethyl, cyclopropylethyl, phenylmethyl, pyridylmethyl, piperidinylmethyl, morpholinylmethyl, morpholinylethyl, morpholinylcarbonyl, dimethylaminocarbonyl, and ethylsulfonyl, wherein the methyl, ethyl, isopropyl, isobutyl, cyclopropyl, cyclopentyl, piperidinyl, tetrahydrofuranyl, tetrahydropyranyl, cyclopropylmethyl, cyclopropylethyl, phenylmethyl, pyridylmethyl, piperidinylmethyl, morpholinylmethyl, and morpholinylethyl of $R^{3A}$ are each optionally substituted with 1, 2, 3, or 4 independently selected $R^{3B}$ substituents.

37. The compound of claim 1, or a pharmaceutically acceptable salt thereof, wherein $R^3$ is selected from phenyl, cyclopropyl, cyclohexenyl, pyrazolyl, pyrrolyl, 4,5,6,7-tetrahydropyrazolo[1,5-a]pyridinyl, 6,7-dihydro-5H-pyrazolo[5,1-b][1,3]oxazinyl, 3,4-dihydro-2H-benzo[b][1,4]oxazinyl, 5,6-dihydro-4H-pyrrolo[1,2-b]pyrazolyl, and pyrazolo[1,5-a]pyrimidinyl, wherein the phenyl, cyclopropyl, cyclohexenyl, pyrazolyl, pyrrolyl, 4,5,6,7-tetrahydropyrazolo[1,5-a]pyridinyl, 6,7-dihydro-5H-pyrazolo[5,1-b][1,3]oxazinyl, 3,4-dihydro-2H-benzo[b][1,4]oxazinyl, 5,6-dihydro-4H-pyrrolo[1,2-b]pyrazolyl, and pyrazolo[1,5-a]pyrimidinyl of $R^3$ are each optionally substituted with 1, 2, 3, or 4 independently selected $R^{3A}$ substituents; and
  each $R^{3A}$ is independently selected from methyl, —$CD_3$, ethyl, isopropyl, isobutyl, difluoroethyl, trifluoroethyl, methoxy, cyclopropyl, cyclopentyl, piperidinyl, tetrahydrofuranyl, tetrahydropyranyl, cyclopropylmethyl, cyclopropylethyl, phenylmethyl, pyridylmethyl, piperidinylmethyl, morpholinylmethyl, morpholinylethyl, morpholinylcarbonyl, dimethylaminocarbonyl, and ethylsulfonyl, wherein the methyl, ethyl, isopropyl, isobutyl, cyclopropyl, cyclopentyl, piperidinyl, tetrahydrofuranyl, tetrahydropyranyl, cyclopropylmethyl, cyclopropylethyl, phenylmethyl, pyridylmethyl, piperidinylmethyl, morpholinylmethyl, and morpholinylethyl of $R^{3A}$ are each optionally substituted with 1 or 2 substituents independently selected from hydroxy, methoxy, methylsulfonyl, methylcarbonyl, and cyano.

38. The compound of claim 1, or a pharmaceutically acceptable salt thereof, wherein $R^4$ is selected from H and $C_{1-3}$ alkyl.

39. The compound of claim 1, or a pharmaceutically acceptable salt thereof, wherein $R^4$ is methyl or $CD_3$.

40. The compound of claim 1, or a pharmaceutically acceptable salt thereof, wherein:
  W is $C(R^W)_2$;
  Y is $C(R^Y)_2$;
  each $R^W$ is independently H or $C_{1-6}$ alkyl;
  each R is independently H or $C_{1-6}$ alkyl;
  Ring A is $C_{3-10}$ cycloalkyl or 4-10 membered heterocycloalkyl, wherein the $C_{3-10}$ cycloalkyl and 4-10 membered heterocycloalkyl of Ring A are each optionally substituted with 1, 2, 3, or 4 independently selected $R^6$ substituents;
  $R^2$ is selected from H, $C_{1-6}$ alkyl, $C_{2-6}$ alkenyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^2$ are each optionally substituted with 1, 2, 3, or 4 independently selected $R^{2A}$ substituents;
  each $R^{2A}$ is independently selected from halo, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, (4-10 membered heterocycloalkyl)-$C_{1-6}$ alkyl-, CN, and $OR^{a21}$, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, and (4-10 membered heterocycloalkyl)-$C_{1-6}$ alkyl- of $R^{2A}$ are each optionally substituted with 1, 2, 3, or 4 independently selected $R^{2B}$ substituents;
  each $R^{a21}$ is independently selected from H, $C_{1-6}$ alkyl, and $C_{1-6}$ haloalkyl;
  each $R^{2B}$ is independently selected from halo, oxo, $C_{1-6}$ alkyl, $C_{1-6}$ haloalkyl, $C_{2-6}$ alkenyl, $C_{2-6}$ alkynyl, $S(O)R^{b22}$, and $S(O)_2R^{b22}$, wherein the $C_{1-6}$ alkyl, $C_{2-6}$ alkenyl, and $C_{2-6}$ alkynyl of $R^{2B}$ are each optionally substituted with 1, 2, 3, or 4 independently selected $R^{2C}$ substituents;
  each $R^{b22}$ is independently selected from H, $C_{1-6}$ alkyl, $C_{1-6}$ haloalkyl, $C_{2-6}$ alkenyl, and $C_{2-6}$ alkynyl;
  each $R^{2C}$ is independently selected from halo, oxo, $C_{1-6}$ alkyl, $C_{1-6}$ haloalkyl, $C_{2-6}$ alkenyl, $C_{2-6}$ alkynyl, CN, and $NO_2$;
  $R^3$ is selected from $C_{6-10}$ aryl, $C_{3-10}$ cycloalkyl, 5-10 membered heteroaryl, and 4-10 membered heterocycloalkyl, wherein the $C_{6-10}$ aryl, $C_{3-10}$ cycloalkyl, 5-10 membered heteroaryl, and 4-10 membered heterocycloalkyl of $R^3$ are each optionally substituted with 1, 2, 3, or 4 independently selected $R^{3A}$ substituents;
  each $R^{3A}$ is independently selected from oxo, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, (4-10 membered heterocycloalkyl)-$C_{1-6}$ alkyl-, $C(O)R^{b31}$, $C(O)NR^{c31}R^{d31}$, $NR^{c31}R^{d31}$, and $S(O)_2R^{b31}$, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{3A}$ are each optionally substituted with 1, 2, 3, or 4 independently selected $R^{3B}$ substituents;

each $R^{b31}$, $R^{c31}$, and $R^{d31}$ is independently selected from H, $C_{1-6}$ alkyl, and 4-10 membered heterocycloalkyl;

each $R^{3B}$ is independently selected from CN, $OR^{a32}$, $C(O)R^{b32}$, and $S(O)_2R^{b32}$;

each $R^{a32}$ and $R^{b32}$ is independently selected from H and $C_{1-6}$ alkyl;

$R^4$ is selected from H and $C_{1-3}$ alkyl;

$R^5$ is H;

each $R^6$ is independently selected from $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, (4-10 membered heterocycloalkyl)-$C_{1-6}$ alkyl-, $C(O)R^{b6}$, $C(O)NR^{c6}R^{d6}$, $C(O)OR^{a6}$, $NR^{c6}C(O)R^{b6}$, $NR^{c6}S(O)_2R^{b6}$, and $S(O)_2R^{b6}$, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^6$ are each optionally substituted with 1, 2, 3, or 4 independently selected $R^{6A}$ substituents;

each $R^{a6}$, $R^{b6}$, $R^{c6}$, and $R^{d6}$ is independently selected from H, $C_{1-6}$ alkyl, $C_{1-6}$ haloalkyl, $C_{2-6}$ alkenyl, $C_{2-6}$ alkynyl, $C_{3-10}$ cycloalkyl, $C_{6-10}$ aryl, and 4-10 membered heterocycloalkyl)-$C_{1-6}$ alkyl-, wherein the $C_{1-6}$ alkyl, $C_{1-6}$ haloalkyl, $C_{2-6}$ alkenyl, $C_{2-6}$ alkynyl, $C_{3-10}$ cycloalkyl, $C_{6-10}$ aryl, and 4-10 membered heterocycloalkyl)-$C_{1-6}$ alkyl- of $R^{a6}$, $R^{b6}$, $R^{c6}$, and $R^{d6}$ are each optionally substituted by 1, 2, 3, or 4 independently selected $R^{6A}$ substituents;

each $R^{6A}$ is independently selected from halo, oxo, $C_{1-6}$ alkyl, 4-10 membered heterocycloalkyl, CN, $OR^{a61}$, $C(O)R^{b61}$, $C(O)NR^{c61}R^{d61}$, $C(O)OR^{a61}$, $NR^{c61}C(O)R^{b61}$, $NR^{c61}C(O)OR^{a61}$, $NR^{c61}C(O)NR^{c61}R^{d61}$, $NR^{c61}S(O)_2R^{b61}$, and $S(O)_2R^{b61}$, wherein each $C_{1-6}$ alkyl and 4-10 membered heterocycloalkyl of $R^{6A}$ are optionally substituted with 1, 2, 3, or 4 independently selected $R^{6B}$ substituents;

each $R^{a61}$, $R^{b61}$, $R^{c61}$, and $R^{d61}$ is independently selected from H, $C_{1-6}$ alkyl, $C_{1-6}$ haloalkyl, $C_{2-6}$ alkenyl, $C_{2-6}$ alkynyl, and $C_{6-10}$ aryl, wherein the $C_{1-6}$ alkyl, $C_{1-6}$ haloalkyl, $C_{2-6}$ alkenyl, $C_{2-6}$ alkynyl, and $C_{6-10}$ aryl of $R^{a61}$, $R^{b61}$, $R^{c61}$, and $R^{d61}$ are each optionally substituted by 1, 2, 3, or 4 independently selected $R^{6B}$ substituents;

each $R^{6B}$ is independently selected from $C_{1-6}$ alkyl, $C_{1-6}$ haloalkyl, $C_{2-6}$ alkenyl, $C_{2-6}$ alkynyl, CN, and $C(O)NR^{e62}R^{d62}$, wherein the $C_{1-6}$ alkyl, $C_{1-6}$ haloalkyl, $C_{2-6}$ alkenyl, and $C_{2-6}$ alkynyl of $R^{6B}$ are each optionally substituted by 1, 2, 3, or 4 independently selected $R^{6C}$ substituents;

each $R^{e62}$ and $R^{d62}$ are independently H or $C_{1-6}$ alkyl; and each $R^{6C}$ is independently selected from halo, oxo, $C_{1-6}$ alkyl, $C_{1-6}$ haloalkyl, $C_{2-6}$ alkenyl, $C_{2-6}$ alkynyl, CN, and $NO_2$.

41. The compound of claim 1, or a pharmaceutically acceptable salt thereof, wherein:

W is $C(R^W)_2$;

Y is $C(R^Y)_2$;

each $R^W$ is independently H or $C_{1-6}$ alkyl;

each R is independently H or $C_{1-6}$ alkyl;

Ring A is $C_{3-10}$ cycloalkyl or 4-10 membered heterocycloalkyl, wherein the $C_{3-10}$ cycloalkyl and 4-10 membered heterocycloalkyl of Ring A are each optionally substituted with 1, 2, 3, or 4 independently selected $R^6$ substituents;

$R^2$ is selected from H, $C_{1-6}$ alkyl, $C_{2-6}$ alkenyl, $C_{6-10}$ aryl, 5-10 membered heteroaryl, and 4-10 membered heterocycloalkyl, wherein the $C_{1-6}$ alkyl, $C_{2-6}$ alkenyl, $C_{6-10}$ aryl, 5-10 membered heteroaryl, and 4-10 membered heterocycloalkyl of $R^2$ are each optionally substituted with 1, 2, 3, or 4 independently selected $R^{2A}$ substituents;

each $R^{2A}$ is independently selected from halo, $C_{1-6}$ alkyl, $C_{1-6}$ haloalkyl, $C_{2-6}$ alkenyl, $C_{2-6}$ alkynyl, phenyl, $C_{3-7}$ cycloalkyl, 5-6 membered heteroaryl, 4-6 membered heterocycloalkyl, (4-6 membered heterocycloalkyl)-$C_{1-6}$ alkyl-, CN, and $OR^{a21}$, wherein the $C_{1-6}$ alkyl, $C_{2-6}$ alkenyl, $C_{2-6}$ alkynyl, phenyl, $C_{3-6}$ cycloalkyl, 5-6 membered heteroaryl, 4-6 membered heterocycloalkyl, and (4-6 membered heterocycloalkyl)-$C_{1-6}$ alkyl- of $R^{2A}$ are each optionally substituted with 1, 2, 3, or 4 independently selected $R^{2B}$ substituents;

each $R^{a21}$ is independently selected from H, $C_{1-6}$ alkyl, and $C_{1-6}$ haloalkyl;

each $R^{2B}$ is independently selected from halo, oxo, $C_{1-6}$ alkyl, $C_{1-6}$ haloalkyl, $C_{2-6}$ alkenyl, $C_{2-6}$ alkynyl, and $S(O)_2R^{b22}$, wherein the $C_{1-6}$ alkyl, $C_{2-6}$ alkenyl, and $C_{2-6}$ alkynyl of $R^{2B}$ are each optionally substituted with 1, 2, 3, or 4 independently selected $R^{2C}$ substituents;

each $R^{b22}$ is independently selected from H, $C_{1-6}$ alkyl, $C_{1-6}$ haloalkyl, $C_{2-6}$ alkenyl, and $C_{2-6}$ alkynyl;

each $R^{2C}$ is independently selected from halo, $C_{1-6}$ alkyl, $C_{1-6}$ haloalkyl, CN, and $NO_2$;

$R^3$ is selected from phenyl, $C_{3-7}$ cycloalkyl, monocyclic 5-6 membered heteroaryl, bicyclic 8-10 membered heteroaryl, and bicyclic 8-10 membered heterocycloalkyl, wherein the phenyl, $C_{3-7}$ cycloalkyl, monocyclic 5-6 membered heteroaryl, bicyclic 8-10 membered heteroaryl, and bicyclic 8-10 membered heterocycloalkyl of $R^3$ are each optionally substituted with 1, 2, 3, or 4 independently selected $R^{3A}$ substituents;

each $R^{3A}$ is independently selected from oxo, $C_{1-6}$ alkyl, $C_{1-6}$ haloalkyl, $C_{3-7}$ cycloalkyl, 4-6 membered heterocycloalkyl, phenyl-$C_{1-6}$ alkyl-, $C_{3-6}$ cycloalkyl-$C_{1-6}$ alkyl-, (5-6 membered heteroaryl)-$C_{1-6}$ alkyl-, (4-6 membered heterocycloalkyl)-$C_{1-6}$ alkyl-, $C(O)R^{b31}$, $C(O)NR^{c31}R^{d31}$, $NR^{c31}R^{d31}$, and $S(O)_2R^{b31}$, wherein the $C_{1-6}$ alkyl, $C_{3-7}$ cycloalkyl, 4-6 membered heterocycloalkyl, phenyl-$C_{1-6}$ alkyl-, $C_{3-6}$ cycloalkyl-$C_{1-6}$ alkyl-, (5-6 membered heteroaryl)-$C_{1-6}$ alkyl-, and (4-6 membered heterocycloalkyl)-$C_{1-6}$ alkyl- of $R^{3A}$ are each optionally substituted with 1, 2, 3, or 4 independently selected $R^{3B}$ substituents;

each $R^{b31}$, $R^{c31}$, and $R^{d31}$ is independently selected from H, $C_{1-6}$ alkyl, and 4-10 membered heterocycloalkyl;

each $R^{3B}$ is independently selected from CN, $OR^{a32}$, $C(O)R^{b32}$, and $S(O)_2R^{b32}$;

each $R^{a32}$ and $R^{b32}$ is independently selected from H and $C_{1-6}$ alkyl;

$R^4$ is selected from H and $C_{1-3}$ alkyl;

$R^5$ is H;

each $R^6$ is independently selected from $C_{1-6}$ alkyl, $C_{1-6}$ haloalkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, (4-7 membered heterocycloalkyl)-$C_{1-6}$ alkyl-, $C(O)R^{b6}$, C(O)NR$^{c6}$R$^{d6}$, C(O)OR$^{a6}$, NR$^{c6}$C(O)R$^{b6}$, NR$^{c6}$S(O)$_2$R$^{b6}$, and S(O)$_2$R$^{b6}$, wherein the C$_{1-6}$ alkyl, C$_{1-6}$ haloalkyl, C$_{2-6}$ alkenyl, C$_{2-6}$ alkynyl, phenyl, C$_{3-7}$ cycloalkyl, 5-6 membered heteroaryl, 4-7 membered heterocycloalkyl, phenyl-C$_{1-6}$ alkyl-, C$_{3-7}$ cycloalkyl-C$_{1-6}$ alkyl-, (5-6 membered heteroaryl)-C$_{1-6}$ alkyl-, and (4-7 membered heterocycloalkyl)-C$_{1-6}$ alkyl- of R$^6$ are each optionally substituted with 1, 2, 3, or 4 independently selected R$^{6A}$ substituents;

each R$^{a6}$, R$^{b6}$, R$^{c6}$, and R$^{d6}$ is independently selected from H, C$_{1-6}$ alkyl, C$_{1-6}$ haloalkyl, C$_{2-6}$ alkenyl, C$_{2-6}$ alkynyl, C$_{3-7}$ cycloalkyl, phenyl, 4-7 membered heterocycloalkyl)-C$_{1-6}$ alkyl-, wherein the C$_{1-6}$ alkyl, C$_{1-6}$ haloalkyl, C$_{2-6}$ alkenyl, C$_{2-6}$ alkynyl, C$_{3-7}$ cycloalkyl, phenyl, and 4-10 membered heterocycloalkyl)-C$_{1-6}$ alkyl- of R$^{a6}$, R$^{b6}$, R$^{c6}$, and R$^{d6}$ are each optionally substituted by 1, 2, 3, or 4 independently selected R$^{6A}$ substituents;

each R$^{6A}$ is independently selected from halo, oxo, C$_{1-6}$ alkyl, 4-10 membered heterocycloalkyl, CN, OR$^{a61}$, C(O)R$^{b61}$, C(O)NR$^{c61}$R$^{d61}$, C(O)OR$^{a61}$, NR$^{c61}$C(O)R$^{b61}$, NR$^{c61}$C(O)OR$^{a61}$, NR$^{c61}$C(O)NR$^{c61}$R$^{d61}$, NR$^{c61}$S(O)$_2$R$^{b61}$, and S(O)$_2$R$^{b61}$, wherein each C$_{1-6}$ alkyl and 4-10 membered heterocycloalkyl of R$^{6A}$ are optionally substituted with 1, 2, 3, or 4 independently selected R$^{6B}$ substituents;

each R$^{a61}$, R$^{b61}$, R$^{c61}$, and R$^{d61}$ is independently selected from H, C$_{1-6}$ alkyl, and phenyl, wherein the C$_{1-6}$ alkyl and phenyl of R$^{a61}$, R$^{b61}$, R$^{c61}$, and R$^{d61}$ are each optionally substituted by 1 or 2 independently selected R$^{6B}$ substituents;

each R$^{6B}$ is independently selected from C$_{1-6}$ alkyl, CN, and C(O)NR$^{c62}$R$^{c62}$, wherein each C$_{1-6}$ alkyl of R$^{6B}$ is optionally substituted by CN; and each R$^{c62}$ and R$^{d62}$ is independently selected from H and C$_{1-3}$ alkyl.

42. The compound of claim 1, or a pharmaceutically acceptable salt thereof, wherein:

W is CH$_2$;

Y is CH$_2$;

Ring A is selected from C$_{3-7}$ cycloalkyl, monocyclic 4-6 membered heterocycloalkyl, and bicyclic 8-10 membered heterocycloalkyl, wherein the C$_{3-7}$ cycloalkyl, monocyclic 4-6 membered heterocycloalkyl, and bicyclic 8-10 membered heterocycloalkyl of Ring A are each optionally substituted by 1, 2, 3, or 4 independently selected R$^6$ substituents;

R$^2$ is selected from phenyl and indazolyl, wherein the phenyl and indazolyl of R$^2$ are each optionally substituted with 1, 2, 3, or 4 independently selected R$^{2A}$ substituents;

each R$^{2A}$ is independently selected from C$_{1-6}$ alkyl, and 5-10 membered heteroaryl, wherein the C$_{1-6}$ alkyl and 5-10 membered heteroaryl of R$^{2A}$ are each optionally substituted with 1 or 2 independently selected R$^{2B}$ substituents;

each R$^{2B}$ is independently selected from H and C$_{1-6}$ alkyl, wherein the C$_{1-6}$ alkyl of R$^{2B}$ is optionally substituted by CN;

R$^3$ is selected from phenyl, cyclopropyl, and pyrazolyl, wherein the phenyl, cyclopropyl, and pyrazolyl of R$^3$ are each optionally substituted with 1, 2, 3, or 4 independently selected R$^{3A}$ substituents;

each R$^{3A}$ is independently selected from C$_{1-6}$ alkyl, (5-10 membered heteroaryl)-C$_{1-6}$ alkyl-, and (4-10 membered heterocycloalkyl)-C$_{1-6}$ alkyl-, wherein the C$_{1-6}$ alkyl, (5-10 membered heteroaryl)-C$_{1-6}$ alkyl-, and (4-10 membered heterocycloalkyl)-C$_{1-6}$ alkyl- of R$^{3A}$ are each optionally substituted with 1, 2, 3, or 4 independently selected R$^{3B}$ substituents;

each R$^{3B}$ is independently selected from S(O)$_2$R$^{b32}$;

each R$^{b32}$ is independently selected from H and C$_{1-6}$ alkyl;

R$^4$ is selected from H and C$_{1-3}$ alkyl;

R$^5$ is H;

each R$^6$ is independently selected from C$_{1-6}$ alkyl, 5-10 membered heteroaryl, 4-10 membered heterocycloalkyl, and C(O)R$^{b6}$, wherein the C$_{1-6}$ alkyl, 5-10 membered heteroaryl, and 4-10 membered heterocycloalkyl of R$^6$ are each optionally substituted with 1, 2, 3, or 4 independently selected R$^{6A}$ substituents;

each R$^{b6}$ is independently selected from H, C$_{1-6}$ alkyl, C$_{1-6}$ haloalkyl, C$_{2-6}$ alkenyl, C$_{2-6}$ alkynyl, wherein the C$_{1-6}$ alkyl, C$_{1-6}$ haloalkyl, C$_{2-6}$ alkenyl, C$_{2-6}$ alkynyl of R$^{b6}$ are each optionally substituted by 1, 2, 3, or 4 independently selected R$^{6A}$ substituents;

each R$^{6A}$ is independently selected from 4-10 membered heterocycloalkyl, CN, and C(O)R$^{b61}$, wherein the 4-10 membered heterocycloalkyl of R$^{6A}$ are each optionally substituted with 1, 2, 3, or 4 independently selected R$^{6B}$ substituents;

each R$^{b61}$ is independently selected from H, C$_{1-6}$ alkyl, C$_{1-6}$ haloalkyl, C$_{2-6}$ alkenyl, C$_{2-6}$ alkynyl, wherein the C$_{1-6}$ alkyl, C$_{1-6}$ haloalkyl, C$_{2-6}$ alkenyl, C$_{2-6}$ alkynyl of R$^{b61}$ are each optionally substituted by 1 or 2 independently selected R$^{6B}$ substituents;

each R$^{6B}$ is independently selected from C$_{1-6}$ alkyl, wherein the C$_{1-6}$ alkyl of R$^{6B}$ is optionally substituted by CN.

43. The compound of claim 1, or a pharmaceutically acceptable salt thereof, wherein:

W is CH$_2$;

Y is CH$_2$;

Ring A is selected from cyclobutyl, cyclopentyl, cyclohexyl, dihydroindenyl, tetrahydro-2H-pyranyl, tetrahydrofuranyl, azetidinyl, piperidinyl, pyrrolidinyl, azepanyl, dihydropyridinyl, azabicyclo[3.2.1]octanyl, 2-azaspiro[3.3]heptanyl, and 7-azaspiro[3.5]nonanyl, wherein the cyclobutyl, cyclopentyl, tetrahydro-2H-pyranyl, tetrahydrofuranyl, azetidinyl, piperidinyl, pyrrolidinyl, azepanyl, dihydropyridinyl, azabicyclo[3.2.1]octanyl, 2-azaspiro[3.3]heptanyl, and 7-azaspiro[3.5]nonanyl of Ring A are each optionally substituted by 1 or 2 independently selected R$^6$ substituents;

R$^2$ is selected from H, ethyl, ethenyl, phenyl, indazolyl, thiazolyl, thieno[3,2-c]pyridinyl, 3,6-dihydro-2H-pyranyl, and indolyl, wherein the ethyl, ethenyl, phenyl, indazolyl, thiazolyl, thieno[3,2-c]pyridinyl, 3,6-dihydro-2H-pyranyl, and indolyl of R$^2$ are each optionally substituted with 1, 2, 3, or 4 independently selected R$^{2A}$ substituents;

each R$^{2A}$ is independently selected from fluoro, methyl, CD$_3$, trifluoromethyl, cyclopropyl, pyrazolyl, piperazinylmethyl, cyano, methoxy, and trifluoromethoxy, wherein the methyl, cyclopropyl, pyrazolyl, and piperazinylmethyl are each optionally substituted with 1 or 2 independently selected R$^{2B}$ substituents;

each R$^{2B}$ is independently selected from C$_{1-6}$ alkyl and S(O)$_2$R$^{b22}$, wherein the C$_{1-6}$ alkyl of R$^{2B}$ are each optionally substituted with CN;

each R$^{b22}$ is independently selected from H or C$_{1-6}$ alkyl;

R$^3$ is selected from phenyl, cyclopropyl, cyclohexenyl, pyrazolyl, pyrrolyl, 4,5,6,7-tetrahydropyrazolo[1,5-a]pyridinyl, 6,7-dihydro-5H-pyrazolo[5,1-b][1,3]oxazinyl, 3,4-dihydro-2H-benzo[b][1,4]oxazinyl, 5,6-dihydro-4H-pyrrolo[1,2-b]pyrazolyl, and pyrazolo[1,5-a]pyrimidinyl, wherein the phenyl, cyclopropyl, cyclohexenyl, pyrazolyl, pyrrolyl, 4,5,6,7-tetrahydropyrazolo[1,5-a]pyridinyl, 6,7-dihydro-5H-pyrazolo[5,1-b][1,3]oxazinyl, 3,4-dihydro-2H-benzo[b][1,4]oxazinyl, 5,6-dihydro-4H-pyrrolo[1,2-b]pyrazolyl, and pyrazolo[1,5-a]pyrimidinyl of $R^3$ are each optionally substituted with 1, 2, 3, or 4 independently selected $R^{3A}$ substituents;

each $R^{3A}$ is independently selected from methyl, trideuteromethyl, ethyl, isopropyl, isobutyl, difluoroethyl, trifluoroethyl, methoxy, cyclopropyl, cyclopentyl, piperidinyl, tetrahydrofuranyl, tetrahydropyranyl, cyclopropylmethyl, cyclopropylethyl, phenylmethyl, pyridylmethyl, piperidinylmethyl, morpholinylmethyl, morpholinylethyl, morpholinylcarbonyl, dimethylaminocarbonyl, and ethylsulfonyl, wherein the methyl, ethyl, isopropyl, isobutyl, cyclopropyl, cyclopentyl, piperidinyl, tetrahydrofuranyl, tetrahydropyranyl, cyclopropylmethyl, cyclopropylethyl, phenylmethyl, pyridylmethyl, piperidinylmethyl, morpholinylmethyl, and morpholinylethyl of $R^{3A}$ are each optionally substituted with 1, 2, 3, or 4 independently selected $R^{3B}$ substituents;

each $R^{3B}$ is independently selected from hydroxy, methoxy, methylsulfonyl, methylcarbonyl, and cyano; $R^4$ is selected from H and $C_{1-3}$ alkyl; $R^5$ is H;

each $R^6$ is independently selected from ethyl, tert-butyl, cyclopropyl, cyclobutyl, cyclopentyl, cyclohexyl, azetidinyl, tetrahydrothiopheneyl, pyrazolyl, piperidinyl, pyrimidinyl, cyclopropylmethyl, spiro[3.3]heptanylmethyl, phenylmethyl, triazolylisopropyl, azetidinylisopropyl, 2-azabicyclo[2.1.1]hexanyl, bicyclo[1.1.1]pentanyl, methylcarbonyl, tetrahydropyranylmethylcarbonyl, propylcarbonyl, dimethylaminocarbonyl, methoxycarbonyl, phenylaminocarbonyl, ethylsulfonyl, cyclobutylcarbonylamino, cyclopropylsulfonyl, and cyclopropylsulfonylamino, wherein the ethyl, tert-butyl, cyclopropyl, cyclobutyl, cyclopentyl, cyclohexyl, azetidinyl, tetrahydrothiopheneyl, pyrazolyl, piperidinyl, pyrimidinyl, cyclopropylmethyl, spiro[3.3]heptanylmethyl, phenylmethyl, triazolylisopropyl, azetidinylisopropyl, 2-azabicyclo[2.1.1]hexanyl, bicyclo[1.1.1]pentanyl, methylcarbonyl, tetrahydropyranylmethylcarbonyl, propylcarbonyl, dimethylaminocarbonyl, methoxycarbonyl, phenylaminocarbonyl, ethylsulfonyl, cyclobutylcarbonylamino, cyclopropylsulfonyl, and cyclopropylsulfonylamino of $R^6$ are each optionally substituted with 1 or 2 independently selected $R^{6A}$ substituents; and each $R^{6A}$ is independently selected from fluoro, oxo, methyl, CN, methoxy, tetrahydropyranyl, methylcarbonyl, aminocarbonyl, methylcarbonylamino, ethylaminocarbonyl, methoxycarbonyl, methoxycarbonylamino, ethylaminocarbonylamino, ethylsulfonyl, and phenylsulfonylamino, wherein each methyl of $R^{6A}$ is optionally substituted by CN or aminocarbonyl; and wherein each tetrahydropyranyl of $R^{6A}$ is optionally substituted by cyanomethyl.

44. The compound of claim 1, wherein the compound of Formula I is a compound of Formula II:

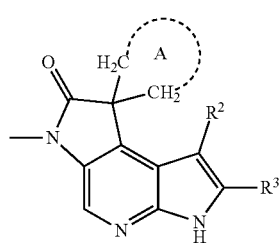

II or a pharmaceutically acceptable salt thereof.

45. The compound of claim 1, wherein the compound of Formula I is a compound of Formula III:

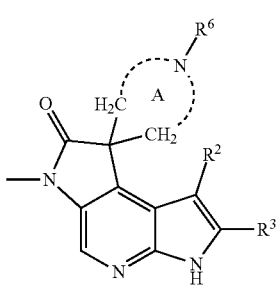

III or a pharmaceutically acceptable salt thereof.

46. The compound of claim 1, wherein the compound of Formula I is a compound of Formula IV:

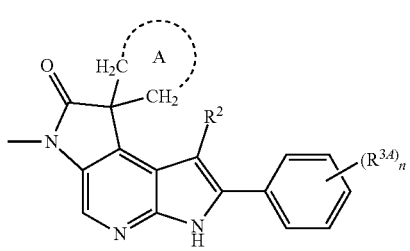

IV or a pharmaceutically acceptable salt thereof, wherein n is 0, 1, 2, 3, 4, or 5.

47. The compound of claim 1, or a pharmaceutically acceptable salt thereof, wherein the compound comprises at least one deuterium atom.

48. The compound of claim 1, or a pharmaceutically acceptable salt thereof, wherein the compound comprises two or more deuterium atoms.

49. The compound of claim 1, or a pharmaceutically acceptable salt thereof, wherein all of the hydrogen atoms in the compound are replaced by deuterium atoms.

50. The compound of claim 1, which is selected from:
6-methyl-2-(4-((4-(methylsulfonyl)piperidin-1-yl)methyl)phenyl)-1-phenyl-2',3,3',5',6,6'-hexahydro-7H-spiro[dipyrrolo[2,3-b:3',2'-d]pyridine-8,4'-pyran]-7-one;
6-methyl-2-(4-((4-(methylsulfonyl)piperidin-1-yl)methyl)phenyl)-1-phenyl-3,4',5',6-tetrahydro-2'H,7H-spiro[dipyrrolo[2,3-b:3',2'-d]pyridine-8,3'-furan]-7-one;

1-(1-acetylpiperidin-4-yl)-6'-methyl-2'-(4-((4-(methylsulfonyl)piperidin-1-yl)methyl)phenyl)-1'-phenyl-3',6'-dihydro-7'H-spiro[azetidine-3,8'-dipyrrolo[2,3-b:3',2'-d]pyridin]-7'-one;

3-(6-methyl-2-(4-((4-(methylsulfonyl)piperidin-1-yl)methyl)phenyl)-7-oxo-1-phenyl-6,7-dihydro-3H-spiro[dipyrrolo[2,3-b:3',2'-d]pyridine-8,4'-piperidin]-1'-yl)propanenitrile;

3-(6-methyl-1-(1-methyl-1H-indazol-5-yl)-2-(4-((4-(methylsulfonyl)piperidin-1-yl)methyl)phenyl)-7-oxo-6,7-dihydro-3H-spiro[dipyrrolo[2,3-b:3',2'-d]pyridine-8,4'-piperidin]-1'-yl)propanenitrile;

2-(4-(4-(6-methyl-2-(1-methyl-1H-pyrazol-4-yl)-7-oxo-1-phenyl-6,7-dihydro-3H-spiro[dipyrrolo[2,3-b:3',2'-d]pyridine-8,4'-piperidin]-1'-yl)-1H-pyrazol-1-yl)tetrahydro-2H-pyran-4-yl)acetonitrile;

3-(6-methyl-1-(1-methyl-1H-indazol-5-yl)-2-(1-(methyl-d3)-1H-pyrazol-4-yl)-7-oxo-6,7-dihydro-3H-spiro[dipyrrolo[2,3-b:3',2'-d]pyridine-8,4'-piperidin]-1'-yl)propanenitrile;

6'-methyl-1'-(1-methyl-1H-indazol-5-yl)-2'-(1-(pyridin-4-ylmethyl)-1H-pyrazol-4-yl)-3',6'-dihydro-7'H-spiro[cyclopentane-1,8'-dipyrrolo[2,3-b:3',2'-d]pyridin]-7'-one;

2'-cyclopropyl-6'-methyl-1'-(1-methyl-1H-indazol-5-yl)-3',6'-dihydro-7'H-spiro[cyclopentane-1,8'-dipyrrolo[2,3-b:3',2'-d]pyridin]-7'-one;

6'-methyl-2'-(4-((4-(methylsulfonyl)piperidin-1-yl)methyl)phenyl)-1'-phenyl-3',6'-dihydro-7'H-spiro[cyclobutane-1,8'-dipyrrolo[2,3-b:3',2'-d]pyridin]-7'-one;

6'-methyl-2'-(4-((4-(methylsulfonyl)piperidin-1-yl)methyl)phenyl)-1'-phenyl-3',6'-dihydro-7'H-spiro[cyclohexane-1,8'-dipyrrolo[2,3-b:3',2'-d]pyridin]-7'-one;

6-methyl-2-(4-((4-(methylsulfonyl)piperidin-1-yl)methyl)phenyl)-1-phenyl-1'-(2-(tetrahydro-2H-pyran-4-yl)acetyl)-3,6-dihydro-7H-spiro[dipyrrolo[2,3-b:3',2'-d]pyridine-8,3'-pyrrolidin]-7-one;

8-acetyl-6'-methyl-2'-(4-((4-(methylsulfonyl)piperidin-1-yl)methyl)phenyl)-1'-phenyl-3',6'-dihydro-7'H-8-azaspiro[bicyclo[3.2.1]octane-3,8'-dipyrrolo[2,3-b:3',2'-d]pyridin]-7'-one; and 3-(4-(4-(6'-methyl-2'-(1-methyl-1H-pyrazol-4-yl)-7'-oxo-6',7'-dihydro-3'H-spiro[cyclopentane-1,8'-dipyrrolo[2,3-b:3',2'-d]pyridin]-1'-yl)phenyl)-1H-pyrazol-1-yl)butanenitrile;

or a pharmaceutically acceptable salt thereof.

51. The compound of claim 1, which is selected from:

6-methyl-2-(4-((4-(methylsulfonyl)piperidin-1-yl)methyl)phenyl)-1-phenyl-1'-(pyrimidin-4-yl)-3,6-dihydro-7H-spiro[dipyrrolo[2,3-b:3',2'-d]pyridine-8,4'-piperidin]-7-one;

(1R,3r,5S)-6'-methyl-2'-(4-((4-(methylsulfonyl)piperidin-1-yl)methyl)phenyl)-1'-phenyl-8-(pyrimidin-4-yl)-3',6'-dihydro-7'H-8-azaspiro[bicyclo[3.2.1]octane-3,8'-dipyrrolo[2,3-b:3',2'-d]pyridin]-7'-one;

6-methyl-2-(1-methyl-1H-pyrazol-4-yl)-1-(2-methylthiazol-5-yl)-1'-(pyrimidin-4-yl)-3,6-dihydro-7H-spiro[dipyrrolo[2,3-b:3',2'-d]pyridine-8,4'-piperidin]-7-one;

6-methyl-2-(1-methyl-1H-pyrazol-4-yl)-1'-(pyrimidin-4-yl)-1-vinyl-3,6-dihydro-7H-spiro[dipyrrolo[2,3-b:3',2'-d]pyridine-8,4'-piperidin]-7-one;

1-ethyl-6-methyl-2-(1-methyl-1H-pyrazol-4-yl)-1'-(pyrimidin-4-yl)-3,6-dihydro-7H-spiro[dipyrrolo[2,3-b:3',2'-d]pyridine-8,4'-piperidin]-7-one;

1-(3,6-dihydro-2H-pyran-4-yl)-6-methyl-2-(1-methyl-1H-pyrazol-4-yl)-1'-(pyrimidin-4-yl)-3,6-dihydro-7H-spiro[dipyrrolo[2,3-b:3',2'-d]pyridine-8,4'-piperidin]-7-one;

N-(3-methoxyphenyl)-6-methyl-2-(4-((4-(methylsulfonyl)piperidin-1-yl)methyl)phenyl)-7-oxo-1-phenyl-6,7-dihydro-3H-spiro[dipyrrolo[2,3-b:3',2'-d]pyridine-8,4'-piperidine]-1'-carboxamide;

6'-methyl-2'-(1-methyl-1H-pyrazol-4-yl)-1'-(4-((4-(methylsulfonyl)piperazin-1-yl)methyl)phenyl)-3',6'-dihydro-7'H-spiro[cyclopentane-1,8'-dipyrrolo[2,3-b:3',2'-d]pyridin]-7'-one;

2-(1-(ethylsulfonyl)-3-(6-methyl-2-(1-methyl-1H-pyrazol-4-yl)-7-oxo-1-phenyl-6,7-dihydro-3H-spiro[dipyrrolo[2,3-b:3',2'-d]pyridine-8,4'-piperidin]-1'-yl)azetidin-3-yl)acetonitrile;

2-(1-acetyl-3-(6-methyl-2-(1-methyl-1H-pyrazol-4-yl)-7-oxo-1-phenyl-6,7-dihydro-3H-spiro[dipyrrolo[2,3-b:3',2'-d]pyridine-8,4'-piperidin]-1'-yl)azetidin-3-yl)acetonitrile;

3-(cyanomethyl)-N-ethyl-3-(6-methyl-2-(1-methyl-1H-pyrazol-4-yl)-7-oxo-1-phenyl-6,7-dihydro-3H-spiro[dipyrrolo[2,3-b:3',2'-d]pyridine-8,4'-piperidin]-1'-yl)azetidine-1-carboxamide;

2-(4-fluorophenyl)-2-(6-methyl-2-(1-methyl-1H-pyrazol-4-yl)-7-oxo-1-phenyl-6,7-dihydro-3H-spiro[dipyrrolo[2,3-b:3',2'-d]pyridine-8,4'-piperidin]-1'-yl)acetamide;

methyl (3-(cyanomethyl)-3-(6-methyl-2-(1-methyl-1H-pyrazol-4-yl)-7-oxo-1-phenyl-6,7-dihydro-3H-spiro[dipyrrolo[2,3-b:3',2'-d]pyridine-8,4'-piperidin]-1'-yl)cyclobutyl)carbamate;

1-(3-(cyanomethyl)-3-(6-methyl-2-(1-methyl-1H-pyrazol-4-yl)-7-oxo-1-phenyl-6,7-dihydro-3H-spiro[dipyrrolo[2,3-b:3',2'-d]pyridine-8,4'-piperidin]-1'-yl)cyclobutyl)-3-ethylurea;

N-(3-(cyanomethyl)-3-(6-methyl-2-(1-methyl-1H-pyrazol-4-yl)-7-oxo-1-phenyl-6,7-dihydro-3H-spiro[dipyrrolo[2,3-b:3',2'-d]pyridine-8,4'-piperidin]-1'-yl)cyclobutyl)benzenesulfonamide;

2-(1-(2-(1-(2,2-difluoroethyl)-1H-pyrazol-4-yl)-6-methyl-1-(1-methyl-1H-indazol-5-yl)-7-oxo-6,7-dihydro-3H-spiro[dipyrrolo[2,3-b:3',2'-d]pyridine-8,4'-piperidin]-1'-yl)cyclobutyl)acetonitrile;

2-(1-(6-methyl-1-(1-methyl-1H-indazol-5-yl)-2-(1-methyl-1H-pyrazol-4-yl)-7-oxo-6,7-dihydro-3H-spiro[dipyrrolo[2,3-b:3',2'-d]pyridine-8,4'-piperidin]-1'-yl)cyclobutyl)acetonitrile;

2-(1-(2-(1-(2-hydroxy-2-methylpropyl)-1H-pyrazol-4-yl)-6-methyl-1-(1-methyl-1H-indazol-5-yl)-7-oxo-6,7-dihydro-3H-spiro[dipyrrolo[2,3-b:3',2'-d]pyridine-8,4'-piperidin]-1'-yl)cyclobutyl)acetonitrile;

2-(1-(6-methyl-1-(1-methyl-1H-indazol-5-yl)-7-oxo-2-(1-(2,2,2-trifluoroethyl)-1H-pyrazol-4-yl)-6,7-dihydro-3H-spiro[dipyrrolo[2,3-b:3',2'-d]pyridine-8,4'-piperidin]-1'-yl)cyclobutyl)acetonitrile;

2-(1-(6-methyl-1-(1-methyl-1H-indazol-5-yl)-2-(4-(morpholine-4-carbonyl)cyclohex-1-en-1-yl)-7-oxo-6,7-dihydro-3H-spiro[dipyrrolo[2,3-b:3',2'-d]pyridine-8,4'-piperidin]-1'-yl)cyclobutyl)acetonitrile;

2-(1-(2-(4-(ethylsulfonyl)phenyl)-6-methyl-1-(1-methyl-1H-indazol-5-yl)-7-oxo-6,7-dihydro-3H-spiro[dipyrrolo[2,3-b:3',2'-d]pyridine-8,4'-piperidin]-1'-yl)cyclobutyl)acetonitrile;

2-(1-(2-(1-(2-methoxyethyl)-1H-pyrazol-4-yl)-6-methyl-1-(1-methyl-1H-indazol-5-yl)-7-oxo-6,7-dihydro-3H-spiro[dipyrrolo[2,3-b:3',2'-d]pyridine-8,4'-piperidin]-1'-yl)cyclobutyl)acetonitrile;

2-(1-(2-(1-(1-hydroxy-2-methylpropan-2-yl)-1H-pyrazol-4-yl)-6-methyl-1-(1-methyl-1H-indazol-5-yl)-7-oxo-6,7-dihydro-3H-spiro[dipyrrolo[2,3-b:3',2'-d]pyridine-8,4'-piperidin]-1'-yl)cyclobutyl)acetonitrile;

2-(1-(6-methyl-1-(1-methyl-H-indazol-5-yl)-2-(1-(2-morpholinoethyl)-1H-pyrazol-4-yl)-7-oxo-6,7-dihydro-3H-spiro[dipyrrolo[2,3-b:3',2'-d]pyridine-8,4'-piperidin]-1'-yl)cyclobutyl)acetonitrile;

2-(1-(2-(1-(cyclopropylmethyl)-1H-pyrazol-4-yl)-6-methyl-1-(1-methyl-1H-indazol-5-yl)-7-oxo-6,7-dihydro-3H-spiro[dipyrrolo[2,3-b:3',2'-d]pyridine-8,4'-piperidin]-1'-yl)cyclobutyl)acetonitrile;

2-(1-(2-(3-cyclopropyl-1-methyl-1H-pyrazol-4-yl)-6-methyl-1-(1-methyl-1H-indazol-5-yl)-7-oxo-6,7-dihydro-3H-spiro[dipyrrolo[2,3-b:3',2'-d]pyridine-8,4'-piperidin]-1'-yl)cyclobutyl)acetonitrile;

2-(1-(2-(1-(1-acetylpiperidin-4-yl)-1H-pyrazol-4-yl)-6-methyl-1-(1-methyl-1H-indazol-5-yl)-7-oxo-6,7-dihydro-3H-spiro[dipyrrolo[2,3-b:3',2'-d]pyridine-8,4'-piperidin]-1'-yl)cyclobutyl)acetonitrile;

2-(1-(6-methyl-1-(1-methyl-H-indazol-5-yl)-2-(1-methyl-H-pyrrol-3-yl)-7-oxo-6,7-dihydro-3H-spiro[dipyrrolo[2,3-b:3',2'-d]pyridine-8,4'-piperidin]-1'-yl)cyclobutyl)acetonitrile;

2-(1-(6-methyl-1-(1-methyl-H-indazol-5-yl)-7-oxo-2-(4,5,6,7-tetrahydropyrazolo[1,5-a]pyridin-3-yl)-6,7-dihydro-3H-spiro[dipyrrolo[2,3-b:3',2'-d]pyridine-8,4'-piperidin]-1'-yl)cyclobutyl)acetonitrile;

2-(1-(2-(1-(2-methoxy-2-methylpropyl)-1H-pyrazol-4-yl)-6-methyl-1-(1-methyl-1H-indazol-5-yl)-7-oxo-6,7-dihydro-3H-spiro[dipyrrolo[2,3-b:3',2'-d]pyridine-8,4'-piperidin]-1'-yl)cyclobutyl)acetonitrile;

2-(1-(6-methyl-1-(1-methyl-1H-indazol-5-yl)-7-oxo-2-(1-(tetrahydrofuran-3-yl)-1H-pyrazol-4-yl)-6,7-dihydro-3H-spiro[dipyrrolo[2,3-b:3',2'-d]pyridine-8,4'-piperidin]-1'-yl)cyclobutyl)acetonitrile;

2-(1-(2-(1-(2-methoxyethyl)-1H-pyrazol-4-yl)-6-methyl-1-(1-(methyl-d$_3$)-1H-indol-5-yl)-7-oxo-6,7-dihydro-3H-spiro[dipyrrolo[2,3-b:3',2'-d]pyridine-8,4'-piperidin]-1'-yl)cyclobutyl)acetonitrile;

2-(1-(1-(3,5-difluoro-4-methoxyphenyl)-2-(1-(2-hydroxy-2-methylpropyl)-1H-pyrazol-4-yl)-6-methyl-7-oxo-6,7-dihydro-3H-spiro[dipyrrolo[2,3-b:3',2'-d]pyridine-8,4'-piperidin]-1'-yl)cyclobutyl)acetonitrile;

2-(1-(2-(1-(2-hydroxy-2-methylpropyl)-1H-pyrazol-4-yl)-6-methyl-7-oxo-1-(thieno[3,2-c]pyridin-2-yl)-6,7-dihydro-3H-spiro[dipyrrolo[2,3-b:3',2'-d]pyridine-8,4'-piperidin]-1'-yl)cyclobutyl)acetonitrile;

2-(1-(1-(4-cyclopropylphenyl)-2-(1-(2-hydroxy-2-methylpropyl)-1H-pyrazol-4-yl)-6-methyl-7-oxo-6,7-dihydro-3H-spiro[dipyrrolo[2,3-b:3',2'-d]pyridine-8,4'-piperidin]-1'-yl)cyclobutyl)acetonitrile;

2-(1-(2-(1-(2-hydroxy-2-methylpropyl)-1H-pyrazol-4-yl)-6-methyl-7-oxo-1-(4-(trifluoromethoxy)phenyl)-6,7-dihydro-3H-spiro[dipyrrolo[2,3-b:3',2'-d]pyridine-8,4'-piperidin]-1'-yl)cyclobutyl)acetonitrile;

4-(1'-(1-(cyanomethyl)cyclobutyl)-2-(1-(2,2-difluoroethyl)-1H-pyrazol-4-yl)-6-methyl-7-oxo-6,7-dihydro-3H-spiro[dipyrrolo[2,3-b:3',2'-d]pyridine-8,4'-piperidin]-1'-yl)benzonitrile;

2-(1-(2-(1-(2-hydroxy-2-methylpropyl)-1H-pyrazol-4-yl)-6-methyl-7-oxo-1-(4-(trifluoromethyl)phenyl)-6,7-dihydro-3H-spiro[dipyrrolo[2,3-b:3',2'-d]pyridine-8,4'-piperidin]-1'-yl)cyclobutyl)acetonitrile;

(R)-1-(ethylsulfonyl)-2'-(1-isopropyl-1H-pyrazol-4-yl)-6'-methyl-1'-(1-methyl-1H-indazol-5-yl)-3',6'-dihydro-7'H-spiro[azepane-4,8'-dipyrrolo[2,3-b:3',2'-d]pyridin]-7'-one;

(S)-1-(ethylsulfonyl)-2'-(1-isopropyl-1H-pyrazol-4-yl)-6'-methyl-1'-(1-methyl-1H-indazol-5-yl)-3',6'-dihydro-7'H-spiro[azepane-4,8'-dipyrrolo[2,3-b:3',2'-d]pyridin]-7'-one;

1-(ethylsulfonyl)-2"-(1-isopropyl-1H-pyrazol-4-yl)-6"-methyl-1"-(1-methyl-1H-indazol-5-yl)-3",6"-dihydro-7"H-dispiro[azetidine-3,1'-cyclobutane-3',8"-dipyrrolo[2,3-b:3',2'-d]pyridin]-7"-one;

N-((1S,3R)-6'-methyl-1'-(1-methyl-1H-indazol-5-yl)-2'-(1-methyl-1H-pyrazol-4-yl)-7'-oxo-6',7'-dihydro-3'H-spiro[cyclopentane-1,8'-dipyrrolo[2,3-b:3',2'-d]pyridin]-3-yl)cyclopropanesulfonamide;

N-((1R,3S)-6'-methyl-1'-(1-methyl-1H-indazol-5-yl)-2'-(1-methyl-1H-pyrazol-4-yl)-7'-oxo-6',7'-dihydro-3'H-spiro[cyclopentane-1,8'-dipyrrolo[2,3-b:3',2'-d]pyridin]-3-yl)cyclopropanesulfonamide;

N-((1S,3S)-6'-methyl-1'-(1-(methyl-d$_3$)-1H-indazol-5-yl)-2'-(1-methyl-1H-pyrazol-4-yl)-7'-oxo-6',7'-dihydro-3'H-spiro[cyclopentane-1,8'-dipyrrolo[2,3-b:3',2'-d]pyridin]-3-yl)cyclopropanesulfonamide;

N-((1R,3R)-6'-methyl-1'-(1-(methyl-d$_3$)-1H-indazol-5-yl)-2'-(1-methyl-1H-pyrazol-4-yl)-7'-oxo-6',7'-dihydro-3'H-spiro[cyclopentane-1,8'-dipyrrolo[2,3-b:3',2'-d]pyridin]-3-yl)cyclopropanesulfonamide;

6-methyl-2-(4-((4-(methylsulfonyl)piperidin-1-yl)methyl)phenyl)-1',3,3',6-tetrahydro-7H-spiro[dipyrrolo[2,3-b:3',2'-d]pyridine-8,2'-inden]-7-one;

methyl 6-methyl-2-(1-methyl-1H-pyrazol-4-yl)-1-(1-(methyl-d$_3$)-1H-indazol-5-yl)-7-oxo-6,7-dihydro-3H-dispiro[dipyrrolo[2,3-b:3',2'-d]pyridine-8,1'-cyclobutane-3',4"-piperidine]-1"-carboxylate;

1"-butyryl-6-methyl-1-(1-methyl-1H-indazol-5-yl)-2-(1-methyl-1H-pyrazol-4-yl)-3,6-dihydro-7H-dispiro[dipyrrolo[2,3-b:3',2'-d]pyridine-8,1'-cyclobutane-3',4"-piperidin]-7-one;

N,N,6-trimethyl-1-(1-methyl-1H-indazol-5-yl)-2-(1-methyl-1H-pyrazol-4-yl)-7-oxo-6,7-dihydro-3H-dispiro[dipyrrolo[2,3-b:3',2'-d]pyridine-8,1'-cyclobutane-3',4"-piperidine]-1"-carboxamide;

methyl 6-methyl-1-(1-methyl-1H-indazol-5-yl)-2-(1-methyl-1H-pyrazol-4-yl)-7-oxo-6,7-dihydro-3H-dispiro [dipyrrolo[2,3-b:3',2'-d]pyridine-8,1'-cyclobutane-3',4"-piperidine]-1"-carboxylate;

1"-((2-methoxy ethyl)sulfonyl)-6-methyl-2-(1-methyl-1H-pyrazol-4-yl)-1-phenyl-3,6-dihydro-7H-dispiro [dipyrrolo[2,3-b:3',2'-d] pyridine-8,1'-cyclobutane-3',4"-piperidin]-7-one;

4-(1"-butyryl-6-methyl-1-(1-methyl-1H-indazol-5-yl)-7-oxo-6,7-dihydro-3H-dispiro [dipyrrolo[2,3-b:3',2'-d]pyridine-8,1'-cyclobutane-3',4"-piperidin]-2-yl)-N,N-dimethyl cyclohex-3-ene-1-carboxamide;

1"-butyryl-6-methyl-1-(1-methyl-1H-indazol-5-yl)-2-(1-methyl-1H-pyrrol-3-yl)-3,6-dihydro-7H-dispiro[dipyrrolo[2,3-b:3',2'-d]pyridine-8,1'-cyclobutane-3',4"-piperidin]-7-one;

(R)-2-(1-(((6-methyl-1-(1-methyl-1H-indazol-5-yl)-2-(1-methyl-1H-pyrazol-4-yl)-7-oxo-6,7-dihydro-3H-spiro[dipyrrolo[2,3-b:3',2'-d]pyridine-8,3'-pyrrolidin]-1'-yl)methyl)cyclopropyl)acetonitrile;

(S)-2-(1-(((6-methyl-1-(1-methyl-1H-indazol-5-yl)-2-(1-methyl-1H-pyrazol-4-yl)-7-oxo-6,7-dihydro-3H-spiro[dipyrrolo[2,3-b:3',2'-d]pyridine-8,3'-pyrrolidin]-1'-yl)methyl)cyclopropyl)acetonitrile;

2-(1-((6-methyl-1-(1-methyl-1H-indazol-5-yl)-7-oxo-2-(3-oxo-3,4-dihydro-2H-benzo[b][1,4]oxazin-7-yl)-6,7-dihydro-3H-spiro[dipyrrolo[2,3-b:3',2'-d]pyridine-8,3'-pyrrolidin]-1'-yl)methyl)cyclopropyl)acetonitrile;

2-(1-((6-methyl-1-(1-methyl-1H-indazol-5-yl)-7-oxo-2-(pyrazolo[1,5-a]pyrimidin-3-yl)-6,7-dihydro-3H-spiro[dipyrrolo[2,3-b:3',2'-d]pyridine-8,3'-pyrrolidin]-1'-yl)methyl)cyclopropyl)acetonitrile;

4-((4-(1'-(((1-(cyanomethyl)cyclopropyl)methyl)-6-methyl-1-(1-methyl-1H-indazol-5-yl)-7-oxo-6,7-dihydro-3H-spiro[dipyrrolo[2,3-b:3',2'-d]pyridine-8,3'-pyrrolidin]-2-yl)-1H-pyrazol-1-yl)methyl)benzonitrile;

2-(2-((6-methyl-1-(1-methyl-1H-indazol-5-yl)-2-(1-methyl-1H-pyrazol-4-yl)-7-oxo-6,7-dihydro-3H-spiro[dipyrrolo[2,3-b:3',2'-d]pyridine-8,3'-pyrrolidin]-1'-yl)methyl)spiro[3.3]heptan-2-yl)acetonitrile;

2-(1-((6-methyl-1-(1-methyl-1H-indazol-5-yl)-2-(1-methyl-1H-pyrazol-4-yl)-7-oxo-6,7-dihydro-3H-spiro[dipyrrolo[2,3-b:3',2'-d]pyridine-8,3'-pyrrolidin]-1'-yl)sulfonyl)cyclopropyl)acetonitrile;

2-(1-((6-methoxy-1-(1-methyl-1H-indazol-5-yl)-2-(1-methyl-1H-pyrazol-4-yl)-7-oxo-6,7-dihydro-3H-spiro[dipyrrolo[2,3-b:3',2'-d]pyridine-8,3'-pyrrolidin]-1'-yl)methyl)cyclopropyl)acetonitrile;

2-(1-(6-methyl-1-(1-methyl-1H-indazol-5-yl)-2-(1-methyl-1H-pyrazol-4-yl)-7-oxo-6,7-dihydro-3H-spiro[dipyrrolo[2,3-b:3',2'-d]pyridine-8,4'-piperidin]-1'-yl)cyclopentyl)acetonitrile;

2-(1-(6-methyl-1-(1-methyl-1H-indazol-5-yl)-2-(1-methyl-1H-pyrazol-4-yl)-7-oxo-6,7-dihydro-1'H,3H-spiro[dipyrrolo[2,3-b:3',2'-d]pyridine-8,4'-pyridin]-1'-yl)cyclopropyl)acetonitrile;

2-(4-methoxy-1-(6-methyl-1-(1-methyl-1H-indazol-5-yl)-2-(1-methyl-1H-pyrazol-4-yl)-7-oxo-6,7-dihydro-3H-spiro[dipyrrolo[2,3-b:3',2'-d]pyridine-8,4'-piperidin]-1'-yl)cyclohexyl)acetonitrile;

1'-(2-(1H-1,2,3-triazol-4-yl)propan-2-yl)-6-methyl-1-(1-methyl-1H-indazol-5-yl)-2-(1-methyl-1H-pyrazol-4-yl)-3,6-dihydro-7H-spiro[dipyrrolo[2,3-b:3',2'-d]pyridine-8,4'-piperidin]-7-one;

1'-(2-(4H-1,2,4-triazol-3-yl)propan-2-yl)-6-methyl-1-(1-methyl-1H-indazol-5-yl)-2-(1-methyl-1H-pyrazol-4-yl)-3,6-dihydro-7H-spiro[dipyrrolo[2,3-b:3',2'-d]pyridine-8,4'-piperidin]-7-one;

6-methyl-1'-(3-methyl-1,1-dioxidotetrahydrothiophen-3-yl)-1-(1-methyl-1H-indazol-5-yl)-2-(1-methyl-1H-pyrazol-4-yl)-3,6-dihydro-7H-spiro[dipyrrolo[2,3-b:3',2'-d]pyridine-8,4'-piperidin]-7-one;

2-(1-(2-(5,6-dihydro-4H-pyrrolo[1,2-b]pyrazol-3-yl)-6-methyl-1-(1-(methyl-d$_3$)-1H-indazol-5-yl)-7-oxo-6,7-dihydro-3H-spiro[dipyrrolo[2,3-b:3',2'-d]pyridine-8,4'-piperidin]-1'-yl)cyclopentyl)acetonitrile;

(R)-4-methoxy-3-methyl-3-(6-methyl-2-(1-methyl-1H-pyrazol-4-yl)-1-(1-(methyl-d$_3$)-1H-indazol-5-yl)-7-oxo-6,7-dihydro-3H-spiro[dipyrrolo[2,3-b:3',2'-d]pyridine-8,4'-piperidin]-1'-yl)butanenitrile;

(S)-4-methoxy-3-methyl-3-(6-methyl-2-(1-methyl-1H-pyrazol-4-yl)-1-(1-(methyl-d$_3$)-1H-indazol-5-yl)-7-oxo-6,7-dihydro-3H-spiro[dipyrrolo[2,3-b:3',2'-d]pyridine-8,4'-piperidin]-1'-yl)butanenitrile;

methyl 4-(cyanomethyl)-4-(6-methyl-1-(1-methyl-1H-indazol-5-yl)-2-(1-methyl-1H-pyrazol-4-yl)-7-oxo-6,7-dihydro-3H-spiro[dipyrrolo[2,3-b:3',2'-d]pyridine-8,4'-piperidin]-1'-yl)piperidine-1-carboxylate;

N-(3-(6-methyl-1-(1-methyl-1H-indazol-5-yl)-2-(1-methyl-1H-pyrazol-4-yl)-7-oxo-6,7-dihydro-3H-spiro[dipyrrolo[2,3-b:3',2'-d]pyridine-8,4'-piperidin]-1'-yl)bicyclo[1.1.1]pentan-1-yl)acetamide;

methyl 4-(6-methyl-1-(1-methyl-1H-indazol-5-yl)-2-(1-methyl-1H-pyrazol-4-yl)-7-oxo-6,7-dihydro-3H-spiro[dipyrrolo[2,3-b:3',2'-d]pyridine-8,4'-piperidin]-1'-yl)-2-azabicyclo[2.1.1]hexane-2-carboxylate;

1'-(2-(azetidin-3-yl)propan-2-yl)-6-methyl-1-(1-methyl-1H-indazol-5-yl)-2-(1-methyl-1H-pyrazol-4-yl)-3,6-dihydro-7H-spiro[dipyrrolo[2,3-b:3',2'-d]pyridine-8,4'-piperidin]-7-one;

1-(ethylsulfonyl)-6"-methyl-1"-(1-(methyl-d$_3$)-1H-indazol-5-yl)-2"-(4-(morpholinomethyl)phenyl)-3",6"-dihydro-7"H-dispiro[azetidine-3,1'-cyclobutane-3',8"-dipyrrolo[2,3-b:3',2'-d]pyridin]-7"-one;

1-(ethylsulfonyl)-6"-methyl-1"-(1-methyl-1H-indazol-5-yl)-2"-(1-methyl-1H-pyrazol-4-yl)-3",6"-dihydro-7"H-dispiro[azetidine-3,1'-cyclobutane-3',8"-dipyrrolo[2,3-b:3',2'-d]pyridin]-7"-one;

2"-(1-(cyclopropylmethyl)-1H-pyrazol-4-yl)-1-(ethylsulfonyl)-6"-methyl-1"-(1-methyl-1H-indazol-5-yl)-3",6"-dihydro-7"H-dispiro[azetidine-3,1'-cyclobutane-3',8"-dipyrrolo[2,3-b:3',2'-d]pyridin]-7"-one;

1-(ethylsulfonyl)-2"-(1-(2-methoxyethyl)-1H-pyrazol-4-yl)-6"-methyl-1"-(1-methyl-1H-indazol-5-yl)-3",6"-dihydro-7"H-dispiro[azetidine-3,1'-cyclobutane-3',8"-dipyrrolo[2,3-b:3',2'-d]pyridin]-7"-one;

1-(ethylsulfonyl)-2"-(1-isopropyl-1H-pyrazol-4-yl)-6"-(methyl-d3)-1"-(1-methyl-1H-indazol-5-yl)-3",6"-dihydro-7"H-dispiro[azetidine-3,1'-cyclobutane-3',8"-dipyrrolo[2,3-b:3',2'-d]pyridin]-7"-one;

2"-(1-cyclopentyl-1H-pyrazol-4-yl)-1-(ethylsulfonyl)-6"-methyl-1"-(1-methyl-1H-indazol-5-yl)-3",6"-dihydro-7"H-dispiro[azetidine-3,1'-cyclobutane-3',8"-dipyrrolo[2,3-b:3',2'-d]pyridin]-7"-one;

1-(4-(1-(ethylsulfonyl)-6"-methyl-1"-(1-(methyl-d$_3$)-1H-indazol-5-yl)-7"-oxo-6",7"-dihydro-3"H-dispiro[azetidine-3,1'-cyclobutane-3',8"-dipyrrolo[2,3-b:3',2'-d]pyridin]-2"-yl)benzyl)piperidine-4-carbonitrile;

1-(ethylsulfonyl)-1"-(4-methoxyphenyl)-6"-(methyl-d$_3$)-2"-(4-(morpholinomethyl)phenyl)-3",6"-dihydro-7"H-dispiro[azetidine-3,1'-cyclobutane-3',8"-dipyrrolo[2,3-b:3',2'-d]pyridin]-7"-one;

2"-(1-(2,2-difluoroethyl)-1H-pyrazol-4-yl)-1-(ethylsulfonyl)-6"-methyl-1"-(1-methyl-1H-indazol-5-yl)-3",6"-dihydro-7"H-dispiro[azetidine-3,1'-cyclobutane-3',8"-dipyrrolo[2,3-b:3',2'-d]pyridin]-7"-one;

2"-(5,6-dihydro-4H-pyrrolo[1,2-b]pyrazol-3-yl)-1-(ethylsulfonyl)-6"-methyl-1"-(1-methyl-1H-indazol-5-yl)-3",6"-dihydro-7"H-dispiro[azetidine-3,1'-cyclobutane-3',8"-dipyrrolo[2,3-b:3',2'-d]pyridin]-7"-one;

2"-(1-ethyl-1H-pyrazol-4-yl)-1-(ethylsulfonyl)-1"-(4-methoxyphenyl)-6"-(methyl-d$_3$)-3",6"-dihydro-7"H-dispiro[azetidine-3,1'-cyclobutane-3',8"-dipyrrolo[2,3-b:3',2'-d]pyridin]-7"-one;

1-(ethylsulfonyl)-2"-(1-(2-methoxy-2-methylpropyl)-1H-pyrazol-4-yl)-6"-methyl-1"-(1-(methyl-d$_3$)-1H-indazol-5-yl)-3",6"-dihydro-7"H-dispiro[azetidine-3,1'-cyclobutane-3',8"-dipyrrolo[2,3-b:3',2'-d]pyridin]-7"-one;

1-(ethylsulfonyl)-6"-methyl-1"-(1-methyl-1H-indazol-5-yl)-2"-(1-((tetrahydro-2H-pyran-4-yl)methyl)-1H-pyrazol-4-yl)-3",6"-dihydro-7"H-dispiro[azetidine-3,1'-cyclobutane-3',8"-dipyrrolo[2,3-b:3',2'-d]pyridin]-7"-one;

2"-(6,7-dihydro-5H-pyrazolo[5,1-b][1,3]oxazin-3-yl)-1-(ethylsulfonyl)-6"-methyl-1"-(1-(methyl-d$_3$)-1H-indazol-5-yl)-3",6"-dihydro-7"H-dispiro[azetidine-3,1'-cyclobutane-3',8"-dipyrrolo[2,3-b:3',2'-d]pyridin]-7"-one;

1-(ethylsulfonyl)-2"-(3-methoxy-1-methyl-1H-pyrazol-4-yl)-6"-methyl-1"-(1-(methyl-$d_3$)-1H-indazol-5-yl)-3",6"-dihydro-7"H-dispiro[azetidine-3,1'-cyclobutane-3',8"-dipyrrolo[2,3-b:3',2'-d]pyridin]-7"-one;

1-(2-amino-2-oxoethyl)-N-((1S,3S)-6'-methyl-2'-(1-methyl-1H-pyrazol-4-yl)-1'-(1-(methyl-$d_3$)-1H-indazol-5-yl)-7'-oxo-6',7'-dihydro-3'H-spiro[cyclopentane-1,8'-dipyrrolo[2,3-b:3',2'-d]pyridin]-3-yl)cyclobutane-1-carboxamide;

1-(2-amino-2-oxoethyl)-N-((1R,3R)-6'-methyl-2'-(1-methyl-1H-pyrazol-4-yl)-1'-(1-(methyl-$d_3$)-1H-indazol-5-yl)-7'-oxo-6',7'-dihydro-3'H-spiro[cyclopentane-1,8'-dipyrrolo[2,3-b:3',2'-d]pyridin]-3-yl)cyclobutane-1-carboxamide;

1"-butyryl-6-methyl-1-(1-methyl-1H-indazol-5-yl)-2-(1-(methyl-$d_3$)-1H-pyrrol-3-yl)-3,6-dihydro-7H-dispiro[dipyrrolo[2,3-b:3',2'-d]pyridine-8,1'-cyclobutane-3',4"-piperidin]-7-one;

1"-butyryl-6-methyl-1-(1-(methyl-$d_3$)-1H-indazol-5-yl)-2-(1-(methyl-$d_3$)-1H-pyrrol-3-yl)-3,6-dihydro-7H-dispiro[dipyrrolo[2,3-b:3',2'-d]pyridine-8,1'-cyclobutane-3',4"-piperidin]-7-one;

2'-(1-isopropyl-1H-pyrazol-4-yl)-6'-(methyl-$d_3$)-1'-(1-methyl-1H-indazol-5-yl)-1-((1-methylcyclopropyl)sulfonyl)-3',6'-dihydro-7'H-spiro[azepane-4,8'-dipyrrolo[2,3-b:3',2'-d]pyridin]-7'-one; and 2'-(1-(1-cyclopropylethyl)-1H-pyrazol-4-yl)-1-(ethylsulfonyl)-6'-(methyl-$d_3$)-1'-(1-methyl-1H-indazol-5-yl)-3',6'-dihydro-7'H-spiro[azepane-4,8'-dipyrrolo[2,3-b:3',2'-d]pyridin]-7'-one;

or a pharmaceutically acceptable salt thereof.

52. The compound of claim 1, or a pharmaceutically acceptable salt thereof, wherein the compound is deuterated.

53. A pharmaceutical composition comprising a compound of claim 1, or a pharmaceutically acceptable salt thereof, and a pharmaceutically acceptable carrier.

54. A method of inhibiting an activity of the V617F variant of JAK2 kinase, comprising contacting the kinase with a compound of claim 1, or a pharmaceutically acceptable salt thereof.

55. A method of treating a myeloproliferative disorder selected from polycythemia vera, essential thrombocythemia, myelofibrosis with myeloid metaplasia, primary myelofibrosis, post-essential thrombocythemia myelofibrosis, and post polycythemia vera myelofibrosis in a patient in need thereof, the method comprising administering to the patient a therapeutically effective amount of a compound of claim 1, or a pharmaceutically acceptable salt thereof.

56. The method of claim 55, wherein the myeloproliferative disorder is polycythemia vera.

57. The method of claim 55, wherein the myeloproliferative disorder is essential thrombocythemia.

58. The method of claim 55, wherein the myeloproliferative disorder is myelofibrosis with myeloid metaplasia.

59. The method of claim 55, wherein the myeloproliferative disorder is primary myelofibrosis.

60. The method of claim 55, wherein the myeloproliferative disorder is post-essential thrombocythemia myelofibrosis.

61. The method of claim 55, wherein the myeloproliferative disorder is post polycythemia vera myelofibrosis.

* * * * *

SEQUENCE LISTING

<160> NUMBER OF SEQ ID NOS: 1

<210> SEQ ID NO 1
<211> LENGTH: 15
<212> TYPE: PRT
<213> ORGANISM: Artificial Sequence
<220> FEATURE:
<223> OTHER INFORMATION: Biotin-labeled peptide, custom synthesis

<400> SEQUENCE: 1

Glu Gln Glu Asp Glu Pro Glu Gly Asp Tyr Phe Glu Trp Leu Glu
1               5                   10                  15